(12) United States Patent
Menges et al.

(10) Patent No.: US 10,512,267 B2
(45) Date of Patent: Dec. 24, 2019

(54) COMPOSITIONS COMPRISING A TRIAZOLE COMPOUND AND A BIOPESTICIDE

(71) Applicant: BASF AGRO BV, EA Arnhem (NL)

(72) Inventors: Frederik Menges, Schriesheim (DE); Martin Semar, Gleiszellen-Gleishorbach (DE); Nadine Riediger, Schifferstadt (DE); Lutz Brahm, Worms (DE); Kristin Klappach, Neustadt (DE); Murat Mertoglu, Ludwigshafen (DE); Winfried Mayer, Bubenheim (DE); Egon Haden, Speyer (DE); Jan Klaas Lohmann, Lambsheim (DE); Nadege Boudet, Hirschberg (DE); Annette Schuster, Schifferstadt (DE)

(73) Assignee: BASF Agro, B.V., Arnhem (NL)

( * ) Notice: Subject to any disclaimer, the term of this patent is extended or adjusted under 35 U.S.C. 154(b) by 95 days.

(21) Appl. No.: 14/902,877

(22) PCT Filed: Jun. 25, 2014

(86) PCT No.: PCT/EP2014/063412
§ 371 (c)(1),
(2) Date: Jan. 5, 2016

(87) PCT Pub. No.: WO2015/003908
PCT Pub. Date: Jan. 15, 2015

(65) Prior Publication Data
US 2016/0150786 A1  Jun. 2, 2016

(30) Foreign Application Priority Data

Jul. 8, 2013 (EP) .................................. 13175463

(51) Int. Cl.
| | | |
|---|---|---|
| *A01N 63/00* | (2006.01) | |
| *A01N 63/02* | (2006.01) | |
| *A01N 63/04* | (2006.01) | |
| *A01N 43/653* | (2006.01) | |
| *A01N 37/18* | (2006.01) | |
| *A01N 43/16* | (2006.01) | |

(52) U.S. Cl.
CPC ........... *A01N 43/653* (2013.01); *A01N 37/18* (2013.01); *A01N 43/16* (2013.01); *A01N 63/02* (2013.01)

(58) Field of Classification Search
None
See application file for complete search history.

(56) References Cited

U.S. PATENT DOCUMENTS

| | | |
|---|---|---|
| 4,242,121 A | 12/1980 | Hawkins |
| 4,599,362 A | 7/1986 | Tachibana |
| 4,940,720 A | 7/1990 | Nevill et al. |
| 4,940,721 A | 7/1990 | Nevill et al. |
| 4,945,100 A | 7/1990 | Nyfeler et al. |
| 4,992,458 A | 2/1991 | Riebli |
| 5,143,932 A | 9/1992 | Dutzmann |
| 5,162,358 A | 11/1992 | Dehne |
| 8,492,312 B2 * | 7/2013 | Thomas ................. A01N 25/00 504/334 |
| 8,546,577 B2 | 10/2013 | Jeschke et al. |
| 2008/0108686 A1 | 5/2008 | Strathmann |
| 2009/0036509 A1 | 2/2009 | Grammenos |
| 2009/0286768 A1 | 11/2009 | Jin |
| 2010/0240619 A1 | 9/2010 | Gregory et al. |
| 2014/0012855 A1 | 1/2014 | Bingham |
| 2014/0127322 A1 | 5/2014 | Oberholzer et al. |
| 2014/0128255 A1 | 5/2014 | Dietz et al. |
| 2014/0155262 A1 | 6/2014 | Dietz et al. |
| 2015/0250173 A1 | 9/2015 | Braun |

FOREIGN PATENT DOCUMENTS

| | | |
|---|---|---|
| AU | 611315 B2 | 6/1991 |
| CA | 1100976 A1 | 5/1981 |
| CA | 1187084 A1 | 5/1985 |
| CA | 1209152 A1 | 8/1986 |
| CA | 1210404 A1 | 8/1986 |
| CN | 101225074 A | 7/2008 |
| CS | 247200 B2 | 12/1986 |
| DE | 2325878 A1 | 12/1974 |
| DE | 3801233 A1 | 8/1988 |
| DE | 3733755 A1 | 4/1989 |
| DE | 4003180 A1 | 8/1991 |
| EP | 0000017 A1 | 12/1978 |
| EP | 0077479 A2 | 4/1983 |
| EP | 0113640 A2 | 7/1984 |
| EP | 0114567 A2 | 8/1984 |
| EP | 0126430 | 11/1984 |
| EP | 0275955 A1 | 7/1988 |
| EP | 0354183 | 2/1990 |
| EP | 354183 A2 | 2/1990 |
| EP | 0440950 A2 | 8/1991 |
| EP | 0470466 A2 | 2/1992 |

(Continued)

OTHER PUBLICATIONS

International Search Report, issued in PCT/EP2014/063412, dated Jul. 28, 2014.
International Preliminary Report on Patentability, issued in PCT/EP2014/063412, dated Jan. 12, 2016.
Search Report, issued in corresponding EP Application No. 13175463, dated Sep. 11, 2013.
Yu et al., "Synthesis and Fungicidal Evaluation of 2-Arylphenyl Ether-3-(1$H$-1,2,4-triazol-1-yl)propan-2-ol Derivatives," J. Agric. Food Chem., vol. 57, (2009), pp. 4854-4860.
Afon'Kin, A.A. et al. "Synthesis of Some Electron-Rich Aryl(hetaryl)oxarines under Phase-Transfer and Homogenous Conditions", Russian Journal of Organic Chemistry, 2008, p. 1776-1779, vol. 44, No. 12.

(Continued)

*Primary Examiner* — Alton N Pryor
(74) *Attorney, Agent, or Firm* — Brinks Gilson & Lione

(57) ABSTRACT

Compositions comprising a triazole compound and a biopesticide.

19 Claims, No Drawings

(56) References Cited

FOREIGN PATENT DOCUMENTS

| | | | |
|---|---|---|---|
| EP | 0735142 B1 | 10/2001 | |
| EP | 1431275 A1 | 6/2004 | |
| EP | 2559688 | 2/2013 | |
| EP | 2559688 A1 | 2/2013 | |
| EP | 2835052 | 2/2015 | |
| FR | 2491924 A1 | 4/1982 | |
| GB | 2064520 A1 | 6/1981 | |
| GB | 2064520 | * | 7/1981 |
| GB | 2132195 A1 | 7/1984 | |
| GB | 2143815 A1 | 2/1985 | |
| JP | 59-222434 | 12/1984 | |
| JP | 2-83304 | 3/1990 | |
| NZ | 230176 A | 1/1992 | |
| WO | 1996041804 | 12/1996 | |
| WO | 02085891 A1 | 10/2002 | |
| WO | 03064572 A1 | 8/2003 | |
| WO | 2005123689 A1 | 12/2005 | |
| WO | 2005123690 A1 | 12/2005 | |
| WO | 06015866 A1 | 2/2006 | |
| WO | 2006015866 A1 | 2/2006 | |
| WO | 2006087373 A1 | 8/2006 | |
| WO | 2006109933 A1 | 10/2006 | |
| WO | 2006119876 A1 | 11/2006 | |
| WO | 2007031308 A2 | 3/2007 | |
| WO | 2007115644 | 10/2007 | |
| WO | 2008082198 A1 | 7/2008 | |
| WO | 10034737 A1 | 4/2010 | |
| WO | 2010146114 A1 | 12/2010 | |
| WO | 2011099804 A2 | 8/2011 | |
| WO | 2012035050 | 3/2012 | |
| WO | 2012037782 A1 | 3/2012 | |
| WO | 12084670 A1 | 6/2012 | |
| WO | 2012090515 | 7/2012 | |
| WO | 2012092115 | 7/2012 | |
| WO | 12143317 A1 | 10/2012 | |
| WO | 2013010885 | 1/2013 | |
| WO | 2013010894 | 1/2013 | |
| WO | WO 2013007767 | 1/2013 | |
| WO | WO 2013010862 | 1/2013 | |
| WO | 2013024075 | 2/2013 | |
| WO | 2013024076 | 2/2013 | |
| WO | 2013024077 | 2/2013 | |
| WO | 2013024082 | 2/2013 | |
| WO | WO 2013024080 | 2/2013 | |
| WO | WO 2013024081 | 2/2013 | |
| WO | WO 2013024083 | 2/2013 | |
| WO | 13189801 A1 | 12/2013 | |
| WO | 2014079719 | 5/2014 | |
| WO | 2014079724 | 5/2014 | |
| WO | 2014079728 | 5/2014 | |
| WO | 2014079730 | 5/2014 | |
| WO | 2014079752 | 5/2014 | |
| WO | 2014079754 | 5/2014 | |
| WO | 2014079764 | 5/2014 | |
| WO | 2014079766 | 5/2014 | |
| WO | 2014079769 | 5/2014 | |
| WO | 2014079770 | 5/2014 | |
| WO | 2014079771 | 5/2014 | |
| WO | 2014079772 | 5/2014 | |
| WO | 2014079773 | 5/2014 | |
| WO | 2014079774 | 5/2014 | |
| WO | 2014079804 | 5/2014 | |
| WO | 2014079813 | 5/2014 | |
| WO | 2014079814 | 5/2014 | |
| WO | 2014079841 | 5/2014 | |
| WO | 2014095994 | 6/2014 | |
| WO | 2015003908 | 1/2015 | |
| WO | 15055497 A1 | 4/2015 | |
| WO | 2015113860 | 8/2015 | |
| WO | 2015135701 | 9/2015 | |
| WO | 2015169711 | 11/2015 | |
| WO | 15189080 A1 | 12/2015 | |
| WO | 15197393 A1 | 12/2015 | |
| WO | 1614224 A1 | 1/2016 | |
| WO | 16008740 A1 | 1/2016 | |
| WO | 16078995 A1 | 5/2016 | |
| WO | 16079043 A1 | 5/2016 | |
| WO | 2014095932 | 6/2016 | |
| WO | 16128239 A1 | 8/2016 | |
| WO | 16128240 A1 | 8/2016 | |
| WO | 16128261 A2 | 8/2016 | |
| WO | 16142456 A1 | 9/2016 | |
| WO | 17001252 A1 | 1/2017 | |

OTHER PUBLICATIONS

Akama, Tsutomu, et al. "Discovery and structure-activity study of a novel benzoxaborole anti-inflammatory agent (AN2728) for the potential topical treatment of psoriasis and atopic dermatitis", Bioorganic & Medicinal Chemistry Letters, 2009, p. 2129-2132, vol. 19.

Brandes, Bridget D., et al., "Synthesis of enantiopure 3-chlorostyrene oxide via an asymmetric epoxidation-hydrolytic kinetic resolution sequence", Tetrahedron; Asymmetry, 1997, p. 3927-3933, vol. 8, No. 23.

Forrester, Julie, et al. "Generation of trimethylsulfonium cation from dimethyl sulfoxide and dimethyl sulfate: implication s for the synthesis of epoxides from aldehydes and ketones", J. Chem. Soc. Perkin Trans. 1, 1995, pp. 2289-2291, vol. 1995.

Kuzenkov, A.V., "Synthesis of substituted 2-azoloyl-1-pyridylethan-1-ols", Chemistry of hererocyclic compounds, 2003, p. 1492-1495 vol. 39, No. 11.

Lima, Lidia Moreira et al., "Bioisosterism: A useful strategy for molecular Modification and drug design", Current Medicinal Chemistry, 2005, p. 23-49, vol. 12.

Mosset, Paul et al. "Trimethylsulfonium Methylsulfate, a simple and efficient epoxidizing agent", Synthetic Communications, 1985, p. 749-757, vol. 15, No. 8.

Office Action, issued in co-pending U.S. Appl. No. 14/653,578, dated Aug. 24, 2016.

Final Office Action, issued in co-pending U.S. Appl. No. 14/653,578, dated Apr. 28, 2017.

Office Action, issued in co-pending U.S. Appl. No. 15/319,963, dated Mar. 8, 2018.

Office Action, issued in co-pending U.S. Appl. No. 14/653,578, dated Oct. 24, 2017.

Final Office Action, issued in co-pending U.S. Appl. No. 14/653,578, dated Jul. 3, 2018.

Database CA [Online], Chemical Abstracts Service, Columbus, Ohio, US, Crew, et al., "Substituted midazopyrazines and imidazotriazines as ACK1 inhibitors and their preparation" retrieved from STN Database accession No. 2009-1436665.

Database CA [Online], Chemical Abstracts Service, Columbus, Ohio, US, Schlafke, et al., "Phenoxy derivatives of trifluoromethylbenzene", retrieved from STN, Database accession No. 1975-170346.

Database CA [Online], Chemical Abstracts Service, Columbus, Ohio, US, Wan, et al., "Preparation of tricyclic compounds as Lp-PLA2 inhibitors", retrieved from STN, Database accession No. 2012-459740.

Office Action, issued in co-pending U.S. Appl. No. 14/653,578, dated Feb. 5, 2019.

Office Action, issued in co-pending U.S. Appl. No. 15/739,876, dated Oct. 15, 2018.

Final Office Action, issued in co-pending U.S. Appl. No. 15/805,679, dated Oct. 12, 2018.

Office Action, issued in co-pending U.S. Appl. No. 15/805,679, dated May 18, 2018.

Final Office Action, issued in co-pending U.S. Appl. No. 15/739,876 dated May 22, 2019.

* cited by examiner

COMPOSITIONS COMPRISING A TRIAZOLE COMPOUND AND A BIOPESTICIDE This application is a National Stage application of International Application No. PCT/EP2014/063412, filed Jun. 25, 2014. This application also claims priority under 35 U.S.C. § 119 to European Patent Application No. 13175463.2, filed Jul. 8, 2013.

The present invention relates to compositions comprising,
1) as component I a compound selected from:
compound I-1 2-[2-chloro-4-(4-chlorophenoxy)phenyl]-1-(1,2,4-triazol-1-yl)pent-3-yn-2-ol;
compound I-2 1-[2-chloro-4-(4-chlorophenoxy)phenyl]-1-cyclopropyl-2-(1,2,4-triazol-1-yl)ethanol;
compound I-3 2-[4-(4-chlorophenoxy)-2-(trifluoromethyl)phenyl]-1-(1,2,4-triazol-1-yl)propan-2-ol;
compound I-4 1-[4-(4-chlorophenoxy)-2-(trifluoromethyl)phenyl]-1-cyclopropyl-2-(1,2,4-triazol-1-yl)ethanol;
compound I-5 2-[4-(4-chlorophenoxy)-2-(trifluoromethyl)phenyl]-3-methyl-1-(1,2,4-triazol-1-yl)butan-2-ol;
compound I-6 1-[2-[2-chloro-4-(4-chlorophenoxy)phenyl]-2-methoxy-pent-3-ynyl]-1,2,4-triazole;
compound I-7 2-[4-(4-chlorophenoxy)-2-(trifluoromethyl)phenyl]-1-(1,2,4-triazol-1-yl)butan-2-ol;
compound I-8 1-[2-[2-chloro-4-(4-chlorophenoxy)phenyl]-2-cyclopropyl-2-methoxy-ethyl]-1,2,4-triazole;
compound I-9 1-[2-[4-(4-chlorophenoxy)-2-(trifluoromethyl)phenyl]-2-methoxy-propyl]-1,2,4-triazole;
compound I-10 2-[2-chloro-4-(4-chlorophenoxy)phenyl]-3,3-dimethyl-1-(1,2,4-triazol-1-yl)butan-2-ol,
compound I-11 1-[2-[4-(4-chlorophenoxy)-2-(trifluoromethyl)phenyl]-2-cyclopropyl-2-methoxy-ethyl]-1,2,4-triazole;
compound I-12 1-[2-[2-chloro-4-(4-chlorophenoxy)phenyl]-2-methoxy-3,3-dimethyl-butyl]-1,2,4-triazole;
compound I-13 1-[2-[4-(4-chlorophenoxy)-2-(trifluoromethyl)phenyl]-2-methoxy-butyl]1,2,4-triazole;
compound I-14 2-[4-(4-chlorophenoxy)-2-(trifluoromethyl)phenyl]-1-(1,2,4-triazol-1-yl)pent-3-yn-2-ol;
compound I-15 1-[2-[4-(4-chlorophenoxy)-2-(trifluoromethyl)phenyl]-2-methoxy-pent-3-ynyl]-1,2,4-triazole;
compound I-16 2-[4-(4-chlorophenoxy)-2-(trifluoromethyl)phenyl]-1-(1,2,4-triazol-1-yl)but-3-yn-2-ol;
compound I-17 2-[2-chloro-4-(4-chlorophenoxy)phenyl]-1-(1,2,4-triazol-1-yl)propan-2-ol;
compound I-18 2-[2-chloro-4-(4-fluorophenoxy)phenyl]-1-(1,2,4-triazol-1-yl)propan-2-ol;
compound I-19 2-[2-chloro-4-(4-chlorophenoxy)phenyl]-3-methyl-1-(1,2,4-triazol-1-yl)butan-2-ol;
compound I-20 1-[2-[2-chloro-4-(4-chlorophenoxy)phenyl]-2-methoxy-propyl]-1,2,4-triazole;
compound I-21 1-[2-[2-chloro-4-(4-chlorophenoxy)phenyl]-2-methoxy-butyl]-1,2,4-triazole;
compound I-22 1-[2-[2-chloro-4-(4-chlorophenoxy)phenyl]-2-methoxy-pentyl]-1,2,4-triazole;
compound I-23 2-[2-chloro-4-(4-chlorophenoxy)phenyl]-1,1,1-trifluoro-3-(1,2,4-triazol-1-yl)propan-2-ol;
compound I-24 2-[2-chloro-4-(4-chlorophenoxy)phenyl]-3-fluoro-1-(1,2,4-triazol-1-yl)butan-2-ol hydrochloride;
compound I-25 2-[2-chloro-4-(4-chlorophenoxy)phenyl]-1-(1,2,4-triazol-1-yl)pent-4-yn-2-ol;
compound I-26 2-[2-chloro-4-(4-chlorophenoxy)phenyl]-1-methoxy-3-(1,2,4-triazol-1-yl)propan-2-ol;
compound I-27 2-[2-chloro-4-(4-fluorophenoxy)phenyl]-1-methoxy-3-(1,2,4-triazol-1-yl)propan-2-ol;
compound I-28 2-[4-(4-chlorophenoxy)-2-(trifluoromethyl)phenyl]-1-(1,2,4-triazol-1-yl)pentan-2-ol;
compound I-29 and 2-[4-(4-fluorophenoxy)-2-(trifluoromethyl)phenyl]-1-(1,2,4-triazol-1-yl)propan-2-ol;
compound I-30 2-[2-chloro-4-(4-chlorophenoxy)phenyl]-1-(1,2,4-triazol-1-yl)butan-2-ol; and
compound I-31 2-[2-chloro-4-(4-chlorophenoxy)phenyl]-1-(1,2,4-triazol-1-yl)pentan-2-ol; and
2) as component II a biopesticide selected from groups L1 to L6:
L1) Microbial pesticides with fungicidal, bactericidal, viricidal and/or plant defense activator activity: *Ampelomyces quisqualis, Aspergillus flavus, Aureobasidium pullulans, Bacillus altitudinis, B. amyloliquefaciens, B. megaterium, B. mojavensis, B. mycoides, B. pumllus, B. simplex, B. solisalsi, B. subtilis, B. subtilis* var. *amyloliquefaciens, Candida oleophlla, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus alvei, Paenibacillus polymyxa, Pantoea vagans, Penicillium bilaiae, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperellum, T. atroviride, T. fertile, T. gamsii, T. harmatum, T. harzianum, T. polysporum, T. stromaticum, T. virens, T. viride, Typhula phacorrhiza, Ulocladium oudemansii, Verticillium dahlia,* zucchini yellow mosaic virus (avirulent strain);
L2) Biochemical pesticides with fungicidal, bactericidal, viricidal and/or plant defense activator activity: chitosan (hydrolysate), harpin protein, laminarin, Menhaden fish oil, natamycin, Plum pox virus coat protein, potassium or sodium bicarbonate, *Reynoutria sachalinensis* extract, salicylic acid, tea tree oil;
L3) Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai,* B. t. ssp. *israelensis,* B. t. ssp. *galleriae,* B. t. ssp. *kurstaki,* B. t. ssp. *tenebrionis, Beauveria bassiana, B. brongniartil, Burkholderia* spp., *Chromobacterium subtsugae, Cydia pomonella* granulovirus (CpGV), *Cryptophlebia leucotreta* granulovirus (CrIeGV), *Flavobacterium* spp., *Helicoverpa armigera* nucleopolyhedrovirus (HearNPV), *Heterorhabditis bacteriophora, Isaria fumosorosea, Lecaniciffium longisporum, L. muscarium, Metarhizium anisopliae, Metarhizium anisopliae* var. *anisopliae, M. anisopliae* var. *acridum, Nomuraea rileyi, Paecilomyces lilacinus, Paenibacillus popilliae, Pasteuria* spp., *P. nishizawae, P. penetrans, P. ramosa, P. thornea, P. usgae, Pseudomonas fluorescens, Spodoptera littoralis* nucleopolyhedrovirus (SpliNPV), *Steinemema carpocapsae, S. feltiae, S. kraussei, Streptomyces galbus, S. microflavus;*
L4) Biochemical pesticides with insecticidal, acaricidal, molluscidal, pheromone and/or nematicidal activity: L-carvone, citral, (E,Z)-7,9-dodecadien-1-ylacetate, ethyl formate, (E,Z)-2,4-ethyl decadienoate (pear ester), (Z,Z, E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13- octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, *Acacia negra* extract, extract of grapefruit seeds and pulp, extract of *Chenopodium ambrosiodes*, Catnip oil, Neem oil, Quillay extract, *Tagetes* oil;

L5) Microbial pesticides with plant stress reducing, plant growth regulator, plant growth promoting and/or yield enhancing activity: *Azospirillum amazonense, A. brasilense, A. lipoferum, A. irakense, A. halopraeferens, Bradyrhizobium* spp., *B. elkanii B. japonicum, B. liaoningense, B. lupini, Delflia acidovorans, Glomus intraradices, Mesorhizobium* spp., *Rhizobium leguminosarum* bv. *phaseoli, R. l.* bv. *trifolii, R. l.* bv. *viciae, R. tropici, Sinorhizobium mellloti,*

L6) Biochemical pesticides with plant stress reducing, plant growth regulator and/or plant yield enhancing activity: abscisic acid, aluminium silicate (kaolin), 3-decen-2-one, formononetin, genistein, hesperetin, homobrassinolide, humates, jasmonic acid and its salts or derivatives thereof, lysophosphatidyl ethanolamine, naringenin, polymeric polyhydroxy acid, *Ascophyllum nodosum* (Norwegian kelp, Brown kelp) extract and *Ecklonia maxima* (kelp) extract.

In particular, L1) to L6) are defined as follows (L1.1) to L.6.1)):

L1.1) Microbial pesticides with: *Ampelomyces quisqualis, Aspergillus flavus, Aureobasidium pullulans, Bacillus amyloliquefaciens, B. mojavensis, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Fusarium oxysporum, Clonostachys rosea* f. *catenulate* (also named *Gliocladium catenulatum*), *Gliocladium roseum, Metschnikowia fructicola, Microdochium dimerum, Paenibacillus polymyxa, Pantoea agglomerans, Phlebiopsis gigantea, Pseudozyma flocculosa, Pythium oligandrum, Sphaerodes mycoparasitica, Streptomyces lydicus, S. violaceusniger, Talaromyces flavus, Trichoderma asperellum, T. atroviride, T. fertile, T. gamsii, T. harmatum*; composition of *T. harzianum* and *T. viride*; composition of *T. polysporum* and *T. harzianum; T. stromaticum, T. virens* (also named *Gliocladium virens), T. viride, Typhula phacorrhiza, Ulocladium oudema, U. oudemansii, Verticillium dahlia*, zucchini yellow mosaic virus (avirulent strain);

L2.1) Biochemical pesticides with fungicidal, bactericidal, viricidal and/or plant defense activator activity: chitosan (hydrolysate), jasmonic acid or salts or derivatives thereof, laminarin, Menhaden fish oil, natamycin, Plum pox virus coat protein, *Reynoutria sachlinensis* extract, salicylic acid, tea tree oil;

L3.1) Microbial pesticides with insecticidal, acaricidal, molluscidal and/or nematicidal: *Bacillus firmus, B. thuringiensis* ssp. *israelensis,* B. t. ssp. *galleriae,* B. t. ssp. *kurstaki, Beauveria bassiana, Burkholderia* sp., *Chromobacterium subtsugae, Cydia pomonella* granulosis virus, *Isaria fumosorosea, Lecanicillium longisporum, L. muscarium* (formerly *Verticillium lecanii), Metarhizium anisopliae, M. anisopliae* var. *acridum, Paecilomyces fumosoroseus, P. lilacinus, Paenibacillus poppiliae, Pasteuria* spp., *P. nishizawae, P. reneformis, P. usagae, Pseudomonas fluorescens, Steinernema feltiae, Streptomyces galbus;*

L4.1) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-ylacetate, Z-7-tetradecen-2-one, Z-9-tetradecen-1-ylacetate, Z-11-tetradecenal, Z-11-tetradecen-1-ol, *Acacia negra* extract, extract of grapefruit seeds and pulp, extract of *Chenopodium ambrosiodae*, Catnip oil, Neem oil, Quillay extract, *Tagetes* oil;

L5.1) Microbial pesticides with plant stress reducing, plant growth regulator, plant growth promoting and/or yield enhancing activity: *Azospirillum amazonense A. brasilense, A. lipoferum, A. irakense, A. halopraeferens, Bradyrhizobium* sp., *B. japonicum, Glomus intraradices, Mesorhizobium* sp., *Paenibacillus alvei, Penicillium bilaiae, Rhizobium leguminosarum* bv. *phaseolii, R. l. trifolii, R. l.* bv. *viciae, Sinorhizobium meliloti;*

L6.1) Biochemical pesticides with plant stress reducing, plant growth regulator and/or plant yield enhancing activity: abscisic acid, aluminium silicate (kaolin), 3-decen-2-one, homobrassinlide, humates, lysophosphatidyl ethanolamine, polymeric polyhydroxy acid, *Ascophyllum nodosum* (Norwegian kelp, Brown kelp) extract and *Ecklonia maxima* (kelp) extract.

The invention furthermore relates to the use of the inventive compositions for controlling phytopathogenic fungi as detailed herein and preparations or compositions comprising them. The invention furthermore also relates to seed comprising the compositions. The invention furthermore also relates to methods for controlling phytopathogenic fungi as detailed herein, wherein the fungi or the materials, plants, the soil or seed to be protected from fungal attack are treated with an effective amount of a compositions according to the invention. The invention furthermore also relates to processes for preparing the compositions according to the invention.

Practical agricultural experience has shown that the repeated and exclusive application of an individual active compound in the control of harmful fungi leads in many cases to a rapid selection of those fungus strains which have developed natural or adapted resistance against the active compound in question. Effective control of these fungi with the active compound in question is then no longer possible.

To reduce the risk of the selection of resistant fungus strains, compositions of different active compounds are nowadays conventionally employed for controlling harmful fungi. By combining active compounds having different mechanisms of action, it is possible to ensure successful control over a relatively long period of time.

It is an object of the present invention to provide, with a view to effective resistance management and effective control of phytopathogenic harmful fungi, at application rates which are as low as possible, compositions which, at a reduced total amount of active compounds applied, have improved activity against the harmful fungi (synergistic compositions) and a broadened activity spectrum, in particular for certain indications.

We have accordingly found that this object is achieved by the compositions, defined herein, comprising a compound I and a compound II. Moreover, we have found that simultaneous, that is joint or separate, application of a compound I and a compound II or successive application of a compound I and of compound II allows better control of harmful fungi than is possible with the individual compounds alone (synergistic compositions).

According to the present invention, compositions may comprise besides a compound I and a biopesticide II, as component III a further active compound. The inventive compositions can, in the use form as fungicides, also be present together with other active substances, e. g. with herbicides, insecticides, growth regulators, fungicides or else with fertilizers, as premix or, if appropriate, not until immediately prior to use (tank mix).

Accordingly we have found the compositions and uses defined at the outset and in the following description. In particular, the present invention relates to compositions comprising component I and component II and to compositions comprising component I, component II and component III, wherein component III is selected from other active substances, e. g. with herbicides, insecticides, growth regulators, fungicides or else with fertilizers. In addition to the components I, II and III mentioned, the compositions according to the invention may also comprise further components (for example component IV or components IV and V).

In the inventive compositions, compounds I and/or the further active compounds comprised in the respective composition can be present in different crystal modifications, which may differ in biological activity.

The compounds I can be obtained by various routes in analogy to prior art processes known (cf. J. Agric. Food Chem. (2009) 57, 4854-4860; EP 0 275 955 A1; DE 40 03 180 A1; EP 0 113 640 A2; EP 0 126 430 A2; U.S. Pat. No. 4,940,720; EP 354183 A2). Furthermore, compounds of formula I or similar compounds from the triazole class, its preparation and use in crop protection are described in WO 2013/024076, WO 2013/024075, WO2013/024077, WO 2013/024080, WO 2013/024083, WO 2013/007767 and WO 2013/010862 which also disclose certain compositions with other active compounds. Some of the compounds I are described in J. Agric. Food Chem. (2009) 57, 4854-4860, EP 0 126 430 A2, U.S. Pat. No. 4,940,720; EP 354183 A2 and EP 0 113 640 A2 DE 40 03 180 A1.

Owing to the basic character of their nitrogen atoms, the component I, i.e in particular compound I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30 and I-31 or any group of compounds I detailed herein, is capable of forming salts or adducts with inorganic or organic acids or with metal ions, in particular salts with inorganic acids.

Examples of inorganic acids are hydrohalic acids, such as hydrogen fluoride, hydrogen chloride, hydrogen bromide and hydrogen iodide, carbonic acid, sulfuric acid, phosphoric acid and nitric acid.

Suitable organic acids are, for example, formic acid and alkanoic acids, such as acetic acid, trifluoroacetic acid, trichloroacetic acid and propionic acid, and also glycolic acid, thiocyanic acid, lactic acid, succinic acid, citric acid, benzoic acid and other arylcarboxylic acids, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfonic acid groups), alkylphosphonic acids (phosphonic acids having straight-chain or branched alkyl radicals with 1 to 20 carbon atoms), arylphosphonic acids or aryldiphosphonic acids (aromatic radicals, such as phenyl and naphthyl, which carry one or two phosphoric acid radicals), where the alkyl or aryl radicals may carry further substituents, for example p-toluenesulfonic acid, salicylic acid, p-aminosalicylic acid, 2-phenoxybenzoic acid, 2-acetoxybenzoic acid etc. Suitable metal ions are in particular the ions of the elements of the second main group, in particular calcium and magnesium, of the third and fourth main group, in particular aluminum, tin and lead, and also of the elements of transition groups one to eight, in particular chromium, manganese, iron, cobalt, nickel, copper, zinc, and others. Particular preference is given to the metal ions of the elements of transition groups of the fourth period. The metals can be present in the various valencies that they can assume.

Components I comprise chiral centers and they are generally obtained in the form of racemates. The R- and S-enantiomers of the compounds according to the invention can be separated and isolated in pure form with methods known by the skilled person, e.g. by using chiral HPLC. Suitable for use as antimicrobial agents are both the enantiomers and compositions thereof. This applies correspondingly to the compositions. Furthermore, components I can be present in different crystal modifications, which may differ in biological activity.

In particular, in each case, a racemic composition is present. Furthermore, any other proportions of the (R)-enantiomer and the (S)-enantiomer may be present according to the present invention. This applies to every composition detailed herein.

According to one embodiment of the present invention, component I is compound I-1. Compound I-1 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-1.

According to one specific embodiment, the compound I-1 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-1 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further embodiment of the present invention, component I is compound I-2. Compound I-2 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-2.

According to one specific embodiment, the compound I-2 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-2 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-3. Compound I-3 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-3.

According to one specific embodiment, the compound I-3 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-3 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-4. Compound I-4 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-4.

According to one specific embodiment, the compound I-4 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-4 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-5. Compound I-5 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-5.

According to one specific embodiment, the compound I-5 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-5 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-6. Compound I-6 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-6.

According to one specific embodiment, the compound I-6 is provided and used as (R)-enantiomer with an enantomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-6 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-7. Compound I-7 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-7.

According to one specific embodiment, the compound I-7 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-7 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-8. Compound I-8 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-8.

According to one specific embodiment, the compound I-8 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-8 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-9. Compound I-9 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-9.

According to one specific embodiment, the compound I-9 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-9 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-10. Compound I-10 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-10.

According to one specific embodiment, the compound I-10 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-10 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-11. Compound I-11 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-11.

According to one specific embodiment, the compound I-11 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-11 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-12. Compound I-12 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-12.

According to one specific embodiment, the compound I-12 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-12 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-13. Compound I-13 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-13.

According to one specific embodiment, the compound I-13 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-13 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-14. Compound I-14 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-14.

According to one specific embodiment, the compound I-14 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-14 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-15. Compound I-15 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-15.

According to one specific embodiment, the compound I-15 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-15 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-16. Compound I-16 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-16.

According to one specific embodiment, the compound I-16 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-16 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-17. Compound I-17 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-17.

According to one specific embodiment, the compound I-17 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-17 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-18. Compound I-18 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-18.

According to one specific embodiment, the compound I-18 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-18 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-19. Compound I-19 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-19.

According to one specific embodiment, the compound I-19 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-19 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-20. Compound I-20 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-20.

According to one specific embodiment, the compound I-20 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-20 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-21. Compound I-21 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-21.

According to one specific embodiment, the compound I-21 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-21 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-22. Compound I-22 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-22.

According to one specific embodiment, the compound I-22 is provided and used as (R)-enantiomer with an enantomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-22 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-23. Compound I-23 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-23.

According to one specific embodiment, the compound I-23 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-23 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-24. Compound I-24 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-24.

According to one specific embodiment, the compound I-24 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-24 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-25. Compound I-25 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-25.

According to one specific embodiment, the compound I-25 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-25 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-26. Compound I-26 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-26.

According to one specific embodiment, the compound I-26 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-26 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-27. Compound I-27 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-27.

According to one specific embodiment, the compound I-27 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-27 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-28. Compound I-28 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-28.

According to one specific embodiment, the compound I-28 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-28 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-29. Compound I-29 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-29.

According to one specific embodiment, the compound I-29 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-29 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-30. Compound I-30 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-30.

According to one specific embodiment, the compound I-30 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-30 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component I is compound I-31. Compound I-31 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-31.

According to one specific embodiment, the compound I-31 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-31 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to one embodiment of the present invention, component I is selected from compounds I-17, I-18, I-19, I-23, I-25 and I-29. According to one further embodiment of the present invention, component I is selected from compounds I-19, I-23, I-25, I-28, I-29, I-30 and I-31. According to still a further embodiment of the present invention, component I is selected from compounds I-17, I-18, I-26 and I-27. According to another more embodiment of the present invention, component I is selected from compounds I-20, I-21, I-22 and I-24.

According to one further embodiment of the present invention, component I is selected from compounds I-1, I-2, I-3, I-4, I-5, I-6, I-7, I-8, I-9, I-10, I-11, I-12, I-13, I-14, I-15 and I-16.

According to a more particular embodiment of the present invention, component I is selected from compounds I-1, I-2, I-6, I-8 and I-12. According to another more particular embodiment of the present invention, component I is selected from compounds I-3, I-4, I-5, I-7, I-9, I-11, I-13, I-14, I-15 and I-16.

According to still a further embodiment of the present invention, component I is selected from compounds I-1, I-2, I-3, I-4, I-5 and I-17.

According to still a further embodiment of the present invention, component I is selected from compounds I-1, I-2, I-3, I-4 and I-5.

According to still a further embodiment of the present invention, component I is selected from compound I-17 and I-18.

A pesticide is generally a chemical or biological agent (such as pestidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term "pesticide" includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

Biopesticides are typically created by growing and concentrating naturally occurring organisms and/or their metabolites including bacteria and other microbes, fungi, viruses, nematodes, proteins, etc. They are often considered to be important components of integrated pest management (IPM) programmes, and have received much practical attention as substitutes to synthetic chemical plant protection products (PPPs).

Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classed as microbial pesticides, even though they are multicellular.

(2) Biochemical pesticides are naturally occurring substances that control pests or provide other crop protection uses as defined below, but are relatively non-toxic to mammals.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary composition may be mixed by the user himself in a spray tank or any other kind of vessel used for applications (e. g. seed treater drums, seed pelleting machinery, knapsack sprayer) and further auxiliaries may be added, if appropriate.

When living microorganisms, such as microbial pesticides from groups L1), L3) and L5), form part of such kit, it must be taken care that choice and amounts of the components (e. g. chemical pesticides) and of the further auxiliaries should not influence the viability of the microbial pesticides in the composition mixed by the user. Especially for bactericides and solvents, compatibility with the respective microbial pesticide has to be taken into account. Consequently, one embodiment of the invention is a kit for preparing a usable pesticidal composition, the kit comprising a) a composition comprising component I as defined herein and at least one auxiliary; and b) a composition comprising component II as defined herein and at least one auxiliary; and optionally c) a composition comprising at least one auxiliary and optionally a further active component III as defined herein.

Many of these biopesticides used according to the invention have been deposited under deposition numbers mentioned herein (the prefices refer to the acronym of the respective culture collection), are referred to in literature, registered and/or are commercially available: aluminium silicate (Screen™ Duo from Certis LLC, USA), *Agrobacterium radiobacter* K1026 (e. g. NoGall® from BASF Agricultural Specialties Pty Ltd, Australia), *A. radiobacter* K84 (Nature 280, 697-699, 1979; e. g. GallTroll® from AG Biochem, Inc., C, USA), *Ampelomyces quisqualis* M-10 (e. g. AQ 10® from Intrachem Bio GmbH & Co. KG, Germany), *Ascophyllum nodosum* (Norwegian kelp, Brown kelp) extract or filtrate (e. g. ORKA GOLD from BASF Agricultural Specialities (Pty) Ltd., South Africa; or Goemar® from Laboratoires Goemar, France), *Aspergillus flavus* NRRL 21882 isolated from a peanut in Georgia in 1991 by USDA, National Peanut Research Laboratory (e. g. in Afla-Guard® from Syngenta, CH), compositions of *Aureobasidium pullulans* DSM 14940 and DSM 14941 (e. g. blastospores in Blossom Protect® from bio-ferm GmbH, Germany), *Azospirillum amazonense* SpY2 (DN: BR 11140; Proc. 9$^{th}$ Int. and 1$^{st}$ Latin American PGPR meeting, Quimara, Medellín, Colombia 2012, p. 60, ISBN 978-958-46-0908-3), *A. brasilense* AZ39 (also called Az 39; INTA Az-39; Eur. J. Soil Biol 45(1), 28-35, 2009), *A. brasilense* XOH (e. g. AZOS from Xtreme Gardening, USA or RTI Reforestation Technologies International; USA), *A. brasilense* BR 11002 (Proc. 9$^{th}$ Int. and 1$^{st}$ Latin American PGPR meeting, Quimara, Medellín, Colombia 2012, p. 60, ISBN 978-958-46-0908-3), *A. brasilense* Sp245 (BR 11005; e. g. in GELFIX Gramíneas from BASF Agricultural Specialties Ltd., Brazil), *A. brasilense* strains Ab-V5 and Ab-V6 (e. g. in AzoMax from Novozymes BioAg Produtos papra Agricultura Ltda., Quattro Barras, Brazil or SinnbioseMaíz® from Simbiose-Agro, Cruz Alta, R S, Brazil; Plant Soil 331, 413-425, 2010), *A. lipoferum* BR 11646 (Sp31) (Proc. 9$^{th}$ Int. and 1$^{st}$ Latin American PGPR meeting, Quimara, Medellín, Colombia 2012, p. 60), *Bacillus altitudinis* 41 KF2b (DSM 21631; Int. J. Syst. Evol. Microbiol. 56(7), 1465-1473, 2006), *Bacillus amyloliquefaciens* strains AP-136 (NRRL B-50614 and B-50330), AP-188 (NRRL B-50615 and B-50331), AP-218 (NRRL B-50618), AP-219 (NRRL B-50619 and B-50332), and AP-295 (NRRL B-50620 and B-50333) all known from U.S. Pat. No. 8,445,255; *B. amyloliquefaciens* IT-45 (CNCM I-3800) (e. g. Rhizocell C from ITHEC, France), *B. amyloliquefaciens* IN937a (J. Microbiol. Biotechnol. 17(2), 280-286, 2007; e. g. BioYield® from Gustafson LLC, TX, USA), *B. amyloliquefaciens* spp. *plantarum* D747 (US 20130236522 A1; FERM BP-8234; e. g. Double Nickel™ 55 WDG or Double Nickel™ LC from Certis LLC, USA), *B. amyloliquefaciens* spp. *plantarum* FZB24 isolated from plant pathogen-infested soil of a sugar beet field in Brandenburg, Germany (also called SB3615; DSM ID 96-2; J. Plant Dis. Prot. 105, 181-197, 1998; e. g. Taegro® from Novozyme Biologicals, Inc., USA),), *B. amyloliquefaciens* spp. *plantarum* SB3615vPPI being a phage-resistant variant of FZB24 (MRRL B-50349; US 2011/023045 A1; from Novozyme Biologicals, Inc., USA), *B. amyloliquefaciens* ssp. *plantarum* FZB42 isolated from plant pathogen-infested soil of a sugar beet field in Brandenburg, Germany (J. Plant Dis. Prot. 105, 181-197, 1998; DSM 23117; e. g. RhizoVital® 42 from AbiTEP GmbH, Berlin, Germany), *B. amyloliquefaciens* ssp. *plantarum* GB03 (also called GBO3; ATCC SD-1397; Phytopathol. 86(11), S36, 1996; e. g. Kodiak® or BioYield® from Gustafson, Inc., USA; or Companion® from Growth Products, Ltd., White Plains, N.Y. 10603, USA), *B. amyloliquefaciens* ssp. *plantarum* MBI600 also referred to as 1430 (NRRL B-50595; Int. J. Microbiol. Res. 3(2) (2011), 120-130; US 2012/0149571 A1; e. g. Integral®, Subtilex® NG from BASF Corp., USA), *B. amyloliquefaciens* spp. *plantarum* TJ 1000 (also called 1BE; CA 2471555 A1; ATCC BAA-390; e. g. QuickRoots™ from TJ Technologies, Watertown, S. Dak., USA), *B. cereus* CNCM I-1562 (U.S. Pat. No. 6,406,690), *B. chitinosporus* AQ746 isolated from roots in Saskatchewan, Canada (NRRL B-21618; U.S. Pat. No. 5,733,544; AgraQuest now Bayer CropScience LP, USA), *B. firmus* CNCM I-1582 (WO 2009/126473, WO 2009/124707, U.S. Pat. No. 6,406,690; e. g. Votivo® from Bayer CropScience LP, USA), *B. megaterium* strains H491 (NRRL B-50769), M018 (NRRL B-50770) and J142 (NRRL B-50771) all known from US 2014/0051571 A1 from Marrone BioInnovations, Inc., USA; *B. mojavensis* AP-209 (NRRL B-50616; U.S. Pat. No. 8,445,255), *B. mycoides* AQ726 (NRRL B-21664; U.S. Pat. No. 5,906,818; from Bayer Crop Science, Germany), *B. mycoides* strain J (e.g. BmJ WG from Certis, USA against potato virus Y), *B. pumilus* GB34 (ATCC 700814; e. g. YieldShield® from Gustafson LLC, TX, USA), *B. pumilus* GHA 180 isolated from apple tree rhizosphere in Mexico (IDAC 260707-01; e. g. in PRO-MIX® BX from Premier Horticulture, 1, avenue Premier, Rivié re-du-Loup, Quebec, Canada G5R6C1), *B. pumilus* KFP9F (NRRL B-50754; WO 2014/029697; e. g. BAC-UP or FUSION-P from BASF Agricultural Specialities (Pty) Ltd., South Africa), *B. pumilus* INR-7 otherwise referred to as BU-F22 and BU-F33 (NRRL B-50185, NRRL B-50153; U.S. Pat. No. 8,445,255), *B. pumilus* QST 2808 (NRRL B-30087; e. g. Sonata® or Ballad® Plus from AgraQuest Inc., USA), *B. sollsalsi* AP-217 (NRRL B-50617; U.S. Pat. No. 8,445,255), *B. subtilis* CX-9060 (Federal Register 77(7), 1633-1637; by Certis U.S.A., L.L.C.), *B. subtilis* FB17 also called UD 1022 or UD10-22 isolated from red beet roots in North America (ATCC PTA-11857; System. Appl. Microbiol. 27, 372-379, 2004; US 2010/0260735; WO 2011/109395); *B. subtilis* GB07 (Phytopathol. 86(11), S36, 1996; Epic® from Gustafson, Inc., USA), *B. subtilis* QST-713 isolated from a California peach orchard in 1995 (NRRL B-21661; e. g. Rhapsody®, Serenade® MAX or Serenade® ASO from AgraQuest Inc., USA), *B. thuringiensis* ssp. *aizawai* ABTS-1857 (also called ABG-6346; ATCC SD-1372; e. g. XenTari® from BioFa AG, Münsingen, Germany), B. t. ssp. *aizawai* SAN 401 I, ABG-6305 (WO 2013/087709); *Bacillus* t. ssp. *israelensis* AM65-52 of Serotype H-14 (ATCC SD-1276; e. g. VectoBac® from Valent BioSciences, IL, USA), *Bacillus thuringiensis* ssp. *kurstaki* SB4 (NRRL B-50753; e. g. Beta Pro® from BASF Agricultural Specialities (Pty) Ltd., South Africa), B. t. ssp. *kurstaki* ABTS-351 identical to HD-1 (ATCC SD-1275; e. g. Dipel® DF from Valent BioSciences, IL, USA), B. t. ssp. *kurstaki* EG 2348 (NRRL B-18208; e. g. Lepinox® or Rapax® from CBC (Europe) S.r.l., Italy), B. t. ssp. *tenebrionis* DSM 2803 of Serotype H 8a, 8b (identical to NRRL B-15939; EP 0 585 215 B1; Mycogen Corp.), B. t. ssp. *tenebrionis* NB-125 (also referred to as SAN 418 1 or ABG-6479; EP 0 585 215 B1; DSM 5526; former production strain of Novo-Nordisk), B. t. ssp. *tenebrionis* NB-176 (or NB-176-1; a gamma-irridated, induced high-yielding mutant of strain NB-125; EP 585 215 B1; DSM 5480; e. g. Novodor® from Valent BioSciences, Switzerland), *Beauveria bassiana* JW-1 (ATCC 74040; e. g. Naturalis® from CBC (Europe) S.r.l., Italy), *B. bassiana* DSM 12256 (US 200020031495; e. g. BioExpert® SC from Live Sytems Technology S.A., Colombia), *B. bassiana* GHA (ATCC 74250; e. g. BotaniGard® 22WGP from Laverlam Int. Corp., USA), *B. bassiana* PPRI 5339 (ARSEF 5339; NRRL 50757; e. g. Broad Band® from BASF Agricultural Specialities (Pty) Ltd., South Africa), *B. brongniartii* for control of cockchafer (J. Appl. Microbiol. 100(5), 1063-72, 2006; e. g. Melocont® from Agrifutur, Agrianello, Italy), *Bradyrhizobium* sp. (e. g. Vault® from BASF Corp., USA), *B.* sp. (*Arachis*) CB1015 presumably originally collected in India (IITA 1006, USDA 3446; from Australian Inoculants Research Group; http://www.qaseeds.com.au/inoculant_applic.php). B. sp. (*Arachis*) strains deposited at SEMIA and known from FEMS Microbiol. Letters 303(2), 123-131, 2010; Revista Brasileira de Ciencia do Solo 35(3), 739-742, 2011, ISSN 0100-0683: SEMIA 6144, SEMIA 6462 (BR 3267) and SEMIA 6464 (BR 3262); B. sp. (*Vigna*) PNL01 (Bisson and Mason, Apr. 29, 2010, Project report, Worcester Polytechnic Institute, Worcester, Mass., USA: http://www-.wpi.edu/Pubs/E-project/Available/E-project-042810-163614/; e. g. Vault® Peanut Liquid from BASF Corp., USA), *B. elkanii* SEMIA 587 (Appl. Environ. Microbiol. 73(8), 2635, 2007; e. g. GELFIX 5 from BASF Agricultural Specialties Ltd., Brazil), *B. elkanii* SEMIA 5019 (=29W; Appl. Environ. Microbiol. 73(8), 2635, 2007; e. g. GELFIX 5 from BASF Agricultural Specialties Ltd., Brazil), *B. elkanii* USDA 76, *B. elkanii* USDA 94 *B. elkanii* USDA 3254, *B. elkanii* U-1301 and U-1302 (e. g. Nitragin® Optimize from Novozymes Bio As S. A., Brazil, or Nlitrasec for soybean from LAGE y Cia, Brazil), *B. japonicum* (e. g. VAULT® from BASF Corp., USA), *B. japonicum* 532c isolated from Wisconsin field (Nitragin 61A152; Can. J. Plant. Sci. 70, 661-666, 1990; e. g. in Rhizoflo®, Histick®, Hicoat® Super from BASF Agricultural Specialties Ltd., Canada), *B. japonicum* E-109 variant of strain USDA 138 (INTA E109, SEMIA 5085; Eur. J. Soil Biol. 45, 28-35, 2009; Biol. Fertil. Soils 47, 81-89, 2011), *B. japonicum* G49 (MSDJ G49; C. R. Acad. Agric. Fr. 73, 163-171, 1987); *B. japonicum* strains deposited at SEMIA known from Appl. Environ. Microbiol. 73(8), 2635, 2007: SEMIA 566 isolated from North American inoculant in 1966 and used in Brazilian commercial inoculants from 1966 to 1978, SEMIA 586 originally isolated in Maryland, USA, in 1961 but received from Australia in 1966 and used in Brazilian inoculants in 1977 (CB 1809, USDA 136, Nitragin 61A136, RCR 3407), SEMIA 5079 a natural variant of SEMIA 566 used in commercial inoculants since 1992 (CPAC 15; e. g. GELFIX 5 or ADHERE 60 from BASF Agricultural Specialties Ltd., Brazil), *B. japonicum* SEMIA 5080 a natural variant of SEMIA 586 used in commercial inoculants since 1992 (CPAC 7; e. g. GELFIX 5 or ADHERE 60 from BASF Agricultural Specialties Ltd., Brazil); *B. japonicum* TA-11 (TA11 NOD$^+$) (NRRL B-18466; U.S. Pat. No. 5,021,076; Appl. Environ. Microbiol. 56, 2399-2403, 1990; e. g. VAULT® NP, from BASF Corp., USA), *B. japonicum* strains deposited at USDA known from U.S. Pat. No. 7,262,151 and Appl. Environ. Microbiol. 60, 940-94, 1994: USDA 3 isolated from *Glycine max* in Virginia (USA) in 1914, USDA 31 (=Nitragin 61A164) od Serogroup 31 isolated from *Glycine max* in Wisconsin (USA) in 1941, USDA 76 isolated from plant passage of strain USDA 74 (Serogroup 76) which has been isolated from *G. max* in California (USA) in 1956, USDA 110 (=IITA 2121, SEMIA 5032, RCR 3427, ARS I-110 and Nitragin 61A89; Serogroup 110) isolated from *G. max* in Florida in 1959, USDA 121 isolated from *G. max* in Ohio (USA) in 1965 (Crop Science 26(5), 911-916, 1986); *B. japonicum* WB74 (e. g. Eco-Rhiz Soya from Plant Health Products (Pty) Ltd, South Africa; or Soybean inoculant from Stimuplant C C, South Africa), *B. lupini* LL13 isolated from *Lupinus iuteus* nodules from French soils (deposited at INRA, France; http://agriculture.gouv.fr/IMG/pdf/ch20060216.pdf), *B. lupini* strains from Australia and known from Palta J. A., Berger J. B. (eds), Proceed. 12$^{th}$ International Lupin Conference, 14-18 Sep. 2008, Fremantle, Western Australia, International Lupin Association, Canterbury, New Zealand, 47-50, http://www.lupins.org/pdf/conference/2008/Agronomy%20and%20Production/John%20Howieson%20and%20G%20O Hara.pdf; Appl. Environ. Microbiol. 71, 7041-7052, 2005; Australian J. Exp. Agricult. 36(1), 63-70, 1996: strains WU425 isolated in Esperance, Western Australia from a non-Australian legume *Ornithopus compressus*, WSM471 isolated from *Ornithopus pinnatus* in Oyster Harbour, Western Australia, and WSM4024 isolated from lupins in Australia by CRS during a 2005 survey; *Burkholderia* sp. A396 (NRRL B-50319; WO 2013/032693; Marrone Bio Innovations, Inc., USA), *Candida oleophila* I-182 (NRRL Y-18846; Phytoparasitica 23(3), 231-234, 1995; e. g. Aspire® from Ecogen Inc., USA;), *C. oleophila* strain O (NRRL Y-2317; Biological Control 51, 403-408, 2009), *Candida saitoana* (e. g. Biocure® [in composition with lysozyme] and BioCoat® from Micro Flo Company, USA (BASF SE) and Arysta), chitosan (e. g. Armour-Zen® from BotriZen Ltd., NZ), *Clonostachys rosea* f. *catenulate* (also named *Gliocladium catenulatum*) J1446 isolated from Finnish field soil (NJF seminar No 389: Pest, disease and weed management in strawberry; Finland 8-9 Nov. 2006 in NJF Report 2(10), 15-15, 2006; DSM 9212; e. g. Primastop® or Prestop® from Verdera Oy, Finland), *Chromobacterium subtsugae* PRAA4-1 isolated from soil under an eastern hemlock (*Tsuga canadensis*) in the Catoctin Mountain region of central Maryland (NRRL B-30655; e. g. Grandevo® from Marrone Bio Innovations, USA), *Coniothyrium minitans* CON/M/91-08 (WO 1996/021358; DSM 9660; e. g. Contans® WG, Intercept® WG from Prophyta Biologischer Pflanzenschutz GmbH, Germany), *Cryphonectria parasitica* (hypovirulent strains; Microbiol. Reviews 56(4), 561-576, 1992; e. g. product *Endothia parasitica* from CNICM, France), *Cryptococcus albidus* (e. g. YIELD PLUS® from Anchor Bio-Technologies, South Africa), *Cryptophlebia leucotreta* granulovirus (CrleGV) (e. g. CRYPTEX from Adermatt Biocontrol, Switzerland), *Cydia pomonella* granulovirus (CpGV) V03 (DSM GV-0006; e. g. Madex® Max from Andermatt Biocontrol, Switzerland), CpGV V22 (DSM GV-0014; e. g. Madex® Twin from Adermatt Biocontrol, Switzerland), *Delftia acidovorans* RAY209 (ATCC PTA-4249; WO 2003/57861; e. g. BioBoost® from Brett Young, Winnipeg, Canada), *Dilophosphora alopecuri* (FarmNote 396, February 2010, Department of Agriculture and Food, Government of Western Australia; e.g. Twist Fungus from BASF Agricultural Specialties Pty Ltd, Australia), *Ecklonia maxima* (kelp) extract (J. Ecological Engineering 14(1), 48-52, 2013; e. g. KELPAK SL from Kelp Products Ltd, South Africa), *Flavobacterium* sp. H492 (ATCC B-505584; WO 2013/138398; e. g. MBI-302 from Marrone Bio Innovations, USA for soybean cyst nematode control), formononetin (U.S. Pat. No. 5,002,603; e. g. Myconate® from Plant Health Care plc, U.K.), *Fusarium oxysporum* Fo47 (non-pathogenic strain isolated from a suppressive soil located at Châteaurenard, France; Appl. Environ. Microbiol 68(8), 4044-4060, 2002; Fusaclean® from Natural Plant Protection, N.P.P. (société anonyme) Route d'Artix F-64150 Nogueres, France), *F. oxysporum* 251/2RB (Prevention Today Vol. 2, n. 1-2, 47-62, 2006; e. g. Biofox® C from S.I.A.P.A., Italy); *Glomus intradices* (e. g. Myc® 4000 from ITHEC, France), *Glomus intradices* RTI-801 (e. g. MYKOS from Xtreme Gardening, USA or RTI Reforestation Technologies International; USA), grapefruit seeds and pulp extract (e. g. BC-1000 from Chemie S. A., Chile), harpin (alpha-beta) protein (Science 257, 85-88, 1992; e. g. Messenger™ or HARP-N-Tek from Plant Health Care plc, U.K.), *Helicoverpa armigera* nucleopolyhedrovirus (HearNPV) (J. Invertebrate Pathol. 107, 112-126, 2011; e. g. Helicovex® from Adermatt Biocontrol, Switzerland), *Heterorhabditis bacteriophora* (e. g. Nemasys® G from BASF Agricultural Specialities Limited, UK), *Isaria*

*fumosorosea* Apopka-97 (ATCC 20874; Biocontrol Science Technol. 22(7), 747-761, 2012; e. g. PFR-97™ or PreFeRal® from Certis LLC, USA), *I. fumosorosea* FE 9901 (ARSEF 4490; Biocontrol Science Technol. 22(7), 747-761, 2012; e. g. blastospores in NoFly™ WP from Natural Industries, Inc., Houston, Tex., USA or from Novozymes, U.S.A.), cis-jasmone (U.S. Pat. Nos. 6,890,525; 8,221,736; Plant Bioscience Limited, Norwich, U.K.), laminarin (e. g. in Vacciplant® from Laboratoires Goemar, St. Malo, France or Stähler S A, Switzerland), *Lecanicillium longisporum* KV42 and KV71 (e. g. Vertalec® from Koppert B V, Netherlands), *L. muscarium* Ve6 (also called KV01; IMI 19-79, CABI 268317, CBS 102071, ARSEF 5128; e. g. Mycotal® from Koppert B V, Netherlands), *Lysobacter antibioticus* 13-1 (Biological Control 45, 288-296, 2008), *L. antibioticus* HS124 (Curr. Microbiol. 59(6), 608-615, 2009), *L. enzymogenes* 3.1T8 (Microbiol. Res. 158, 107-115, 2003; Biological Control 31(2), 145-154, 2004); *Mesorhizobium* spp. strains known from Soil Biol. Biochem. 36(8), 1309-1317, 2004; Plant and Soil 348(1-2), 231-243, 2011: M. sp. WSM1271 collected in Sardinia, Italy, from plant host *Biserrula pelecinus*, M. sp. WSM 1497 collected in Mykonos, Greece, from *Biserrula pelecinus*, *Mesorhizobium ciceri* CC1192 collected in Israel from *Cicer arietinum* nodules (UPM 848, CECT 5549; Can. J. Microbiol. 48, 279-284, 2002; from Horticultural Research Station, Gosford, Australia), *M. huakuii* HN3015 isolated from *Astralagus sinicus* in a rice-growing field of Southern China (World J. Microbiol. Biotechn. 23(6), 845-851, 2007, ISSN 0959-3993), *M. loti* CC829 isolated from *L. ulginosus* nodules in USA (NZP 2012; commercial inoculant for *Lotus pedunculatus* and *L. ulginosus* in Australia), and *M. loti* SU343 isolated from host nodules in USA (commercial inoculant for *Lotus corniculatus* in Australia); *Metarhizium anisopliae* FI-1045 (AGAL V10/0104285; WO 2012/018266; e. g. Biocane® from BASF Agricultural Specialties Pty Ltd, Australia), *M. anisopliae* var. *anisopliae* F52 also called 275 or V275 (DSM 3884, ATCC 90448; e. g. Met52® Novozymes Biologicals BioAg Group, Canada), *M. anisopliae* ICIPE 69 isolated from a soil sample obtained from the Democratic Republic of Congo (DRC) and using the Galleria bait method in 1990 (e. g. Metathripol from ICIPE, Nairobe, Kenya), *M. anisopliae* var. *acridum* IMI 330189 isolated from *Ornithacris cavroisi* in *Niger* (NRRL 50758; e. g. Green Muscle® from BASF Agricultural Specialities (Pty) Ltd., South Africa), M. a. var. *acridum* FI-985 isolated from a spur-throated locust, *Austracris guttulosa* (Walker), near Rockhampton, Queensland, Australia, in 1979 (ARSEF 324; Memoirs of the Entomological Society of Canada 171, 287-300, 1997; e. g. Green Guard® SC from BASF Agricultural Specialties Pty Ltd, Australia), *Metschnikowia fructicola* 277 isolated from the surface of grape berries (cv. Superior) grown in the central part of Israel (U.S. Pat. No. 6,994,849; NRRL Y-30752; e. g. Shemer® from Agrogreen, Israel, now distributed by Bayer CropSciences, Germany), *Microdochium dimerum* L13 (CNCM I-3141; e. g. Antibot® from Agrauxine, France), *Microsphaeropsis ochracea* P130A isolated from apple leaves from an abandoned orchard, St-Joseph-du-Lac, Quebec, Canada in 1993 (ATCC 74412; Mycologia 94(2), 297-301, 2002), *Muscodor albus* QST 20799 also called 620 originally isolated from the bark of a cinnamon tree in Honduras (NRRL 30547; e. g. Muscudor™ or QRD300 from AgraQuest, USA), *Muscodor albus* SA-13 (NRRL B-50774; US 2014/0086879 A1; e. g. MBI-601-EP from Marrone BioInnovations, Inc., USA), Neem oil (e. g. Trilogy®, Triact® 70 EC from Certis LLC, USA), *Nomuraea rileyi* strains SA86101, GU87401, SR86151, CG128 and VA9101 (Braz. Arch. Biol. Technol. 46(1), 13-19, 2003; WO 2013/110594), *Paecilomyces lilacinus* 251 isolated from infected nematode eggs in the Philippines (AGAL 89/030550; WO1991/02051; Crop Protection 27, 352-361, 2008; e. g. BioAct®/MeloCon® from Prophyta, Germany), *P. lilacinus* DSM 15169 (e. g. Nemata® SC from Live Systems Technology S. A., Colombia), *P. lilacinus* BCP2 (NRRL 50756; Acta agriculturae Slovenica, 101-2, 263-275, 2013; e. g. PL Gold from BASF Agricultural Specialities (Pty) Ltd., South Africa), *Paenibacillus alvei* NAS6G6 (WO 2014/029697; NRRL B-50755; e.g. BAC-UP from BASF Agricultural Specialities (Pty) Ltd., South Africa in composition with *Bacillus pumilus* KFP9F), *P. polymyxa* PKB1 (ATCC 202127; Can. J. Microbiol. 48(2), 159-169, 2002), *Pantoea agglomerans* E325 (NRRL B-21856; Phytopathol. 101(10), 1234-41, 2011; Trees 26, 227-238, 2012; Bloomtime Biological™ from Northwest Agricultural Products, Inc., USA), *Pantoea vagans* (formerly *agglomerans*) C9-1 originally isolated in 1994 from apple stem tissue for control of fire blight in apple (J. Bacteriol. 192(24), 6486-6487, 2010; e. g. BlightBan C9-1® from NuFrams America Inc., USA), *Pasteuria* sp. ATCC PTA-9643 (WO 2010/085795), *Pasteuria* sp. Ph3 isolated from turfgrass soil samples collected at the DeBary Golf Course in central Florida (ATCC SD-5832; WO 2012/064527; for control of *Hoplolaimus galeatus* nematode from Pasteuria Bioscience, Inc. now Syngenta Crop Protection, LLC, USA), *Pasteuria* sp. Pr3 isolated from soil samples collected in the southeastern United States (ATCC SD-5834; for control of *Rotylenchulus reniformis* nematode potentially of species *P. ramosa*; Naviva® ST from Syngenta Crop Protection, LLC, USA), *P. nishizawae* (WO 2010/80619), *P. nishizawae* Pn1 (Federal Register 76(22), 5808, Feb. 2, 2011; ATCC SD-5833; e.g. Clariva™ PN from Syngenta Crop Protection, LLC, USA), *P. penetrans* (U.S. Pat. No. 5,248,500; Del Monte Corp.), *P. ramosa* (WO 2010/080619), *P. thornea* (WO 2010/080619), *P. usgae* BL1 (ATCC SD-5835; J. Nematol. 42(2): 87-90, 2010; ibid. 43(2), 101-109, 2011; e. g. Econem™ for control of *Belonolaimus longicaudatus* from Pasteuria BioScience now Syngenta sold by Harell's LLC, Florida, USA for use on turf for management of *Belonolaimus longicaudatus*), *Penicillium bilaiae* (also called *P. bilaii*) strains ATCC 18309 (=ATCC 74319), ATCC 20851 and/or ATCC 22348 (=ATCC 74318) originally isolated from soil in southern Alberta (Fertilizer Res. 39, 97-103, 1994; Can. J. Plant Sci. 78(1), 91-102, 1998; U.S. Pat. No. 5,026,417, WO 1995/017806; e. g. Jump Start®, Provide® from Novozymes Biologicals BioAg Group, Canada), *P. bilaiae* NRRL 50162 and NRRL 50169 (WO 2010/037228), *Phlebiopsis gigantea* (e. g. RotStop® from Verdera Oy, Finland), *Pichia anomala* WRL-076 (NRRL Y-30842; U.S. Pat. No. 8,206,972), potassium bicarbonate (e. g. Amicarb® from Stähler S A, Switzerland), potassium silicate (e. g. Sil-MATRIX™ from Certis LLC, USA), *Pseudozyma flocculosa* PF-A22 UL (e. g. Sporodex® L from Plant Products Co. Ltd., Canada), *Pseudomonas* sp. Proradix (DSM 13134; WO 2001/40441, e. g. PRORADIX from Sourcon Padena GmbH & Co. KG, Hechinger Str. 262, 72072 Tübingen, Germany), *P. chloraphis* MA 342 (Microbiology Monographs 18, 21-43, 2011; e. g. Cerall® or Cedemon® from BioAgri A B, Uppsala, Sweden or Intrachem Bio Deutschland GmbH & Co. KG, Bad Camberg, Germany), *P. fluorescens* (e.g. in Bio Cure-B from T. Stanes & Company Limited, India; or in Blight-End from Agri Naturals, Mumbai, India), *P. fluorescens* A506 (Phytopathol 97(2), 244-249, 2007; ATCC 31948; e. g. BlightBan® from NuFarm Americas, Inc., Morrisville, N.C., USA), *P. fluore-*

*scens* ATCC 13525 of biovar I=biotype A; originally isolated from pre-filter tanks in England (DSM 50090; registered for use in Canada), *P. fluorescens* CHA0 (Mol. Plant Microbe Interact. 5(1), 4-13, 1992), *P. fluorescens* CL 145A (J. Invertebr. Pathol. 113(1), 104-14, 2013; e. g. Zequanox® from Marrone BioInnovations, Davis, Calif., USA), *P. fluorescens* NCIB 12089 (EP 0210734 AI; Victus® from Mauri Laboratories, 9 Moorebank Ave., Moorebank, NSW 2170, Australia), *P. fluorescens* Pf-5 isolated from root surface of cotton (ATCC BAA-477), *P. putida* ATCC 202153 (EMBRAPA 63/88 4 B; WO 2004/0245865), *Pythium oligandrum* DV 74 (US 2013/0035230; ATCC 38472; e. g. Poyversum® from Remeslo SSRO, Biopreparaty, Czech Rep. and from Gowan, USA), *Reynoutria sachalinensis* extract (EP 0307510 B1; e. g. Regalia® SC from Marrone BioInnovations, Davis, Calif., USA or Milsana® from BioFa A G, Germany), *Rhizobium leguminosarum* bv. *phaseoli*(e. g. RHIZO-STICK from BASF Corp., USA), *R. leguminosarum* bv. *phaseoli* RG-B10 (USDA 9041; from Int. J. Syst. Bacteriol. 46(1), 240-244, 1996; Int. J. Syst. Evol. Microbiol. 50, 159-170, 2000; e. g. Nodulator® Dry Bean in Africa, HiStick NT Dry bean in US, and Nodulator® Dry Bean in Canada from BASF Corp., USA, or BASF Agricultural Specialties Ltd., Canada), *R. l.* bv. *trifolii* CB782 (Nodulaid® peat for Kenya white clover from BASF Agricultural Specialties Pty Ltd, Australia), *R. l.* bv. *trifolii* CC275e (Nodulaid® peat for NZ white clover from BASF Agricultural Specialties Pty Ltd, Australia), *R. l.* bv. *trifolii* CC283b (ICMP 4073b; Proc. New Zealand Grassland Assoc. 56, 101-105, 1994; Microbiol. 153, 3184-3195, 2007; Nodulaid® peat for Caucasian clover from BASF Agricultural Specialties Pty Ltd, Australia), *R. l.* bv. *trifolii* CC1099 (Inoculating Legumes: A Practical Guide, ed. Grain Research and Development Corporation, 2012, ISBN 978-1-921779-45-9; e. g. Nodulaid® peat for sainfoin from BASF Agricultural Specialties Pty Ltd, Australia), *R. l.* bv. *trifolii* RP113-7 (Appl. Environ. Microbiol. 44(5), 1096-1101, 1982; e. g. Dormal® from BASF Corp., USA), *R. l.* bv. *trifolii* TA1 (Appl. Environ. Microbiol. 49(1), 127-131, 1985; e. g. Nodulaid® peat for white clover from BASF Agricultural Specialties Pty Ltd, Australia), *R. l.* bv. *trifolii* strain WSM1325 isolated in 1993 from the Greek Island of Serifos (Stand. Genomic Sci. 2(3), 347-356, 2010; Inoculating Legumes: A Practical Guide, ed. Grain Research and Development Corporation, 2012, ISBN 978-1-921779-45-9; Nodulaid® peat for sub clover and Nodulator® granules for sub clover both from BASF Agricultural Specialties Pty Ltd, Australia, for a broad range of annual clovers of Mediterranean origin), *R. l.* bv. *trifolii* strain WSM2304 isolated from *Trifolium polymorphum* in Uruguay in 1998 (Stand. Genomic Sci. 2(1), 66-76, 2010), *R. l.* bv. *viciae* P1NP3Cst being a Streptomycin-resistant mutant of P1NP3C isolated from pea root nodules in Bretenière, France (also referred to as 1435; New Phytol. 176, 680-690, 2007; ibid. 179(1), 224-235, 2008; e. g. Nodulator® PL Peat Granule from BASF Corp., USA; or Nodulator® XL PL from BASF Agricultural Specialties Ltd., Canada), *R. l.* bv. *viciae* RG-P2 also called P2 isolated from pea root nodules in Sakatchewan, Canada (e. g RhizUP peat for peas and lentils in Canada from BASF Agricultural Specialties Ltd., Canada), *R. l.* bv. *viciae* SU303 (e. g. Nodulaid® Group E from BASF Agricultural Specialties Pty Ltd, Australia), *R. l.* bv. *viciae* WSM1455 (e. g. Nodulaid® Group F from BASF Agricultural Specialties Pty Ltd, Australia), *R. tropici* CC511 (Agronomy, N.Z. 36, 4-35, 2006; e. g. Nodulaid® peat for common bean from BASF Agricultural Specialties Pty Ltd, Australia) *R. tropici* CIAT 899 isolated in Colombia (SEMIA 4077; Rev. Ciênc. Agron. 44(4) Fortaleza October/December 2013; e. g. Nitrafix® FEIJÃO peat for beans from BASF Agricultural Specialties Ltd., Brazil in composition with strain SEMIA 4080), *R. tropici* H12 isolated in Planaltina, DF, Cerrados, Brazil (SEMIA 4088; Appl. Microbiol. Biotechnol. 93(5), 2035-49, 2012; e. g. Nitrafix® FEIJÃO from BASF Agricultural Specialties Ltd., Brazil), *R. tropici* PRF 81 isolated in Paraná, Brazil (SEMIA 4080; Soil Biology & Biochemistry 39, 867-876, 2007; BMC Microbiol. 12, 84, 2012; Nitrafix® FEIJÃO peat for beans from BASF Agricultural Specialties Ltd., Brazil in composition with strain SEMIA 4077), *Sinorhizobium meliloti* RCR2011 also called 2011 or SU47 (MSDJ0848; Mol. Gen. Genomics 272, 1-17, 2004; e. g. Dormal® Alfalfa & Luzerne from BASF Corp., USA; Nitragin® Gold from Novozymes Biologicals BioAg Group, Canada), *Sphaerodes mycoparasitica* SMCD2220 also called SMCD2220-01 (IDAC 301008-01; WO 2011/022809), *Spodoptera littoralis* nucleopolyhedrovirus (SpliNPV) (e.g. in LITTOVIR from Adermatt Biocontrol, Switzerland), *Steinernema carpocapsae* (e. g. Millenium® from BASF Agricultural Specialities Limited, UK), *S. feltiae* (Nemashield® from BioWorks, Inc., USA; Nemasys® from BASF Agricultural Specialities Limited, UK), *S. kraussei* L137 (Nemasys® L from BASF Agricultural Specialities Limited, UK), *Streptomyces galbus* AQ6047 (NRRL 30232; WO 2012/135763; AgraQuest now Bayer CropScience LP, USA); *S. galbus* M1064 (NRRL 50334; WO 2012/135763; AgraQuest now Bayer CropScience LP, USA); *S. griseoviridis* K61 (Crop Protection 25, 468-475, 2006; e. g. Mycostop® from Verdera Oy, Espoo, Finland), *S. lydicus* WYEC 108 (U.S. Pat. No. 5,403,584; e. g. Actinovate® from Natural Industries, Inc., USA), *S. violaceusniger* YCED-9 (U.S. Pat. No. 5,968,503; e. g. DT-9® from Natural Industries, Inc., USA), *Talaromyces flavus* V117b isolated from soil (e. g. Protus® WG from Prophyta, Germany), *Trichoderma asperellum* SKT-1 isolated from the rhizosphere of Japanese lawngrass (FERM P-16510; J. Gen. Plant Pathol. 71(5), 351-356, 2005; e. g. Eco-Hope® from Kumiai Chemical Industry Co., Ltd., Japan), *T. asperellum* ICC 012 isolated from a soil in central Italy that was found to suppress plant disease (IMI 392716; e. g. Tenet WP, Remdier WP or Bioten WP from Isagro N.C., USA, Bio-Tam™ from AgraQuest, USA), *T. asperellum* TV1 formerly *T. viride* (MUCL 43093; e. g. *T. viride* TV1 from Agribiotec srl, Italy or Xedavir from Xeda Italia, Italy), *T. atroviride* LC52 (e. g. Sentinel® from Agrimm Technologies Ltd, NZ), *T. atroviride* CNCM I-1237 (e. g. Esquive® WG from Agrauxine S. A., France, e. g. against pruning wound diseases on vine and plant root pathogens), *T. fertile* JM41R (NRRL 50759; e. g. Trichoplus™ from BASF Agricultural Specialities (Pty) Ltd., South Africa), *T. gamsii* ICC 080 (IMI 392151; e. g. Tenet WP, Renndier WP, Bioten WP from Isagro N.C., USA, Bio-Tam™ from AgraQuest, USA), *T. harzianum* T-22 also called KRL-AG2 (ATCC 20847; BioControl 57, 687-696, 2012; e. g. Plantshield® from BioWorks Inc., USA or SabrEx™ from Advanced Biological Marketing Inc., Van Wert, Ohio, USA), *T. harzianum* T-35 and T-315 (ATCC 20691; EP 0133878 B1; e. g. Root Pro® from Mycontrol Ltd., Israel), *T. harzianum* T-39 (CNCM I-952; EP 0466133 B2; e. g. Trichodex® or *Trichoderma* 2000® from Mycontrol Ltd., Israel and Makhteshim Ltd., Israel), composition of *T. harzianum* and *T. viride* (e. g. Trichopel® from Agrimm Technologies Ltd, NZ), composition of *T. harzianum* ICC012 and *T. viride* ICC080 (e. g. Remdier® WP from Isagro Ricerca, Italy), *T. polysporum* IMI 206039 (ATCC 20476; e. g. Binab® from BINAB Bio-Innovation A B, Sweden in composition with *T. atroviride* IMI 206040), *T.*

*stromaticum* (e. g. Tricovab® from C.E.P.L.A.C., Brazil), *T. virens* GI-3 also called G1-3 or GL-3 (CA 2471555 A1; ATCC 58678; e.g. QuickRoots™ from TJ Technologies, Watertown, S. Dak., USA in composition with *B. amyloliquefaciens* TJ1000), *T. virens* GL-21 also called G1-21 isolated from a *sclerotium* of *Sclerotinia minor* (U.S. Pat. No. 7,429,477; e. g. Soilguard® 12G from Certis LLC, USA; EPA Registration Number: 70051-3 and EPA Establishment Number: 067250-IL-001), *T. virens* G-41 also called 041, #41X or ABM 127 isolated from soil samples taken from *Aphanomyces*-suppressive bean fields in Livingston County, New York (ATCC 20906; U.S. Pat. No. 4,996,157; e. g. Rootshield® PLUS from BioWorks, Inc., USA), *T. viride* (J. Biological Control 23(1), 31-36, 2009; e. g. Trieco® from Ecosense Labs. (India) Pvt. Ltd., India; or Bio-Cure® F from T. Stanes & Co. Ltd., India), and *Ulocladium oudemansii* HRU3 (Agronomy 3, 632-647, 2013; e. g. Botry-Zen® from Botry-Zen Ltd, NZ).

(3) Strains can be obtained from culture collections and deposition centers (listed by their acronym=strain prefix here: http://www.wfcc.info/ccinfo/collection/by_acronym/) such as strains with prefices AGAL or NMI from: National Measurement Institute, 1/153 Bertie Street, Port Melbourne, Victoria, Australia 3207; ATCC: American Type Culture Collection, 10801 University Blvd., Manassas, Va. 20110-2209, USA; BR: Embrapa Agrobiology Diazothrophic Microbial Culture Collection, P.O. Box 74.505, Seropedica, Rio de Janeiro, 23.851-970, Brazil; CABI or IMI: CABI Europe—International Mycological Institute, Bakeham Lane, Egham, Surrey, TW20 9TYNRRL, UK; CB: The CB *Rhizobium* Collection, School of Environment and Agriculture, University of Western Sydney, Hawkesbury, Locked Bag 1797, South Penrith Distribution Centre, NSW 1797, Australia; CBS: Centraalbureau voor Schimmelcultures, Fungal Biodiversity Centre, Uppsalaan 8, PO Box 85167, 3508 AD Utrecht, Netherlands; CC: Division of Plant Industry, CSIRO, Canberra, Australia; CNCM: Collection Nationale de Cultures de Microorganismes, Institute Pasteur, 25 rue du Docteur Roux, F-75724 PARIS Cedex 15; CPAC: Embrapa-Cerrados, CX. Postal 08223, Planaltina, DF, 73301-970, Brazil; DSM: Leibniz-Institut DSMZ-Deutsche Sammlung von Mikroorganismen and Zellkulturen GmbH, Inhoffenstraße 7 B, 38124 Braunschweig, Germany; IDAC: International Depositary Authority of Canada Collection, Canada; ICMP: International Collection of Micro-organisms from Plants, Landcare Research, Private Bag 92170, Auckland Mail Centre, Auckland 1142, New Zealand; IITA: IITA, PMB 5320, Ibadan, Nigeria; INTA: Agriculture Collection Laboratory of the Instituto de Microbiologia y Zoologia Agricola (IMYZA), Instituto Nacional de Tecnologi a Agropecuaria (INTA), Castelar, Argentina; MSDJ: Laboratoire de Microbiologie des Sols, INRA, Dijon, France; MUCL: Mycothèque de l'Université catholique de Louvain, Croix du Sud 2, box L7.05.06, 1348 Louvain-la-Neuve, Belgium; NCIMB or NICB: The National Collections of Industrial and Marine Bacteria Ltd., Torry Research Station, P.O. Box 31, 135 Abbey Road, Aberdeen, AB9 8DG, Scotland; Nitragin: Nitragin strain collection, The Nitragin Company, Milwaukee, Wis., USA, NRRL or ARSEF (collection of entomopathogenic fungi): ARS Culture Collection of the National Center for Agricultural Utilization Research, Agricultural Research Service, U.S. Department of Agriculture, 1815 North University Street, Peoria, Ill. 61604, USA; NZP: Department of Scientific and Industrial Research Culture Collection, Applied Biochemistry Division, Palmerston North, New Zealand; PPRI: ARC-Plant Protection Research Institute, Private Bag X134, Queenswood Pretoria, Gauteng, 0121, South Africa; SEMIA: FEPAGRO-Fundação Estadual de Pesquisa Agropecuária, Rua Gonçalves Dias, 570, Bairro Menino Deus, Porto Alegre/RS, Brazil; SRDI: SARDI, Adelaide, South Australia; USDA: U.S. Department of Agriculture, Agricultural Research Service, Soybean and Alfalfa Research Laboratory, BARC-West, 10300 Baltimore Boulevard, Building 011, Beltsville, Md. 20705, USA (Beltsville Rhiz. Cult. Catalog: http://pdf.usaid.gov/pdf_docs/PNAAW891.pdf); and WSM: Murdoch University, Perth, Western Australia. Further strains may be found at: http://gcm.wfcc.info/; http://www.landcareresearch.co.nz/resources/collections/icmp. Jasmonic acid, its salts (jasmonates) or derivatives include without limitation potassium, sodium, lithium, ammonium, dimethylammonium, isopropylammonium, diolammonium and diethtriethanolammonium jasmonate; and also jasmonic acid methyl ester, jasmonic acid amide, jasmonic acid methylamide, jasmonic acid-L-amino acid (amide-linked) conjugates (e. g. conjugates with L-isoleucine, L-valine, L-leucine, or L-phenylalanine), 12-oxo-phytodienoic acid, coronatine, coronalon, coronafacoyl-L-serine, coronafacoyl-L-threonine, methyl esters of 1-oxo-indanoyl-isoleucine, methyl esters of 1-oxo-indanoyl-leucine, cis-jasmone, linoleic acid or derivatives thereof, and combinations of any of the above.

*Bacillus amyloliquefaciens* subsp. *plantarum* MBI600 having the accession number NRRL B-50595 is deposited with the United States Department of Agriculture on Nov. 10, 2011 under the strain designation *Bacillus subtilis* 1430. It has also been deposited at The National Collections of Industrial and Marine Bacteria Ltd. (NCIB), Torry Research Station, P.O. Box 31, 135 Abbey Road, Aberdeen, AB9 8DG, Scotland. under accession number 1237 on Dec. 22, 1986. *Bacillus amyloliquefaciens* MBI600 is known as plant growth-promoting rice seed treatment from Int. J. Microbiol. Res. ISSN 0975-5276, 3(2) (2011), 120-130 and further described e.g. in US 2012/0149571 A1. This strain MBI600 is commercially available as liquid formulation product Integral® (Becker-Underwood Inc., USA). *Metarhizium anisopliae* IMI33 is commercially available from Becker Underwood as product Green Guard. *M. anisopliae* var *acridium* strain IMI 330189 (NRRL-50758) is commercially available from Becker Underwood as product Green Muscle.

According to one embodiment, the microbial pesticides selected from groups L1), L3) and L5) embraces not only the isolated, pure cultures of the respective micro-organism as defined herein, but also its cell-free extract, its suspensions in a whole broth culture or as a metabolite-containing supernatant or a purified metabolite obtained from a whole broth culture of the microorganism or microorganism strain.

According to a further embodiment, the microbial pesticides selected from groups L1), L3 and L5) embraces not only the isolated, pure cultures of the respective microorganism as defined herein, but also a cell-free extract thereof or at least one metabolite thereof, and/or a mutant of the respective micro-organism having all the identifying characteristics thereof and also a cell-free extract or at least one metabolite of the mutant;

"Whole broth culture" refers to a liquid culture containing both cells and media.

"Supernatant" refers to the liquid broth remaining when cells grown in broth are removed by centrifugation, filtration, sedimentation, or other means well known in the art.

The term "metabolite" refers to any compound, substance or byproduct produced by a microorganism (such as fungi and bacteria) that has improves plant growth, water use efficiency of the plant, plant health, plant appearance, or the population of beneficial microorganisms in the soil around the plant activity.

The term "mutant" refers a microorganism obtained by direct mutant selection but also includes microorganisms that have been further mutagenized or otherwise manipulated (e.g., via the introduction of a plasmid). Accordingly, embodiments include mutants, variants, and or derivatives of the respective microorganism, both naturally occurring and artificially induced mutants. For example, mutants may be induced by subjecting the microorganism to known mutagens, such as N-methyl-nitrosoguanidine, using conventional methods.

According to one embodiment of the inventive compositions, the biopesticide component II is selected from the groups L1a) to L6a):

L1a) Microbial pesticides with fungicidal, bactericidal, viricidal and/or plant defense activator activity: *Ampelomyces quisqualis* M-10 (L.1.1), *Aspergillus flavus* NRRL 21882 (L1.2), *Aureobasidium pullulans* DSM 14940 (L1.3), *A. pullulans* DSM 14941 (L.1.4), *Bacillus altitudinis* 41 KF2b (L.1.5), *Bacillus amyloliquefaciens* AP-136 (L.1.6), *B. amyloliquefaciens* AP-188 (L.1.7), *B. amyloliquefaciens* AP-218 (L.1.8), *B. amyloliquefaciens* AP-219 (L.1.9), *B. amyloliquefaciens* AP-295 (L.1.10), *B. amyloliquefaciens* IN937a (L.1.11), *B. amyloliquefaciens* IT-45 (L.1.12), *B. amyloliquefaciens* ssp. *plantarum* D747 (L.1.13), *B. amyloliquefaciens* ssp. *plantarum* FZB24 (L.1.14), *B. amyloliquefaciens* ssp. *plantarum* FZB42 (L.1.15), *B. amyloliquefaciens* ssp. *plantarum* G B03 (L.1.16), *B. amyloliquefaciens* ssp. *plantarum* MBI600 (NRRL B-50595) (L.1.17), *B. amyloliquefaciens* ssp. *plantarum* QST-713 (L.1.18), *B. amyloliquefaciens* ssp. *plantarum* TJ1000 (L.1.19), *B. mojavensis* AP-209 (L.1.20), *B. mycoides* AQ726 (L.1.21), *B. mycoides* strain J (L.1.22), *B. pumilus* INR-7 (L.1.23), *B. pumilus* KFP9F (L.1.24), *B. pumilus* QST 2808 (L.1.25), *B. pumilus* GHA 180 (L.1.26), *B. simplex* ABU 288 (L.1.27), *B. solisalsi* AP-217 (L.1.28), *B. subtilis* CX-9060 (L.1.29), *B. subtilis* FB17 (L.1.30), *B. subtilis* GB07 (L.1.31), *Candida oleophila* I-82 (L.1.32), *C. oleophila* O (L.1.33), *C. saitoana* (L.1.34), *Clavibacter michiganensis* (bacteriophages) (L.1.35), *Coniothyrium minitans* CON/M/91-08 (L.1.36), *Cryphonectria parasitica* (L.1.37), *Cryptococcus albidus* (L.1.38), *Dilophosphora alopecuri* (L.1.39), *Fusarium oxysporum* (L.1.40), *Clonostachys rosea* f. *catenulata* J1446 (L.1.41), *Gliocladium roseum* 321U (L.1.42), *Metschnikowia fructicola* NRRL Y-30752 (L.1.43), *Microdochium dimerum* (L.1.44), *Microsphaeropsis ochracea* P130A (L.1.45), *Muscodor albus* QST 20799 (L.1.46), *Muscodor albus* SA-13 (L.1.47), *Paenibacillus alvei* NAS6G6 (L.1.48), *Paenibacillus polymyxa* PKB1 (L.1.49), *Pantoea agglomerans* E325 (L.1.90), *Pantoea vagans* C9-1 (L.1.50), *Penicillium bilaiae* ATCC 22348 (L.1.51), *P. bilaiae* ATCC 20851 (L.1.52), *Penicillium bilaiae* ATCC 18309 (L.1.53), *Phlebiopsis gigantea* (L.1.54), *Pichia anomala* WRL-76 (L.1.55), *Pseudomonas* sp. Proradix (L.1.56), *Pseudomonas chloraphis* MA 342 (L.1.57), *P. fluorescens* A506 (L.1.58), *P. fluorescens* CL 145A (L.1.91), *P. fluorescens* NCIB 12089 (L.1.92), *P. fluorescens* Pf-5 (L.1.93), *P. fluorescens* WCS 374 (L.1.94), *P. fluorescens* ATCC 13525 (L.1.95), *P. fluorescens* CHA0 (L.1.96), *P. putida* ATCC 202153 (L.1.97), *Pseudozyma flocculosa* PF-A22 UL (L.1.59), *Pythium oligandrum* DV 74 (L.1.60), *Sphaerodes mycoparasitica* SMCD2220 (L.1.61), *Streptomyces griseoviridis* K61 (L.1.62), *S. lydicus* WYEC 108 (L.1.63), *S. violaceusniger* XL-2 (L.1.64), *S. violaceusniger* YCED-9 (L.1.65), *Talaromyces flavus* V117b (L.1.66), *Trichoderma asperellum* T34 (L.1.67), *T. asperellum* SKT-1 (L.1.68), *T. asperellum* ICC 012 (L.1.69), *T. atroviride* LC52 (L.1.70), *T. atroviride* CNCM I-1237 (L.1.71), *T. fertile* JM41R (L.1.72), *T. gamsii* ICC 080 (L.1.73), *T. harmatum* TH 382 (L.1.74), *T. harzianum* T-35 (L.1.75), *T. harzianum* T-22 (L.1.76), *T. harzianum* T-39 (L.1.77); mixture of *T. harzianum* ICC012 and *T. viride* ICC080 (L.1.78); *T. polysporum* (L.1.79); *T. stromaticum* (L.1.80), *T. virens* GI-3 (L.1.81), *T. virens* G-41 (L.1.82), *T. virens* GL-21 (L.1.83), *T. virens* G-41 (L.1.84), *T. viride* TV1 (L.1.85), *Typhula phacorrhiza* 94671 (L.1.86), *Ulocladium oudemansii* HRU3 (L.1.87), *Verticillium dahlia* (L.1.88), zucchini yellow mosaic virus (avirulent strain) (L.1.89);

L2a) Biochemical pesticides with fungicidal, bactericidal, viricidal and/or plant defense activator activity: chitosan (hydrolysate) (L.2.1), harpin protein (L.2.2), laminarin (L.2.3), Menhaden fish oil (L.2.4), natamycin (L.2.5), Plum pox virus coat protein (L.2.6), potassium bicarbonate (L.2.7), *Reynoutria sachalinensis* extract (L.2.8), salicylic acid (L.2.9), potassium or sodium bicarbonate (L.2.10), tea tree oil (L.2.11);

L3a) Microbial pesticides with insecticidal, acaricidal, molluscidal and/or nematicidal activity: *Agrobacterium radiobacter* K1026 (L.3.1), *A. radiobacter* K84 (L.3.2), *Bacillus firmus* I-1582 (L.3.3); *B. thuringiensis* ssp. *aizawai* strains: ABTS-1857 (L.3.4), SAN 401 I (L.3.5), ABG-6305 (L.3.6) and ABG-6346 (L.3.7); B. t. ssp. *israelensis* AM65-52 (L.3.8), B. t. ssp. *israelensis* SUM-6218 (L.3.9), B. t. ssp. *galleriae* SDS-502 (L.3.10), B. t. ssp. *kurstaki* EG 2348 (L.3.11), B. t. ssp. *kurstaki* SB4 (L.3.12), B. t. ssp. *kurstaki* ABTS-351 (HD-1) (L.3.13), *Beauveria bassiana* ATCC 74040 (L.3.14), *B. bassiana* GHA (L.3.15), *B. bassiana* H123 (L.3.16), *B. bassiana* DSM 12256 (L.3.17), *B. bassiana* PPRI 5339 (L.3.18), *B. brongniartii* (L.3.19), *Burkholderia* sp. A396 (L.3.20), *Chromobacterium subtsugae* PRAA4-1 (L.3.21), *Cydia pomonella* granulosis virus V22 (L.3.22), *Cydia pomonella* granulosis virus V1 (L.3.23), *Cryptophlebia leucotreta* granulovirus (CrleGV) (L.3.57), *Flavobacterium* sp. H492 (L.3.60), *Helicoverpa armigera* nucleopolyhedrovirus (HearNPV) (L.3.58), *Isaria fumosorosea* Apopka-97 (L.3.24), *Lecanialium longisporum* KV42 (L.3.25), *L. longisporum* KV71 (L.3.26), *L. muscarium* KV01 (L.3.27), *Metarhizium anisopliae* FI-985 (L.3.28), *M. anisopliae* FI-1045 (L.3.29), *M. anisopliae* F52 (L.3.30), *M. anisopliae* ICIPE 69 (L.3.31), *M. anisopliae* var. *acridum* IMI 330189 (L.3.32); *Nomuraea rileyi* strains: SA86101 (L.3.33), GU87401 (L.3.34), SR86151 (L.3.35), CG128 (L.3.36) and VA9101 (L.3.37); *Paecllomyces fumosoroseus* FE 9901 (L.3.38), *P. lilacinus* 251 (L.3.39), *P. lilacinus* DSM 15169 (L.3.40), *P. lilacinus* BCP2 (L.3.41), *Paenibacillus popilliae* Dutky-1940 (NRRL B-2309=ATCC 14706) (L.3.42), *P. popilliae* Dutky 1 (L.3.43), *P. popilliae* KLN 3 (L.3.56), *Pasteuria* sp. Ph3 (L.3.44), *Pasteuria* sp. ATCC PTA-9643 (L.3.45), *Pasteuria* sp. ATCC SD-5832 (L.3.46), *P. nishizawae* Pn1 (L.3.46), *P. penetrans* (L.3.47), *P. ramosa* (L.3.48), P. sp. Pr-3 (L.3.49), *P. thornea* (L.3.50), *P. usgae* (L.3.51), *Pseudomonas fluorescens* CL 145A (L.3.52), *Spodoptera littoralis* nucleopolyhedrovirus (SpliNPV) (L.3.59), *Steinernema carpocapsae* (L.3.53), *S. feltiae* (L.3.54), *S. kraussei* L137 (L.3.55);

L4a) Biochemical pesticides with insecticidal, acaricidal, molluscidal, pheromone and/or nematicidal activity: L-carvone (L.4.1), citral (L.4.2), (E,Z)-7,9-dodecadien-1- yl acetate (L.4.3), ethyl formate (L.4.4), (E,Z)-2,4-ethyl decadienoate (pear ester) (L.4.5), (Z,Z,E)-7,11,13-hexadecatrienal (L.4.6), heptyl butyrate (L.4.7), isopropyl myristate (L.4.8), cis-jasmone (L.4.9), lavanulyl senecioate (L.4.10), 2-methyl 1-butanol (L.4.11), methyl eugenol (L.4.12), methyl jasmonate (L.4.13), (E,Z)-2,13-octadecadien-1-ol (L.4.14), (E,Z)-2,13-octadecadien-1-ol acetate (L.4.15), (E,Z)-3,13-octadecadien-1-ol (L.4.16), R-1-octen-3-ol (L.4.17), pentatermanone (L.4.18), potassium silicate (L.4.19), sorbitol actanoate (L.4.20), (E,Z, Z)-3,8,11-tetradecatrienyl acetate (L.4.21), (Z,E)-9,12-tetradecadien-1-yl acetate (L.4.22), Z-7-tetradecen-2-one (L.4.23), Z-9-tetradecen-1-yl acetate (L.4.24), Z-11-tetradecenal (L.4.25), Z-11-tetradecen-1-ol (L.4.26), *Acacia negra* extract (L.4.27), extract of grapefruit seeds and pulp (L.4.28), extract of *Chenopodium ambrosiodes* (L.4.29), Catnip oil (L.4.30), Neem oil (L.4.31), Quillay extract (L.4.32), *Tagetes* oil (L.4.33);

L5a) Microbial pesticides with plant stress reducing, plant growth regulator, plant growth promoting and/or yield enhancing activity: *Azospirillum amazonense* BR 11140 (SpY2) (L.5.1), *A. brasilense* Ab-V5 (L.5.74), *A. brasilense* Ab-V6 (L.5.75), A. bras/tense AZ39 (L.5.2), *A. brasilense* XOH (L.5.3), *A. brasilense* Sp245 (BR 11005) (L.5.4), *A. brasilense* BR 11002 (L.5.5), *A. lipoferum* BR 11646 (Sp31) (L.5.6), *A. irakense* (L.5.7), *A. halopraeferens* (L.5.8), *Bradyrhizobium* sp. PNL01 (L.5.9), B. sp. (*Arachis*) CB1015 (L.5.10), B. sp. (*Arachis*) USDA 3446 (L.5.11), B. sp. (*Arachis*) SEMIA 6144 (L.5.12), B. sp. (*Arachis*) SEMIA 6462 (L.5.13), B. sp. (*Arachis*) SEMIA 6464 (L.5.14), B. sp. (*Vigna*) (L.5.15), *B. elkanii* SEMIA 587 (L.5.16), *B. elkanii* SEMIA 5019 (L.5.17), *B. elkanii* U-1301 (L.5.18), *B. elkanii* U-1302 (L.5.19), *B. elkanii* USDA 74 (L.5.20), *B. elkanii* USDA 76 (L.5.21), *B. elkanii* USDA 94 (L.5.22), *B. elkanii* USDA 3254 (L.5.23), *B. japonicum* 532c (L.5.24), *B. japonicum* CPAC 15 (L.5.25), *B. japonicum* E-109 (L.5.26), *B. japonicum* G49 (L.5.27), *B. japonicum* TA-11 (L.5.28), *B. japonicum* USDA 3 (L.5.29), *B. japonicum* USDA 31 (L.5.30), *B. japonicum* USDA 76 (L.5.31), *B. japonicum* USDA 110 (L.5.32), *B. japonicum* USDA 121 (L.5.33), *B. japonicum* USDA 123 (L.5.34), *B. japonicum* USDA 136 (L.5.35), *B. japonicum* SEMIA 566 (L.5.36), *B. japonicum* SEMIA 5079 (L.5.37), *B. japonicum* SEMIA 5080 (L.5.38), *B. japonicum* WB74 (L.5.39), *B. liaoningense* (L.5.40), *B. lupini* LL13 (L.5.41), *B. lupini* WU425 (L.5.42), *B. lupini* WSM471 (L.5.43), *B. lupini* WSM4024 (L.5.44), *Glomus intraradices* RTI-801 (L.5.45), *Mesorhizobium* sp. WSM1271 (L.5.46), M. sp. WSM1497 (L.5.47), *M. ciceri* CC1192 (L.5.48), *M. huakii* (L.5.49), *M. loti* CC829 (L.5.50), *M. loti* SU343 (L.5.51), *Rhizobium leguminosarum* bv. *phaseoli* RG-B10 (L.5.52), *R. l.* bv. *trifolil* RP113-7 (L.5.53), *R. l.* bv. *trifolii* 095 (L.5.57), *R. l.* bv. *trifolii* TA1 (L.5.58), *R. l.* bv. *trifolii* CC283b (L.5.59), *R. l.* bv. *trifolii* CC275e (L.5.60), *R. l.* bv. *trifolii* CB782 (L.5.61), *R. l.* bv. *trifolii* CC1099 (L.5.62), *R. l.* bv. *trifolii* WSM1325 (L.5.63), *R. l.* bv. *viciae* SU303 (L.5.64), *R. l.* bv. *viciae* WSM1455 (L.5.65), *R. l.* bv. *viciae* P1NP3Cst (L.5.66), *R. l.* bv. *viciae* RG-P2 (L.5.67), *R. tropici* PRF 81 (L.5.68), *R. tropici* SEMIA 4077 (L.5.69), *R. tropici* CC511 (L.5.70), *Sinorhizobium meliloti* RCR2011 (L.5.71), *S. meliloti* NRG185 (L.5.72), *S. meliloti* RRI128 (L.5.73);

L6a) Biochemical pesticides with plant stress reducing, plant growth regulator and/or plant yield enhancing activity: abscisic acid (L.6.1), aluminium silicate (kaolin) (L.6.2), 3-decen-2-one (L.6.3), formononetin (L.6.4), genistein (L.6.5), hesperetin (L.6.6), homobrassinolide (L.6.7), humates (L.6.8), methyl jasmonate (L.6.9), cis-jasmone (L.6.10), lysophosphatidyl ethanamine (L.6.11), naringenin (L.6.12), polymeric polyhydroxy acid (L.6.13), salicylic acid (L.6.14), *Ascophyllum nodosum* (Norwegian kelp, Brown kelp) extract (L.6.15) and *Ecklonia maxima* (kelp) extract (L.6.16).

According to a further embodiment of the inventive compositions, the biopesticide component II is *Bacillus amyloliquefaciens* subsp. *plantarum* MBI600. These compositions are particularly suitable in soybean.

According to another embodiment of the inventive compositions, the biopesticide component II is *B. pumilus* strain INR-7 (otherwise referred to as BU-F22 (NRRL B-50153) and BU-F33 (NRRL B-50185; see WO 2012/079073). These compositions are particularly suitable in soybean and corn.

According to another embodiment of the inventive compositions, the biopesticide component II is *Bacillus simplex*, preferably *B. simplex* strain ABU 288 (NRRL B-50340). These compositions are particularly suitable in soybean and corn.

According to another embodiment of the inventive compositions, the biopesticide component II is selected from *Trichoderma asperellum, T. atroviride, T. fertile, T. gamsii, T. harmatum*; composition of *T. harzianum* and *T. viride*; composition of *T. polysporum* and *T. harzianum; T. stromaticum, T. virens* (also named *Gliocladium virens*) and *T. viride*; preferably *Trichoderma fertile*, in particular *T. fertile* strain JM41R. These compositions are particularly suitable in soybean and corn.

According to another embodiment of the inventive compositions, the biopesticide component II is *Sphaerodes mycoparasitica*, preferably *Sphaerodes mycoparasitica* strain IDAC 301008-01 (also referred to as strain SMCD2220-01). These compositions are particularly suitable in soybean and corn.

According to another embodiment of the inventive compositions, the biopesticide component II is *Beauveria bassiana*, preferably *Beauveria bassiana* strain PPRI5339. These compositions are particularly suitable in soybean and corn.

According to another embodiment of the inventive compositions, the biopesticide component II is *Metarhizium anisopliae* or *M. anisopliae* var. *acridium*, preferably selected from *M. anisolpiae* strain IMI33 and *M. anisopliae* var. *acridium* strain IMI 330189. These compositions are particularly suitable in soybean and corn.

According to another embodiment of the inventive compositions, the biopesticide component II is *Bacillus firmus*, preferably strain I-1592. This isolate has been deposited with the Collection Nationale de Cultures de Microorganismes (CNCM), Institute Pasteur, France, on May 29, 1995 under Accession Number CNCMI-1582.

According to another embodiment of the inventive compositions, *Bradyrhizobium* sp. (meaning any *Bradyrhizobium* species and/or strain) as biopesticide II is *Bradyrhizobium japonicum* (*B. japonicum*). These compositions are particularly suitable in soybean. Preferably *B. japonicum* is not one of the strains TA-11 or 532c. *B. japonicum* strains were cultivated using media and fermentation techniques known in the art, e.g. in yeast extract-mannitol broth (YEM) at 27° C. for about 5 days.

References for various *B. japonicum* strains are given e.g. in U.S. Pat. No. 7,262,151 (*B. japonicum* strains USDA 110 (=IITA 2121, SEMIA 5032, RCR 3427, ARS I-110, Nitragin 61A89; isolated from *Glycine max* in Florida in 1959, Serogroup 110; Appl Environ Microbiol 60, 940-94, 1994), USDA 31 (=Nitragin 61A164; isolated from *Glycine max* in Wisconsin in 1941, USA, Serogroup 31), USDA 76 (plant passage of strain USDA 74 which has been isolated from *Glycine max* in California, USA, in 1956, Serogroup 76), USDA 121 (isolated from *Glycine max* in Ohio, USA, in 1965), USDA 3 (isolated from *Glycine max* in Virginia, USA, in 1914, Serogroup 6) and USDA 136 (=CB 1809, SEMIA 586, Nitragin 61A136, RCR 3407; isolated from *Glycine max* in Beltsville, Md. in 1961; Appl Environ Microbiol 60, 940-94, 1994). USDA refers to United States Department of Agriculture Culture Collection, Beltsville, Md., USA (see e.g. Beltsville *Rhizobium* Culture Collection Catalog March 1987 ARS-30). Further suitable *B. japonicum* strain G49 (INRA, Angers, France) is described in Fernandez-Flouret, D. & Cleyet-Marel, J. C. (1987) C R Acad Agric Fr 73, 163-171), especially for soybean grown in Europe, in particular in France. Further suitable *B. japonicum* strain TA-11 (TA11 NOD$^+$) (NRRL B-18466) is i.a. described in U.S. Pat. No. 5,021,076; Appl Environ Microbiol (1990) 56, 2399-2403 and commercially available as liquid inoculant for soybean (VAULT® NP, Becker Underwood, USA). Further *B. japonicum* strains as example for biopesticide component II are described in US2012/0252672A. Further suitable and especially in Canada commercially available strain 532c (The Nitragin Company, Milwaukee, Wis., USA, field isolate from Wisconsin; Nitragin strain collection No. 61A152; Can J Plant Sci 70 (1990), 661-666).

Other suitable and commercially available *B. japonicum* strains (see e.g. Appl Environ Microbiol 2007, 73(8), 2635) are SEMIA 566 (isolated from North American inoculant in 1966 and used in Brazilian commercial inoculants from 1966 to 1978), SEMIA 586 (=CB 1809; originally isolated in Maryland, USA but received from Australia in 1966 and used in Brazilian inoculants in 1977), CPAC 15 (=SEMIA 5079; a natural variant of SEMIA 566 used in commercial inoculants since 1992) and CPAC 7 (=SEMIA 5080; a natural variant of SEMIA 586 used in commercial inoculants since 1992). These strains are especially suitable for soybean grown in Australia or South America, in particular in Brazil. Some of the abovementioned strains have been re-classified as a novel species *Bradyrhizobium elkanii*, e.g. strain USDA 76 (Can. J. Microbiol., 1992, 38, 501-505).

Another suitable and commercially available *B. japonicum* strain is E-109 (variant of strain USDA 138, see e.g. Eur. J. Soil Biol. 45 (2009) 28-35; Biol Fertil Soils (2011) 47:81-89, deposited at Agriculture Collection Laboratory of the Instituto de Microbiologia y Zoologia *Agricola* (IMYZA), Instituto Nacional de Tecnologi'a Agropecuaria (INTA), Castelar, Argentina). This strain is especially suitable for soybean grown in South America, in particular in Argentina.

The present invention also relates to compositions, wherein the biopesticide component II is selected from *Bradyrhizobium elkanii* and *Bradyrhizobium liaoningense* (*B. elkanii* and *B. liaoningense*), more preferably from *B. elkanii*. These compositions are particularly suitable in soybean. *B. elkanii* and liaoningense were cultivated using media and fermentation techniques known in the art, e.g. in yeast extract-mannitol broth (YEM) at 27° C. for about 5 days.

Suitable and commercially available *B. elkanii* strains are SEMIA 587 and SEMIA 5019 (=29W) (see e.g. Appl Environ Microbiol 2007, 73(8), 2635) and USDA 3254 and USDA 76 and USDA 94. Further commercially available *B. elkanii* strains are U-1301 and U-1302 (e.g. product Nitroagin® Optimize from Novozymes Bio As S.A., Brazil or NITRASEC for soybean from LACE y Cia, Brazil). These strains are especially suitable for soybean grown in Australia or South America, in particular in Brazil.

The present invention also relates to compositions, wherein the biopesticide component II is selected from *Bradyrhizobium japonicum* (*B. japonicum*) and further comprises a compound III, wherein compound III is selected from jasmonic acid or salts or derivatives thereof including cis-jasmone, preferably methyl-jasmonate or cis-jasmone.

The present invention also relates to compositions, wherein biopesticide II is selected from *Bradyrhizobium* sp. (*Arachis*) (*B.* sp. *Arachis*) which shall describe the cowpea miscellany cross-inoculation group which includes inter alia indigenous cowpea bradyrhizobia on cowpea (*Vigna unguiculata*), siratro (*Macroptilium atropurpureum*), lima bean (*Phaseolus lunatus*), and peanut (*Arachis hypogaea*). This composition comprising as biopesticide II B. sp. *Arachis* is especially suitable for use in peanut, Cowpea, Mung bean, Moth bean, Dune bean, Rice bean, Snake bean and Creeping *vigna*, in particular peanut.

Suitable and commercially available B. sp. (*Arachis*) strain is CB1015 (=IITA 1006, USDA 3446 presumably originally collected in India; from Australian Inoculants Research Group; see e.g. http://www.qaseeds.com.au/inoculant_applic.php; Beltsville *Rhizobium* Culture Collection Catalog March 1987 USDA-ARS ARS-30). These strains are especially suitable for peanut grown in Australia, North America or South America, in particular in Brazil. Further suitable strain is *Bradyrhizobium* sp. PNL01 (Becker Underwood; ISO Rep Marita McCreary, QC Manager Padma Somasageran; IDENTIFICATION OF *RHIZOBIA* SPECIES THAT CAN ESTABLISH NITROGEN-FIXING NODULES IN CROTALARIA LONGIROSTRATA. Apr. 29, 2010, University of Massachusetts Amherst: http://www.wpi.edu/Pubs/E-project/Available/E-project-042810-163-614/unrestricted/Bisson.Mason._Identification_of_Rhizobia_Species_That_can_Establish_Nitrogen-Fixing_Nodules_in_Crotalia_Longirostrata.pdf).

Suitable and commercially available *Bradyrhizobium* sp. (*Arachis*) strains especially for cowpea and peanut but also for soybean are *Bradyrhizobium* SEMIA 6144, SEMIA 6462 (=BR 3267) and SEMIA 6464 (=BR 3262) (deposited at FEPAGRO-MIRCEN, R. Gonçalves Dias, 570 Porto Alegre—RS, 90130-060, Brazil; see e.g. FEMS Microbiology Letters (2010) 303(2), 123-131; Revista Brasileira de Ciencia do Solo (2011) 35(3); 739-742, ISSN 0100-0683).

The present invention also relates to compositions wherein the biopesticide component II is selected from *Bradyrhizobium* sp. (*Arachis*) and further comprises a compound III, wherein compound III is selected from jasmonic acid or salts or derivatives thereof including cis-jasmone, preferably methyl-jasmonate or cis-jasmone.

The present invention also relates to compositions, wherein the biopesticide component II is selected from *Bradyrhizobium* sp. (Lupine) (also called *B. lupini*, *B. lupines* or *Rhizobium lupini*). This composition is especially suitable for use in dry beans and lupins.

Suitable and commercially available *B. lupini* strain is LL13 (isolated from *Lupinus iuteus* nodules from French soils; deposited at INRA, Dijon and Angers, France; http://agriculture.gouv.fr/IMG/pdf/ch20060216.pdf). This strain is especially suitable for lupins grown in Australia, North America or Europe, in particular in Europe.

Further suitable and commercially available *B. lupini* strains WU425 (isolated in Esperance, Western Australia from a non-Australian legume *Ornthopus compressus*), WSM4024 (isolated from lupins in Australia by CRS during a 2005 survey) and WSM471 (isolated from *Ornithopus pinnatus* in Oyster Harbour, Western Australia) are described e.g. in Palta J. A. and Berger J. B. (eds), 2008, Proceedings 12th International Lupin Conference, 14-18 Sep. 2008, Fremantle, Western Australia. International Lupin Association, Canterbury, New Zealand, 47-50, ISBN 0-86476-153-8:http://www.lupins.org/pdf/conference/2008/Agronomy%20and%20Production/John%20Howieson%20and%20G%20OHara.pdf; Appl Environ Microbiol (2005) 71, 7041-7052 and Australian J. Exp. Agricult. (1996) 36(1), 63-70.

The present invention also relates to compositions wherein the biopesticide component II is selected from *Bradyrhizobium* sp. (Lupine) (*B. lupini*) and further comprises a compound III, wherein compound III is selected from jasmonic acid or salts or derivatives thereof including cis-jasmone, preferably methyl-jasmonate or cis-jasmone.

The present invention also relates to compositions, wherein the biopesticide component II is selected from *Mesorhizobium* sp. (meaning any *Mesorhizobium* species and/or strain), more preferably *Mesorhizobium* ciceri. These compositions are particularly suitable in cowpea.

Suitable and commercially available M. sp. strains are e.g. *M. ciceri* CC1192 (=UPM 848, CECT 5549; from Horticultural Research Station, Gosford, Australia; collected in Israel from *Cicer arietinum* nodules; Can J Microbial (2002) 48, 279-284) and *Mesorhizobium* sp. strains WSM1271 (collected in Sardinia, Italy, from plant host *Biserrula pelecinus*), WSM 1497 (collected in Mykonos, Greece, from plant host *Biserrula pelecinus*), *M. loti* strains CC829 (commercial inoculant for *Lotus pedunculatus* and *L. ulginosus* in Australia, isolated from *L. ulginosus* nodules in USA) and SU343 (commercial inoculant for *Lotus corniculatus* in Australia; isolated from host nodules in USA) all of which are deposited at Western Australian Soil Microbiology (WSM) culture collection, Australia and/or CSIRO collection (CC), Canberra, Australian Capital Territory (see e.g. Soil Biol Biochem (2004) 36(8), 1309-1317; Plant and Soil (2011) 348(1-2), 231-243).

Suitable and commercially available *M. loti* strains are e.g. *M. loti* CC829 for *Lotus pedunculatus*.

The present invention also relates to compositions wherein the biopesticide component II is selected from *Bradyrhizobium* sp. (Lupine) (*B. lupini*) and further comprises a compound III, wherein compound III is selected from jasmonic acid or salts or derivatives thereof including cis-jasmone, preferably methyl-jasmonate or cis-jasmone.

The present invention also relates to compositions wherein the biopesticide component II is selected from *Mesorhizobium huakuii*, also referred to as *Rhizobium huakuii* (see e.g. Appl. Environ. Microbiol. 2011, 77(15), 5513-5516). These compositions are particularly suitable in *Astralagus*, e.g. *Astalagus sinicus* (Chinese milkwetch), *Thermopsis*, e.g. *Thermopsis luinoides* (Goldenbanner) and alike.

Suitable and commercially available *M. huakuii* strain is HN3015 which was isolated from *Astralagus sinicus* in a rice-growing field of Southern China (see e.g. World J. Microbiol. Biotechn. (2007) 23(6), 845-851, ISSN 0959-3993).

The present invention also relates to compositions wherein the biopesticide component II is selected from *Mesorhizobium huakuii* and further comprises a compound III, wherein compound III is selected from jasmonic acid or salts or derivatives thereof including cis-jasmone, preferably methyl-jasmonate or cis-jasmone.

The present invention also relates to compositions, wherein the biopesticide component II is selected from *Azospirillum amazonense, A. brasilense, A. lipoferum, A. irakense, A. halopraeferens*, more preferably from *A. brasilense*, in particular selected from *A. brasilense* strains BR 11005 (SP 245) and AZ39 which are both commercially used in Brazil and are obtainable from EMBRAPA, Brazil. These compositions are particularly suitable in soybean.

Humates are humic and fulvic acids extracted from a form of lignite coal and clay, known as leonardite. Humic acids are organic acids that occur in humus and other organically derived materials such as peat and certain soft coal. They have been shown to increase fertilizer efficiency in phosphate and micro-nutrient uptake by plants as well as aiding in the development of plant root systems.

Salts of jasmonic acid (jasmonate) or derivatives include without limitation the jasmonate salts potassium jasmonate, sodium jasmonate, lithium jasmonate, ammonium jasmonate, dimethylammonium jasmonate, isopropylammonium jasmonate, diolammonium jasmonate, diethtriethanolammonium jasmonate, jasmonic acid methyl ester, jasmonic acid amide, jasmonic acid methylamide, jasmonic acid-L-amino acid (amide-linked) conjugates (e.g., conjugates with L-isoleucine, L-valine, L-leucine, or L-phenylalanine), 12-oxo-phytodienoic acid, coronatine, coronafacoyl-L-serine, coronafacoyl-L-threonine, methyl esters of 1-oxo-indanoyl-isoleucine, methyl esters of 1-oxo-indanoyl-leucine, coronalon (2-[(6-ethyl-1-oxo-indane-4-carbonyl)-amino]-3-methyl-pentanoic acid methyl ester), linoleic acid or derivatives thereof and cis-jasmone, or combinations of any of the above. More preferably, jasmonic acid derivatives are selected from jasmonic acid, methyl jasmonate and cis-jasmone.

According to a further embodiment of the invention, the biopesticide component II is selected from the groups:

La) Microbial pesticides with fungicidal, bactericidal, viricidal and/or plant defense activator activity selected from: *Bacillus altudinis, Bacillus amyloliquefaciens, Bacillus amyloliquefaciens* ssp. *plantarum* MBI 600 (II-27), *B. amyloliquefaciens* ssp. *plantarum* D747, *B. megaterium, B. mojavensis* (II-28), *B. mycoides, B. pumilus* INR-7 (II-29), *B. pumilus* GHA 180, *B. simplex* (II-30), *B. solisalsi* (II-31), *Bacillus subtilis, Burkholderia* sp., *Clavibacter michiganensis* (bacteriophages) (II-32), *Gliocladium roseum* (II-33), *Microsphaeropsis ochracea, Muscodor albus, Paenibacillus alvei, Paenibacillus polymyxa* (II-34), *Pantoea agglomerans* (II-35), *Pantoea vagans, Penicillium bilaiae, Pseudomonas* sp., *Pseudomonas chloraphis, P. fluorescens, Sphaerodes mycoparasitica* (II-36), *Streptomyces lydicus* (II-37), *S. violaceusniger* (II-38), *Trichoderma fertile* JM41R (II-39), *Typhula phacorrhiza* (II-40), *Verticillium dahlia* (II-42), zucchini yellow mosaic virus (avirulent strain);

Lb) Biochemical pesticides with fungicidal, bactericidal, viricidal and/or plant defense activator activity selected from: harpin protein, laminarin, jasmonic acid (II-43) or salts or derivatives thereof, laminarin, Menhaden fish oil, natamycin, Plum pox virus coat protein, potassium or sodium bicarbonate, salicylic acid, tea tree oil;

Lc) Microbial pesticides with insecticidal, acaricidal, molluscidal and/or nematicidal activity selected from: *Agrobacterium radiobacter, Bacillus cereus, Bacillus firmus* (II-44), *B. thuringiensis* ssp. *israelensis*, B. t. ssp. *galleriae*, B. t. ssp. *kurstaki, Beauveria bassiana* (II-45), *Beauveria brongniartii, Burkholderia* sp., *Chromobacterium subtsugae, Cydia pomonella* granulosis virus, *Isaria fumosorosea, Lecanicillium longisporum, L. muscarium* (formerly *Verticillium lecanii*), *Metarhizium anisopliae* (II-46), *M.* anisopliae var. anisopliae, M. anisopliae var. acridum, Paecilomyces fumosoroseus, P. lilacinus, Paenibacillus popilliae, Pasteuria spp., P. nishizawae, P. reneformis, P. usagae, Pseudomonas fluorescens, Pseudomonas putida, Steinernema feltiae, Steinernema kraussei, Streptomces galbus, Streptomyces microflavus;

Ld) Biochemical pesticides with insecticidal, acaricidal, molluscidal, pheromone and/or nematicidal activity selected from: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-ylacetate, Z-7-tetradecen-2-one, Z-9-tetradecen-1-ylacetate, Z-11-tetradecenal, Z-11-tetradecen-1-ol, Acacia negra extract, extract of grapefruit seeds and pulp, extract of Chenopodium ambrosiodae, Catnip oil, Neem oil, Quillay extract (II-47), Tagetes oil;

Le) Microbial pesticides with plant stress reducing, plant growth regulator, plant growth promoting and/or yield enhancing activity selected from: Azospirillum amazonense, A. brasilense (II-48), A. lipoferum, A. irakense, A. halopraeferens, Bradyrhizobium sp. (II-49), B. japonicum (II-50), B. elkanii, B. lupini, B. liaoningense, Delftia acidovorans, Glomus intraradices, Mesorhizobium sp. (II-51), M. ciceri, M. huakii, M. loti, Paenibacillus alvei, Penicillium bilaiae (II-52), Rhizobium leguminosarum bv. phaseoli (II-53), R. l. trifolii, R. l. bv. viciae (II-54), R. tropici, Sinorhizobium meliloti (II-55);

Lf) Biochemical pesticides with plant stress reducing, plant growth regulator and/or plant yield enhancing activity selected from: abscisic acid, aluminium silicate (kaolin), 3-decen-2-one, homobrassinlide, humates, indole-3-acetic acid, lysophosphatidyl ethanlamine, polymeric polyhydroxy acid, Ascophyllum nodosum (Norwegian kelp, Brown kelp) extract and Ecklonia maxima (kelp) extract.

In a further embodiment, La) to Lf) are defined as follows (La.1) to Lf.1)):

La.1) Microbial pesticides with fungicidal, bactericidal, viricidal and/or plant defense activator activity selected from: Bacillus amyloliquefaciens MBI 600 (II-27), B. mojavensis (II-28), B. pumilus INR-7 (II-29), B. simplex (II-30), B. solisalsi (II-31), Clavibacter michiganensis (bacteriophages) (II-32), Gliocladium roseum (II-33), Paenibacillus polymyxa (II-34), Pantoea agglomerans (II-35), Sphaerodes mycoparasitica (II-36), Streptomyces lydicus (II-37), S. violaceusniger (II-38), Trichoderma fertile JM41R (II-39), Typhula phacorrhiza (II-40), Ulocladium oudema (II-41), Verticillium dahlia (II-42), zucchini yellow mosaic virus (avirulent strain);

Lb.1) Biochemical pesticides with fungicidal, bactericidal, viricidal and/or plant defense activator activity selected from: jasmonic acid (II-43) or salts or derivatives thereof, laminarin, Menhaden fish oil, natamycin, Plum pox virus coat protein, Reynoutria sachlinensis extract, salicylic acid, tea tree oil;

Lc.1) Microbial pesticides with insecticidal, acaricidal, molluscidal and/or nematicidal activity selected from: Bacillus firmus (II-44), B. thuringiensis ssp. israelensis, B. t. ssp. galleriae, B. t. ssp. kurstaki, Beauveria bassiana (II-45), Burkholderia sp., Chromobacterium subtsugae, Cydia pomonella granulosis virus, Isaria fumosorosea, Lecanicillium longisporum, L. muscarium (formerly Verticillium lecanii), Metarhizium anisopliae (II-46), M. anisopliae var. acridum, Paecilomyces fumosoroseus, P. lilacinus, Paenibacillus poppiliae, Pasteuria spp., P. nishizawae, P. reneformis, P. usagae, Pseudomonas fluorescens, Steinernema feltiae, Streptomces galbus;

Ld.1) Biochemical pesticides with insecticidal, acaricidal, molluscidal, pheromone and/or nematicidal activity selected from: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-ylacetate, Z-7-tetradecen-2-one, Z-9-tetradecen-1-ylacetate, Z-11-tetradecenal, Z-11-tetradecen-1-ol, Acacia negra extract, extract of grapefruit seeds and pulp, extract of Chenopodium ambrosiodae, Catnip oil, Neem oil, Quillay extract (II-47), Tagetes oil;

Le.1) Microbial pesticides with plant stress reducing, plant growth regulator, plant growth promoting and/or yield enhancing activity selected from: Azospirillum amazonense, A. brasilense (II-48), A. lipoferum, A. irakense, A. halopraeferens, Bradyrhizobium sp. (II-49), B. japonicum (II-50), Glomus intraradices, Mesorhizobium sp. (II-1), Paenibacillus alvei, Penicillium bilaiae (II-52), Rhizobium leguminosarum bv. phaseolii (II-53), R. l. trifolii, R. l. bv. viciae (II-54), Sinorhizobium meliloti (II-55);

Lf.1) Biochemical pesticides with plant stress reducing, plant growth regulator and/or plant yield enhancing activity selected from: abscisic acid, aluminium silicate (kaolin), 3-decen-2-one, homobrassinlide, humates, indole-3-acetic acid, lysophosphatidyl ethanlamine, polymeric polyhydroxy acid, Ascophyllum nodosum (Norwegian kelp, Brown kelp) extract and Ecklonia maxima (kelp) extract.

According to one embodiment of the inventive mixtures, the component 2) is a biopesticide II from the groups D) to I) selected from:

La-1) Microbial pesticides with fungicidal, bactericidal, viricidal and/or plant defense activator activity: Bacillus altitudinis 41 KF2b, Bacillus amyloliquefaciens AP-136, B. amyloliquefaciens AP-188, B. amyloliquefaciens AP-218, B. amyloliquefaciens AP-219, B. amyloliquefaciens AP-295, B. amyloliquefaciens IN937a, B. amyloliquefaciens IT-45, B. amyloliquefaciens ssp. plantarum D747, B. amyloliquefaciens ssp. plantarum MBI600 (NRRL B-50595), B. amyloliquefaciens ssp. plantarum TJ1000, B. mojavensis AP-209, B. mycoides AQ726, B. mycoides strain J, B. pumilus INR-7, B. pumilus GHA 180, B. simplex ABU 288, B. solisalsi AP-217, B. subtilis CX-9060, B. subtilis FB17, B. subtilis GB07, Clavibacter michiganensis (bacteriophages), Gliocladium roseum 321 U, Microsphaeropsis ochracea P130A, Muscodor albus QST 20799, Muscodor albus SA-13, Paenibacillus alvei NAS6G6, Paenibacillus polymyxa PKB1, Pantoea agglomerans E325, Pantoea vagans C9-1, Penicillium bilaiae ATCC 22348, P. bilaiae ATCC 20851, Penicillium bilaiae ATCC 18309, Phlebiopsis gigantea, Pichia anomala WRL-76, Pseudomonas sp. Proradix, Pseudomonas chloraphis MA 342, P. fluorescens A506, P. fluorescens CL 145A, P. fluorescens NCIB 12089, P. fluorescens Pf-5, P.

fluorescens WCS 374, *P. fluorescens* ATCC 13525, *P. fluorescens* CHA0, *P. putida* ATCC 202153, *Sphaerodes mycoparasitica* SMCD2220, *S. lydicus* WYEC 108, *S. violaceusniger* XL-2, *S. violaceusniger* YCED-9, *Trichoderma fertile* JM41R, *Typhula phacorrhiza* 94671, *Verticillium dahlia*, zucchini yellow mosaic virus (avirulent strain);

Lb-1) Biochemical pesticides with fungicidal, bactericidal, viricidal and/or plant defense activator activity: harpin protein, laminarin, Menhaden fish oil, natamycin, Plum pox virus coat protein, potassium bicarbonate, salicylic acid, potassium or sodium bicarbonate, tea tree oil;

Lc-1) Microbial pesticides with insecticidal, acaricidal, molluscidal and/or nematicidal activity: *Agrobacterium radiobacter* K1026, *A. radiobacter* K84, *Bacillus firmus* I-1582; *B. thuringiensis* ssp. *aizawai* strains: ABTS-1857, SAN 401 I, ABG-6305 and ABG-6346; B. t. ssp. *israelensis* AM65-52, B. t. ssp. *israelensis* SUM-6218, B. t. ssp. *galleriae* SDS-502, B. t. ssp. *kurstaki* EG 2348, B. t. ssp. *kurstaki* SB4, B. t. ssp. *kurstaki* ABTS-351 (HD-1), *Beauveria bassiana* ATCC 74040, *B. bassiana* GHA, *B. bassiana* H123, *B. bassiana* DSM 12256, *B. bassiana* PPRI 5339, *B. brongniartii, Burkholderia* sp. A396, *Chromobacterium subtsugae* PRAA4-1, *Cydia pomonella* granulosis virus V22, *Cydia pomonella* granulosis virus V1, *Cryptophlebia leucotreta* granulovirus (CrIeGV), *Flavobacterium* sp. H492, *Helicoverpa armigera* nucleopolyhedrovirus (HearNPV), *Isaria fumosorosea* Apopka-97, *Lecanicillium longisporum* KV42, *L. longisporum* KV71, *L. muscarium* KV01, *Metarhizium anisopliae* FI-985, *M. anisopliae* FI-1045, *M. anisopliae* F52, *M. anisopliae* ICIPE 69, *M. anisopliae* var. *acridum* IMI 330189; *Nomuraea rileyi* strains: SA86101, GU87401, SR86151, CG128 and VA9101; *Paecilomyces fumosoroseus* FE 9901, *P. lilacinus* 251, *P. lilacinus* DSM 15169, *P. lilacinus* BCP2, *Paenibacillus popilliae* Dutky-1940 (NRRL B-2309=ATCC 14706), *P. popilliae* Dutky 1, *P. popilliae* KLN 3, *Pasteuria* sp. Ph3, *Pasteuria* sp. ATCC PTA-9643, *Pasteuria* sp. ATCC SD-5832, *P. nishizawae* Pn1, *P. penetrans, P. ramosa*, P. sp. Pr-3, *P. thornea, P. usgae, Pseudomonas fluorescens* CL 145A, *Spodoptera littoralis* nucleopolyhedrovirus (SpliNPV), *Steinernema carpocapsae, S. feltiae, S. kraussei* L137;

Ld-1) Biochemical pesticides with insecticidal, acaricidal, molluscidal, pheromone and/or nematicidal activity: L-carvone, citral, (E,Z)-7,9-dodecadien-1-ylacetate, ethyl formate, (E,Z)-2,4-ethyl decadienoate (pear ester), (Z,Z,E)-7,11,13-hexadecatrienal, heptyl butyrate, isopropyl myristate, cis-jasmone, lavanulyl senecioate, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-ylacetate, Z-7-tetradecen-2-one, Z-9-tetradecen-1-ylacetate, Z-11-tetradecenal, Z-11-tetradecen-1-ol, *Acacia negra* extract, extract of grapefruit seeds and pulp, extract of *Chenopodium ambrosiodes*, Catnip oil, Neem oil, Quillay extract, *Tagetes* oil;

Le-1) Microbial pesticides with plant stress reducing, plant growth regulator, plant growth promoting and/or yield enhancing activity: *Azospirillum amazonense* BR 11140 (SpY2), *A. brasilense* Ab-V5, *A. brasilense* Ab-V6, *A. brasilense* AZ39, *A. brasilense* XOH, *A. brasilense* Sp245 (BR 11005), *A. brasilense* BR 11002, *A. lipoferum* BR 11646 (Sp31), *A. irakense, A. halopraeferens, Bradyrhizobium* sp. PNL01, B. sp. (*Arachis*) CB1015, B. sp. (*Arachis*) USDA 3446, B. sp. (*Arachis*) SEMIA 6144, B. sp. (*Arachis*) SEMIA 6462, B. sp. (*Arachis*) SEMIA 6464, B. sp. (*Vigna*), *B. elkanii* SEMIA 587, *B. elkanii* SEMIA 5019, *B. elkanii* U-1301, *B. elkanii* U-1302, *B. elkanii* USDA 74, *B. elkanii* USDA 76, *B. elkanii* USDA 94, *B. elkanii* USDA 3254, *B. japonicum* 532c, *B. japonicum* CPAC 15, *B. japonicum* E-109, *B. japonicum* G49, *B. japonicum* TA-11, *B. japonicum* USDA 3, *B. japonicum* USDA 31, *B. japonicum* USDA 76, *B. japonicum* USDA 110, *B. japonicum* USDA 121, *B. japonicum* USDA 123, *B. japonicum* USDA 136, *B. japonicum* SEMIA 566, *B. japonicum* SEMIA 5079, *B. japonicum* SEMIA 5080, *B. japonicum* WB74, *B. liaoningense, B. lupini* LL13, *B. lupini* WU425, *B. lupini* WSM471, *B. lupini* WSM4024, *Glomus intraradices* RTI-801, *Mesorhizobium* sp. WSM1271, M. sp. WSM1497, *M. ciceri* CC1192, *M. huakii, M. loti* CC829, *M. loti* SU343, *Rhizobium leguminosarum* bv. *phaseoli* RG-B10, *R. l.* bv. *trifolii* RP113-7, *R. l.* bv. *trifolii* 095, *R. l.* bv. *trifolii* TA1, *R. l.* bv. *trifolii* CC283b, *R. l.* bv. *trifolii* CC275e, *R. l.* bv. *trifolii* CB782, *R. l.* bv. *trifolii* CC1099, *R. l.* bv. *trifolii* WSM1325, *R. l.* bv. *viciae* SU303, *R. l.* bv. *viciae* WSM1455, *R. l.* bv. *viciae* P1NP3Cst, *R. l.* bv. *viciae* RG-P2, *R. tropici* PRF 81, *R. tropici* SEMIA 4077, *R. tropici* CC511 (L.5.70), *Sinorhizobium meliloti* RCR2011, *S. meliloti* NRG185, *S. meliloti* RRI128;

Lf-1) Biochemical pesticides with plant stress reducing, plant growth regulator and/or plant yield enhancing activity: abscisic acid, aluminium silicate (kaolin), 3-decen-2-one, formononectin, genistein, hesperetin, homobrassinolide, humates, methyl jasmonate, cis-jasmone, lysophosphatidyl ethanlamine, naringenin, polymeric polyhydroxy acid, salicylic acid, *Ascophyllum nodosum* (Norwegian kelp, Brown kelp) extract and *Ecklonia maxima* (kelp) extract.

Preference is also given to compositions comprising as biopesticide component II a biopesticide from group La), preferably selected from *Bacillus amyloliquefaciens* herein even more preferably from strains AP-136, AP-188, AP-218, AP-219, AP-295, IN937a, IT-45; *B. amyloliquefaciens* ssp. *plantarum* herein even more preferably from strains MBI600, D747 and TJ1000; *B. mojavensis* AP-209; *B. pumilus* GHA 180 and INR-7; *B. simplex* herein more preferably strain ABU 288*; B. solisalsi* herein more preferably strain AP-217; *B. subtilis* herein even more preferably selected from strains CX-9060, FB17 and GB07; *Muscodor albus* herein more preferably strains QST 20799 and SA-13; *Paenibacillus alvei* herein more preferably strain NAS6G6, *Paenibacillus polymyxa* herein more preferably strain PKB1, *Penicillium bilaiae* herein more preferably strains ATCC 22348, ATCC 20581 and ATCC 18309; *Pseudomonas fluorescens* herein more preferably strain A506; *Sphaerodes mycoparasitica* herein more preferably strain SMCD2220; *Trichoderma fertile* herein more preferably strain JM41R.

Preference is also given to compositions comprising as biopesticide component II a biopesticide from group La), even more preferably selected from even more preferably from *B. amyloliquefaciens* AP-188, *B. amyloliquefaciens* ssp. *plantarum* MBI600, *B. pumilus* INR-7, *B. simplex* ABU 288, *B. subtilis* FB17, *Paenibacillus alvei* NAS6G6 and *Trichoderma fertile* JM41R.

According to one embodiment of the inventive compositions, the at least one biopesticide component II is *Bacillus amyloliquefaciens* ssp. *plantarum* MBI600. These compositions are particularly suitable in soybean.

According to another embodiment of the inventive compositions, the at least one biopesticide component II is *B. pumilus* INR-7. These compositions are particularly suitable in soybean and corn.

According to a further embodiment, the at least one biopesticide component II is *Bacillus simplex*, preferably *B. simplex* ABU 288. These compositions are particularly suitable in soybean and corn.

According to a further embodiment, the at least one biopesticide component II is *Bacillus subtilis*, preferably *B. subtilis* strain FB17.

According to one embodiment of the inventive compositions, the at least one biopesticide component II is selected from *Bacillus amyloliquefaciens* AP-136, *B. amyloliquefaciens* AP-188, *B. amyloliquefaciens* AP-218, *B. amyloliquefaciens* AP-219, *B. amyloliquefaciens* AP-295, *B. amyloliquefaciens* ssp. *plantarum* TJ1000, *B. amyloliquefaciens* ssp. *plantarum* D747, *B. amyloliquefaciens* ssp. *plantarum* MBI600, *B. mojavensis* AP-209, *B. pumilus* INR-7, *B. pumilus* GHA 180, *B. simplex* ABU 288, *B. solisalsi* AP-217, *B. subtilis* CX-9060, *B. subtilis* FB17 and *B. subtilis* GB07. These compositions are particularly suitable in soybean and corn, in particular for seed treatment.

According to a further embodiment, the at least one biopesticide component II is selected from *Streptomyces* spp., preferably from *S. griseoviridis*, *S. lydicus* and *S. violaceusniger*, in particular from strains *S. griseoviridis* K61, *S. lydicus* WYEC 108, *S. violaceusniger* XL-2 and *S. violaceusniger* YCED-9.

According to a further embodiment, the at least one biopesticide component II is selected from *Pseudomonas* spp., preferably selected from *P. chloraphis* herein more preferably strain MA 342 and *Pseudomonas* sp. DSM 13134; *P. fluorescens* herein more preferably selected from strains A506, WCS 374 and Pf-5; and *P. putida* herein more preferably strain ATCC 202153.

The present invention also relates to compositions wherein the at least one biopesticide component II is selected from the fungal species *Muscodor albus* preferably from the strains SA-13 and QST 20799, which are particularly suitable for soil and seed treatment against soil-borne pathogens and/or nematodes.

Preference is also given to compositions comprising as biopesticide component II a biopesticide from group Lb), preferably selected methyl-jasmonate, cis-jasmone, laminarin, *Reynoutria sachalinensis* extract and tea tree oil; even more preferable from methyl jasmonate, cis-jasmone and laminarin.

Preference is also given to compositions comprising as biopesticide component II a biopesticide from group Lc), preferably selected from *Agrobacterium radiobacter* herein preferably strain K1026, *Bacillus firmus* herein preferably strain I-1582, *Bacillus thuringiensis* ssp. *kurstaki* herein preferably strain SB4, *Beauveria bassiana* herein preferably selected from strains GHA, H123, DSM 12256 and PPRI 5339; *Burkholderia* sp. and herein preferably strain A396, *Metarhizium anisopliae* var. *acridum* herein preferably strain IMI 330189, *M. anisopliae* herein preferably selected from strains FI-985, FI-1045, F52 and ICIPE 69; *Paecilomyces lilacinus* herein preferably selected from strains 251, DSM 15169 and BCP2, *Paenibacillus popilliae* herein preferably selected from strains Dutky-1940, KLN 3 and Dutky 1; *Pasteuria nishazawa* and herein preferably strain Pn1.

Preference is also given to compositions comprising as biopesticide component II a biopesticide from group Lc), even more preferably from *Bacillus thuringiensis* ssp. *kurstaki*SB4, *B. bassiana* DSM 12256, *B. bassiana* PPRI 5339, *Metarhizium anisopliae* var. *acridum* IMI 330189, *M. anisopliae* FI-985, *M. anisopliae* FI-1045, *Paecilomyces lilacinus* DSM 15169, *P. lilacinus* BCP2, *P. lilacinus* 251, *Paenibacillus popilliae* Dutky-1940, *P. popilliae* KLN 3 and *P. popilliae* Dutky 1.

According to a further embodiment, the at least one biopesticide component II is *Beauveria brongniartii*.

According to a further embodiment, the at least one biopesticide component II is *Metarhizium anisopliae* or *M. anisopliae* var. *acridium*, preferably selected from *M. anisopliae* FI-1045, *M. anisopliae* F52, *M. anisopliae* var. *acridum* strains FI-985 and IMI 330189; in particular strain IMI 330189. These compositions are particularly suitable for control of arthropod pests in soybean and corn.

According to a further embodiment, the at least one biopesticide component II is *Lecanicillium* sp., preferably selected from *Lecanicillium longisporum* KV42, *L. longisporum* KV71 and *L. muscarium* KV01.

According to a further embodiment, the at least one biopesticide component II is *Paecilomyces fumosoroseus*, preferably strain FE 9901 especially for white fly control.

According to a further embodiment, the at least one biopesticide component II is selected from *Nomuraea rileyi*, preferably strains SA86101, GU87401, SR86151, CG128 and VA9101; and *P. lilacinus*, preferably strains 251, DSM 15169 or BCP2, in particular BCP2, which strains especially control the growth of plant-pathogenic nematodes.

According to a further embodiment, the at least one biopesticide component II is *Bacillus firmus*, preferably spores of strain CNCM I-1582, preferably useful for seed treatment of soybean and corn against nematodes and insects.

According to a further embodiment, the at least one biopesticide component II is *Bacillus cereus*, preferably spores of CNCM I-1562, preferably useful for seed treatment of soybean and corn against nematodes and insects.

According to a further embodiment, the at least one biopesticide component II is a composition of spores of *B. firmus* and *B. cereus*, preferably compositions spores of above mentioned strains CNCM I-1582 and CNCM I-1562, preferably useful for seed treatment of soybean and corn against nematodes and insects.

According to a further embodiment, the at least one biopesticide component II is selected from *Bacillus* t. ssp. *kurstaki* preferably from strains EG 2348, SB4 and ABTS-351 (HD-1), in particular B. t. ssp. *kurstaki* SB4. These strains are used for control of lepidopteran larvae, but without noctuidae.

According to one embodiment of the inventive compositions, the at least one biopesticide component II is selected from *Bacillus firmus* CNCM I-1582, *Paecilomyces lilcinus* 251, *Pasteuria nishizawa* Pn1 and *Burkholderia* sp. A396 having nematicidal, acaricidal and/or insecticidal activity. These compositions are particularly suitable in soybean and corn, in particular for seed treatment.

Preference is also given to compositions comprising as biopesticide component II a biopesticide from group Ld), preferably selected from methyl jasmonate, *Acacia negra* extract, extract of grapefruit seeds and pulp, Catnip oil, Neem oil, Quillay extract and *Tagetes* oil, in particular methyl jasmonate or water-based Quillay extract.

Preference is also given to compositions comprising as biopesticide component II a biopesticide from group Le), preferably selected from *Azospirillum amazonense*, *A. brasilense*, *A. lipoferum*, *A. irakense*, *A. halopraeferens*, *Bradyrhizobium* sp. (*Arachis*), *Bradyrhizobium* sp. (*Vigna*), *B. elkanii*, *B. japonicum*; *Paenibacillus alvei*, *Penicillium*

*bilaiae, Rhizobium leguminosarum* bv. *phaseoli, R. l.* bv. *trifolii, R. l.* bv. *viciae*, and *Sinorhizobium meliloti.*

Preference is also given to compositions comprising as biopesticide component II a biopesticide from group Le) selected from *Azospirillum amazonense* SpY2, *A. brasilense* XOH, *A. brasilense* Sp245, *A. brasilense* Cd, *A. brasilense* Ab-V5, *A. brasilense* Ab-V6, *A. lipoferum* Sp31, *Bradyrhizobium* sp. (*Vigna*) PNL1, *B. elkanii* SEMIA 587, *B. elkanii* SEMIA 5019, *B. japonicum* SEMIA 5079, *B. japonicum* SEMIA 5080, *B. japonicum* TA-11, *B. japonicum* 532c, *Paenibacillus alvei* NAS6G6, *Penicillium bilaiae* strains ATCC 18309, ATCC 20851 and ATCC 22348; *Rhizobium leguminosarum* bv. *phaseoli* RG-B10, *R. l.* bv. *viciae* P1NP3Cst, *R. l.* bv. *viciae* RG-P2, *R. l.* bv. *trifolii* RP113-7, *R. l.* bv. *viciae* SU303, *R. l.* bv. *viciae* WSM1455, *R. tropici* SEMIA 4077, *R. tropici* PRF 81 and *Sinorhizobium meliloti*; even more preferably selected from *Azospirillum brasilense* Sp245, *Bradyrhizobium* sp. (*Vigna*) PNL1, B *B. elkanii* SEMIA 587, *B. elkanii* SEMIA 5019, *B. japonicum* SEMIA 5079, *B. japonicum* SEMIA 5080, *B. japonicum* TA-11 and *B. japonicum* 532c.

The present invention also relates to compositions, wherein the at least one biopesticide II is selected from *Azospirillum amazonense, A. brasilense, A. lipoferum, A. irakense* and *A. halopraeferens*, more preferably from *A. brasilense*, in particular selected from *A. brasilense* strains Sp245 and AZ39 which are both commercially used in Brazil and are obtainable from EMBRAPA-Agribiologia, Brazil, and strains Ab-V5 and Ab-V6; in particular compositions of these strains Ab-V5 and Ab-V6. These compositions are particularly suitable in soybean, especially as seed treatment.

The present invention also relates to compositions wherein the at least one biopesticide component II is selected from *A. amazonense, A. brasilense, A. lipoferum, A. irakense* and *A. halopraeferens*, more preferably *A. brasilense*, and further comprises a pesticide III, wherein pesticide III is selected from jasmonic acid, its salts and derivatives thereof, preferably methyl-jasmonate or cis-jasmone.

According to another embodiment of the inventive compositions, *Bradyrhizobium* spp. (meaning any *Bradyrhizobium* species and/or strain) as biopesticide component II is *B. japonicum*. These compositions are particularly suitable in soybean. Certain *B. japonicum* strains have been re-classified as a novel species *B. elkanii*, e. g. strain USDA 76 (Can. J. Microbiol. 38, 501-505, 1992). *Bradyrhizobium* spp. are cultivated using media and fermentation techniques known in the art, e. g. in yeast extract-mannitol broth (YEM) at 27° C. for about 5 days.

The present invention also relates to compositions, wherein the at least one biopesticide component II is selected from *Bradyrhizobium* spp., even more preferably from B. sp. (*Arachis*), *B. elkanii, B. japonicum, B. liaoningense* and *B. lupini*, and further comprises a pesticide III (component 3), wherein pesticide III is selected from jasmonic acid, its salts and derivatives thereof, preferably methyl-jasmonate or cis-jasmone.

Preferably, *B. japonicum* is selected from strains E-109, SEMIA 5079, SEMIA 5080, TA-11 and 532c. According to a further embodiment, compositions of *B. japonicum* strains TA-11 and 532c or *B. japonicum* strains SEMIA 5079 and 5080 are used. The strains having a prefix SEMIA are especially suitable for soybean grown in Australia or South America, in particular in Brazil. More preferably, compositions of *B. japonicum* SEMIA 5079 and SEMIA 5080 are used. *B. japonicum* WB74 is especially suitable for soybean grown in South America and Africa, in particular in South Africa. Strain E-109 is especially suitable for soybean grown in South America, in particular in Argentina.

The present invention also relates to compositions, wherein the at least one biopesticide component II is selected from *B. japonicum* and further comprises a pesticide III, wherein pesticide III is selected from jasmonic acid, its salts and derivatives thereof, preferably methyl-jasmonate or cis-jasmone.

The present invention also relates to compositions, wherein the at least one biopesticide component II is selected from *Bradyrhizobium elkanii* and *Bradyrhizobium liaoningense*, more preferably from *B. elkanii* even more preferably *B. elkanii* strains SEMIA 587 and SEMIA 5019; in particular compositions of both. These compositions are particularly suitable in soybean in Australia or South America, in particular in Brazil.

The present invention also relates to compositions, wherein biopesticide component II is selected from *Bradyrhizobium* sp. (*Arachis*) and B. sp. (*Vigna*) which shall describe the cowpea miscellany cross-inoculation group which includes inter alia indigenous cowpea bradyrhizobia on cowpea (*Vigna unguiculata*), siratro (*Macroptilium atropurpureum*), lima bean (*Phaseolus lunatus*), and peanut (*Arachis hypogaea*), in particular in particular B. sp. (*Vigna*) strain PNL1. This composition comprising as biopesticide II B. sp. (*Arachis*) or B. sp. (*Vigna*) is especially suitable for use in peanut, cowpea, Mung bean, Moth bean, Dune bean, Rice bean, Snake bean and Creeping *vigna*, in particular peanut.

The present invention also relates to compositions, wherein the at least one biopesticide component II is selected from *Bradyrhizobium lupini* (also called B. sp. (Lupine), *B. lupines* or *Rhizobium lupini*). These compositions are especially suitable for use in dry beans and lupins. Preferably, *B. lupini* is strain LL13. This strain is especially suitable for lupins grown in Australia, North America or Europe, in particular in Europe.

The present invention also relates to compositions wherein the at least one biopesticide component II is selected from *Rhizobium leguminosarum* bv. *phaseoli* especially for the legume common bean (*Phaseolus vulgaris*), but also for other for various legumes such as alfalfa, clover, peas, beans, lentils, soybeans, peanuts and other crops such as corn and lettuce, even more preferably strain RG-B10 thereof; *R. l.* bv. *trifolii*, especially strain RP113-7 thereof, *R. l.* bv. *viciae*, in particular strains RG-P2, SU303, WSM1455 and P1NP3Cst thereof, in particular P1NP3Cst; *R. tropici*, especially strains CC511, CIAT 899 and PRF 81 thereof; and *Sinorhizobium meliloti*, especially strain RCR2011 thereof. Further *R. l.* bv. *phaseoli* or *R. etli* strains are e. g. known from the above mentioned references and Appl. Environ. Microbiol. 45(3), 737-742, 1983; ibida 54(5), 1280-1283, 1988.

According to a further embodiment, in the inventive compositions biopesticide component II is selected from *Sinorhizobium meliloti* more preferably from RCR2011, *S. meliloti* NRG185, *S. meliloti* RRI128, *S. meliloti* SU277,

*R. tropici* is useful for a range of legume crops especially all kind of clovers e. g. in tropical regions such as Brazil. Preferably, compositions comprise as *R. tropici* at least one strain selected from CC511, CIAT899, H12 and PRF 81.

The present invention also relates to compositions wherein the at least one biopesticide component II is selected from *R. leguminosarum* bv. *phaseoli, R. l.* bv. *trifolii, R. l.* bv. *viciae, R. tropici* and *Sinorhizobium meliloti*, and further comprises a component III, wherein component III is selected from jasmonic acid, its salts and derivatives thereof, preferably methyl-jasmonate or cis-jasmone.

According to a further embodiment, the at least one biopesticide component II is selected from *Delftia acidovorans*, in particular strain RAY209, especially in soybean and canola.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary composition may be mixed by the user himself in a spray tank or any other kind of vessel used for applications (e.g seed treater drums, seed pelleting machinery, knapsack sprayer) and further auxiliaries may be added, if appropriate. Consequently, one embodiment of the invention is a kit for preparing a usable pesticidal composition, the kit comprising a) a composition comprising component I as defined herein and at least one auxiliary; and b) a composition comprising component II as defined herein and at least one auxiliary; and optionally c) a composition comprising component III as defined herein and at least one auxiliary.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

In the following, the inventive compositions and their preferred uses are further described. In each case, according to the present invention, the use of the composition for controlling a particular phytopathogenic fungus is also meant to encompass the respective method for controlling the particular phytopathogenic fungi, wherein the fungi or the materials, plants, the soil or seed to be protected from fungal attack are treated with an effective amount of a composition as defined in that particular context.

According to a further embodiment of the invention, the biopesticide component II is selected from
*Bacillus amyloliquefaciens* MBI 600 ssp. *plantarum* (II-27);

*B. mojavensis* (II-28),
*B. pumilus* INR-7(II-29);
*B. simplex* (II-30);
*B. solisalsi* (II-31);
*Clavibacter michiganensis* (bacteriophages) (II-32);
*Gliocladium roseum* (II-33);
*Paenibacillus polymyxa* (II-34);
*Pantoea agglomerans* (II-35);
*Sphaerodes mycoparasitica* (II-36);
*Streptomyces lydicus* (II-37);
*S. violaceusniger* (II-38);
*Trichoderma fertile* JM41R (II-39);
*Typhula phacorrhiza* (II-40);
*Verticillium dahlia* (II-42);
jasmonic acid (II-43) or salts or derivatives thereof;
*Bacillus firmus* (II-44);
*Beauveria bassiana* (II-45);
*Metarhizium anisopliae* (II-46);

Quillay extract (II-47);
*A. brasilense* (II-48);
*Bradyrhizobium* sp. (II-49);
*B. japonicum* (II-50);
*Mesorhizobium* sp. (II-51);
*Penicillium bilaiae* (II-52);
*Rhizobium leguminosarum* bv. phaseoli (II-53);
*R. l.* bv. viciae (II-54); and
*Sinorhizobium meliloti* (II-55).

According to still a further embodiment of the invention, the biopesticide component II is selected from:

*Bacillus amyloliquefaciens* ssp. Plantarum (II-27))
*Bacillus mojavensis* (II-28)
*Bacillus pumilus* (II-29)
*Bacillus simplex* (II-30)
*Bacillus solisalsi* (II-31)
*Paenibacillus polymyxa* (II-34)
jasmonic acid or salts or derivatives thereof (II-43)
*Bacillus firmus* (II-44)
*Azospirillum brasilense* (II-48)
*Bradyrhizobium* spp. (II-49)
*Bradyrhizobium japonicum* (II-50)
*Mesorhizobium* spp. (II-51)
*Penicillium bilaiae* (II-52)
*Rhizobium leguminosarum* bv. Phaseoli (II-53)
*Rhizobium leguminosarum* bv. Viciae (II-54)
*Sinorhizobium meliloti* (II-55)
*Azospirillum amazonense* (II-56)
*Azospirillum lipoferum* (II-57)
*Azospirillum irakense* (II-58)
*Azospirillum halopraeferens* (II-59)
*Bradyrhizobium* sp. (Arachis) (II-60)
*Bradyrhizobium* sp. (Vigna) (II-61)
*Bradyrhizobium elkanii* (II-62)
*Bradyrhizobium liaoningense* (II-63)
*Bradyrhizobium lupini* (II-64)
*Delftia acidovorans* (II-65)
*Glomus intraradices* (II-66)
*Mesorhizobium ciceri* (II-67)
*Mesorhizobium huakii* (II-68)
*Mesorhizobium loti* (II-69)
*Rhizobium leguminosarum* bv. Trifolii (II-70)
*Rhizobium tropici* (II-71)
*Bacillus altitudinis* (II-72)
*Bacillus amyloliquefaciens* (II-73)
*Bacillus megaterium* (II-74)
*Bacillus mycoides* (II-75)
*Bacillus subtilis* (II-76)
*Burkholderia* sp. (II-77)
*Coniothyrium minitans* (II-78)
*Paecilomyces lilacinus* (II-79)
*Paenibacillus alvei* (II-80)
*Paenibacillus popilliae* (II-81)
*Pasteuria nishizawae* (II-82)
*Pasteuria usgae* (II-83)
*Pseudomonas chloraphis* (II-84)
*Pseudomonas fluorescens* (II-85)
*Pseudomonas putida* (II-86)
abscisic acid (II-87)
harpin (alpha-beta) (II-88)
cis-jasmone (II-89)
methyl jasmonate (II-90)

According to still a further embodiment of the invention, the biopesticide component II is selected from (II-27), (II-29), (II-30), (II-44), (II-48), (II-50), (II-52), (II-62), (II-73), (II-74), (II-76), (II-77), (II-78), (II-79), (II-80), (II-82), (II-88), (II-89) and (II-90).

According to still a further embodiment of the invention, the biopesticide component II is selected from:

*Azospirillum amazonense* SpY2 (II-91)
*Azospirillum brasilense* AZ39 also called Az 39 (II-92)
*Azospirillum brasilense* Cd (II-93)
*Azospirillum brasilense* Sp 245 (II-94)
*Azospirillum brasilense* Ab-V5 (II-95)
*Azospirillum brasilense* Ab-V6 (II-96)
*Azospirillum brasilense* XOH (II-97)
*Azospirillum lipoferunn* Sp31 (II-98)
*Bradyrhizobium elkanii* SEMIA 5019 also called 29W (II-99)
*Bradyrhizobium elkanii* SEMIA 587 (II-100)
*Bradyrhizobium elkanii* U-1301 (II-101)
*Bradyrhizobium elkanii* U-1302 (II-102)
*Bradyrhizobium elkanii* USDA 3254 (II-103)
*Bradyrhizobium elkanii* USDA 76 (II-104)
*Bradyrhizobium elkanii* USDA 94 (II-105)
*Bradyrhizobium japonicum* 532c (II-106)
*Bradyrhizobium japonicum* E-109 (II-107)
*Bradyrhizobium japonicum* G49 (II-108)
*Bradyrhizobium japonicum* SEMIA 5079 (II-109)
*Bradyrhizobium japonicum* SEMIA 5080 (II-110)
*Bradyrhizobium japonicum* SEMIA 566 (II-111)
*Bradyrhizobium japonicum* SEMIA 586 (II-112)
*Bradyrhizobium japonicum* TA-11 (TA11 NOD+) (II-113)
*Bradyrhizobium japonicum* USDA 110 (II-114)
*Bradyrhizobium japonicum* USDA 121 (II-115)
*Bradyrhizobium japonicum* USDA 3 (II-116)
*Bradyrhizobium japonicum* USDA 31 (II-117)
*Bradyrhizobium japonicum* USDA 76 (II-118)
*Bradyrhizobium* sp. (Arachis) CB1015 (II-119)
*Bradyrhizobium* sp. (Arachis) SEMIA 6144 (II-120)
*Bradyrhizobium* sp. (Arachis) SEMIA 6462 (II-121)
*Bradyrhizobium* sp. (Arachis) SEMIA 6464 (II-122)
*Bradyrhizobium* sp. (Vigna) PNL1 (II-123)
*Mesorhizobium* sp. WSM1497 (II-124)
*Rhizobium leguminosarum* bv. phaseoli RG-B10 (II-125)
*Rhizobium leguminosarum* bv. phaseoli (II-126)
*Rhizobium leguminosarum* bv. trifolii 095 (II-127)
*Rhizobium leguminosarum* bv. trifolii CB782 (II-128)
*Rhizobium leguminosarum* bv. trifolii CC1099 (II-129)
*Rhizobium leguminosarum* bv. trifolii CC275e (II-130)
*Rhizobium leguminosarum* bv. trifolii CC283b (II-131)
*Rhizobium leguminosarum* bv. trifolii RP113-7 (II-132)
*Rhizobium leguminosarum* bv. trifolii TA1 (II-133)
*Rhizobium leguminosarum* bv. trifolii WSM1325 (II-134)
*Rhizobium leguminosarum* bv. trifolii WSM2304 (II-135)
*Rhizobium leguminosarum* bv. viciae P1NP3Cst also referred to as 1435 (II-136)
*Rhizobium leguminosarum* bv. viciae RG-P2 also called P2 (II-137)
*Rhizobium leguminosarum* bv. viciae SU303 (II-138)
*Rhizobium leguminosarum* bv. viciae WSM1455 (II-140)
*Rhizobium tropici* CC511 (II-141)
*Rhizobium tropici* CIAT 899 (II-142)
*Rhizobium tropici* H12 (II-143)
*Rhizobium tropici* PRF 81 (II-144)
*Sinorhizobium meliloti* NRG185 (II-145)
*Sinorhizobium meliloti* RCR2011 also called 2011 or SU47 (II-146)
*Sinorhizobium meliloti* RRI128 (II-147)
*Bacillus altitudinis* 41KF2b (II-148)
*Bacillus amyloliquefaciens* AP-136 (II-149)
*Bacillus amyloliquefaciens* AP-188 (II-150)
*Bacillus amyloliquefaciens* AP-218 (II-151)
*Bacillus amyloliquefaciens* AP-219 (II-152)
*Bacillus amyloliquefaciens* AP-295 (II-153)
*Bacillus amyloliquefaciens* ssp. plantarum D747 (II-154)
*Bacillus amyloliquefaciens* ssp. plantarum FZB24 also called SB3615 (II-155)
*Bacillus amyloliquefaciens* ssp. plantarum FZB42 (II-156)
*Bacillus amyloliquefaciens* ssp. plantarum GB03 also called GBO3 formerly *B. subtilis* (II-157)
*Bacillus amyloliquefaciens* ssp. plantarum MBI600 also referred to as 1430, formerly *B. subtilis* (II-158)
*Bacillus amyloliquefaciens* ssp. plantarum QST-713, formerly *B. subtilis* (II-159)
*Bacillus amyloliquefaciens* ssp. plantarum TJ1000, also called 1BE (II-160)
*Bacillus firmus* CNCM I-1582 (II-161)
*Bacillus megaterium* H491 (II-162)
*Bacillus megaterium* J142 (II-163)
*Bacillus megaterium* M018 (II-164)
*Bacillus mojavensis* AP-209 (II-165)
*Bacillus mojavensis* SR11 (II-166)
*Bacillus mycoides* AQ726 (II-167)
*Bacillus mycoides* J also called BmJ (II-168)
*Bacillus pumilus* GB34 (II-169)
*Bacillus pumilus* GHA 180 (II-170)
*Bacillus pumilus* INR-7 otherwise referred to as BU F22 and BU-F33 (II-171)
*Bacillus pumilus* KFP9F (II-172)
*Bacillus pumilus* QST 2808 (II-173)
*Bacillus simplex* ABU 288 (II-174)
*Bacillus subtilis* CX-9060 (II-175)
*Bacillus subtilis* FB17 (II-176)
*Bacillus subtilis* GB07 (II-177)
*Burkholderia* sp. A396 (II-178)
*Coniothyrium minitans* CON/M/91-08 (II-179)
*Paecilomyces lilacinus* 251 (II-180)
*Paecilomyces lilacinus* BCP2 (II-181)
*Paenibacillus alvei* NAS6G6 (II-182)
*Paenibacillus polymyxa* PKB1 (II-183)
*Paenibacilllus popilliae* 14F-D80 also called K14F-0080 (II-184)
*Paenibacilllus popilliae* KLN 3 (II-185)
*Pasteuria nishizawae* Pn1 (II-186)
*Pasteuria* sp, Ph3 (II-187)
*Pasteuria* sp. Pr3 (II-188)
*Pasteuria* sp. ATCC PTA-9643(II-189)
*Pasteuria usgae* BL1 (II-190)
*Penicillium bilaiae* (also called *P. bilaii*) NRRL 50162 (II-191)
*Penicillium bilaiae* (also called *P. bilaii*)

-continued

NRRL 50169 (II-192)
*Penicillium bilaiae* (also called *P. bilaii*)
ATCC 18309 (=ATCC 74319) (II-193)
*Penicillium bilaiae* (also called *P. bilaii*)
ATCC 20851 (II-194)
*Penicillium bilaiae* (also called *P. bilaii*)
ATCC 22348 (=ATCC 74318) (II-195)
*Pseudomonas fluorescens* A506 (II-196)
*Pseudomonas fluorescens* ATCC 13525 (II-197)
*Pseudomonas fluorescens* CHA0 (II-198)
*Pseudomonas fluorescens* CL 145A (II-199)
*Pseudomonas fluorescens* NCIB 12089 (II-200)
*Pseudomonas fluorescens* Pf-5 (II-201)
*Pseudomonas fluorescens* WCS374 (II-202)
*Pseudomonas putida* ATCC 202153 (II-203)

According to still a further embodiment of the invention, the biopesticide component II is selected from (II-94), (II-95), (II-96), (II-99), (II-100), (II-106), (II-107), (II-109), (II-110), (II-154), (II-155), (II-156), (II-158), (II-159), (II-160), (II-161), (II-170), (II-171), (II-173), (II-174), (II-176), (II-178), (II-179), (II-180), (II-182), (II-186), (II-193), (II-194) and (II-195).

Consequently, particularly preferred two-component compositions are compiled in Table B, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE B

Two-component compositions comprising one component I and one component II, in particular binary compositions containing the respective component I and II as only active ingredients.

| composition | I | II |
| --- | --- | --- |
| B-1 | I-1 | II-27 |
| B-2 | I-1 | II-28 |
| B-3 | I-1 | II-29 |
| B-4 | I-1 | II-30 |
| B-5 | I-1 | II-31 |
| B-6 | I-1 | II-32 |
| B-7 | I-1 | II-33 |
| B-8 | I-1 | II-34 |
| B-9 | I-1 | II-35 |
| B-10 | I-1 | II-36 |
| B-11 | I-1 | II-37 |
| B-12 | I-1 | II-38 |
| B-13 | I-1 | II-39 |
| B-14 | I-1 | II-40 |
| B-15 | I-1 | II-41 |
| B-16 | I-1 | II-42 |
| B-17 | I-1 | II-43 |
| B-18 | I-1 | II-44 |
| B-19 | I-1 | II-45 |
| B-20 | I-1 | II-46 |
| B-21 | I-1 | II-47 |
| B-22 | I-1 | II-48 |
| B-23 | I-1 | II-49 |
| B-24 | I-1 | II-50 |
| B-25 | I-1 | II-51 |
| B-26 | I-1 | II-52 |
| B-27 | I-1 | II-53 |
| B-28 | I-1 | II-54 |
| B-29 | I-1 | II-55 |
| B-30 | I-2 | II-27 |
| B-31 | I-2 | II-28 |
| B-32 | I-2 | II-29 |
| B-33 | I-2 | II-30 |
| B-34 | I-2 | II-31 |
| B-35 | I-2 | II-32 |
| B-36 | I-2 | II-33 |
| B-37 | I-2 | II-34 |
| B-38 | I-2 | II-35 |
| B-39 | I-2 | II-36 |
| B-40 | I-2 | II-37 |
| B-41 | I-2 | II-38 |
| B-42 | I-2 | II-39 |
| B-43 | I-2 | II-40 |
| B-44 | I-2 | II-41 |
| B-45 | I-2 | II-42 |
| B-46 | I-2 | II-43 |
| B-47 | I-2 | II-44 |
| B-48 | I-2 | II-45 |
| B-49 | I-2 | II-46 |
| B-50 | I-2 | II-47 |
| B-51 | I-2 | II-48 |
| B-52 | I-2 | II-49 |
| B-53 | I-2 | II-50 |
| B-54 | I-2 | II-51 |
| B-55 | I-2 | II-52 |
| B-56 | I-2 | II-53 |
| B-57 | I-2 | II-54 |
| B-58 | I-2 | II-55 |
| B-59 | I-3 | II-27 |
| B-60 | I-3 | II-28 |
| B-61 | I-3 | II-29 |
| B-62 | I-3 | II-30 |
| B-63 | I-3 | II-31 |
| B-64 | I-3 | II-32 |
| B-65 | I-3 | II-33 |
| B-66 | I-3 | II-34 |
| B-67 | I-3 | II-35 |
| B-68 | I-3 | II-36 |
| B-69 | I-3 | II-37 |
| B-70 | I-3 | II-38 |
| B-71 | I-3 | II-39 |
| B-72 | I-3 | II-40 |
| B-73 | I-3 | II-41 |
| B-74 | I-3 | II-42 |
| B-75 | I-3 | II-43 |
| B-76 | I-3 | II-44 |
| B-77 | I-3 | II-45 |
| B-78 | I-3 | II-46 |
| B-79 | I-3 | II-47 |
| B-80 | I-3 | II-48 |
| B-81 | I-3 | II-49 |
| B-82 | I-3 | II-50 |
| B-83 | I-3 | II-51 |
| B-84 | I-3 | II-52 |
| B-85 | I-3 | II-53 |
| B-86 | I-3 | II-54 |
| B-87 | I-3 | II-55 |
| B-88 | I-4 | II-27 |
| B-89 | I-4 | II-28 |
| B-90 | I-4 | II-29 |
| B-91 | I-4 | II-30 |
| B-92 | I-4 | II-31 |
| B-93 | I-4 | II-32 |
| B-94 | I-4 | II-33 |
| B-95 | I-4 | II-34 |
| B-96 | I-4 | II-35 |
| B-97 | I-4 | II-36 |
| B-98 | I-4 | II-37 |
| B-99 | I-4 | II-38 |
| B-100 | I-4 | II-39 |

TABLE B-continued

Two-component compositions comprising one component I and one component II, in particular binary compositions containing the respective component I and II as only active ingredients.

| composition | I | II |
|---|---|---|
| B-101 | I-4 | II-40 |
| B-102 | I-4 | II-41 |
| B-103 | I-4 | II-42 |
| B-104 | I-4 | II-43 |
| B-105 | I-4 | II-44 |
| B-106 | I-4 | II-45 |
| B-107 | I-4 | II-46 |
| B-108 | I-4 | II-47 |
| B-109 | I-4 | II-48 |
| B-110 | I-4 | II-49 |
| B-111 | I-4 | II-50 |
| B-112 | I-4 | II-51 |
| B-113 | I-4 | II-52 |
| B-114 | I-4 | II-53 |
| B-115 | I-4 | II-54 |
| B-116 | I-4 | II-55 |
| B-117 | I-5 | II-27 |
| B-118 | I-5 | II-28 |
| B-119 | I-5 | II-29 |
| B-120 | I-5 | II-30 |
| B-121 | I-5 | II-31 |
| B-122 | I-5 | II-32 |
| B-123 | I-5 | II-33 |
| B-124 | I-5 | II-34 |
| B-125 | I-5 | II-35 |
| B-126 | I-5 | II-36 |
| B-127 | I-5 | II-37 |
| B-128 | I-5 | II-38 |
| B-129 | I-5 | II-39 |
| B-130 | I-5 | II-40 |
| B-131 | I-5 | II-41 |
| B-132 | I-5 | II-42 |
| B-133 | I-5 | II-43 |
| B-134 | I-5 | II-44 |
| B-135 | I-5 | II-45 |
| B-136 | I-5 | II-46 |
| B-137 | I-5 | II-47 |
| B-138 | I-5 | II-48 |
| B-139 | I-5 | II-49 |
| B-140 | I-5 | II-50 |
| B-141 | I-5 | II-51 |
| B-142 | I-5 | II-52 |
| B-143 | I-5 | II-53 |
| B-144 | I-5 | II-54 |
| B-145 | I-5 | II-55 |
| B-146 | I-6 | II-27 |
| B-147 | I-6 | II-28 |
| B-148 | I-6 | II-29 |
| B-149 | I-6 | II-30 |
| B-150 | I-6 | II-31 |
| B-151 | I-6 | II-32 |
| B-152 | I-6 | II-33 |
| B-153 | I-6 | II-34 |
| B-154 | I-6 | II-35 |
| B-155 | I-6 | II-36 |
| B-156 | I-6 | II-37 |
| B-157 | I-6 | II-38 |
| B-158 | I-6 | II-39 |
| B-159 | I-6 | II-40 |
| B-160 | I-6 | II-41 |
| B-161 | I-6 | II-42 |
| B-162 | I-6 | II-43 |
| B-163 | I-6 | II-44 |
| B-164 | I-6 | II-45 |
| B-165 | I-6 | II-46 |
| B-166 | I-6 | II-47 |
| B-167 | I-6 | II-48 |
| B-168 | I-6 | II-49 |
| B-169 | I-6 | II-50 |
| B-170 | I-6 | II-51 |
| B-171 | I-6 | II-52 |
| B-172 | I-6 | II-53 |
| B-173 | I-6 | II-54 |
| B-174 | I-6 | II-55 |
| B-175 | I-7 | II-27 |
| B-176 | I-7 | II-28 |
| B-177 | I-7 | II-29 |
| B-178 | I-7 | II-30 |
| B-179 | I-7 | II-31 |
| B-180 | I-7 | II-32 |
| B-181 | I-7 | II-33 |
| B-182 | I-7 | II-34 |
| B-183 | I-7 | II-35 |
| B-184 | I-7 | II-36 |
| B-185 | I-7 | II-37 |
| B-186 | I-7 | II-38 |
| B-187 | I-7 | II-39 |
| B-188 | I-7 | II-40 |
| B-189 | I-7 | II-41 |
| B-190 | I-7 | II-42 |
| B-191 | I-7 | II-43 |
| B-192 | I-7 | II-44 |
| B-193 | I-7 | II-45 |
| B-194 | I-7 | II-46 |
| B-195 | I-7 | II-47 |
| B-196 | I-7 | II-48 |
| B-197 | I-7 | II-49 |
| B-198 | I-7 | II-50 |
| B-199 | I-7 | II-51 |
| B-200 | I-7 | II-52 |
| B-201 | I-7 | II-53 |
| B-202 | I-7 | II-54 |
| B-203 | I-7 | II-55 |
| B-204 | I-8 | II-27 |
| B-205 | I-8 | II-28 |
| B-206 | I-8 | II-29 |
| B-207 | I-8 | II-30 |
| B-208 | I-8 | II-31 |
| B-209 | I-8 | II-32 |
| B-210 | I-8 | II-33 |
| B-211 | I-8 | II-34 |
| B-212 | I-8 | II-35 |
| B-213 | I-8 | II-36 |
| B-214 | I-8 | II-37 |
| B-215 | I-8 | II-38 |
| B-216 | I-8 | II-39 |
| B-217 | I-8 | II-40 |
| B-218 | I-8 | II-41 |
| B-219 | I-8 | II-42 |
| B-220 | I-8 | II-43 |
| B-221 | I-8 | II-44 |
| B-222 | I-8 | II-45 |
| B-223 | I-8 | II-46 |
| B-224 | I-8 | II-47 |
| B-225 | I-8 | II-48 |
| B-226 | I-8 | II-49 |
| B-227 | I-8 | II-50 |
| B-228 | I-8 | II-51 |
| B-229 | I-8 | II-52 |
| B-230 | I-8 | II-53 |
| B-231 | I-8 | II-54 |
| B-232 | I-8 | II-55 |
| B-233 | I-9 | II-27 |
| B-234 | I-9 | II-28 |
| B-235 | I-9 | II-29 |
| B-236 | I-9 | II-30 |
| B-237 | I-9 | II-31 |
| B-238 | I-9 | II-32 |
| B-239 | I-9 | II-33 |
| B-240 | I-9 | II-34 |
| B-241 | I-9 | II-35 |
| B-242 | I-9 | II-36 |
| B-243 | I-9 | II-37 |
| B-244 | I-9 | II-38 |
| B-245 | I-9 | II-39 |
| B-246 | I-9 | II-40 |
| B-247 | I-9 | II-41 |
| B-248 | I-9 | II-42 |

TABLE B-continued

Two-component compositions comprising one component I and one component II, in particular binary compositions containing the respective component I and II as only active ingredients.

| composition | I | II |
|---|---|---|
| B-249 | I-9 | II-43 |
| B-250 | I-9 | II-44 |
| B-251 | I-9 | II-45 |
| B-252 | I-9 | II-46 |
| B-253 | I-9 | II-47 |
| B-254 | I-9 | II-48 |
| B-255 | I-9 | II-49 |
| B-256 | I-9 | II-50 |
| B-257 | I-9 | II-51 |
| B-258 | I-9 | II-52 |
| B-259 | I-9 | II-53 |
| B-260 | I-9 | II-54 |
| B-261 | I-9 | II-55 |
| B-262 | I-10 | II-27 |
| B-263 | I-10 | II-28 |
| B-264 | I-10 | II-29 |
| B-265 | I-10 | II-30 |
| B-266 | I-10 | II-31 |
| B-267 | I-10 | II-32 |
| B-268 | I-10 | II-33 |
| B-269 | I-10 | II-34 |
| B-270 | I-10 | II-35 |
| B-271 | I-10 | II-36 |
| B-272 | I-10 | II-37 |
| B-273 | I-10 | II-38 |
| B-274 | I-10 | II-39 |
| B-275 | I-10 | II-40 |
| B-276 | I-10 | II-41 |
| B-277 | I-10 | II-42 |
| B-278 | I-10 | II-43 |
| B-279 | I-10 | II-44 |
| B-280 | I-10 | II-45 |
| B-281 | I-10 | II-46 |
| B-282 | I-10 | II-47 |
| B-283 | I-10 | II-48 |
| B-284 | I-10 | II-49 |
| B-285 | I-10 | II-50 |
| B-286 | I-10 | II-51 |
| B-287 | I-10 | II-52 |
| B-288 | I-10 | II-53 |
| B-289 | I-10 | II-54 |
| B-290 | I-10 | II-55 |
| B-291 | I-11 | II-27 |
| B-292 | I-11 | II-28 |
| B-293 | I-11 | II-29 |
| B-294 | I-11 | II-30 |
| B-295 | I-11 | II-31 |
| B-296 | I-11 | II-32 |
| B-297 | I-11 | II-33 |
| B-298 | I-11 | II-34 |
| B-299 | I-11 | II-35 |
| B-300 | I-11 | II-36 |
| B-301 | I-11 | II-37 |
| B-302 | I-11 | II-38 |
| B-303 | I-11 | II-39 |
| B-304 | I-11 | II-40 |
| B-305 | I-11 | II-41 |
| B-306 | I-11 | II-42 |
| B-307 | I-11 | II-43 |
| B-308 | I-11 | II-44 |
| B-309 | I-11 | II-45 |
| B-310 | I-11 | II-46 |
| B-311 | I-11 | II-47 |
| B-312 | I-11 | II-48 |
| B-313 | I-11 | II-49 |
| B-314 | I-11 | II-50 |
| B-315 | I-11 | II-51 |
| B-316 | I-11 | II-52 |
| B-317 | I-11 | II-53 |
| B-318 | I-11 | II-54 |
| B-319 | I-11 | II-55 |
| B-320 | I-12 | II-27 |
| B-321 | I-12 | II-28 |
| B-322 | I-12 | II-29 |
| B-323 | I-12 | II-30 |
| B-324 | I-12 | II-31 |
| B-325 | I-12 | II-32 |
| B-326 | I-12 | II-33 |
| B-327 | I-12 | II-34 |
| B-328 | I-12 | II-35 |
| B-329 | I-12 | II-36 |
| B-330 | I-12 | II-37 |
| B-331 | I-12 | II-38 |
| B-332 | I-12 | II-39 |
| B-333 | I-12 | II-40 |
| B-334 | I-12 | II-41 |
| B-335 | I-12 | II-42 |
| B-336 | I-12 | II-43 |
| B-337 | I-12 | II-44 |
| B-338 | I-12 | II-45 |
| B-339 | I-12 | II-46 |
| B-340 | I-12 | II-47 |
| B-341 | I-12 | II-48 |
| B-342 | I-12 | II-49 |
| B-343 | I-12 | II-50 |
| B-344 | I-12 | II-51 |
| B-345 | I-12 | II-52 |
| B-346 | I-12 | II-53 |
| B-347 | I-12 | II-54 |
| B-348 | I-12 | II-55 |
| B-349 | I-13 | II-27 |
| B-350 | I-13 | II-28 |
| B-351 | I-13 | II-29 |
| B-352 | I-13 | II-30 |
| B-353 | I-13 | II-31 |
| B-354 | I-13 | II-32 |
| B-355 | I-13 | II-33 |
| B-356 | I-13 | II-34 |
| B-357 | I-13 | II-35 |
| B-358 | I-13 | II-36 |
| B-359 | I-13 | II-37 |
| B-360 | I-13 | II-38 |
| B-361 | I-13 | II-39 |
| B-362 | I-13 | II-40 |
| B-363 | I-13 | II-41 |
| B-364 | I-13 | II-42 |
| B-365 | I-13 | II-43 |
| B-366 | I-13 | II-44 |
| B-367 | I-13 | II-45 |
| B-368 | I-13 | II-46 |
| B-369 | I-13 | II-47 |
| B-370 | I-13 | II-48 |
| B-371 | I-13 | II-49 |
| B-372 | I-13 | II-50 |
| B-373 | I-13 | II-51 |
| B-374 | I-13 | II-52 |
| B-375 | I-13 | II-53 |
| B-376 | I-13 | II-54 |
| B-377 | I-13 | II-55 |
| B-378 | I-14 | II-27 |
| B-379 | I-14 | II-28 |
| B-380 | I-14 | II-29 |
| B-381 | I-14 | II-30 |
| B-382 | I-14 | II-31 |
| B-383 | I-14 | II-32 |
| B-384 | I-14 | II-33 |
| B-385 | I-14 | II-34 |
| B-386 | I-14 | II-35 |
| B-387 | I-14 | II-36 |
| B-388 | I-14 | II-37 |
| B-389 | I-14 | II-38 |
| B-390 | I-14 | II-39 |
| B-391 | I-14 | II-40 |
| B-392 | I-14 | II-41 |
| B-393 | I-14 | II-42 |
| B-394 | I-14 | II-43 |
| B-395 | I-14 | II-44 |
| B-396 | I-14 | II-45 |

TABLE B-continued

Two-component compositions comprising one component I and one component II, in particular binary compositions containing the respective component I and II as only active ingredients.

| composition | I | II |
|---|---|---|
| B-397 | I-14 | II-46 |
| B-398 | I-14 | II-47 |
| B-399 | I-14 | II-48 |
| B-400 | I-14 | II-49 |
| B-401 | I-14 | II-50 |
| B-402 | I-14 | II-51 |
| B-403 | I-14 | II-52 |
| B-404 | I-14 | II-53 |
| B-405 | I-14 | II-54 |
| B-406 | I-14 | II-55 |
| B-407 | I-15 | II-27 |
| B-408 | I-15 | II-28 |
| B-409 | I-15 | II-29 |
| B-410 | I-15 | II-30 |
| B-411 | I-15 | II-31 |
| B-412 | I-15 | II-32 |
| B-413 | I-15 | II-33 |
| B-414 | I-15 | II-34 |
| B-415 | I-15 | II-35 |
| B-416 | I-15 | II-36 |
| B-417 | I-15 | II-37 |
| B-418 | I-15 | II-38 |
| B-419 | I-15 | II-39 |
| B-420 | I-15 | II-40 |
| B-421 | I-15 | II-41 |
| B-422 | I-15 | II-42 |
| B-423 | I-15 | II-43 |
| B-424 | I-15 | II-44 |
| B-425 | I-15 | II-45 |
| B-426 | I-15 | II-46 |
| B-427 | I-15 | II-47 |
| B-428 | I-15 | II-48 |
| B-429 | I-15 | II-49 |
| B-430 | I-15 | II-50 |
| B-431 | I-15 | II-51 |
| B-432 | I-15 | II-52 |
| B-433 | I-15 | II-53 |
| B-434 | I-15 | II-54 |
| B-435 | I-15 | II-55 |
| B-436 | I-16 | II-27 |
| B-437 | I-16 | II-28 |
| B-438 | I-16 | II-29 |
| B-439 | I-16 | II-30 |
| B-440 | I-16 | II-31 |
| B-441 | I-16 | II-32 |
| B-442 | I-16 | II-33 |
| B-443 | I-16 | II-34 |
| B-444 | I-16 | II-35 |
| B-445 | I-16 | II-36 |
| B-446 | I-16 | II-37 |
| B-447 | I-16 | II-38 |
| B-448 | I-16 | II-39 |
| B-449 | I-16 | II-40 |
| B-450 | I-16 | II-41 |
| B-451 | I-16 | II-42 |
| B-452 | I-16 | II-43 |
| B-453 | I-16 | II-44 |
| B-454 | I-16 | II-45 |
| B-455 | I-16 | II-46 |
| B-456 | I-16 | II-47 |
| B-457 | I-16 | II-48 |
| B-458 | I-16 | II-49 |
| B-459 | I-16 | II-50 |
| B-460 | I-16 | II-51 |
| B-461 | I-16 | II-52 |
| B-462 | I-16 | II-53 |
| B-463 | I-16 | II-54 |
| B-464 | I-16 | II-55 |
| B-465 | I-17 | II-27 |
| B-466 | I-17 | II-28 |
| B-467 | I-17 | II-29 |
| B-468 | I-17 | II-30 |
| B-469 | I-17 | II-31 |
| B-470 | I-17 | II-32 |
| B-471 | I-17 | II-33 |
| B-472 | I-17 | II-34 |
| B-473 | I-17 | II-35 |
| B-474 | I-17 | II-36 |
| B-475 | I-17 | II-37 |
| B-476 | I-17 | II-38 |
| B-477 | I-17 | II-39 |
| B-478 | I-17 | II-40 |
| B-479 | I-17 | II-41 |
| B-480 | I-17 | II-42 |
| B-481 | I-17 | II-43 |
| B-482 | I-17 | II-44 |
| B-483 | I-17 | II-45 |
| B-484 | I-17 | II-46 |
| B-485 | I-17 | II-47 |
| B-486 | I-17 | II-48 |
| B-487 | I-17 | II-49 |
| B-488 | I-17 | II-50 |
| B-489 | I-17 | II-51 |
| B-490 | I-17 | II-52 |
| B-491 | I-17 | II-53 |
| B-492 | I-17 | II-54 |
| B-493 | I-17 | II-55 |
| B-494 | I-18 | II-27 |
| B-495 | I-18 | II-28 |
| B-496 | I-18 | II-29 |
| B-497 | I-18 | II-30 |
| B-498 | I-18 | II-31 |
| B-499 | I-18 | II-32 |
| B-500 | I-18 | II-33 |
| B-501 | I-18 | II-34 |
| B-502 | I-18 | II-35 |
| B-503 | I-18 | II-36 |
| B-504 | I-18 | II-37 |
| B-505 | I-18 | II-38 |
| B-506 | I-18 | II-39 |
| B-507 | I-18 | II-40 |
| B-508 | I-18 | II-41 |
| B-509 | I-18 | II-42 |
| B-510 | I-18 | II-43 |
| B-511 | I-18 | II-44 |
| B-512 | I-18 | II-45 |
| B-513 | I-18 | II-46 |
| B-514 | I-18 | II-47 |
| B-515 | I-18 | II-48 |
| B-516 | I-18 | II-49 |
| B-517 | I-18 | II-50 |
| B-518 | I-18 | II-51 |
| B-519 | I-18 | II-52 |
| B-520 | I-18 | II-53 |
| B-521 | I-18 | II-54 |
| B-522 | I-18 | II-55 |
| B-523 | I-19 | II-27 |
| B-524 | I-19 | II-28 |
| B-525 | I-19 | II-29 |
| B-526 | I-19 | II-30 |
| B-527 | I-19 | II-31 |
| B-528 | I-19 | II-32 |
| B-529 | I-19 | II-33 |
| B-530 | I-19 | II-34 |
| B-531 | I-19 | II-35 |
| B-532 | I-19 | II-36 |
| B-533 | I-19 | II-37 |
| B-534 | I-19 | II-38 |
| B-535 | I-19 | II-39 |
| B-536 | I-19 | II-40 |
| B-537 | I-19 | II-41 |
| B-538 | I-19 | II-42 |
| B-539 | I-19 | II-43 |
| B-540 | I-19 | II-44 |
| B-541 | I-19 | II-45 |
| B-542 | I-19 | II-46 |
| B-543 | I-19 | II-47 |
| B-544 | I-19 | II-48 |

TABLE B-continued

Two-component compositions comprising one component I and one component II, in particular binary compositions containing the respective component I and II as only active ingredients.

| composition | I | II |
|---|---|---|
| B-545 | I-19 | II-49 |
| B-546 | I-19 | II-50 |
| B-547 | I-19 | II-51 |
| B-548 | I-19 | II-52 |
| B-549 | I-19 | II-53 |
| B-550 | I-19 | II-54 |
| B-551 | I-19 | II-55 |
| B-552 | I-20 | II-27 |
| B-553 | I-20 | II-28 |
| B-554 | I-20 | II-29 |
| B-555 | I-20 | II-30 |
| B-556 | I-20 | II-31 |
| B-557 | I-20 | II-32 |
| B-558 | I-20 | II-33 |
| B-559 | I-20 | II-34 |
| B-560 | I-20 | II-35 |
| B-561 | I-20 | II-36 |
| B-562 | I-20 | II-37 |
| B-563 | I-20 | II-38 |
| B-564 | I-20 | II-39 |
| B-565 | I-20 | II-40 |
| B-566 | I-20 | II-41 |
| B-567 | I-20 | II-42 |
| B-568 | I-20 | II-43 |
| B-569 | I-20 | II-44 |
| B-570 | I-20 | II-45 |
| B-571 | I-20 | II-46 |
| B-572 | I-20 | II-47 |
| B-573 | I-20 | II-48 |
| B-574 | I-20 | II-49 |
| B-575 | I-20 | II-50 |
| B-576 | I-20 | II-51 |
| B-577 | I-20 | II-52 |
| B-578 | I-20 | II-53 |
| B-579 | I-20 | II-54 |
| B-580 | I-20 | II-55 |
| B-581 | I-21 | II-27 |
| B-582 | I-21 | II-28 |
| B-583 | I-21 | II-29 |
| B-584 | I-21 | II-30 |
| B-585 | I-21 | II-31 |
| B-586 | I-21 | II-32 |
| B-587 | I-21 | II-33 |
| B-588 | I-21 | II-34 |
| B-589 | I-21 | II-35 |
| B-590 | I-21 | II-36 |
| B-591 | I-21 | II-37 |
| B-592 | I-21 | II-38 |
| B-593 | I-21 | II-39 |
| B-594 | I-21 | II-40 |
| B-595 | I-21 | II-41 |
| B-596 | I-21 | II-42 |
| B-597 | I-21 | II-43 |
| B-598 | I-21 | II-44 |
| B-599 | I-21 | II-45 |
| B-600 | I-21 | II-46 |
| B-601 | I-21 | II-47 |
| B-602 | I-21 | II-48 |
| B-603 | I-21 | II-49 |
| B-604 | I-21 | II-50 |
| B-605 | I-21 | II-51 |
| B-606 | I-21 | II-52 |
| B-607 | I-21 | II-53 |
| B-608 | I-21 | II-54 |
| B-609 | I-21 | II-55 |
| B-610 | I-22 | II-27 |
| B-611 | I-22 | II-28 |
| B-612 | I-22 | II-29 |
| B-613 | I-22 | II-30 |
| B-614 | I-22 | II-31 |
| B-615 | I-22 | II-32 |
| B-616 | I-22 | II-33 |
| B-617 | I-22 | II-34 |
| B-618 | I-22 | II-35 |
| B-619 | I-22 | II-36 |
| B-620 | I-22 | II-37 |
| B-621 | I-22 | II-38 |
| B-622 | I-22 | II-39 |
| B-623 | I-22 | II-40 |
| B-624 | I-22 | II-41 |
| B-625 | I-22 | II-42 |
| B-626 | I-22 | II-43 |
| B-627 | I-22 | II-44 |
| B-628 | I-22 | II-45 |
| B-629 | I-22 | II-46 |
| B-630 | I-22 | II-47 |
| B-631 | I-22 | II-48 |
| B-632 | I-22 | II-49 |
| B-633 | I-22 | II-50 |
| B-634 | I-22 | II-51 |
| B-635 | I-22 | II-52 |
| B-636 | I-22 | II-53 |
| B-637 | I-22 | II-54 |
| B-638 | I-22 | II-55 |
| B-639 | I-23 | II-27 |
| B-640 | I-23 | II-28 |
| B-641 | I-23 | II-29 |
| B-642 | I-23 | II-30 |
| B-643 | I-23 | II-31 |
| B-644 | I-23 | II-32 |
| B-645 | I-23 | II-33 |
| B-646 | I-23 | II-34 |
| B-647 | I-23 | II-35 |
| B-648 | I-23 | II-36 |
| B-649 | I-23 | II-37 |
| B-650 | I-23 | II-38 |
| B-651 | I-23 | II-39 |
| B-652 | I-23 | II-40 |
| B-653 | I-23 | II-41 |
| B-654 | I-23 | II-42 |
| B-655 | I-23 | II-43 |
| B-656 | I-23 | II-44 |
| B-657 | I-23 | II-45 |
| B-658 | I-23 | II-46 |
| B-659 | I-23 | II-47 |
| B-660 | I-23 | II-48 |
| B-661 | I-23 | II-49 |
| B-662 | I-23 | II-50 |
| B-663 | I-23 | II-51 |
| B-664 | I-23 | II-52 |
| B-665 | I-23 | II-53 |
| B-666 | I-23 | II-54 |
| B-667 | I-23 | II-55 |
| B-668 | I-24 | II-27 |
| B-669 | I-24 | II-28 |
| B-670 | I-24 | II-29 |
| B-671 | I-24 | II-30 |
| B-672 | I-24 | II-31 |
| B-673 | I-24 | II-32 |
| B-674 | I-24 | II-33 |
| B-675 | I-24 | II-34 |
| B-676 | I-24 | II-35 |
| B-677 | I-24 | II-36 |
| B-678 | I-24 | II-37 |
| B-679 | I-24 | II-38 |
| B-680 | I-24 | II-39 |
| B-681 | I-24 | II-40 |
| B-682 | I-24 | II-41 |
| B-683 | I-24 | II-42 |
| B-684 | I-24 | II-43 |
| B-685 | I-24 | II-44 |
| B-686 | I-24 | II-45 |
| B-687 | I-24 | II-46 |
| B-688 | I-24 | II-47 |
| B-689 | I-24 | II-48 |
| B-690 | I-24 | II-49 |
| B-691 | I-24 | II-50 |
| B-692 | I-24 | II-51 |

TABLE B-continued

Two-component compositions comprising one component I and one component II, in particular binary compositions containing the respective component I and II as only active ingredients.

| composition | I | II |
|---|---|---|
| B-693 | I-24 | II-52 |
| B-694 | I-24 | II-53 |
| B-695 | I-24 | II-54 |
| B-696 | I-24 | II-55 |
| B-697 | I-25 | II-27 |
| B-698 | I-25 | II-28 |
| B-699 | I-25 | II-29 |
| B-700 | I-25 | II-30 |
| B-701 | I-25 | II-31 |
| B-702 | I-25 | II-32 |
| B-703 | I-25 | II-33 |
| B-704 | I-25 | II-34 |
| B-705 | I-25 | II-35 |
| B-706 | I-25 | II-36 |
| B-707 | I-25 | II-37 |
| B-708 | I-25 | II-38 |
| B-709 | I-25 | II-39 |
| B-710 | I-25 | II-40 |
| B-711 | I-25 | II-41 |
| B-712 | I-25 | II-42 |
| B-713 | I-25 | II-43 |
| B-714 | I-25 | II-44 |
| B-715 | I-25 | II-45 |
| B-716 | I-25 | II-46 |
| B-717 | I-25 | II-47 |
| B-718 | I-25 | II-48 |
| B-719 | I-25 | II-49 |
| B-720 | I-25 | II-50 |
| B-721 | I-25 | II-51 |
| B-722 | I-25 | II-52 |
| B-723 | I-25 | II-53 |
| B-724 | I-25 | II-54 |
| B-725 | I-25 | II-55 |
| B-726 | I-26 | II-27 |
| B-727 | I-26 | II-28 |
| B-728 | I-26 | II-29 |
| B-729 | I-26 | II-30 |
| B-730 | I-26 | II-31 |
| B-731 | I-26 | II-32 |
| B-732 | I-26 | II-33 |
| B-733 | I-26 | II-34 |
| B-734 | I-26 | II-35 |
| B-735 | I-26 | II-36 |
| B-736 | I-26 | II-37 |
| B-737 | I-26 | II-38 |
| B-738 | I-26 | II-39 |
| B-739 | I-26 | II-40 |
| B-740 | I-26 | II-41 |
| B-741 | I-26 | II-42 |
| B-742 | I-26 | II-43 |
| B-743 | I-26 | II-44 |
| B-744 | I-26 | II-45 |
| B-745 | I-26 | II-46 |
| B-746 | I-26 | II-47 |
| B-747 | I-26 | II-48 |
| B-748 | I-26 | II-49 |
| B-749 | I-26 | II-50 |
| B-750 | I-26 | II-51 |
| B-751 | I-26 | II-52 |
| B-752 | I-26 | II-53 |
| B-753 | I-26 | II-54 |
| B-754 | I-26 | II-55 |
| B-755 | I-27 | II-27 |
| B-756 | I-27 | II-28 |
| B-757 | I-27 | II-29 |
| B-758 | I-27 | II-30 |
| B-759 | I-27 | II-31 |
| B-760 | I-27 | II-32 |
| B-761 | I-27 | II-33 |
| B-762 | I-27 | II-34 |
| B-763 | I-27 | II-35 |
| B-764 | I-27 | II-36 |
| B-765 | I-27 | II-37 |
| B-766 | I-27 | II-38 |
| B-767 | I-27 | II-39 |
| B-768 | I-27 | II-40 |
| B-769 | I-27 | II-41 |
| B-770 | I-27 | II-42 |
| B-771 | I-27 | II-43 |
| B-772 | I-27 | II-44 |
| B-773 | I-27 | II-45 |
| B-774 | I-27 | II-46 |
| B-775 | I-27 | II-47 |
| B-776 | I-27 | II-48 |
| B-777 | I-27 | II-49 |
| B-778 | I-27 | II-50 |
| B-779 | I-27 | II-51 |
| B-780 | I-27 | II-52 |
| B-781 | I-27 | II-53 |
| B-782 | I-27 | II-54 |
| B-783 | I-27 | II-55 |
| B-784 | I-28 | II-27 |
| B-785 | I-28 | II-28 |
| B-786 | I-28 | II-29 |
| B-787 | I-28 | II-30 |
| B-788 | I-28 | II-31 |
| B-789 | I-28 | II-32 |
| B-790 | I-28 | II-33 |
| B-791 | I-28 | II-34 |
| B-792 | I-28 | II-35 |
| B-793 | I-28 | II-36 |
| B-794 | I-28 | II-37 |
| B-795 | I-28 | II-38 |
| B-796 | I-28 | II-39 |
| B-797 | I-28 | II-40 |
| B-798 | I-28 | II-41 |
| B-799 | I-28 | II-42 |
| B-800 | I-28 | II-43 |
| B-801 | I-28 | II-44 |
| B-802 | I-28 | II-45 |
| B-803 | I-28 | II-46 |
| B-804 | I-28 | II-47 |
| B-805 | I-28 | II-48 |
| B-806 | I-28 | II-49 |
| B-807 | I-28 | II-50 |
| B-808 | I-28 | II-51 |
| B-809 | I-28 | II-52 |
| B-810 | I-28 | II-53 |
| B-811 | I-28 | II-54 |
| B-812 | I-28 | II-55 |
| B-813 | I-29 | II-27 |
| B-814 | I-29 | II-28 |
| B-815 | I-29 | II-29 |
| B-816 | I-29 | II-30 |
| B-817 | I-29 | II-31 |
| B-818 | I-29 | II-32 |
| B-819 | I-29 | II-33 |
| B-820 | I-29 | II-34 |
| B-821 | I-29 | II-35 |
| B-822 | I-29 | II-36 |
| B-823 | I-29 | II-37 |
| B-824 | I-29 | II-38 |
| B-825 | I-29 | II-39 |
| B-826 | I-29 | II-40 |
| B-827 | I-29 | II-41 |
| B-828 | I-29 | II-42 |
| B-829 | I-29 | II-43 |
| B-830 | I-29 | II-44 |
| B-831 | I-29 | II-45 |
| B-832 | I-29 | II-46 |
| B-833 | I-29 | II-47 |
| B-834 | I-29 | II-48 |
| B-835 | I-29 | II-49 |
| B-836 | I-29 | II-50 |
| B-837 | I-29 | II-51 |
| B-838 | I-29 | II-52 |
| B-839 | I-29 | II-53 |
| B-840 | I-29 | II-54 |

TABLE B-continued

Two-component compositions comprising one component I and one component II, in particular binary compositions containing the respective component I and II as only active ingredients.

| composition | I | II |
|---|---|---|
| B-841 | I-29 | II-55 |
| B-842 | I-30 | II-27 |
| B-843 | I-30 | II-28 |
| B-844 | I-30 | II-29 |
| B-845 | I-30 | II-30 |
| B-846 | I-30 | II-31 |
| B-847 | I-30 | II-32 |
| B-848 | I-30 | II-33 |
| B-849 | I-30 | II-34 |
| B-850 | I-30 | II-35 |
| B-851 | I-30 | II-36 |
| B-852 | I-30 | II-37 |
| B-853 | I-30 | II-38 |
| B-854 | I-30 | II-39 |
| B-855 | I-30 | II-40 |
| B-856 | I-30 | II-41 |
| B-857 | I-30 | II-42 |
| B-858 | I-30 | II-43 |
| B-859 | I-30 | II-44 |
| B-860 | I-30 | II-45 |
| B-861 | I-30 | II-46 |
| B-862 | I-30 | II-47 |
| B-863 | I-30 | II-48 |
| B-864 | I-30 | II-49 |
| B-865 | I-30 | II-50 |
| B-866 | I-30 | II-51 |
| B-867 | I-30 | II-52 |
| B-868 | I-30 | II-53 |
| B-869 | I-30 | II-54 |
| B-870 | I-30 | II-55 |
| B-871 | I-31 | II-27 |
| B-872 | I-31 | II-28 |
| B-873 | I-31 | II-29 |
| B-874 | I-31 | II-30 |
| B-875 | I-31 | II-31 |
| B-876 | I-31 | II-32 |
| B-877 | I-31 | II-33 |
| B-878 | I-31 | II-34 |
| B-879 | I-31 | II-35 |
| B-880 | I-31 | II-36 |
| B-881 | I-31 | II-37 |
| B-882 | I-31 | II-38 |
| B-883 | I-31 | II-39 |
| B-884 | I-31 | II-40 |
| B-885 | I-31 | II-41 |
| B-886 | I-31 | II-42 |
| B-887 | I-31 | II-43 |
| B-888 | I-31 | II-44 |
| B-889 | I-31 | II-45 |
| B-890 | I-31 | II-46 |
| B-891 | I-31 | II-47 |
| B-892 | I-31 | II-48 |
| B-893 | I-31 | II-49 |
| B-894 | I-31 | II-50 |
| B-895 | I-31 | II-51 |
| B-896 | I-31 | II-52 |
| B-897 | I-31 | II-53 |
| B-898 | I-31 | II-54 |
| B-899 | I-31 | II-55 |

Further particularly preferred two-component compositions are compiled in Table B1, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE B1

Two-component compositions comprising one component I and one component II, in particular binary compositions containing the respective component I and II as only active ingredients.

| composition | I | II |
|---|---|---|
| B1-1 | I-1 | II-56 |
| B1-2 | I-1 | II-57 |
| B1-3 | I-1 | II-58 |
| B1-4 | I-1 | II-59 |
| B1-5 | I-1 | II-60 |
| B1-6 | I-1 | II-61 |
| B1-7 | I-1 | II-62 |
| B1-8 | I-1 | II-63 |
| B1-9 | I-1 | II-64 |
| B1-10 | I-1 | II-65 |
| B1-11 | I-1 | II-66 |
| B1-12 | I-1 | II-67 |
| B1-13 | I-1 | II-68 |
| B1-14 | I-1 | II-69 |
| B1-15 | I-1 | II-70 |
| B1-16 | I-1 | II-71 |
| B1-17 | I-1 | II-72 |
| B1-18 | I-1 | II-73 |
| B1-19 | I-1 | II-74 |
| B1-20 | I-1 | II-75 |
| B1-21 | I-1 | II-76 |
| B1-22 | I-1 | II-77 |
| B1-23 | I-1 | II-78 |
| B1-24 | I-1 | II-79 |
| B1-25 | I-1 | II-80 |
| B1-26 | I-1 | II-81 |
| B1-27 | I-1 | II-82 |
| B1-28 | I-1 | II-83 |
| B1-29 | I-1 | II-84 |
| B1-30 | I-1 | II-85 |
| B1-31 | I-1 | II-86 |
| B1-32 | I-1 | II-87 |
| B1-33 | I-1 | II-88 |
| B1-34 | I-1 | II-89 |
| B1-35 | I-1 | II-90 |
| B1-36 | I-2 | II-56 |
| B1-37 | I-2 | II-57 |
| B1-38 | I-2 | II-58 |
| B1-39 | I-2 | II-59 |
| B1-40 | I-2 | II-60 |
| B1-41 | I-2 | II-61 |
| B1-42 | I-2 | II-62 |
| B1-43 | I-2 | II-63 |
| B1-44 | I-2 | II-64 |
| B1-45 | I-2 | II-65 |
| B1-46 | I-2 | II-66 |
| B1-47 | I-2 | II-67 |
| B1-48 | I-2 | II-68 |
| B1-49 | I-2 | II-69 |
| B1-50 | I-2 | II-70 |
| B1-51 | I-2 | II-71 |
| B1-52 | I-2 | II-72 |
| B1-53 | I-2 | II-73 |
| B1-54 | I-2 | II-74 |
| B1-55 | I-2 | II-75 |
| B1-56 | I-2 | II-76 |
| B1-57 | I-2 | II-77 |
| B1-58 | I-2 | II-78 |
| B1-59 | I-2 | II-79 |
| B1-60 | I-2 | II-80 |
| B1-61 | I-2 | II-81 |
| B1-62 | I-2 | II-82 |
| B1-63 | I-2 | II-83 |
| B1-64 | I-2 | II-84 |
| B1-65 | I-2 | II-85 |
| B1-66 | I-2 | II-86 |
| B1-67 | I-2 | II-87 |
| B1-68 | I-2 | II-88 |
| B1-69 | I-2 | II-89 |
| B1-70 | I-2 | II-90 |
| B1-71 | I-3 | II-56 |
| B1-72 | I-3 | II-57 |
| B1-73 | I-3 | II-58 |
| B1-74 | I-3 | II-59 |

TABLE B1-continued

Two-component compositions comprising one component I and one component II, in particular binary compositions containing the respective component I and II as only active ingredients.

| composition | I | II |
|---|---|---|
| B1-75 | I-3 | II-60 |
| B1-76 | I-3 | II-61 |
| B1-77 | I-3 | II-62 |
| B1-78 | I-3 | II-63 |
| B1-79 | I-3 | II-64 |
| B1-80 | I-3 | II-65 |
| B1-81 | I-3 | II-66 |
| B1-82 | I-3 | II-67 |
| B1-83 | I-3 | II-68 |
| B1-84 | I-3 | II-69 |
| B1-85 | I-3 | II-70 |
| B1-86 | I-3 | II-71 |
| B1-87 | I-3 | II-72 |
| B1-88 | I-3 | II-73 |
| B1-89 | I-3 | II-74 |
| B1-90 | I-3 | II-75 |
| B1-91 | I-3 | II-76 |
| B1-92 | I-3 | II-77 |
| B1-93 | I-3 | II-78 |
| B1-94 | I-3 | II-79 |
| B1-95 | I-3 | II-80 |
| B1-96 | I-3 | II-81 |
| B1-97 | I-3 | II-82 |
| B1-98 | I-3 | II-83 |
| B1-99 | I-3 | II-84 |
| B1-100 | I-3 | II-85 |
| B1-101 | I-3 | II-86 |
| B1-102 | I-3 | II-87 |
| B1-103 | I-3 | II-88 |
| B1-104 | I-3 | II-89 |
| B1-105 | I-3 | II-90 |
| B1-106 | I-4 | II-56 |
| B1-107 | I-4 | II-57 |
| B1-108 | I-4 | II-58 |
| B1-109 | I-4 | II-59 |
| B1-110 | I-4 | II-60 |
| B1-111 | I-4 | II-61 |
| B1-112 | I-4 | II-62 |
| B1-113 | I-4 | II-63 |
| B1-114 | I-4 | II-64 |
| B1-115 | I-4 | II-65 |
| B1-116 | I-4 | II-66 |
| B1-117 | I-4 | II-67 |
| B1-118 | I-4 | II-68 |
| B1-119 | I-4 | II-69 |
| B1-120 | I-4 | II-70 |
| B1-121 | I-4 | II-71 |
| B1-122 | I-4 | II-72 |
| B1-123 | I-4 | II-73 |
| B1-124 | I-4 | II-74 |
| B1-125 | I-4 | II-75 |
| B1-126 | I-4 | II-76 |
| B1-127 | I-4 | II-77 |
| B1-128 | I-4 | II-78 |
| B1-129 | I-4 | II-79 |
| B1-130 | I-4 | II-80 |
| B1-131 | I-4 | II-81 |
| B1-132 | I-4 | II-82 |
| B1-133 | I-4 | II-83 |
| B1-134 | I-4 | II-84 |
| B1-135 | I-4 | II-85 |
| B1-136 | I-4 | II-86 |
| B1-137 | I-4 | II-87 |
| B1-138 | I-4 | II-88 |
| B1-139 | I-4 | II-89 |
| B1-140 | I-4 | II-90 |
| B1-141 | I-5 | II-56 |
| B1-142 | I-5 | II-57 |
| B1-143 | I-5 | II-58 |
| B1-144 | I-5 | II-59 |
| B1-145 | I-5 | II-60 |
| B1-146 | I-5 | II-61 |
| B1-147 | I-5 | II-62 |
| B1-148 | I-5 | II-63 |
| B1-149 | I-5 | II-64 |
| B1-150 | I-5 | II-65 |
| B1-151 | I-5 | II-66 |
| B1-152 | I-5 | II-67 |
| B1-153 | I-5 | II-68 |
| B1-154 | I-5 | II-69 |
| B1-155 | I-5 | II-70 |
| B1-156 | I-5 | II-71 |
| B1-157 | I-5 | II-72 |
| B1-158 | I-5 | II-73 |
| B1-159 | I-5 | II-74 |
| B1-160 | I-5 | II-75 |
| B1-161 | I-5 | II-76 |
| B1-162 | I-5 | II-77 |
| B1-163 | I-5 | II-78 |
| B1-164 | I-5 | II-79 |
| B1-165 | I-5 | II-80 |
| B1-166 | I-5 | II-81 |
| B1-167 | I-5 | II-82 |
| B1-168 | I-5 | II-83 |
| B1-169 | I-5 | II-84 |
| B1-170 | I-5 | II-85 |
| B1-171 | I-5 | II-86 |
| B1-172 | I-5 | II-87 |
| B1-173 | I-5 | II-88 |
| B1-174 | I-5 | II-89 |
| B1-175 | I-5 | II-90 |
| B1-176 | I-13 | II-56 |
| B1-177 | I-13 | II-57 |
| B1-178 | I-13 | II-58 |
| B1-179 | I-13 | II-59 |
| B1-180 | I-13 | II-60 |
| B1-181 | I-13 | II-61 |
| B1-182 | I-13 | II-62 |
| B1-183 | I-13 | II-63 |
| B1-184 | I-13 | II-64 |
| B1-185 | I-13 | II-65 |
| B1-186 | I-13 | II-66 |
| B1-187 | I-13 | II-67 |
| B1-188 | I-13 | II-68 |
| B1-189 | I-13 | II-69 |
| B1-190 | I-13 | II-70 |
| B1-191 | I-13 | II-71 |
| B1-192 | I-13 | II-72 |
| B1-193 | I-13 | II-73 |
| B1-194 | I-13 | II-74 |
| B1-195 | I-13 | II-75 |
| B1-196 | I-13 | II-76 |
| B1-197 | I-13 | II-77 |
| B1-198 | I-13 | II-78 |
| B1-199 | I-13 | II-79 |
| B1-200 | I-13 | II-80 |
| B1-201 | I-13 | II-81 |
| B1-202 | I-13 | II-82 |
| B1-203 | I-13 | II-83 |
| B1-204 | I-13 | II-84 |
| B1-205 | I-13 | II-85 |
| B1-206 | I-13 | II-86 |
| B1-207 | I-13 | II-87 |
| B1-208 | I-13 | II-88 |
| B1-209 | I-13 | II-89 |
| B1-210 | I-13 | II-90 |

Further particularly preferred two-component compositions are compiled in Table B2, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE B2

Two-component compositions comprising one component I and one component II, in particular binary compositions containing the respective component I and II as only active ingredients.

| composition | I | II |
|---|---|---|
| B2-1 | I-1 | II-91 |
| B2-2 | I-1 | II-92 |
| B2-3 | I-1 | II-93 |
| B2-4 | I-1 | II-94 |
| B2-5 | I-1 | II-95 |
| B2-6 | I-1 | II-96 |
| B2-7 | I-1 | II-97 |
| B2-8 | I-1 | II-98 |
| B2-9 | I-1 | II-99 |
| B2-10 | I-1 | II-100 |
| B2-11 | I-1 | II-101 |
| B2-12 | I-1 | II-102 |
| B2-13 | I-1 | II-103 |
| B2-14 | I-1 | II-104 |
| B2-15 | I-1 | II-105 |
| B2-16 | I-1 | II-106 |
| B2-17 | I-1 | II-107 |
| B2-18 | I-1 | II-108 |
| B2-19 | I-1 | II-109 |
| B2-20 | I-1 | II-110 |
| B2-21 | I-1 | II-111 |
| B2-22 | I-1 | II-112 |
| B2-23 | I-1 | II-113 |
| B2-24 | I-1 | II-114 |
| B2-25 | I-1 | II-115 |
| B2-26 | I-1 | II-116 |
| B2-27 | I-1 | II-117 |
| B2-28 | I-1 | II-118 |
| B2-29 | I-1 | II-119 |
| B2-30 | I-1 | II-120 |
| B2-31 | I-1 | II-121 |
| B2-32 | I-1 | II-122 |
| B2-33 | I-1 | II-123 |
| B2-34 | I-1 | II-124 |
| B2-35 | I-1 | II-125 |
| B2-36 | I-1 | II-126 |
| B2-37 | I-1 | II-127 |
| B2-38 | I-1 | II-128 |
| B2-39 | I-1 | II-129 |
| B2-40 | I-1 | II-130 |
| B2-41 | I-1 | II-131 |
| B2-42 | I-1 | II-132 |
| B2-43 | I-1 | II-133 |
| B2-44 | I-1 | II-134 |
| B2-45 | I-1 | II-135 |
| B2-46 | I-1 | II-136 |
| B2-47 | I-1 | II-137 |
| B2-48 | I-1 | II-138 |
| B2-49 | I-1 | II-140 |
| B2-50 | I-1 | II-141 |
| B2-51 | I-1 | II-142 |
| B2-52 | I-1 | II-143 |
| B2-53 | I-1 | II-144 |
| B2-54 | I-1 | II-145 |
| B2-55 | I-1 | II-146 |
| B2-56 | I-1 | II-147 |
| B2-57 | I-1 | II-148 |
| B2-58 | I-1 | II-149 |
| B2-59 | I-1 | II-150 |
| B2-60 | I-1 | II-151 |
| B2-61 | I-1 | II-152 |
| B2-62 | I-1 | II-153 |
| B2-63 | I-1 | II-154 |
| B2-64 | I-1 | II-155 |
| B2-65 | I-1 | II-156 |
| B2-66 | I-1 | II-157 |
| B2-67 | I-1 | II-158 |
| B2-68 | I-1 | II-159 |
| B2-69 | I-1 | II-160 |
| B2-70 | I-1 | II-161 |
| B2-71 | I-1 | II-162 |
| B2-72 | I-1 | II-163 |
| B2-73 | I-1 | II-164 |
| B2-74 | I-1 | II-165 |
| B2-75 | I-1 | II-166 |
| B2-76 | I-1 | II-167 |
| B2-77 | I-1 | II-168 |
| B2-78 | I-1 | II-169 |
| B2-79 | I-1 | II-170 |
| B2-80 | I-1 | II-171 |
| B2-81 | I-1 | II-172 |
| B2-82 | I-1 | II-173 |
| B2-83 | I-1 | II-174 |
| B2-84 | I-1 | II-175 |
| B2-85 | I-1 | II-176 |
| B2-86 | I-1 | II-177 |
| B2-87 | I-1 | II-178 |
| B2-88 | I-1 | II-179 |
| B2-89 | I-1 | II-180 |
| B2-90 | I-1 | II-181 |
| B2-91 | I-1 | II-182 |
| B2-92 | I-1 | II-183 |
| B2-93 | I-1 | II-184 |
| B2-94 | I-1 | II-185 |
| B2-95 | I-1 | II-186 |
| B2-96 | I-1 | II-187 |
| B2-97 | I-1 | II-188 |
| B2-98 | I-1 | II-189 |
| B2-99 | I-1 | II-190 |
| B2-100 | I-1 | II-191 |
| B2-101 | I-1 | II-192 |
| B2-102 | I-1 | II-193 |
| B2-103 | I-1 | II-194 |
| B2-104 | I-1 | II-195 |
| B2-105 | I-1 | II-196 |
| B2-106 | I-1 | II-197 |
| B2-107 | I-1 | II-198 |
| B2-108 | I-1 | II-199 |
| B2-109 | I-1 | II-200 |
| B2-110 | I-1 | II-201 |
| B2-111 | I-1 | II-202 |
| B2-112 | I-1 | II-203 |
| B2-113 | I-2 | II-91 |
| B2-114 | I-2 | II-92 |
| B2-115 | I-2 | II-93 |
| B2-116 | I-2 | II-94 |
| B2-117 | I-2 | II-95 |
| B2-118 | I-2 | II-96 |
| B2-119 | I-2 | II-97 |
| B2-120 | I-2 | II-98 |
| B2-121 | I-2 | II-99 |
| B2-122 | I-2 | II-100 |
| B2-123 | I-2 | II-101 |
| B2-124 | I-2 | II-102 |
| B2-125 | I-2 | II-103 |
| B2-126 | I-2 | II-104 |
| B2-127 | I-2 | II-105 |
| B2-128 | I-2 | II-106 |
| B2-129 | I-2 | II-107 |
| B2-130 | I-2 | II-108 |
| B2-131 | I-2 | II-109 |
| B2-132 | I-2 | II-110 |
| B2-133 | I-2 | II-111 |
| B2-134 | I-2 | II-112 |
| B2-135 | I-2 | II-113 |
| B2-136 | I-2 | II-114 |
| B2-137 | I-2 | II-115 |
| B2-138 | I-2 | II-116 |
| B2-139 | I-2 | II-117 |
| B2-140 | I-2 | II-118 |
| B2-141 | I-2 | II-119 |
| B2-142 | I-2 | II-120 |
| B2-143 | I-2 | II-121 |
| B2-144 | I-2 | II-122 |
| B2-145 | I-2 | II-123 |
| B2-146 | I-2 | II-124 |
| B2-147 | I-2 | II-125 |
| B2-148 | I-2 | II-126 |

TABLE B2-continued

Two-component compositions comprising one component I and one component II, in particular binary compositions containing the respective component I and II as only active ingredients.

| composition | I | II |
|---|---|---|
| B2-149 | I-2 | II-127 |
| B2-150 | I-2 | II-128 |
| B2-151 | I-2 | II-129 |
| B2-152 | I-2 | II-130 |
| B2-153 | I-2 | II-131 |
| B2-154 | I-2 | II-132 |
| B2-155 | I-2 | II-133 |
| B2-156 | I-2 | II-134 |
| B2-157 | I-2 | II-135 |
| B2-158 | I-2 | II-136 |
| B2-159 | I-2 | II-137 |
| B2-160 | I-2 | II-138 |
| B2-161 | I-2 | II-140 |
| B2-162 | I-2 | II-141 |
| B2-163 | I-2 | II-142 |
| B2-164 | I-2 | II-143 |
| B2-165 | I-2 | II-144 |
| B2-166 | I-2 | II-145 |
| B2-167 | I-2 | II-146 |
| B2-168 | I-2 | II-147 |
| B2-169 | I-2 | II-148 |
| B2-170 | I-2 | II-149 |
| B2-171 | I-2 | II-150 |
| B2-172 | I-2 | II-151 |
| B2-173 | I-2 | II-152 |
| B2-174 | I-2 | II-153 |
| B2-175 | I-2 | II-154 |
| B2-176 | I-2 | II-155 |
| B2-177 | I-2 | II-156 |
| B2-178 | I-2 | II-157 |
| B2-179 | I-2 | II-158 |
| B2-180 | I-2 | II-159 |
| B2-181 | I-2 | II-160 |
| B2-182 | I-2 | II-161 |
| B2-183 | I-2 | II-162 |
| B2-184 | I-2 | II-163 |
| B2-185 | I-2 | II-164 |
| B2-186 | I-2 | II-165 |
| B2-187 | I-2 | II-166 |
| B2-188 | I-2 | II-167 |
| B2-189 | I-2 | II-168 |
| B2-190 | I-2 | II-169 |
| B2-191 | I-2 | II-170 |
| B2-192 | I-2 | II-171 |
| B2-193 | I-2 | II-172 |
| B2-194 | I-2 | II-173 |
| B2-195 | I-2 | II-174 |
| B2-196 | I-2 | II-175 |
| B2-197 | I-2 | II-176 |
| B2-198 | I-2 | II-177 |
| B2-199 | I-2 | II-178 |
| B2-200 | I-2 | II-179 |
| B2-201 | I-2 | II-180 |
| B2-202 | I-2 | II-181 |
| B2-203 | I-2 | II-182 |
| B2-204 | I-2 | II-183 |
| B2-205 | I-2 | II-184 |
| B2-206 | I-2 | II-185 |
| B2-207 | I-2 | II-186 |
| B2-208 | I-2 | II-187 |
| B2-209 | I-2 | II-188 |
| B2-210 | I-2 | II-189 |
| B2-211 | I-2 | II-190 |
| B2-212 | I-2 | II-191 |
| B2-213 | I-2 | II-192 |
| B2-214 | I-2 | II-193 |
| B2-215 | I-2 | II-194 |
| B2-216 | I-2 | II-195 |
| B2-217 | I-2 | II-196 |
| B2-218 | I-2 | II-197 |
| B2-219 | I-2 | II-198 |
| B2-220 | I-2 | II-199 |
| B2-221 | I-2 | II-200 |
| B2-222 | I-2 | II-201 |
| B2-223 | I-2 | II-202 |
| B2-224 | I-2 | II-203 |
| B2-225 | I-3 | II-91 |
| B2-226 | I-3 | II-92 |
| B2-227 | I-3 | II-93 |
| B2-228 | I-3 | II-94 |
| B2-229 | I-3 | II-95 |
| B2-230 | I-3 | II-96 |
| B2-231 | I-3 | II-97 |
| B2-232 | I-3 | II-98 |
| B2-233 | I-3 | II-99 |
| B2-234 | I-3 | II-100 |
| B2-235 | I-3 | II-101 |
| B2-236 | I-3 | II-102 |
| B2-237 | I-3 | II-103 |
| B2-238 | I-3 | II-104 |
| B2-239 | I-3 | II-105 |
| B2-240 | I-3 | II-106 |
| B2-241 | I-3 | II-107 |
| B2-242 | I-3 | II-108 |
| B2-243 | I-3 | II-109 |
| B2-244 | I-3 | II-110 |
| B2-245 | I-3 | II-111 |
| B2-246 | I-3 | II-112 |
| B2-247 | I-3 | II-113 |
| B2-248 | I-3 | II-114 |
| B2-249 | I-3 | II-115 |
| B2-250 | I-3 | II-116 |
| B2-251 | I-3 | II-117 |
| B2-252 | I-3 | II-118 |
| B2-253 | I-3 | II-119 |
| B2-254 | I-3 | II-120 |
| B2-255 | I-3 | II-121 |
| B2-256 | I-3 | II-122 |
| B2-257 | I-3 | II-123 |
| B2-258 | I-3 | II-124 |
| B2-259 | I-3 | II-125 |
| B2-260 | I-3 | II-126 |
| B2-261 | I-3 | II-127 |
| B2-262 | I-3 | II-128 |
| B2-263 | I-3 | II-129 |
| B2-264 | I-3 | II-130 |
| B2-265 | I-3 | II-131 |
| B2-266 | I-3 | II-132 |
| B2-267 | I-3 | II-133 |
| B2-268 | I-3 | II-134 |
| B2-269 | I-3 | II-135 |
| B2-270 | I-3 | II-136 |
| B2-271 | I-3 | II-137 |
| B2-272 | I-3 | II-138 |
| B2-273 | I-3 | II-140 |
| B2-274 | I-3 | II-141 |
| B2-275 | I-3 | II-142 |
| B2-276 | I-3 | II-143 |
| B2-277 | I-3 | II-144 |
| B2-278 | I-3 | II-145 |
| B2-279 | I-3 | II-146 |
| B2-280 | I-3 | II-147 |
| B2-281 | I-3 | II-148 |
| B2-282 | I-3 | II-149 |
| B2-283 | I-3 | II-150 |
| B2-284 | I-3 | II-151 |
| B2-285 | I-3 | II-152 |
| B2-286 | I-3 | II-153 |
| B2-287 | I-3 | II-154 |
| B2-288 | I-3 | II-155 |
| B2-289 | I-3 | II-156 |
| B2-290 | I-3 | II-157 |
| B2-291 | I-3 | II-158 |
| B2-292 | I-3 | II-159 |
| B2-293 | I-3 | II-160 |
| B2-294 | I-3 | II-161 |
| B2-295 | I-3 | II-162 |
| B2-296 | I-3 | II-163 |

TABLE B2-continued

Two-component compositions comprising one component I and one component II, in particular binary compositions containing the respective component I and II as only active ingredients.

| composition | I | II |
|---|---|---|
| B2-297 | I-3 | II-164 |
| B2-298 | I-3 | II-165 |
| B2-299 | I-3 | II-166 |
| B2-300 | I-3 | II-167 |
| B2-301 | I-3 | II-168 |
| B2-302 | I-3 | II-169 |
| B2-303 | I-3 | II-170 |
| B2-304 | I-3 | II-171 |
| B2-305 | I-3 | II-172 |
| B2-306 | I-3 | II-173 |
| B2-307 | I-3 | II-174 |
| B2-308 | I-3 | II-175 |
| B2-309 | I-3 | II-176 |
| B2-310 | I-3 | II-177 |
| B2-311 | I-3 | II-178 |
| B2-312 | I-3 | II-179 |
| B2-313 | I-3 | II-180 |
| B2-314 | I-3 | II-181 |
| B2-315 | I-3 | II-182 |
| B2-316 | I-3 | II-183 |
| B2-317 | I-3 | II-184 |
| B2-318 | I-3 | II-185 |
| B2-319 | I-3 | II-186 |
| B2-320 | I-3 | II-187 |
| B2-321 | I-3 | II-188 |
| B2-322 | I-3 | II-189 |
| B2-323 | I-3 | II-190 |
| B2-324 | I-3 | II-191 |
| B2-325 | I-3 | II-192 |
| B2-326 | I-3 | II-193 |
| B2-327 | I-3 | II-194 |
| B2-328 | I-3 | II-195 |
| B2-329 | I-3 | II-196 |
| B2-330 | I-3 | II-197 |
| B2-331 | I-3 | II-198 |
| B2-332 | I-3 | II-199 |
| B2-333 | I-3 | II-200 |
| B2-334 | I-3 | II-201 |
| B2-335 | I-3 | II-202 |
| B2-336 | I-3 | II-203 |
| B2-337 | I-4 | II-91 |
| B2-338 | I-4 | II-92 |
| B2-339 | I-4 | II-93 |
| B2-340 | I-4 | II-94 |
| B2-341 | I-4 | II-95 |
| B2-342 | I-4 | II-96 |
| B2-343 | I-4 | II-97 |
| B2-344 | I-4 | II-98 |
| B2-345 | I-4 | II-99 |
| B2-346 | I-4 | II-100 |
| B2-347 | I-4 | II-101 |
| B2-348 | I-4 | II-102 |
| B2-349 | I-4 | II-103 |
| B2-350 | I-4 | II-104 |
| B2-351 | I-4 | II-105 |
| B2-352 | I-4 | II-106 |
| B2-353 | I-4 | II-107 |
| B2-354 | I-4 | II-108 |
| B2-355 | I-4 | II-109 |
| B2-356 | I-4 | II-110 |
| B2-357 | I-4 | II-111 |
| B2-358 | I-4 | II-112 |
| B2-359 | I-4 | II-113 |
| B2-360 | I-4 | II-114 |
| B2-361 | I-4 | II-115 |
| B2-362 | I-4 | II-116 |
| B2-363 | I-4 | II-117 |
| B2-364 | I-4 | II-118 |
| B2-365 | I-4 | II-119 |
| B2-366 | I-4 | II-120 |
| B2-367 | I-4 | II-121 |
| B2-368 | I-4 | II-122 |
| B2-369 | I-4 | II-123 |
| B2-370 | I-4 | II-124 |
| B2-371 | I-4 | II-125 |
| B2-372 | I-4 | II-126 |
| B2-373 | I-4 | II-127 |
| B2-374 | I-4 | II-128 |
| B2-375 | I-4 | II-129 |
| B2-376 | I-4 | II-130 |
| B2-377 | I-4 | II-131 |
| B2-378 | I-4 | II-132 |
| B2-379 | I-4 | II-133 |
| B2-380 | I-4 | II-134 |
| B2-381 | I-4 | II-135 |
| B2-382 | I-4 | II-136 |
| B2-383 | I-4 | II-137 |
| B2-384 | I-4 | II-138 |
| B2-385 | I-4 | II-140 |
| B2-386 | I-4 | II-141 |
| B2-387 | I-4 | II-142 |
| B2-388 | I-4 | II-143 |
| B2-389 | I-4 | II-144 |
| B2-390 | I-4 | II-145 |
| B2-391 | I-4 | II-146 |
| B2-392 | I-4 | II-147 |
| B2-393 | I-4 | II-148 |
| B2-394 | I-4 | II-149 |
| B2-395 | I-4 | II-150 |
| B2-396 | I-4 | II-151 |
| B2-397 | I-4 | II-152 |
| B2-398 | I-4 | II-153 |
| B2-399 | I-4 | II-154 |
| B2-400 | I-4 | II-155 |
| B2-401 | I-4 | II-156 |
| B2-402 | I-4 | II-157 |
| B2-403 | I-4 | II-158 |
| B2-404 | I-4 | II-159 |
| B2-405 | I-4 | II-160 |
| B2-406 | I-4 | II-161 |
| B2-407 | I-4 | II-162 |
| B2-408 | I-4 | II-163 |
| B2-409 | I-4 | II-164 |
| B2-410 | I-4 | II-165 |
| B2-411 | I-4 | II-166 |
| B2-412 | I-4 | II-167 |
| B2-413 | I-4 | II-168 |
| B2-414 | I-4 | II-169 |
| B2-415 | I-4 | II-170 |
| B2-416 | I-4 | II-171 |
| B2-417 | I-4 | II-172 |
| B2-418 | I-4 | II-173 |
| B2-419 | I-4 | II-174 |
| B2-420 | I-4 | II-175 |
| B2-421 | I-4 | II-176 |
| B2-422 | I-4 | II-177 |
| B2-423 | I-4 | II-178 |
| B2-424 | I-4 | II-179 |
| B2-425 | I-4 | II-180 |
| B2-426 | I-4 | II-181 |
| B2-427 | I-4 | II-182 |
| B2-428 | I-4 | II-183 |
| B2-429 | I-4 | II-184 |
| B2-430 | I-4 | II-185 |
| B2-431 | I-4 | II-186 |
| B2-432 | I-4 | II-187 |
| B2-433 | I-4 | II-188 |
| B2-434 | I-4 | II-189 |
| B2-435 | I-4 | II-190 |
| B2-436 | I-4 | II-191 |
| B2-437 | I-4 | II-192 |
| B2-438 | I-4 | II-193 |
| B2-439 | I-4 | II-194 |
| B2-440 | I-4 | II-195 |
| B2-441 | I-4 | II-196 |
| B2-442 | I-4 | II-197 |
| B2-443 | I-4 | II-198 |
| B2-444 | I-4 | II-199 |

TABLE B2-continued

Two-component compositions comprising one component I and one component II, in particular binary compositions containing the respective component I and II as only active ingredients.

| composition | I | II |
|---|---|---|
| B2-445 | I-4 | II-200 |
| B2-446 | I-4 | II-201 |
| B2-447 | I-4 | II-202 |
| B2-448 | I-4 | II-203 |
| B2-449 | I-5 | II-91 |
| B2-450 | I-5 | II-92 |
| B2-451 | I-5 | II-93 |
| B2-452 | I-5 | II-94 |
| B2-453 | I-5 | II-95 |
| B2-454 | I-5 | II-96 |
| B2-455 | I-5 | II-97 |
| B2-456 | I-5 | II-98 |
| B2-457 | I-5 | II-99 |
| B2-458 | I-5 | II-100 |
| B2-459 | I-5 | II-101 |
| B2-460 | I-5 | II-102 |
| B2-461 | I-5 | II-103 |
| B2-462 | I-5 | II-104 |
| B2-463 | I-5 | II-105 |
| B2-464 | I-5 | II-106 |
| B2-465 | I-5 | II-107 |
| B2-466 | I-5 | II-108 |
| B2-467 | I-5 | II-109 |
| B2-468 | I-5 | II-110 |
| B2-469 | I-5 | II-111 |
| B2-470 | I-5 | II-112 |
| B2-471 | I-5 | II-113 |
| B2-472 | I-5 | II-114 |
| B2-473 | I-5 | II-115 |
| B2-474 | I-5 | II-116 |
| B2-475 | I-5 | II-117 |
| B2-476 | I-5 | II-118 |
| B2-477 | I-5 | II-119 |
| B2-478 | I-5 | II-120 |
| B2-479 | I-5 | II-121 |
| B2-480 | I-5 | II-122 |
| B2-481 | I-5 | II-123 |
| B2-482 | I-5 | II-124 |
| B2-483 | I-5 | II-125 |
| B2-484 | I-5 | II-126 |
| B2-485 | I-5 | II-127 |
| B2-486 | I-5 | II-128 |
| B2-487 | I-5 | II-129 |
| B2-488 | I-5 | II-130 |
| B2-489 | I-5 | II-131 |
| B2-490 | I-5 | II-132 |
| B2-491 | I-5 | II-133 |
| B2-492 | I-5 | II-134 |
| B2-493 | I-5 | II-135 |
| B2-494 | I-5 | II-136 |
| B2-495 | I-5 | II-137 |
| B2-496 | I-5 | II-138 |
| B2-497 | I-5 | II-140 |
| B2-498 | I-5 | II-141 |
| B2-499 | I-5 | II-142 |
| B2-500 | I-5 | II-143 |
| B2-501 | I-5 | II-144 |
| B2-502 | I-5 | II-145 |
| B2-503 | I-5 | II-146 |
| B2-504 | I-5 | II-147 |
| B2-505 | I-5 | II-148 |
| B2-506 | I-5 | II-149 |
| B2-507 | I-5 | II-150 |
| B2-508 | I-5 | II-151 |
| B2-509 | I-5 | II-152 |
| B2-510 | I-5 | II-153 |
| B2-511 | I-5 | II-154 |
| B2-512 | I-5 | II-155 |
| B2-513 | I-5 | II-156 |
| B2-514 | I-5 | II-157 |
| B2-515 | I-5 | II-158 |
| B2-516 | I-5 | II-159 |
| B2-517 | I-5 | II-160 |
| B2-518 | I-5 | II-161 |
| B2-519 | I-5 | II-162 |
| B2-520 | I-5 | II-163 |
| B2-521 | I-5 | II-164 |
| B2-522 | I-5 | II-165 |
| B2-523 | I-5 | II-166 |
| B2-524 | I-5 | II-167 |
| B2-525 | I-5 | II-168 |
| B2-526 | I-5 | II-169 |
| B2-527 | I-5 | II-170 |
| B2-528 | I-5 | II-171 |
| B2-529 | I-5 | II-172 |
| B2-530 | I-5 | II-173 |
| B2-531 | I-5 | II-174 |
| B2-532 | I-5 | II-175 |
| B2-533 | I-5 | II-176 |
| B2-534 | I-5 | II-177 |
| B2-535 | I-5 | II-178 |
| B2-536 | I-5 | II-179 |
| B2-537 | I-5 | II-180 |
| B2-538 | I-5 | II-181 |
| B2-539 | I-5 | II-182 |
| B2-540 | I-5 | II-183 |
| B2-541 | I-5 | II-184 |
| B2-542 | I-5 | II-185 |
| B2-543 | I-5 | II-186 |
| B2-544 | I-5 | II-187 |
| B2-545 | I-5 | II-188 |
| B2-546 | I-5 | II-189 |
| B2-547 | I-5 | II-190 |
| B2-548 | I-5 | II-191 |
| B2-549 | I-5 | II-192 |
| B2-550 | I-5 | II-193 |
| B2-551 | I-5 | II-194 |
| B2-552 | I-5 | II-195 |
| B2-553 | I-5 | II-196 |
| B2-554 | I-5 | II-197 |
| B2-555 | I-5 | II-198 |
| B2-556 | I-5 | II-199 |
| B2-557 | I-5 | II-200 |
| B2-558 | I-5 | II-201 |
| B2-559 | I-5 | II-202 |
| B2-560 | I-5 | II-203 |
| B2-561 | I-13 | II-91 |
| B2-562 | I-13 | II-92 |
| B2-563 | I-13 | II-93 |
| B2-564 | I-13 | II-94 |
| B2-565 | I-13 | II-95 |
| B2-566 | I-13 | II-96 |
| B2-567 | I-13 | II-97 |
| B2-568 | I-13 | II-98 |
| B2-569 | I-13 | II-99 |
| B2-570 | I-13 | II-100 |
| B2-571 | I-13 | II-101 |
| B2-572 | I-13 | II-102 |
| B2-573 | I-13 | II-103 |
| B2-574 | I-13 | II-104 |
| B2-575 | I-13 | II-105 |
| B2-576 | I-13 | II-106 |
| B2-577 | I-13 | II-107 |
| B2-578 | I-13 | II-108 |
| B2-579 | I-13 | II-109 |
| B2-580 | I-13 | II-110 |
| B2-581 | I-13 | II-111 |
| B2-582 | I-13 | II-112 |
| B2-583 | I-13 | II-113 |
| B2-584 | I-13 | II-114 |
| B2-585 | I-13 | II-115 |
| B2-586 | I-13 | II-116 |
| B2-587 | I-13 | II-117 |
| B2-588 | I-13 | II-118 |
| B2-589 | I-13 | II-119 |
| B2-590 | I-13 | II-120 |
| B2-591 | I-13 | II-121 |
| B2-592 | I-13 | II-122 |

TABLE B2-continued

Two-component compositions comprising one component I and one component II, in particular binary compositions containing the respective component I and II as only active ingredients.

| composition | I | II |
| --- | --- | --- |
| B2-593 | I-13 | II-123 |
| B2-594 | I-13 | II-124 |
| B2-595 | I-13 | II-125 |
| B2-596 | I-13 | II-126 |
| B2-597 | I-13 | II-127 |
| B2-598 | I-13 | II-128 |
| B2-599 | I-13 | II-129 |
| B2-600 | I-13 | II-130 |
| B2-601 | I-13 | II-131 |
| B2-602 | I-13 | II-132 |
| B2-603 | I-13 | II-133 |
| B2-604 | I-13 | II-134 |
| B2-605 | I-13 | II-135 |
| B2-606 | I-13 | II-136 |
| B2-607 | I-13 | II-137 |
| B2-608 | I-13 | II-138 |
| B2-609 | I-13 | II-140 |
| B2-610 | I-13 | II-141 |
| B2-611 | I-13 | II-142 |
| B2-612 | I-13 | II-143 |
| B2-613 | I-13 | II-144 |
| B2-614 | I-13 | II-145 |
| B2-615 | I-13 | II-146 |
| B2-616 | I-13 | II-147 |
| B2-617 | I-13 | II-148 |
| B2-618 | I-13 | II-149 |
| B2-619 | I-13 | II-150 |
| B2-620 | I-13 | II-151 |
| B2-621 | I-13 | II-152 |
| B2-622 | I-13 | II-153 |
| B2-623 | I-13 | II-154 |
| B2-624 | I-13 | II-155 |
| B2-625 | I-13 | II-156 |
| B2-626 | I-13 | II-157 |
| B2-627 | I-13 | II-158 |
| B2-628 | I-13 | II-159 |
| B2-629 | I-13 | II-160 |
| B2-630 | I-13 | II-161 |
| B2-631 | I-13 | II-162 |
| B2-632 | I-13 | II-163 |
| B2-633 | I-13 | II-164 |
| B2-634 | I-13 | II-165 |
| B2-635 | I-13 | II-166 |
| B2-636 | I-13 | II-167 |
| B2-637 | I-13 | II-168 |
| B2-638 | I-13 | II-169 |
| B2-639 | I-13 | II-170 |
| B2-640 | I-13 | II-171 |
| B2-641 | I-13 | II-172 |
| B2-642 | I-13 | II-173 |
| B2-643 | I-13 | II-174 |
| B2-644 | I-13 | II-175 |
| B2-645 | I-13 | II-176 |
| B2-646 | I-13 | II-177 |
| B2-647 | I-13 | II-178 |
| B2-648 | I-13 | II-179 |
| B2-649 | I-13 | II-180 |
| B2-650 | I-13 | II-181 |
| B2-651 | I-13 | II-182 |
| B2-652 | I-13 | II-183 |
| B2-653 | I-13 | II-184 |
| B2-654 | I-13 | II-185 |
| B2-655 | I-13 | II-186 |
| B2-656 | I-13 | II-187 |
| B2-657 | I-13 | II-188 |
| B2-658 | I-13 | II-189 |
| B2-659 | I-13 | II-190 |
| B2-660 | I-13 | II-191 |
| B2-661 | I-13 | II-192 |
| B2-662 | I-13 | II-193 |
| B2-663 | I-13 | II-194 |
| B2-664 | I-13 | II-195 |
| B2-665 | I-13 | II-196 |
| B2-666 | I-13 | II-197 |
| B2-667 | I-13 | II-198 |
| B2-668 | I-13 | II-199 |
| B2-669 | I-13 | II-200 |
| B2-670 | I-13 | II-201 |
| B2-671 | I-13 | II-202 |
| B2-672 | I-13 | II-203 |

As detailed above, the components I contain chirality centers and may, therefore, be present as racemic compositions, as pure enantiomers or in the two enantiomers of one component I may be present in any ratio (S):(R).

According to particular embodiments of the invention, the respective component I is present as (S) enantiomer. Specific two-component compositions comprising the (S) enantiomer of the respective component I are compiled in Table Bs, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE Bs

Two-component compositions comprising one component I as (S) enantiomer (appreviated as (S)-I, e.g. (S)-I-1 for the (S)-enantiomer of I-1) and one component II, in particular binary compositions containing the respective component I as (S) enantiomer and II as only active ingredients.

| composition | (S)-I | II |
| --- | --- | --- |
| Bs-1 | (S)-I-1 | II-27 |
| Bs-2 | (S)-I-1 | II-28 |
| Bs-3 | (S)-I-1 | II-29 |
| Bs-4 | (S)-I-1 | II-30 |
| Bs-5 | (S)-I-1 | II-31 |
| Bs-6 | (S)-I-1 | II-32 |
| Bs-7 | (S)-I-1 | II-33 |
| Bs-8 | (S)-I-1 | II-34 |
| Bs-9 | (S)-I-1 | II-35 |
| Bs-10 | (S)-I-1 | II-36 |
| Bs-11 | (S)-I-1 | II-37 |
| Bs-12 | (S)-I-1 | II-38 |
| Bs-13 | (S)-I-1 | II-39 |
| Bs-14 | (S)-I-1 | II-40 |
| Bs-15 | (S)-I-1 | II-41 |
| Bs-16 | (S)-I-1 | II-42 |
| Bs-17 | (S)-I-1 | II-43 |
| Bs-18 | (S)-I-1 | II-44 |
| Bs-19 | (S)-I-1 | II-45 |
| Bs-20 | (S)-I-1 | II-46 |
| Bs-21 | (S)-I-1 | II-47 |
| Bs-22 | (S)-I-1 | II-48 |
| Bs-23 | (S)-I-1 | II-49 |
| Bs-24 | (S)-I-1 | II-50 |
| Bs-25 | (S)-I-1 | II-51 |
| Bs-26 | (S)-I-1 | II-52 |
| Bs-27 | (S)-I-1 | II-53 |
| Bs-28 | (S)-I-1 | II-54 |
| Bs-29 | (S)-I-1 | II-55 |
| Bs-30 | (S)-I-2 | II-27 |
| Bs-31 | (S)-I-2 | II-28 |
| Bs-32 | (S)-I-2 | II-29 |
| Bs-33 | (S)-I-2 | II-30 |
| Bs-34 | (S)-I-2 | II-31 |

TABLE Bs-continued

Two-component compositions comprising one component I as (S) enantiomer (appreviated as (S)-I, e.g. (S)-I-1 for the (S)-enantiomer of I-1) and one component II, in particular binary compositions containing the respective component I as (S) enantiomer and II as only active ingredients.

| composition | (S)-I | II |
|---|---|---|
| Bs-35 | (S)-I-2 | II-32 |
| Bs-36 | (S)-I-2 | II-33 |
| Bs-37 | (S)-I-2 | II-34 |
| Bs-38 | (S)-I-2 | II-35 |
| Bs-39 | (S)-I-2 | II-36 |
| Bs-40 | (S)-I-2 | II-37 |
| Bs-41 | (S)-I-2 | II-38 |
| Bs-42 | (S)-I-2 | II-39 |
| Bs-43 | (S)-I-2 | II-40 |
| Bs-44 | (S)-I-2 | II-41 |
| Bs-45 | (S)-I-2 | II-42 |
| Bs-46 | (S)-I-2 | II-43 |
| Bs-47 | (S)-I-2 | II-44 |
| Bs-48 | (S)-I-2 | II-45 |
| Bs-49 | (S)-I-2 | II-46 |
| Bs-50 | (S)-I-2 | II-47 |
| Bs-51 | (S)-I-2 | II-48 |
| Bs-52 | (S)-I-2 | II-49 |
| Bs-53 | (S)-I-2 | II-50 |
| Bs-54 | (S)-I-2 | II-51 |
| Bs-55 | (S)-I-2 | II-52 |
| Bs-56 | (S)-I-2 | II-53 |
| Bs-57 | (S)-I-2 | II-54 |
| Bs-58 | (S)-I-2 | II-55 |
| Bs-59 | (S)-I-3 | II-27 |
| Bs-60 | (S)-I-3 | II-28 |
| Bs-61 | (S)-I-3 | II-29 |
| Bs-62 | (S)-I-3 | II-30 |
| Bs-63 | (S)-I-3 | II-31 |
| Bs-64 | (S)-I-3 | II-32 |
| Bs-65 | (S)-I-3 | II-33 |
| Bs-66 | (S)-I-3 | II-34 |
| Bs-67 | (S)-I-3 | II-35 |
| Bs-68 | (S)-I-3 | II-36 |
| Bs-69 | (S)-I-3 | II-37 |
| Bs-70 | (S)-I-3 | II-38 |
| Bs-71 | (S)-I-3 | II-39 |
| Bs-72 | (S)-I-3 | II-40 |
| Bs-73 | (S)-I-3 | II-41 |
| Bs-74 | (S)-I-3 | II-42 |
| Bs-75 | (S)-I-3 | II-43 |
| Bs-76 | (S)-I-3 | II-44 |
| Bs-77 | (S)-I-3 | II-45 |
| Bs-78 | (S)-I-3 | II-46 |
| Bs-79 | (S)-I-3 | II-47 |
| Bs-80 | (S)-I-3 | II-48 |
| Bs-81 | (S)-I-3 | II-49 |
| Bs-82 | (S)-I-3 | II-50 |
| Bs-83 | (S)-I-3 | II-51 |
| Bs-84 | (S)-I-3 | II-52 |
| Bs-85 | (S)-I-3 | II-53 |
| Bs-86 | (S)-I-3 | II-54 |
| Bs-87 | (S)-I-3 | II-55 |
| Bs-88 | (S)-I-4 | II-27 |
| Bs-89 | (S)-I-4 | II-28 |
| Bs-90 | (S)-I-4 | II-29 |
| Bs-91 | (S)-I-4 | II-30 |
| Bs-92 | (S)-I-4 | II-31 |
| Bs-93 | (S)-I-4 | II-32 |
| Bs-94 | (S)-I-4 | II-33 |
| Bs-95 | (S)-I-4 | II-34 |
| Bs-96 | (S)-I-4 | II-35 |
| Bs-97 | (S)-I-4 | II-36 |
| Bs-98 | (S)-I-4 | II-37 |
| Bs-99 | (S)-I-4 | II-38 |
| Bs-100 | (S)-I-4 | II-39 |
| Bs-101 | (S)-I-4 | II-40 |
| Bs-102 | (S)-I-4 | II-41 |
| Bs-103 | (S)-I-4 | II-42 |
| Bs-104 | (S)-I-4 | II-43 |
| Bs-105 | (S)-I-4 | II-44 |
| Bs-106 | (S)-I-4 | II-45 |
| Bs-107 | (S)-I-4 | II-46 |
| Bs-108 | (S)-I-4 | II-47 |
| Bs-109 | (S)-I-4 | II-48 |
| Bs-110 | (S)-I-4 | II-49 |
| Bs-111 | (S)-I-4 | II-50 |
| Bs-112 | (S)-I-4 | II-51 |
| Bs-113 | (S)-I-4 | II-52 |
| Bs-114 | (S)-I-4 | II-53 |
| Bs-115 | (S)-I-4 | II-54 |
| Bs-116 | (S)-I-4 | II-55 |
| Bs-117 | (S)-I-5 | II-27 |
| Bs-118 | (S)-I-5 | II-28 |
| Bs-119 | (S)-I-5 | II-29 |
| Bs-120 | (S)-I-5 | II-30 |
| Bs-121 | (S)-I-5 | II-31 |
| Bs-122 | (S)-I-5 | II-32 |
| Bs-123 | (S)-I-5 | II-33 |
| Bs-124 | (S)-I-5 | II-34 |
| Bs-125 | (S)-I-5 | II-35 |
| Bs-126 | (S)-I-5 | II-36 |
| Bs-127 | (S)-I-5 | II-37 |
| Bs-128 | (S)-I-5 | II-38 |
| Bs-129 | (S)-I-5 | II-39 |
| Bs-130 | (S)-I-5 | II-40 |
| Bs-131 | (S)-I-5 | II-41 |
| Bs-132 | (S)-I-5 | II-42 |
| Bs-133 | (S)-I-5 | II-43 |
| Bs-134 | (S)-I-5 | II-44 |
| Bs-135 | (S)-I-5 | II-45 |
| Bs-136 | (S)-I-5 | II-46 |
| Bs-137 | (S)-I-5 | II-47 |
| Bs-138 | (S)-I-5 | II-48 |
| Bs-139 | (S)-I-5 | II-49 |
| Bs-140 | (S)-I-5 | II-50 |
| Bs-141 | (S)-I-5 | II-51 |
| Bs-142 | (S)-I-5 | II-52 |
| Bs-143 | (S)-I-5 | II-53 |
| Bs-144 | (S)-I-5 | II-54 |
| Bs-145 | (S)-I-5 | II-55 |
| Bs-146 | (S)-I-13 | II-27 |
| Bs-147 | (S)-I-13 | II-28 |
| Bs-148 | (S)-I-13 | II-29 |
| Bs-149 | (S)-I-13 | II-30 |
| Bs-150 | (S)-I-13 | II-31 |
| Bs-151 | (S)-I-13 | II-32 |
| Bs-152 | (S)-I-13 | II-33 |
| Bs-153 | (S)-I-13 | II-34 |
| Bs-154 | (S)-I-13 | II-35 |
| Bs-155 | (S)-I-13 | II-36 |
| Bs-156 | (S)-I-13 | II-37 |
| Bs-157 | (S)-I-13 | II-38 |
| Bs-158 | (S)-I-13 | II-39 |
| Bs-159 | (S)-I-13 | II-40 |
| Bs-160 | (S)-I-13 | II-41 |
| Bs-161 | (S)-I-13 | II-42 |
| Bs-162 | (S)-I-13 | II-43 |
| Bs-163 | (S)-I-13 | II-44 |
| Bs-164 | (S)-I-13 | II-45 |
| Bs-165 | (S)-I-13 | II-46 |
| Bs-166 | (S)-I-13 | II-47 |
| Bs-167 | (S)-I-13 | II-48 |
| Bs-168 | (S)-I-13 | II-49 |
| Bs-169 | (S)-I-13 | II-50 |
| Bs-170 | (S)-I-13 | II-51 |
| Bs-171 | (S)-I-13 | II-52 |
| Bs-172 | (S)-I-13 | II-53 |
| Bs-173 | (S)-I-13 | II-54 |
| Bs-174 | (S)-I-13 | II-55 |

According to particular embodiments of the invention, the respective component I is present as (R) enantiomer. Specific two-component compositions comprising the (R)

enantiomer of the respective component I are compiled in Table Br, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE Br

Two-component compositions comprising one component I as (R) enantiomer (appreviated as (R)-I, e.g. (R)-I-1 for the (R)-enantiomer of I-1) and one component II, in particular binary compositions containing the respective component I as (R) enantiomer and II as only active ingredients.

| composition | (R)-I | II |
|---|---|---|
| Br-1 | (R)-I-1 | II-27 |
| Br-2 | (R)-I-1 | II-28 |
| Br-3 | (R)-I-1 | II-29 |
| Br-4 | (R)-I-1 | II-30 |
| Br-5 | (R)-I-1 | II-31 |
| Br-6 | (R)-I-1 | II-32 |
| Br-7 | (R)-I-1 | II-33 |
| Br-8 | (R)-I-1 | II-34 |
| Br-9 | (R)-I-1 | II-35 |
| Br-10 | (R)-I-1 | II-36 |
| Br-11 | (R)-I-1 | II-37 |
| Br-12 | (R)-I-1 | II-38 |
| Br-13 | (R)-I-1 | II-39 |
| Br-14 | (R)-I-1 | II-40 |
| Br-15 | (R)-I-1 | II-41 |
| Br-16 | (R)-I-1 | II-42 |
| Br-17 | (R)-I-1 | II-43 |
| Br-18 | (R)-I-1 | II-44 |
| Br-19 | (R)-I-1 | II-45 |
| Br-20 | (R)-I-1 | II-46 |
| Br-21 | (R)-I-1 | II-47 |
| Br-22 | (R)-I-1 | II-48 |
| Br-23 | (R)-I-1 | II-49 |
| Br-24 | (R)-I-1 | II-50 |
| Br-25 | (R)-I-1 | II-51 |
| Br-26 | (R)-I-1 | II-52 |
| Br-27 | (R)-I-1 | II-53 |
| Br-28 | (R)-I-1 | II-54 |
| Br-29 | (R)-I-1 | II-55 |
| Br-30 | (R)-I-2 | II-27 |
| Br-31 | (R)-I-2 | II-28 |
| Br-32 | (R)-I-2 | II-29 |
| Br-33 | (R)-I-2 | II-30 |
| Br-34 | (R)-I-2 | II-31 |
| Br-35 | (R)-I-2 | II-32 |
| Br-36 | (R)-I-2 | II-33 |
| Br-37 | (R)-I-2 | II-34 |
| Br-38 | (R)-I-2 | II-35 |
| Br-39 | (R)-I-2 | II-36 |
| Br-40 | (R)-I-2 | II-37 |
| Br-41 | (R)-I-2 | II-38 |
| Br-42 | (R)-I-2 | II-39 |
| Br-43 | (R)-I-2 | II-40 |
| Br-44 | (R)-I-2 | II-41 |
| Br-45 | (R)-I-2 | II-42 |
| Br-46 | (R)-I-2 | II-43 |
| Br-47 | (R)-I-2 | II-44 |
| Br-48 | (R)-I-2 | II-45 |
| Br-49 | (R)-I-2 | II-46 |
| Br-50 | (R)-I-2 | II-47 |
| Br-51 | (R)-I-2 | II-48 |
| Br-52 | (R)-I-2 | II-49 |
| Br-53 | (R)-I-2 | II-50 |
| Br-54 | (R)-I-2 | II-51 |
| Br-55 | (R)-I-2 | II-52 |
| Br-56 | (R)-I-2 | II-53 |
| Br-57 | (R)-I-2 | II-54 |
| Br-58 | (R)-I-2 | II-55 |
| Br-59 | (R)-I-3 | II-27 |
| Br-60 | (R)-I-3 | II-28 |
| Br-61 | (R)-I-3 | II-29 |
| Br-62 | (R)-I-3 | II-30 |
| Br-63 | (R)-I-3 | II-31 |
| Br-64 | (R)-I-3 | II-32 |
| Br-65 | (R)-I-3 | II-33 |
| Br-66 | (R)-I-3 | II-34 |
| Br-67 | (R)-I-3 | II-35 |
| Br-68 | (R)-I-3 | II-36 |
| Br-69 | (R)-I-3 | II-37 |
| Br-70 | (R)-I-3 | II-38 |
| Br-71 | (R)-I-3 | II-39 |
| Br-72 | (R)-I-3 | II-40 |
| Br-73 | (R)-I-3 | II-41 |
| Br-74 | (R)-I-3 | II-42 |
| Br-75 | (R)-I-3 | II-43 |
| Br-76 | (R)-I-3 | II-44 |
| Br-77 | (R)-I-3 | II-45 |
| Br-78 | (R)-I-3 | II-46 |
| Br-79 | (R)-I-3 | II-47 |
| Br-80 | (R)-I-3 | II-48 |
| Br-81 | (R)-I-3 | II-49 |
| Br-82 | (R)-I-3 | II-50 |
| Br-83 | (R)-I-3 | II-51 |
| Br-84 | (R)-I-3 | II-52 |
| Br-85 | (R)-I-3 | II-53 |
| Br-86 | (R)-I-3 | II-54 |
| Br-87 | (R)-I-3 | II-55 |
| Br-88 | (R)-I-4 | II-27 |
| Br-89 | (R)-I-4 | II-28 |
| Br-90 | (R)-I-4 | II-29 |
| Br-91 | (R)-I-4 | II-30 |
| Br-92 | (R)-I-4 | II-31 |
| Br-93 | (R)-I-4 | II-32 |
| Br-94 | (R)-I-4 | II-33 |
| Br-95 | (R)-I-4 | II-34 |
| Br-96 | (R)-I-4 | II-35 |
| Br-97 | (R)-I-4 | II-36 |
| Br-98 | (R)-I-4 | II-37 |
| Br-99 | (R)-I-4 | II-38 |
| Br-100 | (R)-I-4 | II-39 |
| Br-101 | (R)-I-4 | II-40 |
| Br-102 | (R)-I-4 | II-41 |
| Br-103 | (R)-I-4 | II-42 |
| Br-104 | (R)-I-4 | II-43 |
| Br-105 | (R)-I-4 | II-44 |
| Br-106 | (R)-I-4 | II-45 |
| Br-107 | (R)-I-4 | II-46 |
| Br-108 | (R)-I-4 | II-47 |
| Br-109 | (R)-I-4 | II-48 |
| Br-110 | (R)-I-4 | II-49 |
| Br-111 | (R)-I-4 | II-50 |
| Br-112 | (R)-I-4 | II-51 |
| Br-113 | (R)-I-4 | II-52 |
| Br-114 | (R)-I-4 | II-53 |
| Br-115 | (R)-I-4 | II-54 |
| Br-116 | (R)-I-4 | II-55 |
| Br-117 | (R)-I-5 | II-27 |
| Br-118 | (R)-I-5 | II-28 |
| Br-119 | (R)-I-5 | II-29 |
| Br-120 | (R)-I-5 | II-30 |
| Br-121 | (R)-I-5 | II-31 |
| Br-122 | (R)-I-5 | II-32 |
| Br-123 | (R)-I-5 | II-33 |
| Br-124 | (R)-I-5 | II-34 |
| Br-125 | (R)-I-5 | II-35 |
| Br-126 | (R)-I-5 | II-36 |
| Br-127 | (R)-I-5 | II-37 |
| Br-128 | (R)-I-5 | II-38 |
| Br-129 | (R)-I-5 | II-39 |
| Br-130 | (R)-I-5 | II-40 |
| Br-131 | (R)-I-5 | II-41 |
| Br-132 | (R)-I-5 | II-42 |

TABLE Br-continued

Two-component compositions comprising one component I as (R) enantiomer (appreviated as (R)-I, e.g. (R)-I-1 for the (R)-enantiomer of I-1) and one component II, in particular binary compositions containing the respective component I as (R) enantiomer and II as only active ingredients.

| composition | (R)-I | II |
|---|---|---|
| Br-133 | (R)-I-5 | II-43 |
| Br-134 | (R)-I-5 | II-44 |
| Br-135 | (R)-I-5 | II-45 |
| Br-136 | (R)-I-5 | II-46 |
| Br-137 | (R)-I-5 | II-47 |
| Br-138 | (R)-I-5 | II-48 |
| Br-139 | (R)-I-5 | II-49 |
| Br-140 | (R)-I-5 | II-50 |
| Br-141 | (R)-I-5 | II-51 |
| Br-142 | (R)-I-5 | II-52 |
| Br-143 | (R)-I-5 | II-53 |
| Br-144 | (R)-I-5 | II-54 |
| Br-145 | (R)-I-5 | II-55 |
| Br-146 | (R)-I-13 | II-27 |
| Br-147 | (R)-I-13 | II-28 |
| Br-148 | (R)-I-13 | II-29 |
| Br-149 | (R)-I-13 | II-30 |
| Br-150 | (R)-I-13 | II-31 |
| Br-151 | (R)-I-13 | II-32 |
| Br-152 | (R)-I-13 | II-33 |
| Br-153 | (R)-I-13 | II-34 |
| Br-154 | (R)-I-13 | II-35 |
| Br-155 | (R)-I-13 | II-36 |
| Br-156 | (R)-I-13 | II-37 |
| Br-157 | (R)-I-13 | II-38 |
| Br-158 | (R)-I-13 | II-39 |
| Br-159 | (R)-I-13 | II-40 |
| Br-160 | (R)-I-13 | II-41 |
| Br-161 | (R)-I-13 | II-42 |
| Br-162 | (R)-I-13 | II-43 |
| Br-163 | (R)-I-13 | II-44 |
| Br-164 | (R)-I-13 | II-45 |
| Br-165 | (R)-I-13 | II-46 |
| Br-166 | (R)-I-13 | II-47 |
| Br-167 | (R)-I-13 | II-48 |
| Br-168 | (R)-I-13 | II-49 |
| Br-169 | (R)-I-13 | II-50 |
| Br-170 | (R)-I-13 | II-51 |
| Br-171 | (R)-I-13 | II-52 |
| Br-172 | (R)-I-13 | II-53 |
| Br-173 | (R)-I-13 | II-54 |
| Br-174 | (R)-I-13 | II-55 |

According to a further aspect, the present invention relates to three-component compositions, i.e. compositions comprising component I, i.e a compound I, in particular a compound selected from compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30 and I-31 or any group of compounds I detailed above, a component II as detailed above and a component III.

According to one embodiment, the component III is selected from the groups L1 to L6 or any preferred sub group thereof as detailed above.

According to a further embodiment, the component III is selected from the groups L1a to L6a or any preferred sub group thereof as detailed above.

According to still a further embodiment, the component III is selected from the groups La to Lf or any preferred sub group thereof as detailed above.

According to still a further embodiment, the component III is selected from the groups La-1) to Lf-1) or any preferred sub group thereof as detailed above.

According to still a further embodiment, the component III is selected from the following compounds:

*Bacillus altitudinis* (II-72)
*Bacillus amyloliquefaciens* (II-73)
*Bacillus amyloliquefaciens* ssp. Plantarum (II-27)
*Bacillus firmus* (II-44)
*Bacillus megaterium* (II-74)
*Bacillus mojavensis* (II-28)
*Bacillus mycoides* (II-75)
*Bacillus pumilus* (II-29)
*Bacillus simplex* (II-30)
*Bacillus solisalsi* (II-31)
*Bacillus subtilis* (II-76)
*Burkholderia* sp. (II-77)
*Coniothyrium minitans* (II-78)
*Paecilomyces lilacinus* (II-79)
*Paenibacillus alvei* (II-80)
*Paenibacillus polymyxa* (II-34)
*Paenibacillus popilliae* (II-81)
*Pasteuria nishizawae* (II-82)
*Pasteuria usgae* (II-83)
*Penicillium bilaiae* (II-52)
*Pseudomonas chloraphis* (II-84)
*Pseudomonas fluorescens* (II-85)
*Pseudomonas putida* (II-86)
abscisic acid (II-87)
harpin protein (alpha-beta) (II-88)
jasmonic acid or salts or derivatives thereof (II-43)
cis-jasmone (II-89)
methyl jasmonate (II-90)

Particularly preferred three-component compositions are compiled in Tables T1 to T31, wherein each row corresponds to one embodiment of the compositions according to the invention, i.e. one specific individualized composition. According to one specific aspect, these are ternary compositions which each only contain these three components as active compounds. Furthermore, also every combination of the compositions individualized in this table represent embodiments of the present invention.

In these three-component compositions, component I is selected from compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30 and I-31 or any group of compounds 1 detailed above, component II is selected from:

*Azospirillum amazonense* (II-56)
*Azospirillum brasilense* (II-48)
*Azospirillum lipoferum* (II-57)
*Azospirillum irakense* (II-58)
*Azospirillum halopraeferens* (II-59)
*Bradyrhizobium* spp. (II-49)
*Bradyrhizobium* sp. (Arachis) (II-60)
*Bradyrhizobium* sp. (Vigna) (II-61)
*Bradyrhizobium elkanii* (II-62)
*Bradyrhizobium japonicum* (II-50)
*Bradyrhizobium liaoningense* (II-63)
*Bradyrhizobium lupini* (II-64)
*Delftia acidovorans* (II-65)
*Glomus intraradices* (II-66)
*Mesorhizobium* spp. (II-51)
*Mesorhizobium ciceri* (II-67)
*Mesorhizobium huakii* (II-68)
*Mesorhizobium loti* (II-69)
*Rhizobium leguminosarum* bv. Phaseoli (II-53)
*Rhizobium leguminosarum* bv. Trifolii (II-70)
*Rhizobium leguminosarum* bv. Viciae (II-54)
*Rhizobium tropici* (II-71)
*Sinorhizobium meliloti* (II-55)

and component III is selected from:

*Bacillus altitudinis* (II-72)
*Bacillus amyloliquefaciens* (II-73)
*Bacillus amyloliquefaciens* ssp. *Plantarum* (II-27)
*Bacillus firmus* (II-44)
*Bacillus megaterium* (II-74)
*Bacillus mojavensis* (II-28)
*Bacillus mycoides* (II-75)
*Bacillus pumilus* (II-29)
*Bacillus simplex* (II-30)
*Bacillus solisalsi* (II-31)
*Bacillus subtilis* (II-76)
*Burkholderia* sp. (II-77)
*Coniothyrium minitans* (II-78)
*Paecilomyces lilacinus* (II-79)
*Paenibacillus alvei* (II-80)
*Paenibacillus polymyxa* (II-34)
*Paenibacillus popilliae* (II-81)
*Pasteuria nishizawae* (II-82)
*Pasteuria usgae* (II-83)
*Penicillium bilaiae* (II-52)
*Pseudomonas chloraphis* (II-84)
*Pseudomonas fluorescens* (II-85)
*Pseudomonas putida* (II-86)
abscisic acid (II-87)
harpin protein (alpha-beta) (II-88)
jasmonic acid or salts or derivatives thereof (II-43)
cis-jasmone (II-89)
methyl jasmonate (II-90)

TABLE T1

Three-component compositions T1-1 to T1-644 comprising compound I-3, component II and component III, in particular ternary compositions containing compound I-3, II and III as only active ingredients.

| composition | I | II | III |
|---|---|---|---|
| T1-1 | I-3 | II-56 | II-72 |
| T1-2 | I-3 | II-56 | II-73 |
| T1-3 | I-3 | II-56 | II-27 |
| T1-4 | I-3 | II-56 | II-44 |
| T1-5 | I-3 | II-56 | II-74 |
| T1-6 | I-3 | II-56 | II-28 |
| T1-7 | I-3 | II-56 | II-75 |
| T1-8 | I-3 | II-56 | II-29 |
| T1-9 | I-3 | II-56 | II-30 |
| T1-10 | I-3 | II-56 | II-31 |
| T1-11 | I-3 | II-56 | II-76 |
| T1-12 | I-3 | II-56 | II-77 |
| T1-13 | I-3 | II-56 | II-78 |
| T1-14 | I-3 | II-56 | II-79 |
| T1-15 | I-3 | II-56 | II-80 |
| T1-16 | I-3 | II-56 | II-34 |
| T1-17 | I-3 | II-56 | II-81 |
| T1-18 | I-3 | II-56 | II-82 |
| T1-19 | I-3 | II-56 | II-83 |
| T1-20 | I-3 | II-56 | II-52 |
| T1-21 | I-3 | II-56 | II-84 |
| T1-22 | I-3 | II-56 | II-85 |
| T1-23 | I-3 | II-56 | II-86 |
| T1-24 | I-3 | II-56 | II-87 |
| T1-25 | I-3 | II-56 | II-88 |
| T1-26 | I-3 | II-56 | II-43 |
| T1-27 | I-3 | II-56 | II-89 |
| T1-28 | I-3 | II-56 | II-90 |
| T1-29 | I-3 | II-48 | II-72 |
| T1-30 | I-3 | II-48 | II-73 |
| T1-31 | I-3 | II-48 | II-27 |
| T1-32 | I-3 | II-48 | II-44 |
| T1-33 | I-3 | II-48 | II-74 |
| T1-34 | I-3 | II-48 | II-28 |
| T1-35 | I-3 | II-48 | II-75 |
| T1-36 | I-3 | II-48 | II-29 |
| T1-37 | I-3 | II-48 | II-30 |
| T1-38 | I-3 | II-48 | II-31 |
| T1-39 | I-3 | II-48 | II-76 |
| T1-40 | I-3 | II-48 | II-77 |
| T1-41 | I-3 | II-48 | II-78 |
| T1-42 | I-3 | II-48 | II-79 |
| T1-43 | I-3 | II-48 | II-80 |
| T1-44 | I-3 | II-48 | II-34 |
| T1-45 | I-3 | II-48 | II-81 |
| T1-46 | I-3 | II-48 | II-82 |
| T1-47 | I-3 | II-48 | II-83 |
| T1-48 | I-3 | II-48 | II-52 |
| T1-49 | I-3 | II-48 | II-84 |
| T1-50 | I-3 | II-48 | II-85 |
| T1-51 | I-3 | II-48 | II-86 |
| T1-52 | I-3 | II-48 | II-87 |
| T1-53 | I-3 | II-48 | II-88 |
| T1-54 | I-3 | II-48 | II-43 |
| T1-55 | I-3 | II-48 | II-89 |
| T1-56 | I-3 | II-48 | II-90 |
| T1-57 | I-3 | II-57 | II-72 |
| T1-58 | I-3 | II-57 | II-73 |
| T1-59 | I-3 | II-57 | II-27 |
| T1-60 | I-3 | II-57 | II-44 |
| T1-61 | I-3 | II-57 | II-74 |
| T1-62 | I-3 | II-57 | II-28 |
| T1-63 | I-3 | II-57 | II-75 |
| T1-64 | I-3 | II-57 | II-29 |
| T1-65 | I-3 | II-57 | II-30 |
| T1-66 | I-3 | II-57 | II-31 |
| T1-67 | I-3 | II-57 | II-76 |
| T1-68 | I-3 | II-57 | II-77 |
| T1-69 | I-3 | II-57 | II-78 |
| T1-70 | I-3 | II-57 | II-79 |
| T1-71 | I-3 | II-57 | II-80 |
| T1-72 | I-3 | II-57 | II-34 |
| T1-73 | I-3 | II-57 | II-81 |
| T1-74 | I-3 | II-57 | II-82 |
| T1-75 | I-3 | II-57 | II-83 |
| T1-76 | I-3 | II-57 | II-52 |
| T1-77 | I-3 | II-57 | II-84 |
| T1-78 | I-3 | II-57 | II-85 |
| T1-79 | I-3 | II-57 | II-86 |
| T1-80 | I-3 | II-57 | II-87 |
| T1-81 | I-3 | II-57 | II-88 |
| T1-82 | I-3 | II-57 | II-43 |
| T1-83 | I-3 | II-57 | II-89 |
| T1-84 | I-3 | II-57 | II-90 |
| T1-85 | I-3 | II-58 | II-72 |
| T1-86 | I-3 | II-58 | II-73 |
| T1-87 | I-3 | II-58 | II-27 |
| T1-88 | I-3 | II-58 | II-44 |
| T1-89 | I-3 | II-58 | II-74 |
| T1-90 | I-3 | II-58 | II-28 |
| T1-91 | I-3 | II-58 | II-75 |
| T1-92 | I-3 | II-58 | II-29 |
| T1-93 | I-3 | II-58 | II-30 |
| T1-94 | I-3 | II-58 | II-31 |
| T1-95 | I-3 | II-58 | II-76 |
| T1-96 | I-3 | II-58 | II-77 |
| T1-97 | I-3 | II-58 | II-78 |
| T1-98 | I-3 | II-58 | II-79 |
| T1-99 | I-3 | II-58 | II-80 |
| T1-100 | I-3 | II-58 | II-34 |
| T1-101 | I-3 | II-58 | II-81 |
| T1-102 | I-3 | II-58 | II-82 |
| T1-103 | I-3 | II-58 | II-83 |
| T1-104 | I-3 | II-58 | II-52 |
| T1-105 | I-3 | II-58 | II-84 |
| T1-106 | I-3 | II-58 | II-85 |
| T1-107 | I-3 | II-58 | II-86 |
| T1-108 | I-3 | II-58 | II-87 |
| T1-109 | I-3 | II-58 | II-88 |

TABLE T1-continued

Three-component compositions T1-1 to T1-644 comprising compound I-3, component II and component III, in particular ternary compositions containing compound I-3, II and III as only active ingredients.

| composition | I | II | III |
|---|---|---|---|
| T1-110 | I-3 | II-58 | II-43 |
| T1-111 | I-3 | II-58 | II-89 |
| T1-112 | I-3 | II-58 | II-90 |
| T1-113 | I-3 | II-59 | II-72 |
| T1-114 | I-3 | II-59 | II-73 |
| T1-115 | I-3 | II-59 | II-27 |
| T1-116 | I-3 | II-59 | II-44 |
| T1-117 | I-3 | II-59 | II-74 |
| T1-118 | I-3 | II-59 | II-28 |
| T1-119 | I-3 | II-59 | II-75 |
| T1-120 | I-3 | II-59 | II-29 |
| T1-121 | I-3 | II-59 | II-30 |
| T1-122 | I-3 | II-59 | II-31 |
| T1-123 | I-3 | II-59 | II-76 |
| T1-124 | I-3 | II-59 | II-77 |
| T1-125 | I-3 | II-59 | II-78 |
| T1-126 | I-3 | II-59 | II-79 |
| T1-127 | I-3 | II-59 | II-80 |
| T1-128 | I-3 | II-59 | II-34 |
| T1-129 | I-3 | II-59 | II-81 |
| T1-130 | I-3 | II-59 | II-82 |
| T1-131 | I-3 | II-59 | II-83 |
| T1-132 | I-3 | II-59 | II-52 |
| T1-133 | I-3 | II-59 | II-84 |
| T1-134 | I-3 | II-59 | II-85 |
| T1-135 | I-3 | II-59 | II-86 |
| T1-136 | I-3 | II-59 | II-87 |
| T1-137 | I-3 | II-59 | II-88 |
| T1-138 | I-3 | II-59 | II-43 |
| T1-139 | I-3 | II-59 | II-89 |
| T1-140 | I-3 | II-59 | II-90 |
| T1-141 | I-3 | II-49 | II-72 |
| T1-142 | I-3 | II-49 | II-73 |
| T1-143 | I-3 | II-49 | II-27 |
| T1-144 | I-3 | II-49 | II-44 |
| T1-145 | I-3 | II-49 | II-74 |
| T1-146 | I-3 | II-49 | II-28 |
| T1-147 | I-3 | II-49 | II-75 |
| T1-148 | I-3 | II-49 | II-29 |
| T1-149 | I-3 | II-49 | II-30 |
| T1-150 | I-3 | II-49 | II-31 |
| T1-151 | I-3 | II-49 | II-76 |
| T1-152 | I-3 | II-49 | II-77 |
| T1-153 | I-3 | II-49 | II-78 |
| T1-154 | I-3 | II-49 | II-79 |
| T1-155 | I-3 | II-49 | II-80 |
| T1-156 | I-3 | II-49 | II-34 |
| T1-157 | I-3 | II-49 | II-81 |
| T1-158 | I-3 | II-49 | II-82 |
| T1-159 | I-3 | II-49 | II-83 |
| T1-160 | I-3 | II-49 | II-52 |
| T1-161 | I-3 | II-49 | II-84 |
| T1-162 | I-3 | II-49 | II-85 |
| T1-163 | I-3 | II-49 | II-86 |
| T1-164 | I-3 | II-49 | II-87 |
| T1-165 | I-3 | II-49 | II-88 |
| T1-166 | I-3 | II-49 | II-43 |
| T1-167 | I-3 | II-49 | II-89 |
| T1-168 | I-3 | II-49 | II-90 |
| T1-169 | I-3 | II-60 | II-72 |
| T1-170 | I-3 | II-60 | II-73 |
| T1-171 | I-3 | II-60 | II-27 |
| T1-172 | I-3 | II-60 | II-44 |
| T1-173 | I-3 | II-60 | II-74 |
| T1-174 | I-3 | II-60 | II-28 |
| T1-175 | I-3 | II-60 | II-75 |
| T1-176 | I-3 | II-60 | II-29 |
| T1-177 | I-3 | II-60 | II-30 |
| T1-178 | I-3 | II-60 | II-31 |
| T1-179 | I-3 | II-60 | II-76 |
| T1-180 | I-3 | II-60 | II-77 |
| T1-181 | I-3 | II-60 | II-78 |
| T1-182 | I-3 | II-60 | II-79 |
| T1-183 | I-3 | II-60 | II-80 |
| T1-184 | I-3 | II-60 | II-34 |
| T1-185 | I-3 | II-60 | II-81 |
| T1-186 | I-3 | II-60 | II-82 |
| T1-187 | I-3 | II-60 | II-83 |
| T1-188 | I-3 | II-60 | II-52 |
| T1-189 | I-3 | II-60 | II-84 |
| T1-190 | I-3 | II-60 | II-85 |
| T1-191 | I-3 | II-60 | II-86 |
| T1-192 | I-3 | II-60 | II-87 |
| T1-193 | I-3 | II-60 | II-88 |
| T1-194 | I-3 | II-60 | II-43 |
| T1-195 | I-3 | II-60 | II-89 |
| T1-196 | I-3 | II-60 | II-90 |
| T1-197 | I-3 | II-61 | II-72 |
| T1-198 | I-3 | II-61 | II-73 |
| T1-199 | I-3 | II-61 | II-27 |
| T1-200 | I-3 | II-61 | II-44 |
| T1-201 | I-3 | II-61 | II-74 |
| T1-202 | I-3 | II-61 | II-28 |
| T1-203 | I-3 | II-61 | II-75 |
| T1-204 | I-3 | II-61 | II-29 |
| T1-205 | I-3 | II-61 | II-30 |
| T1-206 | I-3 | II-61 | II-31 |
| T1-207 | I-3 | II-61 | II-76 |
| T1-208 | I-3 | II-61 | II-77 |
| T1-209 | I-3 | II-61 | II-78 |
| T1-210 | I-3 | II-61 | II-79 |
| T1-211 | I-3 | II-61 | II-80 |
| T1-212 | I-3 | II-61 | II-34 |
| T1-213 | I-3 | II-61 | II-81 |
| T1-214 | I-3 | II-61 | II-82 |
| T1-215 | I-3 | II-61 | II-83 |
| T1-216 | I-3 | II-61 | II-52 |
| T1-217 | I-3 | II-61 | II-84 |
| T1-218 | I-3 | II-61 | II-85 |
| T1-219 | I-3 | II-61 | II-86 |
| T1-220 | I-3 | II-61 | II-87 |
| T1-221 | I-3 | II-61 | II-88 |
| T1-222 | I-3 | II-61 | II-43 |
| T1-223 | I-3 | II-61 | II-89 |
| T1-224 | I-3 | II-61 | II-90 |
| T1-225 | I-3 | II-62 | II-72 |
| T1-226 | I-3 | II-62 | II-73 |
| T1-227 | I-3 | II-62 | II-27 |
| T1-228 | I-3 | II-62 | II-44 |
| T1-229 | I-3 | II-62 | II-74 |
| T1-230 | I-3 | II-62 | II-28 |
| T1-231 | I-3 | II-62 | II-75 |
| T1-232 | I-3 | II-62 | II-29 |
| T1-233 | I-3 | II-62 | II-30 |
| T1-234 | I-3 | II-62 | II-31 |
| T1-235 | I-3 | II-62 | II-76 |
| T1-236 | I-3 | II-62 | II-77 |
| T1-237 | I-3 | II-62 | II-78 |
| T1-238 | I-3 | II-62 | II-79 |
| T1-239 | I-3 | II-62 | II-80 |
| T1-240 | I-3 | II-62 | II-34 |
| T1-241 | I-3 | II-62 | II-81 |
| T1-242 | I-3 | II-62 | II-82 |
| T1-243 | I-3 | II-62 | II-83 |
| T1-244 | I-3 | II-62 | II-52 |
| T1-245 | I-3 | II-62 | II-84 |
| T1-246 | I-3 | II-62 | II-85 |
| T1-247 | I-3 | II-62 | II-86 |
| T1-248 | I-3 | II-62 | II-87 |
| T1-249 | I-3 | II-62 | II-88 |
| T1-250 | I-3 | II-62 | II-43 |
| T1-251 | I-3 | II-62 | II-89 |
| T1-252 | I-3 | II-62 | II-90 |
| T1-253 | I-3 | II-50 | II-72 |
| T1-254 | I-3 | II-50 | II-73 |
| T1-255 | I-3 | II-50 | II-27 |

TABLE T1-continued

Three-component compositions T1-1 to T1-644 comprising compound I-3, component II and component III, in particular ternary compositions containing compound I-3, II and III as only active ingredients.

| composition | I | II | III |
|---|---|---|---|
| T1-256 | I-3 | II-50 | II-44 |
| T1-257 | I-3 | II-50 | II-74 |
| T1-258 | I-3 | II-50 | II-28 |
| T1-259 | I-3 | II-50 | II-75 |
| T1-260 | I-3 | II-50 | II-29 |
| T1-261 | I-3 | II-50 | II-30 |
| T1-262 | I-3 | II-50 | II-31 |
| T1-263 | I-3 | II-50 | II-76 |
| T1-264 | I-3 | II-50 | II-77 |
| T1-265 | I-3 | II-50 | II-78 |
| T1-266 | I-3 | II-50 | II-79 |
| T1-267 | I-3 | II-50 | II-80 |
| T1-268 | I-3 | II-50 | II-34 |
| T1-269 | I-3 | II-50 | II-81 |
| T1-270 | I-3 | II-50 | II-82 |
| T1-271 | I-3 | II-50 | II-83 |
| T1-272 | I-3 | II-50 | II-52 |
| T1-273 | I-3 | II-50 | II-84 |
| T1-274 | I-3 | II-50 | II-85 |
| T1-275 | I-3 | II-50 | II-86 |
| T1-276 | I-3 | II-50 | II-87 |
| T1-277 | I-3 | II-50 | II-88 |
| T1-278 | I-3 | II-50 | II-43 |
| T1-279 | I-3 | II-50 | II-89 |
| T1-280 | I-3 | II-50 | II-90 |
| T1-281 | I-3 | II-63 | II-72 |
| T1-282 | I-3 | II-63 | II-73 |
| T1-283 | I-3 | II-63 | II-27 |
| T1-284 | I-3 | II-63 | II-44 |
| T1-285 | I-3 | II-63 | II-74 |
| T1-286 | I-3 | II-63 | II-28 |
| T1-287 | I-3 | II-63 | II-75 |
| T1-288 | I-3 | II-63 | II-29 |
| T1-289 | I-3 | II-63 | II-30 |
| T1-290 | I-3 | II-63 | II-31 |
| T1-291 | I-3 | II-63 | II-76 |
| T1-292 | I-3 | II-63 | II-77 |
| T1-293 | I-3 | II-63 | II-78 |
| T1-294 | I-3 | II-63 | II-79 |
| T1-295 | I-3 | II-63 | II-80 |
| T1-296 | I-3 | II-63 | II-34 |
| T1-297 | I-3 | II-63 | II-81 |
| T1-298 | I-3 | II-63 | II-82 |
| T1-299 | I-3 | II-63 | II-83 |
| T1-300 | I-3 | II-63 | II-52 |
| T1-301 | I-3 | II-63 | II-84 |
| T1-302 | I-3 | II-63 | II-85 |
| T1-303 | I-3 | II-63 | II-86 |
| T1-304 | I-3 | II-63 | II-87 |
| T1-305 | I-3 | II-63 | II-88 |
| T1-306 | I-3 | II-63 | II-43 |
| T1-307 | I-3 | II-63 | II-89 |
| T1-308 | I-3 | II-63 | II-90 |
| T1-309 | I-3 | II-64 | II-72 |
| T1-310 | I-3 | II-64 | II-73 |
| T1-311 | I-3 | II-64 | II-27 |
| T1-312 | I-3 | II-64 | II-44 |
| T1-313 | I-3 | II-64 | II-74 |
| T1-314 | I-3 | II-64 | II-28 |
| T1-315 | I-3 | II-64 | II-75 |
| T1-316 | I-3 | II-64 | II-29 |
| T1-317 | I-3 | II-64 | II-30 |
| T1-318 | I-3 | II-64 | II-31 |
| T1-319 | I-3 | II-64 | II-76 |
| T1-320 | I-3 | II-64 | II-77 |
| T1-321 | I-3 | II-64 | II-78 |
| T1-322 | I-3 | II-64 | II-79 |
| T1-323 | I-3 | II-64 | II-80 |
| T1-324 | I-3 | II-64 | II-34 |
| T1-325 | I-3 | II-64 | II-81 |
| T1-326 | I-3 | II-64 | II-82 |
| T1-327 | I-3 | II-64 | II-83 |
| T1-328 | I-3 | II-64 | II-52 |
| T1-329 | I-3 | II-64 | II-84 |
| T1-330 | I-3 | II-64 | II-85 |
| T1-331 | I-3 | II-64 | II-86 |
| T1-332 | I-3 | II-64 | II-87 |
| T1-333 | I-3 | II-64 | II-88 |
| T1-334 | I-3 | II-64 | II-43 |
| T1-335 | I-3 | II-64 | II-89 |
| T1-336 | I-3 | II-64 | II-90 |
| T1-337 | I-3 | II-65 | II-72 |
| T1-338 | I-3 | II-65 | II-73 |
| T1-339 | I-3 | II-65 | II-27 |
| T1-340 | I-3 | II-65 | II-44 |
| T1-341 | I-3 | II-65 | II-74 |
| T1-342 | I-3 | II-65 | II-28 |
| T1-343 | I-3 | II-65 | II-75 |
| T1-344 | I-3 | II-65 | II-29 |
| T1-345 | I-3 | II-65 | II-30 |
| T1-346 | I-3 | II-65 | II-31 |
| T1-347 | I-3 | II-65 | II-76 |
| T1-348 | I-3 | II-65 | II-77 |
| T1-349 | I-3 | II-65 | II-78 |
| T1-350 | I-3 | II-65 | II-79 |
| T1-351 | I-3 | II-65 | II-80 |
| T1-352 | I-3 | II-65 | II-34 |
| T1-353 | I-3 | II-65 | II-81 |
| T1-354 | I-3 | II-65 | II-82 |
| T1-355 | I-3 | II-65 | II-83 |
| T1-356 | I-3 | II-65 | II-52 |
| T1-357 | I-3 | II-65 | II-84 |
| T1-358 | I-3 | II-65 | II-85 |
| T1-359 | I-3 | II-65 | II-86 |
| T1-360 | I-3 | II-65 | II-87 |
| T1-361 | I-3 | II-65 | II-88 |
| T1-362 | I-3 | II-65 | II-43 |
| T1-363 | I-3 | II-65 | II-89 |
| T1-364 | I-3 | II-65 | II-90 |
| T1-365 | I-3 | II-66 | II-72 |
| T1-366 | I-3 | II-66 | II-73 |
| T1-367 | I-3 | II-66 | II-27 |
| T1-368 | I-3 | II-66 | II-44 |
| T1-369 | I-3 | II-66 | II-74 |
| T1-370 | I-3 | II-66 | II-28 |
| T1-371 | I-3 | II-66 | II-75 |
| T1-372 | I-3 | II-66 | II-29 |
| T1-373 | I-3 | II-66 | II-30 |
| T1-374 | I-3 | II-66 | II-31 |
| T1-375 | I-3 | II-66 | II-76 |
| T1-376 | I-3 | II-66 | II-77 |
| T1-377 | I-3 | II-66 | II-78 |
| T1-378 | I-3 | II-66 | II-79 |
| T1-379 | I-3 | II-66 | II-80 |
| T1-380 | I-3 | II-66 | II-34 |
| T1-381 | I-3 | II-66 | II-81 |
| T1-382 | I-3 | II-66 | II-82 |
| T1-383 | I-3 | II-66 | II-83 |
| T1-384 | I-3 | II-66 | II-52 |
| T1-385 | I-3 | II-66 | II-84 |
| T1-386 | I-3 | II-66 | II-85 |
| T1-387 | I-3 | II-66 | II-86 |
| T1-388 | I-3 | II-66 | II-87 |
| T1-389 | I-3 | II-66 | II-88 |
| T1-390 | I-3 | II-66 | II-43 |
| T1-391 | I-3 | II-66 | II-89 |
| T1-392 | I-3 | II-66 | II-90 |
| T1-393 | I-3 | II-51 | II-72 |
| T1-394 | I-3 | II-51 | II-73 |
| T1-395 | I-3 | II-51 | II-27 |
| T1-396 | I-3 | II-51 | II-44 |
| T1-397 | I-3 | II-51 | II-74 |
| T1-398 | I-3 | II-51 | II-28 |
| T1-399 | I-3 | II-51 | II-75 |
| T1-400 | I-3 | II-51 | II-29 |
| T1-401 | I-3 | II-51 | II-30 |

TABLE T1-continued

Three-component compositions T1-1 to T1-644 comprising compound I-3, component II and component III, in particular ternary compositions containing compound I-3, II and III as only active ingredients.

| composition | I | II | III |
|---|---|---|---|
| T1-402 | I-3 | II-51 | II-31 |
| T1-403 | I-3 | II-51 | II-76 |
| T1-404 | I-3 | II-51 | II-77 |
| T1-405 | I-3 | II-51 | II-78 |
| T1-406 | I-3 | II-51 | II-79 |
| T1-407 | I-3 | II-51 | II-80 |
| T1-408 | I-3 | II-51 | II-34 |
| T1-409 | I-3 | II-51 | II-81 |
| T1-410 | I-3 | II-51 | II-82 |
| T1-411 | I-3 | II-51 | II-83 |
| T1-412 | I-3 | II-51 | II-52 |
| T1-413 | I-3 | II-51 | II-84 |
| T1-414 | I-3 | II-51 | II-85 |
| T1-415 | I-3 | II-51 | II-86 |
| T1-416 | I-3 | II-51 | II-87 |
| T1-417 | I-3 | II-51 | II-88 |
| T1-418 | I-3 | II-51 | II-43 |
| T1-419 | I-3 | II-51 | II-89 |
| T1-420 | I-3 | II-51 | II-90 |
| T1-421 | I-3 | II-67 | II-72 |
| T1-422 | I-3 | II-67 | II-73 |
| T1-423 | I-3 | II-67 | II-27 |
| T1-424 | I-3 | II-67 | II-44 |
| T1-425 | I-3 | II-67 | II-74 |
| T1-426 | I-3 | II-67 | II-28 |
| T1-427 | I-3 | II-67 | II-75 |
| T1-428 | I-3 | II-67 | II-29 |
| T1-429 | I-3 | II-67 | II-30 |
| T1-430 | I-3 | II-67 | II-31 |
| T1-431 | I-3 | II-67 | II-76 |
| T1-432 | I-3 | II-67 | II-77 |
| T1-433 | I-3 | II-67 | II-78 |
| T1-434 | I-3 | II-67 | II-79 |
| T1-435 | I-3 | II-67 | II-80 |
| T1-436 | I-3 | II-67 | II-34 |
| T1-437 | I-3 | II-67 | II-81 |
| T1-438 | I-3 | II-67 | II-82 |
| T1-439 | I-3 | II-67 | II-83 |
| T1-440 | I-3 | II-67 | II-52 |
| T1-441 | I-3 | II-67 | II-84 |
| T1-442 | I-3 | II-67 | II-85 |
| T1-443 | I-3 | II-67 | II-86 |
| T1-444 | I-3 | II-67 | II-87 |
| T1-445 | I-3 | II-67 | II-88 |
| T1-446 | I-3 | II-67 | II-43 |
| T1-447 | I-3 | II-67 | II-89 |
| T1-448 | I-3 | II-67 | II-90 |
| T1-449 | I-3 | II-68 | II-72 |
| T1-450 | I-3 | II-68 | II-73 |
| T1-451 | I-3 | II-68 | II-27 |
| T1-452 | I-3 | II-68 | II-44 |
| T1-453 | I-3 | II-68 | II-74 |
| T1-454 | I-3 | II-68 | II-28 |
| T1-455 | I-3 | II-68 | II-75 |
| T1-456 | I-3 | II-68 | II-29 |
| T1-457 | I-3 | II-68 | II-30 |
| T1-458 | I-3 | II-68 | II-31 |
| T1-459 | I-3 | II-68 | II-76 |
| T1-460 | I-3 | II-68 | II-77 |
| T1-461 | I-3 | II-68 | II-78 |
| T1-462 | I-3 | II-68 | II-79 |
| T1-463 | I-3 | II-68 | II-80 |
| T1-464 | I-3 | II-68 | II-34 |
| T1-465 | I-3 | II-68 | II-81 |
| T1-466 | I-3 | II-68 | II-82 |
| T1-467 | I-3 | II-68 | II-83 |
| T1-468 | I-3 | II-68 | II-52 |
| T1-469 | I-3 | II-68 | II-84 |
| T1-470 | I-3 | II-68 | II-85 |
| T1-471 | I-3 | II-68 | II-86 |
| T1-472 | I-3 | II-68 | II-87 |
| T1-473 | I-3 | II-68 | II-88 |
| T1-474 | I-3 | II-68 | II-43 |
| T1-475 | I-3 | II-68 | II-89 |
| T1-476 | I-3 | II-68 | II-90 |
| T1-477 | I-3 | II-69 | II-72 |
| T1-478 | I-3 | II-69 | II-73 |
| T1-479 | I-3 | II-69 | II-27 |
| T1-480 | I-3 | II-69 | II-44 |
| T1-481 | I-3 | II-69 | II-74 |
| T1-482 | I-3 | II-69 | II-28 |
| T1-483 | I-3 | II-69 | II-75 |
| T1-484 | I-3 | II-69 | II-29 |
| T1-485 | I-3 | II-69 | II-30 |
| T1-486 | I-3 | II-69 | II-31 |
| T1-487 | I-3 | II-69 | II-76 |
| T1-488 | I-3 | II-69 | II-77 |
| T1-489 | I-3 | II-69 | II-78 |
| T1-490 | I-3 | II-69 | II-79 |
| T1-491 | I-3 | II-69 | II-80 |
| T1-492 | I-3 | II-69 | II-34 |
| T1-493 | I-3 | II-69 | II-81 |
| T1-494 | I-3 | II-69 | II-82 |
| T1-495 | I-3 | II-69 | II-83 |
| T1-496 | I-3 | II-69 | II-52 |
| T1-497 | I-3 | II-69 | II-84 |
| T1-498 | I-3 | II-69 | II-85 |
| T1-499 | I-3 | II-69 | II-86 |
| T1-500 | I-3 | II-69 | II-87 |
| T1-501 | I-3 | II-69 | II-88 |
| T1-502 | I-3 | II-69 | II-43 |
| T1-503 | I-3 | II-69 | II-89 |
| T1-504 | I-3 | II-69 | II-90 |
| T1-505 | I-3 | II-53 | II-72 |
| T1-506 | I-3 | II-53 | II-73 |
| T1-507 | I-3 | II-53 | II-27 |
| T1-508 | I-3 | II-53 | II-44 |
| T1-509 | I-3 | II-53 | II-74 |
| T1-510 | I-3 | II-53 | II-28 |
| T1-511 | I-3 | II-53 | II-75 |
| T1-512 | I-3 | II-53 | II-29 |
| T1-513 | I-3 | II-53 | II-30 |
| T1-514 | I-3 | II-53 | II-31 |
| T1-515 | I-3 | II-53 | II-76 |
| T1-516 | I-3 | II-53 | II-77 |
| T1-517 | I-3 | II-53 | II-78 |
| T1-518 | I-3 | II-53 | II-79 |
| T1-519 | I-3 | II-53 | II-80 |
| T1-520 | I-3 | II-53 | II-34 |
| T1-521 | I-3 | II-53 | II-81 |
| T1-522 | I-3 | II-53 | II-82 |
| T1-523 | I-3 | II-53 | II-83 |
| T1-524 | I-3 | II-53 | II-52 |
| T1-525 | I-3 | II-53 | II-84 |
| T1-526 | I-3 | II-53 | II-85 |
| T1-527 | I-3 | II-53 | II-86 |
| T1-528 | I-3 | II-53 | II-87 |
| T1-529 | I-3 | II-53 | II-88 |
| T1-530 | I-3 | II-53 | II-43 |
| T1-531 | I-3 | II-53 | II-89 |
| T1-532 | I-3 | II-53 | II-90 |
| T1-533 | I-3 | II-70 | II-72 |
| T1-534 | I-3 | II-70 | II-73 |
| T1-535 | I-3 | II-70 | II-27 |
| T1-536 | I-3 | II-70 | II-44 |
| T1-537 | I-3 | II-70 | II-74 |
| T1-538 | I-3 | II-70 | II-28 |
| T1-539 | I-3 | II-70 | II-75 |
| T1-540 | I-3 | II-70 | II-29 |
| T1-541 | I-3 | II-70 | II-30 |
| T1-542 | I-3 | II-70 | II-31 |
| T1-543 | I-3 | II-70 | II-76 |
| T1-544 | I-3 | II-70 | II-77 |
| T1-545 | I-3 | II-70 | II-78 |
| T1-546 | I-3 | II-70 | II-79 |
| T1-547 | I-3 | II-70 | II-80 |

TABLE T1-continued

Three-component compositions T1-1 to T1-644 comprising compound I-3, component II and component III, in particular ternary compositions containing compound I-3, II and III as only active ingredients.

| composition | I | II | III |
|---|---|---|---|
| T1-548 | I-3 | II-70 | II-34 |
| T1-549 | I-3 | II-70 | II-81 |
| T1-550 | I-3 | II-70 | II-82 |
| T1-551 | I-3 | II-70 | II-83 |
| T1-552 | I-3 | II-70 | II-52 |
| T1-553 | I-3 | II-70 | II-84 |
| T1-554 | I-3 | II-70 | II-85 |
| T1-555 | I-3 | II-70 | II-86 |
| T1-556 | I-3 | II-70 | II-87 |
| T1-557 | I-3 | II-70 | II-88 |
| T1-558 | I-3 | II-70 | II-43 |
| T1-559 | I-3 | II-70 | II-89 |
| T1-560 | I-3 | II-70 | II-90 |
| T1-561 | I-3 | II-54 | II-72 |
| T1-562 | I-3 | II-54 | II-73 |
| T1-563 | I-3 | II-54 | II-27 |
| T1-564 | I-3 | II-54 | II-44 |
| T1-565 | I-3 | II-54 | II-74 |
| T1-566 | I-3 | II-54 | II-28 |
| T1-567 | I-3 | II-54 | II-75 |
| T1-568 | I-3 | II-54 | II-29 |
| T1-569 | I-3 | II-54 | II-30 |
| T1-570 | I-3 | II-54 | II-31 |
| T1-571 | I-3 | II-54 | II-76 |
| T1-572 | I-3 | II-54 | II-77 |
| T1-573 | I-3 | II-54 | II-78 |
| T1-574 | I-3 | II-54 | II-79 |
| T1-575 | I-3 | II-54 | II-80 |
| T1-576 | I-3 | II-54 | II-34 |
| T1-577 | I-3 | II-54 | II-81 |
| T1-578 | I-3 | II-54 | II-82 |
| T1-579 | I-3 | II-54 | II-83 |
| T1-580 | I-3 | II-54 | II-52 |
| T1-581 | I-3 | II-54 | II-84 |
| T1-582 | I-3 | II-54 | II-85 |
| T1-583 | I-3 | II-54 | II-86 |
| T1-584 | I-3 | II-54 | II-87 |
| T1-585 | I-3 | II-54 | II-88 |
| T1-586 | I-3 | II-54 | II-43 |
| T1-587 | I-3 | II-54 | II-89 |
| T1-588 | I-3 | II-54 | II-90 |
| T1-589 | I-3 | II-71 | II-72 |
| T1-590 | I-3 | II-71 | II-73 |
| T1-591 | I-3 | II-71 | II-27 |
| T1-592 | I-3 | II-71 | II-44 |
| T1-593 | I-3 | II-71 | II-74 |
| T1-594 | I-3 | II-71 | II-28 |
| T1-595 | I-3 | II-71 | II-75 |
| T1-596 | I-3 | II-71 | II-29 |
| T1-597 | I-3 | II-71 | II-30 |
| T1-598 | I-3 | II-71 | II-31 |
| T1-599 | I-3 | II-71 | II-76 |
| T1-600 | I-3 | II-71 | II-77 |
| T1-601 | I-3 | II-71 | II-78 |
| T1-602 | I-3 | II-71 | II-79 |
| T1-603 | I-3 | II-71 | II-80 |
| T1-604 | I-3 | II-71 | II-34 |
| T1-605 | I-3 | II-71 | II-81 |
| T1-606 | I-3 | II-71 | II-82 |
| T1-607 | I-3 | II-71 | II-83 |
| T1-608 | I-3 | II-71 | II-52 |
| T1-609 | I-3 | II-71 | II-84 |
| T1-610 | I-3 | II-71 | II-85 |
| T1-611 | I-3 | II-71 | II-86 |
| T1-612 | I-3 | II-71 | II-87 |
| T1-613 | I-3 | II-71 | II-88 |
| T1-614 | I-3 | II-71 | II-43 |
| T1-615 | I-3 | II-71 | II-89 |
| T1-616 | I-3 | II-71 | II-90 |
| T1-617 | I-3 | II-55 | II-72 |
| T1-618 | I-3 | II-55 | II-73 |
| T1-619 | I-3 | II-55 | II-27 |
| T1-620 | I-3 | II-55 | II-44 |
| T1-621 | I-3 | II-55 | II-74 |
| T1-622 | I-3 | II-55 | II-28 |
| T1-623 | I-3 | II-55 | II-75 |
| T1-624 | I-3 | II-55 | II-29 |
| T1-625 | I-3 | II-55 | II-30 |
| T1-626 | I-3 | II-55 | II-31 |
| T1-627 | I-3 | II-55 | II-76 |
| T1-628 | I-3 | II-55 | II-77 |
| T1-629 | I-3 | II-55 | II-78 |
| T1-630 | I-3 | II-55 | II-79 |
| T1-631 | I-3 | II-55 | II-80 |
| T1-632 | I-3 | II-55 | II-34 |
| T1-633 | I-3 | II-55 | II-81 |
| T1-634 | I-3 | II-55 | II-82 |
| T1-635 | I-3 | II-55 | II-83 |
| T1-636 | I-3 | II-55 | II-52 |
| T1-637 | I-3 | II-55 | II-84 |
| T1-638 | I-3 | II-55 | II-85 |
| T1-639 | I-3 | II-55 | II-86 |
| T1-640 | I-3 | II-55 | II-87 |
| T1-641 | I-3 | II-55 | II-88 |
| T1-642 | I-3 | II-55 | II-43 |
| T1-643 | I-3 | II-55 | II-89 |
| T1-644 | I-3 | II-55 | II-90 |

Table T2: Three-component compositions T2-1 to T2-644 corresponding to the respective compositions T1-1 to T1-644, wherein component I is I-2 instead of I-3. Consequently, Table T2 contains compositions T2-1 to T2-644 comprising compound I-2, component II and component III, in particular ternary compositions containing compound I-2, II and III as only active ingredients.

Table T3: Three-component compositions T3-1 to T3-644 corresponding to the respective compositions T1-1 to T1-644, wherein component I is I-1 instead of I-3. Consequently, Table T3 contains compositions T3-1 to T3-644 comprising compound I-3, component II and component III, in particular ternary compositions containing compound I-1, II and III as only active ingredients.

Table T4: Three-component compositions T4-1 to T4-644 corresponding to the respective compositions T1-1 to T1-644, wherein component I is I-4 instead of I-3. Consequently, Table T4 contains compositions T4-1 to T4-644 comprising compound I-4, component II and component III, in particular ternary compositions containing compound I-4, II and III as only active ingredients.

Table T5: Three-component compositions T5-1 to T5-644 corresponding to the respective compositions T1-1 to T1-644, wherein component I is I-5 instead of I-3. Consequently, Table T5 contains compositions T5-1 to T5-644 comprising compound I-5, component II and component III, in particular ternary compositions containing compound I-5, II and III as only active ingredients.

Table T6: Three-component compositions T6-1 to T6-644 corresponding to the respective compositions T1-1 to T1-644, wherein component I is I-6 instead of I-3. Consequently, Table T6 contains compositions T6-1 to T6-644 comprising compound I-6, component II and component III, in particular ternary compositions containing compound I-6, II and III as only active ingredients.

Table T7: Three-component compositions T7-1 to T7-644 corresponding to the respective compositions T1-1 to T1-644, wherein component I is I-7 instead of I-3. Consequently, Table T7 contains compositions T7-1 to T7-644 comprising compound I-7, component II and component III, in particular ternary compositions containing compound I-7, II and III as only active ingredients.

Table T8: Three-component compositions T8-1 to T8-644 corresponding to the respective compositions T1-1 to T1-644, wherein component I is I-8 instead of I-3. Consequently, Table T8 contains compositions T8-1 to T8-644 comprising compound I-8, component II and component III, in particular ternary compositions containing compound I-8, II and III as only active ingredients.

Table T9: Three-component compositions T9-1 to T9-644 corresponding to the respective compositions T1-1 to T1-644, wherein component I is I-9 instead of I-3. Consequently, Table T9 contains compositions T9-1 to T9-644 comprising compound I-9, component II and component III, in particular ternary compositions containing compound I-9, II and III as only active ingredients.

Table T10: Three-component compositions T10-1 to T10-644 corresponding to the respective compositions T1-1 to T1-644, wherein component I is I-10 instead of I-3. Consequently, Table T10 contains compositions T10-1 to T10-644 comprising compound I-10, component II and component III, in particular ternary compositions containing compound 1-10, II and III as only active ingredients.

Table T11: Three-component compositions T11-1 to T11-644 corresponding to the respective compositions T1-1 to T1-644, wherein component I is I-11 instead of I-3. Consequently, Table T11contains compositions T11-1 to T11-644 comprising compound I-11, component II and component III, in particular ternary compositions containing compound I-11, II and III as only active ingredients.

Table T12: Three-component compositions T12-1 to T12-644 corresponding to the respective compositions T1-1 to T1-644, wherein component I is I-12 instead of I-3. Consequently, Table T12 contains compositions T12-1 to T12-644 comprising compound I-12, component II and component III, in particular ternary compositions containing compound I-12, II and III as only active ingredients.

Table T13: Three-component compositions T13-1 to T13-644 corresponding to the respective compositions T1-1 to T1-644, wherein component I is I-13 instead of I-3. Consequently, Table T13 contains compositions T13-1 to T13-644 comprising compound I-13, component II and component III, in particular ternary compositions containing compound I-13, II and III as only active ingredients.

Table T14: Three-component compositions T14-1 to T14-644 corresponding to the respective compositions T1-1 to T1-644, wherein component I is I-14 instead of I-3. Consequently, Table T14 contains compositions T14-1 to T14-644 comprising compound I-14, component II and component III, in particular ternary compositions containing compound I-14, II and III as only active ingredients.

Table T15: Three-component compositions T15-1 to T15-644 corresponding to the respective compositions T1-1 to T1-644, wherein component I is I-15 instead of I-3. Consequently, Table T15 contains compositions T15-1 to T15-644 comprising compound I-15, component II and component III, in particular ternary compositions containing compound I-15, II and III as only active ingredients.

Table T16: Three-component compositions T16-1 to T16-644 corresponding to the respective compositions T1-1 to T1-644, wherein component I is I-16 instead of I-3. Consequently, Table T16 contains compositions T16-1 to T16-644 comprising compound I-16, component II and component III, in particular ternary compositions containing compound I-16, II and III as only active ingredients.

Table T17: Three-component compositions T17-1 to T17-644 corresponding to the respective compositions T1-1 to T1-644, wherein component I is I-17 instead of I-3. Consequently, Table T17 contains compositions T17-1 to T17-644 comprising compound I-17, component II and component III, in particular ternary compositions containing compound I-17, II and III as only active ingredients.

Table T18: Three-component compositions T18-1 to T18-644 corresponding to the respective compositions T1-1 to T1-644, wherein component I is I-18 instead of I-3. Consequently, Table T18 contains compositions T18-1 to T18-644 comprising compound I-18, component II and component III, in particular ternary compositions containing compound I-18, II and II as only active ingredients.

Table T19: Three-component compositions T19-1 to T19-644 corresponding to the respective compositions T1-1 to T1-644, wherein component I is I-19 instead of I-3. Consequently, Table T19 contains compositions T19-1 to T19-644 comprising compound I-19, component II and component III, in particular ternary compositions containing compound I-19, II and III as only active ingredients.

Table T20: Three-component compositions T20-1 to T20-644 corresponding to the respective compositions T1-1 to T1-644, wherein component I is I-20 instead of I-3. Consequently, Table T20 contains compositions T20-1 to T20-644 comprising compound I-20, component II and component III, in particular ternary compositions containing compound I-20, Hand III as only active ingredients.

Table T21: Three-component compositions T21-1 to T21-644 corresponding to the respective compositions T1-1 to T1-644, wherein component I is I-21 instead of I-3. Consequently, Table T21 contains compositions T21-1 to T21-644 comprising compound I-21, component II and component III, in particular ternary compositions containing compound I-21, Hand III as only active ingredients.

Table T22: Three-component compositions T22-1 to T22-644 corresponding to the respective compositions T1-1 to T1-644, wherein component I is I-22 instead of I-3. Consequently, Table T22 contains compositions T22-1 to T22-644 comprising compound I-22, component II and component III, in particular ternary compositions containing compound I-22, Hand III as only active ingredients.

Table T23: Three-component compositions T23-1 to T23-644 corresponding to the respective compositions T1-1 to T1-644, wherein component I is I-23 instead of I-3. Consequently, Table T23 contains compositions T23-1 to T23-644 comprising compound I-23, component II and component III, in particular ternary compositions containing compound I-23, Hand III as only active ingredients.

Table T24: Three-component compositions T24-1 to T24-644 corresponding to the respective compositions T1-1 to T1-644, wherein component I is I-24 instead of I-3. Consequently, Table T24 contains compositions T24-1 to T24-644 comprising compound I-24, component II and component III, in particular ternary compositions containing compound I-24, Hand III as only active ingredients.

Table T25: Three-component compositions T25-1 to T25-644 corresponding to the respective compositions T1-1 to T1-644, wherein component I is I-25 instead of I-3. Consequently, Table T25 contains compositions T25-1 to T25-644 comprising compound I-25, component II and component III, in particular ternary compositions containing compound I-25, Hand III as only active ingredients.

Table T26: Three-component compositions T26-1 to T26-644 corresponding to the respective compositions T1-1 to T1-644, wherein component I is I-26 instead of I-3. Consequently, Table T26 contains compositions T26-1 to T26-

644 comprising compound I-26, component II and component III, in particular ternary compositions containing compound I-26, II and III as only active ingredients.

Table T27: Three-component compositions T27-1 to T27-644 corresponding to the respective compositions T1-1 to T1-644, wherein component I is I-27 instead of I-3. Consequently, Table T27 contains compositions T27-1 to T27-644 comprising compound I-27, component II and component III, in particular ternary compositions containing compound I-27, II and III as only active ingredients.

Table T28: Three-component compositions T28-1 to T28-644 corresponding to the respective compositions T1-1 to T1-644, wherein component I is I-28 instead of I-3. Consequently, Table T28 contains compositions T28-1 to T28-644 comprising compound I-28, component II and component III, in particular ternary compositions containing compound I-28, II and III as only active ingredients.

Table T29: Three-component compositions T29-1 to T29-644 corresponding to the respective compositions T1-1 to T1-644, wherein component I is I-29 instead of I-3. Consequently, Table T29 contains compositions T29-1 to T29-644 comprising compound I-29, component II and component III, in particular ternary compositions containing compound I-29, II and III as only active ingredients.

Table T30: Three-component compositions T30-1 to T30-644 corresponding to the respective compositions T1-1 to T1-644, wherein component I is I-30 instead of I-3. Consequently, Table T30 contains compositions T30-1 to T30-644 comprising compound I-30, component II and component III, in particular ternary compositions containing compound I-30, II and III as only active ingredients.

Table T31: Three-component compositions T31-1 to T31-644 corresponding to the respective compositions T1-1 to T1-644, wherein component I is I-31 instead of I-3. Consequently, Table T31 contains compositions T31-1 to T31-644 comprising compound I-31, component II and component III, in particular ternary compositions containing compound I-31, II and III as only active ingredients.

Further particularly preferred components III are selected from:

*Bacillus altitudinis* 41KF2b (II-148)
*Bacillus amyloliquefaciens* AP-136 (II-149)
*Bacillus amyloliquefaciens* AP-188 (II-150)
*Bacillus amyloliquefaciens* AP-218 (II-151)
*Bacillus amyloliquefaciens* AP-219 (II-152)
*Bacillus amyloliquefaciens* AP-295 (II-153)
*Bacillus amyloliquefaciens* ssp. *plantarum* D747 (II-154)
*Bacillus amyloliquefaciens* ssp. *plantarum* FZB24 also called SB3615 (II-155)
*Bacillus amyloliquefaciens* ssp. *plantarum* FZB42 (II-156)
*Bacillus amyloliquefaciens* ssp. *plantarum* GB03 also called GBO3 formerly *B. subtilis* (II-157)
*Bacillus amyloliquefaciens* ssp. *plantarum* MBI600 also referred to as 1430, formerly *B. subtilis* (II-158)
*Bacillus amyloliquefaciens* ssp. *plantarum* QST-713, formerly *B. subtilis* (II-159)
*Bacillus amyloliquefaciens* ssp. *plantarum* TJ1000, also called 1BE (II-160)
*Bacillus firmus* CNCM I-1582 (II-161)
*Bacillus megaterium* H491 (II-162)
*Bacillus megaterium* J142 (II-163)
*Bacillus megaterium* M018 (II-164)
*Bacillus mojavensis* AP-209 (II-165)
*Bacillus mojavensis* SR11 (II-166)
*Bacillus mycoides* AQ726 (II-167)
*Bacillus mycoides* J also called BmJ (II-168)
*Bacillus pumilus* GB34 (II-169)
*Bacillus pumilus* GHA 180 (II-170)
*Bacillus pumilus* INR-7 otherwise referred to as BU F22 and BU-F33 (II-171)
*Bacillus pumilus* KFP9F (II-172)
*Bacillus pumilus* QST 2808 (II-173)
*Bacillus simplex* ABU 288 (II-174)
*Bacillus subtilis* CX-9060 (II-175)
*Bacillus subtilis* FB17 (II-176)
*Bacillus subtilis* GB07 (II-177)
*Burkholderia* sp. A396 (II-178)
*Coniothyrium minitans* CON/M/91-08 (II-179)
*Paecilomyces lilacinus* 251 (II-180)
*Paecilomyces lilacinus* BCP2 (II-181)
*Paenibacillus alvei* NAS6G6 (II-182)
*Paenibacillus polymyxa* PKB1 (II-183)
*Paenibacilllus popilliae* 14F-D80 also called K14F-0080 (II-184)
*Paenibacilllus popilliae* KLN 3 (II-185)
*Pasteuria nishizawae* Pn1 (II-186)
*Pasteuria* sp, Ph3 (II-187)
*Pasteuria* sp. Pr3 (II-188)
*Pasteuria* sp. ATCC PTA-9643 (II-189)
*Pasteuria usgae* BL1 (II-190)
*Penicillium bilaiae* (also called *P. bilaii*) NRRL 50162 (II-191)
*Penicillium bilaiae* (also called *P. bilaii*) NRRL 50169 (II-192)
*Penicillium bilaiae* (also called *P. bilaii*) ATCC 18309 (=ATCC 74319) (II-193)
*Penicillium bilaiae* (also called *P. bilaii*) ATCC 20851 (II-194)
*Penicillium bilaiae* (also called *P. bilaii*) ATCC 22348 (=ATCC 74318) (II-195)
*Pseudomonas fluorescens* A506 (II-196)
*Pseudomonas fluorescens* ATCC 13525 (II-197)
*Pseudomonas fluorescens* CHA0 (II-198)
*Pseudomonas fluorescens* CL 145A (II-199)
*Pseudomonas fluorescens* NCIB 12089 (II-200)
*Pseudomonas fluorescens* Pf-5 (II-201)
*Pseudomonas fluorescens* WCS374 (II-202)
*Pseudomonas putida* ATCC 202153 (II-203)

Consequently, further particularly preferred three-component compositions are compiled in Table T1a, wherein each row corresponds to one embodiment of the compositions according to the invention, i.e. one specific individualized composition. According to one specific aspect, these are ternary compositions which each only contain these three components as active compounds. Furthermore, also every combination of the compositions individualized in this table represent embodiments of the present invention.

In these three-component compositions, component I is selected from compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30 and I-31 or any group of compounds I detailed above, component II is selected from:

*Azospirillum amazonense* SpY2 (II-91)
*Azospirillum brasilense* AZ39 also called Az 39 (II-92)
*Azospirillum brasilense* Cd (II-93)
*Azospirillum brasilense* Sp 245 (II-94)
*Azospirillum brasilense* Ab-V5 (II-95)
*Azospirillum brasilense* Ab-V6 (II-96)
*Azospirillum brasilense* XOH (II-97)
*Azospirillum lipoferum* Sp31 (II-98)
*Bradyrhizobium elkanii* SEMIA 5019 also called 29W (II-99)
*Bradyrhizobium elkanii* SEMIA 587 (II-100)
*Bradyrhizobium elkanii* U-1301 (II-101)
*Bradyrhizobium elkanii* U-1302 (II-102)
*Bradyrhizobium elkanii* USDA 3254 (II-103)
*Bradyrhizobium elkanii* USDA 76 (II-104)
*Bradyrhizobium elkanii* USDA 94 (II-105)
*Bradyrhizobium japonicum* 532c (II-106)
*Bradyrhizobium japonicum* E-109 (II-107)
*Bradyrhizobium japonicum* G49 (II-108)
*Bradyrhizobium japonicum* SEMIA 5079 (II-109)
*Bradyrhizobium japonicum* SEMIA 5080 (II-110)
*Bradyrhizobium japonicum* SEMIA 566 (II-111)
*Bradyrhizobium japonicum* SEMIA 586 (II-112)
*Bradyrhizobium japonicum* TA-11 (TA11 NOD+) (II-113)
*Bradyrhizobium japonicum* USDA 110 (II-114)
*Bradyrhizobium japonicum* USDA 121 (II-115)
*Bradyrhizobium japonicum* USDA 3 (II-116)
*Bradyrhizobium japonicum* USDA 31 (II-117)
*Bradyrhizobium japonicum* USDA 76 (II-118)
*Bradyrhizobium* sp. (Arachis) CB1015 (II-119)
*Bradyrhizobium* sp. (Arachis) SEMIA 6144 (II-120)
*Bradyrhizobium* sp. (Arachis) SEMIA 6462 (II-121)
*Bradyrhizobium* sp. (Arachis) SEMIA 6464 (II-122)
*Bradyrhizobium* sp. (Vigna) PNL1 (II-123)
*Mesorhizobium* sp. WSM1497 (II-124)
*Rhizobium leguminosarum* bv. phaseoli RG-B10 (II-125)
*Rhizobium leguminosarum* bv. phaseoli (II-126)
*Rhizobium leguminosarum* bv. trifolii 095 (II-127)
*Rhizobium leguminosarum* bv. trifolii CB782 (II-128)
*Rhizobium leguminosarum* bv. trifolii CC1099 (II-129)
*Rhizobium leguminosarum* bv. trifolii CC275e (II-130)
*Rhizobium leguminosarum* bv. trifolii CC283b (II-131)
*Rhizobium leguminosarum* bv. trifolii RP113-7 (II-132)
*Rhizobium leguminosarum* bv. trifolii TA1 (II-133)
*Rhizobium leguminosarum* bv. trifolii WSM1325 (II-134)
*Rhizobium leguminosarum* bv. trifolii WSM2304 (II-135)
*Rhizobium leguminosarum* bv. viciae P1NP3Cst also referred to as 1435 (II-136)
*Rhizobium leguminosarum* bv. viciae RG-P2 also called P2 (II-137)
*Rhizobium leguminosarum* bv. viciae SU303 (II-138)
*Rhizobium leguminosarum* bv. viciae WSM1455 (II-140)
*Rhizobium tropici* CC511 (II-141)
*Rhizobium tropici* CIAT 899 (II-142)
*Rhizobium tropici* H12 (II-143)
*Rhizobium tropici* PRF 81 (II-144)
*Sinorhizobium meliloti* NRG185 (II-145)
*Sinorhizobium meliloti* RCR2011 also called 2011 or SU47 (II-146)
*Sinorhizobium meliloti* RRI128 (II-147)

and component III is selected from:

*Bacillus altitudinis* 41KF2b (II-148)
*Bacillus amyloliquefaciens* AP-136 (II-149)
*Bacillus amyloliquefaciens* AP-188 (II-150)
*Bacillus amyloliquefaciens* AP-218 (II-151)
*Bacillus amyloliquefaciens* AP-219 (II-152)
*Bacillus amyloliquefaciens* AP-295 (II-153)
*Bacillus amyloliquefaciens* ssp. plantarum D747 (II-154)
*Bacillus amyloliquefaciens* ssp. plantarum FZB24 also called SB3615 (II-155)
*Bacillus amyloliquefaciens* ssp. plantarum FZB42 (II-156)
*Bacillus amyloliquefaciens* ssp. plantarum GB03 also called GBO3 formerly *B. subtilis* (II-157)
*Bacillus amyloliquefaciens* ssp. plantarum MBI600 also referred to as 1430, formerly *B. subtilis* (II-158)
*Bacillus amyloliquefaciens* ssp. plantarum QST-713, formerly *B. subtilis* (II-159)
*Bacillus amyloliquefaciens* ssp. plantarum TJ1000, also called 1BE (II-160)
*Bacillus firmus* CNCM I-1582 (II-161)
*Bacillus megaterium* H491 (II-162)
*Bacillus megaterium* J142 (II-163)
*Bacillus megaterium* M018 (II-164)
*Bacillus mojavensis* AP-209 (II-165)
*Bacillus mojavensis* SR11 (II-166)
*Bacillus mycoides* AQ726 (II-167)
*Bacillus mycoides* J also called BmJ (II-168)
*Bacillus pumilus* GB34 (II-169)
*Bacillus pumilus* GHA 180 (II-170)
*Bacillus pumilus* INR-7 otherwise referred to as BU F22 and BU-F33 (II-171)
*Bacillus pumilus* KFP9F (II-172)
*Bacillus pumilus* QST 2808 (II-173)
*Bacillus simplex* ABU 288 (II-174)
*Bacillus subtilis* CX-9060 (II-175)
*Bacillus subtilis* FB17 (II-176)
*Bacillus subtilis* GB07 (II-177)
*Burkholderia* sp. A396 (II-178)
*Coniothyrium minitans* CON/M/91-08 (II-179)
*Paecilomyces lilacinus* 251 (II-180)
*Paecilomyces lilacinus* BCP2 (II-181)
*Paenibacillus alvei* NAS6G6 (II-182)
*Paenibacillus polymyxa* PKB1 (II-183)
*Paenibacilllus popilliae* 14F-D80 also called K14F-0080 (II-184)
*Paenibacilllus popilliae* KLN 3 (II-185)
*Pasteuria nishizawae* Pn1 (II-186)
*Pasteuria* sp, Ph3 (II-187)
*Pasteuria* sp. Pr3 (II-188)
*Pasteuria* sp. ATCC PTA-9643 (II-189)
*Pasteuria usgae* BL1 (II-190)
*Penicillium bilaiae* (also called *P. bilaii*) NRRL 50162 (II-191)

*Penicillium bilaiae* (also called *P. bilaii*)
RRL 50169 (II-192)
*Penicillium bilaiae* (also called *P. bilaii*)
ATCC 18309 (=ATCC 74319) (II-193)
*Penicillium bilaiae* (also called *P. bilaii*)
ATCC 20851 (II-194)
*Penicillium bilaiae* (also called *P. bilaii*)
ATCC 22348 (=ATCC 74318) (II-195)
*Pseudomonas fluorescens* A506 (II-196)
*Pseudomonas fluorescens* ATCC 13525 (II-197)
*Pseudomonas fluorescens* CHA0 (II-198)
*Pseudomonas fluorescens* CL 145A (II-199)
*Pseudomonas fluorescens* NCIB 12089 (II-200)
*Pseudomonas fluorescens* Pf-5 (II-201)
*Pseudomonas fluorescens* WCS374 (II-202)
*Pseudomonas putida* ATCC 202153 (II-203)

TABLE T1a

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-1 | I-3 | II-91 | II-148 |
| T1a-2 | I-3 | II-91 | II-149 |
| T1a-3 | I-3 | II-91 | II-150 |
| T1a-4 | I-3 | II-91 | II-151 |
| T1a-5 | I-3 | II-91 | II-152 |
| T1a-6 | I-3 | II-91 | II-153 |
| T1a-7 | I-3 | II-91 | II-154 |
| T1a-8 | I-3 | II-91 | II-155 |
| T1a-9 | I-3 | II-91 | II-156 |
| T1a-10 | I-3 | II-91 | II-157 |
| T1a-11 | I-3 | II-91 | II-158 |
| T1a-12 | I-3 | II-91 | II-159 |
| T1a-13 | I-3 | II-91 | II-160 |
| T1a-14 | I-3 | II-91 | II-161 |
| T1a-15 | I-3 | II-91 | II-162 |
| T1a-16 | I-3 | II-91 | II-163 |
| T1a-17 | I-3 | II-91 | II-164 |
| T1a-18 | I-3 | II-91 | II-165 |
| T1a-19 | I-3 | II-91 | II-166 |
| T1a-20 | I-3 | II-91 | II-167 |
| T1a-21 | I-3 | II-91 | II-168 |
| T1a-22 | I-3 | II-91 | II-169 |
| T1a-23 | I-3 | II-91 | II-170 |
| T1a-24 | I-3 | II-91 | II-171 |
| T1a-25 | I-3 | II-91 | II-172 |
| T1a-26 | I-3 | II-91 | II-173 |
| T1a-27 | I-3 | II-91 | II-174 |
| T1a-28 | I-3 | II-91 | II-175 |
| T1a-29 | I-3 | II-91 | II-176 |
| T1a-30 | I-3 | II-91 | II-177 |
| T1a-31 | I-3 | II-91 | II-178 |
| T1a-32 | I-3 | II-91 | II-179 |
| T1a-33 | I-3 | II-91 | II-180 |
| T1a-34 | I-3 | II-91 | II-181 |
| T1a-35 | I-3 | II-91 | II-182 |
| T1a-36 | I-3 | II-91 | II-183 |
| T1a-37 | I-3 | II-91 | II-184 |
| T1a-38 | I-3 | II-91 | II-185 |
| T1a-39 | I-3 | II-91 | II-186 |
| T1a-40 | I-3 | II-91 | II-187 |
| T1a-41 | I-3 | II-91 | II-188 |
| T1a-42 | I-3 | II-91 | II-189 |
| T1a-43 | I-3 | II-91 | II-190 |
| T1a-44 | I-3 | II-91 | II-191 |
| T1a-45 | I-3 | II-91 | II-192 |
| T1a-46 | I-3 | II-91 | II-193 |
| T1a-47 | I-3 | II-91 | II-194 |
| T1a-48 | I-3 | II-91 | II-195 |
| T1a-49 | I-3 | II-91 | II-196 |
| T1a-50 | I-3 | II-91 | II-197 |
| T1a-51 | I-3 | II-91 | II-198 |
| T1a-52 | I-3 | II-91 | II-199 |
| T1a-53 | I-3 | II-91 | II-200 |
| T1a-54 | I-3 | II-91 | II-201 |
| T1a-55 | I-3 | II-91 | II-202 |
| T1a-56 | I-3 | II-91 | II-203 |
| T1a-57 | I-3 | II-92 | II-148 |
| T1a-58 | I-3 | II-92 | II-149 |
| T1a-59 | I-3 | II-92 | II-150 |
| T1a-60 | I-3 | II-92 | II-151 |
| T1a-61 | I-3 | II-92 | II-152 |
| T1a-62 | I-3 | II-92 | II-153 |
| T1a-63 | I-3 | II-92 | II-154 |
| T1a-64 | I-3 | II-92 | II-155 |
| T1a-65 | I-3 | II-92 | II-156 |
| T1a-66 | I-3 | II-92 | II-157 |
| T1a-67 | I-3 | II-92 | II-158 |
| T1a-68 | I-3 | II-92 | II-159 |
| T1a-69 | I-3 | II-92 | II-160 |
| T1a-70 | I-3 | II-92 | II-161 |
| T1a-71 | I-3 | II-92 | II-162 |
| T1a-72 | I-3 | II-92 | II-163 |
| T1a-73 | I-3 | II-92 | II-164 |
| T1a-74 | I-3 | II-92 | II-165 |
| T1a-75 | I-3 | II-92 | II-166 |
| T1a-76 | I-3 | II-92 | II-167 |
| T1a-77 | I-3 | II-92 | II-168 |
| T1a-78 | I-3 | II-92 | II-169 |
| T1a-79 | I-3 | II-92 | II-170 |
| T1a-80 | I-3 | II-92 | II-171 |
| T1a-81 | I-3 | II-92 | II-172 |
| T1a-82 | I-3 | II-92 | II-173 |
| T1a-83 | I-3 | II-92 | II-174 |
| T1a-84 | I-3 | II-92 | II-175 |
| T1a-85 | I-3 | II-92 | II-176 |
| T1a-86 | I-3 | II-92 | II-177 |
| T1a-87 | I-3 | II-92 | II-178 |
| T1a-88 | I-3 | II-92 | II-179 |
| T1a-89 | I-3 | II-92 | II-180 |
| T1a-90 | I-3 | II-92 | II-181 |
| T1a-91 | I-3 | II-92 | II-182 |
| T1a-92 | I-3 | II-92 | II-183 |
| T1a-93 | I-3 | II-92 | II-184 |
| T1a-94 | I-3 | II-92 | II-185 |
| T1a-95 | I-3 | II-92 | II-186 |
| T1a-96 | I-3 | II-92 | II-187 |
| T1a-97 | I-3 | II-92 | II-188 |
| T1a-98 | I-3 | II-92 | II-189 |
| T1a-99 | I-3 | II-92 | II-190 |
| T1a-100 | I-3 | II-92 | II-191 |
| T1a-101 | I-3 | II-92 | II-192 |
| T1a-102 | I-3 | II-92 | II-193 |
| T1a-103 | I-3 | II-92 | II-194 |
| T1a-104 | I-3 | II-92 | II-195 |
| T1a-105 | I-3 | II-92 | II-196 |
| T1a-106 | I-3 | II-92 | II-197 |
| T1a-107 | I-3 | II-92 | II-198 |
| T1a-108 | I-3 | II-92 | II-199 |
| T1a-109 | I-3 | II-92 | II-200 |
| T1a-110 | I-3 | II-92 | II-201 |
| T1a-111 | I-3 | II-92 | II-202 |
| T1a-112 | I-3 | II-92 | II-203 |
| T1a-113 | I-3 | II-93 | II-148 |
| T1a-114 | I-3 | II-93 | II-149 |
| T1a-115 | I-3 | II-93 | II-150 |
| T1a-116 | I-3 | II-93 | II-151 |
| T1a-117 | I-3 | II-93 | II-152 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-118 | I-3 | II-93 | II-153 |
| T1a-119 | I-3 | II-93 | II-154 |
| T1a-120 | I-3 | II-93 | II-155 |
| T1a-121 | I-3 | II-93 | II-156 |
| T1a-122 | I-3 | II-93 | II-157 |
| T1a-123 | I-3 | II-93 | II-158 |
| T1a-124 | I-3 | II-93 | II-159 |
| T1a-125 | I-3 | II-93 | II-160 |
| T1a-126 | I-3 | II-93 | II-161 |
| T1a-127 | I-3 | II-93 | II-162 |
| T1a-128 | I-3 | II-93 | II-163 |
| T1a-129 | I-3 | II-93 | II-164 |
| T1a-130 | I-3 | II-93 | II-165 |
| T1a-131 | I-3 | II-93 | II-166 |
| T1a-132 | I-3 | II-93 | II-167 |
| T1a-133 | I-3 | II-93 | II-168 |
| T1a-134 | I-3 | II-93 | II-169 |
| T1a-135 | I-3 | II-93 | II-170 |
| T1a-136 | I-3 | II-93 | II-171 |
| T1a-137 | I-3 | II-93 | II-172 |
| T1a-138 | I-3 | II-93 | II-173 |
| T1a-139 | I-3 | II-93 | II-174 |
| T1a-140 | I-3 | II-93 | II-175 |
| T1a-141 | I-3 | II-93 | II-176 |
| T1a-142 | I-3 | II-93 | II-177 |
| T1a-143 | I-3 | II-93 | II-178 |
| T1a-144 | I-3 | II-93 | II-179 |
| T1a-145 | I-3 | II-93 | II-180 |
| T1a-146 | I-3 | II-93 | II-181 |
| T1a-147 | I-3 | II-93 | II-182 |
| T1a-148 | I-3 | II-93 | II-183 |
| T1a-149 | I-3 | II-93 | II-184 |
| T1a-150 | I-3 | II-93 | II-185 |
| T1a-151 | I-3 | II-93 | II-186 |
| T1a-152 | I-3 | II-93 | II-187 |
| T1a-153 | I-3 | II-93 | II-188 |
| T1a-154 | I-3 | II-93 | II-189 |
| T1a-155 | I-3 | II-93 | II-190 |
| T1a-156 | I-3 | II-93 | II-191 |
| T1a-157 | I-3 | II-93 | II-192 |
| T1a-158 | I-3 | II-93 | II-193 |
| T1a-159 | I-3 | II-93 | II-194 |
| T1a-160 | I-3 | II-93 | II-195 |
| T1a-161 | I-3 | II-93 | II-196 |
| T1a-162 | I-3 | II-93 | II-197 |
| T1a-163 | I-3 | II-93 | II-198 |
| T1a-164 | I-3 | II-93 | II-199 |
| T1a-165 | I-3 | II-93 | II-200 |
| T1a-166 | I-3 | II-93 | II-201 |
| T1a-167 | I-3 | II-93 | II-202 |
| T1a-168 | I-3 | II-93 | II-203 |
| T1a-169 | I-3 | II-94 | II-148 |
| T1a-170 | I-3 | II-94 | II-149 |
| T1a-171 | I-3 | II-94 | II-150 |
| T1a-172 | I-3 | II-94 | II-151 |
| T1a-173 | I-3 | II-94 | II-152 |
| T1a-174 | I-3 | II-94 | II-153 |
| T1a-175 | I-3 | II-94 | II-154 |
| T1a-176 | I-3 | II-94 | II-155 |
| T1a-177 | I-3 | II-94 | II-156 |
| T1a-178 | I-3 | II-94 | II-157 |
| T1a-179 | I-3 | II-94 | II-158 |
| T1a-180 | I-3 | II-94 | II-159 |
| T1a-181 | I-3 | II-94 | II-160 |
| T1a-182 | I-3 | II-94 | II-161 |
| T1a-183 | I-3 | II-94 | II-162 |
| T1a-184 | I-3 | II-94 | II-163 |
| T1a-185 | I-3 | II-94 | II-164 |
| T1a-186 | I-3 | II-94 | II-165 |
| T1a-187 | I-3 | II-94 | II-166 |
| T1a-188 | I-3 | II-94 | II-167 |
| T1a-189 | I-3 | II-94 | II-168 |
| T1a-190 | I-3 | II-94 | II-169 |
| T1a-191 | I-3 | II-94 | II-170 |
| T1a-192 | I-3 | II-94 | II-171 |
| T1a-193 | I-3 | II-94 | II-172 |
| T1a-194 | I-3 | II-94 | II-173 |
| T1a-195 | I-3 | II-94 | II-174 |
| T1a-196 | I-3 | II-94 | II-175 |
| T1a-197 | I-3 | II-94 | II-176 |
| T1a-198 | I-3 | II-94 | II-177 |
| T1a-199 | I-3 | II-94 | II-178 |
| T1a-200 | I-3 | II-94 | II-179 |
| T1a-201 | I-3 | II-94 | II-180 |
| T1a-202 | I-3 | II-94 | II-181 |
| T1a-203 | I-3 | II-94 | II-182 |
| T1a-204 | I-3 | II-94 | II-183 |
| T1a-205 | I-3 | II-94 | II-184 |
| T1a-206 | I-3 | II-94 | II-185 |
| T1a-207 | I-3 | II-94 | II-186 |
| T1a-208 | I-3 | II-94 | II-187 |
| T1a-209 | I-3 | II-94 | II-188 |
| T1a-210 | I-3 | II-94 | II-189 |
| T1a-211 | I-3 | II-94 | II-190 |
| T1a-212 | I-3 | II-94 | II-191 |
| T1a-213 | I-3 | II-94 | II-192 |
| T1a-214 | I-3 | II-94 | II-193 |
| T1a-215 | I-3 | II-94 | II-194 |
| T1a-216 | I-3 | II-94 | II-195 |
| T1a-217 | I-3 | II-94 | II-196 |
| T1a-218 | I-3 | II-94 | II-197 |
| T1a-219 | I-3 | II-94 | II-198 |
| T1a-220 | I-3 | II-94 | II-199 |
| T1a-221 | I-3 | II-94 | II-200 |
| T1a-222 | I-3 | II-94 | II-201 |
| T1a-223 | I-3 | II-94 | II-202 |
| T1a-224 | I-3 | II-94 | II-203 |
| T1a-225 | I-3 | II-95 | II-148 |
| T1a-226 | I-3 | II-95 | II-149 |
| T1a-227 | I-3 | II-95 | II-150 |
| T1a-228 | I-3 | II-95 | II-151 |
| T1a-229 | I-3 | II-95 | II-152 |
| T1a-230 | I-3 | II-95 | II-153 |
| T1a-231 | I-3 | II-95 | II-154 |
| T1a-232 | I-3 | II-95 | II-155 |
| T1a-233 | I-3 | II-95 | II-156 |
| T1a-234 | I-3 | II-95 | II-157 |
| T1a-235 | I-3 | II-95 | II-158 |
| T1a-236 | I-3 | II-95 | II-159 |
| T1a-237 | I-3 | II-95 | II-160 |
| T1a-238 | I-3 | II-95 | II-161 |
| T1a-239 | I-3 | II-95 | II-162 |
| T1a-240 | I-3 | II-95 | II-163 |
| T1a-241 | I-3 | II-95 | II-164 |
| T1a-242 | I-3 | II-95 | II-165 |
| T1a-243 | I-3 | II-95 | II-166 |
| T1a-244 | I-3 | II-95 | II-167 |
| T1a-245 | I-3 | II-95 | II-168 |
| T1a-246 | I-3 | II-95 | II-169 |
| T1a-247 | I-3 | II-95 | II-170 |
| T1a-248 | I-3 | II-95 | II-171 |
| T1a-249 | I-3 | II-95 | II-172 |
| T1a-250 | I-3 | II-95 | II-173 |
| T1a-251 | I-3 | II-95 | II-174 |
| T1a-252 | I-3 | II-95 | II-175 |
| T1a-253 | I-3 | II-95 | II-176 |
| T1a-254 | I-3 | II-95 | II-177 |
| T1a-255 | I-3 | II-95 | II-178 |
| T1a-256 | I-3 | II-95 | II-179 |
| T1a-257 | I-3 | II-95 | II-180 |
| T1a-258 | I-3 | II-95 | II-181 |
| T1a-259 | I-3 | II-95 | II-182 |
| T1a-260 | I-3 | II-95 | II-183 |
| T1a-261 | I-3 | II-95 | II-184 |
| T1a-262 | I-3 | II-95 | II-185 |
| T1a-263 | I-3 | II-95 | II-186 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-264 | I-3 | II-95 | II-187 |
| T1a-265 | I-3 | II-95 | II-188 |
| T1a-266 | I-3 | II-95 | II-189 |
| T1a-267 | I-3 | II-95 | II-190 |
| T1a-268 | I-3 | II-95 | II-191 |
| T1a-269 | I-3 | II-95 | II-192 |
| T1a-270 | I-3 | II-95 | II-193 |
| T1a-271 | I-3 | II-95 | II-194 |
| T1a-272 | I-3 | II-95 | II-195 |
| T1a-273 | I-3 | II-95 | II-196 |
| T1a-274 | I-3 | II-95 | II-197 |
| T1a-275 | I-3 | II-95 | II-198 |
| T1a-276 | I-3 | II-95 | II-199 |
| T1a-277 | I-3 | II-95 | II-200 |
| T1a-278 | I-3 | II-95 | II-201 |
| T1a-279 | I-3 | II-95 | II-202 |
| T1a-280 | I-3 | II-95 | II-203 |
| T1a-281 | I-3 | II-96 | II-148 |
| T1a-282 | I-3 | II-96 | II-149 |
| T1a-283 | I-3 | II-96 | II-150 |
| T1a-284 | I-3 | II-96 | II-151 |
| T1a-285 | I-3 | II-96 | II-152 |
| T1a-286 | I-3 | II-96 | II-153 |
| T1a-287 | I-3 | II-96 | II-154 |
| T1a-288 | I-3 | II-96 | II-155 |
| T1a-289 | I-3 | II-96 | II-156 |
| T1a-290 | I-3 | II-96 | II-157 |
| T1a-291 | I-3 | II-96 | II-158 |
| T1a-292 | I-3 | II-96 | II-159 |
| T1a-293 | I-3 | II-96 | II-160 |
| T1a-294 | I-3 | II-96 | II-161 |
| T1a-295 | I-3 | II-96 | II-162 |
| T1a-296 | I-3 | II-96 | II-163 |
| T1a-297 | I-3 | II-96 | II-164 |
| T1a-298 | I-3 | II-96 | II-165 |
| T1a-299 | I-3 | II-96 | II-166 |
| T1a-300 | I-3 | II-96 | II-167 |
| T1a-301 | I-3 | II-96 | II-168 |
| T1a-302 | I-3 | II-96 | II-169 |
| T1a-303 | I-3 | II-96 | II-170 |
| T1a-304 | I-3 | II-96 | II-171 |
| T1a-305 | I-3 | II-96 | II-172 |
| T1a-306 | I-3 | II-96 | II-173 |
| T1a-307 | I-3 | II-96 | II-174 |
| T1a-308 | I-3 | II-96 | II-175 |
| T1a-309 | I-3 | II-96 | II-176 |
| T1a-310 | I-3 | II-96 | II-177 |
| T1a-311 | I-3 | II-96 | II-178 |
| T1a-312 | I-3 | II-96 | II-179 |
| T1a-313 | I-3 | II-96 | II-180 |
| T1a-314 | I-3 | II-96 | II-181 |
| T1a-315 | I-3 | II-96 | II-182 |
| T1a-316 | I-3 | II-96 | II-183 |
| T1a-317 | I-3 | II-96 | II-184 |
| T1a-318 | I-3 | II-96 | II-185 |
| T1a-319 | I-3 | II-96 | II-186 |
| T1a-320 | I-3 | II-96 | II-187 |
| T1a-321 | I-3 | II-96 | II-188 |
| T1a-322 | I-3 | II-96 | II-189 |
| T1a-323 | I-3 | II-96 | II-190 |
| T1a-324 | I-3 | II-96 | II-191 |
| T1a-325 | I-3 | II-96 | II-192 |
| T1a-326 | I-3 | II-96 | II-193 |
| T1a-327 | I-3 | II-96 | II-194 |
| T1a-328 | I-3 | II-96 | II-195 |
| T1a-329 | I-3 | II-96 | II-196 |
| T1a-330 | I-3 | II-96 | II-197 |
| T1a-331 | I-3 | II-96 | II-198 |
| T1a-332 | I-3 | II-96 | II-199 |
| T1a-333 | I-3 | II-96 | II-200 |
| T1a-334 | I-3 | II-96 | II-201 |
| T1a-335 | I-3 | II-96 | II-202 |
| T1a-336 | I-3 | II-96 | II-203 |
| T1a-337 | I-3 | II-97 | II-148 |
| T1a-338 | I-3 | II-97 | II-149 |
| T1a-339 | I-3 | II-97 | II-150 |
| T1a-340 | I-3 | II-97 | II-151 |
| T1a-341 | I-3 | II-97 | II-152 |
| T1a-342 | I-3 | II-97 | II-153 |
| T1a-343 | I-3 | II-97 | II-154 |
| T1a-344 | I-3 | II-97 | II-155 |
| T1a-345 | I-3 | II-97 | II-156 |
| T1a-346 | I-3 | II-97 | II-157 |
| T1a-347 | I-3 | II-97 | II-158 |
| T1a-348 | I-3 | II-97 | II-159 |
| T1a-349 | I-3 | II-97 | II-160 |
| T1a-350 | I-3 | II-97 | II-161 |
| T1a-351 | I-3 | II-97 | II-162 |
| T1a-352 | I-3 | II-97 | II-163 |
| T1a-353 | I-3 | II-97 | II-164 |
| T1a-354 | I-3 | II-97 | II-165 |
| T1a-355 | I-3 | II-97 | II-166 |
| T1a-356 | I-3 | II-97 | II-167 |
| T1a-357 | I-3 | II-97 | II-168 |
| T1a-358 | I-3 | II-97 | II-169 |
| T1a-359 | I-3 | II-97 | II-170 |
| T1a-360 | I-3 | II-97 | II-171 |
| T1a-361 | I-3 | II-97 | II-172 |
| T1a-362 | I-3 | II-97 | II-173 |
| T1a-363 | I-3 | II-97 | II-174 |
| T1a-364 | I-3 | II-97 | II-175 |
| T1a-365 | I-3 | II-97 | II-176 |
| T1a-366 | I-3 | II-97 | II-177 |
| T1a-367 | I-3 | II-97 | II-178 |
| T1a-368 | I-3 | II-97 | II-179 |
| T1a-369 | I-3 | II-97 | II-180 |
| T1a-370 | I-3 | II-97 | II-181 |
| T1a-371 | I-3 | II-97 | II-182 |
| T1a-372 | I-3 | II-97 | II-183 |
| T1a-373 | I-3 | II-97 | II-184 |
| T1a-374 | I-3 | II-97 | II-185 |
| T1a-375 | I-3 | II-97 | II-186 |
| T1a-376 | I-3 | II-97 | II-187 |
| T1a-377 | I-3 | II-97 | II-188 |
| T1a-378 | I-3 | II-97 | II-189 |
| T1a-379 | I-3 | II-97 | II-190 |
| T1a-380 | I-3 | II-97 | II-191 |
| T1a-381 | I-3 | II-97 | II-192 |
| T1a-382 | I-3 | II-97 | II-193 |
| T1a-383 | I-3 | II-97 | II-194 |
| T1a-384 | I-3 | II-97 | II-195 |
| T1a-385 | I-3 | II-97 | II-196 |
| T1a-386 | I-3 | II-97 | II-197 |
| T1a-387 | I-3 | II-97 | II-198 |
| T1a-388 | I-3 | II-97 | II-199 |
| T1a-389 | I-3 | II-97 | II-200 |
| T1a-390 | I-3 | II-97 | II-201 |
| T1a-391 | I-3 | II-97 | II-202 |
| T1a-392 | I-3 | II-97 | II-203 |
| T1a-393 | I-3 | II-98 | II-148 |
| T1a-394 | I-3 | II-98 | II-149 |
| T1a-395 | I-3 | II-98 | II-150 |
| T1a-396 | I-3 | II-98 | II-151 |
| T1a-397 | I-3 | II-98 | II-152 |
| T1a-398 | I-3 | II-98 | II-153 |
| T1a-399 | I-3 | II-98 | II-154 |
| T1a-400 | I-3 | II-98 | II-155 |
| T1a-401 | I-3 | II-98 | II-156 |
| T1a-402 | I-3 | II-98 | II-157 |
| T1a-403 | I-3 | II-98 | II-158 |
| T1a-404 | I-3 | II-98 | II-159 |
| T1a-405 | I-3 | II-98 | II-160 |
| T1a-406 | I-3 | II-98 | II-161 |
| T1a-407 | I-3 | II-98 | II-162 |
| T1a-408 | I-3 | II-98 | II-163 |
| T1a-409 | I-3 | II-98 | II-164 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-410 | I-3 | II-98 | II-165 |
| T1a-411 | I-3 | II-98 | II-166 |
| T1a-412 | I-3 | II-98 | II-167 |
| T1a-413 | I-3 | II-98 | II-168 |
| T1a-414 | I-3 | II-98 | II-169 |
| T1a-415 | I-3 | II-98 | II-170 |
| T1a-416 | I-3 | II-98 | II-171 |
| T1a-417 | I-3 | II-98 | II-172 |
| T1a-418 | I-3 | II-98 | II-173 |
| T1a-419 | I-3 | II-98 | II-174 |
| T1a-420 | I-3 | II-98 | II-175 |
| T1a-421 | I-3 | II-98 | II-176 |
| T1a-422 | I-3 | II-98 | II-177 |
| T1a-423 | I-3 | II-98 | II-178 |
| T1a-424 | I-3 | II-98 | II-179 |
| T1a-425 | I-3 | II-98 | II-180 |
| T1a-426 | I-3 | II-98 | II-181 |
| T1a-427 | I-3 | II-98 | II-182 |
| T1a-428 | I-3 | II-98 | II-183 |
| T1a-429 | I-3 | II-98 | II-184 |
| T1a-430 | I-3 | II-98 | II-185 |
| T1a-431 | I-3 | II-98 | II-186 |
| T1a-432 | I-3 | II-98 | II-187 |
| T1a-433 | I-3 | II-98 | II-188 |
| T1a-434 | I-3 | II-98 | II-189 |
| T1a-435 | I-3 | II-98 | II-190 |
| T1a-436 | I-3 | II-98 | II-191 |
| T1a-437 | I-3 | II-98 | II-192 |
| T1a-438 | I-3 | II-98 | II-193 |
| T1a-439 | I-3 | II-98 | II-194 |
| T1a-440 | I-3 | II-98 | II-195 |
| T1a-441 | I-3 | II-98 | II-196 |
| T1a-442 | I-3 | II-98 | II-197 |
| T1a-443 | I-3 | II-98 | II-198 |
| T1a-444 | I-3 | II-98 | II-199 |
| T1a-445 | I-3 | II-98 | II-200 |
| T1a-446 | I-3 | II-98 | II-201 |
| T1a-447 | I-3 | II-98 | II-202 |
| T1a-448 | I-3 | II-98 | II-203 |
| T1a-449 | I-3 | II-99 | II-148 |
| T1a-450 | I-3 | II-99 | II-149 |
| T1a-451 | I-3 | II-99 | II-150 |
| T1a-452 | I-3 | II-99 | II-151 |
| T1a-453 | I-3 | II-99 | II-152 |
| T1a-454 | I-3 | II-99 | II-153 |
| T1a-455 | I-3 | II-99 | II-154 |
| T1a-456 | I-3 | II-99 | II-155 |
| T1a-457 | I-3 | II-99 | II-156 |
| T1a-458 | I-3 | II-99 | II-157 |
| T1a-459 | I-3 | II-99 | II-158 |
| T1a-460 | I-3 | II-99 | II-159 |
| T1a-461 | I-3 | II-99 | II-160 |
| T1a-462 | I-3 | II-99 | II-161 |
| T1a-463 | I-3 | II-99 | II-162 |
| T1a-464 | I-3 | II-99 | II-163 |
| T1a-465 | I-3 | II-99 | II-164 |
| T1a-466 | I-3 | II-99 | II-165 |
| T1a-467 | I-3 | II-99 | II-166 |
| T1a-468 | I-3 | II-99 | II-167 |
| T1a-469 | I-3 | II-99 | II-168 |
| T1a-470 | I-3 | II-99 | II-169 |
| T1a-471 | I-3 | II-99 | II-170 |
| T1a-472 | I-3 | II-99 | II-171 |
| T1a-473 | I-3 | II-99 | II-172 |
| T1a-474 | I-3 | II-99 | II-173 |
| T1a-475 | I-3 | II-99 | II-174 |
| T1a-476 | I-3 | II-99 | II-175 |
| T1a-477 | I-3 | II-99 | II-176 |
| T1a-478 | I-3 | II-99 | II-177 |
| T1a-479 | I-3 | II-99 | II-178 |
| T1a-480 | I-3 | II-99 | II-179 |
| T1a-481 | I-3 | II-99 | II-180 |
| T1a-482 | I-3 | II-99 | II-181 |
| T1a-483 | I-3 | II-99 | II-182 |
| T1a-484 | I-3 | II-99 | II-183 |
| T1a-485 | I-3 | II-99 | II-184 |
| T1a-486 | I-3 | II-99 | II-185 |
| T1a-487 | I-3 | II-99 | II-186 |
| T1a-488 | I-3 | II-99 | II-187 |
| T1a-489 | I-3 | II-99 | II-188 |
| T1a-490 | I-3 | II-99 | II-189 |
| T1a-491 | I-3 | II-99 | II-190 |
| T1a-492 | I-3 | II-99 | II-191 |
| T1a-493 | I-3 | II-99 | II-192 |
| T1a-494 | I-3 | II-99 | II-193 |
| T1a-495 | I-3 | II-99 | II-194 |
| T1a-496 | I-3 | II-99 | II-195 |
| T1a-497 | I-3 | II-99 | II-196 |
| T1a-498 | I-3 | II-99 | II-197 |
| T1a-499 | I-3 | II-99 | II-198 |
| T1a-500 | I-3 | II-99 | II-199 |
| T1a-501 | I-3 | II-99 | II-200 |
| T1a-502 | I-3 | II-99 | II-201 |
| T1a-503 | I-3 | II-99 | II-202 |
| T1a-504 | I-3 | II-99 | II-203 |
| T1a-505 | I-3 | II-100 | II-148 |
| T1a-506 | I-3 | II-100 | II-149 |
| T1a-507 | I-3 | II-100 | II-150 |
| T1a-508 | I-3 | II-100 | II-151 |
| T1a-509 | I-3 | II-100 | II-152 |
| T1a-510 | I-3 | II-100 | II-153 |
| T1a-511 | I-3 | II-100 | II-154 |
| T1a-512 | I-3 | II-100 | II-155 |
| T1a-513 | I-3 | II-100 | II-156 |
| T1a-514 | I-3 | II-100 | II-157 |
| T1a-515 | I-3 | II-100 | II-158 |
| T1a-516 | I-3 | II-100 | II-159 |
| T1a-517 | I-3 | II-100 | II-160 |
| T1a-518 | I-3 | II-100 | II-161 |
| T1a-519 | I-3 | II-100 | II-162 |
| T1a-520 | I-3 | II-100 | II-163 |
| T1a-521 | I-3 | II-100 | II-164 |
| T1a-522 | I-3 | II-100 | II-165 |
| T1a-523 | I-3 | II-100 | II-166 |
| T1a-524 | I-3 | II-100 | II-167 |
| T1a-525 | I-3 | II-100 | II-168 |
| T1a-526 | I-3 | II-100 | II-169 |
| T1a-527 | I-3 | II-100 | II-170 |
| T1a-528 | I-3 | II-100 | II-171 |
| T1a-529 | I-3 | II-100 | II-172 |
| T1a-530 | I-3 | II-100 | II-173 |
| T1a-531 | I-3 | II-100 | II-174 |
| T1a-532 | I-3 | II-100 | II-175 |
| T1a-533 | I-3 | II-100 | II-176 |
| T1a-534 | I-3 | II-100 | II-177 |
| T1a-535 | I-3 | II-100 | II-178 |
| T1a-536 | I-3 | II-100 | II-179 |
| T1a-537 | I-3 | II-100 | II-180 |
| T1a-538 | I-3 | II-100 | II-181 |
| T1a-539 | I-3 | II-100 | II-182 |
| T1a-540 | I-3 | II-100 | II-183 |
| T1a-541 | I-3 | II-100 | II-184 |
| T1a-542 | I-3 | II-100 | II-185 |
| T1a-543 | I-3 | II-100 | II-186 |
| T1a-544 | I-3 | II-100 | II-187 |
| T1a-545 | I-3 | II-100 | II-188 |
| T1a-546 | I-3 | II-100 | II-189 |
| T1a-547 | I-3 | II-100 | II-190 |
| T1a-548 | I-3 | II-100 | II-191 |
| T1a-549 | I-3 | II-100 | II-192 |
| T1a-550 | I-3 | II-100 | II-193 |
| T1a-551 | I-3 | II-100 | II-194 |
| T1a-552 | I-3 | II-100 | II-195 |
| T1a-553 | I-3 | II-100 | II-196 |
| T1a-554 | I-3 | II-100 | II-197 |
| T1a-555 | I-3 | II-100 | II-198 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-556 | I-3 | II-100 | II-199 |
| T1a-557 | I-3 | II-100 | II-200 |
| T1a-558 | I-3 | II-100 | II-201 |
| T1a-559 | I-3 | II-100 | II-202 |
| T1a-560 | I-3 | II-100 | II-203 |
| T1a-561 | I-3 | II-101 | II-148 |
| T1a-562 | I-3 | II-101 | II-149 |
| T1a-563 | I-3 | II-101 | II-150 |
| T1a-564 | I-3 | II-101 | II-151 |
| T1a-565 | I-3 | II-101 | II-152 |
| T1a-566 | I-3 | II-101 | II-153 |
| T1a-567 | I-3 | II-101 | II-154 |
| T1a-568 | I-3 | II-101 | II-155 |
| T1a-569 | I-3 | II-101 | II-156 |
| T1a-570 | I-3 | II-101 | II-157 |
| T1a-571 | I-3 | II-101 | II-158 |
| T1a-572 | I-3 | II-101 | II-159 |
| T1a-573 | I-3 | II-101 | II-160 |
| T1a-574 | I-3 | II-101 | II-161 |
| T1a-575 | I-3 | II-101 | II-162 |
| T1a-576 | I-3 | II-101 | II-163 |
| T1a-577 | I-3 | II-101 | II-164 |
| T1a-578 | I-3 | II-101 | II-165 |
| T1a-579 | I-3 | II-101 | II-166 |
| T1a-580 | I-3 | II-101 | II-167 |
| T1a-581 | I-3 | II-101 | II-168 |
| T1a-582 | I-3 | II-101 | II-169 |
| T1a-583 | I-3 | II-101 | II-170 |
| T1a-584 | I-3 | II-101 | II-171 |
| T1a-585 | I-3 | II-101 | II-172 |
| T1a-586 | I-3 | II-101 | II-173 |
| T1a-587 | I-3 | II-101 | II-174 |
| T1a-588 | I-3 | II-101 | II-175 |
| T1a-589 | I-3 | II-101 | II-176 |
| T1a-590 | I-3 | II-101 | II-177 |
| T1a-591 | I-3 | II-101 | II-178 |
| T1a-592 | I-3 | II-101 | II-179 |
| T1a-593 | I-3 | II-101 | II-180 |
| T1a-594 | I-3 | II-101 | II-181 |
| T1a-595 | I-3 | II-101 | II-182 |
| T1a-596 | I-3 | II-101 | II-183 |
| T1a-597 | I-3 | II-101 | II-184 |
| T1a-598 | I-3 | II-101 | II-185 |
| T1a-599 | I-3 | II-101 | II-186 |
| T1a-600 | I-3 | II-101 | II-187 |
| T1a-601 | I-3 | II-101 | II-188 |
| T1a-602 | I-3 | II-101 | II-189 |
| T1a-603 | I-3 | II-101 | II-190 |
| T1a-604 | I-3 | II-101 | II-191 |
| T1a-605 | I-3 | II-101 | II-192 |
| T1a-606 | I-3 | II-101 | II-193 |
| T1a-607 | I-3 | II-101 | II-194 |
| T1a-608 | I-3 | II-101 | II-195 |
| T1a-609 | I-3 | II-101 | II-196 |
| T1a-610 | I-3 | II-101 | II-197 |
| T1a-611 | I-3 | II-101 | II-198 |
| T1a-612 | I-3 | II-101 | II-199 |
| T1a-613 | I-3 | II-101 | II-200 |
| T1a-614 | I-3 | II-101 | II-201 |
| T1a-615 | I-3 | II-101 | II-202 |
| T1a-616 | I-3 | II-101 | II-203 |
| T1a-617 | I-3 | II-102 | II-148 |
| T1a-618 | I-3 | II-102 | II-149 |
| T1a-619 | I-3 | II-102 | II-150 |
| T1a-620 | I-3 | II-102 | II-151 |
| T1a-621 | I-3 | II-102 | II-152 |
| T1a-622 | I-3 | II-102 | II-153 |
| T1a-623 | I-3 | II-102 | II-154 |
| T1a-624 | I-3 | II-102 | II-155 |
| T1a-625 | I-3 | II-102 | II-156 |
| T1a-626 | I-3 | II-102 | II-157 |
| T1a-627 | I-3 | II-102 | II-158 |
| T1a-628 | I-3 | II-102 | II-159 |
| T1a-629 | I-3 | II-102 | II-160 |
| T1a-630 | I-3 | II-102 | II-161 |
| T1a-631 | I-3 | II-102 | II-162 |
| T1a-632 | I-3 | II-102 | II-163 |
| T1a-633 | I-3 | II-102 | II-164 |
| T1a-634 | I-3 | II-102 | II-165 |
| T1a-635 | I-3 | II-102 | II-166 |
| T1a-636 | I-3 | II-102 | II-167 |
| T1a-637 | I-3 | II-102 | II-168 |
| T1a-638 | I-3 | II-102 | II-169 |
| T1a-639 | I-3 | II-102 | II-170 |
| T1a-640 | I-3 | II-102 | II-171 |
| T1a-641 | I-3 | II-102 | II-172 |
| T1a-642 | I-3 | II-102 | II-173 |
| T1a-643 | I-3 | II-102 | II-174 |
| T1a-644 | I-3 | II-102 | II-175 |
| T1a-645 | I-3 | II-102 | II-176 |
| T1a-646 | I-3 | II-102 | II-177 |
| T1a-647 | I-3 | II-102 | II-178 |
| T1a-648 | I-3 | II-102 | II-179 |
| T1a-649 | I-3 | II-102 | II-180 |
| T1a-650 | I-3 | II-102 | II-181 |
| T1a-651 | I-3 | II-102 | II-182 |
| T1a-652 | I-3 | II-102 | II-183 |
| T1a-653 | I-3 | II-102 | II-184 |
| T1a-654 | I-3 | II-102 | II-185 |
| T1a-655 | I-3 | II-102 | II-186 |
| T1a-656 | I-3 | II-102 | II-187 |
| T1a-657 | I-3 | II-102 | II-188 |
| T1a-658 | I-3 | II-102 | II-189 |
| T1a-659 | I-3 | II-102 | II-190 |
| T1a-660 | I-3 | II-102 | II-191 |
| T1a-661 | I-3 | II-102 | II-192 |
| T1a-662 | I-3 | II-102 | II-193 |
| T1a-663 | I-3 | II-102 | II-194 |
| T1a-664 | I-3 | II-102 | II-195 |
| T1a-665 | I-3 | II-102 | II-196 |
| T1a-666 | I-3 | II-102 | II-197 |
| T1a-667 | I-3 | II-102 | II-198 |
| T1a-668 | I-3 | II-102 | II-199 |
| T1a-669 | I-3 | II-102 | II-200 |
| T1a-670 | I-3 | II-102 | II-201 |
| T1a-671 | I-3 | II-102 | II-202 |
| T1a-672 | I-3 | II-102 | II-203 |
| T1a-673 | I-3 | II-103 | II-148 |
| T1a-674 | I-3 | II-103 | II-149 |
| T1a-675 | I-3 | II-103 | II-150 |
| T1a-676 | I-3 | II-103 | II-151 |
| T1a-677 | I-3 | II-103 | II-152 |
| T1a-678 | I-3 | II-103 | II-153 |
| T1a-679 | I-3 | II-103 | II-154 |
| T1a-680 | I-3 | II-103 | II-155 |
| T1a-681 | I-3 | II-103 | II-156 |
| T1a-682 | I-3 | II-103 | II-157 |
| T1a-683 | I-3 | II-103 | II-158 |
| T1a-684 | I-3 | II-103 | II-159 |
| T1a-685 | I-3 | II-103 | II-160 |
| T1a-686 | I-3 | II-103 | II-161 |
| T1a-687 | I-3 | II-103 | II-162 |
| T1a-688 | I-3 | II-103 | II-163 |
| T1a-689 | I-3 | II-103 | II-164 |
| T1a-690 | I-3 | II-103 | II-165 |
| T1a-691 | I-3 | II-103 | II-166 |
| T1a-692 | I-3 | II-103 | II-167 |
| T1a-693 | I-3 | II-103 | II-168 |
| T1a-694 | I-3 | II-103 | II-169 |
| T1a-695 | I-3 | II-103 | II-170 |
| T1a-696 | I-3 | II-103 | II-171 |
| T1a-697 | I-3 | II-103 | II-172 |
| T1a-698 | I-3 | II-103 | II-173 |
| T1a-699 | I-3 | II-103 | II-174 |
| T1a-700 | I-3 | II-103 | II-175 |
| T1a-701 | I-3 | II-103 | II-176 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-702 | I-3 | II-103 | II-177 |
| T1a-703 | I-3 | II-103 | II-178 |
| T1a-704 | I-3 | II-103 | II-179 |
| T1a-705 | I-3 | II-103 | II-180 |
| T1a-706 | I-3 | II-103 | II-181 |
| T1a-707 | I-3 | II-103 | II-182 |
| T1a-708 | I-3 | II-103 | II-183 |
| T1a-709 | I-3 | II-103 | II-184 |
| T1a-710 | I-3 | II-103 | II-185 |
| T1a-711 | I-3 | II-103 | II-186 |
| T1a-712 | I-3 | II-103 | II-187 |
| T1a-713 | I-3 | II-103 | II-188 |
| T1a-714 | I-3 | II-103 | II-189 |
| T1a-715 | I-3 | II-103 | II-190 |
| T1a-716 | I-3 | II-103 | II-191 |
| T1a-717 | I-3 | II-103 | II-192 |
| T1a-718 | I-3 | II-103 | II-193 |
| T1a-719 | I-3 | II-103 | II-194 |
| T1a-720 | I-3 | II-103 | II-195 |
| T1a-721 | I-3 | II-103 | II-196 |
| T1a-722 | I-3 | II-103 | II-197 |
| T1a-723 | I-3 | II-103 | II-198 |
| T1a-724 | I-3 | II-103 | II-199 |
| T1a-725 | I-3 | II-103 | II-200 |
| T1a-726 | I-3 | II-103 | II-201 |
| T1a-727 | I-3 | II-103 | II-202 |
| T1a-728 | I-3 | II-103 | II-203 |
| T1a-729 | I-3 | II-104 | II-148 |
| T1a-730 | I-3 | II-104 | II-149 |
| T1a-731 | I-3 | II-104 | II-150 |
| T1a-732 | I-3 | II-104 | II-151 |
| T1a-733 | I-3 | II-104 | II-152 |
| T1a-734 | I-3 | II-104 | II-153 |
| T1a-735 | I-3 | II-104 | II-154 |
| T1a-736 | I-3 | II-104 | II-155 |
| T1a-737 | I-3 | II-104 | II-156 |
| T1a-738 | I-3 | II-104 | II-157 |
| T1a-739 | I-3 | II-104 | II-158 |
| T1a-740 | I-3 | II-104 | II-159 |
| T1a-741 | I-3 | II-104 | II-160 |
| T1a-742 | I-3 | II-104 | II-161 |
| T1a-743 | I-3 | II-104 | II-162 |
| T1a-744 | I-3 | II-104 | II-163 |
| T1a-745 | I-3 | II-104 | II-164 |
| T1a-746 | I-3 | II-104 | II-165 |
| T1a-747 | I-3 | II-104 | II-166 |
| T1a-748 | I-3 | II-104 | II-167 |
| T1a-749 | I-3 | II-104 | II-168 |
| T1a-750 | I-3 | II-104 | II-169 |
| T1a-751 | I-3 | II-104 | II-170 |
| T1a-752 | I-3 | II-104 | II-171 |
| T1a-753 | I-3 | II-104 | II-172 |
| T1a-754 | I-3 | II-104 | II-173 |
| T1a-755 | I-3 | II-104 | II-174 |
| T1a-756 | I-3 | II-104 | II-175 |
| T1a-757 | I-3 | II-104 | II-176 |
| T1a-758 | I-3 | II-104 | II-177 |
| T1a-759 | I-3 | II-104 | II-178 |
| T1a-760 | I-3 | II-104 | II-179 |
| T1a-761 | I-3 | II-104 | II-180 |
| T1a-762 | I-3 | II-104 | II-181 |
| T1a-763 | I-3 | II-104 | II-182 |
| T1a-764 | I-3 | II-104 | II-183 |
| T1a-765 | I-3 | II-104 | II-184 |
| T1a-766 | I-3 | II-104 | II-185 |
| T1a-767 | I-3 | II-104 | II-186 |
| T1a-768 | I-3 | II-104 | II-187 |
| T1a-769 | I-3 | II-104 | II-188 |
| T1a-770 | I-3 | II-104 | II-189 |
| T1a-771 | I-3 | II-104 | II-190 |
| T1a-772 | I-3 | II-104 | II-191 |
| T1a-773 | I-3 | II-104 | II-192 |
| T1a-774 | I-3 | II-104 | II-193 |
| T1a-775 | I-3 | II-104 | II-194 |
| T1a-776 | I-3 | II-104 | II-195 |
| T1a-777 | I-3 | II-104 | II-196 |
| T1a-778 | I-3 | II-104 | II-197 |
| T1a-779 | I-3 | II-104 | II-198 |
| T1a-780 | I-3 | II-104 | II-199 |
| T1a-781 | I-3 | II-104 | II-200 |
| T1a-782 | I-3 | II-104 | II-201 |
| T1a-783 | I-3 | II-104 | II-202 |
| T1a-784 | I-3 | II-104 | II-203 |
| T1a-785 | I-3 | II-105 | II-148 |
| T1a-786 | I-3 | II-105 | II-149 |
| T1a-787 | I-3 | II-105 | II-150 |
| T1a-788 | I-3 | II-105 | II-151 |
| T1a-789 | I-3 | II-105 | II-152 |
| T1a-790 | I-3 | II-105 | II-153 |
| T1a-791 | I-3 | II-105 | II-154 |
| T1a-792 | I-3 | II-105 | II-155 |
| T1a-793 | I-3 | II-105 | II-156 |
| T1a-794 | I-3 | II-105 | II-157 |
| T1a-795 | I-3 | II-105 | II-158 |
| T1a-796 | I-3 | II-105 | II-159 |
| T1a-797 | I-3 | II-105 | II-160 |
| T1a-798 | I-3 | II-105 | II-161 |
| T1a-799 | I-3 | II-105 | II-162 |
| T1a-800 | I-3 | II-105 | II-163 |
| T1a-801 | I-3 | II-105 | II-164 |
| T1a-802 | I-3 | II-105 | II-165 |
| T1a-803 | I-3 | II-105 | II-166 |
| T1a-804 | I-3 | II-105 | II-167 |
| T1a-805 | I-3 | II-105 | II-168 |
| T1a-806 | I-3 | II-105 | II-169 |
| T1a-807 | I-3 | II-105 | II-170 |
| T1a-808 | I-3 | II-105 | II-171 |
| T1a-809 | I-3 | II-105 | II-172 |
| T1a-810 | I-3 | II-105 | II-173 |
| T1a-811 | I-3 | II-105 | II-174 |
| T1a-812 | I-3 | II-105 | II-175 |
| T1a-813 | I-3 | II-105 | II-176 |
| T1a-814 | I-3 | II-105 | II-177 |
| T1a-815 | I-3 | II-105 | II-178 |
| T1a-816 | I-3 | II-105 | II-179 |
| T1a-817 | I-3 | II-105 | II-180 |
| T1a-818 | I-3 | II-105 | II-181 |
| T1a-819 | I-3 | II-105 | II-182 |
| T1a-820 | I-3 | II-105 | II-183 |
| T1a-821 | I-3 | II-105 | II-184 |
| T1a-822 | I-3 | II-105 | II-185 |
| T1a-823 | I-3 | II-105 | II-186 |
| T1a-824 | I-3 | II-105 | II-187 |
| T1a-825 | I-3 | II-105 | II-188 |
| T1a-826 | I-3 | II-105 | II-189 |
| T1a-827 | I-3 | II-105 | II-190 |
| T1a-828 | I-3 | II-105 | II-191 |
| T1a-829 | I-3 | II-105 | II-192 |
| T1a-830 | I-3 | II-105 | II-193 |
| T1a-831 | I-3 | II-105 | II-194 |
| T1a-832 | I-3 | II-105 | II-195 |
| T1a-833 | I-3 | II-105 | II-196 |
| T1a-834 | I-3 | II-105 | II-197 |
| T1a-835 | I-3 | II-105 | II-198 |
| T1a-836 | I-3 | II-105 | II-199 |
| T1a-837 | I-3 | II-105 | II-200 |
| T1a-838 | I-3 | II-105 | II-201 |
| T1a-839 | I-3 | II-105 | II-202 |
| T1a-840 | I-3 | II-105 | II-203 |
| T1a-841 | I-3 | II-106 | II-148 |
| T1a-842 | I-3 | II-106 | II-149 |
| T1a-843 | I-3 | II-106 | II-150 |
| T1a-844 | I-3 | II-106 | II-151 |
| T1a-845 | I-3 | II-106 | II-152 |
| T1a-846 | I-3 | II-106 | II-153 |
| T1a-847 | I-3 | II-106 | II-154 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-848 | I-3 | II-106 | II-155 |
| T1a-849 | I-3 | II-106 | II-156 |
| T1a-850 | I-3 | II-106 | II-157 |
| T1a-851 | I-3 | II-106 | II-158 |
| T1a-852 | I-3 | II-106 | II-159 |
| T1a-853 | I-3 | II-106 | II-160 |
| T1a-854 | I-3 | II-106 | II-161 |
| T1a-855 | I-3 | II-106 | II-162 |
| T1a-856 | I-3 | II-106 | II-163 |
| T1a-857 | I-3 | II-106 | II-164 |
| T1a-858 | I-3 | II-106 | II-165 |
| T1a-859 | I-3 | II-106 | II-166 |
| T1a-860 | I-3 | II-106 | II-167 |
| T1a-861 | I-3 | II-106 | II-168 |
| T1a-862 | I-3 | II-106 | II-169 |
| T1a-863 | I-3 | II-106 | II-170 |
| T1a-864 | I-3 | II-106 | II-171 |
| T1a-865 | I-3 | II-106 | II-172 |
| T1a-866 | I-3 | II-106 | II-173 |
| T1a-867 | I-3 | II-106 | II-174 |
| T1a-868 | I-3 | II-106 | II-175 |
| T1a-869 | I-3 | II-106 | II-176 |
| T1a-870 | I-3 | II-106 | II-177 |
| T1a-871 | I-3 | II-106 | II-178 |
| T1a-872 | I-3 | II-106 | II-179 |
| T1a-873 | I-3 | II-106 | II-180 |
| T1a-874 | I-3 | II-106 | II-181 |
| T1a-875 | I-3 | II-106 | II-182 |
| T1a-876 | I-3 | II-106 | II-183 |
| T1a-877 | I-3 | II-106 | II-184 |
| T1a-878 | I-3 | II-106 | II-185 |
| T1a-879 | I-3 | II-106 | II-186 |
| T1a-880 | I-3 | II-106 | II-187 |
| T1a-881 | I-3 | II-106 | II-188 |
| T1a-882 | I-3 | II-106 | II-189 |
| T1a-883 | I-3 | II-106 | II-190 |
| T1a-884 | I-3 | II-106 | II-191 |
| T1a-885 | I-3 | II-106 | II-192 |
| T1a-886 | I-3 | II-106 | II-193 |
| T1a-887 | I-3 | II-106 | II-194 |
| T1a-888 | I-3 | II-106 | II-195 |
| T1a-889 | I-3 | II-106 | II-196 |
| T1a-890 | I-3 | II-106 | II-197 |
| T1a-891 | I-3 | II-106 | II-198 |
| T1a-892 | I-3 | II-106 | II-199 |
| T1a-893 | I-3 | II-106 | II-200 |
| T1a-894 | I-3 | II-106 | II-201 |
| T1a-895 | I-3 | II-106 | II-202 |
| T1a-896 | I-3 | II-106 | II-203 |
| T1a-897 | I-3 | II-107 | II-148 |
| T1a-898 | I-3 | II-107 | II-149 |
| T1a-899 | I-3 | II-107 | II-150 |
| T1a-900 | I-3 | II-107 | II-151 |
| T1a-901 | I-3 | II-107 | II-152 |
| T1a-902 | I-3 | II-107 | II-153 |
| T1a-903 | I-3 | II-107 | II-154 |
| T1a-904 | I-3 | II-107 | II-155 |
| T1a-905 | I-3 | II-107 | II-156 |
| T1a-906 | I-3 | II-107 | II-157 |
| T1a-907 | I-3 | II-107 | II-158 |
| T1a-908 | I-3 | II-107 | II-159 |
| T1a-909 | I-3 | II-107 | II-160 |
| T1a-910 | I-3 | II-107 | II-161 |
| T1a-911 | I-3 | II-107 | II-162 |
| T1a-912 | I-3 | II-107 | II-163 |
| T1a-913 | I-3 | II-107 | II-164 |
| T1a-914 | I-3 | II-107 | II-165 |
| T1a-915 | I-3 | II-107 | II-166 |
| T1a-916 | I-3 | II-107 | II-167 |
| T1a-917 | I-3 | II-107 | II-168 |
| T1a-918 | I-3 | II-107 | II-169 |
| T1a-919 | I-3 | II-107 | II-170 |
| T1a-920 | I-3 | II-107 | II-171 |
| T1a-921 | I-3 | II-107 | II-172 |
| T1a-922 | I-3 | II-107 | II-173 |
| T1a-923 | I-3 | II-107 | II-174 |
| T1a-924 | I-3 | II-107 | II-175 |
| T1a-925 | I-3 | II-107 | II-176 |
| T1a-926 | I-3 | II-107 | II-177 |
| T1a-927 | I-3 | II-107 | II-178 |
| T1a-928 | I-3 | II-107 | II-179 |
| T1a-929 | I-3 | II-107 | II-180 |
| T1a-930 | I-3 | II-107 | II-181 |
| T1a-931 | I-3 | II-107 | II-182 |
| T1a-932 | I-3 | II-107 | II-183 |
| T1a-933 | I-3 | II-107 | II-184 |
| T1a-934 | I-3 | II-107 | II-185 |
| T1a-935 | I-3 | II-107 | II-186 |
| T1a-936 | I-3 | II-107 | II-187 |
| T1a-937 | I-3 | II-107 | II-188 |
| T1a-938 | I-3 | II-107 | II-189 |
| T1a-939 | I-3 | II-107 | II-190 |
| T1a-940 | I-3 | II-107 | II-191 |
| T1a-941 | I-3 | II-107 | II-192 |
| T1a-942 | I-3 | II-107 | II-193 |
| T1a-943 | I-3 | II-107 | II-194 |
| T1a-944 | I-3 | II-107 | II-195 |
| T1a-945 | I-3 | II-107 | II-196 |
| T1a-946 | I-3 | II-107 | II-197 |
| T1a-947 | I-3 | II-107 | II-198 |
| T1a-948 | I-3 | II-107 | II-199 |
| T1a-949 | I-3 | II-107 | II-200 |
| T1a-950 | I-3 | II-107 | II-201 |
| T1a-951 | I-3 | II-107 | II-202 |
| T1a-952 | I-3 | II-107 | II-203 |
| T1a-953 | I-3 | II-108 | II-148 |
| T1a-954 | I-3 | II-108 | II-149 |
| T1a-955 | I-3 | II-108 | II-150 |
| T1a-956 | I-3 | II-108 | II-151 |
| T1a-957 | I-3 | II-108 | II-152 |
| T1a-958 | I-3 | II-108 | II-153 |
| T1a-959 | I-3 | II-108 | II-154 |
| T1a-960 | I-3 | II-108 | II-155 |
| T1a-961 | I-3 | II-108 | II-156 |
| T1a-962 | I-3 | II-108 | II-157 |
| T1a-963 | I-3 | II-108 | II-158 |
| T1a-964 | I-3 | II-108 | II-159 |
| T1a-965 | I-3 | II-108 | II-160 |
| T1a-966 | I-3 | II-108 | II-161 |
| T1a-967 | I-3 | II-108 | II-162 |
| T1a-968 | I-3 | II-108 | II-163 |
| T1a-969 | I-3 | II-108 | II-164 |
| T1a-970 | I-3 | II-108 | II-165 |
| T1a-971 | I-3 | II-108 | II-166 |
| T1a-972 | I-3 | II-108 | II-167 |
| T1a-973 | I-3 | II-108 | II-168 |
| T1a-974 | I-3 | II-108 | II-169 |
| T1a-975 | I-3 | II-108 | II-170 |
| T1a-976 | I-3 | II-108 | II-171 |
| T1a-977 | I-3 | II-108 | II-172 |
| T1a-978 | I-3 | II-108 | II-173 |
| T1a-979 | I-3 | II-108 | II-174 |
| T1a-980 | I-3 | II-108 | II-175 |
| T1a-981 | I-3 | II-108 | II-176 |
| T1a-982 | I-3 | II-108 | II-177 |
| T1a-983 | I-3 | II-108 | II-178 |
| T1a-984 | I-3 | II-108 | II-179 |
| T1a-985 | I-3 | II-108 | II-180 |
| T1a-986 | I-3 | II-108 | II-181 |
| T1a-987 | I-3 | II-108 | II-182 |
| T1a-988 | I-3 | II-108 | II-183 |
| T1a-989 | I-3 | II-108 | II-184 |
| T1a-990 | I-3 | II-108 | II-185 |
| T1a-991 | I-3 | II-108 | II-186 |
| T1a-992 | I-3 | II-108 | II-187 |
| T1a-993 | I-3 | II-108 | II-188 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-994 | I-3 | II-108 | II-189 |
| T1a-995 | I-3 | II-108 | II-190 |
| T1a-996 | I-3 | II-108 | II-191 |
| T1a-997 | I-3 | II-108 | II-192 |
| T1a-998 | I-3 | II-108 | II-193 |
| T1a-999 | I-3 | II-108 | II-194 |
| T1a-1000 | I-3 | II-108 | II-195 |
| T1a-1001 | I-3 | II-108 | II-196 |
| T1a-1002 | I-3 | II-108 | II-197 |
| T1a-1003 | I-3 | II-108 | II-198 |
| T1a-1004 | I-3 | II-108 | II-199 |
| T1a-1005 | I-3 | II-108 | II-200 |
| T1a-1006 | I-3 | II-108 | II-201 |
| T1a-1007 | I-3 | II-108 | II-202 |
| T1a-1008 | I-3 | II-108 | II-203 |
| T1a-1009 | I-3 | II-109 | II-148 |
| T1a-1010 | I-3 | II-109 | II-149 |
| T1a-1011 | I-3 | II-109 | II-150 |
| T1a-1012 | I-3 | II-109 | II-151 |
| T1a-1013 | I-3 | II-109 | II-152 |
| T1a-1014 | I-3 | II-109 | II-153 |
| T1a-1015 | I-3 | II-109 | II-154 |
| T1a-1016 | I-3 | II-109 | II-155 |
| T1a-1017 | I-3 | II-109 | II-156 |
| T1a-1018 | I-3 | II-109 | II-157 |
| T1a-1019 | I-3 | II-109 | II-158 |
| T1a-1020 | I-3 | II-109 | II-159 |
| T1a-1021 | I-3 | II-109 | II-160 |
| T1a-1022 | I-3 | II-109 | II-161 |
| T1a-1023 | I-3 | II-109 | II-162 |
| T1a-1024 | I-3 | II-109 | II-163 |
| T1a-1025 | I-3 | II-109 | II-164 |
| T1a-1026 | I-3 | II-109 | II-165 |
| T1a-1027 | I-3 | II-109 | II-166 |
| T1a-1028 | I-3 | II-109 | II-167 |
| T1a-1029 | I-3 | II-109 | II-168 |
| T1a-1030 | I-3 | II-109 | II-169 |
| T1a-1031 | I-3 | II-109 | II-170 |
| T1a-1032 | I-3 | II-109 | II-171 |
| T1a-1033 | I-3 | II-109 | II-172 |
| T1a-1034 | I-3 | II-109 | II-173 |
| T1a-1035 | I-3 | II-109 | II-174 |
| T1a-1036 | I-3 | II-109 | II-175 |
| T1a-1037 | I-3 | II-109 | II-176 |
| T1a-1038 | I-3 | II-109 | II-177 |
| T1a-1039 | I-3 | II-109 | II-178 |
| T1a-1040 | I-3 | II-109 | II-179 |
| T1a-1041 | I-3 | II-109 | II-180 |
| T1a-1042 | I-3 | II-109 | II-181 |
| T1a-1043 | I-3 | II-109 | II-182 |
| T1a-1044 | I-3 | II-109 | II-183 |
| T1a-1045 | I-3 | II-109 | II-184 |
| T1a-1046 | I-3 | II-109 | II-185 |
| T1a-1047 | I-3 | II-109 | II-186 |
| T1a-1048 | I-3 | II-109 | II-187 |
| T1a-1049 | I-3 | II-109 | II-188 |
| T1a-1050 | I-3 | II-109 | II-189 |
| T1a-1051 | I-3 | II-109 | II-190 |
| T1a-1052 | I-3 | II-109 | II-191 |
| T1a-1053 | I-3 | II-109 | II-192 |
| T1a-1054 | I-3 | II-109 | II-193 |
| T1a-1055 | I-3 | II-109 | II-194 |
| T1a-1056 | I-3 | II-109 | II-195 |
| T1a-1057 | I-3 | II-109 | II-196 |
| T1a-1058 | I-3 | II-109 | II-197 |
| T1a-1059 | I-3 | II-109 | II-198 |
| T1a-1060 | I-3 | II-109 | II-199 |
| T1a-1061 | I-3 | II-109 | II-200 |
| T1a-1062 | I-3 | II-109 | II-201 |
| T1a-1063 | I-3 | II-109 | II-202 |
| T1a-1064 | I-3 | II-109 | II-203 |
| T1a-1065 | I-3 | II-110 | II-148 |
| T1a-1066 | I-3 | II-110 | II-149 |
| T1a-1067 | I-3 | II-110 | II-150 |
| T1a-1068 | I-3 | II-110 | II-151 |
| T1a-1069 | I-3 | II-110 | II-152 |
| T1a-1070 | I-3 | II-110 | II-153 |
| T1a-1071 | I-3 | II-110 | II-154 |
| T1a-1072 | I-3 | II-110 | II-155 |
| T1a-1073 | I-3 | II-110 | II-156 |
| T1a-1074 | I-3 | II-110 | II-157 |
| T1a-1075 | I-3 | II-110 | II-158 |
| T1a-1076 | I-3 | II-110 | II-159 |
| T1a-1077 | I-3 | II-110 | II-160 |
| T1a-1078 | I-3 | II-110 | II-161 |
| T1a-1079 | I-3 | II-110 | II-162 |
| T1a-1080 | I-3 | II-110 | II-163 |
| T1a-1081 | I-3 | II-110 | II-164 |
| T1a-1082 | I-3 | II-110 | II-165 |
| T1a-1083 | I-3 | II-110 | II-166 |
| T1a-1084 | I-3 | II-110 | II-167 |
| T1a-1085 | I-3 | II-110 | II-168 |
| T1a-1086 | I-3 | II-110 | II-169 |
| T1a-1087 | I-3 | II-110 | II-170 |
| T1a-1088 | I-3 | II-110 | II-171 |
| T1a-1089 | I-3 | II-110 | II-172 |
| T1a-1090 | I-3 | II-110 | II-173 |
| T1a-1091 | I-3 | II-110 | II-174 |
| T1a-1092 | I-3 | II-110 | II-175 |
| T1a-1093 | I-3 | II-110 | II-176 |
| T1a-1094 | I-3 | II-110 | II-177 |
| T1a-1095 | I-3 | II-110 | II-178 |
| T1a-1096 | I-3 | II-110 | II-179 |
| T1a-1097 | I-3 | II-110 | II-180 |
| T1a-1098 | I-3 | II-110 | II-181 |
| T1a-1099 | I-3 | II-110 | II-182 |
| T1a-1100 | I-3 | II-110 | II-183 |
| T1a-1101 | I-3 | II-110 | II-184 |
| T1a-1102 | I-3 | II-110 | II-185 |
| T1a-1103 | I-3 | II-110 | II-186 |
| T1a-1104 | I-3 | II-110 | II-187 |
| T1a-1105 | I-3 | II-110 | II-188 |
| T1a-1106 | I-3 | II-110 | II-189 |
| T1a-1107 | I-3 | II-110 | II-190 |
| T1a-1108 | I-3 | II-110 | II-191 |
| T1a-1109 | I-3 | II-110 | II-192 |
| T1a-1110 | I-3 | II-110 | II-193 |
| T1a-1111 | I-3 | II-110 | II-194 |
| T1a-1112 | I-3 | II-110 | II-195 |
| T1a-1113 | I-3 | II-110 | II-196 |
| T1a-1114 | I-3 | II-110 | II-197 |
| T1a-1115 | I-3 | II-110 | II-198 |
| T1a-1116 | I-3 | II-110 | II-199 |
| T1a-1117 | I-3 | II-110 | II-200 |
| T1a-1118 | I-3 | II-110 | II-201 |
| T1a-1119 | I-3 | II-110 | II-202 |
| T1a-1120 | I-3 | II-110 | II-203 |
| T1a-1121 | I-3 | II-111 | II-148 |
| T1a-1122 | I-3 | II-111 | II-149 |
| T1a-1123 | I-3 | II-111 | II-150 |
| T1a-1124 | I-3 | II-111 | II-151 |
| T1a-1125 | I-3 | II-111 | II-152 |
| T1a-1126 | I-3 | II-111 | II-153 |
| T1a-1127 | I-3 | II-111 | II-154 |
| T1a-1128 | I-3 | II-111 | II-155 |
| T1a-1129 | I-3 | II-111 | II-156 |
| T1a-1130 | I-3 | II-111 | II-157 |
| T1a-1131 | I-3 | II-111 | II-158 |
| T1a-1132 | I-3 | II-111 | II-159 |
| T1a-1133 | I-3 | II-111 | II-160 |
| T1a-1134 | I-3 | II-111 | II-161 |
| T1a-1135 | I-3 | II-111 | II-162 |
| T1a-1136 | I-3 | II-111 | II-163 |
| T1a-1137 | I-3 | II-111 | II-164 |
| T1a-1138 | I-3 | II-111 | II-165 |
| T1a-1139 | I-3 | II-111 | II-166 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-1140 | I-3 | II-111 | II-167 |
| T1a-1141 | I-3 | II-111 | II-168 |
| T1a-1142 | I-3 | II-111 | II-169 |
| T1a-1143 | I-3 | II-111 | II-170 |
| T1a-1144 | I-3 | II-111 | II-171 |
| T1a-1145 | I-3 | II-111 | II-172 |
| T1a-1146 | I-3 | II-111 | II-173 |
| T1a-1147 | I-3 | II-111 | II-174 |
| T1a-1148 | I-3 | II-111 | II-175 |
| T1a-1149 | I-3 | II-111 | II-176 |
| T1a-1150 | I-3 | II-111 | II-177 |
| T1a-1151 | I-3 | II-111 | II-178 |
| T1a-1152 | I-3 | II-111 | II-179 |
| T1a-1153 | I-3 | II-111 | II-180 |
| T1a-1154 | I-3 | II-111 | II-181 |
| T1a-1155 | I-3 | II-111 | II-182 |
| T1a-1156 | I-3 | II-111 | II-183 |
| T1a-1157 | I-3 | II-111 | II-184 |
| T1a-1158 | I-3 | II-111 | II-185 |
| T1a-1159 | I-3 | II-111 | II-186 |
| T1a-1160 | I-3 | II-111 | II-187 |
| T1a-1161 | I-3 | II-111 | II-188 |
| T1a-1162 | I-3 | II-111 | II-189 |
| T1a-1163 | I-3 | II-111 | II-190 |
| T1a-1164 | I-3 | II-111 | II-191 |
| T1a-1165 | I-3 | II-111 | II-192 |
| T1a-1166 | I-3 | II-111 | II-193 |
| T1a-1167 | I-3 | II-111 | II-194 |
| T1a-1168 | I-3 | II-111 | II-195 |
| T1a-1169 | I-3 | II-111 | II-196 |
| T1a-1170 | I-3 | II-111 | II-197 |
| T1a-1171 | I-3 | II-111 | II-198 |
| T1a-1172 | I-3 | II-111 | II-199 |
| T1a-1173 | I-3 | II-111 | II-200 |
| T1a-1174 | I-3 | II-111 | II-201 |
| T1a-1175 | I-3 | II-111 | II-202 |
| T1a-1176 | I-3 | II-111 | II-203 |
| T1a-1177 | I-3 | II-112 | II-148 |
| T1a-1178 | I-3 | II-112 | II-149 |
| T1a-1179 | I-3 | II-112 | II-150 |
| T1a-1180 | I-3 | II-112 | II-151 |
| T1a-1181 | I-3 | II-112 | II-152 |
| T1a-1182 | I-3 | II-112 | II-153 |
| T1a-1183 | I-3 | II-112 | II-154 |
| T1a-1184 | I-3 | II-112 | II-155 |
| T1a-1185 | I-3 | II-112 | II-156 |
| T1a-1186 | I-3 | II-112 | II-157 |
| T1a-1187 | I-3 | II-112 | II-158 |
| T1a-1188 | I-3 | II-112 | II-159 |
| T1a-1189 | I-3 | II-112 | II-160 |
| T1a-1190 | I-3 | II-112 | II-161 |
| T1a-1191 | I-3 | II-112 | II-162 |
| T1a-1192 | I-3 | II-112 | II-163 |
| T1a-1193 | I-3 | II-112 | II-164 |
| T1a-1194 | I-3 | II-112 | II-165 |
| T1a-1195 | I-3 | II-112 | II-166 |
| T1a-1196 | I-3 | II-112 | II-167 |
| T1a-1197 | I-3 | II-112 | II-168 |
| T1a-1198 | I-3 | II-112 | II-169 |
| T1a-1199 | I-3 | II-112 | II-170 |
| T1a-1200 | I-3 | II-112 | II-171 |
| T1a-1201 | I-3 | II-112 | II-172 |
| T1a-1202 | I-3 | II-112 | II-173 |
| T1a-1203 | I-3 | II-112 | II-174 |
| T1a-1204 | I-3 | II-112 | II-175 |
| T1a-1205 | I-3 | II-112 | II-176 |
| T1a-1206 | I-3 | II-112 | II-177 |
| T1a-1207 | I-3 | II-112 | II-178 |
| T1a-1208 | I-3 | II-112 | II-179 |
| T1a-1209 | I-3 | II-112 | II-180 |
| T1a-1210 | I-3 | II-112 | II-181 |
| T1a-1211 | I-3 | II-112 | II-182 |
| T1a-1212 | I-3 | II-112 | II-183 |
| T1a-1213 | I-3 | II-112 | II-184 |
| T1a-1214 | I-3 | II-112 | II-185 |
| T1a-1215 | I-3 | II-112 | II-186 |
| T1a-1216 | I-3 | II-112 | II-187 |
| T1a-1217 | I-3 | II-112 | II-188 |
| T1a-1218 | I-3 | II-112 | II-189 |
| T1a-1219 | I-3 | II-112 | II-190 |
| T1a-1220 | I-3 | II-112 | II-191 |
| T1a-1221 | I-3 | II-112 | II-192 |
| T1a-1222 | I-3 | II-112 | II-193 |
| T1a-1223 | I-3 | II-112 | II-194 |
| T1a-1224 | I-3 | II-112 | II-195 |
| T1a-1225 | I-3 | II-112 | II-196 |
| T1a-1226 | I-3 | II-112 | II-197 |
| T1a-1227 | I-3 | II-112 | II-198 |
| T1a-1228 | I-3 | II-112 | II-199 |
| T1a-1229 | I-3 | II-112 | II-200 |
| T1a-1230 | I-3 | II-112 | II-201 |
| T1a-1231 | I-3 | II-112 | II-202 |
| T1a-1232 | I-3 | II-112 | II-203 |
| T1a-1233 | I-3 | II-113 | II-148 |
| T1a-1234 | I-3 | II-113 | II-149 |
| T1a-1235 | I-3 | II-113 | II-150 |
| T1a-1236 | I-3 | II-113 | II-151 |
| T1a-1237 | I-3 | II-113 | II-152 |
| T1a-1238 | I-3 | II-113 | II-153 |
| T1a-1239 | I-3 | II-113 | II-154 |
| T1a-1240 | I-3 | II-113 | II-155 |
| T1a-1241 | I-3 | II-113 | II-156 |
| T1a-1242 | I-3 | II-113 | II-157 |
| T1a-1243 | I-3 | II-113 | II-158 |
| T1a-1244 | I-3 | II-113 | II-159 |
| T1a-1245 | I-3 | II-113 | II-160 |
| T1a-1246 | I-3 | II-113 | II-161 |
| T1a-1247 | I-3 | II-113 | II-162 |
| T1a-1248 | I-3 | II-113 | II-163 |
| T1a-1249 | I-3 | II-113 | II-164 |
| T1a-1250 | I-3 | II-113 | II-165 |
| T1a-1251 | I-3 | II-113 | II-166 |
| T1a-1252 | I-3 | II-113 | II-167 |
| T1a-1253 | I-3 | II-113 | II-168 |
| T1a-1254 | I-3 | II-113 | II-169 |
| T1a-1255 | I-3 | II-113 | II-170 |
| T1a-1256 | I-3 | II-113 | II-171 |
| T1a-1257 | I-3 | II-113 | II-172 |
| T1a-1258 | I-3 | II-113 | II-173 |
| T1a-1259 | I-3 | II-113 | II-174 |
| T1a-1260 | I-3 | II-113 | II-175 |
| T1a-1261 | I-3 | II-113 | II-176 |
| T1a-1262 | I-3 | II-113 | II-177 |
| T1a-1263 | I-3 | II-113 | II-178 |
| T1a-1264 | I-3 | II-113 | II-179 |
| T1a-1265 | I-3 | II-113 | II-180 |
| T1a-1266 | I-3 | II-113 | II-181 |
| T1a-1267 | I-3 | II-113 | II-182 |
| T1a-1268 | I-3 | II-113 | II-183 |
| T1a-1269 | I-3 | II-113 | II-184 |
| T1a-1270 | I-3 | II-113 | II-185 |
| T1a-1271 | I-3 | II-113 | II-186 |
| T1a-1272 | I-3 | II-113 | II-187 |
| T1a-1273 | I-3 | II-113 | II-188 |
| T1a-1274 | I-3 | II-113 | II-189 |
| T1a-1275 | I-3 | II-113 | II-190 |
| T1a-1276 | I-3 | II-113 | II-191 |
| T1a-1277 | I-3 | II-113 | II-192 |
| T1a-1278 | I-3 | II-113 | II-193 |
| T1a-1279 | I-3 | II-113 | II-194 |
| T1a-1280 | I-3 | II-113 | II-195 |
| T1a-1281 | I-3 | II-113 | II-196 |
| T1a-1282 | I-3 | II-113 | II-197 |
| T1a-1283 | I-3 | II-113 | II-198 |
| T1a-1284 | I-3 | II-113 | II-199 |
| T1a-1285 | I-3 | II-113 | II-200 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-1286 | I-3 | II-113 | II-201 |
| T1a-1287 | I-3 | II-113 | II-202 |
| T1a-1288 | I-3 | II-113 | II-203 |
| T1a-1289 | I-3 | II-114 | II-148 |
| T1a-1290 | I-3 | II-114 | II-149 |
| T1a-1291 | I-3 | II-114 | II-150 |
| T1a-1292 | I-3 | II-114 | II-151 |
| T1a-1293 | I-3 | II-114 | II-152 |
| T1a-1294 | I-3 | II-114 | II-153 |
| T1a-1295 | I-3 | II-114 | II-154 |
| T1a-1296 | I-3 | II-114 | II-155 |
| T1a-1297 | I-3 | II-114 | II-156 |
| T1a-1298 | I-3 | II-114 | II-157 |
| T1a-1299 | I-3 | II-114 | II-158 |
| T1a-1300 | I-3 | II-114 | II-159 |
| T1a-1301 | I-3 | II-114 | II-160 |
| T1a-1302 | I-3 | II-114 | II-161 |
| T1a-1303 | I-3 | II-114 | II-162 |
| T1a-1304 | I-3 | II-114 | II-163 |
| T1a-1305 | I-3 | II-114 | II-164 |
| T1a-1306 | I-3 | II-114 | II-165 |
| T1a-1307 | I-3 | II-114 | II-166 |
| T1a-1308 | I-3 | II-114 | II-167 |
| T1a-1309 | I-3 | II-114 | II-168 |
| T1a-1310 | I-3 | II-114 | II-169 |
| T1a-1311 | I-3 | II-114 | II-170 |
| T1a-1312 | I-3 | II-114 | II-171 |
| T1a-1313 | I-3 | II-114 | II-172 |
| T1a-1314 | I-3 | II-114 | II-173 |
| T1a-1315 | I-3 | II-114 | II-174 |
| T1a-1316 | I-3 | II-114 | II-175 |
| T1a-1317 | I-3 | II-114 | II-176 |
| T1a-1318 | I-3 | II-114 | II-177 |
| T1a-1319 | I-3 | II-114 | II-178 |
| T1a-1320 | I-3 | II-114 | II-179 |
| T1a-1321 | I-3 | II-114 | II-180 |
| T1a-1322 | I-3 | II-114 | II-181 |
| T1a-1323 | I-3 | II-114 | II-182 |
| T1a-1324 | I-3 | II-114 | II-183 |
| T1a-1325 | I-3 | II-114 | II-184 |
| T1a-1326 | I-3 | II-114 | II-185 |
| T1a-1327 | I-3 | II-114 | II-186 |
| T1a-1328 | I-3 | II-114 | II-187 |
| T1a-1329 | I-3 | II-114 | II-188 |
| T1a-1330 | I-3 | II-114 | II-189 |
| T1a-1331 | I-3 | II-114 | II-190 |
| T1a-1332 | I-3 | II-114 | II-191 |
| T1a-1333 | I-3 | II-114 | II-192 |
| T1a-1334 | I-3 | II-114 | II-193 |
| T1a-1335 | I-3 | II-114 | II-194 |
| T1a-1336 | I-3 | II-114 | II-195 |
| T1a-1337 | I-3 | II-114 | II-196 |
| T1a-1338 | I-3 | II-114 | II-197 |
| T1a-1339 | I-3 | II-114 | II-198 |
| T1a-1340 | I-3 | II-114 | II-199 |
| T1a-1341 | I-3 | II-114 | II-200 |
| T1a-1342 | I-3 | II-114 | II-201 |
| T1a-1343 | I-3 | II-114 | II-202 |
| T1a-1344 | I-3 | II-114 | II-203 |
| T1a-1345 | I-3 | II-115 | II-148 |
| T1a-1346 | I-3 | II-115 | II-149 |
| T1a-1347 | I-3 | II-115 | II-150 |
| T1a-1348 | I-3 | II-115 | II-151 |
| T1a-1349 | I-3 | II-115 | II-152 |
| T1a-1350 | I-3 | II-115 | II-153 |
| T1a-1351 | I-3 | II-115 | II-154 |
| T1a-1352 | I-3 | II-115 | II-155 |
| T1a-1353 | I-3 | II-115 | II-156 |
| T1a-1354 | I-3 | II-115 | II-157 |
| T1a-1355 | I-3 | II-115 | II-158 |
| T1a-1356 | I-3 | II-115 | II-159 |
| T1a-1357 | I-3 | II-115 | II-160 |
| T1a-1358 | I-3 | II-115 | II-161 |
| T1a-1359 | I-3 | II-115 | II-162 |
| T1a-1360 | I-3 | II-115 | II-163 |
| T1a-1361 | I-3 | II-115 | II-164 |
| T1a-1362 | I-3 | II-115 | II-165 |
| T1a-1363 | I-3 | II-115 | II-166 |
| T1a-1364 | I-3 | II-115 | II-167 |
| T1a-1365 | I-3 | II-115 | II-168 |
| T1a-1366 | I-3 | II-115 | II-169 |
| T1a-1367 | I-3 | II-115 | II-170 |
| T1a-1368 | I-3 | II-115 | II-171 |
| T1a-1369 | I-3 | II-115 | II-172 |
| T1a-1370 | I-3 | II-115 | II-173 |
| T1a-1371 | I-3 | II-115 | II-174 |
| T1a-1372 | I-3 | II-115 | II-175 |
| T1a-1373 | I-3 | II-115 | II-176 |
| T1a-1374 | I-3 | II-115 | II-177 |
| T1a-1375 | I-3 | II-115 | II-178 |
| T1a-1376 | I-3 | II-115 | II-179 |
| T1a-1377 | I-3 | II-115 | II-180 |
| T1a-1378 | I-3 | II-115 | II-181 |
| T1a-1379 | I-3 | II-115 | II-182 |
| T1a-1380 | I-3 | II-115 | II-183 |
| T1a-1381 | I-3 | II-115 | II-184 |
| T1a-1382 | I-3 | II-115 | II-185 |
| T1a-1383 | I-3 | II-115 | II-186 |
| T1a-1384 | I-3 | II-115 | II-187 |
| T1a-1385 | I-3 | II-115 | II-188 |
| T1a-1386 | I-3 | II-115 | II-189 |
| T1a-1387 | I-3 | II-115 | II-190 |
| T1a-1388 | I-3 | II-115 | II-191 |
| T1a-1389 | I-3 | II-115 | II-192 |
| T1a-1390 | I-3 | II-115 | II-193 |
| T1a-1391 | I-3 | II-115 | II-194 |
| T1a-1392 | I-3 | II-115 | II-195 |
| T1a-1393 | I-3 | II-115 | II-196 |
| T1a-1394 | I-3 | II-115 | II-197 |
| T1a-1395 | I-3 | II-115 | II-198 |
| T1a-1396 | I-3 | II-115 | II-199 |
| T1a-1397 | I-3 | II-115 | II-200 |
| T1a-1398 | I-3 | II-115 | II-201 |
| T1a-1399 | I-3 | II-115 | II-202 |
| T1a-1400 | I-3 | II-115 | II-203 |
| T1a-1401 | I-3 | II-116 | II-148 |
| T1a-1402 | I-3 | II-116 | II-149 |
| T1a-1403 | I-3 | II-116 | II-150 |
| T1a-1404 | I-3 | II-116 | II-151 |
| T1a-1405 | I-3 | II-116 | II-152 |
| T1a-1406 | I-3 | II-116 | II-153 |
| T1a-1407 | I-3 | II-116 | II-154 |
| T1a-1408 | I-3 | II-116 | II-155 |
| T1a-1409 | I-3 | II-116 | II-156 |
| T1a-1410 | I-3 | II-116 | II-157 |
| T1a-1411 | I-3 | II-116 | II-158 |
| T1a-1412 | I-3 | II-116 | II-159 |
| T1a-1413 | I-3 | II-116 | II-160 |
| T1a-1414 | I-3 | II-116 | II-161 |
| T1a-1415 | I-3 | II-116 | II-162 |
| T1a-1416 | I-3 | II-116 | II-163 |
| T1a-1417 | I-3 | II-116 | II-164 |
| T1a-1418 | I-3 | II-116 | II-165 |
| T1a-1419 | I-3 | II-116 | II-166 |
| T1a-1420 | I-3 | II-116 | II-167 |
| T1a-1421 | I-3 | II-116 | II-168 |
| T1a-1422 | I-3 | II-116 | II-169 |
| T1a-1423 | I-3 | II-116 | II-170 |
| T1a-1424 | I-3 | II-116 | II-171 |
| T1a-1425 | I-3 | II-116 | II-172 |
| T1a-1426 | I-3 | II-116 | II-173 |
| T1a-1427 | I-3 | II-116 | II-174 |
| T1a-1428 | I-3 | II-116 | II-175 |
| T1a-1429 | I-3 | II-116 | II-176 |
| T1a-1430 | I-3 | II-116 | II-177 |
| T1a-1431 | I-3 | II-116 | II-178 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-1432 | I-3 | II-116 | II-179 |
| T1a-1433 | I-3 | II-116 | II-180 |
| T1a-1434 | I-3 | II-116 | II-181 |
| T1a-1435 | I-3 | II-116 | II-182 |
| T1a-1436 | I-3 | II-116 | II-183 |
| T1a-1437 | I-3 | II-116 | II-184 |
| T1a-1438 | I-3 | II-116 | II-185 |
| T1a-1439 | I-3 | II-116 | II-186 |
| T1a-1440 | I-3 | II-116 | II-187 |
| T1a-1441 | I-3 | II-116 | II-188 |
| T1a-1442 | I-3 | II-116 | II-189 |
| T1a-1443 | I-3 | II-116 | II-190 |
| T1a-1444 | I-3 | II-116 | II-191 |
| T1a-1445 | I-3 | II-116 | II-192 |
| T1a-1446 | I-3 | II-116 | II-193 |
| T1a-1447 | I-3 | II-116 | II-194 |
| T1a-1448 | I-3 | II-116 | II-195 |
| T1a-1449 | I-3 | II-116 | II-196 |
| T1a-1450 | I-3 | II-116 | II-197 |
| T1a-1451 | I-3 | II-116 | II-198 |
| T1a-1452 | I-3 | II-116 | II-199 |
| T1a-1453 | I-3 | II-116 | II-200 |
| T1a-1454 | I-3 | II-116 | II-201 |
| T1a-1455 | I-3 | II-116 | II-202 |
| T1a-1456 | I-3 | II-116 | II-203 |
| T1a-1457 | I-3 | II-117 | II-148 |
| T1a-1458 | I-3 | II-117 | II-149 |
| T1a-1459 | I-3 | II-117 | II-150 |
| T1a-1460 | I-3 | II-117 | II-151 |
| T1a-1461 | I-3 | II-117 | II-152 |
| T1a-1462 | I-3 | II-117 | II-153 |
| T1a-1463 | I-3 | II-117 | II-154 |
| T1a-1464 | I-3 | II-117 | II-155 |
| T1a-1465 | I-3 | II-117 | II-156 |
| T1a-1466 | I-3 | II-117 | II-157 |
| T1a-1467 | I-3 | II-117 | II-158 |
| T1a-1468 | I-3 | II-117 | II-159 |
| T1a-1469 | I-3 | II-117 | II-160 |
| T1a-1470 | I-3 | II-117 | II-161 |
| T1a-1471 | I-3 | II-117 | II-162 |
| T1a-1472 | I-3 | II-117 | II-163 |
| T1a-1473 | I-3 | II-117 | II-164 |
| T1a-1474 | I-3 | II-117 | II-165 |
| T1a-1475 | I-3 | II-117 | II-166 |
| T1a-1476 | I-3 | II-117 | II-167 |
| T1a-1477 | I-3 | II-117 | II-168 |
| T1a-1478 | I-3 | II-117 | II-169 |
| T1a-1479 | I-3 | II-117 | II-170 |
| T1a-1480 | I-3 | II-117 | II-171 |
| T1a-1481 | I-3 | II-117 | II-172 |
| T1a-1482 | I-3 | II-117 | II-173 |
| T1a-1483 | I-3 | II-117 | II-174 |
| T1a-1484 | I-3 | II-117 | II-175 |
| T1a-1485 | I-3 | II-117 | II-176 |
| T1a-1486 | I-3 | II-117 | II-177 |
| T1a-1487 | I-3 | II-117 | II-178 |
| T1a-1488 | I-3 | II-117 | II-179 |
| T1a-1489 | I-3 | II-117 | II-180 |
| T1a-1490 | I-3 | II-117 | II-181 |
| T1a-1491 | I-3 | II-117 | II-182 |
| T1a-1492 | I-3 | II-117 | II-183 |
| T1a-1493 | I-3 | II-117 | II-184 |
| T1a-1494 | I-3 | II-117 | II-185 |
| T1a-1495 | I-3 | II-117 | II-186 |
| T1a-1496 | I-3 | II-117 | II-187 |
| T1a-1497 | I-3 | II-117 | II-188 |
| T1a-1498 | I-3 | II-117 | II-189 |
| T1a-1499 | I-3 | II-117 | II-190 |
| T1a-1500 | I-3 | II-117 | II-191 |
| T1a-1501 | I-3 | II-117 | II-192 |
| T1a-1502 | I-3 | II-117 | II-193 |
| T1a-1503 | I-3 | II-117 | II-194 |
| T1a-1504 | I-3 | II-117 | II-195 |
| T1a-1505 | I-3 | II-117 | II-196 |
| T1a-1506 | I-3 | II-117 | II-197 |
| T1a-1507 | I-3 | II-117 | II-198 |
| T1a-1508 | I-3 | II-117 | II-199 |
| T1a-1509 | I-3 | II-117 | II-200 |
| T1a-1510 | I-3 | II-117 | II-201 |
| T1a-1511 | I-3 | II-117 | II-202 |
| T1a-1512 | I-3 | II-117 | II-203 |
| T1a-1513 | I-3 | II-118 | II-148 |
| T1a-1514 | I-3 | II-118 | II-149 |
| T1a-1515 | I-3 | II-118 | II-150 |
| T1a-1516 | I-3 | II-118 | II-151 |
| T1a-1517 | I-3 | II-118 | II-152 |
| T1a-1518 | I-3 | II-118 | II-153 |
| T1a-1519 | I-3 | II-118 | II-154 |
| T1a-1520 | I-3 | II-118 | II-155 |
| T1a-1521 | I-3 | II-118 | II-156 |
| T1a-1522 | I-3 | II-118 | II-157 |
| T1a-1523 | I-3 | II-118 | II-158 |
| T1a-1524 | I-3 | II-118 | II-159 |
| T1a-1525 | I-3 | II-118 | II-160 |
| T1a-1526 | I-3 | II-118 | II-161 |
| T1a-1527 | I-3 | II-118 | II-162 |
| T1a-1528 | I-3 | II-118 | II-163 |
| T1a-1529 | I-3 | II-118 | II-164 |
| T1a-1530 | I-3 | II-118 | II-165 |
| T1a-1531 | I-3 | II-118 | II-166 |
| T1a-1532 | I-3 | II-118 | II-167 |
| T1a-1533 | I-3 | II-118 | II-168 |
| T1a-1534 | I-3 | II-118 | II-169 |
| T1a-1535 | I-3 | II-118 | II-170 |
| T1a-1536 | I-3 | II-118 | II-171 |
| T1a-1537 | I-3 | II-118 | II-172 |
| T1a-1538 | I-3 | II-118 | II-173 |
| T1a-1539 | I-3 | II-118 | II-174 |
| T1a-1540 | I-3 | II-118 | II-175 |
| T1a-1541 | I-3 | II-118 | II-176 |
| T1a-1542 | I-3 | II-118 | II-177 |
| T1a-1543 | I-3 | II-118 | II-178 |
| T1a-1544 | I-3 | II-118 | II-179 |
| T1a-1545 | I-3 | II-118 | II-180 |
| T1a-1546 | I-3 | II-118 | II-181 |
| T1a-1547 | I-3 | II-118 | II-182 |
| T1a-1548 | I-3 | II-118 | II-183 |
| T1a-1549 | I-3 | II-118 | II-184 |
| T1a-1550 | I-3 | II-118 | II-185 |
| T1a-1551 | I-3 | II-118 | II-186 |
| T1a-1552 | I-3 | II-118 | II-187 |
| T1a-1553 | I-3 | II-118 | II-188 |
| T1a-1554 | I-3 | II-118 | II-189 |
| T1a-1555 | I-3 | II-118 | II-190 |
| T1a-1556 | I-3 | II-118 | II-191 |
| T1a-1557 | I-3 | II-118 | II-192 |
| T1a-1558 | I-3 | II-118 | II-193 |
| T1a-1559 | I-3 | II-118 | II-194 |
| T1a-1560 | I-3 | II-118 | II-195 |
| T1a-1561 | I-3 | II-118 | II-196 |
| T1a-1562 | I-3 | II-118 | II-197 |
| T1a-1563 | I-3 | II-118 | II-198 |
| T1a-1564 | I-3 | II-118 | II-199 |
| T1a-1565 | I-3 | II-118 | II-200 |
| T1a-1566 | I-3 | II-118 | II-201 |
| T1a-1567 | I-3 | II-118 | II-202 |
| T1a-1568 | I-3 | II-118 | II-203 |
| T1a-1569 | I-3 | II-119 | II-148 |
| T1a-1570 | I-3 | II-119 | II-149 |
| T1a-1571 | I-3 | II-119 | II-150 |
| T1a-1572 | I-3 | II-119 | II-151 |
| T1a-1573 | I-3 | II-119 | II-152 |
| T1a-1574 | I-3 | II-119 | II-153 |
| T1a-1575 | I-3 | II-119 | II-154 |
| T1a-1576 | I-3 | II-119 | II-155 |
| T1a-1577 | I-3 | II-119 | II-156 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-1578 | I-3 | II-119 | II-157 |
| T1a-1579 | I-3 | II-119 | II-158 |
| T1a-1580 | I-3 | II-119 | II-159 |
| T1a-1581 | I-3 | II-119 | II-160 |
| T1a-1582 | I-3 | II-119 | II-161 |
| T1a-1583 | I-3 | II-119 | II-162 |
| T1a-1584 | I-3 | II-119 | II-163 |
| T1a-1585 | I-3 | II-119 | II-164 |
| T1a-1586 | I-3 | II-119 | II-165 |
| T1a-1587 | I-3 | II-119 | II-166 |
| T1a-1588 | I-3 | II-119 | II-167 |
| T1a-1589 | I-3 | II-119 | II-168 |
| T1a-1590 | I-3 | II-119 | II-169 |
| T1a-1591 | I-3 | II-119 | II-170 |
| T1a-1592 | I-3 | II-119 | II-171 |
| T1a-1593 | I-3 | II-119 | II-172 |
| T1a-1594 | I-3 | II-119 | II-173 |
| T1a-1595 | I-3 | II-119 | II-174 |
| T1a-1596 | I-3 | II-119 | II-175 |
| T1a-1597 | I-3 | II-119 | II-176 |
| T1a-1598 | I-3 | II-119 | II-177 |
| T1a-1599 | I-3 | II-119 | II-178 |
| T1a-1600 | I-3 | II-119 | II-179 |
| T1a-1601 | I-3 | II-119 | II-180 |
| T1a-1602 | I-3 | II-119 | II-181 |
| T1a-1603 | I-3 | II-119 | II-182 |
| T1a-1604 | I-3 | II-119 | II-183 |
| T1a-1605 | I-3 | II-119 | II-184 |
| T1a-1606 | I-3 | II-119 | II-185 |
| T1a-1607 | I-3 | II-119 | II-186 |
| T1a-1608 | I-3 | II-119 | II-187 |
| T1a-1609 | I-3 | II-119 | II-188 |
| T1a-1610 | I-3 | II-119 | II-189 |
| T1a-1611 | I-3 | II-119 | II-190 |
| T1a-1612 | I-3 | II-119 | II-191 |
| T1a-1613 | I-3 | II-119 | II-192 |
| T1a-1614 | I-3 | II-119 | II-193 |
| T1a-1615 | I-3 | II-119 | II-194 |
| T1a-1616 | I-3 | II-119 | II-195 |
| T1a-1617 | I-3 | II-119 | II-196 |
| T1a-1618 | I-3 | II-119 | II-197 |
| T1a-1619 | I-3 | II-119 | II-198 |
| T1a-1620 | I-3 | II-119 | II-199 |
| T1a-1621 | I-3 | II-119 | II-200 |
| T1a-1622 | I-3 | II-119 | II-201 |
| T1a-1623 | I-3 | II-119 | II-202 |
| T1a-1624 | I-3 | II-119 | II-203 |
| T1a-1625 | I-3 | II-120 | II-148 |
| T1a-1626 | I-3 | II-120 | II-149 |
| T1a-1627 | I-3 | II-120 | II-150 |
| T1a-1628 | I-3 | II-120 | II-151 |
| T1a-1629 | I-3 | II-120 | II-152 |
| T1a-1630 | I-3 | II-120 | II-153 |
| T1a-1631 | I-3 | II-120 | II-154 |
| T1a-1632 | I-3 | II-120 | II-155 |
| T1a-1633 | I-3 | II-120 | II-156 |
| T1a-1634 | I-3 | II-120 | II-157 |
| T1a-1635 | I-3 | II-120 | II-158 |
| T1a-1636 | I-3 | II-120 | II-159 |
| T1a-1637 | I-3 | II-120 | II-160 |
| T1a-1638 | I-3 | II-120 | II-161 |
| T1a-1639 | I-3 | II-120 | II-162 |
| T1a-1640 | I-3 | II-120 | II-163 |
| T1a-1641 | I-3 | II-120 | II-164 |
| T1a-1642 | I-3 | II-120 | II-165 |
| T1a-1643 | I-3 | II-120 | II-166 |
| T1a-1644 | I-3 | II-120 | II-167 |
| T1a-1645 | I-3 | II-120 | II-168 |
| T1a-1646 | I-3 | II-120 | II-169 |
| T1a-1647 | I-3 | II-120 | II-170 |
| T1a-1648 | I-3 | II-120 | II-171 |
| T1a-1649 | I-3 | II-120 | II-172 |
| T1a-1650 | I-3 | II-120 | II-173 |
| T1a-1651 | I-3 | II-120 | II-174 |
| T1a-1652 | I-3 | II-120 | II-175 |
| T1a-1653 | I-3 | II-120 | II-176 |
| T1a-1654 | I-3 | II-120 | II-177 |
| T1a-1655 | I-3 | II-120 | II-178 |
| T1a-1656 | I-3 | II-120 | II-179 |
| T1a-1657 | I-3 | II-120 | II-180 |
| T1a-1658 | I-3 | II-120 | II-181 |
| T1a-1659 | I-3 | II-120 | II-182 |
| T1a-1660 | I-3 | II-120 | II-183 |
| T1a-1661 | I-3 | II-120 | II-184 |
| T1a-1662 | I-3 | II-120 | II-185 |
| T1a-1663 | I-3 | II-120 | II-186 |
| T1a-1664 | I-3 | II-120 | II-187 |
| T1a-1665 | I-3 | II-120 | II-188 |
| T1a-1666 | I-3 | II-120 | II-189 |
| T1a-1667 | I-3 | II-120 | II-190 |
| T1a-1668 | I-3 | II-120 | II-191 |
| T1a-1669 | I-3 | II-120 | II-192 |
| T1a-1670 | I-3 | II-120 | II-193 |
| T1a-1671 | I-3 | II-120 | II-194 |
| T1a-1672 | I-3 | II-120 | II-195 |
| T1a-1673 | I-3 | II-120 | II-196 |
| T1a-1674 | I-3 | II-120 | II-197 |
| T1a-1675 | I-3 | II-120 | II-198 |
| T1a-1676 | I-3 | II-120 | II-199 |
| T1a-1677 | I-3 | II-120 | II-200 |
| T1a-1678 | I-3 | II-120 | II-201 |
| T1a-1679 | I-3 | II-120 | II-202 |
| T1a-1680 | I-3 | II-120 | II-203 |
| T1a-1681 | I-3 | II-121 | II-148 |
| T1a-1682 | I-3 | II-121 | II-149 |
| T1a-1683 | I-3 | II-121 | II-150 |
| T1a-1684 | I-3 | II-121 | II-151 |
| T1a-1685 | I-3 | II-121 | II-152 |
| T1a-1686 | I-3 | II-121 | II-153 |
| T1a-1687 | I-3 | II-121 | II-154 |
| T1a-1688 | I-3 | II-121 | II-155 |
| T1a-1689 | I-3 | II-121 | II-156 |
| T1a-1690 | I-3 | II-121 | II-157 |
| T1a-1691 | I-3 | II-121 | II-158 |
| T1a-1692 | I-3 | II-121 | II-159 |
| T1a-1693 | I-3 | II-121 | II-160 |
| T1a-1694 | I-3 | II-121 | II-161 |
| T1a-1695 | I-3 | II-121 | II-162 |
| T1a-1696 | I-3 | II-121 | II-163 |
| T1a-1697 | I-3 | II-121 | II-164 |
| T1a-1698 | I-3 | II-121 | II-165 |
| T1a-1699 | I-3 | II-121 | II-166 |
| T1a-1700 | I-3 | II-121 | II-167 |
| T1a-1701 | I-3 | II-121 | II-168 |
| T1a-1702 | I-3 | II-121 | II-169 |
| T1a-1703 | I-3 | II-121 | II-170 |
| T1a-1704 | I-3 | II-121 | II-171 |
| T1a-1705 | I-3 | II-121 | II-172 |
| T1a-1706 | I-3 | II-121 | II-173 |
| T1a-1707 | I-3 | II-121 | II-174 |
| T1a-1708 | I-3 | II-121 | II-175 |
| T1a-1709 | I-3 | II-121 | II-176 |
| T1a-1710 | I-3 | II-121 | II-177 |
| T1a-1711 | I-3 | II-121 | II-178 |
| T1a-1712 | I-3 | II-121 | II-179 |
| T1a-1713 | I-3 | II-121 | II-180 |
| T1a-1714 | I-3 | II-121 | II-181 |
| T1a-1715 | I-3 | II-121 | II-182 |
| T1a-1716 | I-3 | II-121 | II-183 |
| T1a-1717 | I-3 | II-121 | II-184 |
| T1a-1718 | I-3 | II-121 | II-185 |
| T1a-1719 | I-3 | II-121 | II-186 |
| T1a-1720 | I-3 | II-121 | II-187 |
| T1a-1721 | I-3 | II-121 | II-188 |
| T1a-1722 | I-3 | II-121 | II-189 |
| T1a-1723 | I-3 | II-121 | II-190 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-1724 | I-3 | II-121 | II-191 |
| T1a-1725 | I-3 | II-121 | II-192 |
| T1a-1726 | I-3 | II-121 | II-193 |
| T1a-1727 | I-3 | II-121 | II-194 |
| T1a-1728 | I-3 | II-121 | II-195 |
| T1a-1729 | I-3 | II-121 | II-196 |
| T1a-1730 | I-3 | II-121 | II-197 |
| T1a-1731 | I-3 | II-121 | II-198 |
| T1a-1732 | I-3 | II-121 | II-199 |
| T1a-1733 | I-3 | II-121 | II-200 |
| T1a-1734 | I-3 | II-121 | II-201 |
| T1a-1735 | I-3 | II-121 | II-202 |
| T1a-1736 | I-3 | II-121 | II-203 |
| T1a-1737 | I-3 | II-122 | II-148 |
| T1a-1738 | I-3 | II-122 | II-149 |
| T1a-1739 | I-3 | II-122 | II-150 |
| T1a-1740 | I-3 | II-122 | II-151 |
| T1a-1741 | I-3 | II-122 | II-152 |
| T1a-1742 | I-3 | II-122 | II-153 |
| T1a-1743 | I-3 | II-122 | II-154 |
| T1a-1744 | I-3 | II-122 | II-155 |
| T1a-1745 | I-3 | II-122 | II-156 |
| T1a-1746 | I-3 | II-122 | II-157 |
| T1a-1747 | I-3 | II-122 | II-158 |
| T1a-1748 | I-3 | II-122 | II-159 |
| T1a-1749 | I-3 | II-122 | II-160 |
| T1a-1750 | I-3 | II-122 | II-161 |
| T1a-1751 | I-3 | II-122 | II-162 |
| T1a-1752 | I-3 | II-122 | II-163 |
| T1a-1753 | I-3 | II-122 | II-164 |
| T1a-1754 | I-3 | II-122 | II-165 |
| T1a-1755 | I-3 | II-122 | II-166 |
| T1a-1756 | I-3 | II-122 | II-167 |
| T1a-1757 | I-3 | II-122 | II-168 |
| T1a-1758 | I-3 | II-122 | II-169 |
| T1a-1759 | I-3 | II-122 | II-170 |
| T1a-1760 | I-3 | II-122 | II-171 |
| T1a-1761 | I-3 | II-122 | II-172 |
| T1a-1762 | I-3 | II-122 | II-173 |
| T1a-1763 | I-3 | II-122 | II-174 |
| T1a-1764 | I-3 | II-122 | II-175 |
| T1a-1765 | I-3 | II-122 | II-176 |
| T1a-1766 | I-3 | II-122 | II-177 |
| T1a-1767 | I-3 | II-122 | II-178 |
| T1a-1768 | I-3 | II-122 | II-179 |
| T1a-1769 | I-3 | II-122 | II-180 |
| T1a-1770 | I-3 | II-122 | II-181 |
| T1a-1771 | I-3 | II-122 | II-182 |
| T1a-1772 | I-3 | II-122 | II-183 |
| T1a-1773 | I-3 | II-122 | II-184 |
| T1a-1774 | I-3 | II-122 | II-185 |
| T1a-1775 | I-3 | II-122 | II-186 |
| T1a-1776 | I-3 | II-122 | II-187 |
| T1a-1777 | I-3 | II-122 | II-188 |
| T1a-1778 | I-3 | II-122 | II-189 |
| T1a-1779 | I-3 | II-122 | II-190 |
| T1a-1780 | I-3 | II-122 | II-191 |
| T1a-1781 | I-3 | II-122 | II-192 |
| T1a-1782 | I-3 | II-122 | II-193 |
| T1a-1783 | I-3 | II-122 | II-194 |
| T1a-1784 | I-3 | II-122 | II-195 |
| T1a-1785 | I-3 | II-122 | II-196 |
| T1a-1786 | I-3 | II-122 | II-197 |
| T1a-1787 | I-3 | II-122 | II-198 |
| T1a-1788 | I-3 | II-122 | II-199 |
| T1a-1789 | I-3 | II-122 | II-200 |
| T1a-1790 | I-3 | II-122 | II-201 |
| T1a-1791 | I-3 | II-122 | II-202 |
| T1a-1792 | I-3 | II-122 | II-203 |
| T1a-1793 | I-3 | II-123 | II-148 |
| T1a-1794 | I-3 | II-123 | II-149 |
| T1a-1795 | I-3 | II-123 | II-150 |
| T1a-1796 | I-3 | II-123 | II-151 |
| T1a-1797 | I-3 | II-123 | II-152 |
| T1a-1798 | I-3 | II-123 | II-153 |
| T1a-1799 | I-3 | II-123 | II-154 |
| T1a-1800 | I-3 | II-123 | II-155 |
| T1a-1801 | I-3 | II-123 | II-156 |
| T1a-1802 | I-3 | II-123 | II-157 |
| T1a-1803 | I-3 | II-123 | II-158 |
| T1a-1804 | I-3 | II-123 | II-159 |
| T1a-1805 | I-3 | II-123 | II-160 |
| T1a-1806 | I-3 | II-123 | II-161 |
| T1a-1807 | I-3 | II-123 | II-162 |
| T1a-1808 | I-3 | II-123 | II-163 |
| T1a-1809 | I-3 | II-123 | II-164 |
| T1a-1810 | I-3 | II-123 | II-165 |
| T1a-1811 | I-3 | II-123 | II-166 |
| T1a-1812 | I-3 | II-123 | II-167 |
| T1a-1813 | I-3 | II-123 | II-168 |
| T1a-1814 | I-3 | II-123 | II-169 |
| T1a-1815 | I-3 | II-123 | II-170 |
| T1a-1816 | I-3 | II-123 | II-171 |
| T1a-1817 | I-3 | II-123 | II-172 |
| T1a-1818 | I-3 | II-123 | II-173 |
| T1a-1819 | I-3 | II-123 | II-174 |
| T1a-1820 | I-3 | II-123 | II-175 |
| T1a-1821 | I-3 | II-123 | II-176 |
| T1a-1822 | I-3 | II-123 | II-177 |
| T1a-1823 | I-3 | II-123 | II-178 |
| T1a-1824 | I-3 | II-123 | II-179 |
| T1a-1825 | I-3 | II-123 | II-180 |
| T1a-1826 | I-3 | II-123 | II-181 |
| T1a-1827 | I-3 | II-123 | II-182 |
| T1a-1828 | I-3 | II-123 | II-183 |
| T1a-1829 | I-3 | II-123 | II-184 |
| T1a-1830 | I-3 | II-123 | II-185 |
| T1a-1831 | I-3 | II-123 | II-186 |
| T1a-1832 | I-3 | II-123 | II-187 |
| T1a-1833 | I-3 | II-123 | II-188 |
| T1a-1834 | I-3 | II-123 | II-189 |
| T1a-1835 | I-3 | II-123 | II-190 |
| T1a-1836 | I-3 | II-123 | II-191 |
| T1a-1837 | I-3 | II-123 | II-192 |
| T1a-1838 | I-3 | II-123 | II-193 |
| T1a-1839 | I-3 | II-123 | II-194 |
| T1a-1840 | I-3 | II-123 | II-195 |
| T1a-1841 | I-3 | II-123 | II-196 |
| T1a-1842 | I-3 | II-123 | II-197 |
| T1a-1843 | I-3 | II-123 | II-198 |
| T1a-1844 | I-3 | II-123 | II-199 |
| T1a-1845 | I-3 | II-123 | II-200 |
| T1a-1846 | I-3 | II-123 | II-201 |
| T1a-1847 | I-3 | II-123 | II-202 |
| T1a-1848 | I-3 | II-123 | II-203 |
| T1a-1849 | I-3 | II-124 | II-148 |
| T1a-1850 | I-3 | II-124 | II-149 |
| T1a-1851 | I-3 | II-124 | II-150 |
| T1a-1852 | I-3 | II-124 | II-151 |
| T1a-1853 | I-3 | II-124 | II-152 |
| T1a-1854 | I-3 | II-124 | II-153 |
| T1a-1855 | I-3 | II-124 | II-154 |
| T1a-1856 | I-3 | II-124 | II-155 |
| T1a-1857 | I-3 | II-124 | II-156 |
| T1a-1858 | I-3 | II-124 | II-157 |
| T1a-1859 | I-3 | II-124 | II-158 |
| T1a-1860 | I-3 | II-124 | II-159 |
| T1a-1861 | I-3 | II-124 | II-160 |
| T1a-1862 | I-3 | II-124 | II-161 |
| T1a-1863 | I-3 | II-124 | II-162 |
| T1a-1864 | I-3 | II-124 | II-163 |
| T1a-1865 | I-3 | II-124 | II-164 |
| T1a-1866 | I-3 | II-124 | II-165 |
| T1a-1867 | I-3 | II-124 | II-166 |
| T1a-1868 | I-3 | II-124 | II-167 |
| T1a-1869 | I-3 | II-124 | II-168 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-1870 | I-3 | II-124 | II-169 |
| T1a-1871 | I-3 | II-124 | II-170 |
| T1a-1872 | I-3 | II-124 | II-171 |
| T1a-1873 | I-3 | II-124 | II-172 |
| T1a-1874 | I-3 | II-124 | II-173 |
| T1a-1875 | I-3 | II-124 | II-174 |
| T1a-1876 | I-3 | II-124 | II-175 |
| T1a-1877 | I-3 | II-124 | II-176 |
| T1a-1878 | I-3 | II-124 | II-177 |
| T1a-1879 | I-3 | II-124 | II-178 |
| T1a-1880 | I-3 | II-124 | II-179 |
| T1a-1881 | I-3 | II-124 | II-180 |
| T1a-1882 | I-3 | II-124 | II-181 |
| T1a-1883 | I-3 | II-124 | II-182 |
| T1a-1884 | I-3 | II-124 | II-183 |
| T1a-1885 | I-3 | II-124 | II-184 |
| T1a-1886 | I-3 | II-124 | II-185 |
| T1a-1887 | I-3 | II-124 | II-186 |
| T1a-1888 | I-3 | II-124 | II-187 |
| T1a-1889 | I-3 | II-124 | II-188 |
| T1a-1890 | I-3 | II-124 | II-189 |
| T1a-1891 | I-3 | II-124 | II-190 |
| T1a-1892 | I-3 | II-124 | II-191 |
| T1a-1893 | I-3 | II-124 | II-192 |
| T1a-1894 | I-3 | II-124 | II-193 |
| T1a-1895 | I-3 | II-124 | II-194 |
| T1a-1896 | I-3 | II-124 | II-195 |
| T1a-1897 | I-3 | II-124 | II-196 |
| T1a-1898 | I-3 | II-124 | II-197 |
| T1a-1899 | I-3 | II-124 | II-198 |
| T1a-1900 | I-3 | II-124 | II-199 |
| T1a-1901 | I-3 | II-124 | II-200 |
| T1a-1902 | I-3 | II-124 | II-201 |
| T1a-1903 | I-3 | II-124 | II-202 |
| T1a-1904 | I-3 | II-124 | II-203 |
| T1a-1905 | I-3 | II-125 | II-148 |
| T1a-1906 | I-3 | II-125 | II-149 |
| T1a-1907 | I-3 | II-125 | II-150 |
| T1a-1908 | I-3 | II-125 | II-151 |
| T1a-1909 | I-3 | II-125 | II-152 |
| T1a-1910 | I-3 | II-125 | II-153 |
| T1a-1911 | I-3 | II-125 | II-154 |
| T1a-1912 | I-3 | II-125 | II-155 |
| T1a-1913 | I-3 | II-125 | II-156 |
| T1a-1914 | I-3 | II-125 | II-157 |
| T1a-1915 | I-3 | II-125 | II-158 |
| T1a-1916 | I-3 | II-125 | II-159 |
| T1a-1917 | I-3 | II-125 | II-160 |
| T1a-1918 | I-3 | II-125 | II-161 |
| T1a-1919 | I-3 | II-125 | II-162 |
| T1a-1920 | I-3 | II-125 | II-163 |
| T1a-1921 | I-3 | II-125 | II-164 |
| T1a-1922 | I-3 | II-125 | II-165 |
| T1a-1923 | I-3 | II-125 | II-166 |
| T1a-1924 | I-3 | II-125 | II-167 |
| T1a-1925 | I-3 | II-125 | II-168 |
| T1a-1926 | I-3 | II-125 | II-169 |
| T1a-1927 | I-3 | II-125 | II-170 |
| T1a-1928 | I-3 | II-125 | II-171 |
| T1a-1929 | I-3 | II-125 | II-172 |
| T1a-1930 | I-3 | II-125 | II-173 |
| T1a-1931 | I-3 | II-125 | II-174 |
| T1a-1932 | I-3 | II-125 | II-175 |
| T1a-1933 | I-3 | II-125 | II-176 |
| T1a-1934 | I-3 | II-125 | II-177 |
| T1a-1935 | I-3 | II-125 | II-178 |
| T1a-1936 | I-3 | II-125 | II-179 |
| T1a-1937 | I-3 | II-125 | II-180 |
| T1a-1938 | I-3 | II-125 | II-181 |
| T1a-1939 | I-3 | II-125 | II-182 |
| T1a-1940 | I-3 | II-125 | II-183 |
| T1a-1941 | I-3 | II-125 | II-184 |
| T1a-1942 | I-3 | II-125 | II-185 |
| T1a-1943 | I-3 | II-125 | II-186 |
| T1a-1944 | I-3 | II-125 | II-187 |
| T1a-1945 | I-3 | II-125 | II-188 |
| T1a-1946 | I-3 | II-125 | II-189 |
| T1a-1947 | I-3 | II-125 | II-190 |
| T1a-1948 | I-3 | II-125 | II-191 |
| T1a-1949 | I-3 | II-125 | II-192 |
| T1a-1950 | I-3 | II-125 | II-193 |
| T1a-1951 | I-3 | II-125 | II-194 |
| T1a-1952 | I-3 | II-125 | II-195 |
| T1a-1953 | I-3 | II-125 | II-196 |
| T1a-1954 | I-3 | II-125 | II-197 |
| T1a-1955 | I-3 | II-125 | II-198 |
| T1a-1956 | I-3 | II-125 | II-199 |
| T1a-1957 | I-3 | II-125 | II-200 |
| T1a-1958 | I-3 | II-125 | II-201 |
| T1a-1959 | I-3 | II-125 | II-202 |
| T1a-1960 | I-3 | II-125 | II-203 |
| T1a-1961 | I-3 | II-126 | II-148 |
| T1a-1962 | I-3 | II-126 | II-149 |
| T1a-1963 | I-3 | II-126 | II-150 |
| T1a-1964 | I-3 | II-126 | II-151 |
| T1a-1965 | I-3 | II-126 | II-152 |
| T1a-1966 | I-3 | II-126 | II-153 |
| T1a-1967 | I-3 | II-126 | II-154 |
| T1a-1968 | I-3 | II-126 | II-155 |
| T1a-1969 | I-3 | II-126 | II-156 |
| T1a-1970 | I-3 | II-126 | II-157 |
| T1a-1971 | I-3 | II-126 | II-158 |
| T1a-1972 | I-3 | II-126 | II-159 |
| T1a-1973 | I-3 | II-126 | II-160 |
| T1a-1974 | I-3 | II-126 | II-161 |
| T1a-1975 | I-3 | II-126 | II-162 |
| T1a-1976 | I-3 | II-126 | II-163 |
| T1a-1977 | I-3 | II-126 | II-164 |
| T1a-1978 | I-3 | II-126 | II-165 |
| T1a-1979 | I-3 | II-126 | II-166 |
| T1a-1980 | I-3 | II-126 | II-167 |
| T1a-1981 | I-3 | II-126 | II-168 |
| T1a-1982 | I-3 | II-126 | II-169 |
| T1a-1983 | I-3 | II-126 | II-170 |
| T1a-1984 | I-3 | II-126 | II-171 |
| T1a-1985 | I-3 | II-126 | II-172 |
| T1a-1986 | I-3 | II-126 | II-173 |
| T1a-1987 | I-3 | II-126 | II-174 |
| T1a-1988 | I-3 | II-126 | II-175 |
| T1a-1989 | I-3 | II-126 | II-176 |
| T1a-1990 | I-3 | II-126 | II-177 |
| T1a-1991 | I-3 | II-126 | II-178 |
| T1a-1992 | I-3 | II-126 | II-179 |
| T1a-1993 | I-3 | II-126 | II-180 |
| T1a-1994 | I-3 | II-126 | II-181 |
| T1a-1995 | I-3 | II-126 | II-182 |
| T1a-1996 | I-3 | II-126 | II-183 |
| T1a-1997 | I-3 | II-126 | II-184 |
| T1a-1998 | I-3 | II-126 | II-185 |
| T1a-1999 | I-3 | II-126 | II-186 |
| T1a-2000 | I-3 | II-126 | II-187 |
| T1a-2001 | I-3 | II-126 | II-188 |
| T1a-2002 | I-3 | II-126 | II-189 |
| T1a-2003 | I-3 | II-126 | II-190 |
| T1a-2004 | I-3 | II-126 | II-191 |
| T1a-2005 | I-3 | II-126 | II-192 |
| T1a-2006 | I-3 | II-126 | II-193 |
| T1a-2007 | I-3 | II-126 | II-194 |
| T1a-2008 | I-3 | II-126 | II-195 |
| T1a-2009 | I-3 | II-126 | II-196 |
| T1a-2010 | I-3 | II-126 | II-197 |
| T1a-2011 | I-3 | II-126 | II-198 |
| T1a-2012 | I-3 | II-126 | II-199 |
| T1a-2013 | I-3 | II-126 | II-200 |
| T1a-2014 | I-3 | II-126 | II-201 |
| T1a-2015 | I-3 | II-126 | II-202 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-2016 | I-3 | II-126 | II-203 |
| T1a-2017 | I-3 | II-127 | II-148 |
| T1a-2018 | I-3 | II-127 | II-149 |
| T1a-2019 | I-3 | II-127 | II-150 |
| T1a-2020 | I-3 | II-127 | II-151 |
| T1a-2021 | I-3 | II-127 | II-152 |
| T1a-2022 | I-3 | II-127 | II-153 |
| T1a-2023 | I-3 | II-127 | II-154 |
| T1a-2024 | I-3 | II-127 | II-155 |
| T1a-2025 | I-3 | II-127 | II-156 |
| T1a-2026 | I-3 | II-127 | II-157 |
| T1a-2027 | I-3 | II-127 | II-158 |
| T1a-2028 | I-3 | II-127 | II-159 |
| T1a-2029 | I-3 | II-127 | II-160 |
| T1a-2030 | I-3 | II-127 | II-161 |
| T1a-2031 | I-3 | II-127 | II-162 |
| T1a-2032 | I-3 | II-127 | II-163 |
| T1a-2033 | I-3 | II-127 | II-164 |
| T1a-2034 | I-3 | II-127 | II-165 |
| T1a-2035 | I-3 | II-127 | II-166 |
| T1a-2036 | I-3 | II-127 | II-167 |
| T1a-2037 | I-3 | II-127 | II-168 |
| T1a-2038 | I-3 | II-127 | II-169 |
| T1a-2039 | I-3 | II-127 | II-170 |
| T1a-2040 | I-3 | II-127 | II-171 |
| T1a-2041 | I-3 | II-127 | II-172 |
| T1a-2042 | I-3 | II-127 | II-173 |
| T1a-2043 | I-3 | II-127 | II-174 |
| T1a-2044 | I-3 | II-127 | II-175 |
| T1a-2045 | I-3 | II-127 | II-176 |
| T1a-2046 | I-3 | II-127 | II-177 |
| T1a-2047 | I-3 | II-127 | II-178 |
| T1a-2048 | I-3 | II-127 | II-179 |
| T1a-2049 | I-3 | II-127 | II-180 |
| T1a-2050 | I-3 | II-127 | II-181 |
| T1a-2051 | I-3 | II-127 | II-182 |
| T1a-2052 | I-3 | II-127 | II-183 |
| T1a-2053 | I-3 | II-127 | II-184 |
| T1a-2054 | I-3 | II-127 | II-185 |
| T1a-2055 | I-3 | II-127 | II-186 |
| T1a-2056 | I-3 | II-127 | II-187 |
| T1a-2057 | I-3 | II-127 | II-188 |
| T1a-2058 | I-3 | II-127 | II-189 |
| T1a-2059 | I-3 | II-127 | II-190 |
| T1a-2060 | I-3 | II-127 | II-191 |
| T1a-2061 | I-3 | II-127 | II-192 |
| T1a-2062 | I-3 | II-127 | II-193 |
| T1a-2063 | I-3 | II-127 | II-194 |
| T1a-2064 | I-3 | II-127 | II-195 |
| T1a-2065 | I-3 | II-127 | II-196 |
| T1a-2066 | I-3 | II-127 | II-197 |
| T1a-2067 | I-3 | II-127 | II-198 |
| T1a-2068 | I-3 | II-127 | II-199 |
| T1a-2069 | I-3 | II-127 | II-200 |
| T1a-2070 | I-3 | II-127 | II-201 |
| T1a-2071 | I-3 | II-127 | II-202 |
| T1a-2072 | I-3 | II-127 | II-203 |
| T1a-2073 | I-3 | II-128 | II-148 |
| T1a-2074 | I-3 | II-128 | II-149 |
| T1a-2075 | I-3 | II-128 | II-150 |
| T1a-2076 | I-3 | II-128 | II-151 |
| T1a-2077 | I-3 | II-128 | II-152 |
| T1a-2078 | I-3 | II-128 | II-153 |
| T1a-2079 | I-3 | II-128 | II-154 |
| T1a-2080 | I-3 | II-128 | II-155 |
| T1a-2081 | I-3 | II-128 | II-156 |
| T1a-2082 | I-3 | II-128 | II-157 |
| T1a-2083 | I-3 | II-128 | II-158 |
| T1a-2084 | I-3 | II-128 | II-159 |
| T1a-2085 | I-3 | II-128 | II-160 |
| T1a-2086 | I-3 | II-128 | II-161 |
| T1a-2087 | I-3 | II-128 | II-162 |
| T1a-2088 | I-3 | II-128 | II-163 |
| T1a-2089 | I-3 | II-128 | II-164 |
| T1a-2090 | I-3 | II-128 | II-165 |
| T1a-2091 | I-3 | II-128 | II-166 |
| T1a-2092 | I-3 | II-128 | II-167 |
| T1a-2093 | I-3 | II-128 | II-168 |
| T1a-2094 | I-3 | II-128 | II-169 |
| T1a-2095 | I-3 | II-128 | II-170 |
| T1a-2096 | I-3 | II-128 | II-171 |
| T1a-2097 | I-3 | II-128 | II-172 |
| T1a-2098 | I-3 | II-128 | II-173 |
| T1a-2099 | I-3 | II-128 | II-174 |
| T1a-2100 | I-3 | II-128 | II-175 |
| T1a-2101 | I-3 | II-128 | II-176 |
| T1a-2102 | I-3 | II-128 | II-177 |
| T1a-2103 | I-3 | II-128 | II-178 |
| T1a-2104 | I-3 | II-128 | II-179 |
| T1a-2105 | I-3 | II-128 | II-180 |
| T1a-2106 | I-3 | II-128 | II-181 |
| T1a-2107 | I-3 | II-128 | II-182 |
| T1a-2108 | I-3 | II-128 | II-183 |
| T1a-2109 | I-3 | II-128 | II-184 |
| T1a-2110 | I-3 | II-128 | II-185 |
| T1a-2111 | I-3 | II-128 | II-186 |
| T1a-2112 | I-3 | II-128 | II-187 |
| T1a-2113 | I-3 | II-128 | II-188 |
| T1a-2114 | I-3 | II-128 | II-189 |
| T1a-2115 | I-3 | II-128 | II-190 |
| T1a-2116 | I-3 | II-128 | II-191 |
| T1a-2117 | I-3 | II-128 | II-192 |
| T1a-2118 | I-3 | II-128 | II-193 |
| T1a-2119 | I-3 | II-128 | II-194 |
| T1a-2120 | I-3 | II-128 | II-195 |
| T1a-2121 | I-3 | II-128 | II-196 |
| T1a-2122 | I-3 | II-128 | II-197 |
| T1a-2123 | I-3 | II-128 | II-198 |
| T1a-2124 | I-3 | II-128 | II-199 |
| T1a-2125 | I-3 | II-128 | II-200 |
| T1a-2126 | I-3 | II-128 | II-201 |
| T1a-2127 | I-3 | II-128 | II-202 |
| T1a-2128 | I-3 | II-128 | II-203 |
| T1a-2129 | I-3 | II-129 | II-148 |
| T1a-2130 | I-3 | II-129 | II-149 |
| T1a-2131 | I-3 | II-129 | II-150 |
| T1a-2132 | I-3 | II-129 | II-151 |
| T1a-2133 | I-3 | II-129 | II-152 |
| T1a-2134 | I-3 | II-129 | II-153 |
| T1a-2135 | I-3 | II-129 | II-154 |
| T1a-2136 | I-3 | II-129 | II-155 |
| T1a-2137 | I-3 | II-129 | II-156 |
| T1a-2138 | I-3 | II-129 | II-157 |
| T1a-2139 | I-3 | II-129 | II-158 |
| T1a-2140 | I-3 | II-129 | II-159 |
| T1a-2141 | I-3 | II-129 | II-160 |
| T1a-2142 | I-3 | II-129 | II-161 |
| T1a-2143 | I-3 | II-129 | II-162 |
| T1a-2144 | I-3 | II-129 | II-163 |
| T1a-2145 | I-3 | II-129 | II-164 |
| T1a-2146 | I-3 | II-129 | II-165 |
| T1a-2147 | I-3 | II-129 | II-166 |
| T1a-2148 | I-3 | II-129 | II-167 |
| T1a-2149 | I-3 | II-129 | II-168 |
| T1a-2150 | I-3 | II-129 | II-169 |
| T1a-2151 | I-3 | II-129 | II-170 |
| T1a-2152 | I-3 | II-129 | II-171 |
| T1a-2153 | I-3 | II-129 | II-172 |
| T1a-2154 | I-3 | II-129 | II-173 |
| T1a-2155 | I-3 | II-129 | II-174 |
| T1a-2156 | I-3 | II-129 | II-175 |
| T1a-2157 | I-3 | II-129 | II-176 |
| T1a-2158 | I-3 | II-129 | II-177 |
| T1a-2159 | I-3 | II-129 | II-178 |
| T1a-2160 | I-3 | II-129 | II-179 |
| T1a-2161 | I-3 | II-129 | II-180 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-2162 | I-3 | II-129 | II-181 |
| T1a-2163 | I-3 | II-129 | II-182 |
| T1a-2164 | I-3 | II-129 | II-183 |
| T1a-2165 | I-3 | II-129 | II-184 |
| T1a-2166 | I-3 | II-129 | II-185 |
| T1a-2167 | I-3 | II-129 | II-186 |
| T1a-2168 | I-3 | II-129 | II-187 |
| T1a-2169 | I-3 | II-129 | II-188 |
| T1a-2170 | I-3 | II-129 | II-189 |
| T1a-2171 | I-3 | II-129 | II-190 |
| T1a-2172 | I-3 | II-129 | II-191 |
| T1a-2173 | I-3 | II-129 | II-192 |
| T1a-2174 | I-3 | II-129 | II-193 |
| T1a-2175 | I-3 | II-129 | II-194 |
| T1a-2176 | I-3 | II-129 | II-195 |
| T1a-2177 | I-3 | II-129 | II-196 |
| T1a-2178 | I-3 | II-129 | II-197 |
| T1a-2179 | I-3 | II-129 | II-198 |
| T1a-2180 | I-3 | II-129 | II-199 |
| T1a-2181 | I-3 | II-129 | II-200 |
| T1a-2182 | I-3 | II-129 | II-201 |
| T1a-2183 | I-3 | II-129 | II-202 |
| T1a-2184 | I-3 | II-129 | II-203 |
| T1a-2185 | I-3 | II-130 | II-148 |
| T1a-2186 | I-3 | II-130 | II-149 |
| T1a-2187 | I-3 | II-130 | II-150 |
| T1a-2188 | I-3 | II-130 | II-151 |
| T1a-2189 | I-3 | II-130 | II-152 |
| T1a-2190 | I-3 | II-130 | II-153 |
| T1a-2191 | I-3 | II-130 | II-154 |
| T1a-2192 | I-3 | II-130 | II-155 |
| T1a-2193 | I-3 | II-130 | II-156 |
| T1a-2194 | I-3 | II-130 | II-157 |
| T1a-2195 | I-3 | II-130 | II-158 |
| T1a-2196 | I-3 | II-130 | II-159 |
| T1a-2197 | I-3 | II-130 | II-160 |
| T1a-2198 | I-3 | II-130 | II-161 |
| T1a-2199 | I-3 | II-130 | II-162 |
| T1a-2200 | I-3 | II-130 | II-163 |
| T1a-2201 | I-3 | II-130 | II-164 |
| T1a-2202 | I-3 | II-130 | II-165 |
| T1a-2203 | I-3 | II-130 | II-166 |
| T1a-2204 | I-3 | II-130 | II-167 |
| T1a-2205 | I-3 | II-130 | II-168 |
| T1a-2206 | I-3 | II-130 | II-169 |
| T1a-2207 | I-3 | II-130 | II-170 |
| T1a-2208 | I-3 | II-130 | II-171 |
| T1a-2209 | I-3 | II-130 | II-172 |
| T1a-2210 | I-3 | II-130 | II-173 |
| T1a-2211 | I-3 | II-130 | II-174 |
| T1a-2212 | I-3 | II-130 | II-175 |
| T1a-2213 | I-3 | II-130 | II-176 |
| T1a-2214 | I-3 | II-130 | II-177 |
| T1a-2215 | I-3 | II-130 | II-178 |
| T1a-2216 | I-3 | II-130 | II-179 |
| T1a-2217 | I-3 | II-130 | II-180 |
| T1a-2218 | I-3 | II-130 | II-181 |
| T1a-2219 | I-3 | II-130 | II-182 |
| T1a-2220 | I-3 | II-130 | II-183 |
| T1a-2221 | I-3 | II-130 | II-184 |
| T1a-2222 | I-3 | II-130 | II-185 |
| T1a-2223 | I-3 | II-130 | II-186 |
| T1a-2224 | I-3 | II-130 | II-187 |
| T1a-2225 | I-3 | II-130 | II-188 |
| T1a-2226 | I-3 | II-130 | II-189 |
| T1a-2227 | I-3 | II-130 | II-190 |
| T1a-2228 | I-3 | II-130 | II-191 |
| T1a-2229 | I-3 | II-130 | II-192 |
| T1a-2230 | I-3 | II-130 | II-193 |
| T1a-2231 | I-3 | II-130 | II-194 |
| T1a-2232 | I-3 | II-130 | II-195 |
| T1a-2233 | I-3 | II-130 | II-196 |
| T1a-2234 | I-3 | II-130 | II-197 |
| T1a-2235 | I-3 | II-130 | II-198 |
| T1a-2236 | I-3 | II-130 | II-199 |
| T1a-2237 | I-3 | II-130 | II-200 |
| T1a-2238 | I-3 | II-130 | II-201 |
| T1a-2239 | I-3 | II-130 | II-202 |
| T1a-2240 | I-3 | II-130 | II-203 |
| T1a-2241 | I-3 | II-131 | II-148 |
| T1a-2242 | I-3 | II-131 | II-149 |
| T1a-2243 | I-3 | II-131 | II-150 |
| T1a-2244 | I-3 | II-131 | II-151 |
| T1a-2245 | I-3 | II-131 | II-152 |
| T1a-2246 | I-3 | II-131 | II-153 |
| T1a-2247 | I-3 | II-131 | II-154 |
| T1a-2248 | I-3 | II-131 | II-155 |
| T1a-2249 | I-3 | II-131 | II-156 |
| T1a-2250 | I-3 | II-131 | II-157 |
| T1a-2251 | I-3 | II-131 | II-158 |
| T1a-2252 | I-3 | II-131 | II-159 |
| T1a-2253 | I-3 | II-131 | II-160 |
| T1a-2254 | I-3 | II-131 | II-161 |
| T1a-2255 | I-3 | II-131 | II-162 |
| T1a-2256 | I-3 | II-131 | II-163 |
| T1a-2257 | I-3 | II-131 | II-164 |
| T1a-2258 | I-3 | II-131 | II-165 |
| T1a-2259 | I-3 | II-131 | II-166 |
| T1a-2260 | I-3 | II-131 | II-167 |
| T1a-2261 | I-3 | II-131 | II-168 |
| T1a-2262 | I-3 | II-131 | II-169 |
| T1a-2263 | I-3 | II-131 | II-170 |
| T1a-2264 | I-3 | II-131 | II-171 |
| T1a-2265 | I-3 | II-131 | II-172 |
| T1a-2266 | I-3 | II-131 | II-173 |
| T1a-2267 | I-3 | II-131 | II-174 |
| T1a-2268 | I-3 | II-131 | II-175 |
| T1a-2269 | I-3 | II-131 | II-176 |
| T1a-2270 | I-3 | II-131 | II-177 |
| T1a-2271 | I-3 | II-131 | II-178 |
| T1a-2272 | I-3 | II-131 | II-179 |
| T1a-2273 | I-3 | II-131 | II-180 |
| T1a-2274 | I-3 | II-131 | II-181 |
| T1a-2275 | I-3 | II-131 | II-182 |
| T1a-2276 | I-3 | II-131 | II-183 |
| T1a-2277 | I-3 | II-131 | II-184 |
| T1a-2278 | I-3 | II-131 | II-185 |
| T1a-2279 | I-3 | II-131 | II-186 |
| T1a-2280 | I-3 | II-131 | II-187 |
| T1a-2281 | I-3 | II-131 | II-188 |
| T1a-2282 | I-3 | II-131 | II-189 |
| T1a-2283 | I-3 | II-131 | II-190 |
| T1a-2284 | I-3 | II-131 | II-191 |
| T1a-2285 | I-3 | II-131 | II-192 |
| T1a-2286 | I-3 | II-131 | II-193 |
| T1a-2287 | I-3 | II-131 | II-194 |
| T1a-2288 | I-3 | II-131 | II-195 |
| T1a-2289 | I-3 | II-131 | II-196 |
| T1a-2290 | I-3 | II-131 | II-197 |
| T1a-2291 | I-3 | II-131 | II-198 |
| T1a-2292 | I-3 | II-131 | II-199 |
| T1a-2293 | I-3 | II-131 | II-200 |
| T1a-2294 | I-3 | II-131 | II-201 |
| T1a-2295 | I-3 | II-131 | II-202 |
| T1a-2296 | I-3 | II-131 | II-203 |
| T1a-2297 | I-3 | II-132 | II-148 |
| T1a-2298 | I-3 | II-132 | II-149 |
| T1a-2299 | I-3 | II-132 | II-150 |
| T1a-2300 | I-3 | II-132 | II-151 |
| T1a-2301 | I-3 | II-132 | II-152 |
| T1a-2302 | I-3 | II-132 | II-153 |
| T1a-2303 | I-3 | II-132 | II-154 |
| T1a-2304 | I-3 | II-132 | II-155 |
| T1a-2305 | I-3 | II-132 | II-156 |
| T1a-2306 | I-3 | II-132 | II-157 |
| T1a-2307 | I-3 | II-132 | II-158 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-2308 | I-3 | II-132 | II-159 |
| T1a-2309 | I-3 | II-132 | II-160 |
| T1a-2310 | I-3 | II-132 | II-161 |
| T1a-2311 | I-3 | II-132 | II-162 |
| T1a-2312 | I-3 | II-132 | II-163 |
| T1a-2313 | I-3 | II-132 | II-164 |
| T1a-2314 | I-3 | II-132 | II-165 |
| T1a-2315 | I-3 | II-132 | II-166 |
| T1a-2316 | I-3 | II-132 | II-167 |
| T1a-2317 | I-3 | II-132 | II-168 |
| T1a-2318 | I-3 | II-132 | II-169 |
| T1a-2319 | I-3 | II-132 | II-170 |
| T1a-2320 | I-3 | II-132 | II-171 |
| T1a-2321 | I-3 | II-132 | II-172 |
| T1a-2322 | I-3 | II-132 | II-173 |
| T1a-2323 | I-3 | II-132 | II-174 |
| T1a-2324 | I-3 | II-132 | II-175 |
| T1a-2325 | I-3 | II-132 | II-176 |
| T1a-2326 | I-3 | II-132 | II-177 |
| T1a-2327 | I-3 | II-132 | II-178 |
| T1a-2328 | I-3 | II-132 | II-179 |
| T1a-2329 | I-3 | II-132 | II-180 |
| T1a-2330 | I-3 | II-132 | II-181 |
| T1a-2331 | I-3 | II-132 | II-182 |
| T1a-2332 | I-3 | II-132 | II-183 |
| T1a-2333 | I-3 | II-132 | II-184 |
| T1a-2334 | I-3 | II-132 | II-185 |
| T1a-2335 | I-3 | II-132 | II-186 |
| T1a-2336 | I-3 | II-132 | II-187 |
| T1a-2337 | I-3 | II-132 | II-188 |
| T1a-2338 | I-3 | II-132 | II-189 |
| T1a-2339 | I-3 | II-132 | II-190 |
| T1a-2340 | I-3 | II-132 | II-191 |
| T1a-2341 | I-3 | II-132 | II-192 |
| T1a-2342 | I-3 | II-132 | II-193 |
| T1a-2343 | I-3 | II-132 | II-194 |
| T1a-2344 | I-3 | II-132 | II-195 |
| T1a-2345 | I-3 | II-132 | II-196 |
| T1a-2346 | I-3 | II-132 | II-197 |
| T1a-2347 | I-3 | II-132 | II-198 |
| T1a-2348 | I-3 | II-132 | II-199 |
| T1a-2349 | I-3 | II-132 | II-200 |
| T1a-2350 | I-3 | II-132 | II-201 |
| T1a-2351 | I-3 | II-132 | II-202 |
| T1a-2352 | I-3 | II-132 | II-203 |
| T1a-2353 | I-3 | II-133 | II-148 |
| T1a-2354 | I-3 | II-133 | II-149 |
| T1a-2355 | I-3 | II-133 | II-150 |
| T1a-2356 | I-3 | II-133 | II-151 |
| T1a-2357 | I-3 | II-133 | II-152 |
| T1a-2358 | I-3 | II-133 | II-153 |
| T1a-2359 | I-3 | II-133 | II-154 |
| T1a-2360 | I-3 | II-133 | II-155 |
| T1a-2361 | I-3 | II-133 | II-156 |
| T1a-2362 | I-3 | II-133 | II-157 |
| T1a-2363 | I-3 | II-133 | II-158 |
| T1a-2364 | I-3 | II-133 | II-159 |
| T1a-2365 | I-3 | II-133 | II-160 |
| T1a-2366 | I-3 | II-133 | II-161 |
| T1a-2367 | I-3 | II-133 | II-162 |
| T1a-2368 | I-3 | II-133 | II-163 |
| T1a-2369 | I-3 | II-133 | II-164 |
| T1a-2370 | I-3 | II-133 | II-165 |
| T1a-2371 | I-3 | II-133 | II-166 |
| T1a-2372 | I-3 | II-133 | II-167 |
| T1a-2373 | I-3 | II-133 | II-168 |
| T1a-2374 | I-3 | II-133 | II-169 |
| T1a-2375 | I-3 | II-133 | II-170 |
| T1a-2376 | I-3 | II-133 | II-171 |
| T1a-2377 | I-3 | II-133 | II-172 |
| T1a-2378 | I-3 | II-133 | II-173 |
| T1a-2379 | I-3 | II-133 | II-174 |
| T1a-2380 | I-3 | II-133 | II-175 |
| T1a-2381 | I-3 | II-133 | II-176 |
| T1a-2382 | I-3 | II-133 | II-177 |
| T1a-2383 | I-3 | II-133 | II-178 |
| T1a-2384 | I-3 | II-133 | II-179 |
| T1a-2385 | I-3 | II-133 | II-180 |
| T1a-2386 | I-3 | II-133 | II-181 |
| T1a-2387 | I-3 | II-133 | II-182 |
| T1a-2388 | I-3 | II-133 | II-183 |
| T1a-2389 | I-3 | II-133 | II-184 |
| T1a-2390 | I-3 | II-133 | II-185 |
| T1a-2391 | I-3 | II-133 | II-186 |
| T1a-2392 | I-3 | II-133 | II-187 |
| T1a-2393 | I-3 | II-133 | II-188 |
| T1a-2394 | I-3 | II-133 | II-189 |
| T1a-2395 | I-3 | II-133 | II-190 |
| T1a-2396 | I-3 | II-133 | II-191 |
| T1a-2397 | I-3 | II-133 | II-192 |
| T1a-2398 | I-3 | II-133 | II-193 |
| T1a-2399 | I-3 | II-133 | II-194 |
| T1a-2400 | I-3 | II-133 | II-195 |
| T1a-2401 | I-3 | II-133 | II-196 |
| T1a-2402 | I-3 | II-133 | II-197 |
| T1a-2403 | I-3 | II-133 | II-198 |
| T1a-2404 | I-3 | II-133 | II-199 |
| T1a-2405 | I-3 | II-133 | II-200 |
| T1a-2406 | I-3 | II-133 | II-201 |
| T1a-2407 | I-3 | II-133 | II-202 |
| T1a-2408 | I-3 | II-133 | II-203 |
| T1a-2409 | I-3 | II-134 | II-148 |
| T1a-2410 | I-3 | II-134 | II-149 |
| T1a-2411 | I-3 | II-134 | II-150 |
| T1a-2412 | I-3 | II-134 | II-151 |
| T1a-2413 | I-3 | II-134 | II-152 |
| T1a-2414 | I-3 | II-134 | II-153 |
| T1a-2415 | I-3 | II-134 | II-154 |
| T1a-2416 | I-3 | II-134 | II-155 |
| T1a-2417 | I-3 | II-134 | II-156 |
| T1a-2418 | I-3 | II-134 | II-157 |
| T1a-2419 | I-3 | II-134 | II-158 |
| T1a-2420 | I-3 | II-134 | II-159 |
| T1a-2421 | I-3 | II-134 | II-160 |
| T1a-2422 | I-3 | II-134 | II-161 |
| T1a-2423 | I-3 | II-134 | II-162 |
| T1a-2424 | I-3 | II-134 | II-163 |
| T1a-2425 | I-3 | II-134 | II-164 |
| T1a-2426 | I-3 | II-134 | II-165 |
| T1a-2427 | I-3 | II-134 | II-166 |
| T1a-2428 | I-3 | II-134 | II-167 |
| T1a-2429 | I-3 | II-134 | II-168 |
| T1a-2430 | I-3 | II-134 | II-169 |
| T1a-2431 | I-3 | II-134 | II-170 |
| T1a-2432 | I-3 | II-134 | II-171 |
| T1a-2433 | I-3 | II-134 | II-172 |
| T1a-2434 | I-3 | II-134 | II-173 |
| T1a-2435 | I-3 | II-134 | II-174 |
| T1a-2436 | I-3 | II-134 | II-175 |
| T1a-2437 | I-3 | II-134 | II-176 |
| T1a-2438 | I-3 | II-134 | II-177 |
| T1a-2439 | I-3 | II-134 | II-178 |
| T1a-2440 | I-3 | II-134 | II-179 |
| T1a-2441 | I-3 | II-134 | II-180 |
| T1a-2442 | I-3 | II-134 | II-181 |
| T1a-2443 | I-3 | II-134 | II-182 |
| T1a-2444 | I-3 | II-134 | II-183 |
| T1a-2445 | I-3 | II-134 | II-184 |
| T1a-2446 | I-3 | II-134 | II-185 |
| T1a-2447 | I-3 | II-134 | II-186 |
| T1a-2448 | I-3 | II-134 | II-187 |
| T1a-2449 | I-3 | II-134 | II-188 |
| T1a-2450 | I-3 | II-134 | II-189 |
| T1a-2451 | I-3 | II-134 | II-190 |
| T1a-2452 | I-3 | II-134 | II-191 |
| T1a-2453 | I-3 | II-134 | II-192 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-2454 | I-3 | II-134 | II-193 |
| T1a-2455 | I-3 | II-134 | II-194 |
| T1a-2456 | I-3 | II-134 | II-195 |
| T1a-2457 | I-3 | II-134 | II-196 |
| T1a-2458 | I-3 | II-134 | II-197 |
| T1a-2459 | I-3 | II-134 | II-198 |
| T1a-2460 | I-3 | II-134 | II-199 |
| T1a-2461 | I-3 | II-134 | II-200 |
| T1a-2462 | I-3 | II-134 | II-201 |
| T1a-2463 | I-3 | II-134 | II-202 |
| T1a-2464 | I-3 | II-134 | II-203 |
| T1a-2465 | I-3 | II-135 | II-148 |
| T1a-2466 | I-3 | II-135 | II-149 |
| T1a-2467 | I-3 | II-135 | II-150 |
| T1a-2468 | I-3 | II-135 | II-151 |
| T1a-2469 | I-3 | II-135 | II-152 |
| T1a-2470 | I-3 | II-135 | II-153 |
| T1a-2471 | I-3 | II-135 | II-154 |
| T1a-2472 | I-3 | II-135 | II-155 |
| T1a-2473 | I-3 | II-135 | II-156 |
| T1a-2474 | I-3 | II-135 | II-157 |
| T1a-2475 | I-3 | II-135 | II-158 |
| T1a-2476 | I-3 | II-135 | II-159 |
| T1a-2477 | I-3 | II-135 | II-160 |
| T1a-2478 | I-3 | II-135 | II-161 |
| T1a-2479 | I-3 | II-135 | II-162 |
| T1a-2480 | I-3 | II-135 | II-163 |
| T1a-2481 | I-3 | II-135 | II-164 |
| T1a-2482 | I-3 | II-135 | II-165 |
| T1a-2483 | I-3 | II-135 | II-166 |
| T1a-2484 | I-3 | II-135 | II-167 |
| T1a-2485 | I-3 | II-135 | II-168 |
| T1a-2486 | I-3 | II-135 | II-169 |
| T1a-2487 | I-3 | II-135 | II-170 |
| T1a-2488 | I-3 | II-135 | II-171 |
| T1a-2489 | I-3 | II-135 | II-172 |
| T1a-2490 | I-3 | II-135 | II-173 |
| T1a-2491 | I-3 | II-135 | II-174 |
| T1a-2492 | I-3 | II-135 | II-175 |
| T1a-2493 | I-3 | II-135 | II-176 |
| T1a-2494 | I-3 | II-135 | II-177 |
| T1a-2495 | I-3 | II-135 | II-178 |
| T1a-2496 | I-3 | II-135 | II-179 |
| T1a-2497 | I-3 | II-135 | II-180 |
| T1a-2498 | I-3 | II-135 | II-181 |
| T1a-2499 | I-3 | II-135 | II-182 |
| T1a-2500 | I-3 | II-135 | II-183 |
| T1a-2501 | I-3 | II-135 | II-184 |
| T1a-2502 | I-3 | II-135 | II-185 |
| T1a-2503 | I-3 | II-135 | II-186 |
| T1a-2504 | I-3 | II-135 | II-187 |
| T1a-2505 | I-3 | II-135 | II-188 |
| T1a-2506 | I-3 | II-135 | II-189 |
| T1a-2507 | I-3 | II-135 | II-190 |
| T1a-2508 | I-3 | II-135 | II-191 |
| T1a-2509 | I-3 | II-135 | II-192 |
| T1a-2510 | I-3 | II-135 | II-193 |
| T1a-2511 | I-3 | II-135 | II-194 |
| T1a-2512 | I-3 | II-135 | II-195 |
| T1a-2513 | I-3 | II-135 | II-196 |
| T1a-2514 | I-3 | II-135 | II-197 |
| T1a-2515 | I-3 | II-135 | II-198 |
| T1a-2516 | I-3 | II-135 | II-199 |
| T1a-2517 | I-3 | II-135 | II-200 |
| T1a-2518 | I-3 | II-135 | II-201 |
| T1a-2519 | I-3 | II-135 | II-202 |
| T1a-2520 | I-3 | II-135 | II-203 |
| T1a-2521 | I-3 | II-136 | II-148 |
| T1a-2522 | I-3 | II-136 | II-149 |
| T1a-2523 | I-3 | II-136 | II-150 |
| T1a-2524 | I-3 | II-136 | II-151 |
| T1a-2525 | I-3 | II-136 | II-152 |
| T1a-2526 | I-3 | II-136 | II-153 |
| T1a-2527 | I-3 | II-136 | II-154 |
| T1a-2528 | I-3 | II-136 | II-155 |
| T1a-2529 | I-3 | II-136 | II-156 |
| T1a-2530 | I-3 | II-136 | II-157 |
| T1a-2531 | I-3 | II-136 | II-158 |
| T1a-2532 | I-3 | II-136 | II-159 |
| T1a-2533 | I-3 | II-136 | II-160 |
| T1a-2534 | I-3 | II-136 | II-161 |
| T1a-2535 | I-3 | II-136 | II-162 |
| T1a-2536 | I-3 | II-136 | II-163 |
| T1a-2537 | I-3 | II-136 | II-164 |
| T1a-2538 | I-3 | II-136 | II-165 |
| T1a-2539 | I-3 | II-136 | II-166 |
| T1a-2540 | I-3 | II-136 | II-167 |
| T1a-2541 | I-3 | II-136 | II-168 |
| T1a-2542 | I-3 | II-136 | II-169 |
| T1a-2543 | I-3 | II-136 | II-170 |
| T1a-2544 | I-3 | II-136 | II-171 |
| T1a-2545 | I-3 | II-136 | II-172 |
| T1a-2546 | I-3 | II-136 | II-173 |
| T1a-2547 | I-3 | II-136 | II-174 |
| T1a-2548 | I-3 | II-136 | II-175 |
| T1a-2549 | I-3 | II-136 | II-176 |
| T1a-2550 | I-3 | II-136 | II-177 |
| T1a-2551 | I-3 | II-136 | II-178 |
| T1a-2552 | I-3 | II-136 | II-179 |
| T1a-2553 | I-3 | II-136 | II-180 |
| T1a-2554 | I-3 | II-136 | II-181 |
| T1a-2555 | I-3 | II-136 | II-182 |
| T1a-2556 | I-3 | II-136 | II-183 |
| T1a-2557 | I-3 | II-136 | II-184 |
| T1a-2558 | I-3 | II-136 | II-185 |
| T1a-2559 | I-3 | II-136 | II-186 |
| T1a-2560 | I-3 | II-136 | II-187 |
| T1a-2561 | I-3 | II-136 | II-188 |
| T1a-2562 | I-3 | II-136 | II-189 |
| T1a-2563 | I-3 | II-136 | II-190 |
| T1a-2564 | I-3 | II-136 | II-191 |
| T1a-2565 | I-3 | II-136 | II-192 |
| T1a-2566 | I-3 | II-136 | II-193 |
| T1a-2567 | I-3 | II-136 | II-194 |
| T1a-2568 | I-3 | II-136 | II-195 |
| T1a-2569 | I-3 | II-136 | II-196 |
| T1a-2570 | I-3 | II-136 | II-197 |
| T1a-2571 | I-3 | II-136 | II-198 |
| T1a-2572 | I-3 | II-136 | II-199 |
| T1a-2573 | I-3 | II-136 | II-200 |
| T1a-2574 | I-3 | II-136 | II-201 |
| T1a-2575 | I-3 | II-136 | II-202 |
| T1a-2576 | I-3 | II-136 | II-203 |
| T1a-2577 | I-3 | II-137 | II-148 |
| T1a-2578 | I-3 | II-137 | II-149 |
| T1a-2579 | I-3 | II-137 | II-150 |
| T1a-2580 | I-3 | II-137 | II-151 |
| T1a-2581 | I-3 | II-137 | II-152 |
| T1a-2582 | I-3 | II-137 | II-153 |
| T1a-2583 | I-3 | II-137 | II-154 |
| T1a-2584 | I-3 | II-137 | II-155 |
| T1a-2585 | I-3 | II-137 | II-156 |
| T1a-2586 | I-3 | II-137 | II-157 |
| T1a-2587 | I-3 | II-137 | II-158 |
| T1a-2588 | I-3 | II-137 | II-159 |
| T1a-2589 | I-3 | II-137 | II-160 |
| T1a-2590 | I-3 | II-137 | II-161 |
| T1a-2591 | I-3 | II-137 | II-162 |
| T1a-2592 | I-3 | II-137 | II-163 |
| T1a-2593 | I-3 | II-137 | II-164 |
| T1a-2594 | I-3 | II-137 | II-165 |
| T1a-2595 | I-3 | II-137 | II-166 |
| T1a-2596 | I-3 | II-137 | II-167 |
| T1a-2597 | I-3 | II-137 | II-168 |
| T1a-2598 | I-3 | II-137 | II-169 |
| T1a-2599 | I-3 | II-137 | II-170 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-2600 | I-3 | II-137 | II-171 |
| T1a-2601 | I-3 | II-137 | II-172 |
| T1a-2602 | I-3 | II-137 | II-173 |
| T1a-2603 | I-3 | II-137 | II-174 |
| T1a-2604 | I-3 | II-137 | II-175 |
| T1a-2605 | I-3 | II-137 | II-176 |
| T1a-2606 | I-3 | II-137 | II-177 |
| T1a-2607 | I-3 | II-137 | II-178 |
| T1a-2608 | I-3 | II-137 | II-179 |
| T1a-2609 | I-3 | II-137 | II-180 |
| T1a-2610 | I-3 | II-137 | II-181 |
| T1a-2611 | I-3 | II-137 | II-182 |
| T1a-2612 | I-3 | II-137 | II-183 |
| T1a-2613 | I-3 | II-137 | II-184 |
| T1a-2614 | I-3 | II-137 | II-185 |
| T1a-2615 | I-3 | II-137 | II-186 |
| T1a-2616 | I-3 | II-137 | II-187 |
| T1a-2617 | I-3 | II-137 | II-188 |
| T1a-2618 | I-3 | II-137 | II-189 |
| T1a-2619 | I-3 | II-137 | II-190 |
| T1a-2620 | I-3 | II-137 | II-191 |
| T1a-2621 | I-3 | II-137 | II-192 |
| T1a-2622 | I-3 | II-137 | II-193 |
| T1a-2623 | I-3 | II-137 | II-194 |
| T1a-2624 | I-3 | II-137 | II-195 |
| T1a-2625 | I-3 | II-137 | II-196 |
| T1a-2626 | I-3 | II-137 | II-197 |
| T1a-2627 | I-3 | II-137 | II-198 |
| T1a-2628 | I-3 | II-137 | II-199 |
| T1a-2629 | I-3 | II-137 | II-200 |
| T1a-2630 | I-3 | II-137 | II-201 |
| T1a-2631 | I-3 | II-137 | II-202 |
| T1a-2632 | I-3 | II-137 | II-203 |
| T1a-2633 | I-3 | II-138 | II-148 |
| T1a-2634 | I-3 | II-138 | II-149 |
| T1a-2635 | I-3 | II-138 | II-150 |
| T1a-2636 | I-3 | II-138 | II-151 |
| T1a-2637 | I-3 | II-138 | II-152 |
| T1a-2638 | I-3 | II-138 | II-153 |
| T1a-2639 | I-3 | II-138 | II-154 |
| T1a-2640 | I-3 | II-138 | II-155 |
| T1a-2641 | I-3 | II-138 | II-156 |
| T1a-2642 | I-3 | II-138 | II-157 |
| T1a-2643 | I-3 | II-138 | II-158 |
| T1a-2644 | I-3 | II-138 | II-159 |
| T1a-2645 | I-3 | II-138 | II-160 |
| T1a-2646 | I-3 | II-138 | II-161 |
| T1a-2647 | I-3 | II-138 | II-162 |
| T1a-2648 | I-3 | II-138 | II-163 |
| T1a-2649 | I-3 | II-138 | II-164 |
| T1a-2650 | I-3 | II-138 | II-165 |
| T1a-2651 | I-3 | II-138 | II-166 |
| T1a-2652 | I-3 | II-138 | II-167 |
| T1a-2653 | I-3 | II-138 | II-168 |
| T1a-2654 | I-3 | II-138 | II-169 |
| T1a-2655 | I-3 | II-138 | II-170 |
| T1a-2656 | I-3 | II-138 | II-171 |
| T1a-2657 | I-3 | II-138 | II-172 |
| T1a-2658 | I-3 | II-138 | II-173 |
| T1a-2659 | I-3 | II-138 | II-174 |
| T1a-2660 | I-3 | II-138 | II-175 |
| T1a-2661 | I-3 | II-138 | II-176 |
| T1a-2662 | I-3 | II-138 | II-177 |
| T1a-2663 | I-3 | II-138 | II-178 |
| T1a-2664 | I-3 | II-138 | II-179 |
| T1a-2665 | I-3 | II-138 | II-180 |
| T1a-2666 | I-3 | II-138 | II-181 |
| T1a-2667 | I-3 | II-138 | II-182 |
| T1a-2668 | I-3 | II-138 | II-183 |
| T1a-2669 | I-3 | II-138 | II-184 |
| T1a-2670 | I-3 | II-138 | II-185 |
| T1a-2671 | I-3 | II-138 | II-186 |
| T1a-2672 | I-3 | II-138 | II-187 |
| T1a-2673 | I-3 | II-138 | II-188 |
| T1a-2674 | I-3 | II-138 | II-189 |
| T1a-2675 | I-3 | II-138 | II-190 |
| T1a-2676 | I-3 | II-138 | II-191 |
| T1a-2677 | I-3 | II-138 | II-192 |
| T1a-2678 | I-3 | II-138 | II-193 |
| T1a-2679 | I-3 | II-138 | II-194 |
| T1a-2680 | I-3 | II-138 | II-195 |
| T1a-2681 | I-3 | II-138 | II-196 |
| T1a-2682 | I-3 | II-138 | II-197 |
| T1a-2683 | I-3 | II-138 | II-198 |
| T1a-2684 | I-3 | II-138 | II-199 |
| T1a-2685 | I-3 | II-138 | II-200 |
| T1a-2686 | I-3 | II-138 | II-201 |
| T1a-2687 | I-3 | II-138 | II-202 |
| T1a-2688 | I-3 | II-138 | II-203 |
| T1a-2689 | I-3 | II-140 | II-148 |
| T1a-2690 | I-3 | II-141 | II-149 |
| T1a-2691 | I-3 | II-141 | II-150 |
| T1a-2692 | I-3 | II-141 | II-151 |
| T1a-2693 | I-3 | II-141 | II-152 |
| T1a-2694 | I-3 | II-141 | II-153 |
| T1a-2695 | I-3 | II-141 | II-154 |
| T1a-2696 | I-3 | II-141 | II-155 |
| T1a-2697 | I-3 | II-141 | II-156 |
| T1a-2698 | I-3 | II-141 | II-157 |
| T1a-2699 | I-3 | II-141 | II-158 |
| T1a-2700 | I-3 | II-141 | II-159 |
| T1a-2701 | I-3 | II-141 | II-160 |
| T1a-2702 | I-3 | II-141 | II-161 |
| T1a-2703 | I-3 | II-141 | II-162 |
| T1a-2704 | I-3 | II-141 | II-163 |
| T1a-2705 | I-3 | II-141 | II-164 |
| T1a-2706 | I-3 | II-141 | II-165 |
| T1a-2707 | I-3 | II-141 | II-166 |
| T1a-2708 | I-3 | II-141 | II-167 |
| T1a-2709 | I-3 | II-141 | II-168 |
| T1a-2710 | I-3 | II-141 | II-169 |
| T1a-2711 | I-3 | II-141 | II-170 |
| T1a-2712 | I-3 | II-141 | II-171 |
| T1a-2713 | I-3 | II-141 | II-172 |
| T1a-2714 | I-3 | II-141 | II-173 |
| T1a-2715 | I-3 | II-141 | II-174 |
| T1a-2716 | I-3 | II-141 | II-175 |
| T1a-2717 | I-3 | II-141 | II-176 |
| T1a-2718 | I-3 | II-141 | II-177 |
| T1a-2719 | I-3 | II-141 | II-178 |
| T1a-2720 | I-3 | II-141 | II-179 |
| T1a-2721 | I-3 | II-141 | II-180 |
| T1a-2722 | I-3 | II-141 | II-181 |
| T1a-2723 | I-3 | II-141 | II-182 |
| T1a-2724 | I-3 | II-141 | II-183 |
| T1a-2725 | I-3 | II-141 | II-184 |
| T1a-2726 | I-3 | II-141 | II-185 |
| T1a-2727 | I-3 | II-141 | II-186 |
| T1a-2728 | I-3 | II-141 | II-187 |
| T1a-2729 | I-3 | II-141 | II-188 |
| T1a-2730 | I-3 | II-141 | II-189 |
| T1a-2731 | I-3 | II-141 | II-190 |
| T1a-2732 | I-3 | II-141 | II-191 |
| T1a-2733 | I-3 | II-141 | II-192 |
| T1a-2734 | I-3 | II-141 | II-193 |
| T1a-2735 | I-3 | II-141 | II-194 |
| T1a-2736 | I-3 | II-141 | II-195 |
| T1a-2737 | I-3 | II-141 | II-196 |
| T1a-2738 | I-3 | II-141 | II-197 |
| T1a-2739 | I-3 | II-141 | II-198 |
| T1a-2740 | I-3 | II-141 | II-199 |
| T1a-2741 | I-3 | II-141 | II-200 |
| T1a-2742 | I-3 | II-141 | II-201 |
| T1a-2743 | I-3 | II-141 | II-202 |
| T1a-2744 | I-3 | II-141 | II-203 |
| T1a-2745 | I-3 | II-142 | II-148 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-2746 | I-3 | II-142 | II-149 |
| T1a-2747 | I-3 | II-142 | II-150 |
| T1a-2748 | I-3 | II-142 | II-151 |
| T1a-2749 | I-3 | II-142 | II-152 |
| T1a-2750 | I-3 | II-142 | II-153 |
| T1a-2751 | I-3 | II-142 | II-154 |
| T1a-2752 | I-3 | II-142 | II-155 |
| T1a-2753 | I-3 | II-142 | II-156 |
| T1a-2754 | I-3 | II-142 | II-157 |
| T1a-2755 | I-3 | II-142 | II-158 |
| T1a-2756 | I-3 | II-142 | II-159 |
| T1a-2757 | I-3 | II-142 | II-160 |
| T1a-2758 | I-3 | II-142 | II-161 |
| T1a-2759 | I-3 | II-142 | II-162 |
| T1a-2760 | I-3 | II-142 | II-163 |
| T1a-2761 | I-3 | II-142 | II-164 |
| T1a-2762 | I-3 | II-142 | II-165 |
| T1a-2763 | I-3 | II-142 | II-166 |
| T1a-2764 | I-3 | II-142 | II-167 |
| T1a-2765 | I-3 | II-142 | II-168 |
| T1a-2766 | I-3 | II-142 | II-169 |
| T1a-2767 | I-3 | II-142 | II-170 |
| T1a-2768 | I-3 | II-142 | II-171 |
| T1a-2769 | I-3 | II-142 | II-172 |
| T1a-2770 | I-3 | II-142 | II-173 |
| T1a-2771 | I-3 | II-142 | II-174 |
| T1a-2772 | I-3 | II-142 | II-175 |
| T1a-2773 | I-3 | II-142 | II-176 |
| T1a-2774 | I-3 | II-142 | II-177 |
| T1a-2775 | I-3 | II-142 | II-178 |
| T1a-2776 | I-3 | II-142 | II-179 |
| T1a-2777 | I-3 | II-142 | II-180 |
| T1a-2778 | I-3 | II-142 | II-181 |
| T1a-2779 | I-3 | II-142 | II-182 |
| T1a-2780 | I-3 | II-142 | II-183 |
| T1a-2781 | I-3 | II-142 | II-184 |
| T1a-2782 | I-3 | II-142 | II-185 |
| T1a-2783 | I-3 | II-142 | II-186 |
| T1a-2784 | I-3 | II-142 | II-187 |
| T1a-2785 | I-3 | II-142 | II-188 |
| T1a-2786 | I-3 | II-142 | II-189 |
| T1a-2787 | I-3 | II-142 | II-190 |
| T1a-2788 | I-3 | II-142 | II-191 |
| T1a-2789 | I-3 | II-142 | II-192 |
| T1a-2790 | I-3 | II-142 | II-193 |
| T1a-2791 | I-3 | II-142 | II-194 |
| T1a-2792 | I-3 | II-142 | II-195 |
| T1a-2793 | I-3 | II-142 | II-196 |
| T1a-2794 | I-3 | II-142 | II-197 |
| T1a-2795 | I-3 | II-142 | II-198 |
| T1a-2796 | I-3 | II-142 | II-199 |
| T1a-2797 | I-3 | II-142 | II-200 |
| T1a-2798 | I-3 | II-142 | II-201 |
| T1a-2799 | I-3 | II-142 | II-202 |
| T1a-2800 | I-3 | II-142 | II-203 |
| T1a-2801 | I-3 | II-143 | II-148 |
| T1a-2802 | I-3 | II-143 | II-149 |
| T1a-2803 | I-3 | II-143 | II-150 |
| T1a-2804 | I-3 | II-143 | II-151 |
| T1a-2805 | I-3 | II-143 | II-152 |
| T1a-2806 | I-3 | II-143 | II-153 |
| T1a-2807 | I-3 | II-143 | II-154 |
| T1a-2808 | I-3 | II-143 | II-155 |
| T1a-2809 | I-3 | II-143 | II-156 |
| T1a-2810 | I-3 | II-143 | II-157 |
| T1a-2811 | I-3 | II-143 | II-158 |
| T1a-2812 | I-3 | II-143 | II-159 |
| T1a-2813 | I-3 | II-143 | II-160 |
| T1a-2814 | I-3 | II-143 | II-161 |
| T1a-2815 | I-3 | II-143 | II-162 |
| T1a-2816 | I-3 | II-143 | II-163 |
| T1a-2817 | I-3 | II-143 | II-164 |
| T1a-2818 | I-3 | II-143 | II-165 |
| T1a-2819 | I-3 | II-143 | II-166 |
| T1a-2820 | I-3 | II-143 | II-167 |
| T1a-2821 | I-3 | II-143 | II-168 |
| T1a-2822 | I-3 | II-143 | II-169 |
| T1a-2823 | I-3 | II-143 | II-170 |
| T1a-2824 | I-3 | II-143 | II-171 |
| T1a-2825 | I-3 | II-143 | II-172 |
| T1a-2826 | I-3 | II-143 | II-173 |
| T1a-2827 | I-3 | II-143 | II-174 |
| T1a-2828 | I-3 | II-143 | II-175 |
| T1a-2829 | I-3 | II-143 | II-176 |
| T1a-2830 | I-3 | II-143 | II-177 |
| T1a-2831 | I-3 | II-143 | II-178 |
| T1a-2832 | I-3 | II-143 | II-179 |
| T1a-2833 | I-3 | II-143 | II-180 |
| T1a-2834 | I-3 | II-143 | II-181 |
| T1a-2835 | I-3 | II-143 | II-182 |
| T1a-2836 | I-3 | II-143 | II-183 |
| T1a-2837 | I-3 | II-143 | II-184 |
| T1a-2838 | I-3 | II-143 | II-185 |
| T1a-2839 | I-3 | II-143 | II-186 |
| T1a-2840 | I-3 | II-143 | II-187 |
| T1a-2841 | I-3 | II-143 | II-188 |
| T1a-2842 | I-3 | II-143 | II-189 |
| T1a-2843 | I-3 | II-143 | II-190 |
| T1a-2844 | I-3 | II-143 | II-191 |
| T1a-2845 | I-3 | II-143 | II-192 |
| T1a-2846 | I-3 | II-143 | II-193 |
| T1a-2847 | I-3 | II-143 | II-194 |
| T1a-2848 | I-3 | II-143 | II-195 |
| T1a-2849 | I-3 | II-143 | II-196 |
| T1a-2850 | I-3 | II-143 | II-197 |
| T1a-2851 | I-3 | II-143 | II-198 |
| T1a-2852 | I-3 | II-143 | II-199 |
| T1a-2853 | I-3 | II-143 | II-200 |
| T1a-2854 | I-3 | II-143 | II-201 |
| T1a-2855 | I-3 | II-143 | II-202 |
| T1a-2856 | I-3 | II-143 | II-203 |
| T1a-2857 | I-3 | II-144 | II-148 |
| T1a-2858 | I-3 | II-144 | II-149 |
| T1a-2859 | I-3 | II-144 | II-150 |
| T1a-2860 | I-3 | II-144 | II-151 |
| T1a-2861 | I-3 | II-144 | II-152 |
| T1a-2862 | I-3 | II-144 | II-153 |
| T1a-2863 | I-3 | II-144 | II-154 |
| T1a-2864 | I-3 | II-144 | II-155 |
| T1a-2865 | I-3 | II-144 | II-156 |
| T1a-2866 | I-3 | II-144 | II-157 |
| T1a-2867 | I-3 | II-144 | II-158 |
| T1a-2868 | I-3 | II-144 | II-159 |
| T1a-2869 | I-3 | II-144 | II-160 |
| T1a-2870 | I-3 | II-144 | II-161 |
| T1a-2871 | I-3 | II-144 | II-162 |
| T1a-2872 | I-3 | II-144 | II-163 |
| T1a-2873 | I-3 | II-144 | II-164 |
| T1a-2874 | I-3 | II-144 | II-165 |
| T1a-2875 | I-3 | II-144 | II-166 |
| T1a-2876 | I-3 | II-144 | II-167 |
| T1a-2877 | I-3 | II-144 | II-168 |
| T1a-2878 | I-3 | II-144 | II-169 |
| T1a-2879 | I-3 | II-144 | II-170 |
| T1a-2880 | I-3 | II-144 | II-171 |
| T1a-2881 | I-3 | II-144 | II-172 |
| T1a-2882 | I-3 | II-144 | II-173 |
| T1a-2883 | I-3 | II-144 | II-174 |
| T1a-2884 | I-3 | II-144 | II-175 |
| T1a-2885 | I-3 | II-144 | II-176 |
| T1a-2886 | I-3 | II-144 | II-177 |
| T1a-2887 | I-3 | II-144 | II-178 |
| T1a-2888 | I-3 | II-144 | II-179 |
| T1a-2889 | I-3 | II-144 | II-180 |
| T1a-2890 | I-3 | II-144 | II-181 |
| T1a-2891 | I-3 | II-144 | II-182 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-2892 | I-3 | II-144 | II-183 |
| T1a-2893 | I-3 | II-144 | II-184 |
| T1a-2894 | I-3 | II-144 | II-185 |
| T1a-2895 | I-3 | II-144 | II-186 |
| T1a-2896 | I-3 | II-144 | II-187 |
| T1a-2897 | I-3 | II-144 | II-188 |
| T1a-2898 | I-3 | II-144 | II-189 |
| T1a-2899 | I-3 | II-144 | II-190 |
| T1a-2900 | I-3 | II-144 | II-191 |
| T1a-2901 | I-3 | II-144 | II-192 |
| T1a-2902 | I-3 | II-144 | II-193 |
| T1a-2903 | I-3 | II-144 | II-194 |
| T1a-2904 | I-3 | II-144 | II-195 |
| T1a-2905 | I-3 | II-144 | II-196 |
| T1a-2906 | I-3 | II-144 | II-197 |
| T1a-2907 | I-3 | II-144 | II-198 |
| T1a-2908 | I-3 | II-144 | II-199 |
| T1a-2909 | I-3 | II-144 | II-200 |
| T1a-2910 | I-3 | II-144 | II-201 |
| T1a-2911 | I-3 | II-144 | II-202 |
| T1a-2912 | I-3 | II-144 | II-203 |
| T1a-2913 | I-3 | II-145 | II-148 |
| T1a-2914 | I-3 | II-145 | II-149 |
| T1a-2915 | I-3 | II-145 | II-150 |
| T1a-2916 | I-3 | II-145 | II-151 |
| T1a-2917 | I-3 | II-145 | II-152 |
| T1a-2918 | I-3 | II-145 | II-153 |
| T1a-2919 | I-3 | II-145 | II-154 |
| T1a-2920 | I-3 | II-145 | II-155 |
| T1a-2921 | I-3 | II-145 | II-156 |
| T1a-2922 | I-3 | II-145 | II-157 |
| T1a-2923 | I-3 | II-145 | II-158 |
| T1a-2924 | I-3 | II-145 | II-159 |
| T1a-2925 | I-3 | II-145 | II-160 |
| T1a-2926 | I-3 | II-145 | II-161 |
| T1a-2927 | I-3 | II-145 | II-162 |
| T1a-2928 | I-3 | II-145 | II-163 |
| T1a-2929 | I-3 | II-145 | II-164 |
| T1a-2930 | I-3 | II-145 | II-165 |
| T1a-2931 | I-3 | II-145 | II-166 |
| T1a-2932 | I-3 | II-145 | II-167 |
| T1a-2933 | I-3 | II-145 | II-168 |
| T1a-2934 | I-3 | II-145 | II-169 |
| T1a-2935 | I-3 | II-145 | II-170 |
| T1a-2936 | I-3 | II-145 | II-171 |
| T1a-2937 | I-3 | II-145 | II-172 |
| T1a-2938 | I-3 | II-145 | II-173 |
| T1a-2939 | I-3 | II-145 | II-174 |
| T1a-2940 | I-3 | II-145 | II-175 |
| T1a-2941 | I-3 | II-145 | II-176 |
| T1a-2942 | I-3 | II-145 | II-177 |
| T1a-2943 | I-3 | II-145 | II-178 |
| T1a-2944 | I-3 | II-145 | II-179 |
| T1a-2945 | I-3 | II-145 | II-180 |
| T1a-2946 | I-3 | II-145 | II-181 |
| T1a-2947 | I-3 | II-145 | II-182 |
| T1a-2948 | I-3 | II-145 | II-183 |
| T1a-2949 | I-3 | II-145 | II-184 |
| T1a-2950 | I-3 | II-145 | II-185 |
| T1a-2951 | I-3 | II-145 | II-186 |
| T1a-2952 | I-3 | II-145 | II-187 |
| T1a-2953 | I-3 | II-145 | II-188 |
| T1a-2954 | I-3 | II-145 | II-189 |
| T1a-2955 | I-3 | II-145 | II-190 |
| T1a-2956 | I-3 | II-145 | II-191 |
| T1a-2957 | I-3 | II-145 | II-192 |
| T1a-2958 | I-3 | II-145 | II-193 |
| T1a-2959 | I-3 | II-145 | II-194 |
| T1a-2960 | I-3 | II-145 | II-195 |
| T1a-2961 | I-3 | II-145 | II-196 |
| T1a-2962 | I-3 | II-145 | II-197 |
| T1a-2963 | I-3 | II-145 | II-198 |
| T1a-2964 | I-3 | II-145 | II-199 |
| T1a-2965 | I-3 | II-145 | II-200 |
| T1a-2966 | I-3 | II-145 | II-201 |
| T1a-2967 | I-3 | II-145 | II-202 |
| T1a-2968 | I-3 | II-145 | II-203 |
| T1a-2969 | I-3 | II-146 | II-148 |
| T1a-2970 | I-3 | II-146 | II-149 |
| T1a-2971 | I-3 | II-146 | II-150 |
| T1a-2972 | I-3 | II-146 | II-151 |
| T1a-2973 | I-3 | II-146 | II-152 |
| T1a-2974 | I-3 | II-146 | II-153 |
| T1a-2975 | I-3 | II-146 | II-154 |
| T1a-2976 | I-3 | II-146 | II-155 |
| T1a-2977 | I-3 | II-146 | II-156 |
| T1a-2978 | I-3 | II-146 | II-157 |
| T1a-2979 | I-3 | II-146 | II-158 |
| T1a-2980 | I-3 | II-146 | II-159 |
| T1a-2981 | I-3 | II-146 | II-160 |
| T1a-2982 | I-3 | II-146 | II-161 |
| T1a-2983 | I-3 | II-146 | II-162 |
| T1a-2984 | I-3 | II-146 | II-163 |
| T1a-2985 | I-3 | II-146 | II-164 |
| T1a-2986 | I-3 | II-146 | II-165 |
| T1a-2987 | I-3 | II-146 | II-166 |
| T1a-2988 | I-3 | II-146 | II-167 |
| T1a-2989 | I-3 | II-146 | II-168 |
| T1a-2990 | I-3 | II-146 | II-169 |
| T1a-2991 | I-3 | II-146 | II-170 |
| T1a-2992 | I-3 | II-146 | II-171 |
| T1a-2993 | I-3 | II-146 | II-172 |
| T1a-2994 | I-3 | II-146 | II-173 |
| T1a-2995 | I-3 | II-146 | II-174 |
| T1a-2996 | I-3 | II-146 | II-175 |
| T1a-2997 | I-3 | II-146 | II-176 |
| T1a-2998 | I-3 | II-146 | II-177 |
| T1a-2999 | I-3 | II-146 | II-178 |
| T1a-3000 | I-3 | II-146 | II-179 |
| T1a-3001 | I-3 | II-146 | II-180 |
| T1a-3002 | I-3 | II-146 | II-181 |
| T1a-3003 | I-3 | II-146 | II-182 |
| T1a-3004 | I-3 | II-146 | II-183 |
| T1a-3005 | I-3 | II-146 | II-184 |
| T1a-3006 | I-3 | II-146 | II-185 |
| T1a-3007 | I-3 | II-146 | II-186 |
| T1a-3008 | I-3 | II-146 | II-187 |
| T1a-3009 | I-3 | II-146 | II-188 |
| T1a-3010 | I-3 | II-146 | II-189 |
| T1a-3011 | I-3 | II-146 | II-190 |
| T1a-3012 | I-3 | II-146 | II-191 |
| T1a-3013 | I-3 | II-146 | II-192 |
| T1a-3014 | I-3 | II-146 | II-193 |
| T1a-3015 | I-3 | II-146 | II-194 |
| T1a-3016 | I-3 | II-146 | II-195 |
| T1a-3017 | I-3 | II-146 | II-196 |
| T1a-3018 | I-3 | II-146 | II-197 |
| T1a-3019 | I-3 | II-146 | II-198 |
| T1a-3020 | I-3 | II-146 | II-199 |
| T1a-3021 | I-3 | II-146 | II-200 |
| T1a-3022 | I-3 | II-146 | II-201 |
| T1a-3023 | I-3 | II-146 | II-202 |
| T1a-3024 | I-3 | II-146 | II-203 |
| T1a-3025 | I-3 | II-147 | II-148 |
| T1a-3026 | I-3 | II-147 | II-149 |
| T1a-3027 | I-3 | II-147 | II-150 |
| T1a-3028 | I-3 | II-147 | II-151 |
| T1a-3029 | I-3 | II-147 | II-152 |
| T1a-3030 | I-3 | II-147 | II-153 |
| T1a-3031 | I-3 | II-147 | II-154 |
| T1a-3032 | I-3 | II-147 | II-155 |
| T1a-3033 | I-3 | II-147 | II-156 |
| T1a-3034 | I-3 | II-147 | II-157 |
| T1a-3035 | I-3 | II-147 | II-158 |
| T1a-3036 | I-3 | II-147 | II-159 |
| T1a-3037 | I-3 | II-147 | II-160 |

TABLE T1a-continued

Three-component compositions T1a-1 to T1a-3080 comprising compound I-3, one component II and one component III, in particular ternary compositions containing compound I-3, II and III as only active ingredients.

| composition | I | II | III |
|---|---|---|---|
| T1a-3038 | I-3 | II-147 | II-161 |
| T1a-3039 | I-3 | II-147 | II-162 |
| T1a-3040 | I-3 | II-147 | II-163 |
| T1a-3041 | I-3 | II-147 | II-164 |
| T1a-3042 | I-3 | II-147 | II-165 |
| T1a-3043 | I-3 | II-147 | II-166 |
| T1a-3044 | I-3 | II-147 | II-167 |
| T1a-3045 | I-3 | II-147 | II-168 |
| T1a-3046 | I-3 | II-147 | II-169 |
| T1a-3047 | I-3 | II-147 | II-170 |
| T1a-3048 | I-3 | II-147 | II-171 |
| T1a-3049 | I-3 | II-147 | II-172 |
| T1a-3050 | I-3 | II-147 | II-173 |
| T1a-3051 | I-3 | II-147 | II-174 |
| T1a-3052 | I-3 | II-147 | II-175 |
| T1a-3053 | I-3 | II-147 | II-176 |
| T1a-3054 | I-3 | II-147 | II-177 |
| T1a-3055 | I-3 | II-147 | II-178 |
| T1a-3056 | I-3 | II-147 | II-179 |
| T1a-3057 | I-3 | II-147 | II-180 |
| T1a-3058 | I-3 | II-147 | II-181 |
| T1a-3059 | I-3 | II-147 | II-182 |
| T1a-3060 | I-3 | II-147 | II-183 |
| T1a-3061 | I-3 | II-147 | II-184 |
| T1a-3062 | I-3 | II-147 | II-185 |
| T1a-3063 | I-3 | II-147 | II-186 |
| T1a-3064 | I-3 | II-147 | II-187 |
| T1a-3065 | I-3 | II-147 | II-188 |
| T1a-3066 | I-3 | II-147 | II-189 |
| T1a-3067 | I-3 | II-147 | II-190 |
| T1a-3068 | I-3 | II-147 | II-191 |
| T1a-3069 | I-3 | II-147 | II-192 |
| T1a-3070 | I-3 | II-147 | II-193 |
| T1a-3071 | I-3 | II-147 | II-194 |
| T1a-3072 | I-3 | II-147 | II-195 |
| T1a-3073 | I-3 | II-147 | II-196 |
| T1a-3074 | I-3 | II-147 | II-197 |
| T1a-3075 | I-3 | II-147 | II-198 |
| T1a-3076 | I-3 | II-147 | II-199 |
| T1a-3077 | I-3 | II-147 | II-200 |
| T1a-3078 | I-3 | II-147 | II-201 |
| T1a-3079 | I-3 | II-147 | II-202 |
| T1a-3080 | I-3 | II-147 | II-203 |

Table T2a: Three-component compositions T2a-1 to T2a-3080 corresponding to the respective compositions T1a-1 to T1a-3080, wherein component I is I-2 instead of I-3. Consequently, Table T2a contains compositions T2a-1 to T2a-3080 comprising compound I-2, component II and component III, in particular ternary compositions containing compound I-2, II and III as only active ingredients.

Table T3a: Three-component compositions T3a-1 to T3a-3080 corresponding to the respective compositions T1a-1 to T1a-3080, wherein component I is I-1 instead of I-3. Consequently, Table T3a contains compositions T3a-1 to T3a-3080 comprising compound I-3, component II and component III, in particular ternary compositions containing compound I-1, II and III as only active ingredients.

Table T4a: Three-component compositions T4a-1 to T4a-3080 corresponding to the respective compositions T1a-1 to T1a-3080, wherein component I is I-4 instead of I-3. Consequently, Table T4a contains compositions T4a-1 to T4a-3080 comprising compound I-4, component II and component III, in particular ternary compositions containing compound I-4, II and III as only active ingredients.

Table T5a: Three-component compositions T5a-1 to T5a-3080 corresponding to the respective compositions T1a-1 to T1a-3080, wherein component I is I-5 instead of I-3. Consequently, Table T5a contains compositions T5a-1 to T5a-3080 comprising compound I-5, component II and component III, in particular ternary compositions containing compound I-5, II and III as only active ingredients.

Table T6a: Three-component compositions T6a-1 to T6a-3080 corresponding to the respective compositions T1a-1 to T1a-3080, wherein component I is I-6 instead of I-3. Consequently, Table T6a contains compositions T6a-1 to T6a-3080 comprising compound I-6, component II and component III, in particular ternary compositions containing compound I-6, II and III as only active ingredients.

Table T7a: Three-component compositions T7a-1 to T7a-3080 corresponding to the respective compositions T1a-1 to T1a-3080, wherein component I is I-7 instead of I-3. Consequently, Table T7a contains compositions T7a-1 to T7a-3080 comprising compound I-7, component II and component III, in particular ternary compositions containing compound I-7, II and III as only active ingredients.

Table T8a: Three-component compositions T8a-1 to T8a-3080 corresponding to the respective compositions T1a-1 to T1a-3080, wherein component I is I-8 instead of I-3. Consequently, Table T8a contains compositions T8a-1 to T8a-3080 comprising compound I-8, component II and component III, in particular ternary compositions containing compound I-8, II and III as only active ingredients.

Table T9a: Three-component compositions T9a-1 to T9a-3080 corresponding to the respective compositions T1a-1 to T1a-3080, wherein component I is I-9 instead of I-3. Consequently, Table T9a contains compositions T9a-1 to T9a-3080 comprising compound I-9, component II and component III, in particular ternary compositions containing compound I-9, II and III as only active ingredients.

Table T10a: Three-component compositions T10a-1 to T10a-3080 corresponding to the respective compositions T1a-1 to T1a-3080, wherein component I is I-10 instead of I-3. Consequently, Table T10a contains compositions T10a-1 to T10a-3080 comprising compound I-10, component II and component III, in particular ternary compositions containing compound I-10, II and III as only active ingredients.

Table T11 a: Three-component compositions T11 a-1 to T11 a-3080 corresponding to the respective compositions T1a-1 to T1a-3080, wherein component I is I-11 instead of I-3. Consequently, Table T11a contains compositions T11 a-1 to T11a-3080 comprising compound I-11, component II and component III, in particular ternary compositions containing compound I-11, II and III as only active ingredients.

Table T12a: Three-component compositions T12a-1 to T12a-3080 corresponding to the respective compositions T1a-1 to T1a-3080, wherein component I is I-12 instead of I-3. Consequently, Table T12a contains compositions T12a-1 to T12a-3080 comprising compound I-12, component II and component III, in particular ternary compositions containing compound I-12, II and III as only active ingredients.

Table T13a: Three-component compositions T13a-1 to T13a-3080 corresponding to the respective compositions T1a-1 to T1a-3080, wherein component I is I-13 instead of I-3. Consequently, Table T13a contains compositions T13a-1 to T13a-3080 comprising compound I-13, component II and component III, in particular ternary compositions containing compound I-13, II and III as only active ingredients.

Table T14a: Three-component compositions T14a-1 to T14a-3080 corresponding to the respective compositions T1a-1 to T1a-3080, wherein component I is I-14 instead of I-3. Consequently, Table T14a contains compositions T14a-1 to T14a-3080 comprising compound I-14, component II and component III, in particular ternary compositions containing compound I-14, II and III as only active ingredients.

Table T15a: Three-component compositions T15a-1 to T15a-3080 corresponding to the respective compositions T1a-1 to T1a-3080, wherein component I is I-15 instead of I-3. Consequently, Table T15a contains compositions T15a-1 to T15a-3080 comprising compound I-15, component II and component III, in particular ternary compositions containing compound I-15, II and III as only active ingredients.

Table T16a: Three-component compositions T16a-1 to T16a-3080 corresponding to the respective compositions T1a-1 to T1a-3080, wherein component I is I-16 instead of I-3. Consequently, Table T16a contains compositions T16a-1 to T16a-3080 comprising compound I-16, component II and component III, in particular ternary compositions containing compound I-16, II and III as only active ingredients.

Table T17a: Three-component compositions T17a-1 to T17a-3080 corresponding to the respective compositions T1a-1 to T1a-3080, wherein component I is I-17 instead of I-3. Consequently, Table T17a contains compositions T17a-1 to T17a-3080 comprising compound I-17, component II and component III, in particular ternary compositions containing compound I-17, II and III as only active ingredients.

Table T18a: Three-component compositions T18a-1 to T18a-3080 corresponding to the respective compositions T1a-1 to T1a-3080, wherein component I is I-18 instead of I-3. Consequently, Table T18a contains compositions T18a-1 to T18a-3080 comprising compound I-18, component II and component III, in particular ternary compositions containing compound I-18, 11 and 11 as only active ingredients.

Table T19a: Three-component compositions T19a-1 to T19a-3080 corresponding to the respective compositions T1a-1 to T1a-3080, wherein component I is I-19 instead of I-3. Consequently, Table T19a contains compositions T19a-1 to T19a-3080 comprising compound I-19, component II and component III, in particular ternary compositions containing compound I-19, II and III as only active ingredients.

Table T20a: Three-component compositions T20a-1 to T20a-3080 corresponding to the respective compositions T1a-1 to T1a-3080, wherein component I is I-20 instead of I-3. Consequently, Table T20a contains compositions T20a-1 to T20a-3080 comprising compound I-20, component II and component III, in particular ternary compositions containing compound I-20, II and III as only active ingredients.

Table T21a: Three-component compositions T21a-1 to T21a-3080 corresponding to the respective compositions T1a-1 to T1a-3080, wherein component I is I-21 instead of I-3. Consequently, Table T21a contains compositions T21a-1 to T21a-3080 comprising compound I-21, component II and component III, in particular ternary compositions containing compound I-21, II and III as only active ingredients.

Table T22a: Three-component compositions T22a-1 to T22a-3080 corresponding to the respective compositions T1a-1 to T1a-3080, wherein component I is I-22 instead of I-3. Consequently, Table T22a contains compositions T22a-1 to T22a-3080 comprising compound I-22, component II and component III, in particular ternary compositions containing compound I-22, II and III as only active ingredients.

Table T23a: Three-component compositions T23a-1 to T23a-3080 corresponding to the respective compositions T1a-1 to T1a-3080, wherein component I is I-23 instead of I-3. Consequently, Table T23a contains compositions T23a-1 to T23a-3080 comprising compound I-23, component II and component III, in particular ternary compositions containing compound I-23, II and III as only active ingredients.

Table T24a: Three-component compositions T24a-1 to T24a-3080 corresponding to the respective compositions T1a-1 to T1a-3080, wherein component I is I-24 instead of I-3. Consequently, Table T24a contains compositions T24a-1 to T24a-3080 comprising compound I-24, component II and component III, in particular ternary compositions containing compound I-24, II and III as only active ingredients.

Table T25a: Three-component compositions T25a-1 to T25a-3080 corresponding to the respective compositions T1a-1 to T1a-3080, wherein component I is I-25 instead of I-3. Consequently, Table T25a contains compositions T25a-1 to T25a-3080 comprising compound I-25, component II and component III, in particular ternary compositions containing compound I-25, II and III as only active ingredients.

Table T26a: Three-component compositions T26a-1 to T26a-3080 corresponding to the respective compositions T1a-1 to T1a-3080, wherein component I is I-26 instead of I-3. Consequently, Table T26a contains compositions T26a-1 to T26a-3080 comprising compound I-26, component II and component III, in particular ternary compositions containing compound I-26, II and III as only active ingredients.

Table T27a: Three-component compositions T27a-1 to T27a-3080 corresponding to the respective compositions T1a-1 to T1a-3080, wherein component I is I-27 instead of I-3. Consequently, Table T27a contains compositions T27a-1 to T27a-3080 comprising compound I-27, component II and component III, in particular ternary compositions containing compound I-27, II and III as only active ingredients.

Table T28a: Three-component compositions T28a-1 to T28a-3080 corresponding to the respective compositions T1a-1 to T1a-3080, wherein component I is I-28 instead of I-3. Consequently, Table T28a contains compositions T28a-1 to T28a-3080 comprising compound I-28, component II and component III, in particular ternary compositions containing compound I-28, II and III as only active ingredients.

Table T29a: Three-component compositions T29a-1 to T29a-3080 corresponding to the respective compositions T1a-1 to T1a-3080, wherein component I is I-29 instead of I-3. Consequently, Table T29a contains compositions T29a-1 to T29a-3080 comprising compound I-29, component II and component III, in particular ternary compositions containing compound I-29, II and III as only active ingredients.

Table T30a: Three-component compositions T30a-1 to T30a-3080 corresponding to the respective compositions T1a-1 to T1a-3080, wherein component I is I-30 instead of I-3. Consequently, Table T30a contains compositions T30a-1 to T30a-3080 comprising compound I-30, component II and component III, in particular ternary compositions containing compound I-30, II and III as only active ingredients.

Table T31a: Three-component compositions T31a-1 to T31a-3080 corresponding to the respective compositions T1a-1 to T1a-3080, wherein component I is I-31 instead of I-3. Consequently, Table T31a contains compositions T31a-1 to T31a-3080 comprising compound I-31, component II and component III, in particular ternary compositions containing compound I-31, II and III as only active ingredients.

According to the present invention, it may be preferred that the three-component compositions comprise besides component I and component II a component III that is selected from a further active compound, preferably in a synergistically effective amount. In particular, according to this embodiment, the component III is selected from the following compounds of groups A')

A') Respiration Inhibitors
Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide, pyribencarb, triclopyricarb/chlorodincarb, famoxadone, fenamidone;

inhibitors of complex III at Q site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxypyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxypyridine-2-carbonyl]amino]-6-methyl-4,9-dioxo-1,5-dioxonan-7-yl]2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

inhibitors of complex II (e. g. carboxamides): benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, tecloftalam, thifluzamide,
N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, N-(7-fluoro-1,1,3-trimethylindan-4-yl)-1,3-dimethyl-pyrazole-4-carboxamide, N-[2-(2,4-dichlorophenyl)-2-methoxy-1-methyl-ethyl]-3-(difluoromethyl)-1-methyl-pyrazole-4-carboxamide;

other respiration inhibitors (e.g. complex I, uncouplers): diflumetorim, (5,8-difluoro-quinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B') Sterol Biosynthesis Inhibitors (SBI Fungicides)
C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)-oxiranylmethyl]-2H-[1,2,4]triazole-3-thiol, 2-[2-chloro-4-(4-chlorophenoxy)phenyl]-1-(1,2,4-triazol-1-yl)pentan-2-ol, 1-[4-(4-chlorophenoxy)-2-(trifluoromethyl)phenyl]-1-cyclopropyl-2-(1,2,4-triazol-1-yl)ethanol, 2-[4-(4-chlorophenoxy)-2-(trifluoromethyl)phenyl]-1-(1,2,4-triazol-1-yl)butan-2-ol, 2-[2-chloro-4-(4-chlorophenoxy)phenyl]-1-(1,2,4-triazol-1-yl) butan-2-ol, 2-[4-(4-chlorophenoxy)-2-(trifluoromethyl)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)propan-2-ol, 2-[2-chloro-4-(4-chlorophenoxy)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)pentan-2-ol, 2-[4-(4-fluorophenoxy)-2-(trifluoromethyl)phenyl]-1-(1,2,4-triazol-1-yl)propan-2-ol; imidazoles: imazalil, pefurazoate, prochloraz, triflumizol; pyrimidines, pyridines and piperazines: fenarimol, nuarimol, pyrifenox, triforine, [3-(4-chloro-2-fluoro-phenyl)-5-(2,4-difluorophenyl) isoxazol-4-yl]-(3-pyridyl)methanol;

Delta14-reductase inhibitors: aldimorph, dodemorph, dodemorph-acetate, fenpropimorph, tridemorph, fenpropidin, piperalin, spiroxamine;

Inhibitors of 3-keto reductase: fenhexamid;

C') Nucleic Acid Synthesis Inhibitors
phenylamides or acyl amino acid fungicides: benalaxyl, benalaxyl-M, kiralaxyl, metalaxyl, metalaxyl-M (mefenoxam), ofurace, oxadixyl;
others: hymexazole, octhilinone, oxolinic acid, bupirimate, 5-fluorocytosine, 5-fluoro-2-(p-tolylmethoxy) pyrimidin-4-amine, 5-fluoro-2-(4-fluorophenylmethoxy)pyrimidin-4-amine;

D') Inhibitors of Cell Division and Cytoskeleton
tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine;
other cell division inhibitors: diethofencarb, ethaboxam, pencycuron, fluopicolide, zoxamide, metrafenone, pyriofenone;

E') Inhibitors of Amino Acid and Protein Synthesis
methionine synthesis inhibitors (anilino-pyrimidines): cyprodinil, mepanipyrim, pyrimethanil;

protein synthesis inhibitors: blasticidin-S, kasugamycin, kasugamycin hydrochloride-hydrate, mildiomycin, streptomycin, oxytetracyclin, polyoxine, validamycin A;

F') Signal Transduction Inhibitors
MAP/histidine kinase inhibitors: fluoroimid, iprodione, procymidone, vinclozolin, fenpiclonil, fludioxonil;
G protein inhibitors: quinoxyfen;

G') Lipid and Membrane Synthesis Inhibitors
Phospholipid biosynthesis inhibitors: edifenphos, iprobenfos, pyrazophos, isoprothiolane;
lipid peroxidation: dicloran, quintozene, tecnazene, tolclofos-methyl, biphenyl, chloroneb, etridiazole;
phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;
compounds affecting cell membrane permeability and fatty acids: propamocarb, propannocarb-hydrochlorid
fatty acid amide hydrolase inhibitors: oxathiapiprolin, 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl}phenyl methanesulfonate, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate;

H') Inhibitors with Multi Site Action
inorganic active substances: Bordeaux mixture, copper acetate, copper hydroxide, copper oxychloride, basic copper sulfate, sulfur;
thio- and dithiocarbamates: ferbam, mancozeb, maneb, metam, metiram, propineb, thiram, zineb, ziram;
organochlorine compounds (e.g. phthalimides, sulfamides, chloronitriles): anilazine, chlorothalonil, captafol, captan, folpet, dichlofluanid, dichlorophen, hexachlorbenzene, pentachlorphenole and its salts, phthalide, tolylfluanid, N-(4-chloro-2-nitro-phenyl)-N-ethyl-4-methyl-benzenesulfonamide;
guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

I') Cell Wall Synthesis Inhibitors
inhibitors of glucan synthesis: validamycin, polyoxin B;
melanin synthesis inhibitors: pyroquilon, tricyclazole, carpropamid, dicyclomet, fenoxanil;

J') Plant Defence Inducers
acibenzolar-S-methyl, probenazole, isotianil, tiadinil, prohexadione-calcium; phosphonates: fosetyl, fosetyl-aluminum, phosphorous acid and its salts;

K') Unknown Mode of Action
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, tolprocarb, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoro-methyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine (pyrisoxazole), N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate, tert-butyl N-[6-[[(Z)-[(1-methyltetrazol-5-yl)-phenyl-methylene]amino]oxymethyl]-2-pyridyl]carbamate (picarbutrazox), pentyl N-[6-[[(Z)-[(1-methyltetrazol-5-yl)-phenyl-methylene]amino]oxymethyl]-2-pyridyl]carbamate, 2-[2-[(7,8-difluoro-2-methyl-3-quinolyl)oxy]-6-fluoro-phenyl]propan-2-ol, 2-[2-fluoro-6-[(8-fluoro-2-methyl-3-quinolyl)oxy]phenyl]propan-2-ol, 3-(5-fluoro-3,3,4,4-tetramethyl-3,4-dihydroisoquinolin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl)quinoline, 9-fluoro-2,2-dimethyl-5-(3-quinolyl)-3H-1,4-benzoxazepine;

M') Growth Regulators
abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N') Herbicides
acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;
amino acid derivatives: bilanafos, glyphosate, glufosinate, sulfosate;
aryloxyphenoxypropionates: clodinafop, cyhalofop-butyl, fenoxaprop, fluazifop, haloxyfop, metamifop, propaquizafop, quizalofop, quizalofop-P-tefuryl;
Bipyridyls: diquat, paraquat;
(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;
cyclohexanediones: butroxydim, clethodim, cycloxydim, profoxydim, sethoxydim, tepraloxydim, tralkoxydim;
dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;
hydroxybenzonitriles: bomoxynil, dichlobenil, ioxynil;
imidazolinones: imazamethabenz, imazamox, imazapic, imazapyr, imazaquin, imazethapyr;
phenoxy acetic acids: clomeprop, 2,4-dichlorophenoxy-acetic acid (2,4-D), 2,4-DB, dichlorprop, MCPA, MCPA-thioethyl, MCPB, Mecoprop;
pyrazines: chloridazon, flufenpyr-ethyl, fluthiacet, norflurazon, pyridate;
pyridines: aminopyralid, clopyralid, diflufenican, dithiopyr, fluridone, fluroxypyr, picloram, picolinafen, thiazopyr;
sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;
triazines: ametryn, atrazine, cyanazine, dimethametryn, ethiozin, hexazinone, metamitron, metribuzin, prometryn, simazine, terbuthylazine, terbutryn, triaziflam;
ureas: chlorotoluron, daimuron, diuron, fluometuron, isoproturon, linuron, metha-benzthiazuron, tebuthiuron, trifludimoxazin;
other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;
others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, Drechslera monoceras, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester;

O') Insecticides
organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;
carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;
pyrethroids: allethrin, bifenthrin, cyfluthrin, cyhalothrin, cyphenothrin, cypermethrin, alpha-cypermethrin, beta-cypermethrin, zeta-cypermnethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;
insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;
nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-ylmethyl)-2-nitrimino-3,5-dimethyl-[1,3,5]triazinane;
GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;
macrocyclic lactone insecticides: abamectin, emamectin, milbemectin, lepimectin, spinosad, spinetoram;
mitochondrial electron transport inhibitor (METI) I acaricides: fenazaquin, pyridaben, tebufenpyrad, tolfenpyrad, flufenerim;
METI II and III compounds: acequinocyl, fluacyprim, hydramethylnon;
Uncouplers: chlorfenapyr;
oxidative phosphorylation inhibitors: cyhexatin, diafenthiuron, fenbutatin oxide, propargite;
moulting disruptor compounds: cryomazine;
mixed function oxidase inhibitors: piperonyl butoxide;
sodium channel blockers: indoxacarb, metaflumizone;
ryanodine receptor inhibitors: chlorantraniliprole, cyantraniliprole, flubendiamide, N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; N-[4-chloro-2-[(diethyl-lambda-4-sulfanylidene)-carbamoyl]-6-methyl-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide; N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide; N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

others: benclothiaz, bifenazate, cartap, flonicamid, pyridalyl, pymetrozine, sulfur, thiocyclam, cyenopyrafen, flupyrazofos, cyflumetofen, amidoflumet, imicyafos, bistrifluron, pyrifluquinazon and 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl] cyclopropane-acetic acid ester.

The compounds of groups A'), B'), C'), D'), E'), F'), G'), H'), J'), K'), M'), N') and O'), their preparation and their biological activity e.g. against harmful fungi, pests or weed is known. The fungicidally active compounds II described by common names, their preparation and their activity against harmful fungi is known (cf.: http://www.alanwood.net/pesticides/); these substances are commercially available.

The compounds described by IUPAC nomenclature, their preparation and their fungicidal activity are also known (Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 11/77514; WO13/047749, WO 10/069882, WO 13/047441, WO 03/16303, WO 09/90181, WO 13/007767, WO 13/010862, WO 13/024009 and WO 13/024010).

According to one embodiment, component III is selected from the following compounds:

Azoxystrobin (C-1)
Trifloxistrobin (C-2)
Picoxystrobin (C-3)
Pyraclostrobin (C-4)
Sedaxane (C-5)
Penthiopyrad (C-6)
Penflufen (C-7)
Fluopyram (C-8)
Fluxapyroxad (C-9)
Boscalid (C-10)
Oxathiapiprolin (C-49)
Metalaxyl (C-11)
Metalaxyl-M (C-12)
Ethaboxam (C-13)
DMM (C-14)

-continued

Cyproconazole (C-15)
Difenoconazole (C-16)
Prothioconazole (C-17)
Flutriafol (C-18)
Thiabendazole (C-19)
Ipconazole (C-20)
Tebuconazole (C-21)
Triadimenol (C-50)
Prochloraz (C-22)
Fluquinconazole (C-23)
Ttriticonazole (C-24)
Fludioxinil (C-25)
Carboxin (C-26)
Silthiofam (C-27)
Ziram (C-28)
Thiram (C-29)
Carbendazim (C-30)
Thiophanate-methyl (C-31)
Valifenalyate (C-32)
Insecticides/Nematic.
Fipronil (C-33)
-Clothianidin (C-34)
Thiamethoxam (C-35)
Acetamiprid (C-36)
Dinotefuran (C-37)
Imidacloprid (C-38)
Thiacloprid (C-39)
Sulfoxaflor (C-51)
Methiocarb (C-52)
Tefluthrin (C-40)
Bifenthrin (C-41)
Cypermethrin (C-53)
Alphacypermethrin (C-42)
Spinosad (C-43)
cyantraniliprole (C-44)
chlorantraniliprole (C-45)
Thiodicarb (C-54)
Triflumezopyrim (Mesoionic) (C-55)
Acephate (C-46)
Chlorpyriphos (C-47)
Flupyradifurone (C-56)
Abamectin (C-48)

Consequently, particularly preferred three-component compositions are compiled in Tables T1b to T31b, wherein each row corresponds to one embodiment of the compositions according to the invention, i.e. one specific individualized composition. According to one specific aspect, these are ternary compositions which each only contain these three components as active compounds. Furthermore, also every combination of the compositions individualized in this table represent embodiments of the present invention.

In these three-component compositions, component I is selected from compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30 and I-31 or any group of compounds 1 detailed above, component II is selected from:

*Azospirillum amazonense* (II-56)
*Azospirillum brasilense* (II-48)
*Azospirillum lipoferum* (II-57)
*Azospirillum irakense* (II-58)
*Azospirillum halopraeferens* (II-59)
*Bradyrhizobium* spp. (II-49)
*Bradyrhizobium* sp. (Arachis) (II-60)
*Bradyrhizobium* sp. (Vigna) (II-61)
*Bradyrhizobium elkanii* (II-62)
*Bradyrhizobium japonicum* (II-50)
*Bradyrhizobium liaoningense* (II-63)
*Bradyrhizobium lupini* (II-64)
*Delftia acidovorans* (II-65)
*Glomus intraradices* (II-66)

*Mesorhizobium* spp. (II-51)
*Mesorhizobium ciceri* (II-67)
*Mesorhizobium huakii* (II-68)
*Mesorhizobium loti* (II-69)
*Rhizobium leguminosarum* bv. Phaseoli (II-53)
*Rhizobium leguminosarum* bv. Trifolii (II-70)
*Rhizobium leguminosarum* bv. Viciae (II-54)
*Rhizobium tropici* (II-71)
*Sinorhizobium meliloti* (II-55)
*Bacillus altitudinis* (II-72)
*Bacillus amyloliquefaciens* (II-73)
*Bacillus amyloliquefaciens* ssp. Plantarum (II-27)
*Bacillus firmus* (II-44)
*Bacillus megaterium* (II-74)
*Bacillus mojavensis* (II-28)
*Bacillus mycoides* (II-75)
*Bacillus pumilus* (II-29)
*Bacillus simplex* (II-30)
*Bacillus solisalsi* (II-31)
*Bacillus subtilis* (II-76)
*Burkholderia* sp. (II-77)
*Coniothyrium minitans* (II-78)
*Paecilomyces lilacinus* (II-79)
*Paenibacillus alvei* (II-80)
*Paenibacillus polymyxa* (II-34)
*Paenibacillus popilliae* (II-81)
*Pasteuria nishizawae* (II-82)
*Pasteuria usgae* (II-83)
*Penicillium bilaiae* (II-52)
*Pseudomonas chloraphis* (II-84)
*Pseudomonas fluorescens* (II-85)
*Pseudomonas putida* (II-86)
abscisic acid (II-87)
harpin protein (alpha-beta) (II-88)
jasmonic acid or salts or derivatives thereof (II-43)
cis-jasmone (II-89); and
methyl jasmonate (II-90)

and component III is selected from:

Azoxystrobin (C-1)
Trifloxistrobin (C-2)
Picoxystrobin (C-3)
Pyraclostrobin (C-4)
Sedaxane (C-5)
Penthiopyrad (C-6)
Penflufen (C-7)
Fluopyram (C-8)
Fluxapyroxad (C-9)
Boscalid (C-10)
Oxathiapiprolin (C-49)
Metalaxyl (C-11)
Metalaxyl-M (C-12)
Ethaboxam (C-13)
DMM (C-14)
Cyproconazole (C-15)
Difenoconazole (C-16)
Prothioconazole (C-17)
Flutriafol (C-18)
Thiabendazole (C-19)
Ipconazole (C-20)
Tebuconazole (C-21)
Triadimenol (C-50)
Prochloraz (C-22)
Fluquinconazole (C-23)
Ttriticonazole (C-24)
Fludioxinil (C-25)
Carboxin (C-26)
Silthiofam (C-27)
Ziram (C-28)
Thiram (C-29)
Carbendazim (C-30)
Thiophanate-methyl (C-31)
Valifenalyate (C-32)
Insecticides/Nematic.
Fipronil (C-33)
Clothianidin (C-34)
Thiamethoxam (C-35)
Acetamiprid (C-36)
Dinotefuran (C-37)
Imidacloprid (C-38)
Thiacloprid (C-39)
Sulfoxaflor (C-51)
Methiocarb (C-52)
Tefluthrin (C-40)
Bifenthrin (C-41)
Cypermethrin (C-53)
Alphacypermethrin (C-42)
Spinosad (C-43)
cyantraniliprole (C-44)
chlorantraniliprole (C-45)
Thiodicarb (C-54)
Triflumezopyrim (Mesoionic) (C-55)
Acephate (C-46)
Chlorpyriphos (C-47)
Flupyradifurone (C-56)
Abamectin (C-48)

TABLE T1b

Three-component compositions T1b-1 to T1b-2856 comprising compound I-3 component II and component III, in particular ternary compositions containing compound I-3, II and III as only active ingredients.

| composition | I | II | III |
| --- | --- | --- | --- |
| T1b-1 | I-3 | II-56 | C-1 |
| T1b-2 | I-3 | II-48 | C-1 |
| T1b-3 | I-3 | II-57 | C-1 |
| T1b-4 | I-3 | II-58 | C-1 |
| T1b-5 | I-3 | II-59 | C-1 |
| T1b-6 | I-3 | II-49 | C-1 |
| T1b-7 | I-3 | II-60 | C-1 |
| T1b-8 | I-3 | II-61 | C-1 |
| T1b-9 | I-3 | II-62 | C-1 |
| T1b-10 | I-3 | II-50 | C-1 |
| T1b-11 | I-3 | II-63 | C-1 |
| T1b-12 | I-3 | II-64 | C-1 |
| T1b-13 | I-3 | II-65 | C-1 |
| T1b-14 | I-3 | II-66 | C-1 |
| T1b-15 | I-3 | II-51 | C-1 |
| T1b-16 | I-3 | II-67 | C-1 |
| T1b-17 | I-3 | II-68 | C-1 |
| T1b-18 | I-3 | II-69 | C-1 |
| T1b-19 | I-3 | II-53 | C-1 |
| T1b-20 | I-3 | II-70 | C-1 |
| T1b-21 | I-3 | II-54 | C-1 |
| T1b-22 | I-3 | II-71 | C-1 |
| T1b-23 | I-3 | II-55 | C-1 |
| T1b-24 | I-3 | II-72 | C-1 |
| T1b-25 | I-3 | II-73 | C-1 |
| T1b-26 | I-3 | II-27 | C-1 |
| T1b-27 | I-3 | II-44 | C-1 |
| T1b-28 | I-3 | II-74 | C-1 |
| T1b-29 | I-3 | II-28 | C-1 |
| T1b-30 | I-3 | II-75 | C-1 |
| T1b-31 | I-3 | II-29 | C-1 |
| T1b-32 | I-3 | II-30 | C-1 |
| T1b-33 | I-3 | II-31 | C-1 |
| T1b-34 | I-3 | II-76 | C-1 |
| T1b-35 | I-3 | II-77 | C-1 |
| T1b-36 | I-3 | II-78 | C-1 |
| T1b-37 | I-3 | II-79 | C-1 |
| T1b-38 | I-3 | II-80 | C-1 |
| T1b-39 | I-3 | II-34 | C-1 |
| T1b-40 | I-3 | II-81 | C-1 |
| T1b-41 | I-3 | II-82 | C-1 |
| T1b-42 | I-3 | II-83 | C-1 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-43 | I-3 | II-52 | C-1 |
| T1b-44 | I-3 | II-84 | C-1 |
| T1b-45 | I-3 | II-85 | C-1 |
| T1b-46 | I-3 | II-86 | C-1 |
| T1b-47 | I-3 | II-87 | C-1 |
| T1b-48 | I-3 | II-88 | C-1 |
| T1b-49 | I-3 | II-43 | C-1 |
| T1b-50 | I-3 | II-89 | C-1 |
| T1b-51 | I-3 | II-90 | C-1 |
| T1b-52 | I-3 | II-56 | C-2 |
| T1b-53 | I-3 | II-48 | C-2 |
| T1b-54 | I-3 | II-57 | C-2 |
| T1b-55 | I-3 | II-58 | C-2 |
| T1b-56 | I-3 | II-59 | C-2 |
| T1b-57 | I-3 | II-49 | C-2 |
| T1b-58 | I-3 | II-60 | C-2 |
| T1b-59 | I-3 | II-61 | C-2 |
| T1b-60 | I-3 | II-62 | C-2 |
| T1b-61 | I-3 | II-50 | C-2 |
| T1b-62 | I-3 | II-63 | C-2 |
| T1b-63 | I-3 | II-64 | C-2 |
| T1b-64 | I-3 | II-65 | C-2 |
| T1b-65 | I-3 | II-66 | C-2 |
| T1b-66 | I-3 | II-51 | C-2 |
| T1b-67 | I-3 | II-67 | C-2 |
| T1b-68 | I-3 | II-68 | C-2 |
| T1b-69 | I-3 | II-69 | C-2 |
| T1b-70 | I-3 | II-53 | C-2 |
| T1b-71 | I-3 | II-70 | C-2 |
| T1b-72 | I-3 | II-54 | C-2 |
| T1b-73 | I-3 | II-71 | C-2 |
| T1b-74 | I-3 | II-55 | C-2 |
| T1b-75 | I-3 | II-72 | C-2 |
| T1b-76 | I-3 | II-73 | C-2 |
| T1b-77 | I-3 | II-27 | C-2 |
| T1b-78 | I-3 | II-44 | C-2 |
| T1b-79 | I-3 | II-74 | C-2 |
| T1b-80 | I-3 | II-28 | C-2 |
| T1b-81 | I-3 | II-75 | C-2 |
| T1b-82 | I-3 | II-29 | C-2 |
| T1b-83 | I-3 | II-30 | C-2 |
| T1b-84 | I-3 | II-31 | C-2 |
| T1b-85 | I-3 | II-76 | C-2 |
| T1b-86 | I-3 | II-77 | C-2 |
| T1b-87 | I-3 | II-78 | C-2 |
| T1b-88 | I-3 | II-79 | C-2 |
| T1b-89 | I-3 | II-80 | C-2 |
| T1b-90 | I-3 | II-34 | C-2 |
| T1b-91 | I-3 | II-81 | C-2 |
| T1b-92 | I-3 | II-82 | C-2 |
| T1b-93 | I-3 | II-83 | C-2 |
| T1b-94 | I-3 | II-52 | C-2 |
| T1b-95 | I-3 | II-84 | C-2 |
| T1b-96 | I-3 | II-85 | C-2 |
| T1b-97 | I-3 | II-86 | C-2 |
| T1b-98 | I-3 | II-87 | C-2 |
| T1b-99 | I-3 | II-88 | C-2 |
| T1b-100 | I-3 | II-43 | C-2 |
| T1b-101 | I-3 | II-89 | C-2 |
| T1b-102 | I-3 | II-90 | C-2 |
| T1b-103 | I-3 | II-56 | C-3 |
| T1b-104 | I-3 | II-48 | C-3 |
| T1b-105 | I-3 | II-57 | C-3 |
| T1b-106 | I-3 | II-58 | C-3 |
| T1b-107 | I-3 | II-59 | C-3 |
| T1b-108 | I-3 | II-49 | C-3 |
| T1b-109 | I-3 | II-60 | C-3 |
| T1b-110 | I-3 | II-61 | C-3 |
| T1b-111 | I-3 | II-62 | C-3 |
| T1b-112 | I-3 | II-50 | C-3 |
| T1b-113 | I-3 | II-63 | C-3 |
| T1b-114 | I-3 | II-64 | C-3 |
| T1b-115 | I-3 | II-65 | C-3 |
| T1b-116 | I-3 | II-66 | C-3 |
| T1b-117 | I-3 | II-51 | C-3 |
| T1b-118 | I-3 | II-67 | C-3 |
| T1b-119 | I-3 | II-68 | C-3 |
| T1b-120 | I-3 | II-69 | C-3 |
| T1b-121 | I-3 | II-53 | C-3 |
| T1b-122 | I-3 | II-70 | C-3 |
| T1b-123 | I-3 | II-54 | C-3 |
| T1b-124 | I-3 | II-71 | C-3 |
| T1b-125 | I-3 | II-55 | C-3 |
| T1b-126 | I-3 | II-72 | C-3 |
| T1b-127 | I-3 | II-73 | C-3 |
| T1b-128 | I-3 | II-27 | C-3 |
| T1b-129 | I-3 | II-44 | C-3 |
| T1b-130 | I-3 | II-74 | C-3 |
| T1b-131 | I-3 | II-28 | C-3 |
| T1b-132 | I-3 | II-75 | C-3 |
| T1b-133 | I-3 | II-29 | C-3 |
| T1b-134 | I-3 | II-30 | C-3 |
| T1b-135 | I-3 | II-31 | C-3 |
| T1b-136 | I-3 | II-76 | C-3 |
| T1b-137 | I-3 | II-77 | C-3 |
| T1b-138 | I-3 | II-78 | C-3 |
| T1b-139 | I-3 | II-79 | C-3 |
| T1b-140 | I-3 | II-80 | C-3 |
| T1b-141 | I-3 | II-34 | C-3 |
| T1b-142 | I-3 | II-81 | C-3 |
| T1b-143 | I-3 | II-82 | C-3 |
| T1b-144 | I-3 | II-83 | C-3 |
| T1b-145 | I-3 | II-52 | C-3 |
| T1b-146 | I-3 | II-84 | C-3 |
| T1b-147 | I-3 | II-85 | C-3 |
| T1b-148 | I-3 | II-86 | C-3 |
| T1b-149 | I-3 | II-87 | C-3 |
| T1b-150 | I-3 | II-88 | C-3 |
| T1b-151 | I-3 | II-43 | C-3 |
| T1b-152 | I-3 | II-89 | C-3 |
| T1b-153 | I-3 | II-90 | C-3 |
| T1b-154 | I-3 | II-56 | C-4 |
| T1b-155 | I-3 | II-48 | C-4 |
| T1b-156 | I-3 | II-57 | C-4 |
| T1b-157 | I-3 | II-58 | C-4 |
| T1b-158 | I-3 | II-59 | C-4 |
| T1b-159 | I-3 | II-49 | C-4 |
| T1b-160 | I-3 | II-60 | C-4 |
| T1b-161 | I-3 | II-61 | C-4 |
| T1b-162 | I-3 | II-62 | C-4 |
| T1b-163 | I-3 | II-50 | C-4 |
| T1b-164 | I-3 | II-63 | C-4 |
| T1b-165 | I-3 | II-64 | C-4 |
| T1b-166 | I-3 | II-65 | C-4 |
| T1b-167 | I-3 | II-66 | C-4 |
| T1b-168 | I-3 | II-51 | C-4 |
| T1b-169 | I-3 | II-67 | C-4 |
| T1b-170 | I-3 | II-68 | C-4 |
| T1b-171 | I-3 | II-69 | C-4 |
| T1b-172 | I-3 | II-53 | C-4 |
| T1b-173 | I-3 | II-70 | C-4 |
| T1b-174 | I-3 | II-54 | C-4 |
| T1b-175 | I-3 | II-71 | C-4 |
| T1b-176 | I-3 | II-55 | C-4 |
| T1b-177 | I-3 | II-72 | C-4 |
| T1b-178 | I-3 | II-73 | C-4 |
| T1b-179 | I-3 | II-27 | C-4 |
| T1b-180 | I-3 | II-44 | C-4 |
| T1b-181 | I-3 | II-74 | C-4 |
| T1b-182 | I-3 | II-28 | C-4 |
| T1b-183 | I-3 | II-75 | C-4 |
| T1b-184 | I-3 | II-29 | C-4 |
| T1b-185 | I-3 | II-30 | C-4 |
| T1b-186 | I-3 | II-31 | C-4 |
| T1b-187 | I-3 | II-76 | C-4 |
| T1b-188 | I-3 | II-77 | C-4 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-189 | I-3 | II-78 | C-4 |
| T1b-190 | I-3 | II-79 | C-4 |
| T1b-191 | I-3 | II-80 | C-4 |
| T1b-192 | I-3 | II-34 | C-4 |
| T1b-193 | I-3 | II-81 | C-4 |
| T1b-194 | I-3 | II-82 | C-4 |
| T1b-195 | I-3 | II-83 | C-4 |
| T1b-196 | I-3 | II-52 | C-4 |
| T1b-197 | I-3 | II-84 | C-4 |
| T1b-198 | I-3 | II-85 | C-4 |
| T1b-199 | I-3 | II-86 | C-4 |
| T1b-200 | I-3 | II-87 | C-4 |
| T1b-201 | I-3 | II-88 | C-4 |
| T1b-202 | I-3 | II-43 | C-4 |
| T1b-203 | I-3 | II-89 | C-4 |
| T1b-204 | I-3 | II-90 | C-4 |
| T1b-205 | I-3 | II-56 | C-5 |
| T1b-206 | I-3 | II-48 | C-5 |
| T1b-207 | I-3 | II-57 | C-5 |
| T1b-208 | I-3 | II-58 | C-5 |
| T1b-209 | I-3 | II-59 | C-5 |
| T1b-210 | I-3 | II-49 | C-5 |
| T1b-211 | I-3 | II-60 | C-5 |
| T1b-212 | I-3 | II-61 | C-5 |
| T1b-213 | I-3 | II-62 | C-5 |
| T1b-214 | I-3 | II-50 | C-5 |
| T1b-215 | I-3 | II-63 | C-5 |
| T1b-216 | I-3 | II-64 | C-5 |
| T1b-217 | I-3 | II-65 | C-5 |
| T1b-218 | I-3 | II-66 | C-5 |
| T1b-219 | I-3 | II-51 | C-5 |
| T1b-220 | I-3 | II-67 | C-5 |
| T1b-221 | I-3 | II-68 | C-5 |
| T1b-222 | I-3 | II-69 | C-5 |
| T1b-223 | I-3 | II-53 | C-5 |
| T1b-224 | I-3 | II-70 | C-5 |
| T1b-225 | I-3 | II-54 | C-5 |
| T1b-226 | I-3 | II-71 | C-5 |
| T1b-227 | I-3 | II-55 | C-5 |
| T1b-228 | I-3 | II-72 | C-5 |
| T1b-229 | I-3 | II-73 | C-5 |
| T1b-230 | I-3 | II-27 | C-5 |
| T1b-231 | I-3 | II-44 | C-5 |
| T1b-232 | I-3 | II-74 | C-5 |
| T1b-233 | I-3 | II-28 | C-5 |
| T1b-234 | I-3 | II-75 | C-5 |
| T1b-235 | I-3 | II-29 | C-5 |
| T1b-236 | I-3 | II-30 | C-5 |
| T1b-237 | I-3 | II-31 | C-5 |
| T1b-238 | I-3 | II-76 | C-5 |
| T1b-239 | I-3 | II-77 | C-5 |
| T1b-240 | I-3 | II-78 | C-5 |
| T1b-241 | I-3 | II-79 | C-5 |
| T1b-242 | I-3 | II-80 | C-5 |
| T1b-243 | I-3 | II-34 | C-5 |
| T1b-244 | I-3 | II-81 | C-5 |
| T1b-245 | I-3 | II-82 | C-5 |
| T1b-246 | I-3 | II-83 | C-5 |
| T1b-247 | I-3 | II-52 | C-5 |
| T1b-248 | I-3 | II-84 | C-5 |
| T1b-249 | I-3 | II-85 | C-5 |
| T1b-250 | I-3 | II-86 | C-5 |
| T1b-251 | I-3 | II-87 | C-5 |
| T1b-252 | I-3 | II-88 | C-5 |
| T1b-253 | I-3 | II-43 | C-5 |
| T1b-254 | I-3 | II-89 | C-5 |
| T1b-255 | I-3 | II-90 | C-5 |
| T1b-256 | I-3 | II-56 | C-6 |
| T1b-257 | I-3 | II-48 | C-6 |
| T1b-258 | I-3 | II-57 | C-6 |
| T1b-259 | I-3 | II-58 | C-6 |
| T1b-260 | I-3 | II-59 | C-6 |
| T1b-261 | I-3 | II-49 | C-6 |
| T1b-262 | I-3 | II-60 | C-6 |
| T1b-263 | I-3 | II-61 | C-6 |
| T1b-264 | I-3 | II-62 | C-6 |
| T1b-265 | I-3 | II-50 | C-6 |
| T1b-266 | I-3 | II-63 | C-6 |
| T1b-267 | I-3 | II-64 | C-6 |
| T1b-268 | I-3 | II-65 | C-6 |
| T1b-269 | I-3 | II-66 | C-6 |
| T1b-270 | I-3 | II-51 | C-6 |
| T1b-271 | I-3 | II-67 | C-6 |
| T1b-272 | I-3 | II-68 | C-6 |
| T1b-273 | I-3 | II-69 | C-6 |
| T1b-274 | I-3 | II-53 | C-6 |
| T1b-275 | I-3 | II-70 | C-6 |
| T1b-276 | I-3 | II-54 | C-6 |
| T1b-277 | I-3 | II-71 | C-6 |
| T1b-278 | I-3 | II-55 | C-6 |
| T1b-279 | I-3 | II-72 | C-6 |
| T1b-280 | I-3 | II-73 | C-6 |
| T1b-281 | I-3 | II-27 | C-6 |
| T1b-282 | I-3 | II-44 | C-6 |
| T1b-283 | I-3 | II-74 | C-6 |
| T1b-284 | I-3 | II-28 | C-6 |
| T1b-285 | I-3 | II-75 | C-6 |
| T1b-286 | I-3 | II-29 | C-6 |
| T1b-287 | I-3 | II-30 | C-6 |
| T1b-288 | I-3 | II-31 | C-6 |
| T1b-289 | I-3 | II-76 | C-6 |
| T1b-290 | I-3 | II-77 | C-6 |
| T1b-291 | I-3 | II-78 | C-6 |
| T1b-292 | I-3 | II-79 | C-6 |
| T1b-293 | I-3 | II-80 | C-6 |
| T1b-294 | I-3 | II-34 | C-6 |
| T1b-295 | I-3 | II-81 | C-6 |
| T1b-296 | I-3 | II-82 | C-6 |
| T1b-297 | I-3 | II-83 | C-6 |
| T1b-298 | I-3 | II-52 | C-6 |
| T1b-299 | I-3 | II-84 | C-6 |
| T1b-300 | I-3 | II-85 | C-6 |
| T1b-301 | I-3 | II-86 | C-6 |
| T1b-302 | I-3 | II-87 | C-6 |
| T1b-303 | I-3 | II-88 | C-6 |
| T1b-304 | I-3 | II-43 | C-6 |
| T1b-305 | I-3 | II-89 | C-6 |
| T1b-306 | I-3 | II-90 | C-6 |
| T1b-307 | I-3 | II-56 | C-7 |
| T1b-308 | I-3 | II-48 | C-7 |
| T1b-309 | I-3 | II-57 | C-7 |
| T1b-310 | I-3 | II-58 | C-7 |
| T1b-311 | I-3 | II-59 | C-7 |
| T1b-312 | I-3 | II-49 | C-7 |
| T1b-313 | I-3 | II-60 | C-7 |
| T1b-314 | I-3 | II-61 | C-7 |
| T1b-315 | I-3 | II-62 | C-7 |
| T1b-316 | I-3 | II-50 | C-7 |
| T1b-317 | I-3 | II-63 | C-7 |
| T1b-318 | I-3 | II-64 | C-7 |
| T1b-319 | I-3 | II-65 | C-7 |
| T1b-320 | I-3 | II-66 | C-7 |
| T1b-321 | I-3 | II-51 | C-7 |
| T1b-322 | I-3 | II-67 | C-7 |
| T1b-323 | I-3 | II-68 | C-7 |
| T1b-324 | I-3 | II-69 | C-7 |
| T1b-325 | I-3 | II-53 | C-7 |
| T1b-326 | I-3 | II-70 | C-7 |
| T1b-327 | I-3 | II-54 | C-7 |
| T1b-328 | I-3 | II-71 | C-7 |
| T1b-329 | I-3 | II-55 | C-7 |
| T1b-330 | I-3 | II-72 | C-7 |
| T1b-331 | I-3 | II-73 | C-7 |
| T1b-332 | I-3 | II-27 | C-7 |
| T1b-333 | I-3 | II-44 | C-7 |
| T1b-334 | I-3 | II-74 | C-7 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-335 | I-3 | II-28 | C-7 |
| T1b-336 | I-3 | II-75 | C-7 |
| T1b-337 | I-3 | II-29 | C-7 |
| T1b-338 | I-3 | II-30 | C-7 |
| T1b-339 | I-3 | II-31 | C-7 |
| T1b-340 | I-3 | II-76 | C-7 |
| T1b-341 | I-3 | II-77 | C-7 |
| T1b-342 | I-3 | II-78 | C-7 |
| T1b-343 | I-3 | II-79 | C-7 |
| T1b-344 | I-3 | II-80 | C-7 |
| T1b-345 | I-3 | II-34 | C-7 |
| T1b-346 | I-3 | II-81 | C-7 |
| T1b-347 | I-3 | II-82 | C-7 |
| T1b-348 | I-3 | II-83 | C-7 |
| T1b-349 | I-3 | II-52 | C-7 |
| T1b-350 | I-3 | II-84 | C-7 |
| T1b-351 | I-3 | II-85 | C-7 |
| T1b-352 | I-3 | II-86 | C-7 |
| T1b-353 | I-3 | II-87 | C-7 |
| T1b-354 | I-3 | II-88 | C-7 |
| T1b-355 | I-3 | II-43 | C-7 |
| T1b-356 | I-3 | II-89 | C-7 |
| T1b-357 | I-3 | II-90 | C-7 |
| T1b-358 | I-3 | II-56 | C-8 |
| T1b-359 | I-3 | II-48 | C-8 |
| T1b-360 | I-3 | II-57 | C-8 |
| T1b-361 | I-3 | II-58 | C-8 |
| T1b-362 | I-3 | II-59 | C-8 |
| T1b-363 | I-3 | II-49 | C-8 |
| T1b-364 | I-3 | II-60 | C-8 |
| T1b-365 | I-3 | II-61 | C-8 |
| T1b-366 | I-3 | II-62 | C-8 |
| T1b-367 | I-3 | II-50 | C-8 |
| T1b-368 | I-3 | II-63 | C-8 |
| T1b-369 | I-3 | II-64 | C-8 |
| T1b-370 | I-3 | II-65 | C-8 |
| T1b-371 | I-3 | II-66 | C-8 |
| T1b-372 | I-3 | II-51 | C-8 |
| T1b-373 | I-3 | II-67 | C-8 |
| T1b-374 | I-3 | II-68 | C-8 |
| T1b-375 | I-3 | II-69 | C-8 |
| T1b-376 | I-3 | II-53 | C-8 |
| T1b-377 | I-3 | II-70 | C-8 |
| T1b-378 | I-3 | II-54 | C-8 |
| T1b-379 | I-3 | II-71 | C-8 |
| T1b-380 | I-3 | II-55 | C-8 |
| T1b-381 | I-3 | II-72 | C-8 |
| T1b-382 | I-3 | II-73 | C-8 |
| T1b-383 | I-3 | II-27 | C-8 |
| T1b-384 | I-3 | II-44 | C-8 |
| T1b-385 | I-3 | II-74 | C-8 |
| T1b-386 | I-3 | II-28 | C-8 |
| T1b-387 | I-3 | II-75 | C-8 |
| T1b-388 | I-3 | II-29 | C-8 |
| T1b-389 | I-3 | II-30 | C-8 |
| T1b-390 | I-3 | II-31 | C-8 |
| T1b-391 | I-3 | II-76 | C-8 |
| T1b-392 | I-3 | II-77 | C-8 |
| T1b-393 | I-3 | II-78 | C-8 |
| T1b-394 | I-3 | II-79 | C-8 |
| T1b-395 | I-3 | II-80 | C-8 |
| T1b-396 | I-3 | II-34 | C-8 |
| T1b-397 | I-3 | II-81 | C-8 |
| T1b-398 | I-3 | II-82 | C-8 |
| T1b-399 | I-3 | II-83 | C-8 |
| T1b-400 | I-3 | II-52 | C-8 |
| T1b-401 | I-3 | II-84 | C-8 |
| T1b-402 | I-3 | II-85 | C-8 |
| T1b-403 | I-3 | II-86 | C-8 |
| T1b-404 | I-3 | II-87 | C-8 |
| T1b-405 | I-3 | II-88 | C-8 |
| T1b-406 | I-3 | II-43 | C-8 |
| T1b-407 | I-3 | II-89 | C-8 |
| T1b-408 | I-3 | II-90 | C-8 |
| T1b-409 | I-3 | II-56 | C-9 |
| T1b-410 | I-3 | II-48 | C-9 |
| T1b-411 | I-3 | II-57 | C-9 |
| T1b-412 | I-3 | II-58 | C-9 |
| T1b-413 | I-3 | II-59 | C-9 |
| T1b-414 | I-3 | II-49 | C-9 |
| T1b-415 | I-3 | II-60 | C-9 |
| T1b-416 | I-3 | II-61 | C-9 |
| T1b-417 | I-3 | II-62 | C-9 |
| T1b-418 | I-3 | II-50 | C-9 |
| T1b-419 | I-3 | II-63 | C-9 |
| T1b-420 | I-3 | II-64 | C-9 |
| T1b-421 | I-3 | II-65 | C-9 |
| T1b-422 | I-3 | II-66 | C-9 |
| T1b-423 | I-3 | II-51 | C-9 |
| T1b-424 | I-3 | II-67 | C-9 |
| T1b-425 | I-3 | II-68 | C-9 |
| T1b-426 | I-3 | II-69 | C-9 |
| T1b-427 | I-3 | II-53 | C-9 |
| T1b-428 | I-3 | II-70 | C-9 |
| T1b-429 | I-3 | II-54 | C-9 |
| T1b-430 | I-3 | II-71 | C-9 |
| T1b-431 | I-3 | II-55 | C-9 |
| T1b-432 | I-3 | II-72 | C-9 |
| T1b-433 | I-3 | II-73 | C-9 |
| T1b-434 | I-3 | II-27 | C-9 |
| T1b-435 | I-3 | II-44 | C-9 |
| T1b-436 | I-3 | II-74 | C-9 |
| T1b-437 | I-3 | II-28 | C-9 |
| T1b-438 | I-3 | II-75 | C-9 |
| T1b-439 | I-3 | II-29 | C-9 |
| T1b-440 | I-3 | II-30 | C-9 |
| T1b-441 | I-3 | II-31 | C-9 |
| T1b-442 | I-3 | II-76 | C-9 |
| T1b-443 | I-3 | II-77 | C-9 |
| T1b-444 | I-3 | II-78 | C-9 |
| T1b-445 | I-3 | II-79 | C-9 |
| T1b-446 | I-3 | II-80 | C-9 |
| T1b-447 | I-3 | II-34 | C-9 |
| T1b-448 | I-3 | II-81 | C-9 |
| T1b-449 | I-3 | II-82 | C-9 |
| T1b-450 | I-3 | II-83 | C-9 |
| T1b-451 | I-3 | II-52 | C-9 |
| T1b-452 | I-3 | II-84 | C-9 |
| T1b-453 | I-3 | II-85 | C-9 |
| T1b-454 | I-3 | II-86 | C-9 |
| T1b-455 | I-3 | II-87 | C-9 |
| T1b-456 | I-3 | II-88 | C-9 |
| T1b-457 | I-3 | II-43 | C-9 |
| T1b-458 | I-3 | II-89 | C-9 |
| T1b-459 | I-3 | II-90 | C-9 |
| T1b-460 | I-3 | II-56 | C-10 |
| T1b-461 | I-3 | II-48 | C-10 |
| T1b-462 | I-3 | II-57 | C-10 |
| T1b-463 | I-3 | II-58 | C-10 |
| T1b-464 | I-3 | II-59 | C-10 |
| T1b-465 | I-3 | II-49 | C-10 |
| T1b-466 | I-3 | II-60 | C-10 |
| T1b-467 | I-3 | II-61 | C-10 |
| T1b-468 | I-3 | II-62 | C-10 |
| T1b-469 | I-3 | II-50 | C-10 |
| T1b-470 | I-3 | II-63 | C-10 |
| T1b-471 | I-3 | II-64 | C-10 |
| T1b-472 | I-3 | II-65 | C-10 |
| T1b-473 | I-3 | II-66 | C-10 |
| T1b-474 | I-3 | II-51 | C-10 |
| T1b-475 | I-3 | II-67 | C-10 |
| T1b-476 | I-3 | II-68 | C-10 |
| T1b-477 | I-3 | II-69 | C-10 |
| T1b-478 | I-3 | II-53 | C-10 |
| T1b-479 | I-3 | II-70 | C-10 |
| T1b-480 | I-3 | II-54 | C-10 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-481 | I-3 | II-71 | C-10 |
| T1b-482 | I-3 | II-55 | C-10 |
| T1b-483 | I-3 | II-72 | C-10 |
| T1b-484 | I-3 | II-73 | C-10 |
| T1b-485 | I-3 | II-27 | C-10 |
| T1b-486 | I-3 | II-44 | C-10 |
| T1b-487 | I-3 | II-74 | C-10 |
| T1b-488 | I-3 | II-28 | C-10 |
| T1b-489 | I-3 | II-75 | C-10 |
| T1b-490 | I-3 | II-29 | C-10 |
| T1b-491 | I-3 | II-30 | C-10 |
| T1b-492 | I-3 | II-31 | C-10 |
| T1b-493 | I-3 | II-76 | C-10 |
| T1b-494 | I-3 | II-77 | C-10 |
| T1b-495 | I-3 | II-78 | C-10 |
| T1b-496 | I-3 | II-79 | C-10 |
| T1b-497 | I-3 | II-80 | C-10 |
| T1b-498 | I-3 | II-34 | C-10 |
| T1b-499 | I-3 | II-81 | C-10 |
| T1b-500 | I-3 | II-82 | C-10 |
| T1b-501 | I-3 | II-83 | C-10 |
| T1b-502 | I-3 | II-52 | C-10 |
| T1b-503 | I-3 | II-84 | C-10 |
| T1b-504 | I-3 | II-85 | C-10 |
| T1b-505 | I-3 | II-86 | C-10 |
| T1b-506 | I-3 | II-87 | C-10 |
| T1b-507 | I-3 | II-88 | C-10 |
| T1b-508 | I-3 | II-43 | C-10 |
| T1b-509 | I-3 | II-89 | C-10 |
| T1b-510 | I-3 | II-90 | C-10 |
| T1b-511 | I-3 | II-56 | C-11 |
| T1b-512 | I-3 | II-48 | C-11 |
| T1b-513 | I-3 | II-57 | C-11 |
| T1b-514 | I-3 | II-58 | C-11 |
| T1b-515 | I-3 | II-59 | C-11 |
| T1b-516 | I-3 | II-49 | C-11 |
| T1b-517 | I-3 | II-60 | C-11 |
| T1b-518 | I-3 | II-61 | C-11 |
| T1b-519 | I-3 | II-62 | C-11 |
| T1b-520 | I-3 | II-50 | C-11 |
| T1b-521 | I-3 | II-63 | C-11 |
| T1b-522 | I-3 | II-64 | C-11 |
| T1b-523 | I-3 | II-65 | C-11 |
| T1b-524 | I-3 | II-66 | C-11 |
| T1b-525 | I-3 | II-51 | C-11 |
| T1b-526 | I-3 | II-67 | C-11 |
| T1b-527 | I-3 | II-68 | C-11 |
| T1b-528 | I-3 | II-69 | C-11 |
| T1b-529 | I-3 | II-53 | C-11 |
| T1b-530 | I-3 | II-70 | C-11 |
| T1b-531 | I-3 | II-54 | C-11 |
| T1b-532 | I-3 | II-71 | C-11 |
| T1b-533 | I-3 | II-55 | C-11 |
| T1b-534 | I-3 | II-72 | C-11 |
| T1b-535 | I-3 | II-73 | C-11 |
| T1b-536 | I-3 | II-27 | C-11 |
| T1b-537 | I-3 | II-44 | C-11 |
| T1b-538 | I-3 | II-74 | C-11 |
| T1b-539 | I-3 | II-28 | C-11 |
| T1b-540 | I-3 | II-75 | C-11 |
| T1b-541 | I-3 | II-29 | C-11 |
| T1b-542 | I-3 | II-30 | C-11 |
| T1b-543 | I-3 | II-31 | C-11 |
| T1b-544 | I-3 | II-76 | C-11 |
| T1b-545 | I-3 | II-77 | C-11 |
| T1b-546 | I-3 | II-78 | C-11 |
| T1b-547 | I-3 | II-79 | C-11 |
| T1b-548 | I-3 | II-80 | C-11 |
| T1b-549 | I-3 | II-34 | C-11 |
| T1b-550 | I-3 | II-81 | C-11 |
| T1b-551 | I-3 | II-82 | C-11 |
| T1b-552 | I-3 | II-83 | C-11 |
| T1b-553 | I-3 | II-52 | C-11 |
| T1b-554 | I-3 | II-84 | C-11 |
| T1b-555 | I-3 | II-85 | C-11 |
| T1b-556 | I-3 | II-86 | C-11 |
| T1b-557 | I-3 | II-87 | C-11 |
| T1b-558 | I-3 | II-88 | C-11 |
| T1b-559 | I-3 | II-43 | C-11 |
| T1b-560 | I-3 | II-89 | C-11 |
| T1b-561 | I-3 | II-90 | C-11 |
| T1b-562 | I-3 | II-56 | C-12 |
| T1b-563 | I-3 | II-48 | C-12 |
| T1b-564 | I-3 | II-57 | C-12 |
| T1b-565 | I-3 | II-58 | C-12 |
| T1b-566 | I-3 | II-59 | C-12 |
| T1b-567 | I-3 | II-49 | C-12 |
| T1b-568 | I-3 | II-60 | C-12 |
| T1b-569 | I-3 | II-61 | C-12 |
| T1b-570 | I-3 | II-62 | C-12 |
| T1b-571 | I-3 | II-50 | C-12 |
| T1b-572 | I-3 | II-63 | C-12 |
| T1b-573 | I-3 | II-64 | C-12 |
| T1b-574 | I-3 | II-65 | C-12 |
| T1b-575 | I-3 | II-66 | C-12 |
| T1b-576 | I-3 | II-51 | C-12 |
| T1b-577 | I-3 | II-67 | C-12 |
| T1b-578 | I-3 | II-68 | C-12 |
| T1b-579 | I-3 | II-69 | C-12 |
| T1b-580 | I-3 | II-53 | C-12 |
| T1b-581 | I-3 | II-70 | C-12 |
| T1b-582 | I-3 | II-54 | C-12 |
| T1b-583 | I-3 | II-71 | C-12 |
| T1b-584 | I-3 | II-55 | C-12 |
| T1b-585 | I-3 | II-72 | C-12 |
| T1b-586 | I-3 | II-73 | C-12 |
| T1b-587 | I-3 | II-27 | C-12 |
| T1b-588 | I-3 | II-44 | C-12 |
| T1b-589 | I-3 | II-74 | C-12 |
| T1b-590 | I-3 | II-28 | C-12 |
| T1b-591 | I-3 | II-75 | C-12 |
| T1b-592 | I-3 | II-29 | C-12 |
| T1b-593 | I-3 | II-30 | C-12 |
| T1b-594 | I-3 | II-31 | C-12 |
| T1b-595 | I-3 | II-76 | C-12 |
| T1b-596 | I-3 | II-77 | C-12 |
| T1b-597 | I-3 | II-78 | C-12 |
| T1b-598 | I-3 | II-79 | C-12 |
| T1b-599 | I-3 | II-80 | C-12 |
| T1b-600 | I-3 | II-34 | C-12 |
| T1b-601 | I-3 | II-81 | C-12 |
| T1b-602 | I-3 | II-82 | C-12 |
| T1b-603 | I-3 | II-83 | C-12 |
| T1b-604 | I-3 | II-52 | C-12 |
| T1b-605 | I-3 | II-84 | C-12 |
| T1b-606 | I-3 | II-85 | C-12 |
| T1b-607 | I-3 | II-86 | C-12 |
| T1b-608 | I-3 | II-87 | C-12 |
| T1b-609 | I-3 | II-88 | C-12 |
| T1b-610 | I-3 | II-43 | C-12 |
| T1b-611 | I-3 | II-89 | C-12 |
| T1b-612 | I-3 | II-90 | C-12 |
| T1b-613 | I-3 | II-56 | C-13 |
| T1b-614 | I-3 | II-48 | C-13 |
| T1b-615 | I-3 | II-57 | C-13 |
| T1b-616 | I-3 | II-58 | C-13 |
| T1b-617 | I-3 | II-59 | C-13 |
| T1b-618 | I-3 | II-49 | C-13 |
| T1b-619 | I-3 | II-60 | C-13 |
| T1b-620 | I-3 | II-61 | C-13 |
| T1b-621 | I-3 | II-62 | C-13 |
| T1b-622 | I-3 | II-50 | C-13 |
| T1b-623 | I-3 | II-63 | C-13 |
| T1b-624 | I-3 | II-64 | C-13 |
| T1b-625 | I-3 | II-65 | C-13 |
| T1b-626 | I-3 | II-66 | C-13 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-627 | I-3 | II-51 | C-13 |
| T1b-628 | I-3 | II-67 | C-13 |
| T1b-629 | I-3 | II-68 | C-13 |
| T1b-630 | I-3 | II-69 | C-13 |
| T1b-631 | I-3 | II-53 | C-13 |
| T1b-632 | I-3 | II-70 | C-13 |
| T1b-633 | I-3 | II-54 | C-13 |
| T1b-634 | I-3 | II-71 | C-13 |
| T1b-635 | I-3 | II-55 | C-13 |
| T1b-636 | I-3 | II-72 | C-13 |
| T1b-637 | I-3 | II-73 | C-13 |
| T1b-638 | I-3 | II-27 | C-13 |
| T1b-639 | I-3 | II-44 | C-13 |
| T1b-640 | I-3 | II-74 | C-13 |
| T1b-641 | I-3 | II-28 | C-13 |
| T1b-642 | I-3 | II-75 | C-13 |
| T1b-643 | I-3 | II-29 | C-13 |
| T1b-644 | I-3 | II-30 | C-13 |
| T1b-645 | I-3 | II-31 | C-13 |
| T1b-646 | I-3 | II-76 | C-13 |
| T1b-647 | I-3 | II-77 | C-13 |
| T1b-648 | I-3 | II-78 | C-13 |
| T1b-649 | I-3 | II-79 | C-13 |
| T1b-650 | I-3 | II-80 | C-13 |
| T1b-651 | I-3 | II-34 | C-13 |
| T1b-652 | I-3 | II-81 | C-13 |
| T1b-653 | I-3 | II-82 | C-13 |
| T1b-654 | I-3 | II-83 | C-13 |
| T1b-655 | I-3 | II-52 | C-13 |
| T1b-656 | I-3 | II-84 | C-13 |
| T1b-657 | I-3 | II-85 | C-13 |
| T1b-658 | I-3 | II-86 | C-13 |
| T1b-659 | I-3 | II-87 | C-13 |
| T1b-660 | I-3 | II-88 | C-13 |
| T1b-661 | I-3 | II-43 | C-13 |
| T1b-662 | I-3 | II-89 | C-13 |
| T1b-663 | I-3 | II-90 | C-13 |
| T1b-664 | I-3 | II-56 | C-14 |
| T1b-665 | I-3 | II-48 | C-14 |
| T1b-666 | I-3 | II-57 | C-14 |
| T1b-667 | I-3 | II-58 | C-14 |
| T1b-668 | I-3 | II-59 | C-14 |
| T1b-669 | I-3 | II-49 | C-14 |
| T1b-670 | I-3 | II-60 | C-14 |
| T1b-671 | I-3 | II-61 | C-14 |
| T1b-672 | I-3 | II-62 | C-14 |
| T1b-673 | I-3 | II-50 | C-14 |
| T1b-674 | I-3 | II-63 | C-14 |
| T1b-675 | I-3 | II-64 | C-14 |
| T1b-676 | I-3 | II-65 | C-14 |
| T1b-677 | I-3 | II-66 | C-14 |
| T1b-678 | I-3 | II-51 | C-14 |
| T1b-679 | I-3 | II-67 | C-14 |
| T1b-680 | I-3 | II-68 | C-14 |
| T1b-681 | I-3 | II-69 | C-14 |
| T1b-682 | I-3 | II-53 | C-14 |
| T1b-683 | I-3 | II-70 | C-14 |
| T1b-684 | I-3 | II-54 | C-14 |
| T1b-685 | I-3 | II-71 | C-14 |
| T1b-686 | I-3 | II-55 | C-14 |
| T1b-687 | I-3 | II-72 | C-14 |
| T1b-688 | I-3 | II-73 | C-14 |
| T1b-689 | I-3 | II-27 | C-14 |
| T1b-690 | I-3 | II-44 | C-14 |
| T1b-691 | I-3 | II-74 | C-14 |
| T1b-692 | I-3 | II-28 | C-14 |
| T1b-693 | I-3 | II-75 | C-14 |
| T1b-694 | I-3 | II-29 | C-14 |
| T1b-695 | I-3 | II-30 | C-14 |
| T1b-696 | I-3 | II-31 | C-14 |
| T1b-697 | I-3 | II-76 | C-14 |
| T1b-698 | I-3 | II-77 | C-14 |
| T1b-699 | I-3 | II-78 | C-14 |
| T1b-700 | I-3 | II-79 | C-14 |
| T1b-701 | I-3 | II-80 | C-14 |
| T1b-702 | I-3 | II-34 | C-14 |
| T1b-703 | I-3 | II-81 | C-14 |
| T1b-704 | I-3 | II-82 | C-14 |
| T1b-705 | I-3 | II-83 | C-14 |
| T1b-706 | I-3 | II-52 | C-14 |
| T1b-707 | I-3 | II-84 | C-14 |
| T1b-708 | I-3 | II-85 | C-14 |
| T1b-709 | I-3 | II-86 | C-14 |
| T1b-710 | I-3 | II-87 | C-14 |
| T1b-711 | I-3 | II-88 | C-14 |
| T1b-712 | I-3 | II-43 | C-14 |
| T1b-713 | I-3 | II-89 | C-14 |
| T1b-714 | I-3 | II-90 | C-14 |
| T1b-715 | I-3 | II-56 | C-15 |
| T1b-716 | I-3 | II-48 | C-15 |
| T1b-717 | I-3 | II-57 | C-15 |
| T1b-718 | I-3 | II-58 | C-15 |
| T1b-719 | I-3 | II-59 | C-15 |
| T1b-720 | I-3 | II-49 | C-15 |
| T1b-721 | I-3 | II-60 | C-15 |
| T1b-722 | I-3 | II-61 | C-15 |
| T1b-723 | I-3 | II-62 | C-15 |
| T1b-724 | I-3 | II-50 | C-15 |
| T1b-725 | I-3 | II-63 | C-15 |
| T1b-726 | I-3 | II-64 | C-15 |
| T1b-727 | I-3 | II-65 | C-15 |
| T1b-728 | I-3 | II-66 | C-15 |
| T1b-729 | I-3 | II-51 | C-15 |
| T1b-730 | I-3 | II-67 | C-15 |
| T1b-731 | I-3 | II-68 | C-15 |
| T1b-732 | I-3 | II-69 | C-15 |
| T1b-733 | I-3 | II-53 | C-15 |
| T1b-734 | I-3 | II-70 | C-15 |
| T1b-735 | I-3 | II-54 | C-15 |
| T1b-736 | I-3 | II-71 | C-15 |
| T1b-737 | I-3 | II-55 | C-15 |
| T1b-738 | I-3 | II-72 | C-15 |
| T1b-739 | I-3 | II-73 | C-15 |
| T1b-740 | I-3 | II-27 | C-15 |
| T1b-741 | I-3 | II-44 | C-15 |
| T1b-742 | I-3 | II-74 | C-15 |
| T1b-743 | I-3 | II-28 | C-15 |
| T1b-744 | I-3 | II-75 | C-15 |
| T1b-745 | I-3 | II-29 | C-15 |
| T1b-746 | I-3 | II-30 | C-15 |
| T1b-747 | I-3 | II-31 | C-15 |
| T1b-748 | I-3 | II-76 | C-15 |
| T1b-749 | I-3 | II-77 | C-15 |
| T1b-750 | I-3 | II-78 | C-15 |
| T1b-751 | I-3 | II-79 | C-15 |
| T1b-752 | I-3 | II-80 | C-15 |
| T1b-753 | I-3 | II-34 | C-15 |
| T1b-754 | I-3 | II-81 | C-15 |
| T1b-755 | I-3 | II-82 | C-15 |
| T1b-756 | I-3 | II-83 | C-15 |
| T1b-757 | I-3 | II-52 | C-15 |
| T1b-758 | I-3 | II-84 | C-15 |
| T1b-759 | I-3 | II-85 | C-15 |
| T1b-760 | I-3 | II-86 | C-15 |
| T1b-761 | I-3 | II-87 | C-15 |
| T1b-762 | I-3 | II-88 | C-15 |
| T1b-763 | I-3 | II-43 | C-15 |
| T1b-764 | I-3 | II-89 | C-15 |
| T1b-765 | I-3 | II-90 | C-15 |
| T1b-766 | I-3 | II-56 | C-16 |
| T1b-767 | I-3 | II-48 | C-16 |
| T1b-768 | I-3 | II-57 | C-16 |
| T1b-769 | I-3 | II-58 | C-16 |
| T1b-770 | I-3 | II-59 | C-16 |
| T1b-771 | I-3 | II-49 | C-16 |
| T1b-772 | I-3 | II-60 | C-16 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-773 | I-3 | II-61 | C-16 |
| T1b-774 | I-3 | II-62 | C-16 |
| T1b-775 | I-3 | II-50 | C-16 |
| T1b-776 | I-3 | II-63 | C-16 |
| T1b-777 | I-3 | II-64 | C-16 |
| T1b-778 | I-3 | II-65 | C-16 |
| T1b-779 | I-3 | II-66 | C-16 |
| T1b-780 | I-3 | II-51 | C-16 |
| T1b-781 | I-3 | II-67 | C-16 |
| T1b-782 | I-3 | II-68 | C-16 |
| T1b-783 | I-3 | II-69 | C-16 |
| T1b-784 | I-3 | II-53 | C-16 |
| T1b-785 | I-3 | II-70 | C-16 |
| T1b-786 | I-3 | II-54 | C-16 |
| T1b-787 | I-3 | II-71 | C-16 |
| T1b-788 | I-3 | II-55 | C-16 |
| T1b-789 | I-3 | II-72 | C-16 |
| T1b-790 | I-3 | II-73 | C-16 |
| T1b-791 | I-3 | II-27 | C-16 |
| T1b-792 | I-3 | II-44 | C-16 |
| T1b-793 | I-3 | II-74 | C-16 |
| T1b-794 | I-3 | II-28 | C-16 |
| T1b-795 | I-3 | II-75 | C-16 |
| T1b-796 | I-3 | II-29 | C-16 |
| T1b-797 | I-3 | II-30 | C-16 |
| T1b-798 | I-3 | II-31 | C-16 |
| T1b-799 | I-3 | II-76 | C-16 |
| T1b-800 | I-3 | II-77 | C-16 |
| T1b-801 | I-3 | II-78 | C-16 |
| T1b-802 | I-3 | II-79 | C-16 |
| T1b-803 | I-3 | II-80 | C-16 |
| T1b-804 | I-3 | II-34 | C-16 |
| T1b-805 | I-3 | II-81 | C-16 |
| T1b-806 | I-3 | II-82 | C-16 |
| T1b-807 | I-3 | II-83 | C-16 |
| T1b-808 | I-3 | II-52 | C-16 |
| T1b-809 | I-3 | II-84 | C-16 |
| T1b-810 | I-3 | II-85 | C-16 |
| T1b-811 | I-3 | II-86 | C-16 |
| T1b-812 | I-3 | II-87 | C-16 |
| T1b-813 | I-3 | II-88 | C-16 |
| T1b-814 | I-3 | II-43 | C-16 |
| T1b-815 | I-3 | II-89 | C-16 |
| T1b-816 | I-3 | II-90 | C-16 |
| T1b-817 | I-3 | II-56 | C-17 |
| T1b-818 | I-3 | II-48 | C-17 |
| T1b-819 | I-3 | II-57 | C-17 |
| T1b-820 | I-3 | II-58 | C-17 |
| T1b-821 | I-3 | II-59 | C-17 |
| T1b-822 | I-3 | II-49 | C-17 |
| T1b-823 | I-3 | II-60 | C-17 |
| T1b-824 | I-3 | II-61 | C-17 |
| T1b-825 | I-3 | II-62 | C-17 |
| T1b-826 | I-3 | II-50 | C-17 |
| T1b-827 | I-3 | II-63 | C-17 |
| T1b-828 | I-3 | II-64 | C-17 |
| T1b-829 | I-3 | II-65 | C-17 |
| T1b-830 | I-3 | II-66 | C-17 |
| T1b-831 | I-3 | II-51 | C-17 |
| T1b-832 | I-3 | II-67 | C-17 |
| T1b-833 | I-3 | II-68 | C-17 |
| T1b-834 | I-3 | II-69 | C-17 |
| T1b-835 | I-3 | II-53 | C-17 |
| T1b-836 | I-3 | II-70 | C-17 |
| T1b-837 | I-3 | II-54 | C-17 |
| T1b-838 | I-3 | II-71 | C-17 |
| T1b-839 | I-3 | II-55 | C-17 |
| T1b-840 | I-3 | II-72 | C-17 |
| T1b-841 | I-3 | II-73 | C-17 |
| T1b-842 | I-3 | II-27 | C-17 |
| T1b-843 | I-3 | II-44 | C-17 |
| T1b-844 | I-3 | II-74 | C-17 |
| T1b-845 | I-3 | II-28 | C-17 |
| T1b-846 | I-3 | II-75 | C-17 |
| T1b-847 | I-3 | II-29 | C-17 |
| T1b-848 | I-3 | II-30 | C-17 |
| T1b-849 | I-3 | II-31 | C-17 |
| T1b-850 | I-3 | II-76 | C-17 |
| T1b-851 | I-3 | II-77 | C-17 |
| T1b-852 | I-3 | II-78 | C-17 |
| T1b-853 | I-3 | II-79 | C-17 |
| T1b-854 | I-3 | II-80 | C-17 |
| T1b-855 | I-3 | II-34 | C-17 |
| T1b-856 | I-3 | II-81 | C-17 |
| T1b-857 | I-3 | II-82 | C-17 |
| T1b-858 | I-3 | II-83 | C-17 |
| T1b-859 | I-3 | II-52 | C-17 |
| T1b-860 | I-3 | II-84 | C-17 |
| T1b-861 | I-3 | II-85 | C-17 |
| T1b-862 | I-3 | II-86 | C-17 |
| T1b-863 | I-3 | II-87 | C-17 |
| T1b-864 | I-3 | II-88 | C-17 |
| T1b-865 | I-3 | II-43 | C-17 |
| T1b-866 | I-3 | II-89 | C-17 |
| T1b-867 | I-3 | II-90 | C-17 |
| T1b-868 | I-3 | II-56 | C-18 |
| T1b-869 | I-3 | II-48 | C-18 |
| T1b-870 | I-3 | II-57 | C-18 |
| T1b-871 | I-3 | II-58 | C-18 |
| T1b-872 | I-3 | II-59 | C-18 |
| T1b-873 | I-3 | II-49 | C-18 |
| T1b-874 | I-3 | II-60 | C-18 |
| T1b-875 | I-3 | II-61 | C-18 |
| T1b-876 | I-3 | II-62 | C-18 |
| T1b-877 | I-3 | II-50 | C-18 |
| T1b-878 | I-3 | II-63 | C-18 |
| T1b-879 | I-3 | II-64 | C-18 |
| T1b-880 | I-3 | II-65 | C-18 |
| T1b-881 | I-3 | II-66 | C-18 |
| T1b-882 | I-3 | II-51 | C-18 |
| T1b-883 | I-3 | II-67 | C-18 |
| T1b-884 | I-3 | II-68 | C-18 |
| T1b-885 | I-3 | II-69 | C-18 |
| T1b-886 | I-3 | II-53 | C-18 |
| T1b-887 | I-3 | II-70 | C-18 |
| T1b-888 | I-3 | II-54 | C-18 |
| T1b-889 | I-3 | II-71 | C-18 |
| T1b-890 | I-3 | II-55 | C-18 |
| T1b-891 | I-3 | II-72 | C-18 |
| T1b-892 | I-3 | II-73 | C-18 |
| T1b-893 | I-3 | II-27 | C-18 |
| T1b-894 | I-3 | II-44 | C-18 |
| T1b-895 | I-3 | II-74 | C-18 |
| T1b-896 | I-3 | II-28 | C-18 |
| T1b-897 | I-3 | II-75 | C-18 |
| T1b-898 | I-3 | II-29 | C-18 |
| T1b-899 | I-3 | II-30 | C-18 |
| T1b-900 | I-3 | II-31 | C-18 |
| T1b-901 | I-3 | II-76 | C-18 |
| T1b-902 | I-3 | II-77 | C-18 |
| T1b-903 | I-3 | II-78 | C-18 |
| T1b-904 | I-3 | II-79 | C-18 |
| T1b-905 | I-3 | II-80 | C-18 |
| T1b-906 | I-3 | II-34 | C-18 |
| T1b-907 | I-3 | II-81 | C-18 |
| T1b-908 | I-3 | II-82 | C-18 |
| T1b-909 | I-3 | II-83 | C-18 |
| T1b-910 | I-3 | II-52 | C-18 |
| T1b-911 | I-3 | II-84 | C-18 |
| T1b-912 | I-3 | II-85 | C-18 |
| T1b-913 | I-3 | II-86 | C-18 |
| T1b-914 | I-3 | II-87 | C-18 |
| T1b-915 | I-3 | II-88 | C-18 |
| T1b-916 | I-3 | II-43 | C-18 |
| T1b-917 | I-3 | II-89 | C-18 |
| T1b-918 | I-3 | II-90 | C-18 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-919 | I-3 | II-56 | C-19 |
| T1b-920 | I-3 | II-48 | C-19 |
| T1b-921 | I-3 | II-57 | C-19 |
| T1b-922 | I-3 | II-58 | C-19 |
| T1b-923 | I-3 | II-59 | C-19 |
| T1b-924 | I-3 | II-49 | C-19 |
| T1b-925 | I-3 | II-60 | C-19 |
| T1b-926 | I-3 | II-61 | C-19 |
| T1b-927 | I-3 | II-62 | C-19 |
| T1b-928 | I-3 | II-50 | C-19 |
| T1b-929 | I-3 | II-63 | C-19 |
| T1b-930 | I-3 | II-64 | C-19 |
| T1b-931 | I-3 | II-65 | C-19 |
| T1b-932 | I-3 | II-66 | C-19 |
| T1b-933 | I-3 | II-51 | C-19 |
| T1b-934 | I-3 | II-67 | C-19 |
| T1b-935 | I-3 | II-68 | C-19 |
| T1b-936 | I-3 | II-69 | C-19 |
| T1b-937 | I-3 | II-53 | C-19 |
| T1b-938 | I-3 | II-70 | C-19 |
| T1b-939 | I-3 | II-54 | C-19 |
| T1b-940 | I-3 | II-71 | C-19 |
| T1b-941 | I-3 | II-55 | C-19 |
| T1b-942 | I-3 | II-72 | C-19 |
| T1b-943 | I-3 | II-73 | C-19 |
| T1b-944 | I-3 | II-27 | C-19 |
| T1b-945 | I-3 | II-44 | C-19 |
| T1b-946 | I-3 | II-74 | C-19 |
| T1b-947 | I-3 | II-28 | C-19 |
| T1b-948 | I-3 | II-75 | C-19 |
| T1b-949 | I-3 | II-29 | C-19 |
| T1b-950 | I-3 | II-30 | C-19 |
| T1b-951 | I-3 | II-31 | C-19 |
| T1b-952 | I-3 | II-76 | C-19 |
| T1b-953 | I-3 | II-77 | C-19 |
| T1b-954 | I-3 | II-78 | C-19 |
| T1b-955 | I-3 | II-79 | C-19 |
| T1b-956 | I-3 | II-80 | C-19 |
| T1b-957 | I-3 | II-34 | C-19 |
| T1b-958 | I-3 | II-81 | C-19 |
| T1b-959 | I-3 | II-82 | C-19 |
| T1b-960 | I-3 | II-83 | C-19 |
| T1b-961 | I-3 | II-52 | C-19 |
| T1b-962 | I-3 | II-84 | C-19 |
| T1b-963 | I-3 | II-85 | C-19 |
| T1b-964 | I-3 | II-86 | C-19 |
| T1b-965 | I-3 | II-87 | C-19 |
| T1b-966 | I-3 | II-88 | C-19 |
| T1b-967 | I-3 | II-43 | C-19 |
| T1b-968 | I-3 | II-89 | C-19 |
| T1b-969 | I-3 | II-90 | C-19 |
| T1b-970 | I-3 | II-56 | C-20 |
| T1b-971 | I-3 | II-48 | C-20 |
| T1b-972 | I-3 | II-57 | C-20 |
| T1b-973 | I-3 | II-58 | C-20 |
| T1b-974 | I-3 | II-59 | C-20 |
| T1b-975 | I-3 | II-49 | C-20 |
| T1b-976 | I-3 | II-60 | C-20 |
| T1b-977 | I-3 | II-61 | C-20 |
| T1b-978 | I-3 | II-62 | C-20 |
| T1b-979 | I-3 | II-50 | C-20 |
| T1b-980 | I-3 | II-63 | C-20 |
| T1b-981 | I-3 | II-64 | C-20 |
| T1b-982 | I-3 | II-65 | C-20 |
| T1b-983 | I-3 | II-66 | C-20 |
| T1b-984 | I-3 | II-51 | C-20 |
| T1b-985 | I-3 | II-67 | C-20 |
| T1b-986 | I-3 | II-68 | C-20 |
| T1b-987 | I-3 | II-69 | C-20 |
| T1b-988 | I-3 | II-53 | C-20 |
| T1b-989 | I-3 | II-70 | C-20 |
| T1b-990 | I-3 | II-54 | C-20 |
| T1b-991 | I-3 | II-71 | C-20 |
| T1b-992 | I-3 | II-55 | C-20 |
| T1b-993 | I-3 | II-72 | C-20 |
| T1b-994 | I-3 | II-73 | C-20 |
| T1b-995 | I-3 | II-27 | C-20 |
| T1b-996 | I-3 | II-44 | C-20 |
| T1b-997 | I-3 | II-74 | C-20 |
| T1b-998 | I-3 | II-28 | C-20 |
| T1b-999 | I-3 | II-75 | C-20 |
| T1b-1000 | I-3 | II-29 | C-20 |
| T1b-1001 | I-3 | II-30 | C-20 |
| T1b-1002 | I-3 | II-31 | C-20 |
| T1b-1003 | I-3 | II-76 | C-20 |
| T1b-1004 | I-3 | II-77 | C-20 |
| T1b-1005 | I-3 | II-78 | C-20 |
| T1b-1006 | I-3 | II-79 | C-20 |
| T1b-1007 | I-3 | II-80 | C-20 |
| T1b-1008 | I-3 | II-34 | C-20 |
| T1b-1009 | I-3 | II-81 | C-20 |
| T1b-1010 | I-3 | II-82 | C-20 |
| T1b-1011 | I-3 | II-83 | C-20 |
| T1b-1012 | I-3 | II-52 | C-20 |
| T1b-1013 | I-3 | II-84 | C-20 |
| T1b-1014 | I-3 | II-85 | C-20 |
| T1b-1015 | I-3 | II-86 | C-20 |
| T1b-1016 | I-3 | II-87 | C-20 |
| T1b-1017 | I-3 | II-88 | C-20 |
| T1b-1018 | I-3 | II-43 | C-20 |
| T1b-1019 | I-3 | II-89 | C-20 |
| T1b-1020 | I-3 | II-90 | C-20 |
| T1b-1021 | I-3 | II-56 | C-21 |
| T1b-1022 | I-3 | II-48 | C-21 |
| T1b-1023 | I-3 | II-57 | C-21 |
| T1b-1024 | I-3 | II-58 | C-21 |
| T1b-1025 | I-3 | II-59 | C-21 |
| T1b-1026 | I-3 | II-49 | C-21 |
| T1b-1027 | I-3 | II-60 | C-21 |
| T1b-1028 | I-3 | II-61 | C-21 |
| T1b-1029 | I-3 | II-62 | C-21 |
| T1b-1030 | I-3 | II-50 | C-21 |
| T1b-1031 | I-3 | II-63 | C-21 |
| T1b-1032 | I-3 | II-64 | C-21 |
| T1b-1033 | I-3 | II-65 | C-21 |
| T1b-1034 | I-3 | II-66 | C-21 |
| T1b-1035 | I-3 | II-51 | C-21 |
| T1b-1036 | I-3 | II-67 | C-21 |
| T1b-1037 | I-3 | II-68 | C-21 |
| T1b-1038 | I-3 | II-69 | C-21 |
| T1b-1039 | I-3 | II-53 | C-21 |
| T1b-1040 | I-3 | II-70 | C-21 |
| T1b-1041 | I-3 | II-54 | C-21 |
| T1b-1042 | I-3 | II-71 | C-21 |
| T1b-1043 | I-3 | II-55 | C-21 |
| T1b-1044 | I-3 | II-72 | C-21 |
| T1b-1045 | I-3 | II-73 | C-21 |
| T1b-1046 | I-3 | II-27 | C-21 |
| T1b-1047 | I-3 | II-44 | C-21 |
| T1b-1048 | I-3 | II-74 | C-21 |
| T1b-1049 | I-3 | II-28 | C-21 |
| T1b-1050 | I-3 | II-75 | C-21 |
| T1b-1051 | I-3 | II-29 | C-21 |
| T1b-1052 | I-3 | II-30 | C-21 |
| T1b-1053 | I-3 | II-31 | C-21 |
| T1b-1054 | I-3 | II-76 | C-21 |
| T1b-1055 | I-3 | II-77 | C-21 |
| T1b-1056 | I-3 | II-78 | C-21 |
| T1b-1057 | I-3 | II-79 | C-21 |
| T1b-1058 | I-3 | II-80 | C-21 |
| T1b-1059 | I-3 | II-34 | C-21 |
| T1b-1060 | I-3 | II-81 | C-21 |
| T1b-1061 | I-3 | II-82 | C-21 |
| T1b-1062 | I-3 | II-83 | C-21 |
| T1b-1063 | I-3 | II-52 | C-21 |
| T1b-1064 | I-3 | II-84 | C-21 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-1065 | I-3 | II-85 | C-21 |
| T1b-1066 | I-3 | II-86 | C-21 |
| T1b-1067 | I-3 | II-87 | C-21 |
| T1b-1068 | I-3 | II-88 | C-21 |
| T1b-1069 | I-3 | II-43 | C-21 |
| T1b-1070 | I-3 | II-89 | C-21 |
| T1b-1071 | I-3 | II-90 | C-21 |
| T1b-1072 | I-3 | II-56 | C-22 |
| T1b-1073 | I-3 | II-48 | C-22 |
| T1b-1074 | I-3 | II-57 | C-22 |
| T1b-1075 | I-3 | II-58 | C-22 |
| T1b-1076 | I-3 | II-59 | C-22 |
| T1b-1077 | I-3 | II-49 | C-22 |
| T1b-1078 | I-3 | II-60 | C-22 |
| T1b-1079 | I-3 | II-61 | C-22 |
| T1b-1080 | I-3 | II-62 | C-22 |
| T1b-1081 | I-3 | II-50 | C-22 |
| T1b-1082 | I-3 | II-63 | C-22 |
| T1b-1083 | I-3 | II-64 | C-22 |
| T1b-1084 | I-3 | II-65 | C-22 |
| T1b-1085 | I-3 | II-66 | C-22 |
| T1b-1086 | I-3 | II-51 | C-22 |
| T1b-1087 | I-3 | II-67 | C-22 |
| T1b-1088 | I-3 | II-68 | C-22 |
| T1b-1089 | I-3 | II-69 | C-22 |
| T1b-1090 | I-3 | II-53 | C-22 |
| T1b-1091 | I-3 | II-70 | C-22 |
| T1b-1092 | I-3 | II-54 | C-22 |
| T1b-1093 | I-3 | II-71 | C-22 |
| T1b-1094 | I-3 | II-55 | C-22 |
| T1b-1095 | I-3 | II-72 | C-22 |
| T1b-1096 | I-3 | II-73 | C-22 |
| T1b-1097 | I-3 | II-27 | C-22 |
| T1b-1098 | I-3 | II-44 | C-22 |
| T1b-1099 | I-3 | II-74 | C-22 |
| T1b-1100 | I-3 | II-28 | C-22 |
| T1b-1101 | I-3 | II-75 | C-22 |
| T1b-1102 | I-3 | II-29 | C-22 |
| T1b-1103 | I-3 | II-30 | C-22 |
| T1b-1104 | I-3 | II-31 | C-22 |
| T1b-1105 | I-3 | II-76 | C-22 |
| T1b-1106 | I-3 | II-77 | C-22 |
| T1b-1107 | I-3 | II-78 | C-22 |
| T1b-1108 | I-3 | II-79 | C-22 |
| T1b-1109 | I-3 | II-80 | C-22 |
| T1b-1110 | I-3 | II-34 | C-22 |
| T1b-1111 | I-3 | II-81 | C-22 |
| T1b-1112 | I-3 | II-82 | C-22 |
| T1b-1113 | I-3 | II-83 | C-22 |
| T1b-1114 | I-3 | II-52 | C-22 |
| T1b-1115 | I-3 | II-84 | C-22 |
| T1b-1116 | I-3 | II-85 | C-22 |
| T1b-1117 | I-3 | II-86 | C-22 |
| T1b-1118 | I-3 | II-87 | C-22 |
| T1b-1119 | I-3 | II-88 | C-22 |
| T1b-1120 | I-3 | II-43 | C-22 |
| T1b-1121 | I-3 | II-89 | C-22 |
| T1b-1122 | I-3 | II-90 | C-22 |
| T1b-1123 | I-3 | II-56 | C-23 |
| T1b-1124 | I-3 | II-48 | C-23 |
| T1b-1125 | I-3 | II-57 | C-23 |
| T1b-1126 | I-3 | II-58 | C-23 |
| T1b-1127 | I-3 | II-59 | C-23 |
| T1b-1128 | I-3 | II-49 | C-23 |
| T1b-1129 | I-3 | II-60 | C-23 |
| T1b-1130 | I-3 | II-61 | C-23 |
| T1b-1131 | I-3 | II-62 | C-23 |
| T1b-1132 | I-3 | II-50 | C-23 |
| T1b-1133 | I-3 | II-63 | C-23 |
| T1b-1134 | I-3 | II-64 | C-23 |
| T1b-1135 | I-3 | II-65 | C-23 |
| T1b-1136 | I-3 | II-66 | C-23 |
| T1b-1137 | I-3 | II-51 | C-23 |
| T1b-1138 | I-3 | II-67 | C-23 |
| T1b-1139 | I-3 | II-68 | C-23 |
| T1b-1140 | I-3 | II-69 | C-23 |
| T1b-1141 | I-3 | II-53 | C-23 |
| T1b-1142 | I-3 | II-70 | C-23 |
| T1b-1143 | I-3 | II-54 | C-23 |
| T1b-1144 | I-3 | II-71 | C-23 |
| T1b-1145 | I-3 | II-55 | C-23 |
| T1b-1146 | I-3 | II-72 | C-23 |
| T1b-1147 | I-3 | II-73 | C-23 |
| T1b-1148 | I-3 | II-27 | C-23 |
| T1b-1149 | I-3 | II-44 | C-23 |
| T1b-1150 | I-3 | II-74 | C-23 |
| T1b-1151 | I-3 | II-28 | C-23 |
| T1b-1152 | I-3 | II-75 | C-23 |
| T1b-1153 | I-3 | II-29 | C-23 |
| T1b-1154 | I-3 | II-30 | C-23 |
| T1b-1155 | I-3 | II-31 | C-23 |
| T1b-1156 | I-3 | II-76 | C-23 |
| T1b-1157 | I-3 | II-77 | C-23 |
| T1b-1158 | I-3 | II-78 | C-23 |
| T1b-1159 | I-3 | II-79 | C-23 |
| T1b-1160 | I-3 | II-80 | C-23 |
| T1b-1161 | I-3 | II-34 | C-23 |
| T1b-1162 | I-3 | II-81 | C-23 |
| T1b-1163 | I-3 | II-82 | C-23 |
| T1b-1164 | I-3 | II-83 | C-23 |
| T1b-1165 | I-3 | II-52 | C-23 |
| T1b-1166 | I-3 | II-84 | C-23 |
| T1b-1167 | I-3 | II-85 | C-23 |
| T1b-1168 | I-3 | II-86 | C-23 |
| T1b-1169 | I-3 | II-87 | C-23 |
| T1b-1170 | I-3 | II-88 | C-23 |
| T1b-1171 | I-3 | II-43 | C-23 |
| T1b-1172 | I-3 | II-89 | C-23 |
| T1b-1173 | I-3 | II-90 | C-23 |
| T1b-1174 | I-3 | II-56 | C-24 |
| T1b-1175 | I-3 | II-48 | C-24 |
| T1b-1176 | I-3 | II-57 | C-24 |
| T1b-1177 | I-3 | II-58 | C-24 |
| T1b-1178 | I-3 | II-59 | C-24 |
| T1b-1179 | I-3 | II-49 | C-24 |
| T1b-1180 | I-3 | II-60 | C-24 |
| T1b-1181 | I-3 | II-61 | C-24 |
| T1b-1182 | I-3 | II-62 | C-24 |
| T1b-1183 | I-3 | II-50 | C-24 |
| T1b-1184 | I-3 | II-63 | C-24 |
| T1b-1185 | I-3 | II-64 | C-24 |
| T1b-1186 | I-3 | II-65 | C-24 |
| T1b-1187 | I-3 | II-66 | C-24 |
| T1b-1188 | I-3 | II-51 | C-24 |
| T1b-1189 | I-3 | II-67 | C-24 |
| T1b-1190 | I-3 | II-68 | C-24 |
| T1b-1191 | I-3 | II-69 | C-24 |
| T1b-1192 | I-3 | II-53 | C-24 |
| T1b-1193 | I-3 | II-70 | C-24 |
| T1b-1194 | I-3 | II-54 | C-24 |
| T1b-1195 | I-3 | II-71 | C-24 |
| T1b-1196 | I-3 | II-55 | C-24 |
| T1b-1197 | I-3 | II-72 | C-24 |
| T1b-1198 | I-3 | II-73 | C-24 |
| T1b-1199 | I-3 | II-27 | C-24 |
| T1b-1200 | I-3 | II-44 | C-24 |
| T1b-1201 | I-3 | II-74 | C-24 |
| T1b-1202 | I-3 | II-28 | C-24 |
| T1b-1203 | I-3 | II-75 | C-24 |
| T1b-1204 | I-3 | II-29 | C-24 |
| T1b-1205 | I-3 | II-30 | C-24 |
| T1b-1206 | I-3 | II-31 | C-24 |
| T1b-1207 | I-3 | II-76 | C-24 |
| T1b-1208 | I-3 | II-77 | C-24 |
| T1b-1209 | I-3 | II-78 | C-24 |
| T1b-1210 | I-3 | II-79 | C-24 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-1211 | I-3 | II-80 | C-24 |
| T1b-1212 | I-3 | II-34 | C-24 |
| T1b-1213 | I-3 | II-81 | C-24 |
| T1b-1214 | I-3 | II-82 | C-24 |
| T1b-1215 | I-3 | II-83 | C-24 |
| T1b-1216 | I-3 | II-52 | C-24 |
| T1b-1217 | I-3 | II-84 | C-24 |
| T1b-1218 | I-3 | II-85 | C-24 |
| T1b-1219 | I-3 | II-86 | C-24 |
| T1b-1220 | I-3 | II-87 | C-24 |
| T1b-1221 | I-3 | II-88 | C-24 |
| T1b-1222 | I-3 | II-43 | C-24 |
| T1b-1223 | I-3 | II-89 | C-24 |
| T1b-1224 | I-3 | II-90 | C-24 |
| T1b-1225 | I-3 | II-56 | C-25 |
| T1b-1226 | I-3 | II-48 | C-25 |
| T1b-1227 | I-3 | II-57 | C-25 |
| T1b-1228 | I-3 | II-58 | C-25 |
| T1b-1229 | I-3 | II-59 | C-25 |
| T1b-1230 | I-3 | II-49 | C-25 |
| T1b-1231 | I-3 | II-60 | C-25 |
| T1b-1232 | I-3 | II-61 | C-25 |
| T1b-1233 | I-3 | II-62 | C-25 |
| T1b-1234 | I-3 | II-50 | C-25 |
| T1b-1235 | I-3 | II-63 | C-25 |
| T1b-1236 | I-3 | II-64 | C-25 |
| T1b-1237 | I-3 | II-65 | C-25 |
| T1b-1238 | I-3 | II-66 | C-25 |
| T1b-1239 | I-3 | II-51 | C-25 |
| T1b-1240 | I-3 | II-67 | C-25 |
| T1b-1241 | I-3 | II-68 | C-25 |
| T1b-1242 | I-3 | II-69 | C-25 |
| T1b-1243 | I-3 | II-53 | C-25 |
| T1b-1244 | I-3 | II-70 | C-25 |
| T1b-1245 | I-3 | II-54 | C-25 |
| T1b-1246 | I-3 | II-71 | C-25 |
| T1b-1247 | I-3 | II-55 | C-25 |
| T1b-1248 | I-3 | II-72 | C-25 |
| T1b-1249 | I-3 | II-73 | C-25 |
| T1b-1250 | I-3 | II-27 | C-25 |
| T1b-1251 | I-3 | II-44 | C-25 |
| T1b-1252 | I-3 | II-74 | C-25 |
| T1b-1253 | I-3 | II-28 | C-25 |
| T1b-1254 | I-3 | II-75 | C-25 |
| T1b-1255 | I-3 | II-29 | C-25 |
| T1b-1256 | I-3 | II-30 | C-25 |
| T1b-1257 | I-3 | II-31 | C-25 |
| T1b-1258 | I-3 | II-76 | C-25 |
| T1b-1259 | I-3 | II-77 | C-25 |
| T1b-1260 | I-3 | II-78 | C-25 |
| T1b-1261 | I-3 | II-79 | C-25 |
| T1b-1262 | I-3 | II-80 | C-25 |
| T1b-1263 | I-3 | II-34 | C-25 |
| T1b-1264 | I-3 | II-81 | C-25 |
| T1b-1265 | I-3 | II-82 | C-25 |
| T1b-1266 | I-3 | II-83 | C-25 |
| T1b-1267 | I-3 | II-52 | C-25 |
| T1b-1268 | I-3 | II-84 | C-25 |
| T1b-1269 | I-3 | II-85 | C-25 |
| T1b-1270 | I-3 | II-86 | C-25 |
| T1b-1271 | I-3 | II-87 | C-25 |
| T1b-1272 | I-3 | II-88 | C-25 |
| T1b-1273 | I-3 | II-43 | C-25 |
| T1b-1274 | I-3 | II-89 | C-25 |
| T1b-1275 | I-3 | II-90 | C-25 |
| T1b-1276 | I-3 | II-56 | C-26 |
| T1b-1277 | I-3 | II-48 | C-26 |
| T1b-1278 | I-3 | II-57 | C-26 |
| T1b-1279 | I-3 | II-58 | C-26 |
| T1b-1280 | I-3 | II-59 | C-26 |
| T1b-1281 | I-3 | II-49 | C-26 |
| T1b-1282 | I-3 | II-60 | C-26 |
| T1b-1283 | I-3 | II-61 | C-26 |
| T1b-1284 | I-3 | II-62 | C-26 |
| T1b-1285 | I-3 | II-50 | C-26 |
| T1b-1286 | I-3 | II-63 | C-26 |
| T1b-1287 | I-3 | II-64 | C-26 |
| T1b-1288 | I-3 | II-65 | C-26 |
| T1b-1289 | I-3 | II-66 | C-26 |
| T1b-1290 | I-3 | II-51 | C-26 |
| T1b-1291 | I-3 | II-67 | C-26 |
| T1b-1292 | I-3 | II-68 | C-26 |
| T1b-1293 | I-3 | II-69 | C-26 |
| T1b-1294 | I-3 | II-53 | C-26 |
| T1b-1295 | I-3 | II-70 | C-26 |
| T1b-1296 | I-3 | II-54 | C-26 |
| T1b-1297 | I-3 | II-71 | C-26 |
| T1b-1298 | I-3 | II-55 | C-26 |
| T1b-1299 | I-3 | II-72 | C-26 |
| T1b-1300 | I-3 | II-73 | C-26 |
| T1b-1301 | I-3 | II-27 | C-26 |
| T1b-1302 | I-3 | II-44 | C-26 |
| T1b-1303 | I-3 | II-74 | C-26 |
| T1b-1304 | I-3 | II-28 | C-26 |
| T1b-1305 | I-3 | II-75 | C-26 |
| T1b-1306 | I-3 | II-29 | C-26 |
| T1b-1307 | I-3 | II-30 | C-26 |
| T1b-1308 | I-3 | II-31 | C-26 |
| T1b-1309 | I-3 | II-76 | C-26 |
| T1b-1310 | I-3 | II-77 | C-26 |
| T1b-1311 | I-3 | II-78 | C-26 |
| T1b-1312 | I-3 | II-79 | C-26 |
| T1b-1313 | I-3 | II-80 | C-26 |
| T1b-1314 | I-3 | II-34 | C-26 |
| T1b-1315 | I-3 | II-81 | C-26 |
| T1b-1316 | I-3 | II-82 | C-26 |
| T1b-1317 | I-3 | II-83 | C-26 |
| T1b-1318 | I-3 | II-52 | C-26 |
| T1b-1319 | I-3 | II-84 | C-26 |
| T1b-1320 | I-3 | II-85 | C-26 |
| T1b-1321 | I-3 | II-86 | C-26 |
| T1b-1322 | I-3 | II-87 | C-26 |
| T1b-1323 | I-3 | II-88 | C-26 |
| T1b-1324 | I-3 | II-43 | C-26 |
| T1b-1325 | I-3 | II-89 | C-26 |
| T1b-1326 | I-3 | II-90 | C-26 |
| T1b-1327 | I-3 | II-56 | C-27 |
| T1b-1328 | I-3 | II-48 | C-27 |
| T1b-1329 | I-3 | II-57 | C-27 |
| T1b-1330 | I-3 | II-58 | C-27 |
| T1b-1331 | I-3 | II-59 | C-27 |
| T1b-1332 | I-3 | II-49 | C-27 |
| T1b-1333 | I-3 | II-60 | C-27 |
| T1b-1334 | I-3 | II-61 | C-27 |
| T1b-1335 | I-3 | II-62 | C-27 |
| T1b-1336 | I-3 | II-50 | C-27 |
| T1b-1337 | I-3 | II-63 | C-27 |
| T1b-1338 | I-3 | II-64 | C-27 |
| T1b-1339 | I-3 | II-65 | C-27 |
| T1b-1340 | I-3 | II-66 | C-27 |
| T1b-1341 | I-3 | II-51 | C-27 |
| T1b-1342 | I-3 | II-67 | C-27 |
| T1b-1343 | I-3 | II-68 | C-27 |
| T1b-1344 | I-3 | II-69 | C-27 |
| T1b-1345 | I-3 | II-53 | C-27 |
| T1b-1346 | I-3 | II-70 | C-27 |
| T1b-1347 | I-3 | II-54 | C-27 |
| T1b-1348 | I-3 | II-71 | C-27 |
| T1b-1349 | I-3 | II-55 | C-27 |
| T1b-1350 | I-3 | II-72 | C-27 |
| T1b-1351 | I-3 | II-73 | C-27 |
| T1b-1352 | I-3 | II-27 | C-27 |
| T1b-1353 | I-3 | II-44 | C-27 |
| T1b-1354 | I-3 | II-74 | C-27 |
| T1b-1355 | I-3 | II-28 | C-27 |
| T1b-1356 | I-3 | II-75 | C-27 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-1357 | I-3 | II-29 | C-27 |
| T1b-1358 | I-3 | II-30 | C-27 |
| T1b-1359 | I-3 | II-31 | C-27 |
| T1b-1360 | I-3 | II-76 | C-27 |
| T1b-1361 | I-3 | II-77 | C-27 |
| T1b-1362 | I-3 | II-78 | C-27 |
| T1b-1363 | I-3 | II-79 | C-27 |
| T1b-1364 | I-3 | II-80 | C-27 |
| T1b-1365 | I-3 | II-34 | C-27 |
| T1b-1366 | I-3 | II-81 | C-27 |
| T1b-1367 | I-3 | II-82 | C-27 |
| T1b-1368 | I-3 | II-83 | C-27 |
| T1b-1369 | I-3 | II-52 | C-27 |
| T1b-1370 | I-3 | II-84 | C-27 |
| T1b-1371 | I-3 | II-85 | C-27 |
| T1b-1372 | I-3 | II-86 | C-27 |
| T1b-1373 | I-3 | II-87 | C-27 |
| T1b-1374 | I-3 | II-88 | C-27 |
| T1b-1375 | I-3 | II-43 | C-27 |
| T1b-1376 | I-3 | II-89 | C-27 |
| T1b-1377 | I-3 | II-90 | C-27 |
| T1b-1378 | I-3 | II-56 | C-28 |
| T1b-1379 | I-3 | II-48 | C-28 |
| T1b-1380 | I-3 | II-57 | C-28 |
| T1b-1381 | I-3 | II-58 | C-28 |
| T1b-1382 | I-3 | II-59 | C-28 |
| T1b-1383 | I-3 | II-49 | C-28 |
| T1b-1384 | I-3 | II-60 | C-28 |
| T1b-1385 | I-3 | II-61 | C-28 |
| T1b-1386 | I-3 | II-62 | C-28 |
| T1b-1387 | I-3 | II-50 | C-28 |
| T1b-1388 | I-3 | II-63 | C-28 |
| T1b-1389 | I-3 | II-64 | C-28 |
| T1b-1390 | I-3 | II-65 | C-28 |
| T1b-1391 | I-3 | II-66 | C-28 |
| T1b-1392 | I-3 | II-51 | C-28 |
| T1b-1393 | I-3 | II-67 | C-28 |
| T1b-1394 | I-3 | II-68 | C-28 |
| T1b-1395 | I-3 | II-69 | C-28 |
| T1b-1396 | I-3 | II-53 | C-28 |
| T1b-1397 | I-3 | II-70 | C-28 |
| T1b-1398 | I-3 | II-54 | C-28 |
| T1b-1399 | I-3 | II-71 | C-28 |
| T1b-1400 | I-3 | II-55 | C-28 |
| T1b-1401 | I-3 | II-72 | C-28 |
| T1b-1402 | I-3 | II-73 | C-28 |
| T1b-1403 | I-3 | II-27 | C-28 |
| T1b-1404 | I-3 | II-44 | C-28 |
| T1b-1405 | I-3 | II-74 | C-28 |
| T1b-1406 | I-3 | II-28 | C-28 |
| T1b-1407 | I-3 | II-75 | C-28 |
| T1b-1408 | I-3 | II-29 | C-28 |
| T1b-1409 | I-3 | II-30 | C-28 |
| T1b-1410 | I-3 | II-31 | C-28 |
| T1b-1411 | I-3 | II-76 | C-28 |
| T1b-1412 | I-3 | II-77 | C-28 |
| T1b-1413 | I-3 | II-78 | C-28 |
| T1b-1414 | I-3 | II-79 | C-28 |
| T1b-1415 | I-3 | II-80 | C-28 |
| T1b-1416 | I-3 | II-34 | C-28 |
| T1b-1417 | I-3 | II-81 | C-28 |
| T1b-1418 | I-3 | II-82 | C-28 |
| T1b-1419 | I-3 | II-83 | C-28 |
| T1b-1420 | I-3 | II-52 | C-28 |
| T1b-1421 | I-3 | II-84 | C-28 |
| T1b-1422 | I-3 | II-85 | C-28 |
| T1b-1423 | I-3 | II-86 | C-28 |
| T1b-1424 | I-3 | II-87 | C-28 |
| T1b-1425 | I-3 | II-88 | C-28 |
| T1b-1426 | I-3 | II-43 | C-28 |
| T1b-1427 | I-3 | II-89 | C-28 |
| T1b-1428 | I-3 | II-90 | C-28 |
| T1b-1429 | I-3 | II-56 | C-29 |
| T1b-1430 | I-3 | II-48 | C-29 |
| T1b-1431 | I-3 | II-57 | C-29 |
| T1b-1432 | I-3 | II-58 | C-29 |
| T1b-1433 | I-3 | II-59 | C-29 |
| T1b-1434 | I-3 | II-49 | C-29 |
| T1b-1435 | I-3 | II-60 | C-29 |
| T1b-1436 | I-3 | II-61 | C-29 |
| T1b-1437 | I-3 | II-62 | C-29 |
| T1b-1438 | I-3 | II-50 | C-29 |
| T1b-1439 | I-3 | II-63 | C-29 |
| T1b-1440 | I-3 | II-64 | C-29 |
| T1b-1441 | I-3 | II-65 | C-29 |
| T1b-1442 | I-3 | II-66 | C-29 |
| T1b-1443 | I-3 | II-51 | C-29 |
| T1b-1444 | I-3 | II-67 | C-29 |
| T1b-1445 | I-3 | II-68 | C-29 |
| T1b-1446 | I-3 | II-69 | C-29 |
| T1b-1447 | I-3 | II-53 | C-29 |
| T1b-1448 | I-3 | II-70 | C-29 |
| T1b-1449 | I-3 | II-54 | C-29 |
| T1b-1450 | I-3 | II-71 | C-29 |
| T1b-1451 | I-3 | II-55 | C-29 |
| T1b-1452 | I-3 | II-72 | C-29 |
| T1b-1453 | I-3 | II-73 | C-29 |
| T1b-1454 | I-3 | II-27 | C-29 |
| T1b-1455 | I-3 | II-44 | C-29 |
| T1b-1456 | I-3 | II-74 | C-29 |
| T1b-1457 | I-3 | II-28 | C-29 |
| T1b-1458 | I-3 | II-75 | C-29 |
| T1b-1459 | I-3 | II-29 | C-29 |
| T1b-1460 | I-3 | II-30 | C-29 |
| T1b-1461 | I-3 | II-31 | C-29 |
| T1b-1462 | I-3 | II-76 | C-29 |
| T1b-1463 | I-3 | II-77 | C-29 |
| T1b-1464 | I-3 | II-78 | C-29 |
| T1b-1465 | I-3 | II-79 | C-29 |
| T1b-1466 | I-3 | II-80 | C-29 |
| T1b-1467 | I-3 | II-34 | C-29 |
| T1b-1468 | I-3 | II-81 | C-29 |
| T1b-1469 | I-3 | II-82 | C-29 |
| T1b-1470 | I-3 | II-83 | C-29 |
| T1b-1471 | I-3 | II-52 | C-29 |
| T1b-1472 | I-3 | II-84 | C-29 |
| T1b-1473 | I-3 | II-85 | C-29 |
| T1b-1474 | I-3 | II-86 | C-29 |
| T1b-1475 | I-3 | II-87 | C-29 |
| T1b-1476 | I-3 | II-88 | C-29 |
| T1b-1477 | I-3 | II-43 | C-29 |
| T1b-1478 | I-3 | II-89 | C-29 |
| T1b-1479 | I-3 | II-90 | C-29 |
| T1b-1480 | I-3 | II-56 | C-30 |
| T1b-1481 | I-3 | II-48 | C-30 |
| T1b-1482 | I-3 | II-57 | C-30 |
| T1b-1483 | I-3 | II-58 | C-30 |
| T1b-1484 | I-3 | II-59 | C-30 |
| T1b-1485 | I-3 | II-49 | C-30 |
| T1b-1486 | I-3 | II-60 | C-30 |
| T1b-1487 | I-3 | II-61 | C-30 |
| T1b-1488 | I-3 | II-62 | C-30 |
| T1b-1489 | I-3 | II-50 | C-30 |
| T1b-1490 | I-3 | II-63 | C-30 |
| T1b-1491 | I-3 | II-64 | C-30 |
| T1b-1492 | I-3 | II-65 | C-30 |
| T1b-1493 | I-3 | II-66 | C-30 |
| T1b-1494 | I-3 | II-51 | C-30 |
| T1b-1495 | I-3 | II-67 | C-30 |
| T1b-1496 | I-3 | II-68 | C-30 |
| T1b-1497 | I-3 | II-69 | C-30 |
| T1b-1498 | I-3 | II-53 | C-30 |
| T1b-1499 | I-3 | II-70 | C-30 |
| T1b-1500 | I-3 | II-54 | C-30 |
| T1b-1501 | I-3 | II-71 | C-30 |
| T1b-1502 | I-3 | II-55 | C-30 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-1503 | I-3 | II-72 | C-30 |
| T1b-1504 | I-3 | II-73 | C-30 |
| T1b-1505 | I-3 | II-27 | C-30 |
| T1b-1506 | I-3 | II-44 | C-30 |
| T1b-1507 | I-3 | II-74 | C-30 |
| T1b-1508 | I-3 | II-28 | C-30 |
| T1b-1509 | I-3 | II-75 | C-30 |
| T1b-1510 | I-3 | II-29 | C-30 |
| T1b-1511 | I-3 | II-30 | C-30 |
| T1b-1512 | I-3 | II-31 | C-30 |
| T1b-1513 | I-3 | II-76 | C-30 |
| T1b-1514 | I-3 | II-77 | C-30 |
| T1b-1515 | I-3 | II-78 | C-30 |
| T1b-1516 | I-3 | II-79 | C-30 |
| T1b-1517 | I-3 | II-80 | C-30 |
| T1b-1518 | I-3 | II-34 | C-30 |
| T1b-1519 | I-3 | II-81 | C-30 |
| T1b-1520 | I-3 | II-82 | C-30 |
| T1b-1521 | I-3 | II-83 | C-30 |
| T1b-1522 | I-3 | II-52 | C-30 |
| T1b-1523 | I-3 | II-84 | C-30 |
| T1b-1524 | I-3 | II-85 | C-30 |
| T1b-1525 | I-3 | II-86 | C-30 |
| T1b-1526 | I-3 | II-87 | C-30 |
| T1b-1527 | I-3 | II-88 | C-30 |
| T1b-1528 | I-3 | II-43 | C-30 |
| T1b-1529 | I-3 | II-89 | C-30 |
| T1b-1530 | I-3 | II-90 | C-30 |
| T1b-1531 | I-3 | II-56 | C-31 |
| T1b-1532 | I-3 | II-48 | C-31 |
| T1b-1533 | I-3 | II-57 | C-31 |
| T1b-1534 | I-3 | II-58 | C-31 |
| T1b-1535 | I-3 | II-59 | C-31 |
| T1b-1536 | I-3 | II-49 | C-31 |
| T1b-1537 | I-3 | II-60 | C-31 |
| T1b-1538 | I-3 | II-61 | C-31 |
| T1b-1539 | I-3 | II-62 | C-31 |
| T1b-1540 | I-3 | II-50 | C-31 |
| T1b-1541 | I-3 | II-63 | C-31 |
| T1b-1542 | I-3 | II-64 | C-31 |
| T1b-1543 | I-3 | II-65 | C-31 |
| T1b-1544 | I-3 | II-66 | C-31 |
| T1b-1545 | I-3 | II-51 | C-31 |
| T1b-1546 | I-3 | II-67 | C-31 |
| T1b-1547 | I-3 | II-68 | C-31 |
| T1b-1548 | I-3 | II-69 | C-31 |
| T1b-1549 | I-3 | II-53 | C-31 |
| T1b-1550 | I-3 | II-70 | C-31 |
| T1b-1551 | I-3 | II-54 | C-31 |
| T1b-1552 | I-3 | II-71 | C-31 |
| T1b-1553 | I-3 | II-55 | C-31 |
| T1b-1554 | I-3 | II-72 | C-31 |
| T1b-1555 | I-3 | II-73 | C-31 |
| T1b-1556 | I-3 | II-27 | C-31 |
| T1b-1557 | I-3 | II-44 | C-31 |
| T1b-1558 | I-3 | II-74 | C-31 |
| T1b-1559 | I-3 | II-28 | C-31 |
| T1b-1560 | I-3 | II-75 | C-31 |
| T1b-1561 | I-3 | II-29 | C-31 |
| T1b-1562 | I-3 | II-30 | C-31 |
| T1b-1563 | I-3 | II-31 | C-31 |
| T1b-1564 | I-3 | II-76 | C-31 |
| T1b-1565 | I-3 | II-77 | C-31 |
| T1b-1566 | I-3 | II-78 | C-31 |
| T1b-1567 | I-3 | II-79 | C-31 |
| T1b-1568 | I-3 | II-80 | C-31 |
| T1b-1569 | I-3 | II-34 | C-31 |
| T1b-1570 | I-3 | II-81 | C-31 |
| T1b-1571 | I-3 | II-82 | C-31 |
| T1b-1572 | I-3 | II-83 | C-31 |
| T1b-1573 | I-3 | II-52 | C-31 |
| T1b-1574 | I-3 | II-84 | C-31 |
| T1b-1575 | I-3 | II-85 | C-31 |
| T1b-1576 | I-3 | II-86 | C-31 |
| T1b-1577 | I-3 | II-87 | C-31 |
| T1b-1578 | I-3 | II-88 | C-31 |
| T1b-1579 | I-3 | II-43 | C-31 |
| T1b-1580 | I-3 | II-89 | C-31 |
| T1b-1581 | I-3 | II-90 | C-31 |
| T1b-1582 | I-3 | II-56 | C-32 |
| T1b-1583 | I-3 | II-48 | C-32 |
| T1b-1584 | I-3 | II-57 | C-32 |
| T1b-1585 | I-3 | II-58 | C-32 |
| T1b-1586 | I-3 | II-59 | C-32 |
| T1b-1587 | I-3 | II-49 | C-32 |
| T1b-1588 | I-3 | II-60 | C-32 |
| T1b-1589 | I-3 | II-61 | C-32 |
| T1b-1590 | I-3 | II-62 | C-32 |
| T1b-1591 | I-3 | II-50 | C-32 |
| T1b-1592 | I-3 | II-63 | C-32 |
| T1b-1593 | I-3 | II-64 | C-32 |
| T1b-1594 | I-3 | II-65 | C-32 |
| T1b-1595 | I-3 | II-66 | C-32 |
| T1b-1596 | I-3 | II-51 | C-32 |
| T1b-1597 | I-3 | II-67 | C-32 |
| T1b-1598 | I-3 | II-68 | C-32 |
| T1b-1599 | I-3 | II-69 | C-32 |
| T1b-1600 | I-3 | II-53 | C-32 |
| T1b-1601 | I-3 | II-70 | C-32 |
| T1b-1602 | I-3 | II-54 | C-32 |
| T1b-1603 | I-3 | II-71 | C-32 |
| T1b-1604 | I-3 | II-55 | C-32 |
| T1b-1605 | I-3 | II-72 | C-32 |
| T1b-1606 | I-3 | II-73 | C-32 |
| T1b-1607 | I-3 | II-27 | C-32 |
| T1b-1608 | I-3 | II-44 | C-32 |
| T1b-1609 | I-3 | II-74 | C-32 |
| T1b-1610 | I-3 | II-28 | C-32 |
| T1b-1611 | I-3 | II-75 | C-32 |
| T1b-1612 | I-3 | II-29 | C-32 |
| T1b-1613 | I-3 | II-30 | C-32 |
| T1b-1614 | I-3 | II-31 | C-32 |
| T1b-1615 | I-3 | II-76 | C-32 |
| T1b-1616 | I-3 | II-77 | C-32 |
| T1b-1617 | I-3 | II-78 | C-32 |
| T1b-1618 | I-3 | II-79 | C-32 |
| T1b-1619 | I-3 | II-80 | C-32 |
| T1b-1620 | I-3 | II-34 | C-32 |
| T1b-1621 | I-3 | II-81 | C-32 |
| T1b-1622 | I-3 | II-82 | C-32 |
| T1b-1623 | I-3 | II-83 | C-32 |
| T1b-1624 | I-3 | II-52 | C-32 |
| T1b-1625 | I-3 | II-84 | C-32 |
| T1b-1626 | I-3 | II-85 | C-32 |
| T1b-1627 | I-3 | II-86 | C-32 |
| T1b-1628 | I-3 | II-87 | C-32 |
| T1b-1629 | I-3 | II-88 | C-32 |
| T1b-1630 | I-3 | II-43 | C-32 |
| T1b-1631 | I-3 | II-89 | C-32 |
| T1b-1632 | I-3 | II-90 | C-32 |
| T1b-1633 | I-3 | II-56 | C-33 |
| T1b-1634 | I-3 | II-48 | C-33 |
| T1b-1635 | I-3 | II-57 | C-33 |
| T1b-1636 | I-3 | II-58 | C-33 |
| T1b-1637 | I-3 | II-59 | C-33 |
| T1b-1638 | I-3 | II-49 | C-33 |
| T1b-1639 | I-3 | II-60 | C-33 |
| T1b-1640 | I-3 | II-61 | C-33 |
| T1b-1641 | I-3 | II-62 | C-33 |
| T1b-1642 | I-3 | II-50 | C-33 |
| T1b-1643 | I-3 | II-63 | C-33 |
| T1b-1644 | I-3 | II-64 | C-33 |
| T1b-1645 | I-3 | II-65 | C-33 |
| T1b-1646 | I-3 | II-66 | C-33 |
| T1b-1647 | I-3 | II-51 | C-33 |
| T1b-1648 | I-3 | II-67 | C-33 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-1649 | I-3 | II-68 | C-33 |
| T1b-1650 | I-3 | II-69 | C-33 |
| T1b-1651 | I-3 | II-53 | C-33 |
| T1b-1652 | I-3 | II-70 | C-33 |
| T1b-1653 | I-3 | II-54 | C-33 |
| T1b-1654 | I-3 | II-71 | C-33 |
| T1b-1655 | I-3 | II-55 | C-33 |
| T1b-1656 | I-3 | II-72 | C-33 |
| T1b-1657 | I-3 | II-73 | C-33 |
| T1b-1658 | I-3 | II-27 | C-33 |
| T1b-1659 | I-3 | II-44 | C-33 |
| T1b-1660 | I-3 | II-74 | C-33 |
| T1b-1661 | I-3 | II-28 | C-33 |
| T1b-1662 | I-3 | II-75 | C-33 |
| T1b-1663 | I-3 | II-29 | C-33 |
| T1b-1664 | I-3 | II-30 | C-33 |
| T1b-1665 | I-3 | II-31 | C-33 |
| T1b-1666 | I-3 | II-76 | C-33 |
| T1b-1667 | I-3 | II-77 | C-33 |
| T1b-1668 | I-3 | II-78 | C-33 |
| T1b-1669 | I-3 | II-79 | C-33 |
| T1b-1670 | I-3 | II-80 | C-33 |
| T1b-1671 | I-3 | II-34 | C-33 |
| T1b-1672 | I-3 | II-81 | C-33 |
| T1b-1673 | I-3 | II-82 | C-33 |
| T1b-1674 | I-3 | II-83 | C-33 |
| T1b-1675 | I-3 | II-52 | C-33 |
| T1b-1676 | I-3 | II-84 | C-33 |
| T1b-1677 | I-3 | II-85 | C-33 |
| T1b-1678 | I-3 | II-86 | C-33 |
| T1b-1679 | I-3 | II-87 | C-33 |
| T1b-1680 | I-3 | II-88 | C-33 |
| T1b-1681 | I-3 | II-43 | C-33 |
| T1b-1682 | I-3 | II-89 | C-33 |
| T1b-1683 | I-3 | II-90 | C-33 |
| T1b-1684 | I-3 | II-56 | C-34 |
| T1b-1685 | I-3 | II-48 | C-34 |
| T1b-1686 | I-3 | II-57 | C-34 |
| T1b-1687 | I-3 | II-58 | C-34 |
| T1b-1688 | I-3 | II-59 | C-34 |
| T1b-1689 | I-3 | II-49 | C-34 |
| T1b-1690 | I-3 | II-60 | C-34 |
| T1b-1691 | I-3 | II-61 | C-34 |
| T1b-1692 | I-3 | II-62 | C-34 |
| T1b-1693 | I-3 | II-50 | C-34 |
| T1b-1694 | I-3 | II-63 | C-34 |
| T1b-1695 | I-3 | II-64 | C-34 |
| T1b-1696 | I-3 | II-65 | C-34 |
| T1b-1697 | I-3 | II-66 | C-34 |
| T1b-1698 | I-3 | II-51 | C-34 |
| T1b-1699 | I-3 | II-67 | C-34 |
| T1b-1700 | I-3 | II-68 | C-34 |
| T1b-1701 | I-3 | II-69 | C-34 |
| T1b-1702 | I-3 | II-53 | C-34 |
| T1b-1703 | I-3 | II-70 | C-34 |
| T1b-1704 | I-3 | II-54 | C-34 |
| T1b-1705 | I-3 | II-71 | C-34 |
| T1b-1706 | I-3 | II-55 | C-34 |
| T1b-1707 | I-3 | II-72 | C-34 |
| T1b-1708 | I-3 | II-73 | C-34 |
| T1b-1709 | I-3 | II-27 | C-34 |
| T1b-1710 | I-3 | II-44 | C-34 |
| T1b-1711 | I-3 | II-74 | C-34 |
| T1b-1712 | I-3 | II-28 | C-34 |
| T1b-1713 | I-3 | II-75 | C-34 |
| T1b-1714 | I-3 | II-29 | C-34 |
| T1b-1715 | I-3 | II-30 | C-34 |
| T1b-1716 | I-3 | II-31 | C-34 |
| T1b-1717 | I-3 | II-76 | C-34 |
| T1b-1718 | I-3 | II-77 | C-34 |
| T1b-1719 | I-3 | II-78 | C-34 |
| T1b-1720 | I-3 | II-79 | C-34 |
| T1b-1721 | I-3 | II-80 | C-34 |
| T1b-1722 | I-3 | II-34 | C-34 |
| T1b-1723 | I-3 | II-81 | C-34 |
| T1b-1724 | I-3 | II-82 | C-34 |
| T1b-1725 | I-3 | II-83 | C-34 |
| T1b-1726 | I-3 | II-52 | C-34 |
| T1b-1727 | I-3 | II-84 | C-34 |
| T1b-1728 | I-3 | II-85 | C-34 |
| T1b-1729 | I-3 | II-86 | C-34 |
| T1b-1730 | I-3 | II-87 | C-34 |
| T1b-1731 | I-3 | II-88 | C-34 |
| T1b-1732 | I-3 | II-43 | C-34 |
| T1b-1733 | I-3 | II-89 | C-34 |
| T1b-1734 | I-3 | II-90 | C-34 |
| T1b-1735 | I-3 | II-56 | C-35 |
| T1b-1736 | I-3 | II-48 | C-35 |
| T1b-1737 | I-3 | II-57 | C-35 |
| T1b-1738 | I-3 | II-58 | C-35 |
| T1b-1739 | I-3 | II-59 | C-35 |
| T1b-1740 | I-3 | II-49 | C-35 |
| T1b-1741 | I-3 | II-60 | C-35 |
| T1b-1742 | I-3 | II-61 | C-35 |
| T1b-1743 | I-3 | II-62 | C-35 |
| T1b-1744 | I-3 | II-50 | C-35 |
| T1b-1745 | I-3 | II-63 | C-35 |
| T1b-1746 | I-3 | II-64 | C-35 |
| T1b-1747 | I-3 | II-65 | C-35 |
| T1b-1748 | I-3 | II-66 | C-35 |
| T1b-1749 | I-3 | II-51 | C-35 |
| T1b-1750 | I-3 | II-67 | C-35 |
| T1b-1751 | I-3 | II-68 | C-35 |
| T1b-1752 | I-3 | II-69 | C-35 |
| T1b-1753 | I-3 | II-53 | C-35 |
| T1b-1754 | I-3 | II-70 | C-35 |
| T1b-1755 | I-3 | II-54 | C-35 |
| T1b-1756 | I-3 | II-71 | C-35 |
| T1b-1757 | I-3 | II-55 | C-35 |
| T1b-1758 | I-3 | II-72 | C-35 |
| T1b-1759 | I-3 | II-73 | C-35 |
| T1b-1760 | I-3 | II-27 | C-35 |
| T1b-1761 | I-3 | II-44 | C-35 |
| T1b-1762 | I-3 | II-74 | C-35 |
| T1b-1763 | I-3 | II-28 | C-35 |
| T1b-1764 | I-3 | II-75 | C-35 |
| T1b-1765 | I-3 | II-29 | C-35 |
| T1b-1766 | I-3 | II-30 | C-35 |
| T1b-1767 | I-3 | II-31 | C-35 |
| T1b-1768 | I-3 | II-76 | C-35 |
| T1b-1769 | I-3 | II-77 | C-35 |
| T1b-1770 | I-3 | II-78 | C-35 |
| T1b-1771 | I-3 | II-79 | C-35 |
| T1b-1772 | I-3 | II-80 | C-35 |
| T1b-1773 | I-3 | II-34 | C-35 |
| T1b-1774 | I-3 | II-81 | C-35 |
| T1b-1775 | I-3 | II-82 | C-35 |
| T1b-1776 | I-3 | II-83 | C-35 |
| T1b-1777 | I-3 | II-52 | C-35 |
| T1b-1778 | I-3 | II-84 | C-35 |
| T1b-1779 | I-3 | II-85 | C-35 |
| T1b-1780 | I-3 | II-86 | C-35 |
| T1b-1781 | I-3 | II-87 | C-35 |
| T1b-1782 | I-3 | II-88 | C-35 |
| T1b-1783 | I-3 | II-43 | C-35 |
| T1b-1784 | I-3 | II-89 | C-35 |
| T1b-1785 | I-3 | II-90 | C-35 |
| T1b-1786 | I-3 | II-56 | C-36 |
| T1b-1787 | I-3 | II-48 | C-36 |
| T1b-1788 | I-3 | II-57 | C-36 |
| T1b-1789 | I-3 | II-58 | C-36 |
| T1b-1790 | I-3 | II-59 | C-36 |
| T1b-1791 | I-3 | II-49 | C-36 |
| T1b-1792 | I-3 | II-60 | C-36 |
| T1b-1793 | I-3 | II-61 | C-36 |
| T1b-1794 | I-3 | II-62 | C-36 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-1795 | I-3 | II-50 | C-36 |
| T1b-1796 | I-3 | II-63 | C-36 |
| T1b-1797 | I-3 | II-64 | C-36 |
| T1b-1798 | I-3 | II-65 | C-36 |
| T1b-1799 | I-3 | II-66 | C-36 |
| T1b-1800 | I-3 | II-51 | C-36 |
| T1b-1801 | I-3 | II-67 | C-36 |
| T1b-1802 | I-3 | II-68 | C-36 |
| T1b-1803 | I-3 | II-69 | C-36 |
| T1b-1804 | I-3 | II-53 | C-36 |
| T1b-1805 | I-3 | II-70 | C-36 |
| T1b-1806 | I-3 | II-54 | C-36 |
| T1b-1807 | I-3 | II-71 | C-36 |
| T1b-1808 | I-3 | II-55 | C-36 |
| T1b-1809 | I-3 | II-72 | C-36 |
| T1b-1810 | I-3 | II-73 | C-36 |
| T1b-1811 | I-3 | II-27 | C-36 |
| T1b-1812 | I-3 | II-44 | C-36 |
| T1b-1813 | I-3 | II-74 | C-36 |
| T1b-1814 | I-3 | II-28 | C-36 |
| T1b-1815 | I-3 | II-75 | C-36 |
| T1b-1816 | I-3 | II-29 | C-36 |
| T1b-1817 | I-3 | II-30 | C-36 |
| T1b-1818 | I-3 | II-31 | C-36 |
| T1b-1819 | I-3 | II-76 | C-36 |
| T1b-1820 | I-3 | II-77 | C-36 |
| T1b-1821 | I-3 | II-78 | C-36 |
| T1b-1822 | I-3 | II-79 | C-36 |
| T1b-1823 | I-3 | II-80 | C-36 |
| T1b-1824 | I-3 | II-34 | C-36 |
| T1b-1825 | I-3 | II-81 | C-36 |
| T1b-1826 | I-3 | II-82 | C-36 |
| T1b-1827 | I-3 | II-83 | C-36 |
| T1b-1828 | I-3 | II-52 | C-36 |
| T1b-1829 | I-3 | II-84 | C-36 |
| T1b-1830 | I-3 | II-85 | C-36 |
| T1b-1831 | I-3 | II-86 | C-36 |
| T1b-1832 | I-3 | II-87 | C-36 |
| T1b-1833 | I-3 | II-88 | C-36 |
| T1b-1834 | I-3 | II-43 | C-36 |
| T1b-1835 | I-3 | II-89 | C-36 |
| T1b-1836 | I-3 | II-90 | C-36 |
| T1b-1837 | I-3 | II-56 | C-37 |
| T1b-1838 | I-3 | II-48 | C-37 |
| T1b-1839 | I-3 | II-57 | C-37 |
| T1b-1840 | I-3 | II-58 | C-37 |
| T1b-1841 | I-3 | II-59 | C-37 |
| T1b-1842 | I-3 | II-49 | C-37 |
| T1b-1843 | I-3 | II-60 | C-37 |
| T1b-1844 | I-3 | II-61 | C-37 |
| T1b-1845 | I-3 | II-62 | C-37 |
| T1b-1846 | I-3 | II-50 | C-37 |
| T1b-1847 | I-3 | II-63 | C-37 |
| T1b-1848 | I-3 | II-64 | C-37 |
| T1b-1849 | I-3 | II-65 | C-37 |
| T1b-1850 | I-3 | II-66 | C-37 |
| T1b-1851 | I-3 | II-51 | C-37 |
| T1b-1852 | I-3 | II-67 | C-37 |
| T1b-1853 | I-3 | II-68 | C-37 |
| T1b-1854 | I-3 | II-69 | C-37 |
| T1b-1855 | I-3 | II-53 | C-37 |
| T1b-1856 | I-3 | II-70 | C-37 |
| T1b-1857 | I-3 | II-54 | C-37 |
| T1b-1858 | I-3 | II-71 | C-37 |
| T1b-1859 | I-3 | II-55 | C-37 |
| T1b-1860 | I-3 | II-72 | C-37 |
| T1b-1861 | I-3 | II-73 | C-37 |
| T1b-1862 | I-3 | II-27 | C-37 |
| T1b-1863 | I-3 | II-44 | C-37 |
| T1b-1864 | I-3 | II-74 | C-37 |
| T1b-1865 | I-3 | II-28 | C-37 |
| T1b-1866 | I-3 | II-75 | C-37 |
| T1b-1867 | I-3 | II-29 | C-37 |
| T1b-1868 | I-3 | II-30 | C-37 |
| T1b-1869 | I-3 | II-31 | C-37 |
| T1b-1870 | I-3 | II-76 | C-37 |
| T1b-1871 | I-3 | II-77 | C-37 |
| T1b-1872 | I-3 | II-78 | C-37 |
| T1b-1873 | I-3 | II-79 | C-37 |
| T1b-1874 | I-3 | II-80 | C-37 |
| T1b-1875 | I-3 | II-34 | C-37 |
| T1b-1876 | I-3 | II-81 | C-37 |
| T1b-1877 | I-3 | II-82 | C-37 |
| T1b-1878 | I-3 | II-83 | C-37 |
| T1b-1879 | I-3 | II-52 | C-37 |
| T1b-1880 | I-3 | II-84 | C-37 |
| T1b-1881 | I-3 | II-85 | C-37 |
| T1b-1882 | I-3 | II-86 | C-37 |
| T1b-1883 | I-3 | II-87 | C-37 |
| T1b-1884 | I-3 | II-88 | C-37 |
| T1b-1885 | I-3 | II-43 | C-37 |
| T1b-1886 | I-3 | II-89 | C-37 |
| T1b-1887 | I-3 | II-90 | C-37 |
| T1b-1888 | I-3 | II-56 | C-38 |
| T1b-1889 | I-3 | II-48 | C-38 |
| T1b-1890 | I-3 | II-57 | C-38 |
| T1b-1891 | I-3 | II-58 | C-38 |
| T1b-1892 | I-3 | II-59 | C-38 |
| T1b-1893 | I-3 | II-49 | C-38 |
| T1b-1894 | I-3 | II-60 | C-38 |
| T1b-1895 | I-3 | II-61 | C-38 |
| T1b-1896 | I-3 | II-62 | C-38 |
| T1b-1897 | I-3 | II-50 | C-38 |
| T1b-1898 | I-3 | II-63 | C-38 |
| T1b-1899 | I-3 | II-64 | C-38 |
| T1b-1900 | I-3 | II-65 | C-38 |
| T1b-1901 | I-3 | II-66 | C-38 |
| T1b-1902 | I-3 | II-51 | C-38 |
| T1b-1903 | I-3 | II-67 | C-38 |
| T1b-1904 | I-3 | II-68 | C-38 |
| T1b-1905 | I-3 | II-69 | C-38 |
| T1b-1906 | I-3 | II-53 | C-38 |
| T1b-1907 | I-3 | II-70 | C-38 |
| T1b-1908 | I-3 | II-54 | C-38 |
| T1b-1909 | I-3 | II-71 | C-38 |
| T1b-1910 | I-3 | II-55 | C-38 |
| T1b-1911 | I-3 | II-72 | C-38 |
| T1b-1912 | I-3 | II-73 | C-38 |
| T1b-1913 | I-3 | II-27 | C-38 |
| T1b-1914 | I-3 | II-44 | C-38 |
| T1b-1915 | I-3 | II-74 | C-38 |
| T1b-1916 | I-3 | II-28 | C-38 |
| T1b-1917 | I-3 | II-75 | C-38 |
| T1b-1918 | I-3 | II-29 | C-38 |
| T1b-1919 | I-3 | II-30 | C-38 |
| T1b-1920 | I-3 | II-31 | C-38 |
| T1b-1921 | I-3 | II-76 | C-38 |
| T1b-1922 | I-3 | II-77 | C-38 |
| T1b-1923 | I-3 | II-78 | C-38 |
| T1b-1924 | I-3 | II-79 | C-38 |
| T1b-1925 | I-3 | II-80 | C-38 |
| T1b-1926 | I-3 | II-34 | C-38 |
| T1b-1927 | I-3 | II-81 | C-38 |
| T1b-1928 | I-3 | II-82 | C-38 |
| T1b-1929 | I-3 | II-83 | C-38 |
| T1b-1930 | I-3 | II-52 | C-38 |
| T1b-1931 | I-3 | II-84 | C-38 |
| T1b-1932 | I-3 | II-85 | C-38 |
| T1b-1933 | I-3 | II-86 | C-38 |
| T1b-1934 | I-3 | II-87 | C-38 |
| T1b-1935 | I-3 | II-88 | C-38 |
| T1b-1936 | I-3 | II-43 | C-38 |
| T1b-1937 | I-3 | II-89 | C-38 |
| T1b-1938 | I-3 | II-90 | C-38 |
| T1b-1939 | I-3 | II-56 | C-39 |
| T1b-1940 | I-3 | II-48 | C-39 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-1941 | I-3 | II-57 | C-39 |
| T1b-1942 | I-3 | II-58 | C-39 |
| T1b-1943 | I-3 | II-59 | C-39 |
| T1b-1944 | I-3 | II-49 | C-39 |
| T1b-1945 | I-3 | II-60 | C-39 |
| T1b-1946 | I-3 | II-61 | C-39 |
| T1b-1947 | I-3 | II-62 | C-39 |
| T1b-1948 | I-3 | II-50 | C-39 |
| T1b-1949 | I-3 | II-63 | C-39 |
| T1b-1950 | I-3 | II-64 | C-39 |
| T1b-1951 | I-3 | II-65 | C-39 |
| T1b-1952 | I-3 | II-66 | C-39 |
| T1b-1953 | I-3 | II-51 | C-39 |
| T1b-1954 | I-3 | II-67 | C-39 |
| T1b-1955 | I-3 | II-68 | C-39 |
| T1b-1956 | I-3 | II-69 | C-39 |
| T1b-1957 | I-3 | II-53 | C-39 |
| T1b-1958 | I-3 | II-70 | C-39 |
| T1b-1959 | I-3 | II-54 | C-39 |
| T1b-1960 | I-3 | II-71 | C-39 |
| T1b-1961 | I-3 | II-55 | C-39 |
| T1b-1962 | I-3 | II-72 | C-39 |
| T1b-1963 | I-3 | II-73 | C-39 |
| T1b-1964 | I-3 | II-27 | C-39 |
| T1b-1965 | I-3 | II-44 | C-39 |
| T1b-1966 | I-3 | II-74 | C-39 |
| T1b-1967 | I-3 | II-28 | C-39 |
| T1b-1968 | I-3 | II-75 | C-39 |
| T1b-1969 | I-3 | II-29 | C-39 |
| T1b-1970 | I-3 | II-30 | C-39 |
| T1b-1971 | I-3 | II-31 | C-39 |
| T1b-1972 | I-3 | II-76 | C-39 |
| T1b-1973 | I-3 | II-77 | C-39 |
| T1b-1974 | I-3 | II-78 | C-39 |
| T1b-1975 | I-3 | II-79 | C-39 |
| T1b-1976 | I-3 | II-80 | C-39 |
| T1b-1977 | I-3 | II-34 | C-39 |
| T1b-1978 | I-3 | II-81 | C-39 |
| T1b-1979 | I-3 | II-82 | C-39 |
| T1b-1980 | I-3 | II-83 | C-39 |
| T1b-1981 | I-3 | II-52 | C-39 |
| T1b-1982 | I-3 | II-84 | C-39 |
| T1b-1983 | I-3 | II-85 | C-39 |
| T1b-1984 | I-3 | II-86 | C-39 |
| T1b-1985 | I-3 | II-87 | C-39 |
| T1b-1986 | I-3 | II-88 | C-39 |
| T1b-1987 | I-3 | II-43 | C-39 |
| T1b-1988 | I-3 | II-89 | C-39 |
| T1b-1989 | I-3 | II-90 | C-39 |
| T1b-1990 | I-3 | II-56 | C-40 |
| T1b-1991 | I-3 | II-48 | C-40 |
| T1b-1992 | I-3 | II-57 | C-40 |
| T1b-1993 | I-3 | II-58 | C-40 |
| T1b-1994 | I-3 | II-59 | C-40 |
| T1b-1995 | I-3 | II-49 | C-40 |
| T1b-1996 | I-3 | II-60 | C-40 |
| T1b-1997 | I-3 | II-61 | C-40 |
| T1b-1998 | I-3 | II-62 | C-40 |
| T1b-1999 | I-3 | II-50 | C-40 |
| T1b-2000 | I-3 | II-63 | C-40 |
| T1b-2001 | I-3 | II-64 | C-40 |
| T1b-2002 | I-3 | II-65 | C-40 |
| T1b-2003 | I-3 | II-66 | C-40 |
| T1b-2004 | I-3 | II-51 | C-40 |
| T1b-2005 | I-3 | II-67 | C-40 |
| T1b-2006 | I-3 | II-68 | C-40 |
| T1b-2007 | I-3 | II-69 | C-40 |
| T1b-2008 | I-3 | II-53 | C-40 |
| T1b-2009 | I-3 | II-70 | C-40 |
| T1b-2010 | I-3 | II-54 | C-40 |
| T1b-2011 | I-3 | II-71 | C-40 |
| T1b-2012 | I-3 | II-55 | C-40 |
| T1b-2013 | I-3 | II-72 | C-40 |
| T1b-2014 | I-3 | II-73 | C-40 |
| T1b-2015 | I-3 | II-27 | C-40 |
| T1b-2016 | I-3 | II-44 | C-40 |
| T1b-2017 | I-3 | II-74 | C-40 |
| T1b-2018 | I-3 | II-28 | C-40 |
| T1b-2019 | I-3 | II-75 | C-40 |
| T1b-2020 | I-3 | II-29 | C-40 |
| T1b-2021 | I-3 | II-30 | C-40 |
| T1b-2022 | I-3 | II-31 | C-40 |
| T1b-2023 | I-3 | II-76 | C-40 |
| T1b-2024 | I-3 | II-77 | C-40 |
| T1b-2025 | I-3 | II-78 | C-40 |
| T1b-2026 | I-3 | II-79 | C-40 |
| T1b-2027 | I-3 | II-80 | C-40 |
| T1b-2028 | I-3 | II-34 | C-40 |
| T1b-2029 | I-3 | II-81 | C-40 |
| T1b-2030 | I-3 | II-82 | C-40 |
| T1b-2031 | I-3 | II-83 | C-40 |
| T1b-2032 | I-3 | II-52 | C-40 |
| T1b-2033 | I-3 | II-84 | C-40 |
| T1b-2034 | I-3 | II-85 | C-40 |
| T1b-2035 | I-3 | II-86 | C-40 |
| T1b-2036 | I-3 | II-87 | C-40 |
| T1b-2037 | I-3 | II-88 | C-40 |
| T1b-2038 | I-3 | II-43 | C-40 |
| T1b-2039 | I-3 | II-89 | C-40 |
| T1b-2040 | I-3 | II-90 | C-40 |
| T1b-2041 | I-3 | II-56 | C-41 |
| T1b-2042 | I-3 | II-48 | C-41 |
| T1b-2043 | I-3 | II-57 | C-41 |
| T1b-2044 | I-3 | II-58 | C-41 |
| T1b-2045 | I-3 | II-59 | C-41 |
| T1b-2046 | I-3 | II-49 | C-41 |
| T1b-2047 | I-3 | II-60 | C-41 |
| T1b-2048 | I-3 | II-61 | C-41 |
| T1b-2049 | I-3 | II-62 | C-41 |
| T1b-2050 | I-3 | II-50 | C-41 |
| T1b-2051 | I-3 | II-63 | C-41 |
| T1b-2052 | I-3 | II-64 | C-41 |
| T1b-2053 | I-3 | II-65 | C-41 |
| T1b-2054 | I-3 | II-66 | C-41 |
| T1b-2055 | I-3 | II-51 | C-41 |
| T1b-2056 | I-3 | II-67 | C-41 |
| T1b-2057 | I-3 | II-68 | C-41 |
| T1b-2058 | I-3 | II-69 | C-41 |
| T1b-2059 | I-3 | II-53 | C-41 |
| T1b-2060 | I-3 | II-70 | C-41 |
| T1b-2061 | I-3 | II-54 | C-41 |
| T1b-2062 | I-3 | II-71 | C-41 |
| T1b-2063 | I-3 | II-55 | C-41 |
| T1b-2064 | I-3 | II-72 | C-41 |
| T1b-2065 | I-3 | II-73 | C-41 |
| T1b-2066 | I-3 | II-27 | C-41 |
| T1b-2067 | I-3 | II-44 | C-41 |
| T1b-2068 | I-3 | II-74 | C-41 |
| T1b-2069 | I-3 | II-28 | C-41 |
| T1b-2070 | I-3 | II-75 | C-41 |
| T1b-2071 | I-3 | II-29 | C-41 |
| T1b-2072 | I-3 | II-30 | C-41 |
| T1b-2073 | I-3 | II-31 | C-41 |
| T1b-2074 | I-3 | II-76 | C-41 |
| T1b-2075 | I-3 | II-77 | C-41 |
| T1b-2076 | I-3 | II-78 | C-41 |
| T1b-2077 | I-3 | II-79 | C-41 |
| T1b-2078 | I-3 | II-80 | C-41 |
| T1b-2079 | I-3 | II-34 | C-41 |
| T1b-2080 | I-3 | II-81 | C-41 |
| T1b-2081 | I-3 | II-82 | C-41 |
| T1b-2082 | I-3 | II-83 | C-41 |
| T1b-2083 | I-3 | II-52 | C-41 |
| T1b-2084 | I-3 | II-84 | C-41 |
| T1b-2085 | I-3 | II-85 | C-41 |
| T1b-2086 | I-3 | II-86 | C-41 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-2087 | I-3 | II-87 | C-41 |
| T1b-2088 | I-3 | II-88 | C-41 |
| T1b-2089 | I-3 | II-43 | C-41 |
| T1b-2090 | I-3 | II-89 | C-41 |
| T1b-2091 | I-3 | II-90 | C-41 |
| T1b-2092 | I-3 | II-56 | C-42 |
| T1b-2093 | I-3 | II-48 | C-42 |
| T1b-2094 | I-3 | II-57 | C-42 |
| T1b-2095 | I-3 | II-58 | C-42 |
| T1b-2096 | I-3 | II-59 | C-42 |
| T1b-2097 | I-3 | II-49 | C-42 |
| T1b-2098 | I-3 | II-60 | C-42 |
| T1b-2099 | I-3 | II-61 | C-42 |
| T1b-2100 | I-3 | II-62 | C-42 |
| T1b-2101 | I-3 | II-50 | C-42 |
| T1b-2102 | I-3 | II-63 | C-42 |
| T1b-2103 | I-3 | II-64 | C-42 |
| T1b-2104 | I-3 | II-65 | C-42 |
| T1b-2105 | I-3 | II-66 | C-42 |
| T1b-2106 | I-3 | II-51 | C-42 |
| T1b-2107 | I-3 | II-67 | C-42 |
| T1b-2108 | I-3 | II-68 | C-42 |
| T1b-2109 | I-3 | II-69 | C-42 |
| T1b-2110 | I-3 | II-53 | C-42 |
| T1b-2111 | I-3 | II-70 | C-42 |
| T1b-2112 | I-3 | II-54 | C-42 |
| T1b-2113 | I-3 | II-71 | C-42 |
| T1b-2114 | I-3 | II-55 | C-42 |
| T1b-2115 | I-3 | II-72 | C-42 |
| T1b-2116 | I-3 | II-73 | C-42 |
| T1b-2117 | I-3 | II-27 | C-42 |
| T1b-2118 | I-3 | II-44 | C-42 |
| T1b-2119 | I-3 | II-74 | C-42 |
| T1b-2120 | I-3 | II-28 | C-42 |
| T1b-2121 | I-3 | II-75 | C-42 |
| T1b-2122 | I-3 | II-29 | C-42 |
| T1b-2123 | I-3 | II-30 | C-42 |
| T1b-2124 | I-3 | II-31 | C-42 |
| T1b-2125 | I-3 | II-76 | C-42 |
| T1b-2126 | I-3 | II-77 | C-42 |
| T1b-2127 | I-3 | II-78 | C-42 |
| T1b-2128 | I-3 | II-79 | C-42 |
| T1b-2129 | I-3 | II-80 | C-42 |
| T1b-2130 | I-3 | II-34 | C-42 |
| T1b-2131 | I-3 | II-81 | C-42 |
| T1b-2132 | I-3 | II-82 | C-42 |
| T1b-2133 | I-3 | II-83 | C-42 |
| T1b-2134 | I-3 | II-52 | C-42 |
| T1b-2135 | I-3 | II-84 | C-42 |
| T1b-2136 | I-3 | II-85 | C-42 |
| T1b-2137 | I-3 | II-86 | C-42 |
| T1b-2138 | I-3 | II-87 | C-42 |
| T1b-2139 | I-3 | II-88 | C-42 |
| T1b-2140 | I-3 | II-43 | C-42 |
| T1b-2141 | I-3 | II-89 | C-42 |
| T1b-2142 | I-3 | II-90 | C-42 |
| T1b-2143 | I-3 | II-56 | C-43 |
| T1b-2144 | I-3 | II-48 | C-43 |
| T1b-2145 | I-3 | II-57 | C-43 |
| T1b-2146 | I-3 | II-58 | C-43 |
| T1b-2147 | I-3 | II-59 | C-43 |
| T1b-2148 | I-3 | II-49 | C-43 |
| T1b-2149 | I-3 | II-60 | C-43 |
| T1b-2150 | I-3 | II-61 | C-43 |
| T1b-2151 | I-3 | II-62 | C-43 |
| T1b-2152 | I-3 | II-50 | C-43 |
| T1b-2153 | I-3 | II-63 | C-43 |
| T1b-2154 | I-3 | II-64 | C-43 |
| T1b-2155 | I-3 | II-65 | C-43 |
| T1b-2156 | I-3 | II-66 | C-43 |
| T1b-2157 | I-3 | II-51 | C-43 |
| T1b-2158 | I-3 | II-67 | C-43 |
| T1b-2159 | I-3 | II-68 | C-43 |
| T1b-2160 | I-3 | II-69 | C-43 |
| T1b-2161 | I-3 | II-53 | C-43 |
| T1b-2162 | I-3 | II-70 | C-43 |
| T1b-2163 | I-3 | II-54 | C-43 |
| T1b-2164 | I-3 | II-71 | C-43 |
| T1b-2165 | I-3 | II-55 | C-43 |
| T1b-2166 | I-3 | II-72 | C-43 |
| T1b-2167 | I-3 | II-73 | C-43 |
| T1b-2168 | I-3 | II-27 | C-43 |
| T1b-2169 | I-3 | II-44 | C-43 |
| T1b-2170 | I-3 | II-74 | C-43 |
| T1b-2171 | I-3 | II-28 | C-43 |
| T1b-2172 | I-3 | II-75 | C-43 |
| T1b-2173 | I-3 | II-29 | C-43 |
| T1b-2174 | I-3 | II-30 | C-43 |
| T1b-2175 | I-3 | II-31 | C-43 |
| T1b-2176 | I-3 | II-76 | C-43 |
| T1b-2177 | I-3 | II-77 | C-43 |
| T1b-2178 | I-3 | II-78 | C-43 |
| T1b-2179 | I-3 | II-79 | C-43 |
| T1b-2180 | I-3 | II-80 | C-43 |
| T1b-2181 | I-3 | II-34 | C-43 |
| T1b-2182 | I-3 | II-81 | C-43 |
| T1b-2183 | I-3 | II-82 | C-43 |
| T1b-2184 | I-3 | II-83 | C-43 |
| T1b-2185 | I-3 | II-52 | C-43 |
| T1b-2186 | I-3 | II-84 | C-43 |
| T1b-2187 | I-3 | II-85 | C-43 |
| T1b-2188 | I-3 | II-86 | C-43 |
| T1b-2189 | I-3 | II-87 | C-43 |
| T1b-2190 | I-3 | II-88 | C-43 |
| T1b-2191 | I-3 | II-43 | C-43 |
| T1b-2192 | I-3 | II-89 | C-43 |
| T1b-2193 | I-3 | II-90 | C-43 |
| T1b-2194 | I-3 | II-56 | C-44 |
| T1b-2195 | I-3 | II-48 | C-44 |
| T1b-2196 | I-3 | II-57 | C-44 |
| T1b-2197 | I-3 | II-58 | C-44 |
| T1b-2198 | I-3 | II-59 | C-44 |
| T1b-2199 | I-3 | II-49 | C-44 |
| T1b-2200 | I-3 | II-60 | C-44 |
| T1b-2201 | I-3 | II-61 | C-44 |
| T1b-2202 | I-3 | II-62 | C-44 |
| T1b-2203 | I-3 | II-50 | C-44 |
| T1b-2204 | I-3 | II-63 | C-44 |
| T1b-2205 | I-3 | II-64 | C-44 |
| T1b-2206 | I-3 | II-65 | C-44 |
| T1b-2207 | I-3 | II-66 | C-44 |
| T1b-2208 | I-3 | II-51 | C-44 |
| T1b-2209 | I-3 | II-67 | C-44 |
| T1b-2210 | I-3 | II-68 | C-44 |
| T1b-2211 | I-3 | II-69 | C-44 |
| T1b-2212 | I-3 | II-53 | C-44 |
| T1b-2213 | I-3 | II-70 | C-44 |
| T1b-2214 | I-3 | II-54 | C-44 |
| T1b-2215 | I-3 | II-71 | C-44 |
| T1b-2216 | I-3 | II-55 | C-44 |
| T1b-2217 | I-3 | II-72 | C-44 |
| T1b-2218 | I-3 | II-73 | C-44 |
| T1b-2219 | I-3 | II-27 | C-44 |
| T1b-2220 | I-3 | II-44 | C-44 |
| T1b-2221 | I-3 | II-74 | C-44 |
| T1b-2222 | I-3 | II-28 | C-44 |
| T1b-2223 | I-3 | II-75 | C-44 |
| T1b-2224 | I-3 | II-29 | C-44 |
| T1b-2225 | I-3 | II-30 | C-44 |
| T1b-2226 | I-3 | II-31 | C-44 |
| T1b-2227 | I-3 | II-76 | C-44 |
| T1b-2228 | I-3 | II-77 | C-44 |
| T1b-2229 | I-3 | II-78 | C-44 |
| T1b-2230 | I-3 | II-79 | C-44 |
| T1b-2231 | I-3 | II-80 | C-44 |
| T1b-2232 | I-3 | II-34 | C-44 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-2233 | I-3 | II-81 | C-44 |
| T1b-2234 | I-3 | II-82 | C-44 |
| T1b-2235 | I-3 | II-83 | C-44 |
| T1b-2236 | I-3 | II-52 | C-44 |
| T1b-2237 | I-3 | II-84 | C-44 |
| T1b-2238 | I-3 | II-85 | C-44 |
| T1b-2239 | I-3 | II-86 | C-44 |
| T1b-2240 | I-3 | II-87 | C-44 |
| T1b-2241 | I-3 | II-88 | C-44 |
| T1b-2242 | I-3 | II-43 | C-44 |
| T1b-2243 | I-3 | II-89 | C-44 |
| T1b-2244 | I-3 | II-90 | C-44 |
| T1b-2245 | I-3 | II-56 | C-45 |
| T1b-2246 | I-3 | II-48 | C-45 |
| T1b-2247 | I-3 | II-57 | C-45 |
| T1b-2248 | I-3 | II-58 | C-45 |
| T1b-2249 | I-3 | II-59 | C-45 |
| T1b-2250 | I-3 | II-49 | C-45 |
| T1b-2251 | I-3 | II-60 | C-45 |
| T1b-2252 | I-3 | II-61 | C-45 |
| T1b-2253 | I-3 | II-62 | C-45 |
| T1b-2254 | I-3 | II-50 | C-45 |
| T1b-2255 | I-3 | II-63 | C-45 |
| T1b-2256 | I-3 | II-64 | C-45 |
| T1b-2257 | I-3 | II-65 | C-45 |
| T1b-2258 | I-3 | II-66 | C-45 |
| T1b-2259 | I-3 | II-51 | C-45 |
| T1b-2260 | I-3 | II-67 | C-45 |
| T1b-2261 | I-3 | II-68 | C-45 |
| T1b-2262 | I-3 | II-69 | C-45 |
| T1b-2263 | I-3 | II-53 | C-45 |
| T1b-2264 | I-3 | II-70 | C-45 |
| T1b-2265 | I-3 | II-54 | C-45 |
| T1b-2266 | I-3 | II-71 | C-45 |
| T1b-2267 | I-3 | II-55 | C-45 |
| T1b-2268 | I-3 | II-72 | C-45 |
| T1b-2269 | I-3 | II-73 | C-45 |
| T1b-2270 | I-3 | II-27 | C-45 |
| T1b-2271 | I-3 | II-44 | C-45 |
| T1b-2272 | I-3 | II-74 | C-45 |
| T1b-2273 | I-3 | II-28 | C-45 |
| T1b-2274 | I-3 | II-75 | C-45 |
| T1b-2275 | I-3 | II-29 | C-45 |
| T1b-2276 | I-3 | II-30 | C-45 |
| T1b-2277 | I-3 | II-31 | C-45 |
| T1b-2278 | I-3 | II-76 | C-45 |
| T1b-2279 | I-3 | II-77 | C-45 |
| T1b-2280 | I-3 | II-78 | C-45 |
| T1b-2281 | I-3 | II-79 | C-45 |
| T1b-2282 | I-3 | II-80 | C-45 |
| T1b-2283 | I-3 | II-34 | C-45 |
| T1b-2284 | I-3 | II-81 | C-45 |
| T1b-2285 | I-3 | II-82 | C-45 |
| T1b-2286 | I-3 | II-83 | C-45 |
| T1b-2287 | I-3 | II-52 | C-45 |
| T1b-2288 | I-3 | II-84 | C-45 |
| T1b-2289 | I-3 | II-85 | C-45 |
| T1b-2290 | I-3 | II-86 | C-45 |
| T1b-2291 | I-3 | II-87 | C-45 |
| T1b-2292 | I-3 | II-88 | C-45 |
| T1b-2293 | I-3 | II-43 | C-45 |
| T1b-2294 | I-3 | II-89 | C-45 |
| T1b-2295 | I-3 | II-90 | C-45 |
| T1b-2296 | I-3 | II-56 | C-46 |
| T1b-2297 | I-3 | II-48 | C-46 |
| T1b-2298 | I-3 | II-57 | C-46 |
| T1b-2299 | I-3 | II-58 | C-46 |
| T1b-2300 | I-3 | II-59 | C-46 |
| T1b-2301 | I-3 | II-49 | C-46 |
| T1b-2302 | I-3 | II-60 | C-46 |
| T1b-2303 | I-3 | II-61 | C-46 |
| T1b-2304 | I-3 | II-62 | C-46 |
| T1b-2305 | I-3 | II-50 | C-46 |
| T1b-2306 | I-3 | II-63 | C-46 |
| T1b-2307 | I-3 | II-64 | C-46 |
| T1b-2308 | I-3 | II-65 | C-46 |
| T1b-2309 | I-3 | II-66 | C-46 |
| T1b-2310 | I-3 | II-51 | C-46 |
| T1b-2311 | I-3 | II-67 | C-46 |
| T1b-2312 | I-3 | II-68 | C-46 |
| T1b-2313 | I-3 | II-69 | C-46 |
| T1b-2314 | I-3 | II-53 | C-46 |
| T1b-2315 | I-3 | II-70 | C-46 |
| T1b-2316 | I-3 | II-54 | C-46 |
| T1b-2317 | I-3 | II-71 | C-46 |
| T1b-2318 | I-3 | II-55 | C-46 |
| T1b-2319 | I-3 | II-72 | C-46 |
| T1b-2320 | I-3 | II-73 | C-46 |
| T1b-2321 | I-3 | II-27 | C-46 |
| T1b-2322 | I-3 | II-44 | C-46 |
| T1b-2323 | I-3 | II-74 | C-46 |
| T1b-2324 | I-3 | II-28 | C-46 |
| T1b-2325 | I-3 | II-75 | C-46 |
| T1b-2326 | I-3 | II-29 | C-46 |
| T1b-2327 | I-3 | II-30 | C-46 |
| T1b-2328 | I-3 | II-31 | C-46 |
| T1b-2329 | I-3 | II-76 | C-46 |
| T1b-2330 | I-3 | II-77 | C-46 |
| T1b-2331 | I-3 | II-78 | C-46 |
| T1b-2332 | I-3 | II-79 | C-46 |
| T1b-2333 | I-3 | II-80 | C-46 |
| T1b-2334 | I-3 | II-34 | C-46 |
| T1b-2335 | I-3 | II-81 | C-46 |
| T1b-2336 | I-3 | II-82 | C-46 |
| T1b-2337 | I-3 | II-83 | C-46 |
| T1b-2338 | I-3 | II-52 | C-46 |
| T1b-2339 | I-3 | II-84 | C-46 |
| T1b-2340 | I-3 | II-85 | C-46 |
| T1b-2341 | I-3 | II-86 | C-46 |
| T1b-2342 | I-3 | II-87 | C-46 |
| T1b-2343 | I-3 | II-88 | C-46 |
| T1b-2344 | I-3 | II-43 | C-46 |
| T1b-2345 | I-3 | II-89 | C-46 |
| T1b-2346 | I-3 | II-90 | C-46 |
| T1b-2347 | I-3 | II-56 | C-47 |
| T1b-2348 | I-3 | II-48 | C-47 |
| T1b-2349 | I-3 | II-57 | C-47 |
| T1b-2350 | I-3 | II-58 | C-47 |
| T1b-2351 | I-3 | II-59 | C-47 |
| T1b-2352 | I-3 | II-49 | C-47 |
| T1b-2353 | I-3 | II-60 | C-47 |
| T1b-2354 | I-3 | II-61 | C-47 |
| T1b-2355 | I-3 | II-62 | C-47 |
| T1b-2356 | I-3 | II-50 | C-47 |
| T1b-2357 | I-3 | II-63 | C-47 |
| T1b-2358 | I-3 | II-64 | C-47 |
| T1b-2359 | I-3 | II-65 | C-47 |
| T1b-2360 | I-3 | II-66 | C-47 |
| T1b-2361 | I-3 | II-51 | C-47 |
| T1b-2362 | I-3 | II-67 | C-47 |
| T1b-2363 | I-3 | II-68 | C-47 |
| T1b-2364 | I-3 | II-69 | C-47 |
| T1b-2365 | I-3 | II-53 | C-47 |
| T1b-2366 | I-3 | II-70 | C-47 |
| T1b-2367 | I-3 | II-54 | C-47 |
| T1b-2368 | I-3 | II-71 | C-47 |
| T1b-2369 | I-3 | II-55 | C-47 |
| T1b-2370 | I-3 | II-72 | C-47 |
| T1b-2371 | I-3 | II-73 | C-47 |
| T1b-2372 | I-3 | II-27 | C-47 |
| T1b-2373 | I-3 | II-44 | C-47 |
| T1b-2374 | I-3 | II-74 | C-47 |
| T1b-2375 | I-3 | II-28 | C-47 |
| T1b-2376 | I-3 | II-75 | C-47 |
| T1b-2377 | I-3 | II-29 | C-47 |
| T1b-2378 | I-3 | II-30 | C-47 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-2379 | I-3 | II-31 | C-47 |
| T1b-2380 | I-3 | II-76 | C-47 |
| T1b-2381 | I-3 | II-77 | C-47 |
| T1b-2382 | I-3 | II-78 | C-47 |
| T1b-2383 | I-3 | II-79 | C-47 |
| T1b-2384 | I-3 | II-80 | C-47 |
| T1b-2385 | I-3 | II-34 | C-47 |
| T1b-2386 | I-3 | II-81 | C-47 |
| T1b-2387 | I-3 | II-82 | C-47 |
| T1b-2388 | I-3 | II-83 | C-47 |
| T1b-2389 | I-3 | II-52 | C-47 |
| T1b-2390 | I-3 | II-84 | C-47 |
| T1b-2391 | I-3 | II-85 | C-47 |
| T1b-2392 | I-3 | II-86 | C-47 |
| T1b-2393 | I-3 | II-87 | C-47 |
| T1b-2394 | I-3 | II-88 | C-47 |
| T1b-2395 | I-3 | II-43 | C-47 |
| T1b-2396 | I-3 | II-89 | C-47 |
| T1b-2397 | I-3 | II-90 | C-47 |
| T1b-2398 | I-3 | II-56 | C-48 |
| T1b-2399 | I-3 | II-48 | C-48 |
| T1b-2400 | I-3 | II-57 | C-48 |
| T1b-2401 | I-3 | II-58 | C-48 |
| T1b-2402 | I-3 | II-59 | C-48 |
| T1b-2403 | I-3 | II-49 | C-48 |
| T1b-2404 | I-3 | II-60 | C-48 |
| T1b-2405 | I-3 | II-61 | C-48 |
| T1b-2406 | I-3 | II-62 | C-48 |
| T1b-2407 | I-3 | II-50 | C-48 |
| T1b-2408 | I-3 | II-63 | C-48 |
| T1b-2409 | I-3 | II-64 | C-48 |
| T1b-2410 | I-3 | II-65 | C-48 |
| T1b-2411 | I-3 | II-66 | C-48 |
| T1b-2412 | I-3 | II-51 | C-48 |
| T1b-2413 | I-3 | II-67 | C-48 |
| T1b-2414 | I-3 | II-68 | C-48 |
| T1b-2415 | I-3 | II-69 | C-48 |
| T1b-2416 | I-3 | II-53 | C-48 |
| T1b-2417 | I-3 | II-70 | C-48 |
| T1b-2418 | I-3 | II-54 | C-48 |
| T1b-2419 | I-3 | II-71 | C-48 |
| T1b-2420 | I-3 | II-55 | C-48 |
| T1b-2421 | I-3 | II-72 | C-48 |
| T1b-2422 | I-3 | II-73 | C-48 |
| T1b-2423 | I-3 | II-27 | C-48 |
| T1b-2424 | I-3 | II-44 | C-48 |
| T1b-2425 | I-3 | II-74 | C-48 |
| T1b-2426 | I-3 | II-28 | C-48 |
| T1b-2427 | I-3 | II-75 | C-48 |
| T1b-2428 | I-3 | II-29 | C-48 |
| T1b-2429 | I-3 | II-30 | C-48 |
| T1b-2430 | I-3 | II-31 | C-48 |
| T1b-2431 | I-3 | II-76 | C-48 |
| T1b-2432 | I-3 | II-77 | C-48 |
| T1b-2433 | I-3 | II-78 | C-48 |
| T1b-2434 | I-3 | II-79 | C-48 |
| T1b-2435 | I-3 | II-80 | C-48 |
| T1b-2436 | I-3 | II-34 | C-48 |
| T1b-2437 | I-3 | II-81 | C-48 |
| T1b-2438 | I-3 | II-82 | C-48 |
| T1b-2439 | I-3 | II-83 | C-48 |
| T1b-2440 | I-3 | II-52 | C-48 |
| T1b-2441 | I-3 | II-84 | C-48 |
| T1b-2442 | I-3 | II-85 | C-48 |
| T1b-2443 | I-3 | II-86 | C-48 |
| T1b-2444 | I-3 | II-87 | C-48 |
| T1b-2445 | I-3 | II-88 | C-48 |
| T1b-2446 | I-3 | II-43 | C-48 |
| T1b-2447 | I-3 | II-89 | C-48 |
| T1b-2448 | I-3 | II-90 | C-48 |
| T1b-2449 | I-3 | II-56 | C-49 |
| T1b-2450 | I-3 | II-48 | C-49 |
| T1b-2451 | I-3 | II-57 | C-49 |
| T1b-2452 | I-3 | II-58 | C-49 |
| T1b-2453 | I-3 | II-59 | C-49 |
| T1b-2454 | I-3 | II-49 | C-49 |
| T1b-2455 | I-3 | II-60 | C-49 |
| T1b-2456 | I-3 | II-61 | C-49 |
| T1b-2457 | I-3 | II-62 | C-49 |
| T1b-2458 | I-3 | II-50 | C-49 |
| T1b-2459 | I-3 | II-63 | C-49 |
| T1b-2460 | I-3 | II-64 | C-49 |
| T1b-2461 | I-3 | II-65 | C-49 |
| T1b-2462 | I-3 | II-66 | C-49 |
| T1b-2463 | I-3 | II-51 | C-49 |
| T1b-2464 | I-3 | II-67 | C-49 |
| T1b-2465 | I-3 | II-68 | C-49 |
| T1b-2466 | I-3 | II-69 | C-49 |
| T1b-2467 | I-3 | II-53 | C-49 |
| T1b-2468 | I-3 | II-70 | C-49 |
| T1b-2469 | I-3 | II-54 | C-49 |
| T1b-2470 | I-3 | II-71 | C-49 |
| T1b-2471 | I-3 | II-55 | C-49 |
| T1b-2472 | I-3 | II-72 | C-49 |
| T1b-2473 | I-3 | II-73 | C-49 |
| T1b-2474 | I-3 | II-27 | C-49 |
| T1b-2475 | I-3 | II-44 | C-49 |
| T1b-2476 | I-3 | II-74 | C-49 |
| T1b-2477 | I-3 | II-28 | C-49 |
| T1b-2478 | I-3 | II-75 | C-49 |
| T1b-2479 | I-3 | II-29 | C-49 |
| T1b-2480 | I-3 | II-30 | C-49 |
| T1b-2481 | I-3 | II-31 | C-49 |
| T1b-2482 | I-3 | II-76 | C-49 |
| T1b-2483 | I-3 | II-77 | C-49 |
| T1b-2484 | I-3 | II-78 | C-49 |
| T1b-2485 | I-3 | II-79 | C-49 |
| T1b-2486 | I-3 | II-80 | C-49 |
| T1b-2487 | I-3 | II-34 | C-49 |
| T1b-2488 | I-3 | II-81 | C-49 |
| T1b-2489 | I-3 | II-82 | C-49 |
| T1b-2490 | I-3 | II-83 | C-49 |
| T1b-2491 | I-3 | II-52 | C-49 |
| T1b-2492 | I-3 | II-84 | C-49 |
| T1b-2493 | I-3 | II-85 | C-49 |
| T1b-2494 | I-3 | II-86 | C-49 |
| T1b-2495 | I-3 | II-87 | C-49 |
| T1b-2496 | I-3 | II-88 | C-49 |
| T1b-2497 | I-3 | II-43 | C-49 |
| T1b-2498 | I-3 | II-89 | C-49 |
| T1b-2499 | I-3 | II-90 | C-49 |
| T1b-2500 | I-3 | II-56 | C-50 |
| T1b-2501 | I-3 | II-48 | C-50 |
| T1b-2502 | I-3 | II-57 | C-50 |
| T1b-2503 | I-3 | II-58 | C-50 |
| T1b-2504 | I-3 | II-59 | C-50 |
| T1b-2505 | I-3 | II-49 | C-50 |
| T1b-2506 | I-3 | II-60 | C-50 |
| T1b-2507 | I-3 | II-61 | C-50 |
| T1b-2508 | I-3 | II-62 | C-50 |
| T1b-2509 | I-3 | II-50 | C-50 |
| T1b-2510 | I-3 | II-63 | C-50 |
| T1b-2511 | I-3 | II-64 | C-50 |
| T1b-2512 | I-3 | II-65 | C-50 |
| T1b-2513 | I-3 | II-66 | C-50 |
| T1b-2514 | I-3 | II-51 | C-50 |
| T1b-2515 | I-3 | II-67 | C-50 |
| T1b-2516 | I-3 | II-68 | C-50 |
| T1b-2517 | I-3 | II-69 | C-50 |
| T1b-2518 | I-3 | II-53 | C-50 |
| T1b-2519 | I-3 | II-70 | C-50 |
| T1b-2520 | I-3 | II-54 | C-50 |
| T1b-2521 | I-3 | II-71 | C-50 |
| T1b-2522 | I-3 | II-55 | C-50 |
| T1b-2523 | I-3 | II-72 | C-50 |
| T1b-2524 | I-3 | II-73 | C-50 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-2525 | I-3 | II-27 | C-50 |
| T1b-2526 | I-3 | II-44 | C-50 |
| T1b-2527 | I-3 | II-74 | C-50 |
| T1b-2528 | I-3 | II-28 | C-50 |
| T1b-2529 | I-3 | II-75 | C-50 |
| T1b-2530 | I-3 | II-29 | C-50 |
| T1b-2531 | I-3 | II-30 | C-50 |
| T1b-2532 | I-3 | II-31 | C-50 |
| T1b-2533 | I-3 | II-76 | C-50 |
| T1b-2534 | I-3 | II-77 | C-50 |
| T1b-2535 | I-3 | II-78 | C-50 |
| T1b-2536 | I-3 | II-79 | C-50 |
| T1b-2537 | I-3 | II-80 | C-50 |
| T1b-2538 | I-3 | II-34 | C-50 |
| T1b-2539 | I-3 | II-81 | C-50 |
| T1b-2540 | I-3 | II-82 | C-50 |
| T1b-2541 | I-3 | II-83 | C-50 |
| T1b-2542 | I-3 | II-52 | C-50 |
| T1b-2543 | I-3 | II-84 | C-50 |
| T1b-2544 | I-3 | II-85 | C-50 |
| T1b-2545 | I-3 | II-86 | C-50 |
| T1b-2546 | I-3 | II-87 | C-50 |
| T1b-2547 | I-3 | II-88 | C-50 |
| T1b-2548 | I-3 | II-43 | C-50 |
| T1b-2549 | I-3 | II-89 | C-50 |
| T1b-2550 | I-3 | II-90 | C-50 |
| T1b-2551 | I-3 | II-56 | C-51 |
| T1b-2552 | I-3 | II-48 | C-51 |
| T1b-2553 | I-3 | II-57 | C-51 |
| T1b-2554 | I-3 | II-58 | C-51 |
| T1b-2555 | I-3 | II-59 | C-51 |
| T1b-2556 | I-3 | II-49 | C-51 |
| T1b-2557 | I-3 | II-60 | C-51 |
| T1b-2558 | I-3 | II-61 | C-51 |
| T1b-2559 | I-3 | II-62 | C-51 |
| T1b-2560 | I-3 | II-50 | C-51 |
| T1b-2561 | I-3 | II-63 | C-51 |
| T1b-2562 | I-3 | II-64 | C-51 |
| T1b-2563 | I-3 | II-65 | C-51 |
| T1b-2564 | I-3 | II-66 | C-51 |
| T1b-2565 | I-3 | II-51 | C-51 |
| T1b-2566 | I-3 | II-67 | C-51 |
| T1b-2567 | I-3 | II-68 | C-51 |
| T1b-2568 | I-3 | II-69 | C-51 |
| T1b-2569 | I-3 | II-53 | C-51 |
| T1b-2570 | I-3 | II-70 | C-51 |
| T1b-2571 | I-3 | II-54 | C-51 |
| T1b-2572 | I-3 | II-71 | C-51 |
| T1b-2573 | I-3 | II-55 | C-51 |
| T1b-2574 | I-3 | II-72 | C-51 |
| T1b-2575 | I-3 | II-73 | C-51 |
| T1b-2576 | I-3 | II-27 | C-51 |
| T1b-2577 | I-3 | II-44 | C-51 |
| T1b-2578 | I-3 | II-74 | C-51 |
| T1b-2579 | I-3 | II-28 | C-51 |
| T1b-2580 | I-3 | II-75 | C-51 |
| T1b-2581 | I-3 | II-29 | C-51 |
| T1b-2582 | I-3 | II-30 | C-51 |
| T1b-2583 | I-3 | II-31 | C-51 |
| T1b-2584 | I-3 | II-76 | C-51 |
| T1b-2585 | I-3 | II-77 | C-51 |
| T1b-2586 | I-3 | II-78 | C-51 |
| T1b-2587 | I-3 | II-79 | C-51 |
| T1b-2588 | I-3 | II-80 | C-51 |
| T1b-2589 | I-3 | II-34 | C-51 |
| T1b-2590 | I-3 | II-81 | C-51 |
| T1b-2591 | I-3 | II-82 | C-51 |
| T1b-2592 | I-3 | II-83 | C-51 |
| T1b-2593 | I-3 | II-52 | C-51 |
| T1b-2594 | I-3 | II-84 | C-51 |
| T1b-2595 | I-3 | II-85 | C-51 |
| T1b-2596 | I-3 | II-86 | C-51 |
| T1b-2597 | I-3 | II-87 | C-51 |
| T1b-2598 | I-3 | II-88 | C-51 |
| T1b-2599 | I-3 | II-43 | C-51 |
| T1b-2600 | I-3 | II-89 | C-51 |
| T1b-2601 | I-3 | II-90 | C-51 |
| T1b-2602 | I-3 | II-56 | C-52 |
| T1b-2603 | I-3 | II-48 | C-52 |
| T1b-2604 | I-3 | II-57 | C-52 |
| T1b-2605 | I-3 | II-58 | C-52 |
| T1b-2606 | I-3 | II-59 | C-52 |
| T1b-2607 | I-3 | II-49 | C-52 |
| T1b-2608 | I-3 | II-60 | C-52 |
| T1b-2609 | I-3 | II-61 | C-52 |
| T1b-2610 | I-3 | II-62 | C-52 |
| T1b-2611 | I-3 | II-50 | C-52 |
| T1b-2612 | I-3 | II-63 | C-52 |
| T1b-2613 | I-3 | II-64 | C-52 |
| T1b-2614 | I-3 | II-65 | C-52 |
| T1b-2615 | I-3 | II-66 | C-52 |
| T1b-2616 | I-3 | II-51 | C-52 |
| T1b-2617 | I-3 | II-67 | C-52 |
| T1b-2618 | I-3 | II-68 | C-52 |
| T1b-2619 | I-3 | II-69 | C-52 |
| T1b-2620 | I-3 | II-53 | C-52 |
| T1b-2621 | I-3 | II-70 | C-52 |
| T1b-2622 | I-3 | II-54 | C-52 |
| T1b-2623 | I-3 | II-71 | C-52 |
| T1b-2624 | I-3 | II-55 | C-52 |
| T1b-2625 | I-3 | II-72 | C-52 |
| T1b-2626 | I-3 | II-73 | C-52 |
| T1b-2627 | I-3 | II-27 | C-52 |
| T1b-2628 | I-3 | II-44 | C-52 |
| T1b-2629 | I-3 | II-74 | C-52 |
| T1b-2630 | I-3 | II-28 | C-52 |
| T1b-2631 | I-3 | II-75 | C-52 |
| T1b-2632 | I-3 | II-29 | C-52 |
| T1b-2633 | I-3 | II-30 | C-52 |
| T1b-2634 | I-3 | II-31 | C-52 |
| T1b-2635 | I-3 | II-76 | C-52 |
| T1b-2636 | I-3 | II-77 | C-52 |
| T1b-2637 | I-3 | II-78 | C-52 |
| T1b-2638 | I-3 | II-79 | C-52 |
| T1b-2639 | I-3 | II-80 | C-52 |
| T1b-2640 | I-3 | II-34 | C-52 |
| T1b-2641 | I-3 | II-81 | C-52 |
| T1b-2642 | I-3 | II-82 | C-52 |
| T1b-2643 | I-3 | II-83 | C-52 |
| T1b-2644 | I-3 | II-52 | C-52 |
| T1b-2645 | I-3 | II-84 | C-52 |
| T1b-2646 | I-3 | II-85 | C-52 |
| T1b-2647 | I-3 | II-86 | C-52 |
| T1b-2648 | I-3 | II-87 | C-52 |
| T1b-2649 | I-3 | II-88 | C-52 |
| T1b-2650 | I-3 | II-43 | C-52 |
| T1b-2651 | I-3 | II-89 | C-52 |
| T1b-2652 | I-3 | II-90 | C-52 |
| T1b-2653 | I-3 | II-56 | C-53 |
| T1b-2654 | I-3 | II-48 | C-53 |
| T1b-2655 | I-3 | II-57 | C-53 |
| T1b-2656 | I-3 | II-58 | C-53 |
| T1b-2657 | I-3 | II-59 | C-53 |
| T1b-2658 | I-3 | II-49 | C-53 |
| T1b-2659 | I-3 | II-60 | C-53 |
| T1b-2660 | I-3 | II-61 | C-53 |
| T1b-2661 | I-3 | II-62 | C-53 |
| T1b-2662 | I-3 | II-50 | C-53 |
| T1b-2663 | I-3 | II-63 | C-53 |
| T1b-2664 | I-3 | II-64 | C-53 |
| T1b-2665 | I-3 | II-65 | C-53 |
| T1b-2666 | I-3 | II-66 | C-53 |
| T1b-2667 | I-3 | II-51 | C-53 |
| T1b-2668 | I-3 | II-67 | C-53 |
| T1b-2669 | I-3 | II-68 | C-53 |
| T1b-2670 | I-3 | II-69 | C-53 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-2671 | I-3 | II-53 | C-53 |
| T1b-2672 | I-3 | II-70 | C-53 |
| T1b-2673 | I-3 | II-54 | C-53 |
| T1b-2674 | I-3 | II-71 | C-53 |
| T1b-2675 | I-3 | II-55 | C-53 |
| T1b-2676 | I-3 | II-72 | C-53 |
| T1b-2677 | I-3 | II-73 | C-53 |
| T1b-2678 | I-3 | II-27 | C-53 |
| T1b-2679 | I-3 | II-44 | C-53 |
| T1b-2680 | I-3 | II-74 | C-53 |
| T1b-2681 | I-3 | II-28 | C-53 |
| T1b-2682 | I-3 | II-75 | C-53 |
| T1b-2683 | I-3 | II-29 | C-53 |
| T1b-2684 | I-3 | II-30 | C-53 |
| T1b-2685 | I-3 | II-31 | C-53 |
| T1b-2686 | I-3 | II-76 | C-53 |
| T1b-2687 | I-3 | II-77 | C-53 |
| T1b-2688 | I-3 | II-78 | C-53 |
| T1b-2689 | I-3 | II-79 | C-53 |
| T1b-2690 | I-3 | II-80 | C-53 |
| T1b-2691 | I-3 | II-34 | C-53 |
| T1b-2692 | I-3 | II-81 | C-53 |
| T1b-2693 | I-3 | II-82 | C-53 |
| T1b-2694 | I-3 | II-83 | C-53 |
| T1b-2695 | I-3 | II-52 | C-53 |
| T1b-2696 | I-3 | II-84 | C-53 |
| T1b-2697 | I-3 | II-85 | C-53 |
| T1b-2698 | I-3 | II-86 | C-53 |
| T1b-2699 | I-3 | II-87 | C-53 |
| T1b-2700 | I-3 | II-88 | C-53 |
| T1b-2701 | I-3 | II-43 | C-53 |
| T1b-2702 | I-3 | II-89 | C-53 |
| T1b-2703 | I-3 | II-90 | C-53 |
| T1b-2704 | I-3 | II-56 | C-54 |
| T1b-2705 | I-3 | II-48 | C-54 |
| T1b-2706 | I-3 | II-57 | C-54 |
| T1b-2707 | I-3 | II-58 | C-54 |
| T1b-2708 | I-3 | II-59 | C-54 |
| T1b-2709 | I-3 | II-49 | C-54 |
| T1b-2710 | I-3 | II-60 | C-54 |
| T1b-2711 | I-3 | II-61 | C-54 |
| T1b-2712 | I-3 | II-62 | C-54 |
| T1b-2713 | I-3 | II-50 | C-54 |
| T1b-2714 | I-3 | II-63 | C-54 |
| T1b-2715 | I-3 | II-64 | C-54 |
| T1b-2716 | I-3 | II-65 | C-54 |
| T1b-2717 | I-3 | II-66 | C-54 |
| T1b-2718 | I-3 | II-51 | C-54 |
| T1b-2719 | I-3 | II-67 | C-54 |
| T1b-2720 | I-3 | II-68 | C-54 |
| T1b-2721 | I-3 | II-69 | C-54 |
| T1b-2722 | I-3 | II-53 | C-54 |
| T1b-2723 | I-3 | II-70 | C-54 |
| T1b-2724 | I-3 | II-54 | C-54 |
| T1b-2725 | I-3 | II-71 | C-54 |
| T1b-2726 | I-3 | II-55 | C-54 |
| T1b-2727 | I-3 | II-72 | C-54 |
| T1b-2728 | I-3 | II-73 | C-54 |
| T1b-2729 | I-3 | II-27 | C-54 |
| T1b-2730 | I-3 | II-44 | C-54 |
| T1b-2731 | I-3 | II-74 | C-54 |
| T1b-2732 | I-3 | II-28 | C-54 |
| T1b-2733 | I-3 | II-75 | C-54 |
| T1b-2734 | I-3 | II-29 | C-54 |
| T1b-2735 | I-3 | II-30 | C-54 |
| T1b-2736 | I-3 | II-31 | C-54 |
| T1b-2737 | I-3 | II-76 | C-54 |
| T1b-2738 | I-3 | II-77 | C-54 |
| T1b-2739 | I-3 | II-78 | C-54 |
| T1b-2740 | I-3 | II-79 | C-54 |
| T1b-2741 | I-3 | II-80 | C-54 |
| T1b-2742 | I-3 | II-34 | C-54 |
| T1b-2743 | I-3 | II-81 | C-54 |
| T1b-2744 | I-3 | II-82 | C-54 |
| T1b-2745 | I-3 | II-83 | C-54 |
| T1b-2746 | I-3 | II-52 | C-54 |
| T1b-2747 | I-3 | II-84 | C-54 |
| T1b-2748 | I-3 | II-85 | C-54 |
| T1b-2749 | I-3 | II-86 | C-54 |
| T1b-2750 | I-3 | II-87 | C-54 |
| T1b-2751 | I-3 | II-88 | C-54 |
| T1b-2752 | I-3 | II-43 | C-54 |
| T1b-2753 | I-3 | II-89 | C-54 |
| T1b-2754 | I-3 | II-90 | C-54 |
| T1b-2755 | I-3 | II-56 | C-55 |
| T1b-2756 | I-3 | II-48 | C-55 |
| T1b-2757 | I-3 | II-57 | C-55 |
| T1b-2758 | I-3 | II-58 | C-55 |
| T1b-2759 | I-3 | II-59 | C-55 |
| T1b-2760 | I-3 | II-49 | C-55 |
| T1b-2761 | I-3 | II-60 | C-55 |
| T1b-2762 | I-3 | II-61 | C-55 |
| T1b-2763 | I-3 | II-62 | C-55 |
| T1b-2764 | I-3 | II-50 | C-55 |
| T1b-2765 | I-3 | II-63 | C-55 |
| T1b-2766 | I-3 | II-64 | C-55 |
| T1b-2767 | I-3 | II-65 | C-55 |
| T1b-2768 | I-3 | II-66 | C-55 |
| T1b-2769 | I-3 | II-51 | C-55 |
| T1b-2770 | I-3 | II-67 | C-55 |
| T1b-2771 | I-3 | II-68 | C-55 |
| T1b-2772 | I-3 | II-69 | C-55 |
| T1b-2773 | I-3 | II-53 | C-55 |
| T1b-2774 | I-3 | II-70 | C-55 |
| T1b-2775 | I-3 | II-54 | C-55 |
| T1b-2776 | I-3 | II-71 | C-55 |
| T1b-2777 | I-3 | II-55 | C-55 |
| T1b-2778 | I-3 | II-72 | C-55 |
| T1b-2779 | I-3 | II-73 | C-55 |
| T1b-2780 | I-3 | II-27 | C-55 |
| T1b-2781 | I-3 | II-44 | C-55 |
| T1b-2782 | I-3 | II-74 | C-55 |
| T1b-2783 | I-3 | II-28 | C-55 |
| T1b-2784 | I-3 | II-75 | C-55 |
| T1b-2785 | I-3 | II-29 | C-55 |
| T1b-2786 | I-3 | II-30 | C-55 |
| T1b-2787 | I-3 | II-31 | C-55 |
| T1b-2788 | I-3 | II-76 | C-55 |
| T1b-2789 | I-3 | II-77 | C-55 |
| T1b-2790 | I-3 | II-78 | C-55 |
| T1b-2791 | I-3 | II-79 | C-55 |
| T1b-2792 | I-3 | II-80 | C-55 |
| T1b-2793 | I-3 | II-34 | C-55 |
| T1b-2794 | I-3 | II-81 | C-55 |
| T1b-2795 | I-3 | II-82 | C-55 |
| T1b-2796 | I-3 | II-83 | C-55 |
| T1b-2797 | I-3 | II-52 | C-55 |
| T1b-2798 | I-3 | II-84 | C-55 |
| T1b-2799 | I-3 | II-85 | C-55 |
| T1b-2800 | I-3 | II-86 | C-55 |
| T1b-2801 | I-3 | II-87 | C-55 |
| T1b-2802 | I-3 | II-88 | C-55 |
| T1b-2803 | I-3 | II-43 | C-55 |
| T1b-2804 | I-3 | II-89 | C-55 |
| T1b-2805 | I-3 | II-90 | C-55 |
| T1b-2806 | I-3 | II-56 | C-56 |
| T1b-2807 | I-3 | II-48 | C-56 |
| T1b-2808 | I-3 | II-57 | C-56 |
| T1b-2809 | I-3 | II-58 | C-56 |
| T1b-2810 | I-3 | II-59 | C-56 |
| T1b-2811 | I-3 | II-49 | C-56 |
| T1b-2812 | I-3 | II-60 | C-56 |
| T1b-2813 | I-3 | II-61 | C-56 |
| T1b-2814 | I-3 | II-62 | C-56 |
| T1b-2815 | I-3 | II-50 | C-56 |
| T1b-2816 | I-3 | II-63 | C-56 |

TABLE T1b-continued

Three-component compositions T1b-1 to T1b-2856 comprising compound I-3 component II and component III, in particular ternary compositions containing compound I-3, II and III as only active ingredients.

| composition | I | II | III |
|---|---|---|---|
| T1b-2817 | I-3 | II-64 | C-56 |
| T1b-2818 | I-3 | II-65 | C-56 |
| T1b-2819 | I-3 | II-66 | C-56 |
| T1b-2820 | I-3 | II-51 | C-56 |
| T1b-2821 | I-3 | II-67 | C-56 |
| T1b-2822 | I-3 | II-68 | C-56 |
| T1b-2823 | I-3 | II-69 | C-56 |
| T1b-2824 | I-3 | II-53 | C-56 |
| T1b-2825 | I-3 | II-70 | C-56 |
| T1b-2826 | I-3 | II-54 | C-56 |
| T1b-2827 | I-3 | II-71 | C-56 |
| T1b-2828 | I-3 | II-55 | C-56 |
| T1b-2829 | I-3 | II-72 | C-56 |
| T1b-2830 | I-3 | II-73 | C-56 |
| T1b-2831 | I-3 | II-27 | C-56 |
| T1b-2832 | I-3 | II-44 | C-56 |
| T1b-2833 | I-3 | II-74 | C-56 |
| T1b-2834 | I-3 | II-28 | C-56 |
| T1b-2835 | I-3 | II-75 | C-56 |
| T1b-2836 | I-3 | II-29 | C-56 |
| T1b-2837 | I-3 | II-30 | C-56 |
| T1b-2838 | I-3 | II-31 | C-56 |
| T1b-2839 | I-3 | II-76 | C-56 |
| T1b-2840 | I-3 | II-77 | C-56 |
| T1b-2841 | I-3 | II-78 | C-56 |
| T1b-2842 | I-3 | II-79 | C-56 |
| T1b-2843 | I-3 | II-80 | C-56 |
| T1b-2844 | I-3 | II-34 | C-56 |
| T1b-2845 | I-3 | II-81 | C-56 |
| T1b-2846 | I-3 | II-82 | C-56 |
| T1b-2847 | I-3 | II-83 | C-56 |
| T1b-2848 | I-3 | II-52 | C-56 |
| T1b-2849 | I-3 | II-84 | C-56 |
| T1b-2850 | I-3 | II-85 | C-56 |
| T1b-2851 | I-3 | II-86 | C-56 |
| T1b-2852 | I-3 | II-87 | C-56 |
| T1b-2853 | I-3 | II-88 | C-56 |
| T1b-2854 | I-3 | II-43 | C-56 |
| T1b-2855 | I-3 | II-89 | C-56 |
| T1b-2856 | I-3 | II-90 | C-56 |

Table T2b: Three-component compositions T2b-1 to T2b-2856 corresponding to the respective compositions T1b-1 to T1b-2856, wherein component I is I-2 instead of I-3. Consequently, Table T2b contains compositions T2b-1 to T2b-2856 comprising compound I-2, component II and component III, in particular ternary compositions containing compound I-2, II and III as only active ingredients.

Table T3b: Three-component compositions T3b-1 to T3b-2856 corresponding to the respective compositions T1b-1 to T1b-2856, wherein component I is I-1 instead of I-3. Consequently, Table T3b contains compositions T3b-1 to T3b-2856 comprising compound I-1, component II and component III, in particular ternary compositions containing compound I-1, II and III as only active ingredients.

Table T4b: Three-component compositions T4b-1 to T4b-2856 corresponding to the respective compositions T1b-1 to T1b-2856, wherein component I is I-4 instead of I-3. Consequently, Table T4b contains compositions T4b-1 to T4b-2856 comprising compound I-4, component II and component III, in particular ternary compositions containing compound I-4, II and III as only active ingredients.

Table T5b: Three-component compositions T5b-1 to T5b-2856 corresponding to the respective compositions T1b-1 to T1b-2856, wherein component I is I-5 instead of I-3. Consequently, Table T5b contains compositions T5b-1 to T5b-2856 comprising compound I-5, component II and component III, in particular ternary compositions containing compound I-5, II and III as only active ingredients.

Table T6b: Three-component compositions T6b-1 to T6b-2856 corresponding to the respective compositions T1b-1 to T1b-2856, wherein component I is I-6 instead of I-3. Consequently, Table T6b contains compositions T6b-1 to T6b-2856 comprising compound I-6, component II and component III, in particular ternary compositions containing compound I-6, II and III as only active ingredients.

Table T7b: Three-component compositions T7b-1 to T7b-2856 corresponding to the respective compositions T1b-1 to T1b-2856, wherein component I is I-7 instead of I-3. Consequently, Table T7b contains compositions T7b-1 to T7b-2856 comprising compound I-7, component II and component III, in particular ternary compositions containing compound I-7, II and III as only active ingredients.

Table T8b: Three-component compositions T8b-1 to T8b-2856 corresponding to the respective compositions T1b-1 to T1b-2856, wherein component I is I-8 instead of I-3. Consequently, Table T8b contains compositions T8b-1 to T8b-2856 comprising compound I-8, component II and component III, in particular ternary compositions containing compound I-8, II and III as only active ingredients.

Table T9b: Three-component compositions T9b-1 to T9b-2856 corresponding to the respective compositions T1b-1 to T1b-2856, wherein component I is I-9 instead of I-3. Consequently, Table T9b contains compositions T9b-1 to T9b-2856 comprising compound I-9, component II and component III, in particular ternary compositions containing compound I-9, II and III as only active ingredients.

Table T10b: Three-component compositions T10b-1 to T10b-2856 corresponding to the respective compositions T1b-1 to T1b-2856, wherein component I is I-10 instead of I-3. Consequently, Table T10b contains compositions T10b-1 to T10b-2856 comprising compound I-10, component II and component III, in particular ternary compositions containing compound I-10, II and III as only active ingredients.

Table T11b: Three-component compositions T11b-1 to T11b-2856 corresponding to the respective compositions T1b-1 to T1b-2856, wherein component I is I-11 instead of I-3. Consequently, Table T11b contains compositions T11b-1 to T11b-2856 comprising compound I-11, component II and component III, in particular ternary compositions containing compound I-11, II and III as only active ingredients.

Table T12b: Three-component compositions T12b-1 to T12b-2856 corresponding to the respective compositions T1b-1 to T1b-2856, wherein component I is I-12 instead of I-3. Consequently, Table T12b contains compositions T12b-1 to T12b-2856 comprising compound I-12, component II and component III, in particular ternary compositions containing compound I-12, II and III as only active ingredients.

Table T13b: Three-component compositions T13b-1 to T13b-2856 corresponding to the respective compositions T1b-1 to T1b-2856, wherein component I is I-13 instead of I-3. Consequently, Table T13b contains compositions T13b-1 to T13b-2856 comprising compound I-13, component II and component III, in particular ternary compositions containing compound I-13, II and III as only active ingredients.

Table T14b: Three-component compositions T14b-1 to T14b-2856 corresponding to the respective compositions T1b-1 to T1b-2856, wherein component I is I-14 instead of I-3. Consequently, Table T14b contains compositions T14b-1 to T14b-2856 comprising compound I-14, component II and component III, in particular ternary compositions containing compound I-14, II and III as only active ingredients.

Table T15b: Three-component compositions T15b-1 to T15b-2856 corresponding to the respective compositions T1b-1 to T1b-2856, wherein component I is I-15 instead of I-3. Consequently, Table T15b contains compositions T15b-1 to T15b-2856 comprising compound I-15, component II and component III, in particular ternary compositions containing compound I-15, II and III as only active ingredients.

Table T16b: Three-component compositions T16b-1 to T16b-2856 corresponding to the respective compositions T1b-1 to T1b-2856, wherein component I is I-16 instead of I-3. Consequently, Table T16b contains compositions T16b-1 to T16b-2856 comprising compound I-16, component II and component III, in particular ternary compositions containing compound I-16, II and III as only active ingredients.

Table T17b: Three-component compositions T17b-1 to T17b-2856 corresponding to the respective compositions T1b-1 to T1b-2856, wherein component I is I-17 instead of I-3. Consequently, Table T17b contains compositions T17b-1 to T17b-2856 comprising compound I-17, component II and component III, in particular ternary compositions containing compound I-17, II and III as only active ingredients.

Table T18b: Three-component compositions T18b-1 to T18b-2856 corresponding to the respective compositions T1b-1 to T1b-2856, wherein component I is I-18 instead of I-3. Consequently, Table T18b contains compositions T18b-1 to T18b-2856 comprising compound I-18, component II and component III, in particular ternary compositions containing compound I-18, II and II as only active ingredients.

Table T19b: Three-component compositions T19b-1 to T19b-2856 corresponding to the respective compositions T1b-1 to T1b-2856, wherein component I is I-19 instead of I-3. Consequently, Table T19b contains compositions T19b-1 to T19b-2856 comprising compound I-19, component II and component III, in particular ternary compositions containing compound I-19, II and III as only active ingredients.

Table T20b: Three-component compositions T20b-1 to T20b-2856 corresponding to the respective compositions T1b-1 to T1b-2856, wherein component I is I-20 instead of I-3. Consequently, Table T20b contains compositions T20b-1 to T20b-2856 comprising compound I-20, component II and component III, in particular ternary compositions containing compound I-20, II and III as only active ingredients.

Table T21b: Three-component compositions T21b-1 to T21b-2856 corresponding to the respective compositions T1b-1 to T1b-2856, wherein component I is I-21 instead of I-3. Consequently, Table T21b contains compositions T21b-1 to T21b-2856 comprising compound I-21, component II and component III, in particular ternary compositions containing compound I-21, II and III as only active ingredients.

Table T22b: Three-component compositions T22b-1 to T22b-2856 corresponding to the respective compositions T1b-1 to T1b-2856, wherein component I is I-22 instead of I-3. Consequently, Table T22b contains compositions T22b-1 to T22b-2856 comprising compound I-22, component II and component III, in particular ternary compositions containing compound I-22, II and III as only active ingredients.

Table T23b: Three-component compositions T23b-1 to T23b-2856 corresponding to the respective compositions T1b-1 to T1b-2856, wherein component I is I-23 instead of I-3. Consequently, Table T23b contains compositions T23b-1 to T23b-2856 comprising compound I-23, component II and component III, in particular ternary compositions containing compound I-23, II and III as only active ingredients.

Table T24b: Three-component compositions T24b-1 to T24b-2856 corresponding to the respective compositions T1b-1 to T1b-2856, wherein component I is I-24 instead of I-3. Consequently, Table T24b contains compositions T24b-1 to T24b-2856 comprising compound I-24, component II and component III, in particular ternary compositions containing compound I-24, II and III as only active ingredients.

Table T25b: Three-component compositions T25b-1 to T25b-2856 corresponding to the respective compositions T1b-1 to T1b-2856, wherein component I is I-25 instead of I-3. Consequently, Table T25b contains compositions T25b-1 to T25b-2856 comprising compound I-25, component II and component III, in particular ternary compositions containing compound I-25, II and III as only active ingredients.

Table T26b: Three-component compositions T26b-1 to T26b-2856 corresponding to the respective compositions T1b-1 to T1b-2856, wherein component I is I-26 instead of I-3. Consequently, Table T26b contains compositions T26b-1 to T26b-2856 comprising compound I-26, component II and component III, in particular ternary compositions containing compound I-26, II and III as only active ingredients.

Table T27b: Three-component compositions T27b-1 to T27b-2856 corresponding to the respective compositions T1b-1 to T1b-2856, wherein component I is I-27 instead of I-3. Consequently, Table T27b contains compositions T27b-1 to T27b-2856 comprising compound I-27, component II and component III, in particular ternary compositions containing compound I-27, II and III as only active ingredients.

Table T28b: Three-component compositions T28b-1 to T28b-2856 corresponding to the respective compositions T1b-1 to T1b-2856, wherein component I is I-28 instead of I-3. Consequently, Table T28b contains compositions T28b-1 to T28b-2856 comprising compound I-28, component II and component III, in particular ternary compositions containing compound I-28, II and III as only active ingredients.

Table T29b: Three-component compositions T29b-1 to T29b-2856 corresponding to the respective compositions T1b-1 to T1b-2856, wherein component I is I-29 instead of I-3. Consequently, Table T29b contains compositions T29b-1 to T29b-2856 comprising compound I-29, component II and component III, in particular ternary compositions containing compound I-29, II and III as only active ingredients.

Table T30b: Three-component compositions T30b-1 to T30b-2856 corresponding to the respective compositions T1b-1 to T1b-2856, wherein component I is I-30 instead of I-3. Consequently, Table T30b contains compositions T30b-1 to T30b-2856 comprising compound I-30, component II and component III, in particular ternary compositions containing compound I-30, II and III as only active ingredients.

Table T31b: Three-component compositions T31b-1 to T31b-2856 corresponding to the respective compositions T1b-1 to T1b-2856, wherein component I is I-31 instead of I-3. Consequently, Table T31b contains compositions T31b-1 to T31b-2856 comprising compound I-31, component II and component III, in particular ternary compositions containing compound I-31, II and III as only active ingredients.

According to a further embodiment of the invention, component III is selected from the following compounds: and component III is selected from:

Azoxystrobin (C-1)
Trifloxistrobin (C-2)
Picoxystrobin (C-3)
Pyraclostrobin (C-4)
Sedaxane (C-5)
Penthiopyrad (C-6)
Penflufen (C-7)
Fluopyram (C-8)
Fluxapyroxad (C-9)
Boscalid (C-10)
Oxathiapiprolin (C-49)
Metalaxyl (C-11)
Metalaxyl-M (C-12)
Ethaboxam (C-13)
DMM (C-14)
Cyproconazole (C-15)
Difenoconazole (C-16)
Prothioconazole (C-17)
Flutriafol (C-18)
Thiabendazole (C-19)
Ipconazole (C-20)
Tebuconazole (C-21)
Triadimenol (C-50)
Prochloraz (C-22)
Fluquinconazole (C-23)
Ttriticonazole (C-24)
Fludioxinil (C-25)
Carboxin (C-26)
Silthiofam (C-27)
Ziram (C-28)
Thiram (C-29)
Carbendazim (C-30)
Thiophanate-methyl (C-31)
Valifenalyate (C-32)
Insecticides/Nematic.
Fipronil (C-33)
Clothianidin (C-34)
Thiamethoxam (C-35)
Acetamiprid (C-36)
Dinotefuran (C-37)
Imidacloprid (C-38)
Thiacloprid (C-39)
Sulfoxaflor (C-51)
Methiocarb (C-52)
Tefluthrin (C-40)
Bifenthrin (C-41)
Cypermethrin (C-53)
Alphacypermethrin (C-42)
Spinosad (C-43)
cyantraniliprole (C-44)
chlorantraniliprole (C-45)
Thiodicarb (C-54)
Triflumezopyrim (Mesoionic) (C-55)
Acephate (C-46)
Chlorpyriphos (C-47)
Flupyradifurone (C-56)
Abamectin (C-48)

Consequently, further particularly preferred three-component compositions are compiled in Table T1c, wherein each row corresponds to one embodiment of the compositions according to the invention, i.e. one specific individualized composition. According to one specific aspect, these are ternary compositions which each only contain these three components as active compounds. Furthermore, also every combination of the compositions individualized in this table represent embodiments of the present invention.

In these three-component compositions, component I is selected from compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30 and I-31 or any group of compounds 1 detailed above, component II is selected from:

*Azospirillum amazonense* SpY2 (II-91)
*Azospirillum brasilense* AZ39 also called Az 39 (II-92)
*Azospirillum brasilense* Cd (II-93)
*Azospirillum brasilense* Sp 245 (II-94)
*Azospirillum brasilense* Ab-V5 (II-95)
*Azospirillum brasilense* Ab-V6 (II-96)
*Azospirillum brasilense* XOH (II-97)
*Azospirillum lipoferunn* Sp31 (II-98)
*Bradyrhizobium elkanii* SEMIA 5019 also called 29W (II-99)
*Bradyrhizobium elkanii* SEMIA 587 (II-100)
*Bradyrhizobium elkanii* U-1301 (II-101)
*Bradyrhizobium elkanii* U-1302 (II-102)
*Bradyrhizobium elkanii* USDA 3254 (II-103)
*Bradyrhizobium elkanii* USDA 76 (II-104)
*Bradyrhizobium elkanii* USDA 94 (II-105)
*Bradyrhizobium japonicum* 532c (II-106)
*Bradyrhizobium japonicum* E-109 (II-107)
*Bradyrhizobium japonicum* G49 (II-108)
*Bradyrhizobium japonicum* SEMIA 5079 (II-109)
*Bradyrhizobium japonicum* SEMIA 5080 (II-110)
*Bradyrhizobium japonicum* SEMIA 566 (II-111)
*Bradyrhizobium japonicum* SEMIA 586 (II-112)
*Bradyrhizobium japonicum* TA-11 (TA11 NOD+) (II-113)
*Bradyrhizobium japonicum* USDA 110 (II-114)
*Bradyrhizobium japonicum* USDA 121 (II-115)
*Bradyrhizobium japonicum* USDA 3 (II-116)
*Bradyrhizobium japonicum* USDA 31 (II-117)
*Bradyrhizobium japonicum* USDA 76 (II-118)
*Bradyrhizobium* sp. (Arachis) CB1015 (II-119)
*Bradyrhizobium* sp. (Arachis) SEMIA 6144 (II-120)
*Bradyrhizobium* sp. (Arachis) SEMIA 6462 (II-121)
*Bradyrhizobium* sp. (Arachis) SEMIA 6464 (II-122)
*Bradyrhizobium* sp. (Vigna) PNL1 (II-123)
*Mesorhizobium* sp. WSM1497 (II-124)
*Rhizobium leguminosarum* bv. phaseoli RG-B10 (II-125)
*Rhizobium leguminosarum* bv. phaseoli (II-126)
*Rhizobium leguminosarum* bv. trifolii 095 (II-127)
*Rhizobium leguminosarum* bv. trifolii CB782 (II-128)
*Rhizobium leguminosarum* bv. trifolii CC1099 (II-129)
*Rhizobium leguminosarum* bv. trifolii CC275e (II-130)
*Rhizobium leguminosarum* bv. trifolii CC283b (II-131)
*Rhizobium leguminosarum* bv. trifolii RP113-7 (II-132)
*Rhizobium leguminosarum* bv. trifolii TA1 (II-133)
*Rhizobium leguminosarum* bv. trifolii -continued WSM1325 (II-134)
*Rhizobium leguminosarum* bv. trifolii
WSM2304 (II-135)
*Rhizobium leguminosarum* bv. viciae
P1NP3Cst also referred to as 1435
(II-136)
*Rhizobium leguminosarum* bv. viciae RG-
P2 also called P2 (II-137)
*Rhizobium leguminosarum* bv. viciae
SU303 (II-138)
*Rhizobium leguminosarum* bv. viciae
WSM1455 (II-140)
*Rhizobium tropici* CC511 (II-141)
*Rhizobium tropici* CIAT 899 (II-142)
*Rhizobium tropici* VH12 (II-143)
*Rhizobium tropici* PRF 81 (II-144)
*Sinorhizobium meliloti* NRG185 (II-145)
*Sinorhizobium meliloti* RCR2011 also
called 2011 or SU47 (II-146)
*Sinorhizobium meliloti* RRI128 (II-147)
*Bacillus altitudinis* 41KF2b (II-148)
*Bacillus amyloliquefaciens* AP-136
(II-149)
*Bacillus amyloliquefaciens* AP-188
(II-150)
*Bacillus amyloliquefaciens* AP-218
(II-151)
*Bacillus amyloliquefaciens* AP-219
(II-152)
*Bacillus amyloliquefaciens* AP-295
(II-153)
*Bacillus amyloliquefaciens* ssp. plantarum
D747 (II-154)
*Bacillus amyloliquefaciens* ssp. plantarum
FZB24 also called SB3615 (II-155)
*Bacillus amyloliquefaciens* ssp. plantarum
FZB42 (II-156)
*Bacillus amyloliquefaciens* ssp. plantarum
GB03 also called GBO3 formerly *B. subtilis*
(II-157)
*Bacillus amyloliquefaciens* ssp. plantarum
MBI600 also referred to as 1430, formerly
*B. subtilis* (II-158)
*Bacillus amyloliquefaciens* ssp. plantarum
QST-713, formerly *B. subtilis* (II-159)
*Bacillus amyloliquefaciens* ssp. plantarum
TJ1000, also called 1BE (II-160)
*Bacillus firmus* CNCM I-1582 (II-161)
*Bacillus megaterium* H491 (II-162)
*Bacillus megaterium* J142 (II-163)
*Bacillus megaterium* M018 (II-164)
*Bacillus mojavensis* AP-209 (II-165)
*Bacillus mojavensis* SR11 (II-166)
*Bacillus mycoides* AQ726 (II-167)
*Bacillus mycoides* J also called BmJ
(II-168)
*Bacillus pumilus* GB34 (II-169)
*Bacillus pumilus* GHA 180 (II-170)
*Bacillus pumilus* INR-7 otherwise referred
to as BU F22 and BU-F33 (II-171)
*Bacillus pumilus* KFP9F (II-172)
*Bacillus pumilus* QST 2808 (II-173)
*Bacillus simplex* ABU 288 (II-174)
*Bacillus subtilis* CX-9060 (II-175)
*Bacillus subtilis* FB17 (II-176)
*Bacillus subtilis* GB07 (II-177)
*Burkholderia* sp. A396 (II-178)
*Coniothyrium minitans* CON/M/91-08
(II-179)
*Paecilomyces lilacinus* 251 (II-180)
*Paecilomyces lilacinus* BCP2 (II-181)
*Paenibacillus alvei* NAS6G6 (II-182)
*Paenibacillus polymyxa* PKB1 (II-183)
*Paenibacilllus popilliae* 14F-D80 also
called K14F-0080 (II-184)
*Paenibacillus popilliae* KLN 3 (II-185)
*Pasteuria nishizawae* Pn1 (II-186)
*Pasteuria* sp. Ph3 (II-187)
*Pasteuria* sp. Pr3 (II-188)

-continued

*Pasteuria* sp. ATCC PTA-9643 (II-189)
*Pasteuria usgae* BL1 (II-190)
*Penicillium bilaiae* (also called *P. bilaii*)
NRRL 50162 (II-191)
*Penicillium bilaiae* (also called *P. bilaii*)
NRRL 50169 (II-192)
*Penicillium bilaiae* (also called *P. bilaii*)
ATCC 18309 (=ATCC 74319) (II-193)
*Penicillium bilaiae* (also called *P. bilaii*)
ATCC 20851 (II-194)
*Penicillium bilaiae* (also called *P. bilaii*)
ATCC 22348 (=ATCC 74318) (II-195)
*Pseudomonas fluorescens* A506 (II-196)
*Pseudomonas fluorescens* ATCC 13525
(II-197)
*Pseudomonas fluorescens* CHA0
(II-198)
*Pseudomonas fluorescens* CL 145A
(II-199)
*Pseudomonas fluorescens* NCIB 12089
(II-200)
*Pseudomonas fluorescens* Pf-5
(II-201)
*Pseudomonas fluorescens* WCS374
(II-202)
*Pseudomonas putida* ATCC 202153
(II-203)

and component III is selected from:

Azoxystrobin (C-1)
Trifloxistrobin (C-2)
Picoxystrobin (C-3)
Pyraclostrobin (C-4)
Sedaxane (C-5)
Penthiopyrad (C-6)
Penflufen (C-7)
Fluopyram (C-8)
Fluxapyroxad (C-9)
Boscalid (C-10)
Oxathiapiprolin (C-49)
Metalaxyl (C-11)
Metalaxyl-M (C-12)
Ethaboxam (C-13)
DMM (C-14)
Cyproconazole (C-15)
Difenoconazole (C-16)
Prothioconazole (C-17)
Flutriafol (C-18)
Thiabendazole (C-19)
Ipconazole (C-20)
Tebuconazole (C-21)
Triadimenol (C-50)
Prochloraz (C-22)
Fluquinconazole (C-23)
Ttriticonazole (C-24)
Fludioxinil (C-25)
Carboxin (C-26)
Silthiofam (C-27)
Ziram (C-28)
Thiram (C-29)
Carbendazim (C-30)
Thiophanate-methyl (C-31)
Valifenalyate (C-32)
Insecticides/Nematic.
Fipronil (C-33)
Clothianidin (C-34)
Thiamethoxam (C-35)
Acetamiprid (C-36)
Dinotefuran (C-37)
Imidacloprid (C-38)
Thiacloprid (C-39)
Sulfoxaflor (C-51)
Methiocarb (C-52)
Tefluthrin (C-40)
Bifenthrin (C-41)
Cypermethrin (C-53)

-continued

Alphacypermethrin (C-42)
Spinosad (C-43)
cyantraniliprole (C-44)
chlorantraniliprole (C-45)
Thiodicarb (C-54)
Triflumezopyrim (Mesoionic) (C-55)
Acephate (C-46)
Chlorpyriphos (C-47)
Flupyradifurone (C-56)
Abamectin (C-48)

TABLE T1c

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-1 | I-3 | II-91 | C-1 |
| T1c-2 | I-3 | II-92 | C-1 |
| T1c-3 | I-3 | II-93 | C-1 |
| T1c-4 | I-3 | II-94 | C-1 |
| T1c-5 | I-3 | II-95 | C-1 |
| T1c-6 | I-3 | II-96 | C-1 |
| T1c-7 | I-3 | II-97 | C-1 |
| T1c-8 | I-3 | II-98 | C-1 |
| T1c-9 | I-3 | II-99 | C-1 |
| T1c-10 | I-3 | II-100 | C-1 |
| T1c-11 | I-3 | II-101 | C-1 |
| T1c-12 | I-3 | II-102 | C-1 |
| T1c-13 | I-3 | II-103 | C-1 |
| T1c-14 | I-3 | II-104 | C-1 |
| T1c-15 | I-3 | II-105 | C-1 |
| T1c-16 | I-3 | II-106 | C-1 |
| T1c-17 | I-3 | II-107 | C-1 |
| T1c-18 | I-3 | II-108 | C-1 |
| T1c-19 | I-3 | II-109 | C-1 |
| T1c-20 | I-3 | II-110 | C-1 |
| T1c-21 | I-3 | II-111 | C-1 |
| T1c-22 | I-3 | II-112 | C-1 |
| T1c-23 | I-3 | II-113 | C-1 |
| T1c-24 | I-3 | II-114 | C-1 |
| T1c-25 | I-3 | II-115 | C-1 |
| T1c-26 | I-3 | II-116 | C-1 |
| T1c-27 | I-3 | II-117 | C-1 |
| T1c-28 | I-3 | II-118 | C-1 |
| T1c-29 | I-3 | II-119 | C-1 |
| T1c-30 | I-3 | II-120 | C-1 |
| T1c-31 | I-3 | II-121 | C-1 |
| T1c-32 | I-3 | II-122 | C-1 |
| T1c-33 | I-3 | II-123 | C-1 |
| T1c-34 | I-3 | II-124 | C-1 |
| T1c-35 | I-3 | II-125 | C-1 |
| T1c-36 | I-3 | II-126 | C-1 |
| T1c-37 | I-3 | II-127 | C-1 |
| T1c-38 | I-3 | II-128 | C-1 |
| T1c-39 | I-3 | II-129 | C-1 |
| T1c-40 | I-3 | II-130 | C-1 |
| T1c-41 | I-3 | II-131 | C-1 |
| T1c-42 | I-3 | II-132 | C-1 |
| T1c-43 | I-3 | II-133 | C-1 |
| T1c-44 | I-3 | II-134 | C-1 |
| T1c-45 | I-3 | II-135 | C-1 |
| T1c-46 | I-3 | II-136 | C-1 |
| T1c-47 | I-3 | II-137 | C-1 |
| T1c-48 | I-3 | II-138 | C-1 |
| T1c-49 | I-3 | II-139 | C-1 |
| T1c-50 | I-3 | II-140 | C-1 |
| T1c-51 | I-3 | II-141 | C-1 |
| T1c-52 | I-3 | II-142 | C-1 |
| T1c-53 | I-3 | II-143 | C-1 |
| T1c-54 | I-3 | II-144 | C-1 |
| T1c-55 | I-3 | II-145 | C-1 |
| T1c-56 | I-3 | II-146 | C-1 |
| T1c-57 | I-3 | II-147 | C-1 |
| T1c-58 | I-3 | II-148 | C-1 |
| T1c-59 | I-3 | II-149 | C-1 |
| T1c-60 | I-3 | II-150 | C-1 |
| T1c-61 | I-3 | II-151 | C-1 |
| T1c-62 | I-3 | II-152 | C-1 |
| T1c-63 | I-3 | II-153 | C-1 |
| T1c-64 | I-3 | II-154 | C-1 |
| T1c-65 | I-3 | II-155 | C-1 |
| T1c-66 | I-3 | II-156 | C-1 |
| T1c-67 | I-3 | II-157 | C-1 |
| T1c-68 | I-3 | II-158 | C-1 |
| T1c-69 | I-3 | II-159 | C-1 |
| T1c-70 | I-3 | II-160 | C-1 |
| T1c-71 | I-3 | II-161 | C-1 |
| T1c-72 | I-3 | II-162 | C-1 |
| T1c-73 | I-3 | II-163 | C-1 |
| T1c-74 | I-3 | II-164 | C-1 |
| T1c-75 | I-3 | II-165 | C-1 |
| T1c-76 | I-3 | II-166 | C-1 |
| T1c-77 | I-3 | II-167 | C-1 |
| T1c-78 | I-3 | II-168 | C-1 |
| T1c-79 | I-3 | II-169 | C-1 |
| T1c-80 | I-3 | II-170 | C-1 |
| T1c-81 | I-3 | II-171 | C-1 |
| T1c-82 | I-3 | II-172 | C-1 |
| T1c-83 | I-3 | II-173 | C-1 |
| T1c-84 | I-3 | II-174 | C-1 |
| T1c-85 | I-3 | II-175 | C-1 |
| T1c-86 | I-3 | II-176 | C-1 |
| T1c-87 | I-3 | II-177 | C-1 |
| T1c-88 | I-3 | II-178 | C-1 |
| T1c-89 | I-3 | II-179 | C-1 |
| T1c-90 | I-3 | II-180 | C-1 |
| T1c-91 | I-3 | II-181 | C-1 |
| T1c-92 | I-3 | II-182 | C-1 |
| T1c-93 | I-3 | II-183 | C-1 |
| T1c-94 | I-3 | II-184 | C-1 |
| T1c-95 | I-3 | II-185 | C-1 |
| T1c-96 | I-3 | II-186 | C-1 |
| T1c-97 | I-3 | II-187 | C-1 |
| T1c-98 | I-3 | II-188 | C-1 |
| T1c-99 | I-3 | II-189 | C-1 |
| T1c-100 | I-3 | II-190 | C-1 |
| T1c-101 | I-3 | II-191 | C-1 |
| T1c-102 | I-3 | II-192 | C-1 |
| T1c-103 | I-3 | II-193 | C-1 |
| T1c-104 | I-3 | II-194 | C-1 |
| T1c-105 | I-3 | II-195 | C-1 |
| T1c-106 | I-3 | II-196 | C-1 |
| T1c-107 | I-3 | II-197 | C-1 |
| T1c-108 | I-3 | II-198 | C-1 |
| T1c-109 | I-3 | II-199 | C-1 |
| T1c-110 | I-3 | II-200 | C-1 |
| T1c-111 | I-3 | II-201 | C-1 |
| T1c-112 | I-3 | II-202 | C-1 |
| T1c-113 | I-3 | II-203 | C-1 |
| T1c-114 | I-3 | II-91 | C-2 |
| T1c-115 | I-3 | II-92 | C-2 |
| T1c-116 | I-3 | II-93 | C-2 |
| T1c-117 | I-3 | II-94 | C-2 |
| T1c-118 | I-3 | II-95 | C-2 |
| T1c-119 | I-3 | II-96 | C-2 |
| T1c-120 | I-3 | II-97 | C-2 |
| T1c-121 | I-3 | II-98 | C-2 |
| T1c-122 | I-3 | II-99 | C-2 |
| T1c-123 | I-3 | II-100 | C-2 |
| T1c-124 | I-3 | II-101 | C-2 |
| T1c-125 | I-3 | II-102 | C-2 |
| T1c-126 | I-3 | II-103 | C-2 |
| T1c-127 | I-3 | II-104 | C-2 |
| T1c-128 | I-3 | II-105 | C-2 |
| T1c-129 | I-3 | II-106 | C-2 |
| T1c-130 | I-3 | II-107 | C-2 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-131 | I-3 | II-108 | C-2 |
| T1c-132 | I-3 | II-109 | C-2 |
| T1c-133 | I-3 | II-110 | C-2 |
| T1c-134 | I-3 | II-111 | C-2 |
| T1c-135 | I-3 | II-112 | C-2 |
| T1c-136 | I-3 | II-113 | C-2 |
| T1c-137 | I-3 | II-114 | C-2 |
| T1c-138 | I-3 | II-115 | C-2 |
| T1c-139 | I-3 | II-116 | C-2 |
| T1c-140 | I-3 | II-117 | C-2 |
| T1c-141 | I-3 | II-118 | C-2 |
| T1c-142 | I-3 | II-119 | C-2 |
| T1c-143 | I-3 | II-120 | C-2 |
| T1c-144 | I-3 | II-121 | C-2 |
| T1c-145 | I-3 | II-122 | C-2 |
| T1c-146 | I-3 | II-123 | C-2 |
| T1c-147 | I-3 | II-124 | C-2 |
| T1c-148 | I-3 | II-125 | C-2 |
| T1c-149 | I-3 | II-126 | C-2 |
| T1c-150 | I-3 | II-127 | C-2 |
| T1c-151 | I-3 | II-128 | C-2 |
| T1c-152 | I-3 | II-129 | C-2 |
| T1c-153 | I-3 | II-130 | C-2 |
| T1c-154 | I-3 | II-131 | C-2 |
| T1c-155 | I-3 | II-132 | C-2 |
| T1c-156 | I-3 | II-133 | C-2 |
| T1c-157 | I-3 | II-134 | C-2 |
| T1c-158 | I-3 | II-135 | C-2 |
| T1c-159 | I-3 | II-136 | C-2 |
| T1c-160 | I-3 | II-137 | C-2 |
| T1c-161 | I-3 | II-138 | C-2 |
| T1c-162 | I-3 | II-139 | C-2 |
| T1c-163 | I-3 | II-140 | C-2 |
| T1c-164 | I-3 | II-141 | C-2 |
| T1c-165 | I-3 | II-142 | C-2 |
| T1c-166 | I-3 | II-143 | C-2 |
| T1c-167 | I-3 | II-144 | C-2 |
| T1c-168 | I-3 | II-145 | C-2 |
| T1c-169 | I-3 | II-146 | C-2 |
| T1c-170 | I-3 | II-147 | C-2 |
| T1c-171 | I-3 | II-148 | C-2 |
| T1c-172 | I-3 | II-149 | C-2 |
| T1c-173 | I-3 | II-150 | C-2 |
| T1c-174 | I-3 | II-151 | C-2 |
| T1c-175 | I-3 | II-152 | C-2 |
| T1c-176 | I-3 | II-153 | C-2 |
| T1c-177 | I-3 | II-154 | C-2 |
| T1c-178 | I-3 | II-155 | C-2 |
| T1c-179 | I-3 | II-156 | C-2 |
| T1c-180 | I-3 | II-157 | C-2 |
| T1c-181 | I-3 | II-158 | C-2 |
| T1c-182 | I-3 | II-159 | C-2 |
| T1c-183 | I-3 | II-160 | C-2 |
| T1c-184 | I-3 | II-161 | C-2 |
| T1c-185 | I-3 | II-162 | C-2 |
| T1c-186 | I-3 | II-163 | C-2 |
| T1c-187 | I-3 | II-164 | C-2 |
| T1c-188 | I-3 | II-165 | C-2 |
| T1c-189 | I-3 | II-166 | C-2 |
| T1c-190 | I-3 | II-167 | C-2 |
| T1c-191 | I-3 | II-168 | C-2 |
| T1c-192 | I-3 | II-169 | C-2 |
| T1c-193 | I-3 | II-170 | C-2 |
| T1c-194 | I-3 | II-171 | C-2 |
| T1c-195 | I-3 | II-172 | C-2 |
| T1c-196 | I-3 | II-173 | C-2 |
| T1c-197 | I-3 | II-174 | C-2 |
| T1c-198 | I-3 | II-175 | C-2 |
| T1c-199 | I-3 | II-176 | C-2 |
| T1c-200 | I-3 | II-177 | C-2 |
| T1c-201 | I-3 | II-178 | C-2 |
| T1c-202 | I-3 | II-179 | C-2 |
| T1c-203 | I-3 | II-180 | C-2 |
| T1c-204 | I-3 | II-181 | C-2 |
| T1c-205 | I-3 | II-182 | C-2 |
| T1c-206 | I-3 | II-183 | C-2 |
| T1c-207 | I-3 | II-184 | C-2 |
| T1c-208 | I-3 | II-185 | C-2 |
| T1c-209 | I-3 | II-186 | C-2 |
| T1c-210 | I-3 | II-187 | C-2 |
| T1c-211 | I-3 | II-188 | C-2 |
| T1c-212 | I-3 | II-189 | C-2 |
| T1c-213 | I-3 | II-190 | C-2 |
| T1c-214 | I-3 | II-191 | C-2 |
| T1c-215 | I-3 | II-192 | C-2 |
| T1c-216 | I-3 | II-193 | C-2 |
| T1c-217 | I-3 | II-194 | C-2 |
| T1c-218 | I-3 | II-195 | C-2 |
| T1c-219 | I-3 | II-196 | C-2 |
| T1c-220 | I-3 | II-197 | C-2 |
| T1c-221 | I-3 | II-198 | C-2 |
| T1c-222 | I-3 | II-199 | C-2 |
| T1c-223 | I-3 | II-200 | C-2 |
| T1c-224 | I-3 | II-201 | C-2 |
| T1c-225 | I-3 | II-202 | C-2 |
| T1c-226 | I-3 | II-203 | C-2 |
| T1c-227 | I-3 | II-91 | C-3 |
| T1c-228 | I-3 | II-92 | C-3 |
| T1c-229 | I-3 | II-93 | C-3 |
| T1c-230 | I-3 | II-94 | C-3 |
| T1c-231 | I-3 | II-95 | C-3 |
| T1c-232 | I-3 | II-96 | C-3 |
| T1c-233 | I-3 | II-97 | C-3 |
| T1c-234 | I-3 | II-98 | C-3 |
| T1c-235 | I-3 | II-99 | C-3 |
| T1c-236 | I-3 | II-100 | C-3 |
| T1c-237 | I-3 | II-101 | C-3 |
| T1c-238 | I-3 | II-102 | C-3 |
| T1c-239 | I-3 | II-103 | C-3 |
| T1c-240 | I-3 | II-104 | C-3 |
| T1c-241 | I-3 | II-105 | C-3 |
| T1c-242 | I-3 | II-106 | C-3 |
| T1c-243 | I-3 | II-107 | C-3 |
| T1c-244 | I-3 | II-108 | C-3 |
| T1c-245 | I-3 | II-109 | C-3 |
| T1c-246 | I-3 | II-110 | C-3 |
| T1c-247 | I-3 | II-111 | C-3 |
| T1c-248 | I-3 | II-112 | C-3 |
| T1c-249 | I-3 | II-113 | C-3 |
| T1c-250 | I-3 | II-114 | C-3 |
| T1c-251 | I-3 | II-115 | C-3 |
| T1c-252 | I-3 | II-116 | C-3 |
| T1c-253 | I-3 | II-117 | C-3 |
| T1c-254 | I-3 | II-118 | C-3 |
| T1c-255 | I-3 | II-119 | C-3 |
| T1c-256 | I-3 | II-120 | C-3 |
| T1c-257 | I-3 | II-121 | C-3 |
| T1c-258 | I-3 | II-122 | C-3 |
| T1c-259 | I-3 | II-123 | C-3 |
| T1c-260 | I-3 | II-124 | C-3 |
| T1c-261 | I-3 | II-125 | C-3 |
| T1c-262 | I-3 | II-126 | C-3 |
| T1c-263 | I-3 | II-127 | C-3 |
| T1c-264 | I-3 | II-128 | C-3 |
| T1c-265 | I-3 | II-129 | C-3 |
| T1c-266 | I-3 | II-130 | C-3 |
| T1c-267 | I-3 | II-131 | C-3 |
| T1c-268 | I-3 | II-132 | C-3 |
| T1c-269 | I-3 | II-133 | C-3 |
| T1c-270 | I-3 | II-134 | C-3 |
| T1c-271 | I-3 | II-135 | C-3 |
| T1c-272 | I-3 | II-136 | C-3 |
| T1c-273 | I-3 | II-137 | C-3 |
| T1c-274 | I-3 | II-138 | C-3 |
| T1c-275 | I-3 | II-139 | C-3 |
| T1c-276 | I-3 | II-140 | C-3 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-277 | I-3 | II-141 | C-3 |
| T1c-278 | I-3 | II-142 | C-3 |
| T1c-279 | I-3 | II-143 | C-3 |
| T1c-280 | I-3 | II-144 | C-3 |
| T1c-281 | I-3 | II-145 | C-3 |
| T1c-282 | I-3 | II-146 | C-3 |
| T1c-283 | I-3 | II-147 | C-3 |
| T1c-284 | I-3 | II-148 | C-3 |
| T1c-285 | I-3 | II-149 | C-3 |
| T1c-286 | I-3 | II-150 | C-3 |
| T1c-287 | I-3 | II-151 | C-3 |
| T1c-288 | I-3 | II-152 | C-3 |
| T1c-289 | I-3 | II-153 | C-3 |
| T1c-290 | I-3 | II-154 | C-3 |
| T1c-291 | I-3 | II-155 | C-3 |
| T1c-292 | I-3 | II-156 | C-3 |
| T1c-293 | I-3 | II-157 | C-3 |
| T1c-294 | I-3 | II-158 | C-3 |
| T1c-295 | I-3 | II-159 | C-3 |
| T1c-296 | I-3 | II-160 | C-3 |
| T1c-297 | I-3 | II-161 | C-3 |
| T1c-298 | I-3 | II-162 | C-3 |
| T1c-299 | I-3 | II-163 | C-3 |
| T1c-300 | I-3 | II-164 | C-3 |
| T1c-301 | I-3 | II-165 | C-3 |
| T1c-302 | I-3 | II-166 | C-3 |
| T1c-303 | I-3 | II-167 | C-3 |
| T1c-304 | I-3 | II-168 | C-3 |
| T1c-305 | I-3 | II-169 | C-3 |
| T1c-306 | I-3 | II-170 | C-3 |
| T1c-307 | I-3 | II-171 | C-3 |
| T1c-308 | I-3 | II-172 | C-3 |
| T1c-309 | I-3 | II-173 | C-3 |
| T1c-310 | I-3 | II-174 | C-3 |
| T1c-311 | I-3 | II-175 | C-3 |
| T1c-312 | I-3 | II-176 | C-3 |
| T1c-313 | I-3 | II-177 | C-3 |
| T1c-314 | I-3 | II-178 | C-3 |
| T1c-315 | I-3 | II-179 | C-3 |
| T1c-316 | I-3 | II-180 | C-3 |
| T1c-317 | I-3 | II-181 | C-3 |
| T1c-318 | I-3 | II-182 | C-3 |
| T1c-319 | I-3 | II-183 | C-3 |
| T1c-320 | I-3 | II-184 | C-3 |
| T1c-321 | I-3 | II-185 | C-3 |
| T1c-322 | I-3 | II-186 | C-3 |
| T1c-323 | I-3 | II-187 | C-3 |
| T1c-324 | I-3 | II-188 | C-3 |
| T1c-325 | I-3 | II-189 | C-3 |
| T1c-326 | I-3 | II-190 | C-3 |
| T1c-327 | I-3 | II-191 | C-3 |
| T1c-328 | I-3 | II-192 | C-3 |
| T1c-329 | I-3 | II-193 | C-3 |
| T1c-330 | I-3 | II-194 | C-3 |
| T1c-331 | I-3 | II-195 | C-3 |
| T1c-332 | I-3 | II-196 | C-3 |
| T1c-333 | I-3 | II-197 | C-3 |
| T1c-334 | I-3 | II-198 | C-3 |
| T1c-335 | I-3 | II-199 | C-3 |
| T1c-336 | I-3 | II-200 | C-3 |
| T1c-337 | I-3 | II-201 | C-3 |
| T1c-338 | I-3 | II-202 | C-3 |
| T1c-339 | I-3 | II-203 | C-3 |
| T1c-340 | I-3 | II-91 | C-4 |
| T1c-341 | I-3 | II-92 | C-4 |
| T1c-342 | I-3 | II-93 | C-4 |
| T1c-343 | I-3 | II-94 | C-4 |
| T1c-344 | I-3 | II-95 | C-4 |
| T1c-345 | I-3 | II-96 | C-4 |
| T1c-346 | I-3 | II-97 | C-4 |
| T1c-347 | I-3 | II-98 | C-4 |
| T1c-348 | I-3 | II-99 | C-4 |
| T1c-349 | I-3 | II-100 | C-4 |
| T1c-350 | I-3 | II-101 | C-4 |
| T1c-351 | I-3 | II-102 | C-4 |
| T1c-352 | I-3 | II-103 | C-4 |
| T1c-353 | I-3 | II-104 | C-4 |
| T1c-354 | I-3 | II-105 | C-4 |
| T1c-355 | I-3 | II-106 | C-4 |
| T1c-356 | I-3 | II-107 | C-4 |
| T1c-357 | I-3 | II-108 | C-4 |
| T1c-358 | I-3 | II-109 | C-4 |
| T1c-359 | I-3 | II-110 | C-4 |
| T1c-360 | I-3 | II-111 | C-4 |
| T1c-361 | I-3 | II-112 | C-4 |
| T1c-362 | I-3 | II-113 | C-4 |
| T1c-363 | I-3 | II-114 | C-4 |
| T1c-364 | I-3 | II-115 | C-4 |
| T1c-365 | I-3 | II-116 | C-4 |
| T1c-366 | I-3 | II-117 | C-4 |
| T1c-367 | I-3 | II-118 | C-4 |
| T1c-368 | I-3 | II-119 | C-4 |
| T1c-369 | I-3 | II-120 | C-4 |
| T1c-370 | I-3 | II-121 | C-4 |
| T1c-371 | I-3 | II-122 | C-4 |
| T1c-372 | I-3 | II-123 | C-4 |
| T1c-373 | I-3 | II-124 | C-4 |
| T1c-374 | I-3 | II-125 | C-4 |
| T1c-375 | I-3 | II-126 | C-4 |
| T1c-376 | I-3 | II-127 | C-4 |
| T1c-377 | I-3 | II-128 | C-4 |
| T1c-378 | I-3 | II-129 | C-4 |
| T1c-379 | I-3 | II-130 | C-4 |
| T1c-380 | I-3 | II-131 | C-4 |
| T1c-381 | I-3 | II-132 | C-4 |
| T1c-382 | I-3 | II-133 | C-4 |
| T1c-383 | I-3 | II-134 | C-4 |
| T1c-384 | I-3 | II-135 | C-4 |
| T1c-385 | I-3 | II-136 | C-4 |
| T1c-386 | I-3 | II-137 | C-4 |
| T1c-387 | I-3 | II-138 | C-4 |
| T1c-388 | I-3 | II-139 | C-4 |
| T1c-389 | I-3 | II-140 | C-4 |
| T1c-390 | I-3 | II-141 | C-4 |
| T1c-391 | I-3 | II-142 | C-4 |
| T1c-392 | I-3 | II-143 | C-4 |
| T1c-393 | I-3 | II-144 | C-4 |
| T1c-394 | I-3 | II-145 | C-4 |
| T1c-395 | I-3 | II-146 | C-4 |
| T1c-396 | I-3 | II-147 | C-4 |
| T1c-397 | I-3 | II-148 | C-4 |
| T1c-398 | I-3 | II-149 | C-4 |
| T1c-399 | I-3 | II-150 | C-4 |
| T1c-400 | I-3 | II-151 | C-4 |
| T1c-401 | I-3 | II-152 | C-4 |
| T1c-402 | I-3 | II-153 | C-4 |
| T1c-403 | I-3 | II-154 | C-4 |
| T1c-404 | I-3 | II-155 | C-4 |
| T1c-405 | I-3 | II-156 | C-4 |
| T1c-406 | I-3 | II-157 | C-4 |
| T1c-407 | I-3 | II-158 | C-4 |
| T1c-408 | I-3 | II-159 | C-4 |
| T1c-409 | I-3 | II-160 | C-4 |
| T1c-410 | I-3 | II-161 | C-4 |
| T1c-411 | I-3 | II-162 | C-4 |
| T1c-412 | I-3 | II-163 | C-4 |
| T1c-413 | I-3 | II-164 | C-4 |
| T1c-414 | I-3 | II-165 | C-4 |
| T1c-415 | I-3 | II-166 | C-4 |
| T1c-416 | I-3 | II-167 | C-4 |
| T1c-417 | I-3 | II-168 | C-4 |
| T1c-418 | I-3 | II-169 | C-4 |
| T1c-419 | I-3 | II-170 | C-4 |
| T1c-420 | I-3 | II-171 | C-4 |
| T1c-421 | I-3 | II-172 | C-4 |
| T1c-422 | I-3 | II-173 | C-4 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-423 | I-3 | II-174 | C-4 |
| T1c-424 | I-3 | II-175 | C-4 |
| T1c-425 | I-3 | II-176 | C-4 |
| T1c-426 | I-3 | II-177 | C-4 |
| T1c-427 | I-3 | II-178 | C-4 |
| T1c-428 | I-3 | II-179 | C-4 |
| T1c-429 | I-3 | II-180 | C-4 |
| T1c-430 | I-3 | II-181 | C-4 |
| T1c-431 | I-3 | II-182 | C-4 |
| T1c-432 | I-3 | II-183 | C-4 |
| T1c-433 | I-3 | II-184 | C-4 |
| T1c-434 | I-3 | II-185 | C-4 |
| T1c-435 | I-3 | II-186 | C-4 |
| T1c-436 | I-3 | II-187 | C-4 |
| T1c-437 | I-3 | II-188 | C-4 |
| T1c-438 | I-3 | II-189 | C-4 |
| T1c-439 | I-3 | II-190 | C-4 |
| T1c-440 | I-3 | II-191 | C-4 |
| T1c-441 | I-3 | II-192 | C-4 |
| T1c-442 | I-3 | II-193 | C-4 |
| T1c-443 | I-3 | II-194 | C-4 |
| T1c-444 | I-3 | II-195 | C-4 |
| T1c-445 | I-3 | II-196 | C-4 |
| T1c-446 | I-3 | II-197 | C-4 |
| T1c-447 | I-3 | II-198 | C-4 |
| T1c-448 | I-3 | II-199 | C-4 |
| T1c-449 | I-3 | II-200 | C-4 |
| T1c-450 | I-3 | II-201 | C-4 |
| T1c-451 | I-3 | II-202 | C-4 |
| T1c-452 | I-3 | II-203 | C-4 |
| T1c-453 | I-3 | II-91 | C-5 |
| T1c-454 | I-3 | II-92 | C-5 |
| T1c-455 | I-3 | II-93 | C-5 |
| T1c-456 | I-3 | II-94 | C-5 |
| T1c-457 | I-3 | II-95 | C-5 |
| T1c-458 | I-3 | II-96 | C-5 |
| T1c-459 | I-3 | II-97 | C-5 |
| T1c-460 | I-3 | II-98 | C-5 |
| T1c-461 | I-3 | II-99 | C-5 |
| T1c-462 | I-3 | II-100 | C-5 |
| T1c-463 | I-3 | II-101 | C-5 |
| T1c-464 | I-3 | II-102 | C-5 |
| T1c-465 | I-3 | II-103 | C-5 |
| T1c-466 | I-3 | II-104 | C-5 |
| T1c-467 | I-3 | II-105 | C-5 |
| T1c-468 | I-3 | II-106 | C-5 |
| T1c-469 | I-3 | II-107 | C-5 |
| T1c-470 | I-3 | II-108 | C-5 |
| T1c-471 | I-3 | II-109 | C-5 |
| T1c-472 | I-3 | II-110 | C-5 |
| T1c-473 | I-3 | II-111 | C-5 |
| T1c-474 | I-3 | II-112 | C-5 |
| T1c-475 | I-3 | II-113 | C-5 |
| T1c-476 | I-3 | II-114 | C-5 |
| T1c-477 | I-3 | II-115 | C-5 |
| T1c-478 | I-3 | II-116 | C-5 |
| T1c-479 | I-3 | II-117 | C-5 |
| T1c-480 | I-3 | II-118 | C-5 |
| T1c-481 | I-3 | II-119 | C-5 |
| T1c-482 | I-3 | II-120 | C-5 |
| T1c-483 | I-3 | II-121 | C-5 |
| T1c-484 | I-3 | II-122 | C-5 |
| T1c-485 | I-3 | II-123 | C-5 |
| T1c-486 | I-3 | II-124 | C-5 |
| T1c-487 | I-3 | II-125 | C-5 |
| T1c-488 | I-3 | II-126 | C-5 |
| T1c-489 | I-3 | II-127 | C-5 |
| T1c-490 | I-3 | II-128 | C-5 |
| T1c-491 | I-3 | II-129 | C-5 |
| T1c-492 | I-3 | II-130 | C-5 |
| T1c-493 | I-3 | II-131 | C-5 |
| T1c-494 | I-3 | II-132 | C-5 |
| T1c-495 | I-3 | II-133 | C-5 |
| T1c-496 | I-3 | II-134 | C-5 |
| T1c-497 | I-3 | II-135 | C-5 |
| T1c-498 | I-3 | II-136 | C-5 |
| T1c-499 | I-3 | II-137 | C-5 |
| T1c-500 | I-3 | II-138 | C-5 |
| T1c-501 | I-3 | II-139 | C-5 |
| T1c-502 | I-3 | II-140 | C-5 |
| T1c-503 | I-3 | II-141 | C-5 |
| T1c-504 | I-3 | II-142 | C-5 |
| T1c-505 | I-3 | II-143 | C-5 |
| T1c-506 | I-3 | II-144 | C-5 |
| T1c-507 | I-3 | II-145 | C-5 |
| T1c-508 | I-3 | II-146 | C-5 |
| T1c-509 | I-3 | II-147 | C-5 |
| T1c-510 | I-3 | II-148 | C-5 |
| T1c-511 | I-3 | II-149 | C-5 |
| T1c-512 | I-3 | II-150 | C-5 |
| T1c-513 | I-3 | II-151 | C-5 |
| T1c-514 | I-3 | II-152 | C-5 |
| T1c-515 | I-3 | II-153 | C-5 |
| T1c-516 | I-3 | II-154 | C-5 |
| T1c-517 | I-3 | II-155 | C-5 |
| T1c-518 | I-3 | II-156 | C-5 |
| T1c-519 | I-3 | II-157 | C-5 |
| T1c-520 | I-3 | II-158 | C-5 |
| T1c-521 | I-3 | II-159 | C-5 |
| T1c-522 | I-3 | II-160 | C-5 |
| T1c-523 | I-3 | II-161 | C-5 |
| T1c-524 | I-3 | II-162 | C-5 |
| T1c-525 | I-3 | II-163 | C-5 |
| T1c-526 | I-3 | II-164 | C-5 |
| T1c-527 | I-3 | II-165 | C-5 |
| T1c-528 | I-3 | II-166 | C-5 |
| T1c-529 | I-3 | II-167 | C-5 |
| T1c-530 | I-3 | II-168 | C-5 |
| T1c-531 | I-3 | II-169 | C-5 |
| T1c-532 | I-3 | II-170 | C-5 |
| T1c-533 | I-3 | II-171 | C-5 |
| T1c-534 | I-3 | II-172 | C-5 |
| T1c-535 | I-3 | II-173 | C-5 |
| T1c-536 | I-3 | II-174 | C-5 |
| T1c-537 | I-3 | II-175 | C-5 |
| T1c-538 | I-3 | II-176 | C-5 |
| T1c-539 | I-3 | II-177 | C-5 |
| T1c-540 | I-3 | II-178 | C-5 |
| T1c-541 | I-3 | II-179 | C-5 |
| T1c-542 | I-3 | II-180 | C-5 |
| T1c-543 | I-3 | II-181 | C-5 |
| T1c-544 | I-3 | II-182 | C-5 |
| T1c-545 | I-3 | II-183 | C-5 |
| T1c-546 | I-3 | II-184 | C-5 |
| T1c-547 | I-3 | II-185 | C-5 |
| T1c-548 | I-3 | II-186 | C-5 |
| T1c-549 | I-3 | II-187 | C-5 |
| T1c-550 | I-3 | II-188 | C-5 |
| T1c-551 | I-3 | II-189 | C-5 |
| T1c-552 | I-3 | II-190 | C-5 |
| T1c-553 | I-3 | II-191 | C-5 |
| T1c-554 | I-3 | II-192 | C-5 |
| T1c-555 | I-3 | II-193 | C-5 |
| T1c-556 | I-3 | II-194 | C-5 |
| T1c-557 | I-3 | II-195 | C-5 |
| T1c-558 | I-3 | II-196 | C-5 |
| T1c-559 | I-3 | II-197 | C-5 |
| T1c-560 | I-3 | II-198 | C-5 |
| T1c-561 | I-3 | II-199 | C-5 |
| T1c-562 | I-3 | II-200 | C-5 |
| T1c-563 | I-3 | II-201 | C-5 |
| T1c-564 | I-3 | II-202 | C-5 |
| T1c-565 | I-3 | II-203 | C-5 |
| T1c-566 | I-3 | II-91 | C-6 |
| T1c-567 | I-3 | II-92 | C-6 |
| T1c-568 | I-3 | II-93 | C-6 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-569 | I-3 | II-94 | C-6 |
| T1c-570 | I-3 | II-95 | C-6 |
| T1c-571 | I-3 | II-96 | C-6 |
| T1c-572 | I-3 | II-97 | C-6 |
| T1c-573 | I-3 | II-98 | C-6 |
| T1c-574 | I-3 | II-99 | C-6 |
| T1c-575 | I-3 | II-100 | C-6 |
| T1c-576 | I-3 | II-101 | C-6 |
| T1c-577 | I-3 | II-102 | C-6 |
| T1c-578 | I-3 | II-103 | C-6 |
| T1c-579 | I-3 | II-104 | C-6 |
| T1c-580 | I-3 | II-105 | C-6 |
| T1c-581 | I-3 | II-106 | C-6 |
| T1c-582 | I-3 | II-107 | C-6 |
| T1c-583 | I-3 | II-108 | C-6 |
| T1c-584 | I-3 | II-109 | C-6 |
| T1c-585 | I-3 | II-110 | C-6 |
| T1c-586 | I-3 | II-111 | C-6 |
| T1c-587 | I-3 | II-112 | C-6 |
| T1c-588 | I-3 | II-113 | C-6 |
| T1c-589 | I-3 | II-114 | C-6 |
| T1c-590 | I-3 | II-115 | C-6 |
| T1c-591 | I-3 | II-116 | C-6 |
| T1c-592 | I-3 | II-117 | C-6 |
| T1c-593 | I-3 | II-118 | C-6 |
| T1c-594 | I-3 | II-119 | C-6 |
| T1c-595 | I-3 | II-120 | C-6 |
| T1c-596 | I-3 | II-121 | C-6 |
| T1c-597 | I-3 | II-122 | C-6 |
| T1c-598 | I-3 | II-123 | C-6 |
| T1c-599 | I-3 | II-124 | C-6 |
| T1c-600 | I-3 | II-125 | C-6 |
| T1c-601 | I-3 | II-126 | C-6 |
| T1c-602 | I-3 | II-127 | C-6 |
| T1c-603 | I-3 | II-128 | C-6 |
| T1c-604 | I-3 | II-129 | C-6 |
| T1c-605 | I-3 | II-130 | C-6 |
| T1c-606 | I-3 | II-131 | C-6 |
| T1c-607 | I-3 | II-132 | C-6 |
| T1c-608 | I-3 | II-133 | C-6 |
| T1c-609 | I-3 | II-134 | C-6 |
| T1c-610 | I-3 | II-135 | C-6 |
| T1c-611 | I-3 | II-136 | C-6 |
| T1c-612 | I-3 | II-137 | C-6 |
| T1c-613 | I-3 | II-138 | C-6 |
| T1c-614 | I-3 | II-139 | C-6 |
| T1c-615 | I-3 | II-140 | C-6 |
| T1c-616 | I-3 | II-141 | C-6 |
| T1c-617 | I-3 | II-142 | C-6 |
| T1c-618 | I-3 | II-143 | C-6 |
| T1c-619 | I-3 | II-144 | C-6 |
| T1c-620 | I-3 | II-145 | C-6 |
| T1c-621 | I-3 | II-146 | C-6 |
| T1c-622 | I-3 | II-147 | C-6 |
| T1c-623 | I-3 | II-148 | C-6 |
| T1c-624 | I-3 | II-149 | C-6 |
| T1c-625 | I-3 | II-150 | C-6 |
| T1c-626 | I-3 | II-151 | C-6 |
| T1c-627 | I-3 | II-152 | C-6 |
| T1c-628 | I-3 | II-153 | C-6 |
| T1c-629 | I-3 | II-154 | C-6 |
| T1c-630 | I-3 | II-155 | C-6 |
| T1c-631 | I-3 | II-156 | C-6 |
| T1c-632 | I-3 | II-157 | C-6 |
| T1c-633 | I-3 | II-158 | C-6 |
| T1c-634 | I-3 | II-159 | C-6 |
| T1c-635 | I-3 | II-160 | C-6 |
| T1c-636 | I-3 | II-161 | C-6 |
| T1c-637 | I-3 | II-162 | C-6 |
| T1c-638 | I-3 | II-163 | C-6 |
| T1c-639 | I-3 | II-164 | C-6 |
| T1c-640 | I-3 | II-165 | C-6 |
| T1c-641 | I-3 | II-166 | C-6 |
| T1c-642 | I-3 | II-167 | C-6 |
| T1c-643 | I-3 | II-168 | C-6 |
| T1c-644 | I-3 | II-169 | C-6 |
| T1c-645 | I-3 | II-170 | C-6 |
| T1c-646 | I-3 | II-171 | C-6 |
| T1c-647 | I-3 | II-172 | C-6 |
| T1c-648 | I-3 | II-173 | C-6 |
| T1c-649 | I-3 | II-174 | C-6 |
| T1c-650 | I-3 | II-175 | C-6 |
| T1c-651 | I-3 | II-176 | C-6 |
| T1c-652 | I-3 | II-177 | C-6 |
| T1c-653 | I-3 | II-178 | C-6 |
| T1c-654 | I-3 | II-179 | C-6 |
| T1c-655 | I-3 | II-180 | C-6 |
| T1c-656 | I-3 | II-181 | C-6 |
| T1c-657 | I-3 | II-182 | C-6 |
| T1c-658 | I-3 | II-183 | C-6 |
| T1c-659 | I-3 | II-184 | C-6 |
| T1c-660 | I-3 | II-185 | C-6 |
| T1c-661 | I-3 | II-186 | C-6 |
| T1c-662 | I-3 | II-187 | C-6 |
| T1c-663 | I-3 | II-188 | C-6 |
| T1c-664 | I-3 | II-189 | C-6 |
| T1c-665 | I-3 | II-190 | C-6 |
| T1c-666 | I-3 | II-191 | C-6 |
| T1c-667 | I-3 | II-192 | C-6 |
| T1c-668 | I-3 | II-193 | C-6 |
| T1c-669 | I-3 | II-194 | C-6 |
| T1c-670 | I-3 | II-195 | C-6 |
| T1c-671 | I-3 | II-196 | C-6 |
| T1c-672 | I-3 | II-197 | C-6 |
| T1c-673 | I-3 | II-198 | C-6 |
| T1c-674 | I-3 | II-199 | C-6 |
| T1c-675 | I-3 | II-200 | C-6 |
| T1c-676 | I-3 | II-201 | C-6 |
| T1c-677 | I-3 | II-202 | C-6 |
| T1c-678 | I-3 | II-203 | C-6 |
| T1c-679 | I-3 | II-91 | C-7 |
| T1c-680 | I-3 | II-92 | C-7 |
| T1c-681 | I-3 | II-93 | C-7 |
| T1c-682 | I-3 | II-94 | C-7 |
| T1c-683 | I-3 | II-95 | C-7 |
| T1c-684 | I-3 | II-96 | C-7 |
| T1c-685 | I-3 | II-97 | C-7 |
| T1c-686 | I-3 | II-98 | C-7 |
| T1c-687 | I-3 | II-99 | C-7 |
| T1c-688 | I-3 | II-100 | C-7 |
| T1c-689 | I-3 | II-101 | C-7 |
| T1c-690 | I-3 | II-102 | C-7 |
| T1c-691 | I-3 | II-103 | C-7 |
| T1c-692 | I-3 | II-104 | C-7 |
| T1c-693 | I-3 | II-105 | C-7 |
| T1c-694 | I-3 | II-106 | C-7 |
| T1c-695 | I-3 | II-107 | C-7 |
| T1c-696 | I-3 | II-108 | C-7 |
| T1c-697 | I-3 | II-109 | C-7 |
| T1c-698 | I-3 | II-110 | C-7 |
| T1c-699 | I-3 | II-111 | C-7 |
| T1c-700 | I-3 | II-112 | C-7 |
| T1c-701 | I-3 | II-113 | C-7 |
| T1c-702 | I-3 | II-114 | C-7 |
| T1c-703 | I-3 | II-115 | C-7 |
| T1c-704 | I-3 | II-116 | C-7 |
| T1c-705 | I-3 | II-117 | C-7 |
| T1c-706 | I-3 | II-118 | C-7 |
| T1c-707 | I-3 | II-119 | C-7 |
| T1c-708 | I-3 | II-120 | C-7 |
| T1c-709 | I-3 | II-121 | C-7 |
| T1c-710 | I-3 | II-122 | C-7 |
| T1c-711 | I-3 | II-123 | C-7 |
| T1c-712 | I-3 | II-124 | C-7 |
| T1c-713 | I-3 | II-125 | C-7 |
| T1c-714 | I-3 | II-126 | C-7 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-715 | I-3 | II-127 | C-7 |
| T1c-716 | I-3 | II-128 | C-7 |
| T1c-717 | I-3 | II-129 | C-7 |
| T1c-718 | I-3 | II-130 | C-7 |
| T1c-719 | I-3 | II-131 | C-7 |
| T1c-720 | I-3 | II-132 | C-7 |
| T1c-721 | I-3 | II-133 | C-7 |
| T1c-722 | I-3 | II-134 | C-7 |
| T1c-723 | I-3 | II-135 | C-7 |
| T1c-724 | I-3 | II-136 | C-7 |
| T1c-725 | I-3 | II-137 | C-7 |
| T1c-726 | I-3 | II-138 | C-7 |
| T1c-727 | I-3 | II-139 | C-7 |
| T1c-728 | I-3 | II-140 | C-7 |
| T1c-729 | I-3 | II-141 | C-7 |
| T1c-730 | I-3 | II-142 | C-7 |
| T1c-731 | I-3 | II-143 | C-7 |
| T1c-732 | I-3 | II-144 | C-7 |
| T1c-733 | I-3 | II-145 | C-7 |
| T1c-734 | I-3 | II-146 | C-7 |
| T1c-735 | I-3 | II-147 | C-7 |
| T1c-736 | I-3 | II-148 | C-7 |
| T1c-737 | I-3 | II-149 | C-7 |
| T1c-738 | I-3 | II-150 | C-7 |
| T1c-739 | I-3 | II-151 | C-7 |
| T1c-740 | I-3 | II-152 | C-7 |
| T1c-741 | I-3 | II-153 | C-7 |
| T1c-742 | I-3 | II-154 | C-7 |
| T1c-743 | I-3 | II-155 | C-7 |
| T1c-744 | I-3 | II-156 | C-7 |
| T1c-745 | I-3 | II-157 | C-7 |
| T1c-746 | I-3 | II-158 | C-7 |
| T1c-747 | I-3 | II-159 | C-7 |
| T1c-748 | I-3 | II-160 | C-7 |
| T1c-749 | I-3 | II-161 | C-7 |
| T1c-750 | I-3 | II-162 | C-7 |
| T1c-751 | I-3 | II-163 | C-7 |
| T1c-752 | I-3 | II-164 | C-7 |
| T1c-753 | I-3 | II-165 | C-7 |
| T1c-754 | I-3 | II-166 | C-7 |
| T1c-755 | I-3 | II-167 | C-7 |
| T1c-756 | I-3 | II-168 | C-7 |
| T1c-757 | I-3 | II-169 | C-7 |
| T1c-758 | I-3 | II-170 | C-7 |
| T1c-759 | I-3 | II-171 | C-7 |
| T1c-760 | I-3 | II-172 | C-7 |
| T1c-761 | I-3 | II-173 | C-7 |
| T1c-762 | I-3 | II-174 | C-7 |
| T1c-763 | I-3 | II-175 | C-7 |
| T1c-764 | I-3 | II-176 | C-7 |
| T1c-765 | I-3 | II-177 | C-7 |
| T1c-766 | I-3 | II-178 | C-7 |
| T1c-767 | I-3 | II-179 | C-7 |
| T1c-768 | I-3 | II-180 | C-7 |
| T1c-769 | I-3 | II-181 | C-7 |
| T1c-770 | I-3 | II-182 | C-7 |
| T1c-771 | I-3 | II-183 | C-7 |
| T1c-772 | I-3 | II-184 | C-7 |
| T1c-773 | I-3 | II-185 | C-7 |
| T1c-774 | I-3 | II-186 | C-7 |
| T1c-775 | I-3 | II-187 | C-7 |
| T1c-776 | I-3 | II-188 | C-7 |
| T1c-777 | I-3 | II-189 | C-7 |
| T1c-778 | I-3 | II-190 | C-7 |
| T1c-779 | I-3 | II-191 | C-7 |
| T1c-780 | I-3 | II-192 | C-7 |
| T1c-781 | I-3 | II-193 | C-7 |
| T1c-782 | I-3 | II-194 | C-7 |
| T1c-783 | I-3 | II-195 | C-7 |
| T1c-784 | I-3 | II-196 | C-7 |
| T1c-785 | I-3 | II-197 | C-7 |
| T1c-786 | I-3 | II-198 | C-7 |
| T1c-787 | I-3 | II-199 | C-7 |
| T1c-788 | I-3 | II-200 | C-7 |
| T1c-789 | I-3 | II-201 | C-7 |
| T1c-790 | I-3 | II-202 | C-7 |
| T1c-791 | I-3 | II-203 | C-7 |
| T1c-792 | I-3 | II-91 | C-8 |
| T1c-793 | I-3 | II-92 | C-8 |
| T1c-794 | I-3 | II-93 | C-8 |
| T1c-795 | I-3 | II-94 | C-8 |
| T1c-796 | I-3 | II-95 | C-8 |
| T1c-797 | I-3 | II-96 | C-8 |
| T1c-798 | I-3 | II-97 | C-8 |
| T1c-799 | I-3 | II-98 | C-8 |
| T1c-800 | I-3 | II-99 | C-8 |
| T1c-801 | I-3 | II-100 | C-8 |
| T1c-802 | I-3 | II-101 | C-8 |
| T1c-803 | I-3 | II-102 | C-8 |
| T1c-804 | I-3 | II-103 | C-8 |
| T1c-805 | I-3 | II-104 | C-8 |
| T1c-806 | I-3 | II-105 | C-8 |
| T1c-807 | I-3 | II-106 | C-8 |
| T1c-808 | I-3 | II-107 | C-8 |
| T1c-809 | I-3 | II-108 | C-8 |
| T1c-810 | I-3 | II-109 | C-8 |
| T1c-811 | I-3 | II-110 | C-8 |
| T1c-812 | I-3 | II-111 | C-8 |
| T1c-813 | I-3 | II-112 | C-8 |
| T1c-814 | I-3 | II-113 | C-8 |
| T1c-815 | I-3 | II-114 | C-8 |
| T1c-816 | I-3 | II-115 | C-8 |
| T1c-817 | I-3 | II-116 | C-8 |
| T1c-818 | I-3 | II-117 | C-8 |
| T1c-819 | I-3 | II-118 | C-8 |
| T1c-820 | I-3 | II-119 | C-8 |
| T1c-821 | I-3 | II-120 | C-8 |
| T1c-822 | I-3 | II-121 | C-8 |
| T1c-823 | I-3 | II-122 | C-8 |
| T1c-824 | I-3 | II-123 | C-8 |
| T1c-825 | I-3 | II-124 | C-8 |
| T1c-826 | I-3 | II-125 | C-8 |
| T1c-827 | I-3 | II-126 | C-8 |
| T1c-828 | I-3 | II-127 | C-8 |
| T1c-829 | I-3 | II-128 | C-8 |
| T1c-830 | I-3 | II-129 | C-8 |
| T1c-831 | I-3 | II-130 | C-8 |
| T1c-832 | I-3 | II-131 | C-8 |
| T1c-833 | I-3 | II-132 | C-8 |
| T1c-834 | I-3 | II-133 | C-8 |
| T1c-835 | I-3 | II-134 | C-8 |
| T1c-836 | I-3 | II-135 | C-8 |
| T1c-837 | I-3 | II-136 | C-8 |
| T1c-838 | I-3 | II-137 | C-8 |
| T1c-839 | I-3 | II-138 | C-8 |
| T1c-840 | I-3 | II-139 | C-8 |
| T1c-841 | I-3 | II-140 | C-8 |
| T1c-842 | I-3 | II-141 | C-8 |
| T1c-843 | I-3 | II-142 | C-8 |
| T1c-844 | I-3 | II-143 | C-8 |
| T1c-845 | I-3 | II-144 | C-8 |
| T1c-846 | I-3 | II-145 | C-8 |
| T1c-847 | I-3 | II-146 | C-8 |
| T1c-848 | I-3 | II-147 | C-8 |
| T1c-849 | I-3 | II-148 | C-8 |
| T1c-850 | I-3 | II-149 | C-8 |
| T1c-851 | I-3 | II-150 | C-8 |
| T1c-852 | I-3 | II-151 | C-8 |
| T1c-853 | I-3 | II-152 | C-8 |
| T1c-854 | I-3 | II-153 | C-8 |
| T1c-855 | I-3 | II-154 | C-8 |
| T1c-856 | I-3 | II-155 | C-8 |
| T1c-857 | I-3 | II-156 | C-8 |
| T1c-858 | I-3 | II-157 | C-8 |
| T1c-859 | I-3 | II-158 | C-8 |
| T1c-860 | I-3 | II-159 | C-8 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-861 | I-3 | II-160 | C-8 |
| T1c-862 | I-3 | II-161 | C-8 |
| T1c-863 | I-3 | II-162 | C-8 |
| T1c-864 | I-3 | II-163 | C-8 |
| T1c-865 | I-3 | II-164 | C-8 |
| T1c-866 | I-3 | II-165 | C-8 |
| T1c-867 | I-3 | II-166 | C-8 |
| T1c-868 | I-3 | II-167 | C-8 |
| T1c-869 | I-3 | II-168 | C-8 |
| T1c-870 | I-3 | II-169 | C-8 |
| T1c-871 | I-3 | II-170 | C-8 |
| T1c-872 | I-3 | II-171 | C-8 |
| T1c-873 | I-3 | II-172 | C-8 |
| T1c-874 | I-3 | II-173 | C-8 |
| T1c-875 | I-3 | II-174 | C-8 |
| T1c-876 | I-3 | II-175 | C-8 |
| T1c-877 | I-3 | II-176 | C-8 |
| T1c-878 | I-3 | II-177 | C-8 |
| T1c-879 | I-3 | II-178 | C-8 |
| T1c-880 | I-3 | II-179 | C-8 |
| T1c-881 | I-3 | II-180 | C-8 |
| T1c-882 | I-3 | II-181 | C-8 |
| T1c-883 | I-3 | II-182 | C-8 |
| T1c-884 | I-3 | II-183 | C-8 |
| T1c-885 | I-3 | II-184 | C-8 |
| T1c-886 | I-3 | II-185 | C-8 |
| T1c-887 | I-3 | II-186 | C-8 |
| T1c-888 | I-3 | II-187 | C-8 |
| T1c-889 | I-3 | II-188 | C-8 |
| T1c-890 | I-3 | II-189 | C-8 |
| T1c-891 | I-3 | II-190 | C-8 |
| T1c-892 | I-3 | II-191 | C-8 |
| T1c-893 | I-3 | II-192 | C-8 |
| T1c-894 | I-3 | II-193 | C-8 |
| T1c-895 | I-3 | II-194 | C-8 |
| T1c-896 | I-3 | II-195 | C-8 |
| T1c-897 | I-3 | II-196 | C-8 |
| T1c-898 | I-3 | II-197 | C-8 |
| T1c-899 | I-3 | II-198 | C-8 |
| T1c-900 | I-3 | II-199 | C-8 |
| T1c-901 | I-3 | II-200 | C-8 |
| T1c-902 | I-3 | II-201 | C-8 |
| T1c-903 | I-3 | II-202 | C-8 |
| T1c-904 | I-3 | II-203 | C-8 |
| T1c-905 | I-3 | II-91 | C-9 |
| T1c-906 | I-3 | II-92 | C-9 |
| T1c-907 | I-3 | II-93 | C-9 |
| T1c-908 | I-3 | II-94 | C-9 |
| T1c-909 | I-3 | II-95 | C-9 |
| T1c-910 | I-3 | II-96 | C-9 |
| T1c-911 | I-3 | II-97 | C-9 |
| T1c-912 | I-3 | II-98 | C-9 |
| T1c-913 | I-3 | II-99 | C-9 |
| T1c-914 | I-3 | II-100 | C-9 |
| T1c-915 | I-3 | II-101 | C-9 |
| T1c-916 | I-3 | II-102 | C-9 |
| T1c-917 | I-3 | II-103 | C-9 |
| T1c-918 | I-3 | II-104 | C-9 |
| T1c-919 | I-3 | II-105 | C-9 |
| T1c-920 | I-3 | II-106 | C-9 |
| T1c-921 | I-3 | II-107 | C-9 |
| T1c-922 | I-3 | II-108 | C-9 |
| T1c-923 | I-3 | II-109 | C-9 |
| T1c-924 | I-3 | II-110 | C-9 |
| T1c-925 | I-3 | II-111 | C-9 |
| T1c-926 | I-3 | II-112 | C-9 |
| T1c-927 | I-3 | II-113 | C-9 |
| T1c-928 | I-3 | II-114 | C-9 |
| T1c-929 | I-3 | II-115 | C-9 |
| T1c-930 | I-3 | II-116 | C-9 |
| T1c-931 | I-3 | II-117 | C-9 |
| T1c-932 | I-3 | II-118 | C-9 |
| T1c-933 | I-3 | II-119 | C-9 |
| T1c-934 | I-3 | II-120 | C-9 |
| T1c-935 | I-3 | II-121 | C-9 |
| T1c-936 | I-3 | II-122 | C-9 |
| T1c-937 | I-3 | II-123 | C-9 |
| T1c-938 | I-3 | II-124 | C-9 |
| T1c-939 | I-3 | II-125 | C-9 |
| T1c-940 | I-3 | II-126 | C-9 |
| T1c-941 | I-3 | II-127 | C-9 |
| T1c-942 | I-3 | II-128 | C-9 |
| T1c-943 | I-3 | II-129 | C-9 |
| T1c-944 | I-3 | II-130 | C-9 |
| T1c-945 | I-3 | II-131 | C-9 |
| T1c-946 | I-3 | II-132 | C-9 |
| T1c-947 | I-3 | II-133 | C-9 |
| T1c-948 | I-3 | II-134 | C-9 |
| T1c-949 | I-3 | II-135 | C-9 |
| T1c-950 | I-3 | II-136 | C-9 |
| T1c-951 | I-3 | II-137 | C-9 |
| T1c-952 | I-3 | II-138 | C-9 |
| T1c-953 | I-3 | II-139 | C-9 |
| T1c-954 | I-3 | II-140 | C-9 |
| T1c-955 | I-3 | II-141 | C-9 |
| T1c-956 | I-3 | II-142 | C-9 |
| T1c-957 | I-3 | II-143 | C-9 |
| T1c-958 | I-3 | II-144 | C-9 |
| T1c-959 | I-3 | II-145 | C-9 |
| T1c-960 | I-3 | II-146 | C-9 |
| T1c-961 | I-3 | II-147 | C-9 |
| T1c-962 | I-3 | II-148 | C-9 |
| T1c-963 | I-3 | II-149 | C-9 |
| T1c-964 | I-3 | II-150 | C-9 |
| T1c-965 | I-3 | II-151 | C-9 |
| T1c-966 | I-3 | II-152 | C-9 |
| T1c-967 | I-3 | II-153 | C-9 |
| T1c-968 | I-3 | II-154 | C-9 |
| T1c-969 | I-3 | II-155 | C-9 |
| T1c-970 | I-3 | II-156 | C-9 |
| T1c-971 | I-3 | II-157 | C-9 |
| T1c-972 | I-3 | II-158 | C-9 |
| T1c-973 | I-3 | II-159 | C-9 |
| T1c-974 | I-3 | II-160 | C-9 |
| T1c-975 | I-3 | II-161 | C-9 |
| T1c-976 | I-3 | II-162 | C-9 |
| T1c-977 | I-3 | II-163 | C-9 |
| T1c-978 | I-3 | II-164 | C-9 |
| T1c-979 | I-3 | II-165 | C-9 |
| T1c-980 | I-3 | II-166 | C-9 |
| T1c-981 | I-3 | II-167 | C-9 |
| T1c-982 | I-3 | II-168 | C-9 |
| T1c-983 | I-3 | II-169 | C-9 |
| T1c-984 | I-3 | II-170 | C-9 |
| T1c-985 | I-3 | II-171 | C-9 |
| T1c-986 | I-3 | II-172 | C-9 |
| T1c-987 | I-3 | II-173 | C-9 |
| T1c-988 | I-3 | II-174 | C-9 |
| T1c-989 | I-3 | II-175 | C-9 |
| T1c-990 | I-3 | II-176 | C-9 |
| T1c-991 | I-3 | II-177 | C-9 |
| T1c-992 | I-3 | II-178 | C-9 |
| T1c-993 | I-3 | II-179 | C-9 |
| T1c-994 | I-3 | II-180 | C-9 |
| T1c-995 | I-3 | II-181 | C-9 |
| T1c-996 | I-3 | II-182 | C-9 |
| T1c-997 | I-3 | II-183 | C-9 |
| T1c-998 | I-3 | II-184 | C-9 |
| T1c-999 | I-3 | II-185 | C-9 |
| T1c-1000 | I-3 | II-186 | C-9 |
| T1c-1001 | I-3 | II-187 | C-9 |
| T1c-1002 | I-3 | II-188 | C-9 |
| T1c-1003 | I-3 | II-189 | C-9 |
| T1c-1004 | I-3 | II-190 | C-9 |
| T1c-1005 | I-3 | II-191 | C-9 |
| T1c-1006 | I-3 | II-192 | C-9 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-1007 | I-3 | II-193 | C-9 |
| T1c-1008 | I-3 | II-194 | C-9 |
| T1c-1009 | I-3 | II-195 | C-9 |
| T1c-1010 | I-3 | II-196 | C-9 |
| T1c-1011 | I-3 | II-197 | C-9 |
| T1c-1012 | I-3 | II-198 | C-9 |
| T1c-1013 | I-3 | II-199 | C-9 |
| T1c-1014 | I-3 | II-200 | C-9 |
| T1c-1015 | I-3 | II-201 | C-9 |
| T1c-1016 | I-3 | II-202 | C-9 |
| T1c-1017 | I-3 | II-203 | C-9 |
| T1c-1018 | I-3 | II-91 | C-10 |
| T1c-1019 | I-3 | II-92 | C-10 |
| T1c-1020 | I-3 | II-93 | C-10 |
| T1c-1021 | I-3 | II-94 | C-10 |
| T1c-1022 | I-3 | II-95 | C-10 |
| T1c-1023 | I-3 | II-96 | C-10 |
| T1c-1024 | I-3 | II-97 | C-10 |
| T1c-1025 | I-3 | II-98 | C-10 |
| T1c-1026 | I-3 | II-99 | C-10 |
| T1c-1027 | I-3 | II-100 | C-10 |
| T1c-1028 | I-3 | II-101 | C-10 |
| T1c-1029 | I-3 | II-102 | C-10 |
| T1c-1030 | I-3 | II-103 | C-10 |
| T1c-1031 | I-3 | II-104 | C-10 |
| T1c-1032 | I-3 | II-105 | C-10 |
| T1c-1033 | I-3 | II-106 | C-10 |
| T1c-1034 | I-3 | II-107 | C-10 |
| T1c-1035 | I-3 | II-108 | C-10 |
| T1c-1036 | I-3 | II-109 | C-10 |
| T1c-1037 | I-3 | II-110 | C-10 |
| T1c-1038 | I-3 | II-111 | C-10 |
| T1c-1039 | I-3 | II-112 | C-10 |
| T1c-1040 | I-3 | II-113 | C-10 |
| T1c-1041 | I-3 | II-114 | C-10 |
| T1c-1042 | I-3 | II-115 | C-10 |
| T1c-1043 | I-3 | II-116 | C-10 |
| T1c-1044 | I-3 | II-117 | C-10 |
| T1c-1045 | I-3 | II-118 | C-10 |
| T1c-1046 | I-3 | II-119 | C-10 |
| T1c-1047 | I-3 | II-120 | C-10 |
| T1c-1048 | I-3 | II-121 | C-10 |
| T1c-1049 | I-3 | II-122 | C-10 |
| T1c-1050 | I-3 | II-123 | C-10 |
| T1c-1051 | I-3 | II-124 | C-10 |
| T1c-1052 | I-3 | II-125 | C-10 |
| T1c-1053 | I-3 | II-126 | C-10 |
| T1c-1054 | I-3 | II-127 | C-10 |
| T1c-1055 | I-3 | II-128 | C-10 |
| T1c-1056 | I-3 | II-129 | C-10 |
| T1c-1057 | I-3 | II-130 | C-10 |
| T1c-1058 | I-3 | II-131 | C-10 |
| T1c-1059 | I-3 | II-132 | C-10 |
| T1c-1060 | I-3 | II-133 | C-10 |
| T1c-1061 | I-3 | II-134 | C-10 |
| T1c-1062 | I-3 | II-135 | C-10 |
| T1c-1063 | I-3 | II-136 | C-10 |
| T1c-1064 | I-3 | II-137 | C-10 |
| T1c-1065 | I-3 | II-138 | C-10 |
| T1c-1066 | I-3 | II-139 | C-10 |
| T1c-1067 | I-3 | II-140 | C-10 |
| T1c-1068 | I-3 | II-141 | C-10 |
| T1c-1069 | I-3 | II-142 | C-10 |
| T1c-1070 | I-3 | II-143 | C-10 |
| T1c-1071 | I-3 | II-144 | C-10 |
| T1c-1072 | I-3 | II-145 | C-10 |
| T1c-1073 | I-3 | II-146 | C-10 |
| T1c-1074 | I-3 | II-147 | C-10 |
| T1c-1075 | I-3 | II-148 | C-10 |
| T1c-1076 | I-3 | II-149 | C-10 |
| T1c-1077 | I-3 | II-150 | C-10 |
| T1c-1078 | I-3 | II-151 | C-10 |
| T1c-1079 | I-3 | II-152 | C-10 |
| T1c-1080 | I-3 | II-153 | C-10 |
| T1c-1081 | I-3 | II-154 | C-10 |
| T1c-1082 | I-3 | II-155 | C-10 |
| T1c-1083 | I-3 | II-156 | C-10 |
| T1c-1084 | I-3 | II-157 | C-10 |
| T1c-1085 | I-3 | II-158 | C-10 |
| T1c-1086 | I-3 | II-159 | C-10 |
| T1c-1087 | I-3 | II-160 | C-10 |
| T1c-1088 | I-3 | II-161 | C-10 |
| T1c-1089 | I-3 | II-162 | C-10 |
| T1c-1090 | I-3 | II-163 | C-10 |
| T1c-1091 | I-3 | II-164 | C-10 |
| T1c-1092 | I-3 | II-165 | C-10 |
| T1c-1093 | I-3 | II-166 | C-10 |
| T1c-1094 | I-3 | II-167 | C-10 |
| T1c-1095 | I-3 | II-168 | C-10 |
| T1c-1096 | I-3 | II-169 | C-10 |
| T1c-1097 | I-3 | II-170 | C-10 |
| T1c-1098 | I-3 | II-171 | C-10 |
| T1c-1099 | I-3 | II-172 | C-10 |
| T1c-1100 | I-3 | II-173 | C-10 |
| T1c-1101 | I-3 | II-174 | C-10 |
| T1c-1102 | I-3 | II-175 | C-10 |
| T1c-1103 | I-3 | II-176 | C-10 |
| T1c-1104 | I-3 | II-177 | C-10 |
| T1c-1105 | I-3 | II-178 | C-10 |
| T1c-1106 | I-3 | II-179 | C-10 |
| T1c-1107 | I-3 | II-180 | C-10 |
| T1c-1108 | I-3 | II-181 | C-10 |
| T1c-1109 | I-3 | II-182 | C-10 |
| T1c-1110 | I-3 | II-183 | C-10 |
| T1c-1111 | I-3 | II-184 | C-10 |
| T1c-1112 | I-3 | II-185 | C-10 |
| T1c-1113 | I-3 | II-186 | C-10 |
| T1c-1114 | I-3 | II-187 | C-10 |
| T1c-1115 | I-3 | II-188 | C-10 |
| T1c-1116 | I-3 | II-189 | C-10 |
| T1c-1117 | I-3 | II-190 | C-10 |
| T1c-1118 | I-3 | II-191 | C-10 |
| T1c-1119 | I-3 | II-192 | C-10 |
| T1c-1120 | I-3 | II-193 | C-10 |
| T1c-1121 | I-3 | II-194 | C-10 |
| T1c-1122 | I-3 | II-195 | C-10 |
| T1c-1123 | I-3 | II-196 | C-10 |
| T1c-1124 | I-3 | II-197 | C-10 |
| T1c-1125 | I-3 | II-198 | C-10 |
| T1c-1126 | I-3 | II-199 | C-10 |
| T1c-1127 | I-3 | II-200 | C-10 |
| T1c-1128 | I-3 | II-201 | C-10 |
| T1c-1129 | I-3 | II-202 | C-10 |
| T1c-1130 | I-3 | II-203 | C-10 |
| T1c-1131 | I-3 | II-91 | C-11 |
| T1c-1132 | I-3 | II-92 | C-11 |
| T1c-1133 | I-3 | II-93 | C-11 |
| T1c-1134 | I-3 | II-94 | C-11 |
| T1c-1135 | I-3 | II-95 | C-11 |
| T1c-1136 | I-3 | II-96 | C-11 |
| T1c-1137 | I-3 | II-97 | C-11 |
| T1c-1138 | I-3 | II-98 | C-11 |
| T1c-1139 | I-3 | II-99 | C-11 |
| T1c-1140 | I-3 | II-100 | C-11 |
| T1c-1141 | I-3 | II-101 | C-11 |
| T1c-1142 | I-3 | II-102 | C-11 |
| T1c-1143 | I-3 | II-103 | C-11 |
| T1c-1144 | I-3 | II-104 | C-11 |
| T1c-1145 | I-3 | II-105 | C-11 |
| T1c-1146 | I-3 | II-106 | C-11 |
| T1c-1147 | I-3 | II-107 | C-11 |
| T1c-1148 | I-3 | II-108 | C-11 |
| T1c-1149 | I-3 | II-109 | C-11 |
| T1c-1150 | I-3 | II-110 | C-11 |
| T1c-1151 | I-3 | II-111 | C-11 |
| T1c-1152 | I-3 | II-112 | C-11 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-1153 | I-3 | II-113 | C-11 |
| T1c-1154 | I-3 | II-114 | C-11 |
| T1c-1155 | I-3 | II-115 | C-11 |
| T1c-1156 | I-3 | II-116 | C-11 |
| T1c-1157 | I-3 | II-117 | C-11 |
| T1c-1158 | I-3 | II-118 | C-11 |
| T1c-1159 | I-3 | II-119 | C-11 |
| T1c-1160 | I-3 | II-120 | C-11 |
| T1c-1161 | I-3 | II-121 | C-11 |
| T1c-1162 | I-3 | II-122 | C-11 |
| T1c-1163 | I-3 | II-123 | C-11 |
| T1c-1164 | I-3 | II-124 | C-11 |
| T1c-1165 | I-3 | II-125 | C-11 |
| T1c-1166 | I-3 | II-126 | C-11 |
| T1c-1167 | I-3 | II-127 | C-11 |
| T1c-1168 | I-3 | II-128 | C-11 |
| T1c-1169 | I-3 | II-129 | C-11 |
| T1c-1170 | I-3 | II-130 | C-11 |
| T1c-1171 | I-3 | II-131 | C-11 |
| T1c-1172 | I-3 | II-132 | C-11 |
| T1c-1173 | I-3 | II-133 | C-11 |
| T1c-1174 | I-3 | II-134 | C-11 |
| T1c-1175 | I-3 | II-135 | C-11 |
| T1c-1176 | I-3 | II-136 | C-11 |
| T1c-1177 | I-3 | II-137 | C-11 |
| T1c-1178 | I-3 | II-138 | C-11 |
| T1c-1179 | I-3 | II-139 | C-11 |
| T1c-1180 | I-3 | II-140 | C-11 |
| T1c-1181 | I-3 | II-141 | C-11 |
| T1c-1182 | I-3 | II-142 | C-11 |
| T1c-1183 | I-3 | II-143 | C-11 |
| T1c-1184 | I-3 | II-144 | C-11 |
| T1c-1185 | I-3 | II-145 | C-11 |
| T1c-1186 | I-3 | II-146 | C-11 |
| T1c-1187 | I-3 | II-147 | C-11 |
| T1c-1188 | I-3 | II-148 | C-11 |
| T1c-1189 | I-3 | II-149 | C-11 |
| T1c-1190 | I-3 | II-150 | C-11 |
| T1c-1191 | I-3 | II-151 | C-11 |
| T1c-1192 | I-3 | II-152 | C-11 |
| T1c-1193 | I-3 | II-153 | C-11 |
| T1c-1194 | I-3 | II-154 | C-11 |
| T1c-1195 | I-3 | II-155 | C-11 |
| T1c-1196 | I-3 | II-156 | C-11 |
| T1c-1197 | I-3 | II-157 | C-11 |
| T1c-1198 | I-3 | II-158 | C-11 |
| T1c-1199 | I-3 | II-159 | C-11 |
| T1c-1200 | I-3 | II-160 | C-11 |
| T1c-1201 | I-3 | II-161 | C-11 |
| T1c-1202 | I-3 | II-162 | C-11 |
| T1c-1203 | I-3 | II-163 | C-11 |
| T1c-1204 | I-3 | II-164 | C-11 |
| T1c-1205 | I-3 | II-165 | C-11 |
| T1c-1206 | I-3 | II-166 | C-11 |
| T1c-1207 | I-3 | II-167 | C-11 |
| T1c-1208 | I-3 | II-168 | C-11 |
| T1c-1209 | I-3 | II-169 | C-11 |
| T1c-1210 | I-3 | II-170 | C-11 |
| T1c-1211 | I-3 | II-171 | C-11 |
| T1c-1212 | I-3 | II-172 | C-11 |
| T1c-1213 | I-3 | II-173 | C-11 |
| T1c-1214 | I-3 | II-174 | C-11 |
| T1c-1215 | I-3 | II-175 | C-11 |
| T1c-1216 | I-3 | II-176 | C-11 |
| T1c-1217 | I-3 | II-177 | C-11 |
| T1c-1218 | I-3 | II-178 | C-11 |
| T1c-1219 | I-3 | II-179 | C-11 |
| T1c-1220 | I-3 | II-180 | C-11 |
| T1c-1221 | I-3 | II-181 | C-11 |
| T1c-1222 | I-3 | II-182 | C-11 |
| T1c-1223 | I-3 | II-183 | C-11 |
| T1c-1224 | I-3 | II-184 | C-11 |
| T1c-1225 | I-3 | II-185 | C-11 |
| T1c-1226 | I-3 | II-186 | C-11 |
| T1c-1227 | I-3 | II-187 | C-11 |
| T1c-1228 | I-3 | II-188 | C-11 |
| T1c-1229 | I-3 | II-189 | C-11 |
| T1c-1230 | I-3 | II-190 | C-11 |
| T1c-1231 | I-3 | II-191 | C-11 |
| T1c-1232 | I-3 | II-192 | C-11 |
| T1c-1233 | I-3 | II-193 | C-11 |
| T1c-1234 | I-3 | II-194 | C-11 |
| T1c-1235 | I-3 | II-195 | C-11 |
| T1c-1236 | I-3 | II-196 | C-11 |
| T1c-1237 | I-3 | II-197 | C-11 |
| T1c-1238 | I-3 | II-198 | C-11 |
| T1c-1239 | I-3 | II-199 | C-11 |
| T1c-1240 | I-3 | II-200 | C-11 |
| T1c-1241 | I-3 | II-201 | C-11 |
| T1c-1242 | I-3 | II-202 | C-11 |
| T1c-1243 | I-3 | II-203 | C-11 |
| T1c-1244 | I-3 | II-91 | C-12 |
| T1c-1245 | I-3 | II-92 | C-12 |
| T1c-1246 | I-3 | II-93 | C-12 |
| T1c-1247 | I-3 | II-94 | C-12 |
| T1c-1248 | I-3 | II-95 | C-12 |
| T1c-1249 | I-3 | II-96 | C-12 |
| T1c-1250 | I-3 | II-97 | C-12 |
| T1c-1251 | I-3 | II-98 | C-12 |
| T1c-1252 | I-3 | II-99 | C-12 |
| T1c-1253 | I-3 | II-100 | C-12 |
| T1c-1254 | I-3 | II-101 | C-12 |
| T1c-1255 | I-3 | II-102 | C-12 |
| T1c-1256 | I-3 | II-103 | C-12 |
| T1c-1257 | I-3 | II-104 | C-12 |
| T1c-1258 | I-3 | II-105 | C-12 |
| T1c-1259 | I-3 | II-106 | C-12 |
| T1c-1260 | I-3 | II-107 | C-12 |
| T1c-1261 | I-3 | II-108 | C-12 |
| T1c-1262 | I-3 | II-109 | C-12 |
| T1c-1263 | I-3 | II-110 | C-12 |
| T1c-1264 | I-3 | II-111 | C-12 |
| T1c-1265 | I-3 | II-112 | C-12 |
| T1c-1266 | I-3 | II-113 | C-12 |
| T1c-1267 | I-3 | II-114 | C-12 |
| T1c-1268 | I-3 | II-115 | C-12 |
| T1c-1269 | I-3 | II-116 | C-12 |
| T1c-1270 | I-3 | II-117 | C-12 |
| T1c-1271 | I-3 | II-118 | C-12 |
| T1c-1272 | I-3 | II-119 | C-12 |
| T1c-1273 | I-3 | II-120 | C-12 |
| T1c-1274 | I-3 | II-121 | C-12 |
| T1c-1275 | I-3 | II-122 | C-12 |
| T1c-1276 | I-3 | II-123 | C-12 |
| T1c-1277 | I-3 | II-124 | C-12 |
| T1c-1278 | I-3 | II-125 | C-12 |
| T1c-1279 | I-3 | II-126 | C-12 |
| T1c-1280 | I-3 | II-127 | C-12 |
| T1c-1281 | I-3 | II-128 | C-12 |
| T1c-1282 | I-3 | II-129 | C-12 |
| T1c-1283 | I-3 | II-130 | C-12 |
| T1c-1284 | I-3 | II-131 | C-12 |
| T1c-1285 | I-3 | II-132 | C-12 |
| T1c-1286 | I-3 | II-133 | C-12 |
| T1c-1287 | I-3 | II-134 | C-12 |
| T1c-1288 | I-3 | II-135 | C-12 |
| T1c-1289 | I-3 | II-136 | C-12 |
| T1c-1290 | I-3 | II-137 | C-12 |
| T1c-1291 | I-3 | II-138 | C-12 |
| T1c-1292 | I-3 | II-139 | C-12 |
| T1c-1293 | I-3 | II-140 | C-12 |
| T1c-1294 | I-3 | II-141 | C-12 |
| T1c-1295 | I-3 | II-142 | C-12 |
| T1c-1296 | I-3 | II-143 | C-12 |
| T1c-1297 | I-3 | II-144 | C-12 |
| T1c-1298 | I-3 | II-145 | C-12 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
| --- | --- | --- | --- |
| T1c-1299 | I-3 | II-146 | C-12 |
| T1c-1300 | I-3 | II-147 | C-12 |
| T1c-1301 | I-3 | II-148 | C-12 |
| T1c-1302 | I-3 | II-149 | C-12 |
| T1c-1303 | I-3 | II-150 | C-12 |
| T1c-1304 | I-3 | II-151 | C-12 |
| T1c-1305 | I-3 | II-152 | C-12 |
| T1c-1306 | I-3 | II-153 | C-12 |
| T1c-1307 | I-3 | II-154 | C-12 |
| T1c-1308 | I-3 | II-155 | C-12 |
| T1c-1309 | I-3 | II-156 | C-12 |
| T1c-1310 | I-3 | II-157 | C-12 |
| T1c-1311 | I-3 | II-158 | C-12 |
| T1c-1312 | I-3 | II-159 | C-12 |
| T1c-1313 | I-3 | II-160 | C-12 |
| T1c-1314 | I-3 | II-161 | C-12 |
| T1c-1315 | I-3 | II-162 | C-12 |
| T1c-1316 | I-3 | II-163 | C-12 |
| T1c-1317 | I-3 | II-164 | C-12 |
| T1c-1318 | I-3 | II-165 | C-12 |
| T1c-1319 | I-3 | II-166 | C-12 |
| T1c-1320 | I-3 | II-167 | C-12 |
| T1c-1321 | I-3 | II-168 | C-12 |
| T1c-1322 | I-3 | II-169 | C-12 |
| T1c-1323 | I-3 | II-170 | C-12 |
| T1c-1324 | I-3 | II-171 | C-12 |
| T1c-1325 | I-3 | II-172 | C-12 |
| T1c-1326 | I-3 | II-173 | C-12 |
| T1c-1327 | I-3 | II-174 | C-12 |
| T1c-1328 | I-3 | II-175 | C-12 |
| T1c-1329 | I-3 | II-176 | C-12 |
| T1c-1330 | I-3 | II-177 | C-12 |
| T1c-1331 | I-3 | II-178 | C-12 |
| T1c-1332 | I-3 | II-179 | C-12 |
| T1c-1333 | I-3 | II-180 | C-12 |
| T1c-1334 | I-3 | II-181 | C-12 |
| T1c-1335 | I-3 | II-182 | C-12 |
| T1c-1336 | I-3 | II-183 | C-12 |
| T1c-1337 | I-3 | II-184 | C-12 |
| T1c-1338 | I-3 | II-185 | C-12 |
| T1c-1339 | I-3 | II-186 | C-12 |
| T1c-1340 | I-3 | II-187 | C-12 |
| T1c-1341 | I-3 | II-188 | C-12 |
| T1c-1342 | I-3 | II-189 | C-12 |
| T1c-1343 | I-3 | II-190 | C-12 |
| T1c-1344 | I-3 | II-191 | C-12 |
| T1c-1345 | I-3 | II-192 | C-12 |
| T1c-1346 | I-3 | II-193 | C-12 |
| T1c-1347 | I-3 | II-194 | C-12 |
| T1c-1348 | I-3 | II-195 | C-12 |
| T1c-1349 | I-3 | II-196 | C-12 |
| T1c-1350 | I-3 | II-197 | C-12 |
| T1c-1351 | I-3 | II-198 | C-12 |
| T1c-1352 | I-3 | II-199 | C-12 |
| T1c-1353 | I-3 | II-200 | C-12 |
| T1c-1354 | I-3 | II-201 | C-12 |
| T1c-1355 | I-3 | II-202 | C-12 |
| T1c-1356 | I-3 | II-203 | C-12 |
| T1c-1357 | I-3 | II-91 | C-13 |
| T1c-1358 | I-3 | II-92 | C-13 |
| T1c-1359 | I-3 | II-93 | C-13 |
| T1c-1360 | I-3 | II-94 | C-13 |
| T1c-1361 | I-3 | II-95 | C-13 |
| T1c-1362 | I-3 | II-96 | C-13 |
| T1c-1363 | I-3 | II-97 | C-13 |
| T1c-1364 | I-3 | II-98 | C-13 |
| T1c-1365 | I-3 | II-99 | C-13 |
| T1c-1366 | I-3 | II-100 | C-13 |
| T1c-1367 | I-3 | II-101 | C-13 |
| T1c-1368 | I-3 | II-102 | C-13 |
| T1c-1369 | I-3 | II-103 | C-13 |
| T1c-1370 | I-3 | II-104 | C-13 |
| T1c-1371 | I-3 | II-105 | C-13 |
| T1c-1372 | I-3 | II-106 | C-13 |
| T1c-1373 | I-3 | II-107 | C-13 |
| T1c-1374 | I-3 | II-108 | C-13 |
| T1c-1375 | I-3 | II-109 | C-13 |
| T1c-1376 | I-3 | II-110 | C-13 |
| T1c-1377 | I-3 | II-111 | C-13 |
| T1c-1378 | I-3 | II-112 | C-13 |
| T1c-1379 | I-3 | II-113 | C-13 |
| T1c-1380 | I-3 | II-114 | C-13 |
| T1c-1381 | I-3 | II-115 | C-13 |
| T1c-1382 | I-3 | II-116 | C-13 |
| T1c-1383 | I-3 | II-117 | C-13 |
| T1c-1384 | I-3 | II-118 | C-13 |
| T1c-1385 | I-3 | II-119 | C-13 |
| T1c-1386 | I-3 | II-120 | C-13 |
| T1c-1387 | I-3 | II-121 | C-13 |
| T1c-1388 | I-3 | II-122 | C-13 |
| T1c-1389 | I-3 | II-123 | C-13 |
| T1c-1390 | I-3 | II-124 | C-13 |
| T1c-1391 | I-3 | II-125 | C-13 |
| T1c-1392 | I-3 | II-126 | C-13 |
| T1c-1393 | I-3 | II-127 | C-13 |
| T1c-1394 | I-3 | II-128 | C-13 |
| T1c-1395 | I-3 | II-129 | C-13 |
| T1c-1396 | I-3 | II-130 | C-13 |
| T1c-1397 | I-3 | II-131 | C-13 |
| T1c-1398 | I-3 | II-132 | C-13 |
| T1c-1399 | I-3 | II-133 | C-13 |
| T1c-1400 | I-3 | II-134 | C-13 |
| T1c-1401 | I-3 | II-135 | C-13 |
| T1c-1402 | I-3 | II-136 | C-13 |
| T1c-1403 | I-3 | II-137 | C-13 |
| T1c-1404 | I-3 | II-138 | C-13 |
| T1c-1405 | I-3 | II-139 | C-13 |
| T1c-1406 | I-3 | II-140 | C-13 |
| T1c-1407 | I-3 | II-141 | C-13 |
| T1c-1408 | I-3 | II-142 | C-13 |
| T1c-1409 | I-3 | II-143 | C-13 |
| T1c-1410 | I-3 | II-144 | C-13 |
| T1c-1411 | I-3 | II-145 | C-13 |
| T1c-1412 | I-3 | II-146 | C-13 |
| T1c-1413 | I-3 | II-147 | C-13 |
| T1c-1414 | I-3 | II-148 | C-13 |
| T1c-1415 | I-3 | II-149 | C-13 |
| T1c-1416 | I-3 | II-150 | C-13 |
| T1c-1417 | I-3 | II-151 | C-13 |
| T1c-1418 | I-3 | II-152 | C-13 |
| T1c-1419 | I-3 | II-153 | C-13 |
| T1c-1420 | I-3 | II-154 | C-13 |
| T1c-1421 | I-3 | II-155 | C-13 |
| T1c-1422 | I-3 | II-156 | C-13 |
| T1c-1423 | I-3 | II-157 | C-13 |
| T1c-1424 | I-3 | II-158 | C-13 |
| T1c-1425 | I-3 | II-159 | C-13 |
| T1c-1426 | I-3 | II-160 | C-13 |
| T1c-1427 | I-3 | II-161 | C-13 |
| T1c-1428 | I-3 | II-162 | C-13 |
| T1c-1429 | I-3 | II-163 | C-13 |
| T1c-1430 | I-3 | II-164 | C-13 |
| T1c-1431 | I-3 | II-165 | C-13 |
| T1c-1432 | I-3 | II-166 | C-13 |
| T1c-1433 | I-3 | II-167 | C-13 |
| T1c-1434 | I-3 | II-168 | C-13 |
| T1c-1435 | I-3 | II-169 | C-13 |
| T1c-1436 | I-3 | II-170 | C-13 |
| T1c-1437 | I-3 | II-171 | C-13 |
| T1c-1438 | I-3 | II-172 | C-13 |
| T1c-1439 | I-3 | II-173 | C-13 |
| T1c-1440 | I-3 | II-174 | C-13 |
| T1c-1441 | I-3 | II-175 | C-13 |
| T1c-1442 | I-3 | II-176 | C-13 |
| T1c-1443 | I-3 | II-177 | C-13 |
| T1c-1444 | I-3 | II-178 | C-13 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-1445 | I-3 | II-179 | C-13 |
| T1c-1446 | I-3 | II-180 | C-13 |
| T1c-1447 | I-3 | II-181 | C-13 |
| T1c-1448 | I-3 | II-182 | C-13 |
| T1c-1449 | I-3 | II-183 | C-13 |
| T1c-1450 | I-3 | II-184 | C-13 |
| T1c-1451 | I-3 | II-185 | C-13 |
| T1c-1452 | I-3 | II-186 | C-13 |
| T1c-1453 | I-3 | II-187 | C-13 |
| T1c-1454 | I-3 | II-188 | C-13 |
| T1c-1455 | I-3 | II-189 | C-13 |
| T1c-1456 | I-3 | II-190 | C-13 |
| T1c-1457 | I-3 | II-191 | C-13 |
| T1c-1458 | I-3 | II-192 | C-13 |
| T1c-1459 | I-3 | II-193 | C-13 |
| T1c-1460 | I-3 | II-194 | C-13 |
| T1c-1461 | I-3 | II-195 | C-13 |
| T1c-1462 | I-3 | II-196 | C-13 |
| T1c-1463 | I-3 | II-197 | C-13 |
| T1c-1464 | I-3 | II-198 | C-13 |
| T1c-1465 | I-3 | II-199 | C-13 |
| T1c-1466 | I-3 | II-200 | C-13 |
| T1c-1467 | I-3 | II-201 | C-13 |
| T1c-1468 | I-3 | II-202 | C-13 |
| T1c-1469 | I-3 | II-203 | C-13 |
| T1c-1470 | I-3 | II-91 | C-14 |
| T1c-1471 | I-3 | II-92 | C-14 |
| T1c-1472 | I-3 | II-93 | C-14 |
| T1c-1473 | I-3 | II-94 | C-14 |
| T1c-1474 | I-3 | II-95 | C-14 |
| T1c-1475 | I-3 | II-96 | C-14 |
| T1c-1476 | I-3 | II-97 | C-14 |
| T1c-1477 | I-3 | II-98 | C-14 |
| T1c-1478 | I-3 | II-99 | C-14 |
| T1c-1479 | I-3 | II-100 | C-14 |
| T1c-1480 | I-3 | II-101 | C-14 |
| T1c-1481 | I-3 | II-102 | C-14 |
| T1c-1482 | I-3 | II-103 | C-14 |
| T1c-1483 | I-3 | II-104 | C-14 |
| T1c-1484 | I-3 | II-105 | C-14 |
| T1c-1485 | I-3 | II-106 | C-14 |
| T1c-1486 | I-3 | II-107 | C-14 |
| T1c-1487 | I-3 | II-108 | C-14 |
| T1c-1488 | I-3 | II-109 | C-14 |
| T1c-1489 | I-3 | II-110 | C-14 |
| T1c-1490 | I-3 | II-111 | C-14 |
| T1c-1491 | I-3 | II-112 | C-14 |
| T1c-1492 | I-3 | II-113 | C-14 |
| T1c-1493 | I-3 | II-114 | C-14 |
| T1c-1494 | I-3 | II-115 | C-14 |
| T1c-1495 | I-3 | II-116 | C-14 |
| T1c-1496 | I-3 | II-117 | C-14 |
| T1c-1497 | I-3 | II-118 | C-14 |
| T1c-1498 | I-3 | II-119 | C-14 |
| T1c-1499 | I-3 | II-120 | C-14 |
| T1c-1500 | I-3 | II-121 | C-14 |
| T1c-1501 | I-3 | II-122 | C-14 |
| T1c-1502 | I-3 | II-123 | C-14 |
| T1c-1503 | I-3 | II-124 | C-14 |
| T1c-1504 | I-3 | II-125 | C-14 |
| T1c-1505 | I-3 | II-126 | C-14 |
| T1c-1506 | I-3 | II-127 | C-14 |
| T1c-1507 | I-3 | II-128 | C-14 |
| T1c-1508 | I-3 | II-129 | C-14 |
| T1c-1509 | I-3 | II-130 | C-14 |
| T1c-1510 | I-3 | II-131 | C-14 |
| T1c-1511 | I-3 | II-132 | C-14 |
| T1c-1512 | I-3 | II-133 | C-14 |
| T1c-1513 | I-3 | II-134 | C-14 |
| T1c-1514 | I-3 | II-135 | C-14 |
| T1c-1515 | I-3 | II-136 | C-14 |
| T1c-1516 | I-3 | II-137 | C-14 |
| T1c-1517 | I-3 | II-138 | C-14 |
| T1c-1518 | I-3 | II-139 | C-14 |
| T1c-1519 | I-3 | II-140 | C-14 |
| T1c-1520 | I-3 | II-141 | C-14 |
| T1c-1521 | I-3 | II-142 | C-14 |
| T1c-1522 | I-3 | II-143 | C-14 |
| T1c-1523 | I-3 | II-144 | C-14 |
| T1c-1524 | I-3 | II-145 | C-14 |
| T1c-1525 | I-3 | II-146 | C-14 |
| T1c-1526 | I-3 | II-147 | C-14 |
| T1c-1527 | I-3 | II-148 | C-14 |
| T1c-1528 | I-3 | II-149 | C-14 |
| T1c-1529 | I-3 | II-150 | C-14 |
| T1c-1530 | I-3 | II-151 | C-14 |
| T1c-1531 | I-3 | II-152 | C-14 |
| T1c-1532 | I-3 | II-153 | C-14 |
| T1c-1533 | I-3 | II-154 | C-14 |
| T1c-1534 | I-3 | II-155 | C-14 |
| T1c-1535 | I-3 | II-156 | C-14 |
| T1c-1536 | I-3 | II-157 | C-14 |
| T1c-1537 | I-3 | II-158 | C-14 |
| T1c-1538 | I-3 | II-159 | C-14 |
| T1c-1539 | I-3 | II-160 | C-14 |
| T1c-1540 | I-3 | II-161 | C-14 |
| T1c-1541 | I-3 | II-162 | C-14 |
| T1c-1542 | I-3 | II-163 | C-14 |
| T1c-1543 | I-3 | II-164 | C-14 |
| T1c-1544 | I-3 | II-165 | C-14 |
| T1c-1545 | I-3 | II-166 | C-14 |
| T1c-1546 | I-3 | II-167 | C-14 |
| T1c-1547 | I-3 | II-168 | C-14 |
| T1c-1548 | I-3 | II-169 | C-14 |
| T1c-1549 | I-3 | II-170 | C-14 |
| T1c-1550 | I-3 | II-171 | C-14 |
| T1c-1551 | I-3 | II-172 | C-14 |
| T1c-1552 | I-3 | II-173 | C-14 |
| T1c-1553 | I-3 | II-174 | C-14 |
| T1c-1554 | I-3 | II-175 | C-14 |
| T1c-1555 | I-3 | II-176 | C-14 |
| T1c-1556 | I-3 | II-177 | C-14 |
| T1c-1557 | I-3 | II-178 | C-14 |
| T1c-1558 | I-3 | II-179 | C-14 |
| T1c-1559 | I-3 | II-180 | C-14 |
| T1c-1560 | I-3 | II-181 | C-14 |
| T1c-1561 | I-3 | II-182 | C-14 |
| T1c-1562 | I-3 | II-183 | C-14 |
| T1c-1563 | I-3 | II-184 | C-14 |
| T1c-1564 | I-3 | II-185 | C-14 |
| T1c-1565 | I-3 | II-186 | C-14 |
| T1c-1566 | I-3 | II-187 | C-14 |
| T1c-1567 | I-3 | II-188 | C-14 |
| T1c-1568 | I-3 | II-189 | C-14 |
| T1c-1569 | I-3 | II-190 | C-14 |
| T1c-1570 | I-3 | II-191 | C-14 |
| T1c-1571 | I-3 | II-192 | C-14 |
| T1c-1572 | I-3 | II-193 | C-14 |
| T1c-1573 | I-3 | II-194 | C-14 |
| T1c-1574 | I-3 | II-195 | C-14 |
| T1c-1575 | I-3 | II-196 | C-14 |
| T1c-1576 | I-3 | II-197 | C-14 |
| T1c-1577 | I-3 | II-198 | C-14 |
| T1c-1578 | I-3 | II-199 | C-14 |
| T1c-1579 | I-3 | II-200 | C-14 |
| T1c-1580 | I-3 | II-201 | C-14 |
| T1c-1581 | I-3 | II-202 | C-14 |
| T1c-1582 | I-3 | II-203 | C-14 |
| T1c-1583 | I-3 | II-91 | C-15 |
| T1c-1584 | I-3 | II-92 | C-15 |
| T1c-1585 | I-3 | II-93 | C-15 |
| T1c-1586 | I-3 | II-94 | C-15 |
| T1c-1587 | I-3 | II-95 | C-15 |
| T1c-1588 | I-3 | II-96 | C-15 |
| T1c-1589 | I-3 | II-97 | C-15 |
| T1c-1590 | I-3 | II-98 | C-15 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-1591 | I-3 | II-99 | C-15 |
| T1c-1592 | I-3 | II-100 | C-15 |
| T1c-1593 | I-3 | II-101 | C-15 |
| T1c-1594 | I-3 | II-102 | C-15 |
| T1c-1595 | I-3 | II-103 | C-15 |
| T1c-1596 | I-3 | II-104 | C-15 |
| T1c-1597 | I-3 | II-105 | C-15 |
| T1c-1598 | I-3 | II-106 | C-15 |
| T1c-1599 | I-3 | II-107 | C-15 |
| T1c-1600 | I-3 | II-108 | C-15 |
| T1c-1601 | I-3 | II-109 | C-15 |
| T1c-1602 | I-3 | II-110 | C-15 |
| T1c-1603 | I-3 | II-111 | C-15 |
| T1c-1604 | I-3 | II-112 | C-15 |
| T1c-1605 | I-3 | II-113 | C-15 |
| T1c-1606 | I-3 | II-114 | C-15 |
| T1c-1607 | I-3 | II-115 | C-15 |
| T1c-1608 | I-3 | II-116 | C-15 |
| T1c-1609 | I-3 | II-117 | C-15 |
| T1c-1610 | I-3 | II-118 | C-15 |
| T1c-1611 | I-3 | II-119 | C-15 |
| T1c-1612 | I-3 | II-120 | C-15 |
| T1c-1613 | I-3 | II-121 | C-15 |
| T1c-1614 | I-3 | II-122 | C-15 |
| T1c-1615 | I-3 | II-123 | C-15 |
| T1c-1616 | I-3 | II-124 | C-15 |
| T1c-1617 | I-3 | II-125 | C-15 |
| T1c-1618 | I-3 | II-126 | C-15 |
| T1c-1619 | I-3 | II-127 | C-15 |
| T1c-1620 | I-3 | II-128 | C-15 |
| T1c-1621 | I-3 | II-129 | C-15 |
| T1c-1622 | I-3 | II-130 | C-15 |
| T1c-1623 | I-3 | II-131 | C-15 |
| T1c-1624 | I-3 | II-132 | C-15 |
| T1c-1625 | I-3 | II-133 | C-15 |
| T1c-1626 | I-3 | II-134 | C-15 |
| T1c-1627 | I-3 | II-135 | C-15 |
| T1c-1628 | I-3 | II-136 | C-15 |
| T1c-1629 | I-3 | II-137 | C-15 |
| T1c-1630 | I-3 | II-138 | C-15 |
| T1c-1631 | I-3 | II-139 | C-15 |
| T1c-1632 | I-3 | II-140 | C-15 |
| T1c-1633 | I-3 | II-141 | C-15 |
| T1c-1634 | I-3 | II-142 | C-15 |
| T1c-1635 | I-3 | II-143 | C-15 |
| T1c-1636 | I-3 | II-144 | C-15 |
| T1c-1637 | I-3 | II-145 | C-15 |
| T1c-1638 | I-3 | II-146 | C-15 |
| T1c-1639 | I-3 | II-147 | C-15 |
| T1c-1640 | I-3 | II-148 | C-15 |
| T1c-1641 | I-3 | II-149 | C-15 |
| T1c-1642 | I-3 | II-150 | C-15 |
| T1c-1643 | I-3 | II-151 | C-15 |
| T1c-1644 | I-3 | II-152 | C-15 |
| T1c-1645 | I-3 | II-153 | C-15 |
| T1c-1646 | I-3 | II-154 | C-15 |
| T1c-1647 | I-3 | II-155 | C-15 |
| T1c-1648 | I-3 | II-156 | C-15 |
| T1c-1649 | I-3 | II-157 | C-15 |
| T1c-1650 | I-3 | II-158 | C-15 |
| T1c-1651 | I-3 | II-159 | C-15 |
| T1c-1652 | I-3 | II-160 | C-15 |
| T1c-1653 | I-3 | II-161 | C-15 |
| T1c-1654 | I-3 | II-162 | C-15 |
| T1c-1655 | I-3 | II-163 | C-15 |
| T1c-1656 | I-3 | II-164 | C-15 |
| T1c-1657 | I-3 | II-165 | C-15 |
| T1c-1658 | I-3 | II-166 | C-15 |
| T1c-1659 | I-3 | II-167 | C-15 |
| T1c-1660 | I-3 | II-168 | C-15 |
| T1c-1661 | I-3 | II-169 | C-15 |
| T1c-1662 | I-3 | II-170 | C-15 |
| T1c-1663 | I-3 | II-171 | C-15 |
| T1c-1664 | I-3 | II-172 | C-15 |
| T1c-1665 | I-3 | II-173 | C-15 |
| T1c-1666 | I-3 | II-174 | C-15 |
| T1c-1667 | I-3 | II-175 | C-15 |
| T1c-1668 | I-3 | II-176 | C-15 |
| T1c-1669 | I-3 | II-177 | C-15 |
| T1c-1670 | I-3 | II-178 | C-15 |
| T1c-1671 | I-3 | II-179 | C-15 |
| T1c-1672 | I-3 | II-180 | C-15 |
| T1c-1673 | I-3 | II-181 | C-15 |
| T1c-1674 | I-3 | II-182 | C-15 |
| T1c-1675 | I-3 | II-183 | C-15 |
| T1c-1676 | I-3 | II-184 | C-15 |
| T1c-1677 | I-3 | II-185 | C-15 |
| T1c-1678 | I-3 | II-186 | C-15 |
| T1c-1679 | I-3 | II-187 | C-15 |
| T1c-1680 | I-3 | II-188 | C-15 |
| T1c-1681 | I-3 | II-189 | C-15 |
| T1c-1682 | I-3 | II-190 | C-15 |
| T1c-1683 | I-3 | II-191 | C-15 |
| T1c-1684 | I-3 | II-192 | C-15 |
| T1c-1685 | I-3 | II-193 | C-15 |
| T1c-1686 | I-3 | II-194 | C-15 |
| T1c-1687 | I-3 | II-195 | C-15 |
| T1c-1688 | I-3 | II-196 | C-15 |
| T1c-1689 | I-3 | II-197 | C-15 |
| T1c-1690 | I-3 | II-198 | C-15 |
| T1c-1691 | I-3 | II-199 | C-15 |
| T1c-1692 | I-3 | II-200 | C-15 |
| T1c-1693 | I-3 | II-201 | C-15 |
| T1c-1694 | I-3 | II-202 | C-15 |
| T1c-1695 | I-3 | II-203 | C-15 |
| T1c-1696 | I-3 | II-91 | C-16 |
| T1c-1697 | I-3 | II-92 | C-16 |
| T1c-1698 | I-3 | II-93 | C-16 |
| T1c-1699 | I-3 | II-94 | C-16 |
| T1c-1700 | I-3 | II-95 | C-16 |
| T1c-1701 | I-3 | II-96 | C-16 |
| T1c-1702 | I-3 | II-97 | C-16 |
| T1c-1703 | I-3 | II-98 | C-16 |
| T1c-1704 | I-3 | II-99 | C-16 |
| T1c-1705 | I-3 | II-100 | C-16 |
| T1c-1706 | I-3 | II-101 | C-16 |
| T1c-1707 | I-3 | II-102 | C-16 |
| T1c-1708 | I-3 | II-103 | C-16 |
| T1c-1709 | I-3 | II-104 | C-16 |
| T1c-1710 | I-3 | II-105 | C-16 |
| T1c-1711 | I-3 | II-106 | C-16 |
| T1c-1712 | I-3 | II-107 | C-16 |
| T1c-1713 | I-3 | II-108 | C-16 |
| T1c-1714 | I-3 | II-109 | C-16 |
| T1c-1715 | I-3 | II-110 | C-16 |
| T1c-1716 | I-3 | II-111 | C-16 |
| T1c-1717 | I-3 | II-112 | C-16 |
| T1c-1718 | I-3 | II-113 | C-16 |
| T1c-1719 | I-3 | II-114 | C-16 |
| T1c-1720 | I-3 | II-115 | C-16 |
| T1c-1721 | I-3 | II-116 | C-16 |
| T1c-1722 | I-3 | II-117 | C-16 |
| T1c-1723 | I-3 | II-118 | C-16 |
| T1c-1724 | I-3 | II-119 | C-16 |
| T1c-1725 | I-3 | II-120 | C-16 |
| T1c-1726 | I-3 | II-121 | C-16 |
| T1c-1727 | I-3 | II-122 | C-16 |
| T1c-1728 | I-3 | II-123 | C-16 |
| T1c-1729 | I-3 | II-124 | C-16 |
| T1c-1730 | I-3 | II-125 | C-16 |
| T1c-1731 | I-3 | II-126 | C-16 |
| T1c-1732 | I-3 | II-127 | C-16 |
| T1c-1733 | I-3 | II-128 | C-16 |
| T1c-1734 | I-3 | II-129 | C-16 |
| T1c-1735 | I-3 | II-130 | C-16 |
| T1c-1736 | I-3 | II-131 | C-16 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-1737 | I-3 | II-132 | C-16 |
| T1c-1738 | I-3 | II-133 | C-16 |
| T1c-1739 | I-3 | II-134 | C-16 |
| T1c-1740 | I-3 | II-135 | C-16 |
| T1c-1741 | I-3 | II-136 | C-16 |
| T1c-1742 | I-3 | II-137 | C-16 |
| T1c-1743 | I-3 | II-138 | C-16 |
| T1c-1744 | I-3 | II-139 | C-16 |
| T1c-1745 | I-3 | II-140 | C-16 |
| T1c-1746 | I-3 | II-141 | C-16 |
| T1c-1747 | I-3 | II-142 | C-16 |
| T1c-1748 | I-3 | II-143 | C-16 |
| T1c-1749 | I-3 | II-144 | C-16 |
| T1c-1750 | I-3 | II-145 | C-16 |
| T1c-1751 | I-3 | II-146 | C-16 |
| T1c-1752 | I-3 | II-147 | C-16 |
| T1c-1753 | I-3 | II-148 | C-16 |
| T1c-1754 | I-3 | II-149 | C-16 |
| T1c-1755 | I-3 | II-150 | C-16 |
| T1c-1756 | I-3 | II-151 | C-16 |
| T1c-1757 | I-3 | II-152 | C-16 |
| T1c-1758 | I-3 | II-153 | C-16 |
| T1c-1759 | I-3 | II-154 | C-16 |
| T1c-1760 | I-3 | II-155 | C-16 |
| T1c-1761 | I-3 | II-156 | C-16 |
| T1c-1762 | I-3 | II-157 | C-16 |
| T1c-1763 | I-3 | II-158 | C-16 |
| T1c-1764 | I-3 | II-159 | C-16 |
| T1c-1765 | I-3 | II-160 | C-16 |
| T1c-1766 | I-3 | II-161 | C-16 |
| T1c-1767 | I-3 | II-162 | C-16 |
| T1c-1768 | I-3 | II-163 | C-16 |
| T1c-1769 | I-3 | II-164 | C-16 |
| T1c-1770 | I-3 | II-165 | C-16 |
| T1c-1771 | I-3 | II-166 | C-16 |
| T1c-1772 | I-3 | II-167 | C-16 |
| T1c-1773 | I-3 | II-168 | C-16 |
| T1c-1774 | I-3 | II-169 | C-16 |
| T1c-1775 | I-3 | II-170 | C-16 |
| T1c-1776 | I-3 | II-171 | C-16 |
| T1c-1777 | I-3 | II-172 | C-16 |
| T1c-1778 | I-3 | II-173 | C-16 |
| T1c-1779 | I-3 | II-174 | C-16 |
| T1c-1780 | I-3 | II-175 | C-16 |
| T1c-1781 | I-3 | II-176 | C-16 |
| T1c-1782 | I-3 | II-177 | C-16 |
| T1c-1783 | I-3 | II-178 | C-16 |
| T1c-1784 | I-3 | II-179 | C-16 |
| T1c-1785 | I-3 | II-180 | C-16 |
| T1c-1786 | I-3 | II-181 | C-16 |
| T1c-1787 | I-3 | II-182 | C-16 |
| T1c-1788 | I-3 | II-183 | C-16 |
| T1c-1789 | I-3 | II-184 | C-16 |
| T1c-1790 | I-3 | II-185 | C-16 |
| T1c-1791 | I-3 | II-186 | C-16 |
| T1c-1792 | I-3 | II-187 | C-16 |
| T1c-1793 | I-3 | II-188 | C-16 |
| T1c-1794 | I-3 | II-189 | C-16 |
| T1c-1795 | I-3 | II-190 | C-16 |
| T1c-1796 | I-3 | II-191 | C-16 |
| T1c-1797 | I-3 | II-192 | C-16 |
| T1c-1798 | I-3 | II-193 | C-16 |
| T1c-1799 | I-3 | II-194 | C-16 |
| T1c-1800 | I-3 | II-195 | C-16 |
| T1c-1801 | I-3 | II-196 | C-16 |
| T1c-1802 | I-3 | II-197 | C-16 |
| T1c-1803 | I-3 | II-198 | C-16 |
| T1c-1804 | I-3 | II-199 | C-16 |
| T1c-1805 | I-3 | II-200 | C-16 |
| T1c-1806 | I-3 | II-201 | C-16 |
| T1c-1807 | I-3 | II-202 | C-16 |
| T1c-1808 | I-3 | II-203 | C-16 |
| T1c-1809 | I-3 | II-91 | C-17 |
| T1c-1810 | I-3 | II-92 | C-17 |
| T1c-1811 | I-3 | II-93 | C-17 |
| T1c-1812 | I-3 | II-94 | C-17 |
| T1c-1813 | I-3 | II-95 | C-17 |
| T1c-1814 | I-3 | II-96 | C-17 |
| T1c-1815 | I-3 | II-97 | C-17 |
| T1c-1816 | I-3 | II-98 | C-17 |
| T1c-1817 | I-3 | II-99 | C-17 |
| T1c-1818 | I-3 | II-100 | C-17 |
| T1c-1819 | I-3 | II-101 | C-17 |
| T1c-1820 | I-3 | II-102 | C-17 |
| T1c-1821 | I-3 | II-103 | C-17 |
| T1c-1822 | I-3 | II-104 | C-17 |
| T1c-1823 | I-3 | II-105 | C-17 |
| T1c-1824 | I-3 | II-106 | C-17 |
| T1c-1825 | I-3 | II-107 | C-17 |
| T1c-1826 | I-3 | II-108 | C-17 |
| T1c-1827 | I-3 | II-109 | C-17 |
| T1c-1828 | I-3 | II-110 | C-17 |
| T1c-1829 | I-3 | II-111 | C-17 |
| T1c-1830 | I-3 | II-112 | C-17 |
| T1c-1831 | I-3 | II-113 | C-17 |
| T1c-1832 | I-3 | II-114 | C-17 |
| T1c-1833 | I-3 | II-115 | C-17 |
| T1c-1834 | I-3 | II-116 | C-17 |
| T1c-1835 | I-3 | II-117 | C-17 |
| T1c-1836 | I-3 | II-118 | C-17 |
| T1c-1837 | I-3 | II-119 | C-17 |
| T1c-1838 | I-3 | II-120 | C-17 |
| T1c-1839 | I-3 | II-121 | C-17 |
| T1c-1840 | I-3 | II-122 | C-17 |
| T1c-1841 | I-3 | II-123 | C-17 |
| T1c-1842 | I-3 | II-124 | C-17 |
| T1c-1843 | I-3 | II-125 | C-17 |
| T1c-1844 | I-3 | II-126 | C-17 |
| T1c-1845 | I-3 | II-127 | C-17 |
| T1c-1846 | I-3 | II-128 | C-17 |
| T1c-1847 | I-3 | II-129 | C-17 |
| T1c-1848 | I-3 | II-130 | C-17 |
| T1c-1849 | I-3 | II-131 | C-17 |
| T1c-1850 | I-3 | II-132 | C-17 |
| T1c-1851 | I-3 | II-133 | C-17 |
| T1c-1852 | I-3 | II-134 | C-17 |
| T1c-1853 | I-3 | II-135 | C-17 |
| T1c-1854 | I-3 | II-136 | C-17 |
| T1c-1855 | I-3 | II-137 | C-17 |
| T1c-1856 | I-3 | II-138 | C-17 |
| T1c-1857 | I-3 | II-139 | C-17 |
| T1c-1858 | I-3 | II-140 | C-17 |
| T1c-1859 | I-3 | II-141 | C-17 |
| T1c-1860 | I-3 | II-142 | C-17 |
| T1c-1861 | I-3 | II-143 | C-17 |
| T1c-1862 | I-3 | II-144 | C-17 |
| T1c-1863 | I-3 | II-145 | C-17 |
| T1c-1864 | I-3 | II-146 | C-17 |
| T1c-1865 | I-3 | II-147 | C-17 |
| T1c-1866 | I-3 | II-148 | C-17 |
| T1c-1867 | I-3 | II-149 | C-17 |
| T1c-1868 | I-3 | II-150 | C-17 |
| T1c-1869 | I-3 | II-151 | C-17 |
| T1c-1870 | I-3 | II-152 | C-17 |
| T1c-1871 | I-3 | II-153 | C-17 |
| T1c-1872 | I-3 | II-154 | C-17 |
| T1c-1873 | I-3 | II-155 | C-17 |
| T1c-1874 | I-3 | II-156 | C-17 |
| T1c-1875 | I-3 | II-157 | C-17 |
| T1c-1876 | I-3 | II-158 | C-17 |
| T1c-1877 | I-3 | II-159 | C-17 |
| T1c-1878 | I-3 | II-160 | C-17 |
| T1c-1879 | I-3 | II-161 | C-17 |
| T1c-1880 | I-3 | II-162 | C-17 |
| T1c-1881 | I-3 | II-163 | C-17 |
| T1c-1882 | I-3 | II-164 | C-17 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-1883 | I-3 | II-165 | C-17 |
| T1c-1884 | I-3 | II-166 | C-17 |
| T1c-1885 | I-3 | II-167 | C-17 |
| T1c-1886 | I-3 | II-168 | C-17 |
| T1c-1887 | I-3 | II-169 | C-17 |
| T1c-1888 | I-3 | II-170 | C-17 |
| T1c-1889 | I-3 | II-171 | C-17 |
| T1c-1890 | I-3 | II-172 | C-17 |
| T1c-1891 | I-3 | II-173 | C-17 |
| T1c-1892 | I-3 | II-174 | C-17 |
| T1c-1893 | I-3 | II-175 | C-17 |
| T1c-1894 | I-3 | II-176 | C-17 |
| T1c-1895 | I-3 | II-177 | C-17 |
| T1c-1896 | I-3 | II-178 | C-17 |
| T1c-1897 | I-3 | II-179 | C-17 |
| T1c-1898 | I-3 | II-180 | C-17 |
| T1c-1899 | I-3 | II-181 | C-17 |
| T1c-1900 | I-3 | II-182 | C-17 |
| T1c-1901 | I-3 | II-183 | C-17 |
| T1c-1902 | I-3 | II-184 | C-17 |
| T1c-1903 | I-3 | II-185 | C-17 |
| T1c-1904 | I-3 | II-186 | C-17 |
| T1c-1905 | I-3 | II-187 | C-17 |
| T1c-1906 | I-3 | II-188 | C-17 |
| T1c-1907 | I-3 | II-189 | C-17 |
| T1c-1908 | I-3 | II-190 | C-17 |
| T1c-1909 | I-3 | II-191 | C-17 |
| T1c-1910 | I-3 | II-192 | C-17 |
| T1c-1911 | I-3 | II-193 | C-17 |
| T1c-1912 | I-3 | II-194 | C-17 |
| T1c-1913 | I-3 | II-195 | C-17 |
| T1c-1914 | I-3 | II-196 | C-17 |
| T1c-1915 | I-3 | II-197 | C-17 |
| T1c-1916 | I-3 | II-198 | C-17 |
| T1c-1917 | I-3 | II-199 | C-17 |
| T1c-1918 | I-3 | II-200 | C-17 |
| T1c-1919 | I-3 | II-201 | C-17 |
| T1c-1920 | I-3 | II-202 | C-17 |
| T1c-1921 | I-3 | II-203 | C-17 |
| T1c-1922 | I-3 | II-91 | C-18 |
| T1c-1923 | I-3 | II-92 | C-18 |
| T1c-1924 | I-3 | II-93 | C-18 |
| T1c-1925 | I-3 | II-94 | C-18 |
| T1c-1926 | I-3 | II-95 | C-18 |
| T1c-1927 | I-3 | II-96 | C-18 |
| T1c-1928 | I-3 | II-97 | C-18 |
| T1c-1929 | I-3 | II-98 | C-18 |
| T1c-1930 | I-3 | II-99 | C-18 |
| T1c-1931 | I-3 | II-100 | C-18 |
| T1c-1932 | I-3 | II-101 | C-18 |
| T1c-1933 | I-3 | II-102 | C-18 |
| T1c-1934 | I-3 | II-103 | C-18 |
| T1c-1935 | I-3 | II-104 | C-18 |
| T1c-1936 | I-3 | II-105 | C-18 |
| T1c-1937 | I-3 | II-106 | C-18 |
| T1c-1938 | I-3 | II-107 | C-18 |
| T1c-1939 | I-3 | II-108 | C-18 |
| T1c-1940 | I-3 | II-109 | C-18 |
| T1c-1941 | I-3 | II-110 | C-18 |
| T1c-1942 | I-3 | II-111 | C-18 |
| T1c-1943 | I-3 | II-112 | C-18 |
| T1c-1944 | I-3 | II-113 | C-18 |
| T1c-1945 | I-3 | II-114 | C-18 |
| T1c-1946 | I-3 | II-115 | C-18 |
| T1c-1947 | I-3 | II-116 | C-18 |
| T1c-1948 | I-3 | II-117 | C-18 |
| T1c-1949 | I-3 | II-118 | C-18 |
| T1c-1950 | I-3 | II-119 | C-18 |
| T1c-1951 | I-3 | II-120 | C-18 |
| T1c-1952 | I-3 | II-121 | C-18 |
| T1c-1953 | I-3 | II-122 | C-18 |
| T1c-1954 | I-3 | II-123 | C-18 |
| T1c-1955 | I-3 | II-124 | C-18 |
| T1c-1956 | I-3 | II-125 | C-18 |
| T1c-1957 | I-3 | II-126 | C-18 |
| T1c-1958 | I-3 | II-127 | C-18 |
| T1c-1959 | I-3 | II-128 | C-18 |
| T1c-1960 | I-3 | II-129 | C-18 |
| T1c-1961 | I-3 | II-130 | C-18 |
| T1c-1962 | I-3 | II-131 | C-18 |
| T1c-1963 | I-3 | II-132 | C-18 |
| T1c-1964 | I-3 | II-133 | C-18 |
| T1c-1965 | I-3 | II-134 | C-18 |
| T1c-1966 | I-3 | II-135 | C-18 |
| T1c-1967 | I-3 | II-136 | C-18 |
| T1c-1968 | I-3 | II-137 | C-18 |
| T1c-1969 | I-3 | II-138 | C-18 |
| T1c-1970 | I-3 | II-139 | C-18 |
| T1c-1971 | I-3 | II-140 | C-18 |
| T1c-1972 | I-3 | II-141 | C-18 |
| T1c-1973 | I-3 | II-142 | C-18 |
| T1c-1974 | I-3 | II-143 | C-18 |
| T1c-1975 | I-3 | II-144 | C-18 |
| T1c-1976 | I-3 | II-145 | C-18 |
| T1c-1977 | I-3 | II-146 | C-18 |
| T1c-1978 | I-3 | II-147 | C-18 |
| T1c-1979 | I-3 | II-148 | C-18 |
| T1c-1980 | I-3 | II-149 | C-18 |
| T1c-1981 | I-3 | II-150 | C-18 |
| T1c-1982 | I-3 | II-151 | C-18 |
| T1c-1983 | I-3 | II-152 | C-18 |
| T1c-1984 | I-3 | II-153 | C-18 |
| T1c-1985 | I-3 | II-154 | C-18 |
| T1c-1986 | I-3 | II-155 | C-18 |
| T1c-1987 | I-3 | II-156 | C-18 |
| T1c-1988 | I-3 | II-157 | C-18 |
| T1c-1989 | I-3 | II-158 | C-18 |
| T1c-1990 | I-3 | II-159 | C-18 |
| T1c-1991 | I-3 | II-160 | C-18 |
| T1c-1992 | I-3 | II-161 | C-18 |
| T1c-1993 | I-3 | II-162 | C-18 |
| T1c-1994 | I-3 | II-163 | C-18 |
| T1c-1995 | I-3 | II-164 | C-18 |
| T1c-1996 | I-3 | II-165 | C-18 |
| T1c-1997 | I-3 | II-166 | C-18 |
| T1c-1998 | I-3 | II-167 | C-18 |
| T1c-1999 | I-3 | II-168 | C-18 |
| T1c-2000 | I-3 | II-169 | C-18 |
| T1c-2001 | I-3 | II-170 | C-18 |
| T1c-2002 | I-3 | II-171 | C-18 |
| T1c-2003 | I-3 | II-172 | C-18 |
| T1c-2004 | I-3 | II-173 | C-18 |
| T1c-2005 | I-3 | II-174 | C-18 |
| T1c-2006 | I-3 | II-175 | C-18 |
| T1c-2007 | I-3 | II-176 | C-18 |
| T1c-2008 | I-3 | II-177 | C-18 |
| T1c-2009 | I-3 | II-178 | C-18 |
| T1c-2010 | I-3 | II-179 | C-18 |
| T1c-2011 | I-3 | II-180 | C-18 |
| T1c-2012 | I-3 | II-181 | C-18 |
| T1c-2013 | I-3 | II-182 | C-18 |
| T1c-2014 | I-3 | II-183 | C-18 |
| T1c-2015 | I-3 | II-184 | C-18 |
| T1c-2016 | I-3 | II-185 | C-18 |
| T1c-2017 | I-3 | II-186 | C-18 |
| T1c-2018 | I-3 | II-187 | C-18 |
| T1c-2019 | I-3 | II-188 | C-18 |
| T1c-2020 | I-3 | II-189 | C-18 |
| T1c-2021 | I-3 | II-190 | C-18 |
| T1c-2022 | I-3 | II-191 | C-18 |
| T1c-2023 | I-3 | II-192 | C-18 |
| T1c-2024 | I-3 | II-193 | C-18 |
| T1c-2025 | I-3 | II-194 | C-18 |
| T1c-2026 | I-3 | II-195 | C-18 |
| T1c-2027 | I-3 | II-196 | C-18 |
| T1c-2028 | I-3 | II-197 | C-18 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-2029 | I-3 | II-198 | C-18 |
| T1c-2030 | I-3 | II-199 | C-18 |
| T1c-2031 | I-3 | II-200 | C-18 |
| T1c-2032 | I-3 | II-201 | C-18 |
| T1c-2033 | I-3 | II-202 | C-18 |
| T1c-2034 | I-3 | II-203 | C-18 |
| T1c-2035 | I-3 | II-91 | C-19 |
| T1c-2036 | I-3 | II-92 | C-20 |
| T1c-2037 | I-3 | II-93 | C-20 |
| T1c-2038 | I-3 | II-94 | C-20 |
| T1c-2039 | I-3 | II-95 | C-20 |
| T1c-2040 | I-3 | II-96 | C-20 |
| T1c-2041 | I-3 | II-97 | C-20 |
| T1c-2042 | I-3 | II-98 | C-20 |
| T1c-2043 | I-3 | II-99 | C-20 |
| T1c-2044 | I-3 | II-100 | C-20 |
| T1c-2045 | I-3 | II-101 | C-20 |
| T1c-2046 | I-3 | II-102 | C-20 |
| T1c-2047 | I-3 | II-103 | C-20 |
| T1c-2048 | I-3 | II-104 | C-20 |
| T1c-2049 | I-3 | II-105 | C-20 |
| T1c-2050 | I-3 | II-106 | C-20 |
| T1c-2051 | I-3 | II-107 | C-20 |
| T1c-2052 | I-3 | II-108 | C-20 |
| T1c-2053 | I-3 | II-109 | C-20 |
| T1c-2054 | I-3 | II-110 | C-20 |
| T1c-2055 | I-3 | II-111 | C-20 |
| T1c-2056 | I-3 | II-112 | C-20 |
| T1c-2057 | I-3 | II-113 | C-20 |
| T1c-2058 | I-3 | II-114 | C-20 |
| T1c-2059 | I-3 | II-115 | C-20 |
| T1c-2060 | I-3 | II-116 | C-20 |
| T1c-2061 | I-3 | II-117 | C-20 |
| T1c-2062 | I-3 | II-118 | C-20 |
| T1c-2063 | I-3 | II-119 | C-20 |
| T1c-2064 | I-3 | II-120 | C-20 |
| T1c-2065 | I-3 | II-121 | C-20 |
| T1c-2066 | I-3 | II-122 | C-20 |
| T1c-2067 | I-3 | II-123 | C-20 |
| T1c-2068 | I-3 | II-124 | C-20 |
| T1c-2069 | I-3 | II-125 | C-20 |
| T1c-2070 | I-3 | II-126 | C-20 |
| T1c-2071 | I-3 | II-127 | C-20 |
| T1c-2072 | I-3 | II-128 | C-20 |
| T1c-2073 | I-3 | II-129 | C-20 |
| T1c-2074 | I-3 | II-130 | C-20 |
| T1c-2075 | I-3 | II-131 | C-20 |
| T1c-2076 | I-3 | II-132 | C-20 |
| T1c-2077 | I-3 | II-133 | C-20 |
| T1c-2078 | I-3 | II-134 | C-20 |
| T1c-2079 | I-3 | II-135 | C-20 |
| T1c-2080 | I-3 | II-136 | C-20 |
| T1c-2081 | I-3 | II-137 | C-20 |
| T1c-2082 | I-3 | II-138 | C-20 |
| T1c-2083 | I-3 | II-139 | C-20 |
| T1c-2084 | I-3 | II-140 | C-20 |
| T1c-2085 | I-3 | II-141 | C-20 |
| T1c-2086 | I-3 | II-142 | C-20 |
| T1c-2087 | I-3 | II-143 | C-20 |
| T1c-2088 | I-3 | II-144 | C-20 |
| T1c-2089 | I-3 | II-145 | C-20 |
| T1c-2090 | I-3 | II-146 | C-20 |
| T1c-2091 | I-3 | II-147 | C-20 |
| T1c-2092 | I-3 | II-148 | C-20 |
| T1c-2093 | I-3 | II-149 | C-20 |
| T1c-2094 | I-3 | II-150 | C-20 |
| T1c-2095 | I-3 | II-151 | C-20 |
| T1c-2096 | I-3 | II-152 | C-20 |
| T1c-2097 | I-3 | II-153 | C-20 |
| T1c-2098 | I-3 | II-154 | C-20 |
| T1c-2099 | I-3 | II-155 | C-20 |
| T1c-2100 | I-3 | II-156 | C-20 |
| T1c-2101 | I-3 | II-157 | C-20 |
| T1c-2102 | I-3 | II-158 | C-20 |
| T1c-2103 | I-3 | II-159 | C-20 |
| T1c-2104 | I-3 | II-160 | C-20 |
| T1c-2105 | I-3 | II-161 | C-20 |
| T1c-2106 | I-3 | II-162 | C-20 |
| T1c-2107 | I-3 | II-163 | C-20 |
| T1c-2108 | I-3 | II-164 | C-20 |
| T1c-2109 | I-3 | II-165 | C-20 |
| T1c-2110 | I-3 | II-166 | C-20 |
| T1c-2111 | I-3 | II-167 | C-20 |
| T1c-2112 | I-3 | II-168 | C-20 |
| T1c-2113 | I-3 | II-169 | C-20 |
| T1c-2114 | I-3 | II-170 | C-20 |
| T1c-2115 | I-3 | II-171 | C-20 |
| T1c-2116 | I-3 | II-172 | C-20 |
| T1c-2117 | I-3 | II-173 | C-20 |
| T1c-2118 | I-3 | II-174 | C-20 |
| T1c-2119 | I-3 | II-175 | C-20 |
| T1c-2120 | I-3 | II-176 | C-20 |
| T1c-2121 | I-3 | II-177 | C-20 |
| T1c-2122 | I-3 | II-178 | C-20 |
| T1c-2123 | I-3 | II-179 | C-20 |
| T1c-2124 | I-3 | II-180 | C-20 |
| T1c-2125 | I-3 | II-181 | C-20 |
| T1c-2126 | I-3 | II-182 | C-20 |
| T1c-2127 | I-3 | II-183 | C-20 |
| T1c-2128 | I-3 | II-184 | C-20 |
| T1c-2129 | I-3 | II-185 | C-20 |
| T1c-2130 | I-3 | II-186 | C-20 |
| T1c-2131 | I-3 | II-187 | C-20 |
| T1c-2132 | I-3 | II-188 | C-20 |
| T1c-2133 | I-3 | II-189 | C-20 |
| T1c-2134 | I-3 | II-190 | C-20 |
| T1c-2135 | I-3 | II-191 | C-20 |
| T1c-2136 | I-3 | II-192 | C-20 |
| T1c-2137 | I-3 | II-193 | C-20 |
| T1c-2138 | I-3 | II-194 | C-20 |
| T1c-2139 | I-3 | II-195 | C-20 |
| T1c-2140 | I-3 | II-196 | C-20 |
| T1c-2141 | I-3 | II-197 | C-20 |
| T1c-2142 | I-3 | II-198 | C-20 |
| T1c-2143 | I-3 | II-199 | C-20 |
| T1c-2144 | I-3 | II-200 | C-20 |
| T1c-2145 | I-3 | II-201 | C-20 |
| T1c-2146 | I-3 | II-202 | C-20 |
| T1c-2147 | I-3 | II-203 | C-20 |
| T1c-2148 | I-3 | II-91 | C-21 |
| T1c-2149 | I-3 | II-92 | C-21 |
| T1c-2150 | I-3 | II-93 | C-21 |
| T1c-2151 | I-3 | II-94 | C-21 |
| T1c-2152 | I-3 | II-95 | C-21 |
| T1c-2153 | I-3 | II-96 | C-21 |
| T1c-2154 | I-3 | II-97 | C-21 |
| T1c-2155 | I-3 | II-98 | C-21 |
| T1c-2156 | I-3 | II-99 | C-21 |
| T1c-2157 | I-3 | II-100 | C-21 |
| T1c-2158 | I-3 | II-101 | C-21 |
| T1c-2159 | I-3 | II-102 | C-21 |
| T1c-2160 | I-3 | II-103 | C-21 |
| T1c-2161 | I-3 | II-104 | C-21 |
| T1c-2162 | I-3 | II-105 | C-21 |
| T1c-2163 | I-3 | II-106 | C-21 |
| T1c-2164 | I-3 | II-107 | C-21 |
| T1c-2165 | I-3 | II-108 | C-21 |
| T1c-2166 | I-3 | II-109 | C-21 |
| T1c-2167 | I-3 | II-110 | C-21 |
| T1c-2168 | I-3 | II-111 | C-21 |
| T1c-2169 | I-3 | II-112 | C-21 |
| T1c-2170 | I-3 | II-113 | C-21 |
| T1c-2171 | I-3 | II-114 | C-21 |
| T1c-2172 | I-3 | II-115 | C-21 |
| T1c-2173 | I-3 | II-116 | C-21 |
| T1c-2174 | I-3 | II-117 | C-21 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-2175 | I-3 | II-118 | C-21 |
| T1c-2176 | I-3 | II-119 | C-21 |
| T1c-2177 | I-3 | II-120 | C-21 |
| T1c-2178 | I-3 | II-121 | C-21 |
| T1c-2179 | I-3 | II-122 | C-21 |
| T1c-2180 | I-3 | II-123 | C-21 |
| T1c-2181 | I-3 | II-124 | C-21 |
| T1c-2182 | I-3 | II-125 | C-21 |
| T1c-2183 | I-3 | II-126 | C-21 |
| T1c-2184 | I-3 | II-127 | C-21 |
| T1c-2185 | I-3 | II-128 | C-21 |
| T1c-2186 | I-3 | II-129 | C-21 |
| T1c-2187 | I-3 | II-130 | C-21 |
| T1c-2188 | I-3 | II-131 | C-21 |
| T1c-2189 | I-3 | II-132 | C-21 |
| T1c-2190 | I-3 | II-133 | C-21 |
| T1c-2191 | I-3 | II-134 | C-21 |
| T1c-2192 | I-3 | II-135 | C-21 |
| T1c-2193 | I-3 | II-136 | C-21 |
| T1c-2194 | I-3 | II-137 | C-21 |
| T1c-2195 | I-3 | II-138 | C-21 |
| T1c-2196 | I-3 | II-139 | C-21 |
| T1c-2197 | I-3 | II-140 | C-21 |
| T1c-2198 | I-3 | II-141 | C-21 |
| T1c-2199 | I-3 | II-142 | C-21 |
| T1c-2200 | I-3 | II-143 | C-21 |
| T1c-2201 | I-3 | II-144 | C-21 |
| T1c-2202 | I-3 | II-145 | C-21 |
| T1c-2203 | I-3 | II-146 | C-21 |
| T1c-2204 | I-3 | II-147 | C-21 |
| T1c-2205 | I-3 | II-148 | C-21 |
| T1c-2206 | I-3 | II-149 | C-21 |
| T1c-2207 | I-3 | II-150 | C-21 |
| T1c-2208 | I-3 | II-151 | C-21 |
| T1c-2209 | I-3 | II-152 | C-21 |
| T1c-2210 | I-3 | II-153 | C-21 |
| T1c-2211 | I-3 | II-154 | C-21 |
| T1c-2212 | I-3 | II-155 | C-21 |
| T1c-2213 | I-3 | II-156 | C-21 |
| T1c-2214 | I-3 | II-157 | C-21 |
| T1c-2215 | I-3 | II-158 | C-21 |
| T1c-2216 | I-3 | II-159 | C-21 |
| T1c-2217 | I-3 | II-160 | C-21 |
| T1c-2218 | I-3 | II-161 | C-21 |
| T1c-2219 | I-3 | II-162 | C-21 |
| T1c-2220 | I-3 | II-163 | C-21 |
| T1c-2221 | I-3 | II-164 | C-21 |
| T1c-2222 | I-3 | II-165 | C-21 |
| T1c-2223 | I-3 | II-166 | C-21 |
| T1c-2224 | I-3 | II-167 | C-21 |
| T1c-2225 | I-3 | II-168 | C-21 |
| T1c-2226 | I-3 | II-169 | C-21 |
| T1c-2227 | I-3 | II-170 | C-21 |
| T1c-2228 | I-3 | II-171 | C-21 |
| T1c-2229 | I-3 | II-172 | C-21 |
| T1c-2230 | I-3 | II-173 | C-21 |
| T1c-2231 | I-3 | II-174 | C-21 |
| T1c-2232 | I-3 | II-175 | C-21 |
| T1c-2233 | I-3 | II-176 | C-21 |
| T1c-2234 | I-3 | II-177 | C-21 |
| T1c-2235 | I-3 | II-178 | C-21 |
| T1c-2236 | I-3 | II-179 | C-21 |
| T1c-2237 | I-3 | II-180 | C-21 |
| T1c-2238 | I-3 | II-181 | C-21 |
| T1c-2239 | I-3 | II-182 | C-21 |
| T1c-2240 | I-3 | II-183 | C-21 |
| T1c-2241 | I-3 | II-184 | C-21 |
| T1c-2242 | I-3 | II-185 | C-21 |
| T1c-2243 | I-3 | II-186 | C-21 |
| T1c-2244 | I-3 | II-187 | C-21 |
| T1c-2245 | I-3 | II-188 | C-21 |
| T1c-2246 | I-3 | II-189 | C-21 |
| T1c-2247 | I-3 | II-190 | C-21 |
| T1c-2248 | I-3 | II-191 | C-21 |
| T1c-2249 | I-3 | II-192 | C-21 |
| T1c-2250 | I-3 | II-193 | C-21 |
| T1c-2251 | I-3 | II-194 | C-21 |
| T1c-2252 | I-3 | II-195 | C-21 |
| T1c-2253 | I-3 | II-196 | C-21 |
| T1c-2254 | I-3 | II-197 | C-21 |
| T1c-2255 | I-3 | II-198 | C-21 |
| T1c-2256 | I-3 | II-199 | C-21 |
| T1c-2257 | I-3 | II-200 | C-21 |
| T1c-2258 | I-3 | II-201 | C-21 |
| T1c-2259 | I-3 | II-202 | C-21 |
| T1c-2260 | I-3 | II-203 | C-21 |
| T1c-2261 | I-3 | II-91 | C-22 |
| T1c-2262 | I-3 | II-92 | C-22 |
| T1c-2263 | I-3 | II-93 | C-22 |
| T1c-2264 | I-3 | II-94 | C-22 |
| T1c-2265 | I-3 | II-95 | C-22 |
| T1c-2266 | I-3 | II-96 | C-22 |
| T1c-2267 | I-3 | II-97 | C-22 |
| T1c-2268 | I-3 | II-98 | C-22 |
| T1c-2269 | I-3 | II-99 | C-22 |
| T1c-2270 | I-3 | II-100 | C-22 |
| T1c-2271 | I-3 | II-101 | C-22 |
| T1c-2272 | I-3 | II-102 | C-22 |
| T1c-2273 | I-3 | II-103 | C-22 |
| T1c-2274 | I-3 | II-104 | C-22 |
| T1c-2275 | I-3 | II-105 | C-22 |
| T1c-2276 | I-3 | II-106 | C-22 |
| T1c-2277 | I-3 | II-107 | C-22 |
| T1c-2278 | I-3 | II-108 | C-22 |
| T1c-2279 | I-3 | II-109 | C-22 |
| T1c-2280 | I-3 | II-110 | C-22 |
| T1c-2281 | I-3 | II-111 | C-22 |
| T1c-2282 | I-3 | II-112 | C-22 |
| T1c-2283 | I-3 | II-113 | C-22 |
| T1c-2284 | I-3 | II-114 | C-22 |
| T1c-2285 | I-3 | II-115 | C-22 |
| T1c-2286 | I-3 | II-116 | C-22 |
| T1c-2287 | I-3 | II-117 | C-22 |
| T1c-2288 | I-3 | II-118 | C-22 |
| T1c-2289 | I-3 | II-119 | C-22 |
| T1c-2290 | I-3 | II-120 | C-22 |
| T1c-2291 | I-3 | II-121 | C-22 |
| T1c-2292 | I-3 | II-122 | C-22 |
| T1c-2293 | I-3 | II-123 | C-22 |
| T1c-2294 | I-3 | II-124 | C-22 |
| T1c-2295 | I-3 | II-125 | C-22 |
| T1c-2296 | I-3 | II-126 | C-22 |
| T1c-2297 | I-3 | II-127 | C-22 |
| T1c-2298 | I-3 | II-128 | C-22 |
| T1c-2299 | I-3 | II-129 | C-22 |
| T1c-2300 | I-3 | II-130 | C-22 |
| T1c-2301 | I-3 | II-131 | C-22 |
| T1c-2302 | I-3 | II-132 | C-22 |
| T1c-2303 | I-3 | II-133 | C-22 |
| T1c-2304 | I-3 | II-134 | C-22 |
| T1c-2305 | I-3 | II-135 | C-22 |
| T1c-2306 | I-3 | II-136 | C-22 |
| T1c-2307 | I-3 | II-137 | C-22 |
| T1c-2308 | I-3 | II-138 | C-22 |
| T1c-2309 | I-3 | II-139 | C-22 |
| T1c-2310 | I-3 | II-140 | C-22 |
| T1c-2311 | I-3 | II-141 | C-22 |
| T1c-2312 | I-3 | II-142 | C-22 |
| T1c-2313 | I-3 | II-143 | C-22 |
| T1c-2314 | I-3 | II-144 | C-22 |
| T1c-2315 | I-3 | II-145 | C-22 |
| T1c-2316 | I-3 | II-146 | C-22 |
| T1c-2317 | I-3 | II-147 | C-22 |
| T1c-2318 | I-3 | II-148 | C-22 |
| T1c-2319 | I-3 | II-149 | C-22 |
| T1c-2320 | I-3 | II-150 | C-22 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-2321 | I-3 | II-151 | C-22 |
| T1c-2322 | I-3 | II-152 | C-22 |
| T1c-2323 | I-3 | II-153 | C-22 |
| T1c-2324 | I-3 | II-154 | C-22 |
| T1c-2325 | I-3 | II-155 | C-22 |
| T1c-2326 | I-3 | II-156 | C-22 |
| T1c-2327 | I-3 | II-157 | C-22 |
| T1c-2328 | I-3 | II-158 | C-22 |
| T1c-2329 | I-3 | II-159 | C-22 |
| T1c-2330 | I-3 | II-160 | C-22 |
| T1c-2331 | I-3 | II-161 | C-22 |
| T1c-2332 | I-3 | II-162 | C-22 |
| T1c-2333 | I-3 | II-163 | C-22 |
| T1c-2334 | I-3 | II-164 | C-22 |
| T1c-2335 | I-3 | II-165 | C-22 |
| T1c-2336 | I-3 | II-166 | C-22 |
| T1c-2337 | I-3 | II-167 | C-22 |
| T1c-2338 | I-3 | II-168 | C-22 |
| T1c-2339 | I-3 | II-169 | C-22 |
| T1c-2340 | I-3 | II-170 | C-22 |
| T1c-2341 | I-3 | II-171 | C-22 |
| T1c-2342 | I-3 | II-172 | C-22 |
| T1c-2343 | I-3 | II-173 | C-22 |
| T1c-2344 | I-3 | II-174 | C-22 |
| T1c-2345 | I-3 | II-175 | C-22 |
| T1c-2346 | I-3 | II-176 | C-22 |
| T1c-2347 | I-3 | II-177 | C-22 |
| T1c-2348 | I-3 | II-178 | C-22 |
| T1c-2349 | I-3 | II-179 | C-22 |
| T1c-2350 | I-3 | II-180 | C-22 |
| T1c-2351 | I-3 | II-181 | C-22 |
| T1c-2352 | I-3 | II-182 | C-22 |
| T1c-2353 | I-3 | II-183 | C-22 |
| T1c-2354 | I-3 | II-184 | C-22 |
| T1c-2355 | I-3 | II-185 | C-22 |
| T1c-2356 | I-3 | II-186 | C-22 |
| T1c-2357 | I-3 | II-187 | C-22 |
| T1c-2358 | I-3 | II-188 | C-22 |
| T1c-2359 | I-3 | II-189 | C-22 |
| T1c-2360 | I-3 | II-190 | C-22 |
| T1c-2361 | I-3 | II-191 | C-22 |
| T1c-2362 | I-3 | II-192 | C-22 |
| T1c-2363 | I-3 | II-193 | C-22 |
| T1c-2364 | I-3 | II-194 | C-22 |
| T1c-2365 | I-3 | II-195 | C-22 |
| T1c-2366 | I-3 | II-196 | C-22 |
| T1c-2367 | I-3 | II-197 | C-22 |
| T1c-2368 | I-3 | II-198 | C-22 |
| T1c-2369 | I-3 | II-199 | C-22 |
| T1c-2370 | I-3 | II-200 | C-22 |
| T1c-2371 | I-3 | II-201 | C-22 |
| T1c-2372 | I-3 | II-202 | C-22 |
| T1c-2373 | I-3 | II-203 | C-22 |
| T1c-2374 | I-3 | II-91 | C-23 |
| T1c-2375 | I-3 | II-92 | C-23 |
| T1c-2376 | I-3 | II-93 | C-23 |
| T1c-2377 | I-3 | II-94 | C-23 |
| T1c-2378 | I-3 | II-95 | C-23 |
| T1c-2379 | I-3 | II-96 | C-23 |
| T1c-2380 | I-3 | II-97 | C-23 |
| T1c-2381 | I-3 | II-98 | C-23 |
| T1c-2382 | I-3 | II-99 | C-23 |
| T1c-2383 | I-3 | II-100 | C-23 |
| T1c-2384 | I-3 | II-101 | C-23 |
| T1c-2385 | I-3 | II-102 | C-23 |
| T1c-2386 | I-3 | II-103 | C-23 |
| T1c-2387 | I-3 | II-104 | C-23 |
| T1c-2388 | I-3 | II-105 | C-23 |
| T1c-2389 | I-3 | II-106 | C-23 |
| T1c-2390 | I-3 | II-107 | C-23 |
| T1c-2391 | I-3 | II-108 | C-23 |
| T1c-2392 | I-3 | II-109 | C-23 |
| T1c-2393 | I-3 | II-110 | C-23 |
| T1c-2394 | I-3 | II-111 | C-23 |
| T1c-2395 | I-3 | II-112 | C-23 |
| T1c-2396 | I-3 | II-113 | C-23 |
| T1c-2397 | I-3 | II-114 | C-23 |
| T1c-2398 | I-3 | II-115 | C-23 |
| T1c-2399 | I-3 | II-116 | C-23 |
| T1c-2400 | I-3 | II-117 | C-23 |
| T1c-2401 | I-3 | II-118 | C-23 |
| T1c-2402 | I-3 | II-119 | C-23 |
| T1c-2403 | I-3 | II-120 | C-23 |
| T1c-2404 | I-3 | II-121 | C-23 |
| T1c-2405 | I-3 | II-122 | C-23 |
| T1c-2406 | I-3 | II-123 | C-23 |
| T1c-2407 | I-3 | II-124 | C-23 |
| T1c-2408 | I-3 | II-125 | C-23 |
| T1c-2409 | I-3 | II-126 | C-23 |
| T1c-2410 | I-3 | II-127 | C-23 |
| T1c-2411 | I-3 | II-128 | C-23 |
| T1c-2412 | I-3 | II-129 | C-23 |
| T1c-2413 | I-3 | II-130 | C-23 |
| T1c-2414 | I-3 | II-131 | C-23 |
| T1c-2415 | I-3 | II-132 | C-23 |
| T1c-2416 | I-3 | II-133 | C-23 |
| T1c-2417 | I-3 | II-134 | C-23 |
| T1c-2418 | I-3 | II-135 | C-23 |
| T1c-2419 | I-3 | II-136 | C-23 |
| T1c-2420 | I-3 | II-137 | C-23 |
| T1c-2421 | I-3 | II-138 | C-23 |
| T1c-2422 | I-3 | II-139 | C-23 |
| T1c-2423 | I-3 | II-140 | C-23 |
| T1c-2424 | I-3 | II-141 | C-23 |
| T1c-2425 | I-3 | II-142 | C-23 |
| T1c-2426 | I-3 | II-143 | C-23 |
| T1c-2427 | I-3 | II-144 | C-23 |
| T1c-2428 | I-3 | II-145 | C-23 |
| T1c-2429 | I-3 | II-146 | C-23 |
| T1c-2430 | I-3 | II-147 | C-23 |
| T1c-2431 | I-3 | II-148 | C-23 |
| T1c-2432 | I-3 | II-149 | C-23 |
| T1c-2433 | I-3 | II-150 | C-23 |
| T1c-2434 | I-3 | II-151 | C-23 |
| T1c-2435 | I-3 | II-152 | C-23 |
| T1c-2436 | I-3 | II-153 | C-23 |
| T1c-2437 | I-3 | II-154 | C-23 |
| T1c-2438 | I-3 | II-155 | C-23 |
| T1c-2439 | I-3 | II-156 | C-23 |
| T1c-2440 | I-3 | II-157 | C-23 |
| T1c-2441 | I-3 | II-158 | C-23 |
| T1c-2442 | I-3 | II-159 | C-23 |
| T1c-2443 | I-3 | II-160 | C-23 |
| T1c-2444 | I-3 | II-161 | C-23 |
| T1c-2445 | I-3 | II-162 | C-23 |
| T1c-2446 | I-3 | II-163 | C-23 |
| T1c-2447 | I-3 | II-164 | C-23 |
| T1c-2448 | I-3 | II-165 | C-23 |
| T1c-2449 | I-3 | II-166 | C-23 |
| T1c-2450 | I-3 | II-167 | C-23 |
| T1c-2451 | I-3 | II-168 | C-23 |
| T1c-2452 | I-3 | II-169 | C-23 |
| T1c-2453 | I-3 | II-170 | C-23 |
| T1c-2454 | I-3 | II-171 | C-23 |
| T1c-2455 | I-3 | II-172 | C-23 |
| T1c-2456 | I-3 | II-173 | C-23 |
| T1c-2457 | I-3 | II-174 | C-23 |
| T1c-2458 | I-3 | II-175 | C-23 |
| T1c-2459 | I-3 | II-176 | C-23 |
| T1c-2460 | I-3 | II-177 | C-23 |
| T1c-2461 | I-3 | II-178 | C-23 |
| T1c-2462 | I-3 | II-179 | C-23 |
| T1c-2463 | I-3 | II-180 | C-23 |
| T1c-2464 | I-3 | II-181 | C-23 |
| T1c-2465 | I-3 | II-182 | C-23 |
| T1c-2466 | I-3 | II-183 | C-23 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-2467 | I-3 | II-184 | C-23 |
| T1c-2468 | I-3 | II-185 | C-23 |
| T1c-2469 | I-3 | II-186 | C-23 |
| T1c-2470 | I-3 | II-187 | C-23 |
| T1c-2471 | I-3 | II-188 | C-23 |
| T1c-2472 | I-3 | II-189 | C-23 |
| T1c-2473 | I-3 | II-190 | C-23 |
| T1c-2474 | I-3 | II-191 | C-23 |
| T1c-2475 | I-3 | II-192 | C-23 |
| T1c-2476 | I-3 | II-193 | C-23 |
| T1c-2477 | I-3 | II-194 | C-23 |
| T1c-2478 | I-3 | II-195 | C-23 |
| T1c-2479 | I-3 | II-196 | C-23 |
| T1c-2480 | I-3 | II-197 | C-23 |
| T1c-2481 | I-3 | II-198 | C-23 |
| T1c-2482 | I-3 | II-199 | C-23 |
| T1c-2483 | I-3 | II-200 | C-23 |
| T1c-2484 | I-3 | II-201 | C-23 |
| T1c-2485 | I-3 | II-202 | C-23 |
| T1c-2486 | I-3 | II-203 | C-23 |
| T1c-2487 | I-3 | II-91 | C-24 |
| T1c-2488 | I-3 | II-92 | C-24 |
| T1c-2489 | I-3 | II-93 | C-24 |
| T1c-2490 | I-3 | II-94 | C-24 |
| T1c-2491 | I-3 | II-95 | C-24 |
| T1c-2492 | I-3 | II-96 | C-24 |
| T1c-2493 | I-3 | II-97 | C-24 |
| T1c-2494 | I-3 | II-98 | C-24 |
| T1c-2495 | I-3 | II-99 | C-24 |
| T1c-2496 | I-3 | II-100 | C-24 |
| T1c-2497 | I-3 | II-101 | C-24 |
| T1c-2498 | I-3 | II-102 | C-24 |
| T1c-2499 | I-3 | II-103 | C-24 |
| T1c-2500 | I-3 | II-104 | C-24 |
| T1c-2501 | I-3 | II-105 | C-24 |
| T1c-2502 | I-3 | II-106 | C-24 |
| T1c-2503 | I-3 | II-107 | C-24 |
| T1c-2504 | I-3 | II-108 | C-24 |
| T1c-2505 | I-3 | II-109 | C-24 |
| T1c-2506 | I-3 | II-110 | C-24 |
| T1c-2507 | I-3 | II-111 | C-24 |
| T1c-2508 | I-3 | II-112 | C-24 |
| T1c-2509 | I-3 | II-113 | C-24 |
| T1c-2510 | I-3 | II-114 | C-24 |
| T1c-2511 | I-3 | II-115 | C-24 |
| T1c-2512 | I-3 | II-116 | C-24 |
| T1c-2513 | I-3 | II-117 | C-24 |
| T1c-2514 | I-3 | II-118 | C-24 |
| T1c-2515 | I-3 | II-119 | C-24 |
| T1c-2516 | I-3 | II-120 | C-24 |
| T1c-2517 | I-3 | II-121 | C-24 |
| T1c-2518 | I-3 | II-122 | C-24 |
| T1c-2519 | I-3 | II-123 | C-24 |
| T1c-2520 | I-3 | II-124 | C-24 |
| T1c-2521 | I-3 | II-125 | C-24 |
| T1c-2522 | I-3 | II-126 | C-24 |
| T1c-2523 | I-3 | II-127 | C-24 |
| T1c-2524 | I-3 | II-128 | C-24 |
| T1c-2525 | I-3 | II-129 | C-24 |
| T1c-2526 | I-3 | II-130 | C-24 |
| T1c-2527 | I-3 | II-131 | C-24 |
| T1c-2528 | I-3 | II-132 | C-24 |
| T1c-2529 | I-3 | II-133 | C-24 |
| T1c-2530 | I-3 | II-134 | C-24 |
| T1c-2531 | I-3 | II-135 | C-24 |
| T1c-2532 | I-3 | II-136 | C-24 |
| T1c-2533 | I-3 | II-137 | C-24 |
| T1c-2534 | I-3 | II-138 | C-24 |
| T1c-2535 | I-3 | II-139 | C-24 |
| T1c-2536 | I-3 | II-140 | C-24 |
| T1c-2537 | I-3 | II-141 | C-24 |
| T1c-2538 | I-3 | II-142 | C-24 |
| T1c-2539 | I-3 | II-143 | C-24 |
| T1c-2540 | I-3 | II-144 | C-24 |
| T1c-2541 | I-3 | II-145 | C-24 |
| T1c-2542 | I-3 | II-146 | C-24 |
| T1c-2543 | I-3 | II-147 | C-24 |
| T1c-2544 | I-3 | II-148 | C-24 |
| T1c-2545 | I-3 | II-149 | C-24 |
| T1c-2546 | I-3 | II-150 | C-24 |
| T1c-2547 | I-3 | II-151 | C-24 |
| T1c-2548 | I-3 | II-152 | C-24 |
| T1c-2549 | I-3 | II-153 | C-24 |
| T1c-2550 | I-3 | II-154 | C-24 |
| T1c-2551 | I-3 | II-155 | C-24 |
| T1c-2552 | I-3 | II-156 | C-24 |
| T1c-2553 | I-3 | II-157 | C-24 |
| T1c-2554 | I-3 | II-158 | C-24 |
| T1c-2555 | I-3 | II-159 | C-24 |
| T1c-2556 | I-3 | II-160 | C-24 |
| T1c-2557 | I-3 | II-161 | C-24 |
| T1c-2558 | I-3 | II-162 | C-24 |
| T1c-2559 | I-3 | II-163 | C-24 |
| T1c-2560 | I-3 | II-164 | C-24 |
| T1c-2561 | I-3 | II-165 | C-24 |
| T1c-2562 | I-3 | II-166 | C-24 |
| T1c-2563 | I-3 | II-167 | C-24 |
| T1c-2564 | I-3 | II-168 | C-24 |
| T1c-2565 | I-3 | II-169 | C-24 |
| T1c-2566 | I-3 | II-170 | C-24 |
| T1c-2567 | I-3 | II-171 | C-24 |
| T1c-2568 | I-3 | II-172 | C-24 |
| T1c-2569 | I-3 | II-173 | C-24 |
| T1c-2570 | I-3 | II-174 | C-24 |
| T1c-2571 | I-3 | II-175 | C-24 |
| T1c-2572 | I-3 | II-176 | C-24 |
| T1c-2573 | I-3 | II-177 | C-24 |
| T1c-2574 | I-3 | II-178 | C-24 |
| T1c-2575 | I-3 | II-179 | C-24 |
| T1c-2576 | I-3 | II-180 | C-24 |
| T1c-2577 | I-3 | II-181 | C-24 |
| T1c-2578 | I-3 | II-182 | C-24 |
| T1c-2579 | I-3 | II-183 | C-24 |
| T1c-2580 | I-3 | II-184 | C-24 |
| T1c-2581 | I-3 | II-185 | C-24 |
| T1c-2582 | I-3 | II-186 | C-24 |
| T1c-2583 | I-3 | II-187 | C-24 |
| T1c-2584 | I-3 | II-188 | C-24 |
| T1c-2585 | I-3 | II-189 | C-24 |
| T1c-2586 | I-3 | II-190 | C-24 |
| T1c-2587 | I-3 | II-191 | C-24 |
| T1c-2588 | I-3 | II-192 | C-24 |
| T1c-2589 | I-3 | II-193 | C-24 |
| T1c-2590 | I-3 | II-194 | C-24 |
| T1c-2591 | I-3 | II-195 | C-24 |
| T1c-2592 | I-3 | II-196 | C-24 |
| T1c-2593 | I-3 | II-197 | C-24 |
| T1c-2594 | I-3 | II-198 | C-24 |
| T1c-2595 | I-3 | II-199 | C-24 |
| T1c-2596 | I-3 | II-200 | C-24 |
| T1c-2597 | I-3 | II-201 | C-24 |
| T1c-2598 | I-3 | II-202 | C-24 |
| T1c-2599 | I-3 | II-203 | C-24 |
| T1c-2600 | I-3 | II-91 | C-25 |
| T1c-2601 | I-3 | II-92 | C-25 |
| T1c-2602 | I-3 | II-93 | C-25 |
| T1c-2603 | I-3 | II-94 | C-25 |
| T1c-2604 | I-3 | II-95 | C-25 |
| T1c-2605 | I-3 | II-96 | C-25 |
| T1c-2606 | I-3 | II-97 | C-25 |
| T1c-2607 | I-3 | II-98 | C-25 |
| T1c-2608 | I-3 | II-99 | C-25 |
| T1c-2609 | I-3 | II-100 | C-25 |
| T1c-2610 | I-3 | II-101 | C-25 |
| T1c-2611 | I-3 | II-102 | C-25 |
| T1c-2612 | I-3 | II-103 | C-25 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-2613 | I-3 | II-104 | C-25 |
| T1c-2614 | I-3 | II-105 | C-25 |
| T1c-2615 | I-3 | II-106 | C-25 |
| T1c-2616 | I-3 | II-107 | C-25 |
| T1c-2617 | I-3 | II-108 | C-25 |
| T1c-2618 | I-3 | II-109 | C-25 |
| T1c-2619 | I-3 | II-110 | C-25 |
| T1c-2620 | I-3 | II-111 | C-25 |
| T1c-2621 | I-3 | II-112 | C-25 |
| T1c-2622 | I-3 | II-113 | C-25 |
| T1c-2623 | I-3 | II-114 | C-25 |
| T1c-2624 | I-3 | II-115 | C-25 |
| T1c-2625 | I-3 | II-116 | C-25 |
| T1c-2626 | I-3 | II-117 | C-25 |
| T1c-2627 | I-3 | II-118 | C-25 |
| T1c-2628 | I-3 | II-119 | C-25 |
| T1c-2629 | I-3 | II-120 | C-25 |
| T1c-2630 | I-3 | II-121 | C-25 |
| T1c-2631 | I-3 | II-122 | C-25 |
| T1c-2632 | I-3 | II-123 | C-25 |
| T1c-2633 | I-3 | II-124 | C-25 |
| T1c-2634 | I-3 | II-125 | C-25 |
| T1c-2635 | I-3 | II-126 | C-25 |
| T1c-2636 | I-3 | II-127 | C-25 |
| T1c-2637 | I-3 | II-128 | C-25 |
| T1c-2638 | I-3 | II-129 | C-25 |
| T1c-2639 | I-3 | II-130 | C-25 |
| T1c-2640 | I-3 | II-131 | C-25 |
| T1c-2641 | I-3 | II-132 | C-25 |
| T1c-2642 | I-3 | II-133 | C-25 |
| T1c-2643 | I-3 | II-134 | C-25 |
| T1c-2644 | I-3 | II-135 | C-25 |
| T1c-2645 | I-3 | II-136 | C-25 |
| T1c-2646 | I-3 | II-137 | C-25 |
| T1c-2647 | I-3 | II-138 | C-25 |
| T1c-2648 | I-3 | II-139 | C-25 |
| T1c-2649 | I-3 | II-140 | C-25 |
| T1c-2650 | I-3 | II-141 | C-25 |
| T1c-2651 | I-3 | II-142 | C-25 |
| T1c-2652 | I-3 | II-143 | C-25 |
| T1c-2653 | I-3 | II-144 | C-25 |
| T1c-2654 | I-3 | II-145 | C-25 |
| T1c-2655 | I-3 | II-146 | C-25 |
| T1c-2656 | I-3 | II-147 | C-25 |
| T1c-2657 | I-3 | II-148 | C-25 |
| T1c-2658 | I-3 | II-149 | C-25 |
| T1c-2659 | I-3 | II-150 | C-25 |
| T1c-2660 | I-3 | II-151 | C-25 |
| T1c-2661 | I-3 | II-152 | C-25 |
| T1c-2662 | I-3 | II-153 | C-25 |
| T1c-2663 | I-3 | II-154 | C-25 |
| T1c-2664 | I-3 | II-155 | C-25 |
| T1c-2665 | I-3 | II-156 | C-25 |
| T1c-2666 | I-3 | II-157 | C-25 |
| T1c-2667 | I-3 | II-158 | C-25 |
| T1c-2668 | I-3 | II-159 | C-25 |
| T1c-2669 | I-3 | II-160 | C-25 |
| T1c-2670 | I-3 | II-161 | C-25 |
| T1c-2671 | I-3 | II-162 | C-25 |
| T1c-2672 | I-3 | II-163 | C-25 |
| T1c-2673 | I-3 | II-164 | C-25 |
| T1c-2674 | I-3 | II-165 | C-25 |
| T1c-2675 | I-3 | II-166 | C-25 |
| T1c-2676 | I-3 | II-167 | C-25 |
| T1c-2677 | I-3 | II-168 | C-25 |
| T1c-2678 | I-3 | II-169 | C-25 |
| T1c-2679 | I-3 | II-170 | C-25 |
| T1c-2680 | I-3 | II-171 | C-25 |
| T1c-2681 | I-3 | II-172 | C-25 |
| T1c-2682 | I-3 | II-173 | C-25 |
| T1c-2683 | I-3 | II-174 | C-25 |
| T1c-2684 | I-3 | II-175 | C-25 |
| T1c-2685 | I-3 | II-176 | C-25 |
| T1c-2686 | I-3 | II-177 | C-25 |
| T1c-2687 | I-3 | II-178 | C-25 |
| T1c-2688 | I-3 | II-179 | C-25 |
| T1c-2689 | I-3 | II-180 | C-25 |
| T1c-2690 | I-3 | II-181 | C-25 |
| T1c-2691 | I-3 | II-182 | C-25 |
| T1c-2692 | I-3 | II-183 | C-25 |
| T1c-2693 | I-3 | II-184 | C-25 |
| T1c-2694 | I-3 | II-185 | C-25 |
| T1c-2695 | I-3 | II-186 | C-25 |
| T1c-2696 | I-3 | II-187 | C-25 |
| T1c-2697 | I-3 | II-188 | C-25 |
| T1c-2698 | I-3 | II-189 | C-25 |
| T1c-2699 | I-3 | II-190 | C-25 |
| T1c-2700 | I-3 | II-191 | C-25 |
| T1c-2701 | I-3 | II-192 | C-25 |
| T1c-2702 | I-3 | II-193 | C-25 |
| T1c-2703 | I-3 | II-194 | C-25 |
| T1c-2704 | I-3 | II-195 | C-25 |
| T1c-2705 | I-3 | II-196 | C-25 |
| T1c-2706 | I-3 | II-197 | C-25 |
| T1c-2707 | I-3 | II-198 | C-25 |
| T1c-2708 | I-3 | II-199 | C-25 |
| T1c-2709 | I-3 | II-200 | C-25 |
| T1c-2710 | I-3 | II-201 | C-25 |
| T1c-2711 | I-3 | II-202 | C-25 |
| T1c-2712 | I-3 | II-203 | C-25 |
| T1c-2713 | I-3 | II-91 | C-26 |
| T1c-2714 | I-3 | II-92 | C-26 |
| T1c-2715 | I-3 | II-93 | C-26 |
| T1c-2716 | I-3 | II-94 | C-26 |
| T1c-2717 | I-3 | II-95 | C-26 |
| T1c-2718 | I-3 | II-96 | C-26 |
| T1c-2719 | I-3 | II-97 | C-26 |
| T1c-2720 | I-3 | II-98 | C-26 |
| T1c-2721 | I-3 | II-99 | C-26 |
| T1c-2722 | I-3 | II-100 | C-26 |
| T1c-2723 | I-3 | II-101 | C-26 |
| T1c-2724 | I-3 | II-102 | C-26 |
| T1c-2725 | I-3 | II-103 | C-26 |
| T1c-2726 | I-3 | II-104 | C-26 |
| T1c-2727 | I-3 | II-105 | C-26 |
| T1c-2728 | I-3 | II-106 | C-26 |
| T1c-2729 | I-3 | II-107 | C-26 |
| T1c-2730 | I-3 | II-108 | C-26 |
| T1c-2731 | I-3 | II-109 | C-26 |
| T1c-2732 | I-3 | II-110 | C-26 |
| T1c-2733 | I-3 | II-111 | C-26 |
| T1c-2734 | I-3 | II-112 | C-26 |
| T1c-2735 | I-3 | II-113 | C-26 |
| T1c-2736 | I-3 | II-114 | C-26 |
| T1c-2737 | I-3 | II-115 | C-26 |
| T1c-2738 | I-3 | II-116 | C-26 |
| T1c-2739 | I-3 | II-117 | C-26 |
| T1c-2740 | I-3 | II-118 | C-26 |
| T1c-2741 | I-3 | II-119 | C-26 |
| T1c-2742 | I-3 | II-120 | C-26 |
| T1c-2743 | I-3 | II-121 | C-26 |
| T1c-2744 | I-3 | II-122 | C-26 |
| T1c-2745 | I-3 | II-123 | C-26 |
| T1c-2746 | I-3 | II-124 | C-26 |
| T1c-2747 | I-3 | II-125 | C-26 |
| T1c-2748 | I-3 | II-126 | C-26 |
| T1c-2749 | I-3 | II-127 | C-26 |
| T1c-2750 | I-3 | II-128 | C-26 |
| T1c-2751 | I-3 | II-129 | C-26 |
| T1c-2752 | I-3 | II-130 | C-26 |
| T1c-2753 | I-3 | II-131 | C-26 |
| T1c-2754 | I-3 | II-132 | C-26 |
| T1c-2755 | I-3 | II-133 | C-26 |
| T1c-2756 | I-3 | II-134 | C-26 |
| T1c-2757 | I-3 | II-135 | C-26 |
| T1c-2758 | I-3 | II-136 | C-26 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-2759 | I-3 | II-137 | C-26 |
| T1c-2760 | I-3 | II-138 | C-26 |
| T1c-2761 | I-3 | II-139 | C-26 |
| T1c-2762 | I-3 | II-140 | C-26 |
| T1c-2763 | I-3 | II-141 | C-26 |
| T1c-2764 | I-3 | II-142 | C-26 |
| T1c-2765 | I-3 | II-143 | C-26 |
| T1c-2766 | I-3 | II-144 | C-26 |
| T1c-2767 | I-3 | II-145 | C-26 |
| T1c-2768 | I-3 | II-146 | C-26 |
| T1c-2769 | I-3 | II-147 | C-26 |
| T1c-2770 | I-3 | II-148 | C-26 |
| T1c-2771 | I-3 | II-149 | C-26 |
| T1c-2772 | I-3 | II-150 | C-26 |
| T1c-2773 | I-3 | II-151 | C-26 |
| T1c-2774 | I-3 | II-152 | C-26 |
| T1c-2775 | I-3 | II-153 | C-26 |
| T1c-2776 | I-3 | II-154 | C-26 |
| T1c-2777 | I-3 | II-155 | C-26 |
| T1c-2778 | I-3 | II-156 | C-26 |
| T1c-2779 | I-3 | II-157 | C-26 |
| T1c-2780 | I-3 | II-158 | C-26 |
| T1c-2781 | I-3 | II-159 | C-26 |
| T1c-2782 | I-3 | II-160 | C-26 |
| T1c-2783 | I-3 | II-161 | C-26 |
| T1c-2784 | I-3 | II-162 | C-26 |
| T1c-2785 | I-3 | II-163 | C-26 |
| T1c-2786 | I-3 | II-164 | C-26 |
| T1c-2787 | I-3 | II-165 | C-26 |
| T1c-2788 | I-3 | II-166 | C-26 |
| T1c-2789 | I-3 | II-167 | C-26 |
| T1c-2790 | I-3 | II-168 | C-26 |
| T1c-2791 | I-3 | II-169 | C-26 |
| T1c-2792 | I-3 | II-170 | C-26 |
| T1c-2793 | I-3 | II-171 | C-26 |
| T1c-2794 | I-3 | II-172 | C-26 |
| T1c-2795 | I-3 | II-173 | C-26 |
| T1c-2796 | I-3 | II-174 | C-26 |
| T1c-2797 | I-3 | II-175 | C-26 |
| T1c-2798 | I-3 | II-176 | C-26 |
| T1c-2799 | I-3 | II-177 | C-26 |
| T1c-2800 | I-3 | II-178 | C-26 |
| T1c-2801 | I-3 | II-179 | C-26 |
| T1c-2802 | I-3 | II-180 | C-26 |
| T1c-2803 | I-3 | II-181 | C-26 |
| T1c-2804 | I-3 | II-182 | C-26 |
| T1c-2805 | I-3 | II-183 | C-26 |
| T1c-2806 | I-3 | II-184 | C-26 |
| T1c-2807 | I-3 | II-185 | C-26 |
| T1c-2808 | I-3 | II-186 | C-26 |
| T1c-2809 | I-3 | II-187 | C-26 |
| T1c-2810 | I-3 | II-188 | C-26 |
| T1c-2811 | I-3 | II-189 | C-26 |
| T1c-2812 | I-3 | II-190 | C-26 |
| T1c-2813 | I-3 | II-191 | C-26 |
| T1c-2814 | I-3 | II-192 | C-26 |
| T1c-2815 | I-3 | II-193 | C-26 |
| T1c-2816 | I-3 | II-194 | C-26 |
| T1c-2817 | I-3 | II-195 | C-26 |
| T1c-2818 | I-3 | II-196 | C-26 |
| T1c-2819 | I-3 | II-197 | C-26 |
| T1c-2820 | I-3 | II-198 | C-26 |
| T1c-2821 | I-3 | II-199 | C-26 |
| T1c-2822 | I-3 | II-200 | C-26 |
| T1c-2823 | I-3 | II-201 | C-26 |
| T1c-2824 | I-3 | II-202 | C-26 |
| T1c-2825 | I-3 | II-203 | C-26 |
| T1c-2826 | I-3 | II-91 | C-27 |
| T1c-2827 | I-3 | II-92 | C-27 |
| T1c-2828 | I-3 | II-93 | C-27 |
| T1c-2829 | I-3 | II-94 | C-27 |
| T1c-2830 | I-3 | II-95 | C-27 |
| T1c-2831 | I-3 | II-96 | C-27 |
| T1c-2832 | I-3 | II-97 | C-27 |
| T1c-2833 | I-3 | II-98 | C-27 |
| T1c-2834 | I-3 | II-99 | C-27 |
| T1c-2835 | I-3 | II-100 | C-27 |
| T1c-2836 | I-3 | II-101 | C-27 |
| T1c-2837 | I-3 | II-102 | C-27 |
| T1c-2838 | I-3 | II-103 | C-27 |
| T1c-2839 | I-3 | II-104 | C-27 |
| T1c-2840 | I-3 | II-105 | C-27 |
| T1c-2841 | I-3 | II-106 | C-27 |
| T1c-2842 | I-3 | II-107 | C-27 |
| T1c-2843 | I-3 | II-108 | C-27 |
| T1c-2844 | I-3 | II-109 | C-27 |
| T1c-2845 | I-3 | II-110 | C-27 |
| T1c-2846 | I-3 | II-111 | C-27 |
| T1c-2847 | I-3 | II-112 | C-27 |
| T1c-2848 | I-3 | II-113 | C-27 |
| T1c-2849 | I-3 | II-114 | C-27 |
| T1c-2850 | I-3 | II-115 | C-27 |
| T1c-2851 | I-3 | II-116 | C-27 |
| T1c-2852 | I-3 | II-117 | C-27 |
| T1c-2853 | I-3 | II-118 | C-27 |
| T1c-2854 | I-3 | II-119 | C-27 |
| T1c-2855 | I-3 | II-120 | C-27 |
| T1c-2856 | I-3 | II-121 | C-27 |
| T1c-2857 | I-3 | II-122 | C-27 |
| T1c-2858 | I-3 | II-123 | C-27 |
| T1c-2859 | I-3 | II-124 | C-27 |
| T1c-2860 | I-3 | II-125 | C-27 |
| T1c-2861 | I-3 | II-126 | C-27 |
| T1c-2862 | I-3 | II-127 | C-27 |
| T1c-2863 | I-3 | II-128 | C-27 |
| T1c-2864 | I-3 | II-129 | C-27 |
| T1c-2865 | I-3 | II-130 | C-27 |
| T1c-2866 | I-3 | II-131 | C-27 |
| T1c-2867 | I-3 | II-132 | C-27 |
| T1c-2868 | I-3 | II-133 | C-27 |
| T1c-2869 | I-3 | II-134 | C-27 |
| T1c-2870 | I-3 | II-135 | C-27 |
| T1c-2871 | I-3 | II-136 | C-27 |
| T1c-2872 | I-3 | II-137 | C-27 |
| T1c-2873 | I-3 | II-138 | C-27 |
| T1c-2874 | I-3 | II-139 | C-27 |
| T1c-2875 | I-3 | II-140 | C-27 |
| T1c-2876 | I-3 | II-141 | C-27 |
| T1c-2877 | I-3 | II-142 | C-27 |
| T1c-2878 | I-3 | II-143 | C-27 |
| T1c-2879 | I-3 | II-144 | C-27 |
| T1c-2880 | I-3 | II-145 | C-27 |
| T1c-2881 | I-3 | II-146 | C-27 |
| T1c-2882 | I-3 | II-147 | C-27 |
| T1c-2883 | I-3 | II-148 | C-27 |
| T1c-2884 | I-3 | II-149 | C-27 |
| T1c-2885 | I-3 | II-150 | C-27 |
| T1c-2886 | I-3 | II-151 | C-27 |
| T1c-2887 | I-3 | II-152 | C-27 |
| T1c-2888 | I-3 | II-153 | C-27 |
| T1c-2889 | I-3 | II-154 | C-27 |
| T1c-2890 | I-3 | II-155 | C-27 |
| T1c-2891 | I-3 | II-156 | C-27 |
| T1c-2892 | I-3 | II-157 | C-27 |
| T1c-2893 | I-3 | II-158 | C-27 |
| T1c-2894 | I-3 | II-159 | C-27 |
| T1c-2895 | I-3 | II-160 | C-27 |
| T1c-2896 | I-3 | II-161 | C-27 |
| T1c-2897 | I-3 | II-162 | C-27 |
| T1c-2898 | I-3 | II-163 | C-27 |
| T1c-2899 | I-3 | II-164 | C-27 |
| T1c-2900 | I-3 | II-165 | C-27 |
| T1c-2901 | I-3 | II-166 | C-27 |
| T1c-2902 | I-3 | II-167 | C-27 |
| T1c-2903 | I-3 | II-168 | C-27 |
| T1c-2904 | I-3 | II-169 | C-27 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-2905 | I-3 | II-170 | C-27 |
| T1c-2906 | I-3 | II-171 | C-27 |
| T1c-2907 | I-3 | II-172 | C-27 |
| T1c-2908 | I-3 | II-173 | C-27 |
| T1c-2909 | I-3 | II-174 | C-27 |
| T1c-2910 | I-3 | II-175 | C-27 |
| T1c-2911 | I-3 | II-176 | C-27 |
| T1c-2912 | I-3 | II-177 | C-27 |
| T1c-2913 | I-3 | II-178 | C-27 |
| T1c-2914 | I-3 | II-179 | C-27 |
| T1c-2915 | I-3 | II-180 | C-27 |
| T1c-2916 | I-3 | II-181 | C-27 |
| T1c-2917 | I-3 | II-182 | C-27 |
| T1c-2918 | I-3 | II-183 | C-27 |
| T1c-2919 | I-3 | II-184 | C-27 |
| T1c-2920 | I-3 | II-185 | C-27 |
| T1c-2921 | I-3 | II-186 | C-27 |
| T1c-2922 | I-3 | II-187 | C-27 |
| T1c-2923 | I-3 | II-188 | C-27 |
| T1c-2924 | I-3 | II-189 | C-27 |
| T1c-2925 | I-3 | II-190 | C-27 |
| T1c-2926 | I-3 | II-191 | C-27 |
| T1c-2927 | I-3 | II-192 | C-27 |
| T1c-2928 | I-3 | II-193 | C-27 |
| T1c-2929 | I-3 | II-194 | C-27 |
| T1c-2930 | I-3 | II-195 | C-27 |
| T1c-2931 | I-3 | II-196 | C-27 |
| T1c-2932 | I-3 | II-197 | C-27 |
| T1c-2933 | I-3 | II-198 | C-27 |
| T1c-2934 | I-3 | II-199 | C-27 |
| T1c-2935 | I-3 | II-200 | C-27 |
| T1c-2936 | I-3 | II-201 | C-27 |
| T1c-2937 | I-3 | II-202 | C-27 |
| T1c-2938 | I-3 | II-203 | C-27 |
| T1c-2939 | I-3 | II-91 | C-28 |
| T1c-2940 | I-3 | II-92 | C-28 |
| T1c-2941 | I-3 | II-93 | C-28 |
| T1c-2942 | I-3 | II-94 | C-28 |
| T1c-2943 | I-3 | II-95 | C-28 |
| T1c-2944 | I-3 | II-96 | C-28 |
| T1c-2945 | I-3 | II-97 | C-28 |
| T1c-2946 | I-3 | II-98 | C-28 |
| T1c-2947 | I-3 | II-99 | C-28 |
| T1c-2948 | I-3 | II-100 | C-28 |
| T1c-2949 | I-3 | II-101 | C-28 |
| T1c-2950 | I-3 | II-102 | C-28 |
| T1c-2951 | I-3 | II-103 | C-28 |
| T1c-2952 | I-3 | II-104 | C-28 |
| T1c-2953 | I-3 | II-105 | C-28 |
| T1c-2954 | I-3 | II-106 | C-28 |
| T1c-2955 | I-3 | II-107 | C-28 |
| T1c-2956 | I-3 | II-108 | C-28 |
| T1c-2957 | I-3 | II-109 | C-28 |
| T1c-2958 | I-3 | II-110 | C-28 |
| T1c-2959 | I-3 | II-111 | C-28 |
| T1c-2960 | I-3 | II-112 | C-28 |
| T1c-2961 | I-3 | II-113 | C-28 |
| T1c-2962 | I-3 | II-114 | C-28 |
| T1c-2963 | I-3 | II-115 | C-28 |
| T1c-2964 | I-3 | II-116 | C-28 |
| T1c-2965 | I-3 | II-117 | C-28 |
| T1c-2966 | I-3 | II-118 | C-28 |
| T1c-2967 | I-3 | II-119 | C-28 |
| T1c-2968 | I-3 | II-120 | C-28 |
| T1c-2969 | I-3 | II-121 | C-28 |
| T1c-2970 | I-3 | II-122 | C-28 |
| T1c-2971 | I-3 | II-123 | C-28 |
| T1c-2972 | I-3 | II-124 | C-28 |
| T1c-2973 | I-3 | II-125 | C-28 |
| T1c-2974 | I-3 | II-126 | C-28 |
| T1c-2975 | I-3 | II-127 | C-28 |
| T1c-2976 | I-3 | II-128 | C-28 |
| T1c-2977 | I-3 | II-129 | C-28 |
| T1c-2978 | I-3 | II-130 | C-28 |
| T1c-2979 | I-3 | II-131 | C-28 |
| T1c-2980 | I-3 | II-132 | C-28 |
| T1c-2981 | I-3 | II-133 | C-28 |
| T1c-2982 | I-3 | II-134 | C-28 |
| T1c-2983 | I-3 | II-135 | C-28 |
| T1c-2984 | I-3 | II-136 | C-28 |
| T1c-2985 | I-3 | II-137 | C-28 |
| T1c-2986 | I-3 | II-138 | C-28 |
| T1c-2987 | I-3 | II-139 | C-28 |
| T1c-2988 | I-3 | II-140 | C-28 |
| T1c-2989 | I-3 | II-141 | C-28 |
| T1c-2990 | I-3 | II-142 | C-28 |
| T1c-2991 | I-3 | II-143 | C-28 |
| T1c-2992 | I-3 | II-144 | C-28 |
| T1c-2993 | I-3 | II-145 | C-28 |
| T1c-2994 | I-3 | II-146 | C-28 |
| T1c-2995 | I-3 | II-147 | C-28 |
| T1c-2996 | I-3 | II-148 | C-28 |
| T1c-2997 | I-3 | II-149 | C-28 |
| T1c-2998 | I-3 | II-150 | C-28 |
| T1c-2999 | I-3 | II-151 | C-28 |
| T1c-3000 | I-3 | II-152 | C-28 |
| T1c-3001 | I-3 | II-153 | C-28 |
| T1c-3002 | I-3 | II-154 | C-28 |
| T1c-3003 | I-3 | II-155 | C-28 |
| T1c-3004 | I-3 | II-156 | C-28 |
| T1c-3005 | I-3 | II-157 | C-28 |
| T1c-3006 | I-3 | II-158 | C-28 |
| T1c-3007 | I-3 | II-159 | C-28 |
| T1c-3008 | I-3 | II-160 | C-28 |
| T1c-3009 | I-3 | II-161 | C-28 |
| T1c-3010 | I-3 | II-162 | C-28 |
| T1c-3011 | I-3 | II-163 | C-28 |
| T1c-3012 | I-3 | II-164 | C-28 |
| T1c-3013 | I-3 | II-165 | C-28 |
| T1c-3014 | I-3 | II-166 | C-28 |
| T1c-3015 | I-3 | II-167 | C-28 |
| T1c-3016 | I-3 | II-168 | C-28 |
| T1c-3017 | I-3 | II-169 | C-28 |
| T1c-3018 | I-3 | II-170 | C-28 |
| T1c-3019 | I-3 | II-171 | C-28 |
| T1c-3020 | I-3 | II-172 | C-28 |
| T1c-3021 | I-3 | II-173 | C-28 |
| T1c-3022 | I-3 | II-174 | C-28 |
| T1c-3023 | I-3 | II-175 | C-28 |
| T1c-3024 | I-3 | II-176 | C-28 |
| T1c-3025 | I-3 | II-177 | C-28 |
| T1c-3026 | I-3 | II-178 | C-28 |
| T1c-3027 | I-3 | II-179 | C-28 |
| T1c-3028 | I-3 | II-180 | C-28 |
| T1c-3029 | I-3 | II-181 | C-28 |
| T1c-3030 | I-3 | II-182 | C-28 |
| T1c-3031 | I-3 | II-183 | C-28 |
| T1c-3032 | I-3 | II-184 | C-28 |
| T1c-3033 | I-3 | II-185 | C-28 |
| T1c-3034 | I-3 | II-186 | C-28 |
| T1c-3035 | I-3 | II-187 | C-28 |
| T1c-3036 | I-3 | II-188 | C-28 |
| T1c-3037 | I-3 | II-189 | C-28 |
| T1c-3038 | I-3 | II-190 | C-28 |
| T1c-3039 | I-3 | II-191 | C-28 |
| T1c-3040 | I-3 | II-192 | C-28 |
| T1c-3041 | I-3 | II-193 | C-28 |
| T1c-3042 | I-3 | II-194 | C-28 |
| T1c-3043 | I-3 | II-195 | C-28 |
| T1c-3044 | I-3 | II-196 | C-28 |
| T1c-3045 | I-3 | II-197 | C-28 |
| T1c-3046 | I-3 | II-198 | C-28 |
| T1c-3047 | I-3 | II-199 | C-28 |
| T1c-3048 | I-3 | II-200 | C-28 |
| T1c-3049 | I-3 | II-201 | C-28 |
| T1c-3050 | I-3 | II-202 | C-28 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-3051 | I-3 | II-203 | C-28 |
| T1c-3052 | I-3 | II-91 | C-29 |
| T1c-3053 | I-3 | II-92 | C-29 |
| T1c-3054 | I-3 | II-93 | C-29 |
| T1c-3055 | I-3 | II-94 | C-29 |
| T1c-3056 | I-3 | II-95 | C-29 |
| T1c-3057 | I-3 | II-96 | C-29 |
| T1c-3058 | I-3 | II-97 | C-29 |
| T1c-3059 | I-3 | II-98 | C-29 |
| T1c-3060 | I-3 | II-99 | C-29 |
| T1c-3061 | I-3 | II-100 | C-29 |
| T1c-3062 | I-3 | II-101 | C-29 |
| T1c-3063 | I-3 | II-102 | C-29 |
| T1c-3064 | I-3 | II-103 | C-29 |
| T1c-3065 | I-3 | II-104 | C-29 |
| T1c-3066 | I-3 | II-105 | C-29 |
| T1c-3067 | I-3 | II-106 | C-29 |
| T1c-3068 | I-3 | II-107 | C-29 |
| T1c-3069 | I-3 | II-108 | C-29 |
| T1c-3070 | I-3 | II-109 | C-29 |
| T1c-3071 | I-3 | II-110 | C-29 |
| T1c-3072 | I-3 | II-111 | C-29 |
| T1c-3073 | I-3 | II-112 | C-29 |
| T1c-3074 | I-3 | II-113 | C-29 |
| T1c-3075 | I-3 | II-114 | C-29 |
| T1c-3076 | I-3 | II-115 | C-29 |
| T1c-3077 | I-3 | II-116 | C-29 |
| T1c-3078 | I-3 | II-117 | C-29 |
| T1c-3079 | I-3 | II-118 | C-29 |
| T1c-3080 | I-3 | II-119 | C-29 |
| T1c-3081 | I-3 | II-120 | C-29 |
| T1c-3082 | I-3 | II-121 | C-29 |
| T1c-3083 | I-3 | II-122 | C-29 |
| T1c-3084 | I-3 | II-123 | C-29 |
| T1c-3085 | I-3 | II-124 | C-29 |
| T1c-3086 | I-3 | II-125 | C-29 |
| T1c-3087 | I-3 | II-126 | C-29 |
| T1c-3088 | I-3 | II-127 | C-29 |
| T1c-3089 | I-3 | II-128 | C-29 |
| T1c-3090 | I-3 | II-129 | C-29 |
| T1c-3091 | I-3 | II-130 | C-29 |
| T1c-3092 | I-3 | II-131 | C-29 |
| T1c-3093 | I-3 | II-132 | C-29 |
| T1c-3094 | I-3 | II-133 | C-29 |
| T1c-3095 | I-3 | II-134 | C-29 |
| T1c-3096 | I-3 | II-135 | C-29 |
| T1c-3097 | I-3 | II-136 | C-29 |
| T1c-3098 | I-3 | II-137 | C-29 |
| T1c-3099 | I-3 | II-138 | C-29 |
| T1c-3100 | I-3 | II-139 | C-29 |
| T1c-3101 | I-3 | II-140 | C-29 |
| T1c-3102 | I-3 | II-141 | C-29 |
| T1c-3103 | I-3 | II-142 | C-29 |
| T1c-3104 | I-3 | II-143 | C-29 |
| T1c-3105 | I-3 | II-144 | C-29 |
| T1c-3106 | I-3 | II-145 | C-29 |
| T1c-3107 | I-3 | II-146 | C-29 |
| T1c-3108 | I-3 | II-147 | C-29 |
| T1c-3109 | I-3 | II-148 | C-29 |
| T1c-3110 | I-3 | II-149 | C-29 |
| T1c-3111 | I-3 | II-150 | C-29 |
| T1c-3112 | I-3 | II-151 | C-29 |
| T1c-3113 | I-3 | II-152 | C-29 |
| T1c-3114 | I-3 | II-153 | C-29 |
| T1c-3115 | I-3 | II-154 | C-29 |
| T1c-3116 | I-3 | II-155 | C-29 |
| T1c-3117 | I-3 | II-156 | C-29 |
| T1c-3118 | I-3 | II-157 | C-29 |
| T1c-3119 | I-3 | II-158 | C-29 |
| T1c-3120 | I-3 | II-159 | C-29 |
| T1c-3121 | I-3 | II-160 | C-29 |
| T1c-3122 | I-3 | II-161 | C-29 |
| T1c-3123 | I-3 | II-162 | C-29 |
| T1c-3124 | I-3 | II-163 | C-29 |
| T1c-3125 | I-3 | II-164 | C-29 |
| T1c-3126 | I-3 | II-165 | C-29 |
| T1c-3127 | I-3 | II-166 | C-29 |
| T1c-3128 | I-3 | II-167 | C-29 |
| T1c-3129 | I-3 | II-168 | C-29 |
| T1c-3130 | I-3 | II-169 | C-29 |
| T1c-3131 | I-3 | II-170 | C-29 |
| T1c-3132 | I-3 | II-171 | C-29 |
| T1c-3133 | I-3 | II-172 | C-29 |
| T1c-3134 | I-3 | II-173 | C-29 |
| T1c-3135 | I-3 | II-174 | C-29 |
| T1c-3136 | I-3 | II-175 | C-29 |
| T1c-3137 | I-3 | II-176 | C-29 |
| T1c-3138 | I-3 | II-177 | C-29 |
| T1c-3139 | I-3 | II-178 | C-29 |
| T1c-3140 | I-3 | II-179 | C-29 |
| T1c-3141 | I-3 | II-180 | C-29 |
| T1c-3142 | I-3 | II-181 | C-29 |
| T1c-3143 | I-3 | II-182 | C-29 |
| T1c-3144 | I-3 | II-183 | C-29 |
| T1c-3145 | I-3 | II-184 | C-29 |
| T1c-3146 | I-3 | II-185 | C-29 |
| T1c-3147 | I-3 | II-186 | C-29 |
| T1c-3148 | I-3 | II-187 | C-29 |
| T1c-3149 | I-3 | II-188 | C-29 |
| T1c-3150 | I-3 | II-189 | C-29 |
| T1c-3151 | I-3 | II-190 | C-29 |
| T1c-3152 | I-3 | II-191 | C-29 |
| T1c-3153 | I-3 | II-192 | C-29 |
| T1c-3154 | I-3 | II-193 | C-29 |
| T1c-3155 | I-3 | II-194 | C-29 |
| T1c-3156 | I-3 | II-195 | C-29 |
| T1c-3157 | I-3 | II-196 | C-29 |
| T1c-3158 | I-3 | II-197 | C-29 |
| T1c-3159 | I-3 | II-198 | C-29 |
| T1c-3160 | I-3 | II-199 | C-29 |
| T1c-3161 | I-3 | II-200 | C-29 |
| T1c-3162 | I-3 | II-201 | C-29 |
| T1c-3163 | I-3 | II-202 | C-29 |
| T1c-3164 | I-3 | II-203 | C-29 |
| T1c-3165 | I-3 | II-91 | C-30 |
| T1c-3166 | I-3 | II-92 | C-30 |
| T1c-3167 | I-3 | II-93 | C-30 |
| T1c-3168 | I-3 | II-94 | C-30 |
| T1c-3169 | I-3 | II-95 | C-30 |
| T1c-3170 | I-3 | II-96 | C-30 |
| T1c-3171 | I-3 | II-97 | C-30 |
| T1c-3172 | I-3 | II-98 | C-30 |
| T1c-3173 | I-3 | II-99 | C-30 |
| T1c-3174 | I-3 | II-100 | C-30 |
| T1c-3175 | I-3 | II-101 | C-30 |
| T1c-3176 | I-3 | II-102 | C-30 |
| T1c-3177 | I-3 | II-103 | C-30 |
| T1c-3178 | I-3 | II-104 | C-30 |
| T1c-3179 | I-3 | II-105 | C-30 |
| T1c-3180 | I-3 | II-106 | C-30 |
| T1c-3181 | I-3 | II-107 | C-30 |
| T1c-3182 | I-3 | II-108 | C-30 |
| T1c-3183 | I-3 | II-109 | C-30 |
| T1c-3184 | I-3 | II-110 | C-30 |
| T1c-3185 | I-3 | II-111 | C-30 |
| T1c-3186 | I-3 | II-112 | C-30 |
| T1c-3187 | I-3 | II-113 | C-30 |
| T1c-3188 | I-3 | II-114 | C-30 |
| T1c-3189 | I-3 | II-115 | C-30 |
| T1c-3190 | I-3 | II-116 | C-30 |
| T1c-3191 | I-3 | II-117 | C-30 |
| T1c-3192 | I-3 | II-118 | C-30 |
| T1c-3193 | I-3 | II-119 | C-30 |
| T1c-3194 | I-3 | II-120 | C-30 |
| T1c-3195 | I-3 | II-121 | C-30 |
| T1c-3196 | I-3 | II-122 | C-30 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-3197 | I-3 | II-123 | C-30 |
| T1c-3198 | I-3 | II-124 | C-30 |
| T1c-3199 | I-3 | II-125 | C-30 |
| T1c-3200 | I-3 | II-126 | C-30 |
| T1c-3201 | I-3 | II-127 | C-30 |
| T1c-3202 | I-3 | II-128 | C-30 |
| T1c-3203 | I-3 | II-129 | C-30 |
| T1c-3204 | I-3 | II-130 | C-30 |
| T1c-3205 | I-3 | II-131 | C-30 |
| T1c-3206 | I-3 | II-132 | C-30 |
| T1c-3207 | I-3 | II-133 | C-30 |
| T1c-3208 | I-3 | II-134 | C-30 |
| T1c-3209 | I-3 | II-135 | C-30 |
| T1c-3210 | I-3 | II-136 | C-30 |
| T1c-3211 | I-3 | II-137 | C-30 |
| T1c-3212 | I-3 | II-138 | C-30 |
| T1c-3213 | I-3 | II-139 | C-30 |
| T1c-3214 | I-3 | II-140 | C-30 |
| T1c-3215 | I-3 | II-141 | C-30 |
| T1c-3216 | I-3 | II-142 | C-30 |
| T1c-3217 | I-3 | II-143 | C-30 |
| T1c-3218 | I-3 | II-144 | C-30 |
| T1c-3219 | I-3 | II-145 | C-30 |
| T1c-3220 | I-3 | II-146 | C-30 |
| T1c-3221 | I-3 | II-147 | C-30 |
| T1c-3222 | I-3 | II-148 | C-30 |
| T1c-3223 | I-3 | II-149 | C-30 |
| T1c-3224 | I-3 | II-150 | C-30 |
| T1c-3225 | I-3 | II-151 | C-30 |
| T1c-3226 | I-3 | II-152 | C-30 |
| T1c-3227 | I-3 | II-153 | C-30 |
| T1c-3228 | I-3 | II-154 | C-30 |
| T1c-3229 | I-3 | II-155 | C-30 |
| T1c-3230 | I-3 | II-156 | C-30 |
| T1c-3231 | I-3 | II-157 | C-30 |
| T1c-3232 | I-3 | II-158 | C-30 |
| T1c-3233 | I-3 | II-159 | C-30 |
| T1c-3234 | I-3 | II-160 | C-30 |
| T1c-3235 | I-3 | II-161 | C-30 |
| T1c-3236 | I-3 | II-162 | C-30 |
| T1c-3237 | I-3 | II-163 | C-30 |
| T1c-3238 | I-3 | II-164 | C-30 |
| T1c-3239 | I-3 | II-165 | C-30 |
| T1c-3240 | I-3 | II-166 | C-30 |
| T1c-3241 | I-3 | II-167 | C-30 |
| T1c-3242 | I-3 | II-168 | C-30 |
| T1c-3243 | I-3 | II-169 | C-30 |
| T1c-3244 | I-3 | II-170 | C-30 |
| T1c-3245 | I-3 | II-171 | C-30 |
| T1c-3246 | I-3 | II-172 | C-30 |
| T1c-3247 | I-3 | II-173 | C-30 |
| T1c-3248 | I-3 | II-174 | C-30 |
| T1c-3249 | I-3 | II-175 | C-30 |
| T1c-3250 | I-3 | II-176 | C-30 |
| T1c-3251 | I-3 | II-177 | C-30 |
| T1c-3252 | I-3 | II-178 | C-30 |
| T1c-3253 | I-3 | II-179 | C-30 |
| T1c-3254 | I-3 | II-180 | C-30 |
| T1c-3255 | I-3 | II-181 | C-30 |
| T1c-3256 | I-3 | II-182 | C-30 |
| T1c-3257 | I-3 | II-183 | C-30 |
| T1c-3258 | I-3 | II-184 | C-30 |
| T1c-3259 | I-3 | II-185 | C-30 |
| T1c-3260 | I-3 | II-186 | C-30 |
| T1c-3261 | I-3 | II-187 | C-30 |
| T1c-3262 | I-3 | II-188 | C-30 |
| T1c-3263 | I-3 | II-189 | C-30 |
| T1c-3264 | I-3 | II-190 | C-30 |
| T1c-3265 | I-3 | II-191 | C-30 |
| T1c-3266 | I-3 | II-192 | C-30 |
| T1c-3267 | I-3 | II-193 | C-30 |
| T1c-3268 | I-3 | II-194 | C-30 |
| T1c-3269 | I-3 | II-195 | C-30 |
| T1c-3270 | I-3 | II-196 | C-30 |
| T1c-3271 | I-3 | II-197 | C-30 |
| T1c-3272 | I-3 | II-198 | C-30 |
| T1c-3273 | I-3 | II-199 | C-30 |
| T1c-3274 | I-3 | II-200 | C-30 |
| T1c-3275 | I-3 | II-201 | C-30 |
| T1c-3276 | I-3 | II-202 | C-30 |
| T1c-3277 | I-3 | II-203 | C-30 |
| T1c-3278 | I-3 | II-91 | C-31 |
| T1c-3279 | I-3 | II-92 | C-31 |
| T1c-3280 | I-3 | II-93 | C-31 |
| T1c-3281 | I-3 | II-94 | C-31 |
| T1c-3282 | I-3 | II-95 | C-31 |
| T1c-3283 | I-3 | II-96 | C-31 |
| T1c-3284 | I-3 | II-97 | C-31 |
| T1c-3285 | I-3 | II-98 | C-31 |
| T1c-3286 | I-3 | II-99 | C-31 |
| T1c-3287 | I-3 | II-100 | C-31 |
| T1c-3288 | I-3 | II-101 | C-31 |
| T1c-3289 | I-3 | II-102 | C-31 |
| T1c-3290 | I-3 | II-103 | C-31 |
| T1c-3291 | I-3 | II-104 | C-31 |
| T1c-3292 | I-3 | II-105 | C-31 |
| T1c-3293 | I-3 | II-106 | C-31 |
| T1c-3294 | I-3 | II-107 | C-31 |
| T1c-3295 | I-3 | II-108 | C-31 |
| T1c-3296 | I-3 | II-109 | C-31 |
| T1c-3297 | I-3 | II-110 | C-31 |
| T1c-3298 | I-3 | II-111 | C-31 |
| T1c-3299 | I-3 | II-112 | C-31 |
| T1c-3300 | I-3 | II-113 | C-31 |
| T1c-3301 | I-3 | II-114 | C-31 |
| T1c-3302 | I-3 | II-115 | C-31 |
| T1c-3303 | I-3 | II-116 | C-31 |
| T1c-3304 | I-3 | II-117 | C-31 |
| T1c-3305 | I-3 | II-118 | C-31 |
| T1c-3306 | I-3 | II-119 | C-31 |
| T1c-3307 | I-3 | II-120 | C-31 |
| T1c-3308 | I-3 | II-121 | C-31 |
| T1c-3309 | I-3 | II-122 | C-31 |
| T1c-3310 | I-3 | II-123 | C-31 |
| T1c-3311 | I-3 | II-124 | C-31 |
| T1c-3312 | I-3 | II-125 | C-31 |
| T1c-3313 | I-3 | II-126 | C-31 |
| T1c-3314 | I-3 | II-127 | C-31 |
| T1c-3315 | I-3 | II-128 | C-31 |
| T1c-3316 | I-3 | II-129 | C-31 |
| T1c-3317 | I-3 | II-130 | C-31 |
| T1c-3318 | I-3 | II-131 | C-31 |
| T1c-3319 | I-3 | II-132 | C-31 |
| T1c-3320 | I-3 | II-133 | C-31 |
| T1c-3321 | I-3 | II-134 | C-31 |
| T1c-3322 | I-3 | II-135 | C-31 |
| T1c-3323 | I-3 | II-136 | C-31 |
| T1c-3324 | I-3 | II-137 | C-31 |
| T1c-3325 | I-3 | II-138 | C-31 |
| T1c-3326 | I-3 | II-139 | C-31 |
| T1c-3327 | I-3 | II-140 | C-31 |
| T1c-3328 | I-3 | II-141 | C-31 |
| T1c-3329 | I-3 | II-142 | C-31 |
| T1c-3330 | I-3 | II-143 | C-31 |
| T1c-3331 | I-3 | II-144 | C-31 |
| T1c-3332 | I-3 | II-145 | C-31 |
| T1c-3333 | I-3 | II-146 | C-31 |
| T1c-3334 | I-3 | II-147 | C-31 |
| T1c-3335 | I-3 | II-148 | C-31 |
| T1c-3336 | I-3 | II-149 | C-31 |
| T1c-3337 | I-3 | II-150 | C-31 |
| T1c-3338 | I-3 | II-151 | C-31 |
| T1c-3339 | I-3 | II-152 | C-31 |
| T1c-3340 | I-3 | II-153 | C-31 |
| T1c-3341 | I-3 | II-154 | C-31 |
| T1c-3342 | I-3 | II-155 | C-31 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-3343 | I-3 | II-156 | C-31 |
| T1c-3344 | I-3 | II-157 | C-31 |
| T1c-3345 | I-3 | II-158 | C-31 |
| T1c-3346 | I-3 | II-159 | C-31 |
| T1c-3347 | I-3 | II-160 | C-31 |
| T1c-3348 | I-3 | II-161 | C-31 |
| T1c-3349 | I-3 | II-162 | C-31 |
| T1c-3350 | I-3 | II-163 | C-31 |
| T1c-3351 | I-3 | II-164 | C-31 |
| T1c-3352 | I-3 | II-165 | C-31 |
| T1c-3353 | I-3 | II-166 | C-31 |
| T1c-3354 | I-3 | II-167 | C-31 |
| T1c-3355 | I-3 | II-168 | C-31 |
| T1c-3356 | I-3 | II-169 | C-31 |
| T1c-3357 | I-3 | II-170 | C-31 |
| T1c-3358 | I-3 | II-171 | C-31 |
| T1c-3359 | I-3 | II-172 | C-31 |
| T1c-3360 | I-3 | II-173 | C-31 |
| T1c-3361 | I-3 | II-174 | C-31 |
| T1c-3362 | I-3 | II-175 | C-31 |
| T1c-3363 | I-3 | II-176 | C-31 |
| T1c-3364 | I-3 | II-177 | C-31 |
| T1c-3365 | I-3 | II-178 | C-31 |
| T1c-3366 | I-3 | II-179 | C-31 |
| T1c-3367 | I-3 | II-180 | C-31 |
| T1c-3368 | I-3 | II-181 | C-31 |
| T1c-3369 | I-3 | II-182 | C-31 |
| T1c-3370 | I-3 | II-183 | C-31 |
| T1c-3371 | I-3 | II-184 | C-31 |
| T1c-3372 | I-3 | II-185 | C-31 |
| T1c-3373 | I-3 | II-186 | C-31 |
| T1c-3374 | I-3 | II-187 | C-31 |
| T1c-3375 | I-3 | II-188 | C-31 |
| T1c-3376 | I-3 | II-189 | C-31 |
| T1c-3377 | I-3 | II-190 | C-31 |
| T1c-3378 | I-3 | II-191 | C-31 |
| T1c-3379 | I-3 | II-192 | C-31 |
| T1c-3380 | I-3 | II-193 | C-31 |
| T1c-3381 | I-3 | II-194 | C-31 |
| T1c-3382 | I-3 | II-195 | C-31 |
| T1c-3383 | I-3 | II-196 | C-31 |
| T1c-3384 | I-3 | II-197 | C-31 |
| T1c-3385 | I-3 | II-198 | C-31 |
| T1c-3386 | I-3 | II-199 | C-31 |
| T1c-3387 | I-3 | II-200 | C-31 |
| T1c-3388 | I-3 | II-201 | C-31 |
| T1c-3389 | I-3 | II-202 | C-31 |
| T1c-3390 | I-3 | II-203 | C-31 |
| T1c-3391 | I-3 | II-91 | C-32 |
| T1c-3392 | I-3 | II-92 | C-32 |
| T1c-3393 | I-3 | II-93 | C-32 |
| T1c-3394 | I-3 | II-94 | C-32 |
| T1c-3395 | I-3 | II-95 | C-32 |
| T1c-3396 | I-3 | II-96 | C-32 |
| T1c-3397 | I-3 | II-97 | C-32 |
| T1c-3398 | I-3 | II-98 | C-32 |
| T1c-3399 | I-3 | II-99 | C-32 |
| T1c-3400 | I-3 | II-100 | C-32 |
| T1c-3401 | I-3 | II-101 | C-32 |
| T1c-3402 | I-3 | II-102 | C-32 |
| T1c-3403 | I-3 | II-103 | C-32 |
| T1c-3404 | I-3 | II-104 | C-32 |
| T1c-3405 | I-3 | II-105 | C-32 |
| T1c-3406 | I-3 | II-106 | C-32 |
| T1c-3407 | I-3 | II-107 | C-32 |
| T1c-3408 | I-3 | II-108 | C-32 |
| T1c-3409 | I-3 | II-109 | C-32 |
| T1c-3410 | I-3 | II-110 | C-32 |
| T1c-3411 | I-3 | II-111 | C-32 |
| T1c-3412 | I-3 | II-112 | C-32 |
| T1c-3413 | I-3 | II-113 | C-32 |
| T1c-3414 | I-3 | II-114 | C-32 |
| T1c-3415 | I-3 | II-115 | C-32 |
| T1c-3416 | I-3 | II-116 | C-32 |
| T1c-3417 | I-3 | II-117 | C-32 |
| T1c-3418 | I-3 | II-118 | C-32 |
| T1c-3419 | I-3 | II-119 | C-32 |
| T1c-3420 | I-3 | II-120 | C-32 |
| T1c-3421 | I-3 | II-121 | C-32 |
| T1c-3422 | I-3 | II-122 | C-32 |
| T1c-3423 | I-3 | II-123 | C-32 |
| T1c-3424 | I-3 | II-124 | C-32 |
| T1c-3425 | I-3 | II-125 | C-32 |
| T1c-3426 | I-3 | II-126 | C-32 |
| T1c-3427 | I-3 | II-127 | C-32 |
| T1c-3428 | I-3 | II-128 | C-32 |
| T1c-3429 | I-3 | II-129 | C-32 |
| T1c-3430 | I-3 | II-130 | C-32 |
| T1c-3431 | I-3 | II-131 | C-32 |
| T1c-3432 | I-3 | II-132 | C-32 |
| T1c-3433 | I-3 | II-133 | C-32 |
| T1c-3434 | I-3 | II-134 | C-32 |
| T1c-3435 | I-3 | II-135 | C-32 |
| T1c-3436 | I-3 | II-136 | C-32 |
| T1c-3437 | I-3 | II-137 | C-32 |
| T1c-3438 | I-3 | II-138 | C-32 |
| T1c-3439 | I-3 | II-139 | C-32 |
| T1c-3440 | I-3 | II-140 | C-32 |
| T1c-3441 | I-3 | II-141 | C-32 |
| T1c-3442 | I-3 | II-142 | C-32 |
| T1c-3443 | I-3 | II-143 | C-32 |
| T1c-3444 | I-3 | II-144 | C-32 |
| T1c-3445 | I-3 | II-145 | C-32 |
| T1c-3446 | I-3 | II-146 | C-32 |
| T1c-3447 | I-3 | II-147 | C-32 |
| T1c-3448 | I-3 | II-148 | C-32 |
| T1c-3449 | I-3 | II-149 | C-32 |
| T1c-3450 | I-3 | II-150 | C-32 |
| T1c-3451 | I-3 | II-151 | C-32 |
| T1c-3452 | I-3 | II-152 | C-32 |
| T1c-3453 | I-3 | II-153 | C-32 |
| T1c-3454 | I-3 | II-154 | C-32 |
| T1c-3455 | I-3 | II-155 | C-32 |
| T1c-3456 | I-3 | II-156 | C-32 |
| T1c-3457 | I-3 | II-157 | C-32 |
| T1c-3458 | I-3 | II-158 | C-32 |
| T1c-3459 | I-3 | II-159 | C-32 |
| T1c-3460 | I-3 | II-160 | C-32 |
| T1c-3461 | I-3 | II-161 | C-32 |
| T1c-3462 | I-3 | II-162 | C-32 |
| T1c-3463 | I-3 | II-163 | C-32 |
| T1c-3464 | I-3 | II-164 | C-32 |
| T1c-3465 | I-3 | II-165 | C-32 |
| T1c-3466 | I-3 | II-166 | C-32 |
| T1c-3467 | I-3 | II-167 | C-32 |
| T1c-3468 | I-3 | II-168 | C-32 |
| T1c-3469 | I-3 | II-169 | C-32 |
| T1c-3470 | I-3 | II-170 | C-32 |
| T1c-3471 | I-3 | II-171 | C-32 |
| T1c-3472 | I-3 | II-172 | C-32 |
| T1c-3473 | I-3 | II-173 | C-32 |
| T1c-3474 | I-3 | II-174 | C-32 |
| T1c-3475 | I-3 | II-175 | C-32 |
| T1c-3476 | I-3 | II-176 | C-32 |
| T1c-3477 | I-3 | II-177 | C-32 |
| T1c-3478 | I-3 | II-178 | C-32 |
| T1c-3479 | I-3 | II-179 | C-32 |
| T1c-3480 | I-3 | II-180 | C-32 |
| T1c-3481 | I-3 | II-181 | C-32 |
| T1c-3482 | I-3 | II-182 | C-32 |
| T1c-3483 | I-3 | II-183 | C-32 |
| T1c-3484 | I-3 | II-184 | C-32 |
| T1c-3485 | I-3 | II-185 | C-32 |
| T1c-3486 | I-3 | II-186 | C-32 |
| T1c-3487 | I-3 | II-187 | C-32 |
| T1c-3488 | I-3 | II-188 | C-32 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-3489 | I-3 | II-189 | C-32 |
| T1c-3490 | I-3 | II-190 | C-32 |
| T1c-3491 | I-3 | II-191 | C-32 |
| T1c-3492 | I-3 | II-192 | C-32 |
| T1c-3493 | I-3 | II-193 | C-32 |
| T1c-3494 | I-3 | II-194 | C-32 |
| T1c-3495 | I-3 | II-195 | C-32 |
| T1c-3496 | I-3 | II-196 | C-32 |
| T1c-3497 | I-3 | II-197 | C-32 |
| T1c-3498 | I-3 | II-198 | C-32 |
| T1c-3499 | I-3 | II-199 | C-32 |
| T1c-3500 | I-3 | II-200 | C-32 |
| T1c-3501 | I-3 | II-201 | C-32 |
| T1c-3502 | I-3 | II-202 | C-32 |
| T1c-3503 | I-3 | II-203 | C-32 |
| T1c-3504 | I-3 | II-91 | C-33 |
| T1c-3505 | I-3 | II-92 | C-33 |
| T1c-3506 | I-3 | II-93 | C-33 |
| T1c-3507 | I-3 | II-94 | C-33 |
| T1c-3508 | I-3 | II-95 | C-33 |
| T1c-3509 | I-3 | II-96 | C-33 |
| T1c-3510 | I-3 | II-97 | C-33 |
| T1c-3511 | I-3 | II-98 | C-33 |
| T1c-3512 | I-3 | II-99 | C-33 |
| T1c-3513 | I-3 | II-100 | C-33 |
| T1c-3514 | I-3 | II-101 | C-33 |
| T1c-3515 | I-3 | II-102 | C-33 |
| T1c-3516 | I-3 | II-103 | C-33 |
| T1c-3517 | I-3 | II-104 | C-33 |
| T1c-3518 | I-3 | II-105 | C-33 |
| T1c-3519 | I-3 | II-106 | C-33 |
| T1c-3520 | I-3 | II-107 | C-33 |
| T1c-3521 | I-3 | II-108 | C-33 |
| T1c-3522 | I-3 | II-109 | C-33 |
| T1c-3523 | I-3 | II-110 | C-33 |
| T1c-3524 | I-3 | II-111 | C-33 |
| T1c-3525 | I-3 | II-112 | C-33 |
| T1c-3526 | I-3 | II-113 | C-33 |
| T1c-3527 | I-3 | II-114 | C-33 |
| T1c-3528 | I-3 | II-115 | C-33 |
| T1c-3529 | I-3 | II-116 | C-33 |
| T1c-3530 | I-3 | II-117 | C-33 |
| T1c-3531 | I-3 | II-118 | C-33 |
| T1c-3532 | I-3 | II-119 | C-33 |
| T1c-3533 | I-3 | II-120 | C-33 |
| T1c-3534 | I-3 | II-121 | C-33 |
| T1c-3535 | I-3 | II-122 | C-33 |
| T1c-3536 | I-3 | II-123 | C-33 |
| T1c-3537 | I-3 | II-124 | C-33 |
| T1c-3538 | I-3 | II-125 | C-33 |
| T1c-3539 | I-3 | II-126 | C-33 |
| T1c-3540 | I-3 | II-127 | C-33 |
| T1c-3541 | I-3 | II-128 | C-33 |
| T1c-3542 | I-3 | II-129 | C-33 |
| T1c-3543 | I-3 | II-130 | C-33 |
| T1c-3544 | I-3 | II-131 | C-33 |
| T1c-3545 | I-3 | II-132 | C-33 |
| T1c-3546 | I-3 | II-133 | C-33 |
| T1c-3547 | I-3 | II-134 | C-33 |
| T1c-3548 | I-3 | II-135 | C-33 |
| T1c-3549 | I-3 | II-136 | C-33 |
| T1c-3550 | I-3 | II-137 | C-33 |
| T1c-3551 | I-3 | II-138 | C-33 |
| T1c-3552 | I-3 | II-139 | C-33 |
| T1c-3553 | I-3 | II-140 | C-33 |
| T1c-3554 | I-3 | II-141 | C-33 |
| T1c-3555 | I-3 | II-142 | C-33 |
| T1c-3556 | I-3 | II-143 | C-33 |
| T1c-3557 | I-3 | II-144 | C-33 |
| T1c-3558 | I-3 | II-145 | C-33 |
| T1c-3559 | I-3 | II-146 | C-33 |
| T1c-3560 | I-3 | II-147 | C-33 |
| T1c-3561 | I-3 | II-148 | C-33 |
| T1c-3562 | I-3 | II-149 | C-33 |
| T1c-3563 | I-3 | II-150 | C-33 |
| T1c-3564 | I-3 | II-151 | C-33 |
| T1c-3565 | I-3 | II-152 | C-33 |
| T1c-3566 | I-3 | II-153 | C-33 |
| T1c-3567 | I-3 | II-154 | C-33 |
| T1c-3568 | I-3 | II-155 | C-33 |
| T1c-3569 | I-3 | II-156 | C-33 |
| T1c-3570 | I-3 | II-157 | C-33 |
| T1c-3571 | I-3 | II-158 | C-33 |
| T1c-3572 | I-3 | II-159 | C-33 |
| T1c-3573 | I-3 | II-160 | C-33 |
| T1c-3574 | I-3 | II-161 | C-33 |
| T1c-3575 | I-3 | II-162 | C-33 |
| T1c-3576 | I-3 | II-163 | C-33 |
| T1c-3577 | I-3 | II-164 | C-33 |
| T1c-3578 | I-3 | II-165 | C-33 |
| T1c-3579 | I-3 | II-166 | C-33 |
| T1c-3580 | I-3 | II-167 | C-33 |
| T1c-3581 | I-3 | II-168 | C-33 |
| T1c-3582 | I-3 | II-169 | C-33 |
| T1c-3583 | I-3 | II-170 | C-33 |
| T1c-3584 | I-3 | II-171 | C-33 |
| T1c-3585 | I-3 | II-172 | C-33 |
| T1c-3586 | I-3 | II-173 | C-33 |
| T1c-3587 | I-3 | II-174 | C-33 |
| T1c-3588 | I-3 | II-175 | C-33 |
| T1c-3589 | I-3 | II-176 | C-33 |
| T1c-3590 | I-3 | II-177 | C-33 |
| T1c-3591 | I-3 | II-178 | C-33 |
| T1c-3592 | I-3 | II-179 | C-33 |
| T1c-3593 | I-3 | II-180 | C-33 |
| T1c-3594 | I-3 | II-181 | C-33 |
| T1c-3595 | I-3 | II-182 | C-33 |
| T1c-3596 | I-3 | II-183 | C-33 |
| T1c-3597 | I-3 | II-184 | C-33 |
| T1c-3598 | I-3 | II-185 | C-33 |
| T1c-3599 | I-3 | II-186 | C-33 |
| T1c-3600 | I-3 | II-187 | C-33 |
| T1c-3601 | I-3 | II-188 | C-33 |
| T1c-3602 | I-3 | II-189 | C-33 |
| T1c-3603 | I-3 | II-190 | C-33 |
| T1c-3604 | I-3 | II-191 | C-33 |
| T1c-3605 | I-3 | II-192 | C-33 |
| T1c-3606 | I-3 | II-193 | C-33 |
| T1c-3607 | I-3 | II-194 | C-33 |
| T1c-3608 | I-3 | II-195 | C-33 |
| T1c-3609 | I-3 | II-196 | C-33 |
| T1c-3610 | I-3 | II-197 | C-33 |
| T1c-3611 | I-3 | II-198 | C-33 |
| T1c-3612 | I-3 | II-199 | C-33 |
| T1c-3613 | I-3 | II-200 | C-33 |
| T1c-3614 | I-3 | II-201 | C-33 |
| T1c-3615 | I-3 | II-202 | C-33 |
| T1c-3616 | I-3 | II-203 | C-33 |
| T1c-3617 | I-3 | II-91 | C-34 |
| T1c-3618 | I-3 | II-92 | C-34 |
| T1c-3619 | I-3 | II-93 | C-34 |
| T1c-3620 | I-3 | II-94 | C-34 |
| T1c-3621 | I-3 | II-95 | C-34 |
| T1c-3622 | I-3 | II-96 | C-34 |
| T1c-3623 | I-3 | II-97 | C-34 |
| T1c-3624 | I-3 | II-98 | C-34 |
| T1c-3625 | I-3 | II-99 | C-34 |
| T1c-3626 | I-3 | II-100 | C-34 |
| T1c-3627 | I-3 | II-101 | C-34 |
| T1c-3628 | I-3 | II-102 | C-34 |
| T1c-3629 | I-3 | II-103 | C-34 |
| T1c-3630 | I-3 | II-104 | C-34 |
| T1c-3631 | I-3 | II-105 | C-34 |
| T1c-3632 | I-3 | II-106 | C-34 |
| T1c-3633 | I-3 | II-107 | C-34 |
| T1c-3634 | I-3 | II-108 | C-34 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-3635 | I-3 | II-109 | C-34 |
| T1c-3636 | I-3 | II-110 | C-34 |
| T1c-3637 | I-3 | II-111 | C-34 |
| T1c-3638 | I-3 | II-112 | C-34 |
| T1c-3639 | I-3 | II-113 | C-34 |
| T1c-3640 | I-3 | II-114 | C-34 |
| T1c-3641 | I-3 | II-115 | C-34 |
| T1c-3642 | I-3 | II-116 | C-34 |
| T1c-3643 | I-3 | II-117 | C-34 |
| T1c-3644 | I-3 | II-118 | C-34 |
| T1c-3645 | I-3 | II-119 | C-34 |
| T1c-3646 | I-3 | II-120 | C-34 |
| T1c-3647 | I-3 | II-121 | C-34 |
| T1c-3648 | I-3 | II-122 | C-34 |
| T1c-3649 | I-3 | II-123 | C-34 |
| T1c-3650 | I-3 | II-124 | C-34 |
| T1c-3651 | I-3 | II-125 | C-34 |
| T1c-3652 | I-3 | II-126 | C-34 |
| T1c-3653 | I-3 | II-127 | C-34 |
| T1c-3654 | I-3 | II-128 | C-34 |
| T1c-3655 | I-3 | II-129 | C-34 |
| T1c-3656 | I-3 | II-130 | C-34 |
| T1c-3657 | I-3 | II-131 | C-34 |
| T1c-3658 | I-3 | II-132 | C-34 |
| T1c-3659 | I-3 | II-133 | C-34 |
| T1c-3660 | I-3 | II-134 | C-34 |
| T1c-3661 | I-3 | II-135 | C-34 |
| T1c-3662 | I-3 | II-136 | C-34 |
| T1c-3663 | I-3 | II-137 | C-34 |
| T1c-3664 | I-3 | II-138 | C-34 |
| T1c-3665 | I-3 | II-139 | C-34 |
| T1c-3666 | I-3 | II-140 | C-34 |
| T1c-3667 | I-3 | II-141 | C-34 |
| T1c-3668 | I-3 | II-142 | C-34 |
| T1c-3669 | I-3 | II-143 | C-34 |
| T1c-3670 | I-3 | II-144 | C-34 |
| T1c-3671 | I-3 | II-145 | C-34 |
| T1c-3672 | I-3 | II-146 | C-34 |
| T1c-3673 | I-3 | II-147 | C-34 |
| T1c-3674 | I-3 | II-148 | C-34 |
| T1c-3675 | I-3 | II-149 | C-34 |
| T1c-3676 | I-3 | II-150 | C-34 |
| T1c-3677 | I-3 | II-151 | C-34 |
| T1c-3678 | I-3 | II-152 | C-34 |
| T1c-3679 | I-3 | II-153 | C-34 |
| T1c-3680 | I-3 | II-154 | C-34 |
| T1c-3681 | I-3 | II-155 | C-34 |
| T1c-3682 | I-3 | II-156 | C-34 |
| T1c-3683 | I-3 | II-157 | C-34 |
| T1c-3684 | I-3 | II-158 | C-34 |
| T1c-3685 | I-3 | II-159 | C-34 |
| T1c-3686 | I-3 | II-160 | C-34 |
| T1c-3687 | I-3 | II-161 | C-34 |
| T1c-3688 | I-3 | II-162 | C-34 |
| T1c-3689 | I-3 | II-163 | C-34 |
| T1c-3690 | I-3 | II-164 | C-34 |
| T1c-3691 | I-3 | II-165 | C-34 |
| T1c-3692 | I-3 | II-166 | C-34 |
| T1c-3693 | I-3 | II-167 | C-34 |
| T1c-3694 | I-3 | II-168 | C-34 |
| T1c-3695 | I-3 | II-169 | C-34 |
| T1c-3696 | I-3 | II-170 | C-34 |
| T1c-3697 | I-3 | II-171 | C-34 |
| T1c-3698 | I-3 | II-172 | C-34 |
| T1c-3699 | I-3 | II-173 | C-34 |
| T1c-3700 | I-3 | II-174 | C-34 |
| T1c-3701 | I-3 | II-175 | C-34 |
| T1c-3702 | I-3 | II-176 | C-34 |
| T1c-3703 | I-3 | II-177 | C-34 |
| T1c-3704 | I-3 | II-178 | C-34 |
| T1c-3705 | I-3 | II-179 | C-34 |
| T1c-3706 | I-3 | II-180 | C-34 |
| T1c-3707 | I-3 | II-181 | C-34 |
| T1c-3708 | I-3 | II-182 | C-34 |
| T1c-3709 | I-3 | II-183 | C-34 |
| T1c-3710 | I-3 | II-184 | C-34 |
| T1c-3711 | I-3 | II-185 | C-34 |
| T1c-3712 | I-3 | II-186 | C-34 |
| T1c-3713 | I-3 | II-187 | C-34 |
| T1c-3714 | I-3 | II-188 | C-34 |
| T1c-3715 | I-3 | II-189 | C-34 |
| T1c-3716 | I-3 | II-190 | C-34 |
| T1c-3717 | I-3 | II-191 | C-34 |
| T1c-3718 | I-3 | II-192 | C-34 |
| T1c-3719 | I-3 | II-193 | C-34 |
| T1c-3720 | I-3 | II-194 | C-34 |
| T1c-3721 | I-3 | II-195 | C-34 |
| T1c-3722 | I-3 | II-196 | C-34 |
| T1c-3723 | I-3 | II-197 | C-34 |
| T1c-3724 | I-3 | II-198 | C-34 |
| T1c-3725 | I-3 | II-199 | C-34 |
| T1c-3726 | I-3 | II-200 | C-34 |
| T1c-3727 | I-3 | II-201 | C-34 |
| T1c-3728 | I-3 | II-202 | C-34 |
| T1c-3729 | I-3 | II-203 | C-34 |
| T1c-3730 | I-3 | II-91 | C-35 |
| T1c-3731 | I-3 | II-92 | C-35 |
| T1c-3732 | I-3 | II-93 | C-35 |
| T1c-3733 | I-3 | II-94 | C-35 |
| T1c-3734 | I-3 | II-95 | C-35 |
| T1c-3735 | I-3 | II-96 | C-35 |
| T1c-3736 | I-3 | II-97 | C-35 |
| T1c-3737 | I-3 | II-98 | C-35 |
| T1c-3738 | I-3 | II-99 | C-35 |
| T1c-3739 | I-3 | II-100 | C-35 |
| T1c-3740 | I-3 | II-101 | C-35 |
| T1c-3741 | I-3 | II-102 | C-35 |
| T1c-3742 | I-3 | II-103 | C-35 |
| T1c-3743 | I-3 | II-104 | C-35 |
| T1c-3744 | I-3 | II-105 | C-35 |
| T1c-3745 | I-3 | II-106 | C-35 |
| T1c-3746 | I-3 | II-107 | C-35 |
| T1c-3747 | I-3 | II-108 | C-35 |
| T1c-3748 | I-3 | II-109 | C-35 |
| T1c-3749 | I-3 | II-110 | C-35 |
| T1c-3750 | I-3 | II-111 | C-35 |
| T1c-3751 | I-3 | II-112 | C-35 |
| T1c-3752 | I-3 | II-113 | C-35 |
| T1c-3753 | I-3 | II-114 | C-35 |
| T1c-3754 | I-3 | II-115 | C-35 |
| T1c-3755 | I-3 | II-116 | C-35 |
| T1c-3756 | I-3 | II-117 | C-35 |
| T1c-3757 | I-3 | II-118 | C-35 |
| T1c-3758 | I-3 | II-119 | C-35 |
| T1c-3759 | I-3 | II-120 | C-35 |
| T1c-3760 | I-3 | II-121 | C-35 |
| T1c-3761 | I-3 | II-122 | C-35 |
| T1c-3762 | I-3 | II-123 | C-35 |
| T1c-3763 | I-3 | II-124 | C-35 |
| T1c-3764 | I-3 | II-125 | C-35 |
| T1c-3765 | I-3 | II-126 | C-35 |
| T1c-3766 | I-3 | II-127 | C-35 |
| T1c-3767 | I-3 | II-128 | C-35 |
| T1c-3768 | I-3 | II-129 | C-35 |
| T1c-3769 | I-3 | II-130 | C-35 |
| T1c-3770 | I-3 | II-131 | C-35 |
| T1c-3771 | I-3 | II-132 | C-35 |
| T1c-3772 | I-3 | II-133 | C-35 |
| T1c-3773 | I-3 | II-134 | C-35 |
| T1c-3774 | I-3 | II-135 | C-35 |
| T1c-3775 | I-3 | II-136 | C-35 |
| T1c-3776 | I-3 | II-137 | C-35 |
| T1c-3777 | I-3 | II-138 | C-35 |
| T1c-3778 | I-3 | II-139 | C-35 |
| T1c-3779 | I-3 | II-140 | C-35 |
| T1c-3780 | I-3 | II-141 | C-35 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-3781 | I-3 | II-142 | C-35 |
| T1c-3782 | I-3 | II-143 | C-35 |
| T1c-3783 | I-3 | II-144 | C-35 |
| T1c-3784 | I-3 | II-145 | C-35 |
| T1c-3785 | I-3 | II-146 | C-35 |
| T1c-3786 | I-3 | II-147 | C-35 |
| T1c-3787 | I-3 | II-148 | C-35 |
| T1c-3788 | I-3 | II-149 | C-35 |
| T1c-3789 | I-3 | II-150 | C-35 |
| T1c-3790 | I-3 | II-151 | C-35 |
| T1c-3791 | I-3 | II-152 | C-35 |
| T1c-3792 | I-3 | II-153 | C-35 |
| T1c-3793 | I-3 | II-154 | C-35 |
| T1c-3794 | I-3 | II-155 | C-35 |
| T1c-3795 | I-3 | II-156 | C-35 |
| T1c-3796 | I-3 | II-157 | C-35 |
| T1c-3797 | I-3 | II-158 | C-35 |
| T1c-3798 | I-3 | II-159 | C-35 |
| T1c-3799 | I-3 | II-160 | C-35 |
| T1c-3800 | I-3 | II-161 | C-35 |
| T1c-3801 | I-3 | II-162 | C-35 |
| T1c-3802 | I-3 | II-163 | C-35 |
| T1c-3803 | I-3 | II-164 | C-35 |
| T1c-3804 | I-3 | II-165 | C-35 |
| T1c-3805 | I-3 | II-166 | C-35 |
| T1c-3806 | I-3 | II-167 | C-35 |
| T1c-3807 | I-3 | II-168 | C-35 |
| T1c-3808 | I-3 | II-169 | C-35 |
| T1c-3809 | I-3 | II-170 | C-35 |
| T1c-3810 | I-3 | II-171 | C-35 |
| T1c-3811 | I-3 | II-172 | C-35 |
| T1c-3812 | I-3 | II-173 | C-35 |
| T1c-3813 | I-3 | II-174 | C-35 |
| T1c-3814 | I-3 | II-175 | C-35 |
| T1c-3815 | I-3 | II-176 | C-35 |
| T1c-3816 | I-3 | II-177 | C-35 |
| T1c-3817 | I-3 | II-178 | C-35 |
| T1c-3818 | I-3 | II-179 | C-35 |
| T1c-3819 | I-3 | II-180 | C-35 |
| T1c-3820 | I-3 | II-181 | C-35 |
| T1c-3821 | I-3 | II-182 | C-35 |
| T1c-3822 | I-3 | II-183 | C-35 |
| T1c-3823 | I-3 | II-184 | C-35 |
| T1c-3824 | I-3 | II-185 | C-35 |
| T1c-3825 | I-3 | II-186 | C-35 |
| T1c-3826 | I-3 | II-187 | C-35 |
| T1c-3827 | I-3 | II-188 | C-35 |
| T1c-3828 | I-3 | II-189 | C-35 |
| T1c-3829 | I-3 | II-190 | C-35 |
| T1c-3830 | I-3 | II-191 | C-35 |
| T1c-3831 | I-3 | II-192 | C-35 |
| T1c-3832 | I-3 | II-193 | C-35 |
| T1c-3833 | I-3 | II-194 | C-35 |
| T1c-3834 | I-3 | II-195 | C-35 |
| T1c-3835 | I-3 | II-196 | C-35 |
| T1c-3836 | I-3 | II-197 | C-35 |
| T1c-3837 | I-3 | II-198 | C-35 |
| T1c-3838 | I-3 | II-199 | C-35 |
| T1c-3839 | I-3 | II-200 | C-35 |
| T1c-3840 | I-3 | II-201 | C-35 |
| T1c-3841 | I-3 | II-202 | C-35 |
| T1c-3842 | I-3 | II-203 | C-35 |
| T1c-3843 | I-3 | II-91 | C-36 |
| T1c-3844 | I-3 | II-92 | C-36 |
| T1c-3845 | I-3 | II-93 | C-36 |
| T1c-3846 | I-3 | II-94 | C-36 |
| T1c-3847 | I-3 | II-95 | C-36 |
| T1c-3848 | I-3 | II-96 | C-36 |
| T1c-3849 | I-3 | II-97 | C-36 |
| T1c-3850 | I-3 | II-98 | C-36 |
| T1c-3851 | I-3 | II-99 | C-36 |
| T1c-3852 | I-3 | II-100 | C-36 |
| T1c-3853 | I-3 | II-101 | C-36 |
| T1c-3854 | I-3 | II-102 | C-36 |
| T1c-3855 | I-3 | II-103 | C-36 |
| T1c-3856 | I-3 | II-104 | C-36 |
| T1c-3857 | I-3 | II-105 | C-36 |
| T1c-3858 | I-3 | II-106 | C-36 |
| T1c-3859 | I-3 | II-107 | C-36 |
| T1c-3860 | I-3 | II-108 | C-36 |
| T1c-3861 | I-3 | II-109 | C-36 |
| T1c-3862 | I-3 | II-110 | C-36 |
| T1c-3863 | I-3 | II-111 | C-36 |
| T1c-3864 | I-3 | II-112 | C-36 |
| T1c-3865 | I-3 | II-113 | C-36 |
| T1c-3866 | I-3 | II-114 | C-36 |
| T1c-3867 | I-3 | II-115 | C-36 |
| T1c-3868 | I-3 | II-116 | C-36 |
| T1c-3869 | I-3 | II-117 | C-36 |
| T1c-3870 | I-3 | II-118 | C-36 |
| T1c-3871 | I-3 | II-119 | C-36 |
| T1c-3872 | I-3 | II-120 | C-36 |
| T1c-3873 | I-3 | II-121 | C-36 |
| T1c-3874 | I-3 | II-122 | C-36 |
| T1c-3875 | I-3 | II-123 | C-36 |
| T1c-3876 | I-3 | II-124 | C-36 |
| T1c-3877 | I-3 | II-125 | C-36 |
| T1c-3878 | I-3 | II-126 | C-36 |
| T1c-3879 | I-3 | II-127 | C-36 |
| T1c-3880 | I-3 | II-128 | C-36 |
| T1c-3881 | I-3 | II-129 | C-36 |
| T1c-3882 | I-3 | II-130 | C-36 |
| T1c-3883 | I-3 | II-131 | C-36 |
| T1c-3884 | I-3 | II-132 | C-36 |
| T1c-3885 | I-3 | II-133 | C-36 |
| T1c-3886 | I-3 | II-134 | C-36 |
| T1c-3887 | I-3 | II-135 | C-36 |
| T1c-3888 | I-3 | II-136 | C-36 |
| T1c-3889 | I-3 | II-137 | C-36 |
| T1c-3890 | I-3 | II-138 | C-36 |
| T1c-3891 | I-3 | II-139 | C-36 |
| T1c-3892 | I-3 | II-140 | C-36 |
| T1c-3893 | I-3 | II-141 | C-36 |
| T1c-3894 | I-3 | II-142 | C-36 |
| T1c-3895 | I-3 | II-143 | C-36 |
| T1c-3896 | I-3 | II-144 | C-36 |
| T1c-3897 | I-3 | II-145 | C-36 |
| T1c-3898 | I-3 | II-146 | C-36 |
| T1c-3899 | I-3 | II-147 | C-36 |
| T1c-3900 | I-3 | II-148 | C-36 |
| T1c-3901 | I-3 | II-149 | C-36 |
| T1c-3902 | I-3 | II-150 | C-36 |
| T1c-3903 | I-3 | II-151 | C-36 |
| T1c-3904 | I-3 | II-152 | C-36 |
| T1c-3905 | I-3 | II-153 | C-36 |
| T1c-3906 | I-3 | II-154 | C-36 |
| T1c-3907 | I-3 | II-155 | C-36 |
| T1c-3908 | I-3 | II-156 | C-36 |
| T1c-3909 | I-3 | II-157 | C-36 |
| T1c-3910 | I-3 | II-158 | C-36 |
| T1c-3911 | I-3 | II-159 | C-36 |
| T1c-3912 | I-3 | II-160 | C-36 |
| T1c-3913 | I-3 | II-161 | C-36 |
| T1c-3914 | I-3 | II-162 | C-36 |
| T1c-3915 | I-3 | II-163 | C-36 |
| T1c-3916 | I-3 | II-164 | C-36 |
| T1c-3917 | I-3 | II-165 | C-36 |
| T1c-3918 | I-3 | II-166 | C-36 |
| T1c-3919 | I-3 | II-167 | C-36 |
| T1c-3920 | I-3 | II-168 | C-36 |
| T1c-3921 | I-3 | II-169 | C-36 |
| T1c-3922 | I-3 | II-170 | C-36 |
| T1c-3923 | I-3 | II-171 | C-36 |
| T1c-3924 | I-3 | II-172 | C-36 |
| T1c-3925 | I-3 | II-173 | C-36 |
| T1c-3926 | I-3 | II-174 | C-36 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-3927 | I-3 | II-175 | C-36 |
| T1c-3928 | I-3 | II-176 | C-36 |
| T1c-3929 | I-3 | II-177 | C-36 |
| T1c-3930 | I-3 | II-178 | C-36 |
| T1c-3931 | I-3 | II-179 | C-36 |
| T1c-3932 | I-3 | II-180 | C-36 |
| T1c-3933 | I-3 | II-181 | C-36 |
| T1c-3934 | I-3 | II-182 | C-36 |
| T1c-3935 | I-3 | II-183 | C-36 |
| T1c-3936 | I-3 | II-184 | C-36 |
| T1c-3937 | I-3 | II-185 | C-36 |
| T1c-3938 | I-3 | II-186 | C-36 |
| T1c-3939 | I-3 | II-187 | C-36 |
| T1c-3940 | I-3 | II-188 | C-36 |
| T1c-3941 | I-3 | II-189 | C-36 |
| T1c-3942 | I-3 | II-190 | C-36 |
| T1c-3943 | I-3 | II-191 | C-36 |
| T1c-3944 | I-3 | II-192 | C-36 |
| T1c-3945 | I-3 | II-193 | C-36 |
| T1c-3946 | I-3 | II-194 | C-36 |
| T1c-3947 | I-3 | II-195 | C-36 |
| T1c-3948 | I-3 | II-196 | C-36 |
| T1c-3949 | I-3 | II-197 | C-36 |
| T1c-3950 | I-3 | II-198 | C-36 |
| T1c-3951 | I-3 | II-199 | C-36 |
| T1c-3952 | I-3 | II-200 | C-36 |
| T1c-3953 | I-3 | II-201 | C-36 |
| T1c-3954 | I-3 | II-202 | C-36 |
| T1c-3955 | I-3 | II-203 | C-36 |
| T1c-3956 | I-3 | II-91 | C-37 |
| T1c-3957 | I-3 | II-92 | C-37 |
| T1c-3958 | I-3 | II-93 | C-37 |
| T1c-3959 | I-3 | II-94 | C-37 |
| T1c-3960 | I-3 | II-95 | C-37 |
| T1c-3961 | I-3 | II-96 | C-37 |
| T1c-3962 | I-3 | II-97 | C-37 |
| T1c-3963 | I-3 | II-98 | C-37 |
| T1c-3964 | I-3 | II-99 | C-37 |
| T1c-3965 | I-3 | II-100 | C-37 |
| T1c-3966 | I-3 | II-101 | C-37 |
| T1c-3967 | I-3 | II-102 | C-37 |
| T1c-3968 | I-3 | II-103 | C-37 |
| T1c-3969 | I-3 | II-104 | C-37 |
| T1c-3970 | I-3 | II-105 | C-37 |
| T1c-3971 | I-3 | II-106 | C-37 |
| T1c-3972 | I-3 | II-107 | C-37 |
| T1c-3973 | I-3 | II-108 | C-37 |
| T1c-3974 | I-3 | II-109 | C-37 |
| T1c-3975 | I-3 | II-110 | C-37 |
| T1c-3976 | I-3 | II-111 | C-37 |
| T1c-3977 | I-3 | II-112 | C-37 |
| T1c-3978 | I-3 | II-113 | C-37 |
| T1c-3979 | I-3 | II-114 | C-37 |
| T1c-3980 | I-3 | II-115 | C-37 |
| T1c-3981 | I-3 | II-116 | C-37 |
| T1c-3982 | I-3 | II-117 | C-37 |
| T1c-3983 | I-3 | II-118 | C-37 |
| T1c-3984 | I-3 | II-119 | C-37 |
| T1c-3985 | I-3 | II-120 | C-37 |
| T1c-3986 | I-3 | II-121 | C-37 |
| T1c-3987 | I-3 | II-122 | C-37 |
| T1c-3988 | I-3 | II-123 | C-37 |
| T1c-3989 | I-3 | II-124 | C-37 |
| T1c-3990 | I-3 | II-125 | C-37 |
| T1c-3991 | I-3 | II-126 | C-37 |
| T1c-3992 | I-3 | II-127 | C-37 |
| T1c-3993 | I-3 | II-128 | C-37 |
| T1c-3994 | I-3 | II-129 | C-37 |
| T1c-3995 | I-3 | II-130 | C-37 |
| T1c-3996 | I-3 | II-131 | C-37 |
| T1c-3997 | I-3 | II-132 | C-37 |
| T1c-3998 | I-3 | II-133 | C-37 |
| T1c-3999 | I-3 | II-134 | C-37 |
| T1c-4000 | I-3 | II-135 | C-37 |
| T1c-4001 | I-3 | II-136 | C-37 |
| T1c-4002 | I-3 | II-137 | C-37 |
| T1c-4003 | I-3 | II-138 | C-37 |
| T1c-4004 | I-3 | II-139 | C-37 |
| T1c-4005 | I-3 | II-140 | C-37 |
| T1c-4006 | I-3 | II-141 | C-37 |
| T1c-4007 | I-3 | II-142 | C-37 |
| T1c-4008 | I-3 | II-143 | C-37 |
| T1c-4009 | I-3 | II-144 | C-37 |
| T1c-4010 | I-3 | II-145 | C-37 |
| T1c-4011 | I-3 | II-146 | C-37 |
| T1c-4012 | I-3 | II-147 | C-37 |
| T1c-4013 | I-3 | II-148 | C-37 |
| T1c-4014 | I-3 | II-149 | C-37 |
| T1c-4015 | I-3 | II-150 | C-37 |
| T1c-4016 | I-3 | II-151 | C-37 |
| T1c-4017 | I-3 | II-152 | C-37 |
| T1c-4018 | I-3 | II-153 | C-37 |
| T1c-4019 | I-3 | II-154 | C-37 |
| T1c-4020 | I-3 | II-155 | C-37 |
| T1c-4021 | I-3 | II-156 | C-37 |
| T1c-4022 | I-3 | II-157 | C-37 |
| T1c-4023 | I-3 | II-158 | C-37 |
| T1c-4024 | I-3 | II-159 | C-37 |
| T1c-4025 | I-3 | II-160 | C-37 |
| T1c-4026 | I-3 | II-161 | C-37 |
| T1c-4027 | I-3 | II-162 | C-37 |
| T1c-4028 | I-3 | II-163 | C-37 |
| T1c-4029 | I-3 | II-164 | C-37 |
| T1c-4030 | I-3 | II-165 | C-37 |
| T1c-4031 | I-3 | II-166 | C-37 |
| T1c-4032 | I-3 | II-167 | C-37 |
| T1c-4033 | I-3 | II-168 | C-37 |
| T1c-4034 | I-3 | II-169 | C-37 |
| T1c-4035 | I-3 | II-170 | C-37 |
| T1c-4036 | I-3 | II-171 | C-37 |
| T1c-4037 | I-3 | II-172 | C-37 |
| T1c-4038 | I-3 | II-173 | C-37 |
| T1c-4039 | I-3 | II-174 | C-37 |
| T1c-4040 | I-3 | II-175 | C-37 |
| T1c-4041 | I-3 | II-176 | C-37 |
| T1c-4042 | I-3 | II-177 | C-37 |
| T1c-4043 | I-3 | II-178 | C-37 |
| T1c-4044 | I-3 | II-179 | C-37 |
| T1c-4045 | I-3 | II-180 | C-37 |
| T1c-4046 | I-3 | II-181 | C-37 |
| T1c-4047 | I-3 | II-182 | C-37 |
| T1c-4048 | I-3 | II-183 | C-37 |
| T1c-4049 | I-3 | II-184 | C-37 |
| T1c-4050 | I-3 | II-185 | C-37 |
| T1c-4051 | I-3 | II-186 | C-37 |
| T1c-4052 | I-3 | II-187 | C-37 |
| T1c-4053 | I-3 | II-188 | C-37 |
| T1c-4054 | I-3 | II-189 | C-37 |
| T1c-4055 | I-3 | II-190 | C-37 |
| T1c-4056 | I-3 | II-191 | C-37 |
| T1c-4057 | I-3 | II-192 | C-37 |
| T1c-4058 | I-3 | II-193 | C-37 |
| T1c-4059 | I-3 | II-194 | C-37 |
| T1c-4060 | I-3 | II-195 | C-37 |
| T1c-4061 | I-3 | II-196 | C-37 |
| T1c-4062 | I-3 | II-197 | C-37 |
| T1c-4063 | I-3 | II-198 | C-37 |
| T1c-4064 | I-3 | II-199 | C-37 |
| T1c-4065 | I-3 | II-200 | C-37 |
| T1c-4066 | I-3 | II-201 | C-37 |
| T1c-4067 | I-3 | II-202 | C-37 |
| T1c-4068 | I-3 | II-203 | C-37 |
| T1c-4069 | I-3 | II-91 | C-38 |
| T1c-4070 | I-3 | II-92 | C-38 |
| T1c-4071 | I-3 | II-93 | C-38 |
| T1c-4072 | I-3 | II-94 | C-38 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-4073 | I-3 | II-95 | C-38 |
| T1c-4074 | I-3 | II-96 | C-38 |
| T1c-4075 | I-3 | II-97 | C-38 |
| T1c-4076 | I-3 | II-98 | C-38 |
| T1c-4077 | I-3 | II-99 | C-38 |
| T1c-4078 | I-3 | II-100 | C-38 |
| T1c-4079 | I-3 | II-101 | C-38 |
| T1c-4080 | I-3 | II-102 | C-38 |
| T1c-4081 | I-3 | II-103 | C-38 |
| T1c-4082 | I-3 | II-104 | C-38 |
| T1c-4083 | I-3 | II-105 | C-38 |
| T1c-4084 | I-3 | II-106 | C-38 |
| T1c-4085 | I-3 | II-107 | C-38 |
| T1c-4086 | I-3 | II-108 | C-38 |
| T1c-4087 | I-3 | II-109 | C-38 |
| T1c-4088 | I-3 | II-110 | C-38 |
| T1c-4089 | I-3 | II-111 | C-38 |
| T1c-4090 | I-3 | II-112 | C-38 |
| T1c-4091 | I-3 | II-113 | C-38 |
| T1c-4092 | I-3 | II-114 | C-38 |
| T1c-4093 | I-3 | II-115 | C-38 |
| T1c-4094 | I-3 | II-116 | C-38 |
| T1c-4095 | I-3 | II-117 | C-38 |
| T1c-4096 | I-3 | II-118 | C-38 |
| T1c-4097 | I-3 | II-119 | C-38 |
| T1c-4098 | I-3 | II-120 | C-38 |
| T1c-4099 | I-3 | II-121 | C-38 |
| T1c-4100 | I-3 | II-122 | C-38 |
| T1c-4101 | I-3 | II-123 | C-38 |
| T1c-4102 | I-3 | II-124 | C-38 |
| T1c-4103 | I-3 | II-125 | C-38 |
| T1c-4104 | I-3 | II-126 | C-38 |
| T1c-4105 | I-3 | II-127 | C-38 |
| T1c-4106 | I-3 | II-128 | C-38 |
| T1c-4107 | I-3 | II-129 | C-38 |
| T1c-4108 | I-3 | II-130 | C-38 |
| T1c-4109 | I-3 | II-131 | C-38 |
| T1c-4110 | I-3 | II-132 | C-38 |
| T1c-4111 | I-3 | II-133 | C-38 |
| T1c-4112 | I-3 | II-134 | C-38 |
| T1c-4113 | I-3 | II-135 | C-38 |
| T1c-4114 | I-3 | II-136 | C-38 |
| T1c-4115 | I-3 | II-137 | C-38 |
| T1c-4116 | I-3 | II-138 | C-38 |
| T1c-4117 | I-3 | II-139 | C-38 |
| T1c-4118 | I-3 | II-140 | C-38 |
| T1c-4119 | I-3 | II-141 | C-38 |
| T1c-4120 | I-3 | II-142 | C-38 |
| T1c-4121 | I-3 | II-143 | C-38 |
| T1c-4122 | I-3 | II-144 | C-38 |
| T1c-4123 | I-3 | II-145 | C-38 |
| T1c-4124 | I-3 | II-146 | C-38 |
| T1c-4125 | I-3 | II-147 | C-38 |
| T1c-4126 | I-3 | II-148 | C-38 |
| T1c-4127 | I-3 | II-149 | C-38 |
| T1c-4128 | I-3 | II-150 | C-38 |
| T1c-4129 | I-3 | II-151 | C-38 |
| T1c-4130 | I-3 | II-152 | C-38 |
| T1c-4131 | I-3 | II-153 | C-38 |
| T1c-4132 | I-3 | II-154 | C-38 |
| T1c-4133 | I-3 | II-155 | C-38 |
| T1c-4134 | I-3 | II-156 | C-38 |
| T1c-4135 | I-3 | II-157 | C-38 |
| T1c-4136 | I-3 | II-158 | C-38 |
| T1c-4137 | I-3 | II-159 | C-38 |
| T1c-4138 | I-3 | II-160 | C-38 |
| T1c-4139 | I-3 | II-161 | C-38 |
| T1c-4140 | I-3 | II-162 | C-38 |
| T1c-4141 | I-3 | II-163 | C-38 |
| T1c-4142 | I-3 | II-164 | C-38 |
| T1c-4143 | I-3 | II-165 | C-38 |
| T1c-4144 | I-3 | II-166 | C-38 |
| T1c-4145 | I-3 | II-167 | C-38 |
| T1c-4146 | I-3 | II-168 | C-38 |
| T1c-4147 | I-3 | II-169 | C-38 |
| T1c-4148 | I-3 | II-170 | C-38 |
| T1c-4149 | I-3 | II-171 | C-38 |
| T1c-4150 | I-3 | II-172 | C-38 |
| T1c-4151 | I-3 | II-173 | C-38 |
| T1c-4152 | I-3 | II-174 | C-38 |
| T1c-4153 | I-3 | II-175 | C-38 |
| T1c-4154 | I-3 | II-176 | C-38 |
| T1c-4155 | I-3 | II-177 | C-38 |
| T1c-4156 | I-3 | II-178 | C-38 |
| T1c-4157 | I-3 | II-179 | C-38 |
| T1c-4158 | I-3 | II-180 | C-38 |
| T1c-4159 | I-3 | II-181 | C-38 |
| T1c-4160 | I-3 | II-182 | C-38 |
| T1c-4161 | I-3 | II-183 | C-38 |
| T1c-4162 | I-3 | II-184 | C-38 |
| T1c-4163 | I-3 | II-185 | C-38 |
| T1c-4164 | I-3 | II-186 | C-38 |
| T1c-4165 | I-3 | II-187 | C-38 |
| T1c-4166 | I-3 | II-188 | C-38 |
| T1c-4167 | I-3 | II-189 | C-38 |
| T1c-4168 | I-3 | II-190 | C-38 |
| T1c-4169 | I-3 | II-191 | C-38 |
| T1c-4170 | I-3 | II-192 | C-38 |
| T1c-4171 | I-3 | II-193 | C-38 |
| T1c-4172 | I-3 | II-194 | C-38 |
| T1c-4173 | I-3 | II-195 | C-38 |
| T1c-4174 | I-3 | II-196 | C-38 |
| T1c-4175 | I-3 | II-197 | C-38 |
| T1c-4176 | I-3 | II-198 | C-38 |
| T1c-4177 | I-3 | II-199 | C-38 |
| T1c-4178 | I-3 | II-200 | C-38 |
| T1c-4179 | I-3 | II-201 | C-38 |
| T1c-4180 | I-3 | II-202 | C-38 |
| T1c-4181 | I-3 | II-203 | C-38 |
| T1c-4182 | I-3 | II-91 | C-39 |
| T1c-4183 | I-3 | II-92 | C-39 |
| T1c-4184 | I-3 | II-93 | C-39 |
| T1c-4185 | I-3 | II-94 | C-39 |
| T1c-4186 | I-3 | II-95 | C-39 |
| T1c-4187 | I-3 | II-96 | C-39 |
| T1c-4188 | I-3 | II-97 | C-39 |
| T1c-4189 | I-3 | II-98 | C-39 |
| T1c-4190 | I-3 | II-99 | C-39 |
| T1c-4191 | I-3 | II-100 | C-39 |
| T1c-4192 | I-3 | II-101 | C-39 |
| T1c-4193 | I-3 | II-102 | C-39 |
| T1c-4194 | I-3 | II-103 | C-39 |
| T1c-4195 | I-3 | II-104 | C-39 |
| T1c-4196 | I-3 | II-105 | C-39 |
| T1c-4197 | I-3 | II-106 | C-39 |
| T1c-4198 | I-3 | II-107 | C-39 |
| T1c-4199 | I-3 | II-108 | C-39 |
| T1c-4200 | I-3 | II-109 | C-39 |
| T1c-4201 | I-3 | II-110 | C-39 |
| T1c-4202 | I-3 | II-111 | C-39 |
| T1c-4203 | I-3 | II-112 | C-39 |
| T1c-4204 | I-3 | II-113 | C-39 |
| T1c-4205 | I-3 | II-114 | C-39 |
| T1c-4206 | I-3 | II-115 | C-39 |
| T1c-4207 | I-3 | II-116 | C-39 |
| T1c-4208 | I-3 | II-117 | C-39 |
| T1c-4209 | I-3 | II-118 | C-39 |
| T1c-4210 | I-3 | II-119 | C-39 |
| T1c-4211 | I-3 | II-120 | C-39 |
| T1c-4212 | I-3 | II-121 | C-39 |
| T1c-4213 | I-3 | II-122 | C-39 |
| T1c-4214 | I-3 | II-123 | C-39 |
| T1c-4215 | I-3 | II-124 | C-39 |
| T1c-4216 | I-3 | II-125 | C-39 |
| T1c-4217 | I-3 | II-126 | C-39 |
| T1c-4218 | I-3 | II-127 | C-39 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-4219 | I-3 | II-128 | C-39 |
| T1c-4220 | I-3 | II-129 | C-39 |
| T1c-4221 | I-3 | II-130 | C-39 |
| T1c-4222 | I-3 | II-131 | C-39 |
| T1c-4223 | I-3 | II-132 | C-39 |
| T1c-4224 | I-3 | II-133 | C-39 |
| T1c-4225 | I-3 | II-134 | C-39 |
| T1c-4226 | I-3 | II-135 | C-39 |
| T1c-4227 | I-3 | II-136 | C-39 |
| T1c-4228 | I-3 | II-137 | C-39 |
| T1c-4229 | I-3 | II-138 | C-39 |
| T1c-4230 | I-3 | II-139 | C-39 |
| T1c-4231 | I-3 | II-140 | C-39 |
| T1c-4232 | I-3 | II-141 | C-39 |
| T1c-4233 | I-3 | II-142 | C-39 |
| T1c-4234 | I-3 | II-143 | C-39 |
| T1c-4235 | I-3 | II-144 | C-39 |
| T1c-4236 | I-3 | II-145 | C-39 |
| T1c-4237 | I-3 | II-146 | C-39 |
| T1c-4238 | I-3 | II-147 | C-39 |
| T1c-4239 | I-3 | II-148 | C-39 |
| T1c-4240 | I-3 | II-149 | C-39 |
| T1c-4241 | I-3 | II-150 | C-39 |
| T1c-4242 | I-3 | II-151 | C-39 |
| T1c-4243 | I-3 | II-152 | C-39 |
| T1c-4244 | I-3 | II-153 | C-39 |
| T1c-4245 | I-3 | II-154 | C-39 |
| T1c-4246 | I-3 | II-155 | C-39 |
| T1c-4247 | I-3 | II-156 | C-39 |
| T1c-4248 | I-3 | II-157 | C-39 |
| T1c-4249 | I-3 | II-158 | C-39 |
| T1c-4250 | I-3 | II-159 | C-39 |
| T1c-4251 | I-3 | II-160 | C-39 |
| T1c-4252 | I-3 | II-161 | C-39 |
| T1c-4253 | I-3 | II-162 | C-39 |
| T1c-4254 | I-3 | II-163 | C-39 |
| T1c-4255 | I-3 | II-164 | C-39 |
| T1c-4256 | I-3 | II-165 | C-39 |
| T1c-4257 | I-3 | II-166 | C-39 |
| T1c-4258 | I-3 | II-167 | C-39 |
| T1c-4259 | I-3 | II-168 | C-39 |
| T1c-4260 | I-3 | II-169 | C-39 |
| T1c-4261 | I-3 | II-170 | C-39 |
| T1c-4262 | I-3 | II-171 | C-39 |
| T1c-4263 | I-3 | II-172 | C-39 |
| T1c-4264 | I-3 | II-173 | C-39 |
| T1c-4265 | I-3 | II-174 | C-39 |
| T1c-4266 | I-3 | II-175 | C-39 |
| T1c-4267 | I-3 | II-176 | C-39 |
| T1c-4268 | I-3 | II-177 | C-39 |
| T1c-4269 | I-3 | II-178 | C-39 |
| T1c-4270 | I-3 | II-179 | C-39 |
| T1c-4271 | I-3 | II-180 | C-39 |
| T1c-4272 | I-3 | II-181 | C-39 |
| T1c-4273 | I-3 | II-182 | C-39 |
| T1c-4274 | I-3 | II-183 | C-39 |
| T1c-4275 | I-3 | II-184 | C-39 |
| T1c-4276 | I-3 | II-185 | C-39 |
| T1c-4277 | I-3 | II-186 | C-39 |
| T1c-4278 | I-3 | II-187 | C-39 |
| T1c-4279 | I-3 | II-188 | C-39 |
| T1c-4280 | I-3 | II-189 | C-39 |
| T1c-4281 | I-3 | II-190 | C-39 |
| T1c-4282 | I-3 | II-191 | C-39 |
| T1c-4283 | I-3 | II-192 | C-39 |
| T1c-4284 | I-3 | II-193 | C-39 |
| T1c-4285 | I-3 | II-194 | C-39 |
| T1c-4286 | I-3 | II-195 | C-39 |
| T1c-4287 | I-3 | II-196 | C-39 |
| T1c-4288 | I-3 | II-197 | C-39 |
| T1c-4289 | I-3 | II-198 | C-39 |
| T1c-4290 | I-3 | II-199 | C-39 |
| T1c-4291 | I-3 | II-200 | C-39 |
| T1c-4292 | I-3 | II-201 | C-39 |
| T1c-4293 | I-3 | II-202 | C-39 |
| T1c-4294 | I-3 | II-203 | C-39 |
| T1c-4295 | I-3 | II-91 | C-40 |
| T1c-4296 | I-3 | II-92 | C-40 |
| T1c-4297 | I-3 | II-93 | C-40 |
| T1c-4298 | I-3 | II-94 | C-40 |
| T1c-4299 | I-3 | II-95 | C-40 |
| T1c-4300 | I-3 | II-96 | C-40 |
| T1c-4301 | I-3 | II-97 | C-40 |
| T1c-4302 | I-3 | II-98 | C-40 |
| T1c-4303 | I-3 | II-99 | C-40 |
| T1c-4304 | I-3 | II-100 | C-40 |
| T1c-4305 | I-3 | II-101 | C-40 |
| T1c-4306 | I-3 | II-102 | C-40 |
| T1c-4307 | I-3 | II-103 | C-40 |
| T1c-4308 | I-3 | II-104 | C-40 |
| T1c-4309 | I-3 | II-105 | C-40 |
| T1c-4310 | I-3 | II-106 | C-40 |
| T1c-4311 | I-3 | II-107 | C-40 |
| T1c-4312 | I-3 | II-108 | C-40 |
| T1c-4313 | I-3 | II-109 | C-40 |
| T1c-4314 | I-3 | II-110 | C-40 |
| T1c-4315 | I-3 | II-111 | C-40 |
| T1c-4316 | I-3 | II-112 | C-40 |
| T1c-4317 | I-3 | II-113 | C-40 |
| T1c-4318 | I-3 | II-114 | C-40 |
| T1c-4319 | I-3 | II-115 | C-40 |
| T1c-4320 | I-3 | II-116 | C-40 |
| T1c-4321 | I-3 | II-117 | C-40 |
| T1c-4322 | I-3 | II-118 | C-40 |
| T1c-4323 | I-3 | II-119 | C-40 |
| T1c-4324 | I-3 | II-120 | C-40 |
| T1c-4325 | I-3 | II-121 | C-40 |
| T1c-4326 | I-3 | II-122 | C-40 |
| T1c-4327 | I-3 | II-123 | C-40 |
| T1c-4328 | I-3 | II-124 | C-40 |
| T1c-4329 | I-3 | II-125 | C-40 |
| T1c-4330 | I-3 | II-126 | C-40 |
| T1c-4331 | I-3 | II-127 | C-40 |
| T1c-4332 | I-3 | II-128 | C-40 |
| T1c-4333 | I-3 | II-129 | C-40 |
| T1c-4334 | I-3 | II-130 | C-40 |
| T1c-4335 | I-3 | II-131 | C-40 |
| T1c-4336 | I-3 | II-132 | C-40 |
| T1c-4337 | I-3 | II-133 | C-40 |
| T1c-4338 | I-3 | II-134 | C-40 |
| T1c-4339 | I-3 | II-135 | C-40 |
| T1c-4340 | I-3 | II-136 | C-40 |
| T1c-4341 | I-3 | II-137 | C-40 |
| T1c-4342 | I-3 | II-138 | C-40 |
| T1c-4343 | I-3 | II-139 | C-40 |
| T1c-4344 | I-3 | II-140 | C-40 |
| T1c-4345 | I-3 | II-141 | C-40 |
| T1c-4346 | I-3 | II-142 | C-40 |
| T1c-4347 | I-3 | II-143 | C-40 |
| T1c-4348 | I-3 | II-144 | C-40 |
| T1c-4349 | I-3 | II-145 | C-40 |
| T1c-4350 | I-3 | II-146 | C-40 |
| T1c-4351 | I-3 | II-147 | C-40 |
| T1c-4352 | I-3 | II-148 | C-40 |
| T1c-4353 | I-3 | II-149 | C-40 |
| T1c-4354 | I-3 | II-150 | C-40 |
| T1c-4355 | I-3 | II-151 | C-40 |
| T1c-4356 | I-3 | II-152 | C-40 |
| T1c-4357 | I-3 | II-153 | C-40 |
| T1c-4358 | I-3 | II-154 | C-40 |
| T1c-4359 | I-3 | II-155 | C-40 |
| T1c-4360 | I-3 | II-156 | C-40 |
| T1c-4361 | I-3 | II-157 | C-40 |
| T1c-4362 | I-3 | II-158 | C-40 |
| T1c-4363 | I-3 | II-159 | C-40 |
| T1c-4364 | I-3 | II-160 | C-40 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-4365 | I-3 | II-161 | C-40 |
| T1c-4366 | I-3 | II-162 | C-40 |
| T1c-4367 | I-3 | II-163 | C-40 |
| T1c-4368 | I-3 | II-164 | C-40 |
| T1c-4369 | I-3 | II-165 | C-40 |
| T1c-4370 | I-3 | II-166 | C-40 |
| T1c-4371 | I-3 | II-167 | C-40 |
| T1c-4372 | I-3 | II-168 | C-40 |
| T1c-4373 | I-3 | II-169 | C-40 |
| T1c-4374 | I-3 | II-170 | C-40 |
| T1c-4375 | I-3 | II-171 | C-40 |
| T1c-4376 | I-3 | II-172 | C-40 |
| T1c-4377 | I-3 | II-173 | C-40 |
| T1c-4378 | I-3 | II-174 | C-40 |
| T1c-4379 | I-3 | II-175 | C-40 |
| T1c-4380 | I-3 | II-176 | C-40 |
| T1c-4381 | I-3 | II-177 | C-40 |
| T1c-4382 | I-3 | II-178 | C-40 |
| T1c-4383 | I-3 | II-179 | C-40 |
| T1c-4384 | I-3 | II-180 | C-40 |
| T1c-4385 | I-3 | II-181 | C-40 |
| T1c-4386 | I-3 | II-182 | C-40 |
| T1c-4387 | I-3 | II-183 | C-40 |
| T1c-4388 | I-3 | II-184 | C-40 |
| T1c-4389 | I-3 | II-185 | C-40 |
| T1c-4390 | I-3 | II-186 | C-40 |
| T1c-4391 | I-3 | II-187 | C-40 |
| T1c-4392 | I-3 | II-188 | C-40 |
| T1c-4393 | I-3 | II-189 | C-40 |
| T1c-4394 | I-3 | II-190 | C-40 |
| T1c-4395 | I-3 | II-191 | C-40 |
| T1c-4396 | I-3 | II-192 | C-40 |
| T1c-4397 | I-3 | II-193 | C-40 |
| T1c-4398 | I-3 | II-194 | C-40 |
| T1c-4399 | I-3 | II-195 | C-40 |
| T1c-4400 | I-3 | II-196 | C-40 |
| T1c-4401 | I-3 | II-197 | C-40 |
| T1c-4402 | I-3 | II-198 | C-40 |
| T1c-4403 | I-3 | II-199 | C-40 |
| T1c-4404 | I-3 | II-200 | C-40 |
| T1c-4405 | I-3 | II-201 | C-40 |
| T1c-4406 | I-3 | II-202 | C-40 |
| T1c-4407 | I-3 | II-203 | C-40 |
| T1c-4408 | I-3 | II-91 | C-41 |
| T1c-4409 | I-3 | II-92 | C-41 |
| T1c-4410 | I-3 | II-93 | C-41 |
| T1c-4411 | I-3 | II-94 | C-41 |
| T1c-4412 | I-3 | II-95 | C-41 |
| T1c-4413 | I-3 | II-96 | C-41 |
| T1c-4414 | I-3 | II-97 | C-41 |
| T1c-4415 | I-3 | II-98 | C-41 |
| T1c-4416 | I-3 | II-99 | C-41 |
| T1c-4417 | I-3 | II-100 | C-41 |
| T1c-4418 | I-3 | II-101 | C-41 |
| T1c-4419 | I-3 | II-102 | C-41 |
| T1c-4420 | I-3 | II-103 | C-41 |
| T1c-4421 | I-3 | II-104 | C-41 |
| T1c-4422 | I-3 | II-105 | C-41 |
| T1c-4423 | I-3 | II-106 | C-41 |
| T1c-4424 | I-3 | II-107 | C-41 |
| T1c-4425 | I-3 | II-108 | C-41 |
| T1c-4426 | I-3 | II-109 | C-41 |
| T1c-4427 | I-3 | II-110 | C-41 |
| T1c-4428 | I-3 | II-111 | C-41 |
| T1c-4429 | I-3 | II-112 | C-41 |
| T1c-4430 | I-3 | II-113 | C-41 |
| T1c-4431 | I-3 | II-114 | C-41 |
| T1c-4432 | I-3 | II-115 | C-41 |
| T1c-4433 | I-3 | II-116 | C-41 |
| T1c-4434 | I-3 | II-117 | C-41 |
| T1c-4435 | I-3 | II-118 | C-41 |
| T1c-4436 | I-3 | II-119 | C-41 |
| T1c-4437 | I-3 | II-120 | C-41 |
| T1c-4438 | I-3 | II-121 | C-41 |
| T1c-4439 | I-3 | II-122 | C-41 |
| T1c-4440 | I-3 | II-123 | C-41 |
| T1c-4441 | I-3 | II-124 | C-41 |
| T1c-4442 | I-3 | II-125 | C-41 |
| T1c-4443 | I-3 | II-126 | C-41 |
| T1c-4444 | I-3 | II-127 | C-41 |
| T1c-4445 | I-3 | II-128 | C-41 |
| T1c-4446 | I-3 | II-129 | C-41 |
| T1c-4447 | I-3 | II-130 | C-41 |
| T1c-4448 | I-3 | II-131 | C-41 |
| T1c-4449 | I-3 | II-132 | C-41 |
| T1c-4450 | I-3 | II-133 | C-41 |
| T1c-4451 | I-3 | II-134 | C-41 |
| T1c-4452 | I-3 | II-135 | C-41 |
| T1c-4453 | I-3 | II-136 | C-41 |
| T1c-4454 | I-3 | II-137 | C-41 |
| T1c-4455 | I-3 | II-138 | C-41 |
| T1c-4456 | I-3 | II-139 | C-41 |
| T1c-4457 | I-3 | II-140 | C-41 |
| T1c-4458 | I-3 | II-141 | C-41 |
| T1c-4459 | I-3 | II-142 | C-41 |
| T1c-4460 | I-3 | II-143 | C-41 |
| T1c-4461 | I-3 | II-144 | C-41 |
| T1c-4462 | I-3 | II-145 | C-41 |
| T1c-4463 | I-3 | II-146 | C-41 |
| T1c-4464 | I-3 | II-147 | C-41 |
| T1c-4465 | I-3 | II-148 | C-41 |
| T1c-4466 | I-3 | II-149 | C-41 |
| T1c-4467 | I-3 | II-150 | C-41 |
| T1c-4468 | I-3 | II-151 | C-41 |
| T1c-4469 | I-3 | II-152 | C-41 |
| T1c-4470 | I-3 | II-153 | C-41 |
| T1c-4471 | I-3 | II-154 | C-41 |
| T1c-4472 | I-3 | II-155 | C-41 |
| T1c-4473 | I-3 | II-156 | C-41 |
| T1c-4474 | I-3 | II-157 | C-41 |
| T1c-4475 | I-3 | II-158 | C-41 |
| T1c-4476 | I-3 | II-159 | C-41 |
| T1c-4477 | I-3 | II-160 | C-41 |
| T1c-4478 | I-3 | II-161 | C-41 |
| T1c-4479 | I-3 | II-162 | C-41 |
| T1c-4480 | I-3 | II-163 | C-41 |
| T1c-4481 | I-3 | II-164 | C-41 |
| T1c-4482 | I-3 | II-165 | C-41 |
| T1c-4483 | I-3 | II-166 | C-41 |
| T1c-4484 | I-3 | II-167 | C-41 |
| T1c-4485 | I-3 | II-168 | C-41 |
| T1c-4486 | I-3 | II-169 | C-41 |
| T1c-4487 | I-3 | II-170 | C-41 |
| T1c-4488 | I-3 | II-171 | C-41 |
| T1c-4489 | I-3 | II-172 | C-41 |
| T1c-4490 | I-3 | II-173 | C-41 |
| T1c-4491 | I-3 | II-174 | C-41 |
| T1c-4492 | I-3 | II-175 | C-41 |
| T1c-4493 | I-3 | II-176 | C-41 |
| T1c-4494 | I-3 | II-177 | C-41 |
| T1c-4495 | I-3 | II-178 | C-41 |
| T1c-4496 | I-3 | II-179 | C-41 |
| T1c-4497 | I-3 | II-180 | C-41 |
| T1c-4498 | I-3 | II-181 | C-41 |
| T1c-4499 | I-3 | II-182 | C-41 |
| T1c-4500 | I-3 | II-183 | C-41 |
| T1c-4501 | I-3 | II-184 | C-41 |
| T1c-4502 | I-3 | II-185 | C-41 |
| T1c-4503 | I-3 | II-186 | C-41 |
| T1c-4504 | I-3 | II-187 | C-41 |
| T1c-4505 | I-3 | II-188 | C-41 |
| T1c-4506 | I-3 | II-189 | C-41 |
| T1c-4507 | I-3 | II-190 | C-41 |
| T1c-4508 | I-3 | II-191 | C-41 |
| T1c-4509 | I-3 | II-192 | C-41 |
| T1c-4510 | I-3 | II-193 | C-41 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-4511 | I-3 | II-194 | C-41 |
| T1c-4512 | I-3 | II-195 | C-41 |
| T1c-4513 | I-3 | II-196 | C-41 |
| T1c-4514 | I-3 | II-197 | C-41 |
| T1c-4515 | I-3 | II-198 | C-41 |
| T1c-4516 | I-3 | II-199 | C-41 |
| T1c-4517 | I-3 | II-200 | C-41 |
| T1c-4518 | I-3 | II-201 | C-41 |
| T1c-4519 | I-3 | II-202 | C-41 |
| T1c-4520 | I-3 | II-203 | C-41 |
| T1c-4521 | I-3 | II-91 | C-42 |
| T1c-4522 | I-3 | II-92 | C-42 |
| T1c-4523 | I-3 | II-93 | C-42 |
| T1c-4524 | I-3 | II-94 | C-42 |
| T1c-4525 | I-3 | II-95 | C-42 |
| T1c-4526 | I-3 | II-96 | C-42 |
| T1c-4527 | I-3 | II-97 | C-42 |
| T1c-4528 | I-3 | II-98 | C-42 |
| T1c-4529 | I-3 | II-99 | C-42 |
| T1c-4530 | I-3 | II-100 | C-42 |
| T1c-4531 | I-3 | II-101 | C-42 |
| T1c-4532 | I-3 | II-102 | C-42 |
| T1c-4533 | I-3 | II-103 | C-42 |
| T1c-4534 | I-3 | II-104 | C-42 |
| T1c-4535 | I-3 | II-105 | C-42 |
| T1c-4536 | I-3 | II-106 | C-42 |
| T1c-4537 | I-3 | II-107 | C-42 |
| T1c-4538 | I-3 | II-108 | C-42 |
| T1c-4539 | I-3 | II-109 | C-42 |
| T1c-4540 | I-3 | II-110 | C-42 |
| T1c-4541 | I-3 | II-111 | C-42 |
| T1c-4542 | I-3 | II-112 | C-42 |
| T1c-4543 | I-3 | II-113 | C-42 |
| T1c-4544 | I-3 | II-114 | C-42 |
| T1c-4545 | I-3 | II-115 | C-42 |
| T1c-4546 | I-3 | II-116 | C-42 |
| T1c-4547 | I-3 | II-117 | C-42 |
| T1c-4548 | I-3 | II-118 | C-42 |
| T1c-4549 | I-3 | II-119 | C-42 |
| T1c-4550 | I-3 | II-120 | C-42 |
| T1c-4551 | I-3 | II-121 | C-42 |
| T1c-4552 | I-3 | II-122 | C-42 |
| T1c-4553 | I-3 | II-123 | C-42 |
| T1c-4554 | I-3 | II-124 | C-42 |
| T1c-4555 | I-3 | II-125 | C-42 |
| T1c-4556 | I-3 | II-126 | C-42 |
| T1c-4557 | I-3 | II-127 | C-42 |
| T1c-4558 | I-3 | II-128 | C-42 |
| T1c-4559 | I-3 | II-129 | C-42 |
| T1c-4560 | I-3 | II-130 | C-42 |
| T1c-4561 | I-3 | II-131 | C-42 |
| T1c-4562 | I-3 | II-132 | C-42 |
| T1c-4563 | I-3 | II-133 | C-42 |
| T1c-4564 | I-3 | II-134 | C-42 |
| T1c-4565 | I-3 | II-135 | C-42 |
| T1c-4566 | I-3 | II-136 | C-42 |
| T1c-4567 | I-3 | II-137 | C-42 |
| T1c-4568 | I-3 | II-138 | C-42 |
| T1c-4569 | I-3 | II-139 | C-42 |
| T1c-4570 | I-3 | II-140 | C-42 |
| T1c-4571 | I-3 | II-141 | C-42 |
| T1c-4572 | I-3 | II-142 | C-42 |
| T1c-4573 | I-3 | II-143 | C-42 |
| T1c-4574 | I-3 | II-144 | C-42 |
| T1c-4575 | I-3 | II-145 | C-42 |
| T1c-4576 | I-3 | II-146 | C-42 |
| T1c-4577 | I-3 | II-147 | C-42 |
| T1c-4578 | I-3 | II-148 | C-42 |
| T1c-4579 | I-3 | II-149 | C-42 |
| T1c-4580 | I-3 | II-150 | C-42 |
| T1c-4581 | I-3 | II-151 | C-42 |
| T1c-4582 | I-3 | II-152 | C-42 |
| T1c-4583 | I-3 | II-153 | C-42 |
| T1c-4584 | I-3 | II-154 | C-42 |
| T1c-4585 | I-3 | II-155 | C-42 |
| T1c-4586 | I-3 | II-156 | C-42 |
| T1c-4587 | I-3 | II-157 | C-42 |
| T1c-4588 | I-3 | II-158 | C-42 |
| T1c-4589 | I-3 | II-159 | C-42 |
| T1c-4590 | I-3 | II-160 | C-42 |
| T1c-4591 | I-3 | II-161 | C-42 |
| T1c-4592 | I-3 | II-162 | C-42 |
| T1c-4593 | I-3 | II-163 | C-42 |
| T1c-4594 | I-3 | II-164 | C-42 |
| T1c-4595 | I-3 | II-165 | C-42 |
| T1c-4596 | I-3 | II-166 | C-42 |
| T1c-4597 | I-3 | II-167 | C-42 |
| T1c-4598 | I-3 | II-168 | C-42 |
| T1c-4599 | I-3 | II-169 | C-42 |
| T1c-4600 | I-3 | II-170 | C-42 |
| T1c-4601 | I-3 | II-171 | C-42 |
| T1c-4602 | I-3 | II-172 | C-42 |
| T1c-4603 | I-3 | II-173 | C-42 |
| T1c-4604 | I-3 | II-174 | C-42 |
| T1c-4605 | I-3 | II-175 | C-42 |
| T1c-4606 | I-3 | II-176 | C-42 |
| T1c-4607 | I-3 | II-177 | C-42 |
| T1c-4608 | I-3 | II-178 | C-42 |
| T1c-4609 | I-3 | II-179 | C-42 |
| T1c-4610 | I-3 | II-180 | C-42 |
| T1c-4611 | I-3 | II-181 | C-42 |
| T1c-4612 | I-3 | II-182 | C-42 |
| T1c-4613 | I-3 | II-183 | C-42 |
| T1c-4614 | I-3 | II-184 | C-42 |
| T1c-4615 | I-3 | II-185 | C-42 |
| T1c-4616 | I-3 | II-186 | C-42 |
| T1c-4617 | I-3 | II-187 | C-42 |
| T1c-4618 | I-3 | II-188 | C-42 |
| T1c-4619 | I-3 | II-189 | C-42 |
| T1c-4620 | I-3 | II-190 | C-42 |
| T1c-4621 | I-3 | II-191 | C-42 |
| T1c-4622 | I-3 | II-192 | C-42 |
| T1c-4623 | I-3 | II-193 | C-42 |
| T1c-4624 | I-3 | II-194 | C-42 |
| T1c-4625 | I-3 | II-195 | C-42 |
| T1c-4626 | I-3 | II-196 | C-42 |
| T1c-4627 | I-3 | II-197 | C-42 |
| T1c-4628 | I-3 | II-198 | C-42 |
| T1c-4629 | I-3 | II-199 | C-42 |
| T1c-4630 | I-3 | II-200 | C-42 |
| T1c-4631 | I-3 | II-201 | C-42 |
| T1c-4632 | I-3 | II-202 | C-42 |
| T1c-4633 | I-3 | II-203 | C-42 |
| T1c-4634 | I-3 | II-91 | C-43 |
| T1c-4635 | I-3 | II-92 | C-43 |
| T1c-4636 | I-3 | II-93 | C-43 |
| T1c-4637 | I-3 | II-94 | C-43 |
| T1c-4638 | I-3 | II-95 | C-43 |
| T1c-4639 | I-3 | II-96 | C-43 |
| T1c-4640 | I-3 | II-97 | C-43 |
| T1c-4641 | I-3 | II-98 | C-43 |
| T1c-4642 | I-3 | II-99 | C-43 |
| T1c-4643 | I-3 | II-100 | C-43 |
| T1c-4644 | I-3 | II-101 | C-43 |
| T1c-4645 | I-3 | II-102 | C-43 |
| T1c-4646 | I-3 | II-103 | C-43 |
| T1c-4647 | I-3 | II-104 | C-43 |
| T1c-4648 | I-3 | II-105 | C-43 |
| T1c-4649 | I-3 | II-106 | C-43 |
| T1c-4650 | I-3 | II-107 | C-43 |
| T1c-4651 | I-3 | II-108 | C-43 |
| T1c-4652 | I-3 | II-109 | C-43 |
| T1c-4653 | I-3 | II-110 | C-43 |
| T1c-4654 | I-3 | II-111 | C-43 |
| T1c-4655 | I-3 | II-112 | C-43 |
| T1c-4656 | I-3 | II-113 | C-43 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-4657 | I-3 | II-114 | C-43 |
| T1c-4658 | I-3 | II-115 | C-43 |
| T1c-4659 | I-3 | II-116 | C-43 |
| T1c-4660 | I-3 | II-117 | C-43 |
| T1c-4661 | I-3 | II-118 | C-43 |
| T1c-4662 | I-3 | II-119 | C-43 |
| T1c-4663 | I-3 | II-120 | C-43 |
| T1c-4664 | I-3 | II-121 | C-43 |
| T1c-4665 | I-3 | II-122 | C-43 |
| T1c-4666 | I-3 | II-123 | C-43 |
| T1c-4667 | I-3 | II-124 | C-43 |
| T1c-4668 | I-3 | II-125 | C-43 |
| T1c-4669 | I-3 | II-126 | C-43 |
| T1c-4670 | I-3 | II-127 | C-43 |
| T1c-4671 | I-3 | II-128 | C-43 |
| T1c-4672 | I-3 | II-129 | C-43 |
| T1c-4673 | I-3 | II-130 | C-43 |
| T1c-4674 | I-3 | II-131 | C-43 |
| T1c-4675 | I-3 | II-132 | C-43 |
| T1c-4676 | I-3 | II-133 | C-43 |
| T1c-4677 | I-3 | II-134 | C-43 |
| T1c-4678 | I-3 | II-135 | C-43 |
| T1c-4679 | I-3 | II-136 | C-43 |
| T1c-4680 | I-3 | II-137 | C-43 |
| T1c-4681 | I-3 | II-138 | C-43 |
| T1c-4682 | I-3 | II-139 | C-43 |
| T1c-4683 | I-3 | II-140 | C-43 |
| T1c-4684 | I-3 | II-141 | C-43 |
| T1c-4685 | I-3 | II-142 | C-43 |
| T1c-4686 | I-3 | II-143 | C-43 |
| T1c-4687 | I-3 | II-144 | C-43 |
| T1c-4688 | I-3 | II-145 | C-43 |
| T1c-4689 | I-3 | II-146 | C-43 |
| T1c-4690 | I-3 | II-147 | C-43 |
| T1c-4691 | I-3 | II-148 | C-43 |
| T1c-4692 | I-3 | II-149 | C-43 |
| T1c-4693 | I-3 | II-150 | C-43 |
| T1c-4694 | I-3 | II-151 | C-43 |
| T1c-4695 | I-3 | II-152 | C-43 |
| T1c-4696 | I-3 | II-153 | C-43 |
| T1c-4697 | I-3 | II-154 | C-43 |
| T1c-4698 | I-3 | II-155 | C-43 |
| T1c-4699 | I-3 | II-156 | C-43 |
| T1c-4700 | I-3 | II-157 | C-43 |
| T1c-4701 | I-3 | II-158 | C-43 |
| T1c-4702 | I-3 | II-159 | C-43 |
| T1c-4703 | I-3 | II-160 | C-43 |
| T1c-4704 | I-3 | II-161 | C-43 |
| T1c-4705 | I-3 | II-162 | C-43 |
| T1c-4706 | I-3 | II-163 | C-43 |
| T1c-4707 | I-3 | II-164 | C-43 |
| T1c-4708 | I-3 | II-165 | C-43 |
| T1c-4709 | I-3 | II-166 | C-43 |
| T1c-4710 | I-3 | II-167 | C-43 |
| T1c-4711 | I-3 | II-168 | C-43 |
| T1c-4712 | I-3 | II-169 | C-43 |
| T1c-4713 | I-3 | II-170 | C-43 |
| T1c-4714 | I-3 | II-171 | C-43 |
| T1c-4715 | I-3 | II-172 | C-43 |
| T1c-4716 | I-3 | II-173 | C-43 |
| T1c-4717 | I-3 | II-174 | C-43 |
| T1c-4718 | I-3 | II-175 | C-43 |
| T1c-4719 | I-3 | II-176 | C-43 |
| T1c-4720 | I-3 | II-177 | C-43 |
| T1c-4721 | I-3 | II-178 | C-43 |
| T1c-4722 | I-3 | II-179 | C-43 |
| T1c-4723 | I-3 | II-180 | C-43 |
| T1c-4724 | I-3 | II-181 | C-43 |
| T1c-4725 | I-3 | II-182 | C-43 |
| T1c-4726 | I-3 | II-183 | C-43 |
| T1c-4727 | I-3 | II-184 | C-43 |
| T1c-4728 | I-3 | II-185 | C-43 |
| T1c-4729 | I-3 | II-186 | C-43 |
| T1c-4730 | I-3 | II-187 | C-43 |
| T1c-4731 | I-3 | II-188 | C-43 |
| T1c-4732 | I-3 | II-189 | C-43 |
| T1c-4733 | I-3 | II-190 | C-43 |
| T1c-4734 | I-3 | II-191 | C-43 |
| T1c-4735 | I-3 | II-192 | C-43 |
| T1c-4736 | I-3 | II-193 | C-43 |
| T1c-4737 | I-3 | II-194 | C-43 |
| T1c-4738 | I-3 | II-195 | C-43 |
| T1c-4739 | I-3 | II-196 | C-43 |
| T1c-4740 | I-3 | II-197 | C-43 |
| T1c-4741 | I-3 | II-198 | C-43 |
| T1c-4742 | I-3 | II-199 | C-43 |
| T1c-4743 | I-3 | II-200 | C-43 |
| T1c-4744 | I-3 | II-201 | C-43 |
| T1c-4745 | I-3 | II-202 | C-43 |
| T1c-4746 | I-3 | II-203 | C-43 |
| T1c-4747 | I-3 | II-91 | C-44 |
| T1c-4748 | I-3 | II-92 | C-44 |
| T1c-4749 | I-3 | II-93 | C-44 |
| T1c-4750 | I-3 | II-94 | C-44 |
| T1c-4751 | I-3 | II-95 | C-44 |
| T1c-4752 | I-3 | II-96 | C-44 |
| T1c-4753 | I-3 | II-97 | C-44 |
| T1c-4754 | I-3 | II-98 | C-44 |
| T1c-4755 | I-3 | II-99 | C-44 |
| T1c-4756 | I-3 | II-100 | C-44 |
| T1c-4757 | I-3 | II-101 | C-44 |
| T1c-4758 | I-3 | II-102 | C-44 |
| T1c-4759 | I-3 | II-103 | C-44 |
| T1c-4760 | I-3 | II-104 | C-44 |
| T1c-4761 | I-3 | II-105 | C-44 |
| T1c-4762 | I-3 | II-106 | C-44 |
| T1c-4763 | I-3 | II-107 | C-44 |
| T1c-4764 | I-3 | II-108 | C-44 |
| T1c-4765 | I-3 | II-109 | C-44 |
| T1c-4766 | I-3 | II-110 | C-44 |
| T1c-4767 | I-3 | II-111 | C-44 |
| T1c-4768 | I-3 | II-112 | C-44 |
| T1c-4769 | I-3 | II-113 | C-44 |
| T1c-4770 | I-3 | II-114 | C-44 |
| T1c-4771 | I-3 | II-115 | C-44 |
| T1c-4772 | I-3 | II-116 | C-44 |
| T1c-4773 | I-3 | II-117 | C-44 |
| T1c-4774 | I-3 | II-118 | C-44 |
| T1c-4775 | I-3 | II-119 | C-44 |
| T1c-4776 | I-3 | II-120 | C-44 |
| T1c-4777 | I-3 | II-121 | C-44 |
| T1c-4778 | I-3 | II-122 | C-44 |
| T1c-4779 | I-3 | II-123 | C-44 |
| T1c-4780 | I-3 | II-124 | C-44 |
| T1c-4781 | I-3 | II-125 | C-44 |
| T1c-4782 | I-3 | II-126 | C-44 |
| T1c-4783 | I-3 | II-127 | C-44 |
| T1c-4784 | I-3 | II-128 | C-44 |
| T1c-4785 | I-3 | II-129 | C-44 |
| T1c-4786 | I-3 | II-130 | C-44 |
| T1c-4787 | I-3 | II-131 | C-44 |
| T1c-4788 | I-3 | II-132 | C-44 |
| T1c-4789 | I-3 | II-133 | C-44 |
| T1c-4790 | I-3 | II-134 | C-44 |
| T1c-4791 | I-3 | II-135 | C-44 |
| T1c-4792 | I-3 | II-136 | C-44 |
| T1c-4793 | I-3 | II-137 | C-44 |
| T1c-4794 | I-3 | II-138 | C-44 |
| T1c-4795 | I-3 | II-139 | C-44 |
| T1c-4796 | I-3 | II-140 | C-44 |
| T1c-4797 | I-3 | II-141 | C-44 |
| T1c-4798 | I-3 | II-142 | C-44 |
| T1c-4799 | I-3 | II-143 | C-44 |
| T1c-4800 | I-3 | II-144 | C-44 |
| T1c-4801 | I-3 | II-145 | C-44 |
| T1c-4802 | I-3 | II-146 | C-44 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-4803 | I-3 | II-147 | C-44 |
| T1c-4804 | I-3 | II-148 | C-44 |
| T1c-4805 | I-3 | II-149 | C-44 |
| T1c-4806 | I-3 | II-150 | C-44 |
| T1c-4807 | I-3 | II-151 | C-44 |
| T1c-4808 | I-3 | II-152 | C-44 |
| T1c-4809 | I-3 | II-153 | C-44 |
| T1c-4810 | I-3 | II-154 | C-44 |
| T1c-4811 | I-3 | II-155 | C-44 |
| T1c-4812 | I-3 | II-156 | C-44 |
| T1c-4813 | I-3 | II-157 | C-44 |
| T1c-4814 | I-3 | II-158 | C-44 |
| T1c-4815 | I-3 | II-159 | C-44 |
| T1c-4816 | I-3 | II-160 | C-44 |
| T1c-4817 | I-3 | II-161 | C-44 |
| T1c-4818 | I-3 | II-162 | C-44 |
| T1c-4819 | I-3 | II-163 | C-44 |
| T1c-4820 | I-3 | II-164 | C-44 |
| T1c-4821 | I-3 | II-165 | C-44 |
| T1c-4822 | I-3 | II-166 | C-44 |
| T1c-4823 | I-3 | II-167 | C-44 |
| T1c-4824 | I-3 | II-168 | C-44 |
| T1c-4825 | I-3 | II-169 | C-44 |
| T1c-4826 | I-3 | II-170 | C-44 |
| T1c-4827 | I-3 | II-171 | C-44 |
| T1c-4828 | I-3 | II-172 | C-44 |
| T1c-4829 | I-3 | II-173 | C-44 |
| T1c-4830 | I-3 | II-174 | C-44 |
| T1c-4831 | I-3 | II-175 | C-44 |
| T1c-4832 | I-3 | II-176 | C-44 |
| T1c-4833 | I-3 | II-177 | C-44 |
| T1c-4834 | I-3 | II-178 | C-44 |
| T1c-4835 | I-3 | II-179 | C-44 |
| T1c-4836 | I-3 | II-180 | C-44 |
| T1c-4837 | I-3 | II-181 | C-44 |
| T1c-4838 | I-3 | II-182 | C-44 |
| T1c-4839 | I-3 | II-183 | C-44 |
| T1c-4840 | I-3 | II-184 | C-44 |
| T1c-4841 | I-3 | II-185 | C-44 |
| T1c-4842 | I-3 | II-186 | C-44 |
| T1c-4843 | I-3 | II-187 | C-44 |
| T1c-4844 | I-3 | II-188 | C-44 |
| T1c-4845 | I-3 | II-189 | C-44 |
| T1c-4846 | I-3 | II-190 | C-44 |
| T1c-4847 | I-3 | II-191 | C-44 |
| T1c-4848 | I-3 | II-192 | C-44 |
| T1c-4849 | I-3 | II-193 | C-44 |
| T1c-4850 | I-3 | II-194 | C-44 |
| T1c-4851 | I-3 | II-195 | C-44 |
| T1c-4852 | I-3 | II-196 | C-44 |
| T1c-4853 | I-3 | II-197 | C-44 |
| T1c-4854 | I-3 | II-198 | C-44 |
| T1c-4855 | I-3 | II-199 | C-44 |
| T1c-4856 | I-3 | II-200 | C-44 |
| T1c-4857 | I-3 | II-201 | C-44 |
| T1c-4858 | I-3 | II-202 | C-44 |
| T1c-4859 | I-3 | II-203 | C-44 |
| T1c-4860 | I-3 | II-91 | C-45 |
| T1c-4861 | I-3 | II-92 | C-45 |
| T1c-4862 | I-3 | II-93 | C-45 |
| T1c-4863 | I-3 | II-94 | C-45 |
| T1c-4864 | I-3 | II-95 | C-45 |
| T1c-4865 | I-3 | II-96 | C-45 |
| T1c-4866 | I-3 | II-97 | C-45 |
| T1c-4867 | I-3 | II-98 | C-45 |
| T1c-4868 | I-3 | II-99 | C-45 |
| T1c-4869 | I-3 | II-100 | C-45 |
| T1c-4870 | I-3 | II-101 | C-45 |
| T1c-4871 | I-3 | II-102 | C-45 |
| T1c-4872 | I-3 | II-103 | C-45 |
| T1c-4873 | I-3 | II-104 | C-45 |
| T1c-4874 | I-3 | II-105 | C-45 |
| T1c-4875 | I-3 | II-106 | C-45 |
| T1c-4876 | I-3 | II-107 | C-45 |
| T1c-4877 | I-3 | II-108 | C-45 |
| T1c-4878 | I-3 | II-109 | C-45 |
| T1c-4879 | I-3 | II-110 | C-45 |
| T1c-4880 | I-3 | II-111 | C-45 |
| T1c-4881 | I-3 | II-112 | C-45 |
| T1c-4882 | I-3 | II-113 | C-45 |
| T1c-4883 | I-3 | II-114 | C-45 |
| T1c-4884 | I-3 | II-115 | C-45 |
| T1c-4885 | I-3 | II-116 | C-45 |
| T1c-4886 | I-3 | II-117 | C-45 |
| T1c-4887 | I-3 | II-118 | C-45 |
| T1c-4888 | I-3 | II-119 | C-45 |
| T1c-4889 | I-3 | II-120 | C-45 |
| T1c-4890 | I-3 | II-121 | C-45 |
| T1c-4891 | I-3 | II-122 | C-45 |
| T1c-4892 | I-3 | II-123 | C-45 |
| T1c-4893 | I-3 | II-124 | C-45 |
| T1c-4894 | I-3 | II-125 | C-45 |
| T1c-4895 | I-3 | II-126 | C-45 |
| T1c-4896 | I-3 | II-127 | C-45 |
| T1c-4897 | I-3 | II-128 | C-45 |
| T1c-4898 | I-3 | II-129 | C-45 |
| T1c-4899 | I-3 | II-130 | C-45 |
| T1c-4900 | I-3 | II-131 | C-45 |
| T1c-4901 | I-3 | II-132 | C-45 |
| T1c-4902 | I-3 | II-133 | C-45 |
| T1c-4903 | I-3 | II-134 | C-45 |
| T1c-4904 | I-3 | II-135 | C-45 |
| T1c-4905 | I-3 | II-136 | C-45 |
| T1c-4906 | I-3 | II-137 | C-45 |
| T1c-4907 | I-3 | II-138 | C-45 |
| T1c-4908 | I-3 | II-139 | C-45 |
| T1c-4909 | I-3 | II-140 | C-45 |
| T1c-4910 | I-3 | II-141 | C-45 |
| T1c-4911 | I-3 | II-142 | C-45 |
| T1c-4912 | I-3 | II-143 | C-45 |
| T1c-4913 | I-3 | II-144 | C-45 |
| T1c-4914 | I-3 | II-145 | C-45 |
| T1c-4915 | I-3 | II-146 | C-45 |
| T1c-4916 | I-3 | II-147 | C-45 |
| T1c-4917 | I-3 | II-148 | C-45 |
| T1c-4918 | I-3 | II-149 | C-45 |
| T1c-4919 | I-3 | II-150 | C-45 |
| T1c-4920 | I-3 | II-151 | C-45 |
| T1c-4921 | I-3 | II-152 | C-45 |
| T1c-4922 | I-3 | II-153 | C-45 |
| T1c-4923 | I-3 | II-154 | C-45 |
| T1c-4924 | I-3 | II-155 | C-45 |
| T1c-4925 | I-3 | II-156 | C-45 |
| T1c-4926 | I-3 | II-157 | C-45 |
| T1c-4927 | I-3 | II-158 | C-45 |
| T1c-4928 | I-3 | II-159 | C-45 |
| T1c-4929 | I-3 | II-160 | C-45 |
| T1c-4930 | I-3 | II-161 | C-45 |
| T1c-4931 | I-3 | II-162 | C-45 |
| T1c-4932 | I-3 | II-163 | C-45 |
| T1c-4933 | I-3 | II-164 | C-45 |
| T1c-4934 | I-3 | II-165 | C-45 |
| T1c-4935 | I-3 | II-166 | C-45 |
| T1c-4936 | I-3 | II-167 | C-45 |
| T1c-4937 | I-3 | II-168 | C-45 |
| T1c-4938 | I-3 | II-169 | C-45 |
| T1c-4939 | I-3 | II-170 | C-45 |
| T1c-4940 | I-3 | II-171 | C-45 |
| T1c-4941 | I-3 | II-172 | C-45 |
| T1c-4942 | I-3 | II-173 | C-45 |
| T1c-4943 | I-3 | II-174 | C-45 |
| T1c-4944 | I-3 | II-175 | C-45 |
| T1c-4945 | I-3 | II-176 | C-45 |
| T1c-4946 | I-3 | II-177 | C-45 |
| T1c-4947 | I-3 | II-178 | C-45 |
| T1c-4948 | I-3 | II-179 | C-45 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-4949 | I-3 | II-180 | C-45 |
| T1c-4950 | I-3 | II-181 | C-45 |
| T1c-4951 | I-3 | II-182 | C-45 |
| T1c-4952 | I-3 | II-183 | C-45 |
| T1c-4953 | I-3 | II-184 | C-45 |
| T1c-4954 | I-3 | II-185 | C-45 |
| T1c-4955 | I-3 | II-186 | C-45 |
| T1c-4956 | I-3 | II-187 | C-45 |
| T1c-4957 | I-3 | II-188 | C-45 |
| T1c-4958 | I-3 | II-189 | C-45 |
| T1c-4959 | I-3 | II-190 | C-45 |
| T1c-4960 | I-3 | II-191 | C-45 |
| T1c-4961 | I-3 | II-192 | C-45 |
| T1c-4962 | I-3 | II-193 | C-45 |
| T1c-4963 | I-3 | II-194 | C-45 |
| T1c-4964 | I-3 | II-195 | C-45 |
| T1c-4965 | I-3 | II-196 | C-45 |
| T1c-4966 | I-3 | II-197 | C-45 |
| T1c-4967 | I-3 | II-198 | C-45 |
| T1c-4968 | I-3 | II-199 | C-45 |
| T1c-4969 | I-3 | II-200 | C-45 |
| T1c-4970 | I-3 | II-201 | C-45 |
| T1c-4971 | I-3 | II-202 | C-45 |
| T1c-4972 | I-3 | II-203 | C-45 |
| T1c-4973 | I-3 | II-91 | C-46 |
| T1c-4974 | I-3 | II-92 | C-46 |
| T1c-4975 | I-3 | II-93 | C-46 |
| T1c-4976 | I-3 | II-94 | C-46 |
| T1c-4977 | I-3 | II-95 | C-46 |
| T1c-4978 | I-3 | II-96 | C-46 |
| T1c-4979 | I-3 | II-97 | C-46 |
| T1c-4980 | I-3 | II-98 | C-46 |
| T1c-4981 | I-3 | II-99 | C-46 |
| T1c-4982 | I-3 | II-100 | C-46 |
| T1c-4983 | I-3 | II-101 | C-46 |
| T1c-4984 | I-3 | II-102 | C-46 |
| T1c-4985 | I-3 | II-103 | C-46 |
| T1c-4986 | I-3 | II-104 | C-46 |
| T1c-4987 | I-3 | II-105 | C-46 |
| T1c-4988 | I-3 | II-106 | C-46 |
| T1c-4989 | I-3 | II-107 | C-46 |
| T1c-4990 | I-3 | II-108 | C-46 |
| T1c-4991 | I-3 | II-109 | C-46 |
| T1c-4992 | I-3 | II-110 | C-46 |
| T1c-4993 | I-3 | II-111 | C-46 |
| T1c-4994 | I-3 | II-112 | C-46 |
| T1c-4995 | I-3 | II-113 | C-46 |
| T1c-4996 | I-3 | II-114 | C-46 |
| T1c-4997 | I-3 | II-115 | C-46 |
| T1c-4998 | I-3 | II-116 | C-46 |
| T1c-4999 | I-3 | II-117 | C-46 |
| T1c-5000 | I-3 | II-118 | C-46 |
| T1c-5001 | I-3 | II-119 | C-46 |
| T1c-5002 | I-3 | II-120 | C-46 |
| T1c-5003 | I-3 | II-121 | C-46 |
| T1c-5004 | I-3 | II-122 | C-46 |
| T1c-5005 | I-3 | II-123 | C-46 |
| T1c-5006 | I-3 | II-124 | C-46 |
| T1c-5007 | I-3 | II-125 | C-46 |
| T1c-5008 | I-3 | II-126 | C-46 |
| T1c-5009 | I-3 | II-127 | C-46 |
| T1c-5010 | I-3 | II-128 | C-46 |
| T1c-5011 | I-3 | II-129 | C-46 |
| T1c-5012 | I-3 | II-130 | C-46 |
| T1c-5013 | I-3 | II-131 | C-46 |
| T1c-5014 | I-3 | II-132 | C-46 |
| T1c-5015 | I-3 | II-133 | C-46 |
| T1c-5016 | I-3 | II-134 | C-46 |
| T1c-5017 | I-3 | II-135 | C-46 |
| T1c-5018 | I-3 | II-136 | C-46 |
| T1c-5019 | I-3 | II-137 | C-46 |
| T1c-5020 | I-3 | II-138 | C-46 |
| T1c-5021 | I-3 | II-139 | C-46 |
| T1c-5022 | I-3 | II-140 | C-46 |
| T1c-5023 | I-3 | II-141 | C-46 |
| T1c-5024 | I-3 | II-142 | C-46 |
| T1c-5025 | I-3 | II-143 | C-46 |
| T1c-5026 | I-3 | II-144 | C-46 |
| T1c-5027 | I-3 | II-145 | C-46 |
| T1c-5028 | I-3 | II-146 | C-46 |
| T1c-5029 | I-3 | II-147 | C-46 |
| T1c-5030 | I-3 | II-148 | C-46 |
| T1c-5031 | I-3 | II-149 | C-46 |
| T1c-5032 | I-3 | II-150 | C-46 |
| T1c-5033 | I-3 | II-151 | C-46 |
| T1c-5034 | I-3 | II-152 | C-46 |
| T1c-5035 | I-3 | II-153 | C-46 |
| T1c-5036 | I-3 | II-154 | C-46 |
| T1c-5037 | I-3 | II-155 | C-46 |
| T1c-5038 | I-3 | II-156 | C-46 |
| T1c-5039 | I-3 | II-157 | C-46 |
| T1c-5040 | I-3 | II-158 | C-46 |
| T1c-5041 | I-3 | II-159 | C-46 |
| T1c-5042 | I-3 | II-160 | C-46 |
| T1c-5043 | I-3 | II-161 | C-46 |
| T1c-5044 | I-3 | II-162 | C-46 |
| T1c-5045 | I-3 | II-163 | C-46 |
| T1c-5046 | I-3 | II-164 | C-46 |
| T1c-5047 | I-3 | II-165 | C-46 |
| T1c-5048 | I-3 | II-166 | C-46 |
| T1c-5049 | I-3 | II-167 | C-46 |
| T1c-5050 | I-3 | II-168 | C-46 |
| T1c-5051 | I-3 | II-169 | C-46 |
| T1c-5052 | I-3 | II-170 | C-46 |
| T1c-5053 | I-3 | II-171 | C-46 |
| T1c-5054 | I-3 | II-172 | C-46 |
| T1c-5055 | I-3 | II-173 | C-46 |
| T1c-5056 | I-3 | II-174 | C-46 |
| T1c-5057 | I-3 | II-175 | C-46 |
| T1c-5058 | I-3 | II-176 | C-46 |
| T1c-5059 | I-3 | II-177 | C-46 |
| T1c-5060 | I-3 | II-178 | C-46 |
| T1c-5061 | I-3 | II-179 | C-46 |
| T1c-5062 | I-3 | II-180 | C-46 |
| T1c-5063 | I-3 | II-181 | C-46 |
| T1c-5064 | I-3 | II-182 | C-46 |
| T1c-5065 | I-3 | II-183 | C-46 |
| T1c-5066 | I-3 | II-184 | C-46 |
| T1c-5067 | I-3 | II-185 | C-46 |
| T1c-5068 | I-3 | II-186 | C-46 |
| T1c-5069 | I-3 | II-187 | C-46 |
| T1c-5070 | I-3 | II-188 | C-46 |
| T1c-5071 | I-3 | II-189 | C-46 |
| T1c-5072 | I-3 | II-190 | C-46 |
| T1c-5073 | I-3 | II-191 | C-46 |
| T1c-5074 | I-3 | II-192 | C-46 |
| T1c-5075 | I-3 | II-193 | C-46 |
| T1c-5076 | I-3 | II-194 | C-46 |
| T1c-5077 | I-3 | II-195 | C-46 |
| T1c-5078 | I-3 | II-196 | C-46 |
| T1c-5079 | I-3 | II-197 | C-46 |
| T1c-5080 | I-3 | II-198 | C-46 |
| T1c-5081 | I-3 | II-199 | C-46 |
| T1c-5082 | I-3 | II-200 | C-46 |
| T1c-5083 | I-3 | II-201 | C-46 |
| T1c-5084 | I-3 | II-202 | C-46 |
| T1c-5085 | I-3 | II-203 | C-46 |
| T1c-5086 | I-3 | II-91 | C-47 |
| T1c-5087 | I-3 | II-92 | C-47 |
| T1c-5088 | I-3 | II-93 | C-47 |
| T1c-5089 | I-3 | II-94 | C-47 |
| T1c-5090 | I-3 | II-95 | C-47 |
| T1c-5091 | I-3 | II-96 | C-47 |
| T1c-5092 | I-3 | II-97 | C-47 |
| T1c-5093 | I-3 | II-98 | C-47 |
| T1c-5094 | I-3 | II-99 | C-47 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-5095 | I-3 | II-100 | C-47 |
| T1c-5096 | I-3 | II-101 | C-47 |
| T1c-5097 | I-3 | II-102 | C-47 |
| T1c-5098 | I-3 | II-103 | C-47 |
| T1c-5099 | I-3 | II-104 | C-47 |
| T1c-5100 | I-3 | II-105 | C-47 |
| T1c-5101 | I-3 | II-106 | C-47 |
| T1c-5102 | I-3 | II-107 | C-47 |
| T1c-5103 | I-3 | II-108 | C-47 |
| T1c-5104 | I-3 | II-109 | C-47 |
| T1c-5105 | I-3 | II-110 | C-47 |
| T1c-5106 | I-3 | II-111 | C-47 |
| T1c-5107 | I-3 | II-112 | C-47 |
| T1c-5108 | I-3 | II-113 | C-47 |
| T1c-5109 | I-3 | II-114 | C-47 |
| T1c-5110 | I-3 | II-115 | C-47 |
| T1c-5111 | I-3 | II-116 | C-47 |
| T1c-5112 | I-3 | II-117 | C-47 |
| T1c-5113 | I-3 | II-118 | C-47 |
| T1c-5114 | I-3 | II-119 | C-47 |
| T1c-5115 | I-3 | II-120 | C-47 |
| T1c-5116 | I-3 | II-121 | C-47 |
| T1c-5117 | I-3 | II-122 | C-47 |
| T1c-5118 | I-3 | II-123 | C-47 |
| T1c-5119 | I-3 | II-124 | C-47 |
| T1c-5120 | I-3 | II-125 | C-47 |
| T1c-5121 | I-3 | II-126 | C-47 |
| T1c-5122 | I-3 | II-127 | C-47 |
| T1c-5123 | I-3 | II-128 | C-47 |
| T1c-5124 | I-3 | II-129 | C-47 |
| T1c-5125 | I-3 | II-130 | C-47 |
| T1c-5126 | I-3 | II-131 | C-47 |
| T1c-5127 | I-3 | II-132 | C-47 |
| T1c-5128 | I-3 | II-133 | C-47 |
| T1c-5129 | I-3 | II-134 | C-47 |
| T1c-5130 | I-3 | II-135 | C-47 |
| T1c-5131 | I-3 | II-136 | C-47 |
| T1c-5132 | I-3 | II-137 | C-47 |
| T1c-5133 | I-3 | II-138 | C-47 |
| T1c-5134 | I-3 | II-139 | C-47 |
| T1c-5135 | I-3 | II-140 | C-47 |
| T1c-5136 | I-3 | II-141 | C-47 |
| T1c-5137 | I-3 | II-142 | C-47 |
| T1c-5138 | I-3 | II-143 | C-47 |
| T1c-5139 | I-3 | II-144 | C-47 |
| T1c-5140 | I-3 | II-145 | C-47 |
| T1c-5141 | I-3 | II-146 | C-47 |
| T1c-5142 | I-3 | II-147 | C-47 |
| T1c-5143 | I-3 | II-148 | C-47 |
| T1c-5144 | I-3 | II-149 | C-47 |
| T1c-5145 | I-3 | II-150 | C-47 |
| T1c-5146 | I-3 | II-151 | C-47 |
| T1c-5147 | I-3 | II-152 | C-47 |
| T1c-5148 | I-3 | II-153 | C-47 |
| T1c-5149 | I-3 | II-154 | C-47 |
| T1c-5150 | I-3 | II-155 | C-47 |
| T1c-5151 | I-3 | II-156 | C-47 |
| T1c-5152 | I-3 | II-157 | C-47 |
| T1c-5153 | I-3 | II-158 | C-47 |
| T1c-5154 | I-3 | II-159 | C-47 |
| T1c-5155 | I-3 | II-160 | C-47 |
| T1c-5156 | I-3 | II-161 | C-47 |
| T1c-5157 | I-3 | II-162 | C-47 |
| T1c-5158 | I-3 | II-163 | C-47 |
| T1c-5159 | I-3 | II-164 | C-47 |
| T1c-5160 | I-3 | II-165 | C-47 |
| T1c-5161 | I-3 | II-166 | C-47 |
| T1c-5162 | I-3 | II-167 | C-47 |
| T1c-5163 | I-3 | II-168 | C-47 |
| T1c-5164 | I-3 | II-169 | C-47 |
| T1c-5165 | I-3 | II-170 | C-47 |
| T1c-5166 | I-3 | II-171 | C-47 |
| T1c-5167 | I-3 | II-172 | C-47 |
| T1c-5168 | I-3 | II-173 | C-47 |
| T1c-5169 | I-3 | II-174 | C-47 |
| T1c-5170 | I-3 | II-175 | C-47 |
| T1c-5171 | I-3 | II-176 | C-47 |
| T1c-5172 | I-3 | II-177 | C-47 |
| T1c-5173 | I-3 | II-178 | C-47 |
| T1c-5174 | I-3 | II-179 | C-47 |
| T1c-5175 | I-3 | II-180 | C-47 |
| T1c-5176 | I-3 | II-181 | C-47 |
| T1c-5177 | I-3 | II-182 | C-47 |
| T1c-5178 | I-3 | II-183 | C-47 |
| T1c-5179 | I-3 | II-184 | C-47 |
| T1c-5180 | I-3 | II-185 | C-47 |
| T1c-5181 | I-3 | II-186 | C-47 |
| T1c-5182 | I-3 | II-187 | C-47 |
| T1c-5183 | I-3 | II-188 | C-47 |
| T1c-5184 | I-3 | II-189 | C-47 |
| T1c-5185 | I-3 | II-190 | C-47 |
| T1c-5186 | I-3 | II-191 | C-47 |
| T1c-5187 | I-3 | II-192 | C-47 |
| T1c-5188 | I-3 | II-193 | C-47 |
| T1c-5189 | I-3 | II-194 | C-47 |
| T1c-5190 | I-3 | II-195 | C-47 |
| T1c-5191 | I-3 | II-196 | C-47 |
| T1c-5192 | I-3 | II-197 | C-47 |
| T1c-5193 | I-3 | II-198 | C-47 |
| T1c-5194 | I-3 | II-199 | C-47 |
| T1c-5195 | I-3 | II-200 | C-47 |
| T1c-5196 | I-3 | II-201 | C-47 |
| T1c-5197 | I-3 | II-202 | C-47 |
| T1c-5198 | I-3 | II-203 | C-47 |
| T1c-5199 | I-3 | II-91 | C-48 |
| T1c-5200 | I-3 | II-92 | C-48 |
| T1c-5201 | I-3 | II-93 | C-48 |
| T1c-5202 | I-3 | II-94 | C-48 |
| T1c-5203 | I-3 | II-95 | C-48 |
| T1c-5204 | I-3 | II-96 | C-48 |
| T1c-5205 | I-3 | II-97 | C-48 |
| T1c-5206 | I-3 | II-98 | C-48 |
| T1c-5207 | I-3 | II-99 | C-48 |
| T1c-5208 | I-3 | II-100 | C-48 |
| T1c-5209 | I-3 | II-101 | C-48 |
| T1c-5210 | I-3 | II-102 | C-48 |
| T1c-5211 | I-3 | II-103 | C-48 |
| T1c-5212 | I-3 | II-104 | C-48 |
| T1c-5213 | I-3 | II-105 | C-48 |
| T1c-5214 | I-3 | II-106 | C-48 |
| T1c-5215 | I-3 | II-107 | C-48 |
| T1c-5216 | I-3 | II-108 | C-48 |
| T1c-5217 | I-3 | II-109 | C-48 |
| T1c-5218 | I-3 | II-110 | C-48 |
| T1c-5219 | I-3 | II-111 | C-48 |
| T1c-5220 | I-3 | II-112 | C-48 |
| T1c-5221 | I-3 | II-113 | C-48 |
| T1c-5222 | I-3 | II-114 | C-48 |
| T1c-5223 | I-3 | II-115 | C-48 |
| T1c-5224 | I-3 | II-116 | C-48 |
| T1c-5225 | I-3 | II-117 | C-48 |
| T1c-5226 | I-3 | II-118 | C-48 |
| T1c-5227 | I-3 | II-119 | C-48 |
| T1c-5228 | I-3 | II-120 | C-48 |
| T1c-5229 | I-3 | II-121 | C-48 |
| T1c-5230 | I-3 | II-122 | C-48 |
| T1c-5231 | I-3 | II-123 | C-48 |
| T1c-5232 | I-3 | II-124 | C-48 |
| T1c-5233 | I-3 | II-125 | C-48 |
| T1c-5234 | I-3 | II-126 | C-48 |
| T1c-5235 | I-3 | II-127 | C-48 |
| T1c-5236 | I-3 | II-128 | C-48 |
| T1c-5237 | I-3 | II-129 | C-48 |
| T1c-5238 | I-3 | II-130 | C-48 |
| T1c-5239 | I-3 | II-131 | C-48 |
| T1c-5240 | I-3 | II-132 | C-48 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-5241 | I-3 | II-133 | C-48 |
| T1c-5242 | I-3 | II-134 | C-48 |
| T1c-5243 | I-3 | II-135 | C-48 |
| T1c-5244 | I-3 | II-136 | C-48 |
| T1c-5245 | I-3 | II-137 | C-48 |
| T1c-5246 | I-3 | II-138 | C-48 |
| T1c-5247 | I-3 | II-139 | C-48 |
| T1c-5248 | I-3 | II-140 | C-48 |
| T1c-5249 | I-3 | II-141 | C-48 |
| T1c-5250 | I-3 | II-142 | C-48 |
| T1c-5251 | I-3 | II-143 | C-48 |
| T1c-5252 | I-3 | II-144 | C-48 |
| T1c-5253 | I-3 | II-145 | C-48 |
| T1c-5254 | I-3 | II-146 | C-48 |
| T1c-5255 | I-3 | II-147 | C-48 |
| T1c-5256 | I-3 | II-148 | C-48 |
| T1c-5257 | I-3 | II-149 | C-48 |
| T1c-5258 | I-3 | II-150 | C-48 |
| T1c-5259 | I-3 | II-151 | C-48 |
| T1c-5260 | I-3 | II-152 | C-48 |
| T1c-5261 | I-3 | II-153 | C-48 |
| T1c-5262 | I-3 | II-154 | C-48 |
| T1c-5263 | I-3 | II-155 | C-48 |
| T1c-5264 | I-3 | II-156 | C-48 |
| T1c-5265 | I-3 | II-157 | C-48 |
| T1c-5266 | I-3 | II-158 | C-48 |
| T1c-5267 | I-3 | II-159 | C-48 |
| T1c-5268 | I-3 | II-160 | C-48 |
| T1c-5269 | I-3 | II-161 | C-48 |
| T1c-5270 | I-3 | II-162 | C-48 |
| T1c-5271 | I-3 | II-163 | C-48 |
| T1c-5272 | I-3 | II-164 | C-48 |
| T1c-5273 | I-3 | II-165 | C-48 |
| T1c-5274 | I-3 | II-166 | C-48 |
| T1c-5275 | I-3 | II-167 | C-48 |
| T1c-5276 | I-3 | II-168 | C-48 |
| T1c-5277 | I-3 | II-169 | C-48 |
| T1c-5278 | I-3 | II-170 | C-48 |
| T1c-5279 | I-3 | II-171 | C-48 |
| T1c-5280 | I-3 | II-172 | C-48 |
| T1c-5281 | I-3 | II-173 | C-48 |
| T1c-5282 | I-3 | II-174 | C-48 |
| T1c-5283 | I-3 | II-175 | C-48 |
| T1c-5284 | I-3 | II-176 | C-48 |
| T1c-5285 | I-3 | II-177 | C-48 |
| T1c-5286 | I-3 | II-178 | C-48 |
| T1c-5287 | I-3 | II-179 | C-48 |
| T1c-5288 | I-3 | II-180 | C-48 |
| T1c-5289 | I-3 | II-181 | C-48 |
| T1c-5290 | I-3 | II-182 | C-48 |
| T1c-5291 | I-3 | II-183 | C-48 |
| T1c-5292 | I-3 | II-184 | C-48 |
| T1c-5293 | I-3 | II-185 | C-48 |
| T1c-5294 | I-3 | II-186 | C-48 |
| T1c-5295 | I-3 | II-187 | C-48 |
| T1c-5296 | I-3 | II-188 | C-48 |
| T1c-5297 | I-3 | II-189 | C-48 |
| T1c-5298 | I-3 | II-190 | C-48 |
| T1c-5299 | I-3 | II-191 | C-48 |
| T1c-5300 | I-3 | II-192 | C-48 |
| T1c-5301 | I-3 | II-193 | C-48 |
| T1c-5302 | I-3 | II-194 | C-48 |
| T1c-5303 | I-3 | II-195 | C-48 |
| T1c-5304 | I-3 | II-196 | C-48 |
| T1c-5305 | I-3 | II-197 | C-48 |
| T1c-5306 | I-3 | II-198 | C-48 |
| T1c-5307 | I-3 | II-199 | C-48 |
| T1c-5308 | I-3 | II-200 | C-48 |
| T1c-5309 | I-3 | II-201 | C-48 |
| T1c-5310 | I-3 | II-202 | C-48 |
| T1c-5311 | I-3 | II-203 | C-48 |
| T1c-5312 | I-3 | II-91 | C-49 |
| T1c-5313 | I-3 | II-92 | C-49 |
| T1c-5314 | I-3 | II-93 | C-49 |
| T1c-5315 | I-3 | II-94 | C-49 |
| T1c-5316 | I-3 | II-95 | C-49 |
| T1c-5317 | I-3 | II-96 | C-49 |
| T1c-5318 | I-3 | II-97 | C-49 |
| T1c-5319 | I-3 | II-98 | C-49 |
| T1c-5320 | I-3 | II-99 | C-49 |
| T1c-5321 | I-3 | II-100 | C-49 |
| T1c-5322 | I-3 | II-101 | C-49 |
| T1c-5323 | I-3 | II-102 | C-49 |
| T1c-5324 | I-3 | II-103 | C-49 |
| T1c-5325 | I-3 | II-104 | C-49 |
| T1c-5326 | I-3 | II-105 | C-49 |
| T1c-5327 | I-3 | II-106 | C-49 |
| T1c-5328 | I-3 | II-107 | C-49 |
| T1c-5329 | I-3 | II-108 | C-49 |
| T1c-5330 | I-3 | II-109 | C-49 |
| T1c-5331 | I-3 | II-110 | C-49 |
| T1c-5332 | I-3 | II-111 | C-49 |
| T1c-5333 | I-3 | II-112 | C-49 |
| T1c-5334 | I-3 | II-113 | C-49 |
| T1c-5335 | I-3 | II-114 | C-49 |
| T1c-5336 | I-3 | II-115 | C-49 |
| T1c-5337 | I-3 | II-116 | C-49 |
| T1c-5338 | I-3 | II-117 | C-49 |
| T1c-5339 | I-3 | II-118 | C-49 |
| T1c-5340 | I-3 | II-119 | C-49 |
| T1c-5341 | I-3 | II-120 | C-49 |
| T1c-5342 | I-3 | II-121 | C-49 |
| T1c-5343 | I-3 | II-122 | C-49 |
| T1c-5344 | I-3 | II-123 | C-49 |
| T1c-5345 | I-3 | II-124 | C-49 |
| T1c-5346 | I-3 | II-125 | C-49 |
| T1c-5347 | I-3 | II-126 | C-49 |
| T1c-5348 | I-3 | II-127 | C-49 |
| T1c-5349 | I-3 | II-128 | C-49 |
| T1c-5350 | I-3 | II-129 | C-49 |
| T1c-5351 | I-3 | II-130 | C-49 |
| T1c-5352 | I-3 | II-131 | C-49 |
| T1c-5353 | I-3 | II-132 | C-49 |
| T1c-5354 | I-3 | II-133 | C-49 |
| T1c-5355 | I-3 | II-134 | C-49 |
| T1c-5356 | I-3 | II-135 | C-49 |
| T1c-5357 | I-3 | II-136 | C-49 |
| T1c-5358 | I-3 | II-137 | C-49 |
| T1c-5359 | I-3 | II-138 | C-49 |
| T1c-5360 | I-3 | II-139 | C-49 |
| T1c-5361 | I-3 | II-140 | C-49 |
| T1c-5362 | I-3 | II-141 | C-49 |
| T1c-5363 | I-3 | II-142 | C-49 |
| T1c-5364 | I-3 | II-143 | C-49 |
| T1c-5365 | I-3 | II-144 | C-49 |
| T1c-5366 | I-3 | II-145 | C-49 |
| T1c-5367 | I-3 | II-146 | C-49 |
| T1c-5368 | I-3 | II-147 | C-49 |
| T1c-5369 | I-3 | II-148 | C-49 |
| T1c-5370 | I-3 | II-149 | C-49 |
| T1c-5371 | I-3 | II-150 | C-49 |
| T1c-5372 | I-3 | II-151 | C-49 |
| T1c-5373 | I-3 | II-152 | C-49 |
| T1c-5374 | I-3 | II-153 | C-49 |
| T1c-5375 | I-3 | II-154 | C-49 |
| T1c-5376 | I-3 | II-155 | C-49 |
| T1c-5377 | I-3 | II-156 | C-49 |
| T1c-5378 | I-3 | II-157 | C-49 |
| T1c-5379 | I-3 | II-158 | C-49 |
| T1c-5380 | I-3 | II-159 | C-49 |
| T1c-5381 | I-3 | II-160 | C-49 |
| T1c-5382 | I-3 | II-161 | C-49 |
| T1c-5383 | I-3 | II-162 | C-49 |
| T1c-5384 | I-3 | II-163 | C-49 |
| T1c-5385 | I-3 | II-164 | C-49 |
| T1c-5386 | I-3 | II-165 | C-49 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-5387 | I-3 | II-166 | C-49 |
| T1c-5388 | I-3 | II-167 | C-49 |
| T1c-5389 | I-3 | II-168 | C-49 |
| T1c-5390 | I-3 | II-169 | C-49 |
| T1c-5391 | I-3 | II-170 | C-49 |
| T1c-5392 | I-3 | II-171 | C-49 |
| T1c-5393 | I-3 | II-172 | C-49 |
| T1c-5394 | I-3 | II-173 | C-49 |
| T1c-5395 | I-3 | II-174 | C-49 |
| T1c-5396 | I-3 | II-175 | C-49 |
| T1c-5397 | I-3 | II-176 | C-49 |
| T1c-5398 | I-3 | II-177 | C-49 |
| T1c-5399 | I-3 | II-178 | C-49 |
| T1c-5400 | I-3 | II-179 | C-49 |
| T1c-5401 | I-3 | II-180 | C-49 |
| T1c-5402 | I-3 | II-181 | C-49 |
| T1c-5403 | I-3 | II-182 | C-49 |
| T1c-5404 | I-3 | II-183 | C-49 |
| T1c-5405 | I-3 | II-184 | C-49 |
| T1c-5406 | I-3 | II-185 | C-49 |
| T1c-5407 | I-3 | II-186 | C-49 |
| T1c-5408 | I-3 | II-187 | C-49 |
| T1c-5409 | I-3 | II-188 | C-49 |
| T1c-5410 | I-3 | II-189 | C-49 |
| T1c-5411 | I-3 | II-190 | C-49 |
| T1c-5412 | I-3 | II-191 | C-49 |
| T1c-5413 | I-3 | II-192 | C-49 |
| T1c-5414 | I-3 | II-193 | C-49 |
| T1c-5415 | I-3 | II-194 | C-49 |
| T1c-5416 | I-3 | II-195 | C-49 |
| T1c-5417 | I-3 | II-196 | C-49 |
| T1c-5418 | I-3 | II-197 | C-49 |
| T1c-5419 | I-3 | II-198 | C-49 |
| T1c-5420 | I-3 | II-199 | C-49 |
| T1c-5421 | I-3 | II-200 | C-49 |
| T1c-5422 | I-3 | II-201 | C-49 |
| T1c-5423 | I-3 | II-202 | C-49 |
| T1c-5424 | I-3 | II-203 | C-49 |
| T1c-5425 | I-3 | II-91 | C-50 |
| T1c-5426 | I-3 | II-92 | C-50 |
| T1c-5427 | I-3 | II-93 | C-50 |
| T1c-5428 | I-3 | II-94 | C-50 |
| T1c-5429 | I-3 | II-95 | C-50 |
| T1c-5430 | I-3 | II-96 | C-50 |
| T1c-5431 | I-3 | II-97 | C-50 |
| T1c-5432 | I-3 | II-98 | C-50 |
| T1c-5433 | I-3 | II-99 | C-50 |
| T1c-5434 | I-3 | II-100 | C-50 |
| T1c-5435 | I-3 | II-101 | C-50 |
| T1c-5436 | I-3 | II-102 | C-50 |
| T1c-5437 | I-3 | II-103 | C-50 |
| T1c-5438 | I-3 | II-104 | C-50 |
| T1c-5439 | I-3 | II-105 | C-50 |
| T1c-5440 | I-3 | II-106 | C-50 |
| T1c-5441 | I-3 | II-107 | C-50 |
| T1c-5442 | I-3 | II-108 | C-50 |
| T1c-5443 | I-3 | II-109 | C-50 |
| T1c-5444 | I-3 | II-110 | C-50 |
| T1c-5445 | I-3 | II-111 | C-50 |
| T1c-5446 | I-3 | II-112 | C-50 |
| T1c-5447 | I-3 | II-113 | C-50 |
| T1c-5448 | I-3 | II-114 | C-50 |
| T1c-5449 | I-3 | II-115 | C-50 |
| T1c-5450 | I-3 | II-116 | C-50 |
| T1c-5451 | I-3 | II-117 | C-50 |
| T1c-5452 | I-3 | II-118 | C-50 |
| T1c-5453 | I-3 | II-119 | C-50 |
| T1c-5454 | I-3 | II-120 | C-50 |
| T1c-5455 | I-3 | II-121 | C-50 |
| T1c-5456 | I-3 | II-122 | C-50 |
| T1c-5457 | I-3 | II-123 | C-50 |
| T1c-5458 | I-3 | II-124 | C-50 |
| T1c-5459 | I-3 | II-125 | C-50 |
| T1c-5460 | I-3 | II-126 | C-50 |
| T1c-5461 | I-3 | II-127 | C-50 |
| T1c-5462 | I-3 | II-128 | C-50 |
| T1c-5463 | I-3 | II-129 | C-50 |
| T1c-5464 | I-3 | II-130 | C-50 |
| T1c-5465 | I-3 | II-131 | C-50 |
| T1c-5466 | I-3 | II-132 | C-50 |
| T1c-5467 | I-3 | II-133 | C-50 |
| T1c-5468 | I-3 | II-134 | C-50 |
| T1c-5469 | I-3 | II-135 | C-50 |
| T1c-5470 | I-3 | II-136 | C-50 |
| T1c-5471 | I-3 | II-137 | C-50 |
| T1c-5472 | I-3 | II-138 | C-50 |
| T1c-5473 | I-3 | II-139 | C-50 |
| T1c-5474 | I-3 | II-140 | C-50 |
| T1c-5475 | I-3 | II-141 | C-50 |
| T1c-5476 | I-3 | II-142 | C-50 |
| T1c-5477 | I-3 | II-143 | C-50 |
| T1c-5478 | I-3 | II-144 | C-50 |
| T1c-5479 | I-3 | II-145 | C-50 |
| T1c-5480 | I-3 | II-146 | C-50 |
| T1c-5481 | I-3 | II-147 | C-50 |
| T1c-5482 | I-3 | II-148 | C-50 |
| T1c-5483 | I-3 | II-149 | C-50 |
| T1c-5484 | I-3 | II-150 | C-50 |
| T1c-5485 | I-3 | II-151 | C-50 |
| T1c-5486 | I-3 | II-152 | C-50 |
| T1c-5487 | I-3 | II-153 | C-50 |
| T1c-5488 | I-3 | II-154 | C-50 |
| T1c-5489 | I-3 | II-155 | C-50 |
| T1c-5490 | I-3 | II-156 | C-50 |
| T1c-5491 | I-3 | II-157 | C-50 |
| T1c-5492 | I-3 | II-158 | C-50 |
| T1c-5493 | I-3 | II-159 | C-50 |
| T1c-5494 | I-3 | II-160 | C-50 |
| T1c-5495 | I-3 | II-161 | C-50 |
| T1c-5496 | I-3 | II-162 | C-50 |
| T1c-5497 | I-3 | II-163 | C-50 |
| T1c-5498 | I-3 | II-164 | C-50 |
| T1c-5499 | I-3 | II-165 | C-50 |
| T1c-5500 | I-3 | II-166 | C-50 |
| T1c-5501 | I-3 | II-167 | C-50 |
| T1c-5502 | I-3 | II-168 | C-50 |
| T1c-5503 | I-3 | II-169 | C-50 |
| T1c-5504 | I-3 | II-170 | C-50 |
| T1c-5505 | I-3 | II-171 | C-50 |
| T1c-5506 | I-3 | II-172 | C-50 |
| T1c-5507 | I-3 | II-173 | C-50 |
| T1c-5508 | I-3 | II-174 | C-50 |
| T1c-5509 | I-3 | II-175 | C-50 |
| T1c-5510 | I-3 | II-176 | C-50 |
| T1c-5511 | I-3 | II-177 | C-50 |
| T1c-5512 | I-3 | II-178 | C-50 |
| T1c-5513 | I-3 | II-179 | C-50 |
| T1c-5514 | I-3 | II-180 | C-50 |
| T1c-5515 | I-3 | II-181 | C-50 |
| T1c-5516 | I-3 | II-182 | C-50 |
| T1c-5517 | I-3 | II-183 | C-50 |
| T1c-5518 | I-3 | II-184 | C-50 |
| T1c-5519 | I-3 | II-185 | C-50 |
| T1c-5520 | I-3 | II-186 | C-50 |
| T1c-5521 | I-3 | II-187 | C-50 |
| T1c-5522 | I-3 | II-188 | C-50 |
| T1c-5523 | I-3 | II-189 | C-50 |
| T1c-5524 | I-3 | II-190 | C-50 |
| T1c-5525 | I-3 | II-191 | C-50 |
| T1c-5526 | I-3 | II-192 | C-50 |
| T1c-5527 | I-3 | II-193 | C-50 |
| T1c-5528 | I-3 | II-194 | C-50 |
| T1c-5529 | I-3 | II-195 | C-50 |
| T1c-5530 | I-3 | II-196 | C-50 |
| T1c-5531 | I-3 | II-197 | C-50 |
| T1c-5532 | I-3 | II-198 | C-50 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-5533 | I-3 | II-199 | C-50 |
| T1c-5534 | I-3 | II-200 | C-50 |
| T1c-5535 | I-3 | II-201 | C-50 |
| T1c-5536 | I-3 | II-202 | C-50 |
| T1c-5537 | I-3 | II-203 | C-50 |
| T1c-5538 | I-3 | II-91 | C-51 |
| T1c-5539 | I-3 | II-92 | C-51 |
| T1c-5540 | I-3 | II-93 | C-51 |
| T1c-5541 | I-3 | II-94 | C-51 |
| T1c-5542 | I-3 | II-95 | C-51 |
| T1c-5543 | I-3 | II-96 | C-51 |
| T1c-5544 | I-3 | II-97 | C-51 |
| T1c-5545 | I-3 | II-98 | C-51 |
| T1c-5546 | I-3 | II-99 | C-51 |
| T1c-5547 | I-3 | II-100 | C-51 |
| T1c-5548 | I-3 | II-101 | C-51 |
| T1c-5549 | I-3 | II-102 | C-51 |
| T1c-5550 | I-3 | II-103 | C-51 |
| T1c-5551 | I-3 | II-104 | C-51 |
| T1c-5552 | I-3 | II-105 | C-51 |
| T1c-5553 | I-3 | II-106 | C-51 |
| T1c-5554 | I-3 | II-107 | C-51 |
| T1c-5555 | I-3 | II-108 | C-51 |
| T1c-5556 | I-3 | II-109 | C-51 |
| T1c-5557 | I-3 | II-110 | C-51 |
| T1c-5558 | I-3 | II-111 | C-51 |
| T1c-5559 | I-3 | II-112 | C-51 |
| T1c-5560 | I-3 | II-113 | C-51 |
| T1c-5561 | I-3 | II-114 | C-51 |
| T1c-5562 | I-3 | II-115 | C-51 |
| T1c-5563 | I-3 | II-116 | C-51 |
| T1c-5564 | I-3 | II-117 | C-51 |
| T1c-5565 | I-3 | II-118 | C-51 |
| T1c-5566 | I-3 | II-119 | C-51 |
| T1c-5567 | I-3 | II-120 | C-51 |
| T1c-5568 | I-3 | II-121 | C-51 |
| T1c-5569 | I-3 | II-122 | C-51 |
| T1c-5570 | I-3 | II-123 | C-51 |
| T1c-5571 | I-3 | II-124 | C-51 |
| T1c-5572 | I-3 | II-125 | C-51 |
| T1c-5573 | I-3 | II-126 | C-51 |
| T1c-5574 | I-3 | II-127 | C-51 |
| T1c-5575 | I-3 | II-128 | C-51 |
| T1c-5576 | I-3 | II-129 | C-51 |
| T1c-5577 | I-3 | II-130 | C-51 |
| T1c-5578 | I-3 | II-131 | C-51 |
| T1c-5579 | I-3 | II-132 | C-51 |
| T1c-5580 | I-3 | II-133 | C-51 |
| T1c-5581 | I-3 | II-134 | C-51 |
| T1c-5582 | I-3 | II-135 | C-51 |
| T1c-5583 | I-3 | II-136 | C-51 |
| T1c-5584 | I-3 | II-137 | C-51 |
| T1c-5585 | I-3 | II-138 | C-51 |
| T1c-5586 | I-3 | II-139 | C-51 |
| T1c-5587 | I-3 | II-140 | C-51 |
| T1c-5588 | I-3 | II-141 | C-51 |
| T1c-5589 | I-3 | II-142 | C-51 |
| T1c-5590 | I-3 | II-143 | C-51 |
| T1c-5591 | I-3 | II-144 | C-51 |
| T1c-5592 | I-3 | II-145 | C-51 |
| T1c-5593 | I-3 | II-146 | C-51 |
| T1c-5594 | I-3 | II-147 | C-51 |
| T1c-5595 | I-3 | II-148 | C-51 |
| T1c-5596 | I-3 | II-149 | C-51 |
| T1c-5597 | I-3 | II-150 | C-51 |
| T1c-5598 | I-3 | II-151 | C-51 |
| T1c-5599 | I-3 | II-152 | C-51 |
| T1c-5600 | I-3 | II-153 | C-51 |
| T1c-5601 | I-3 | II-154 | C-51 |
| T1c-5602 | I-3 | II-155 | C-51 |
| T1c-5603 | I-3 | II-156 | C-51 |
| T1c-5604 | I-3 | II-157 | C-51 |
| T1c-5605 | I-3 | II-158 | C-51 |
| T1c-5606 | I-3 | II-159 | C-51 |
| T1c-5607 | I-3 | II-160 | C-51 |
| T1c-5608 | I-3 | II-161 | C-51 |
| T1c-5609 | I-3 | II-162 | C-51 |
| T1c-5610 | I-3 | II-163 | C-51 |
| T1c-5611 | I-3 | II-164 | C-51 |
| T1c-5612 | I-3 | II-165 | C-51 |
| T1c-5613 | I-3 | II-166 | C-51 |
| T1c-5614 | I-3 | II-167 | C-51 |
| T1c-5615 | I-3 | II-168 | C-51 |
| T1c-5616 | I-3 | II-169 | C-51 |
| T1c-5617 | I-3 | II-170 | C-51 |
| T1c-5618 | I-3 | II-171 | C-51 |
| T1c-5619 | I-3 | II-172 | C-51 |
| T1c-5620 | I-3 | II-173 | C-51 |
| T1c-5621 | I-3 | II-174 | C-51 |
| T1c-5622 | I-3 | II-175 | C-51 |
| T1c-5623 | I-3 | II-176 | C-51 |
| T1c-5624 | I-3 | II-177 | C-51 |
| T1c-5625 | I-3 | II-178 | C-51 |
| T1c-5626 | I-3 | II-179 | C-51 |
| T1c-5627 | I-3 | II-180 | C-51 |
| T1c-5628 | I-3 | II-181 | C-51 |
| T1c-5629 | I-3 | II-182 | C-51 |
| T1c-5630 | I-3 | II-183 | C-51 |
| T1c-5631 | I-3 | II-184 | C-51 |
| T1c-5632 | I-3 | II-185 | C-51 |
| T1c-5633 | I-3 | II-186 | C-51 |
| T1c-5634 | I-3 | II-187 | C-51 |
| T1c-5635 | I-3 | II-188 | C-51 |
| T1c-5636 | I-3 | II-189 | C-51 |
| T1c-5637 | I-3 | II-190 | C-51 |
| T1c-5638 | I-3 | II-191 | C-51 |
| T1c-5639 | I-3 | II-192 | C-51 |
| T1c-5640 | I-3 | II-193 | C-51 |
| T1c-5641 | I-3 | II-194 | C-51 |
| T1c-5642 | I-3 | II-195 | C-51 |
| T1c-5643 | I-3 | II-196 | C-51 |
| T1c-5644 | I-3 | II-197 | C-51 |
| T1c-5645 | I-3 | II-198 | C-51 |
| T1c-5646 | I-3 | II-199 | C-51 |
| T1c-5647 | I-3 | II-200 | C-51 |
| T1c-5648 | I-3 | II-201 | C-51 |
| T1c-5649 | I-3 | II-202 | C-51 |
| T1c-5650 | I-3 | II-203 | C-51 |
| T1c-5651 | I-3 | II-91 | C-52 |
| T1c-5652 | I-3 | II-92 | C-52 |
| T1c-5653 | I-3 | II-93 | C-52 |
| T1c-5654 | I-3 | II-94 | C-52 |
| T1c-5655 | I-3 | II-95 | C-52 |
| T1c-5656 | I-3 | II-96 | C-52 |
| T1c-5657 | I-3 | II-97 | C-52 |
| T1c-5658 | I-3 | II-98 | C-52 |
| T1c-5659 | I-3 | II-99 | C-52 |
| T1c-5660 | I-3 | II-100 | C-52 |
| T1c-5661 | I-3 | II-101 | C-52 |
| T1c-5662 | I-3 | II-102 | C-52 |
| T1c-5663 | I-3 | II-103 | C-52 |
| T1c-5664 | I-3 | II-104 | C-52 |
| T1c-5665 | I-3 | II-105 | C-52 |
| T1c-5666 | I-3 | II-106 | C-52 |
| T1c-5667 | I-3 | II-107 | C-52 |
| T1c-5668 | I-3 | II-108 | C-52 |
| T1c-5669 | I-3 | II-109 | C-52 |
| T1c-5670 | I-3 | II-110 | C-52 |
| T1c-5671 | I-3 | II-111 | C-52 |
| T1c-5672 | I-3 | II-112 | C-52 |
| T1c-5673 | I-3 | II-113 | C-52 |
| T1c-5674 | I-3 | II-114 | C-52 |
| T1c-5675 | I-3 | II-115 | C-52 |
| T1c-5676 | I-3 | II-116 | C-52 |
| T1c-5677 | I-3 | II-117 | C-52 |
| T1c-5678 | I-3 | II-118 | C-52 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-5679 | I-3 | II-119 | C-52 |
| T1c-5680 | I-3 | II-120 | C-52 |
| T1c-5681 | I-3 | II-121 | C-52 |
| T1c-5682 | I-3 | II-122 | C-52 |
| T1c-5683 | I-3 | II-123 | C-52 |
| T1c-5684 | I-3 | II-124 | C-52 |
| T1c-5685 | I-3 | II-125 | C-52 |
| T1c-5686 | I-3 | II-126 | C-52 |
| T1c-5687 | I-3 | II-127 | C-52 |
| T1c-5688 | I-3 | II-128 | C-52 |
| T1c-5689 | I-3 | II-129 | C-52 |
| T1c-5690 | I-3 | II-130 | C-52 |
| T1c-5691 | I-3 | II-131 | C-52 |
| T1c-5692 | I-3 | II-132 | C-52 |
| T1c-5693 | I-3 | II-133 | C-52 |
| T1c-5694 | I-3 | II-134 | C-52 |
| T1c-5695 | I-3 | II-135 | C-52 |
| T1c-5696 | I-3 | II-136 | C-52 |
| T1c-5697 | I-3 | II-137 | C-52 |
| T1c-5698 | I-3 | II-138 | C-52 |
| T1c-5699 | I-3 | II-139 | C-52 |
| T1c-5700 | I-3 | II-140 | C-52 |
| T1c-5701 | I-3 | II-141 | C-52 |
| T1c-5702 | I-3 | II-142 | C-52 |
| T1c-5703 | I-3 | II-143 | C-52 |
| T1c-5704 | I-3 | II-144 | C-52 |
| T1c-5705 | I-3 | II-145 | C-52 |
| T1c-5706 | I-3 | II-146 | C-52 |
| T1c-5707 | I-3 | II-147 | C-52 |
| T1c-5708 | I-3 | II-148 | C-52 |
| T1c-5709 | I-3 | II-149 | C-52 |
| T1c-5710 | I-3 | II-150 | C-52 |
| T1c-5711 | I-3 | II-151 | C-52 |
| T1c-5712 | I-3 | II-152 | C-52 |
| T1c-5713 | I-3 | II-153 | C-52 |
| T1c-5714 | I-3 | II-154 | C-52 |
| T1c-5715 | I-3 | II-155 | C-52 |
| T1c-5716 | I-3 | II-156 | C-52 |
| T1c-5717 | I-3 | II-157 | C-52 |
| T1c-5718 | I-3 | II-158 | C-52 |
| T1c-5719 | I-3 | II-159 | C-52 |
| T1c-5720 | I-3 | II-160 | C-52 |
| T1c-5721 | I-3 | II-161 | C-52 |
| T1c-5722 | I-3 | II-162 | C-52 |
| T1c-5723 | I-3 | II-163 | C-52 |
| T1c-5724 | I-3 | II-164 | C-52 |
| T1c-5725 | I-3 | II-165 | C-52 |
| T1c-5726 | I-3 | II-166 | C-52 |
| T1c-5727 | I-3 | II-167 | C-52 |
| T1c-5728 | I-3 | II-168 | C-52 |
| T1c-5729 | I-3 | II-169 | C-52 |
| T1c-5730 | I-3 | II-170 | C-52 |
| T1c-5731 | I-3 | II-171 | C-52 |
| T1c-5732 | I-3 | II-172 | C-52 |
| T1c-5733 | I-3 | II-173 | C-52 |
| T1c-5734 | I-3 | II-174 | C-52 |
| T1c-5735 | I-3 | II-175 | C-52 |
| T1c-5736 | I-3 | II-176 | C-52 |
| T1c-5737 | I-3 | II-177 | C-52 |
| T1c-5738 | I-3 | II-178 | C-52 |
| T1c-5739 | I-3 | II-179 | C-52 |
| T1c-5740 | I-3 | II-180 | C-52 |
| T1c-5741 | I-3 | II-181 | C-52 |
| T1c-5742 | I-3 | II-182 | C-52 |
| T1c-5743 | I-3 | II-183 | C-52 |
| T1c-5744 | I-3 | II-184 | C-52 |
| T1c-5745 | I-3 | II-185 | C-52 |
| T1c-5746 | I-3 | II-186 | C-52 |
| T1c-5747 | I-3 | II-187 | C-52 |
| T1c-5748 | I-3 | II-188 | C-52 |
| T1c-5749 | I-3 | II-189 | C-52 |
| T1c-5750 | I-3 | II-190 | C-52 |
| T1c-5751 | I-3 | II-191 | C-52 |
| T1c-5752 | I-3 | II-192 | C-52 |
| T1c-5753 | I-3 | II-193 | C-52 |
| T1c-5754 | I-3 | II-194 | C-52 |
| T1c-5755 | I-3 | II-195 | C-52 |
| T1c-5756 | I-3 | II-196 | C-52 |
| T1c-5757 | I-3 | II-197 | C-52 |
| T1c-5758 | I-3 | II-198 | C-52 |
| T1c-5759 | I-3 | II-199 | C-52 |
| T1c-5760 | I-3 | II-200 | C-52 |
| T1c-5761 | I-3 | II-201 | C-52 |
| T1c-5762 | I-3 | II-202 | C-52 |
| T1c-5763 | I-3 | II-203 | C-52 |
| T1c-5764 | I-3 | II-91 | C-53 |
| T1c-5765 | I-3 | II-92 | C-53 |
| T1c-5766 | I-3 | II-93 | C-53 |
| T1c-5767 | I-3 | II-94 | C-53 |
| T1c-5768 | I-3 | II-95 | C-53 |
| T1c-5769 | I-3 | II-96 | C-53 |
| T1c-5770 | I-3 | II-97 | C-53 |
| T1c-5771 | I-3 | II-98 | C-53 |
| T1c-5772 | I-3 | II-99 | C-53 |
| T1c-5773 | I-3 | II-100 | C-53 |
| T1c-5774 | I-3 | II-101 | C-53 |
| T1c-5775 | I-3 | II-102 | C-53 |
| T1c-5776 | I-3 | II-103 | C-53 |
| T1c-5777 | I-3 | II-104 | C-53 |
| T1c-5778 | I-3 | II-105 | C-53 |
| T1c-5779 | I-3 | II-106 | C-53 |
| T1c-5780 | I-3 | II-107 | C-53 |
| T1c-5781 | I-3 | II-108 | C-53 |
| T1c-5782 | I-3 | II-109 | C-53 |
| T1c-5783 | I-3 | II-110 | C-53 |
| T1c-5784 | I-3 | II-111 | C-53 |
| T1c-5785 | I-3 | II-112 | C-53 |
| T1c-5786 | I-3 | II-113 | C-53 |
| T1c-5787 | I-3 | II-114 | C-53 |
| T1c-5788 | I-3 | II-115 | C-53 |
| T1c-5789 | I-3 | II-116 | C-53 |
| T1c-5790 | I-3 | II-117 | C-53 |
| T1c-5791 | I-3 | II-118 | C-53 |
| T1c-5792 | I-3 | II-119 | C-53 |
| T1c-5793 | I-3 | II-120 | C-53 |
| T1c-5794 | I-3 | II-121 | C-53 |
| T1c-5795 | I-3 | II-122 | C-53 |
| T1c-5796 | I-3 | II-123 | C-53 |
| T1c-5797 | I-3 | II-124 | C-53 |
| T1c-5798 | I-3 | II-125 | C-53 |
| T1c-5799 | I-3 | II-126 | C-53 |
| T1c-5800 | I-3 | II-127 | C-53 |
| T1c-5801 | I-3 | II-128 | C-53 |
| T1c-5802 | I-3 | II-129 | C-53 |
| T1c-5803 | I-3 | II-130 | C-53 |
| T1c-5804 | I-3 | II-131 | C-53 |
| T1c-5805 | I-3 | II-132 | C-53 |
| T1c-5806 | I-3 | II-133 | C-53 |
| T1c-5807 | I-3 | II-134 | C-53 |
| T1c-5808 | I-3 | II-135 | C-53 |
| T1c-5809 | I-3 | II-136 | C-53 |
| T1c-5810 | I-3 | II-137 | C-53 |
| T1c-5811 | I-3 | II-138 | C-53 |
| T1c-5812 | I-3 | II-139 | C-53 |
| T1c-5813 | I-3 | II-140 | C-53 |
| T1c-5814 | I-3 | II-141 | C-53 |
| T1c-5815 | I-3 | II-142 | C-53 |
| T1c-5816 | I-3 | II-143 | C-53 |
| T1c-5817 | I-3 | II-144 | C-53 |
| T1c-5818 | I-3 | II-145 | C-53 |
| T1c-5819 | I-3 | II-146 | C-53 |
| T1c-5820 | I-3 | II-147 | C-53 |
| T1c-5821 | I-3 | II-148 | C-53 |
| T1c-5822 | I-3 | II-149 | C-53 |
| T1c-5823 | I-3 | II-150 | C-53 |
| T1c-5824 | I-3 | II-151 | C-53 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-5825 | I-3 | II-152 | C-53 |
| T1c-5826 | I-3 | II-153 | C-53 |
| T1c-5827 | I-3 | II-154 | C-53 |
| T1c-5828 | I-3 | II-155 | C-53 |
| T1c-5829 | I-3 | II-156 | C-53 |
| T1c-5830 | I-3 | II-157 | C-53 |
| T1c-5831 | I-3 | II-158 | C-53 |
| T1c-5832 | I-3 | II-159 | C-53 |
| T1c-5833 | I-3 | II-160 | C-53 |
| T1c-5834 | I-3 | II-161 | C-53 |
| T1c-5835 | I-3 | II-162 | C-53 |
| T1c-5836 | I-3 | II-163 | C-53 |
| T1c-5837 | I-3 | II-164 | C-53 |
| T1c-5838 | I-3 | II-165 | C-53 |
| T1c-5839 | I-3 | II-166 | C-53 |
| T1c-5840 | I-3 | II-167 | C-53 |
| T1c-5841 | I-3 | II-168 | C-53 |
| T1c-5842 | I-3 | II-169 | C-53 |
| T1c-5843 | I-3 | II-170 | C-53 |
| T1c-5844 | I-3 | II-171 | C-53 |
| T1c-5845 | I-3 | II-172 | C-53 |
| T1c-5846 | I-3 | II-173 | C-53 |
| T1c-5847 | I-3 | II-174 | C-53 |
| T1c-5848 | I-3 | II-175 | C-53 |
| T1c-5849 | I-3 | II-176 | C-53 |
| T1c-5850 | I-3 | II-177 | C-53 |
| T1c-5851 | I-3 | II-178 | C-53 |
| T1c-5852 | I-3 | II-179 | C-53 |
| T1c-5853 | I-3 | II-180 | C-53 |
| T1c-5854 | I-3 | II-181 | C-53 |
| T1c-5855 | I-3 | II-182 | C-53 |
| T1c-5856 | I-3 | II-183 | C-53 |
| T1c-5857 | I-3 | II-184 | C-53 |
| T1c-5858 | I-3 | II-185 | C-53 |
| T1c-5859 | I-3 | II-186 | C-53 |
| T1c-5860 | I-3 | II-187 | C-53 |
| T1c-5861 | I-3 | II-188 | C-53 |
| T1c-5862 | I-3 | II-189 | C-53 |
| T1c-5863 | I-3 | II-190 | C-53 |
| T1c-5864 | I-3 | II-191 | C-53 |
| T1c-5865 | I-3 | II-192 | C-53 |
| T1c-5866 | I-3 | II-193 | C-53 |
| T1c-5867 | I-3 | II-194 | C-53 |
| T1c-5868 | I-3 | II-195 | C-53 |
| T1c-5869 | I-3 | II-196 | C-53 |
| T1c-5870 | I-3 | II-197 | C-53 |
| T1c-5871 | I-3 | II-198 | C-53 |
| T1c-5872 | I-3 | II-199 | C-53 |
| T1c-5873 | I-3 | II-200 | C-53 |
| T1c-5874 | I-3 | II-201 | C-53 |
| T1c-5875 | I-3 | II-202 | C-53 |
| T1c-5876 | I-3 | II-203 | C-53 |
| T1c-5877 | I-3 | II-91 | C-54 |
| T1c-5878 | I-3 | II-92 | C-54 |
| T1c-5879 | I-3 | II-93 | C-54 |
| T1c-5880 | I-3 | II-94 | C-54 |
| T1c-5881 | I-3 | II-95 | C-54 |
| T1c-5882 | I-3 | II-96 | C-54 |
| T1c-5883 | I-3 | II-97 | C-54 |
| T1c-5884 | I-3 | II-98 | C-54 |
| T1c-5885 | I-3 | II-99 | C-54 |
| T1c-5886 | I-3 | II-100 | C-54 |
| T1c-5887 | I-3 | II-101 | C-54 |
| T1c-5888 | I-3 | II-102 | C-54 |
| T1c-5889 | I-3 | II-103 | C-54 |
| T1c-5890 | I-3 | II-104 | C-54 |
| T1c-5891 | I-3 | II-105 | C-54 |
| T1c-5892 | I-3 | II-106 | C-54 |
| T1c-5893 | I-3 | II-107 | C-54 |
| T1c-5894 | I-3 | II-108 | C-54 |
| T1c-5895 | I-3 | II-109 | C-54 |
| T1c-5896 | I-3 | II-110 | C-54 |
| T1c-5897 | I-3 | II-111 | C-54 |
| T1c-5898 | I-3 | II-112 | C-54 |
| T1c-5899 | I-3 | II-113 | C-54 |
| T1c-5900 | I-3 | II-114 | C-54 |
| T1c-5901 | I-3 | II-115 | C-54 |
| T1c-5902 | I-3 | II-116 | C-54 |
| T1c-5903 | I-3 | II-117 | C-54 |
| T1c-5904 | I-3 | II-118 | C-54 |
| T1c-5905 | I-3 | II-119 | C-54 |
| T1c-5906 | I-3 | II-120 | C-54 |
| T1c-5907 | I-3 | II-121 | C-54 |
| T1c-5908 | I-3 | II-122 | C-54 |
| T1c-5909 | I-3 | II-123 | C-54 |
| T1c-5910 | I-3 | II-124 | C-54 |
| T1c-5911 | I-3 | II-125 | C-54 |
| T1c-5912 | I-3 | II-126 | C-54 |
| T1c-5913 | I-3 | II-127 | C-54 |
| T1c-5914 | I-3 | II-128 | C-54 |
| T1c-5915 | I-3 | II-129 | C-54 |
| T1c-5916 | I-3 | II-130 | C-54 |
| T1c-5917 | I-3 | II-131 | C-54 |
| T1c-5918 | I-3 | II-132 | C-54 |
| T1c-5919 | I-3 | II-133 | C-54 |
| T1c-5920 | I-3 | II-134 | C-54 |
| T1c-5921 | I-3 | II-135 | C-54 |
| T1c-5922 | I-3 | II-136 | C-54 |
| T1c-5923 | I-3 | II-137 | C-54 |
| T1c-5924 | I-3 | II-138 | C-54 |
| T1c-5925 | I-3 | II-139 | C-54 |
| T1c-5926 | I-3 | II-140 | C-54 |
| T1c-5927 | I-3 | II-141 | C-54 |
| T1c-5928 | I-3 | II-142 | C-54 |
| T1c-5929 | I-3 | II-143 | C-54 |
| T1c-5930 | I-3 | II-144 | C-54 |
| T1c-5931 | I-3 | II-145 | C-54 |
| T1c-5932 | I-3 | II-146 | C-54 |
| T1c-5933 | I-3 | II-147 | C-54 |
| T1c-5934 | I-3 | II-148 | C-54 |
| T1c-5935 | I-3 | II-149 | C-54 |
| T1c-5936 | I-3 | II-150 | C-54 |
| T1c-5937 | I-3 | II-151 | C-54 |
| T1c-5938 | I-3 | II-152 | C-54 |
| T1c-5939 | I-3 | II-153 | C-54 |
| T1c-5940 | I-3 | II-154 | C-54 |
| T1c-5941 | I-3 | II-155 | C-54 |
| T1c-5942 | I-3 | II-156 | C-54 |
| T1c-5943 | I-3 | II-157 | C-54 |
| T1c-5944 | I-3 | II-158 | C-54 |
| T1c-5945 | I-3 | II-159 | C-54 |
| T1c-5946 | I-3 | II-160 | C-54 |
| T1c-5947 | I-3 | II-161 | C-54 |
| T1c-5948 | I-3 | II-162 | C-54 |
| T1c-5949 | I-3 | II-163 | C-54 |
| T1c-5950 | I-3 | II-164 | C-54 |
| T1c-5951 | I-3 | II-165 | C-54 |
| T1c-5952 | I-3 | II-166 | C-54 |
| T1c-5953 | I-3 | II-167 | C-54 |
| T1c-5954 | I-3 | II-168 | C-54 |
| T1c-5955 | I-3 | II-169 | C-54 |
| T1c-5956 | I-3 | II-170 | C-54 |
| T1c-5957 | I-3 | II-171 | C-54 |
| T1c-5958 | I-3 | II-172 | C-54 |
| T1c-5959 | I-3 | II-173 | C-54 |
| T1c-5960 | I-3 | II-174 | C-54 |
| T1c-5961 | I-3 | II-175 | C-54 |
| T1c-5962 | I-3 | II-176 | C-54 |
| T1c-5963 | I-3 | II-177 | C-54 |
| T1c-5964 | I-3 | II-178 | C-54 |
| T1c-5965 | I-3 | II-179 | C-54 |
| T1c-5966 | I-3 | II-180 | C-54 |
| T1c-5967 | I-3 | II-181 | C-54 |
| T1c-5968 | I-3 | II-182 | C-54 |
| T1c-5969 | I-3 | II-183 | C-54 |
| T1c-5970 | I-3 | II-184 | C-54 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-5971 | I-3 | II-185 | C-54 |
| T1c-5972 | I-3 | II-186 | C-54 |
| T1c-5973 | I-3 | II-187 | C-54 |
| T1c-5974 | I-3 | II-188 | C-54 |
| T1c-5975 | I-3 | II-189 | C-54 |
| T1c-5976 | I-3 | II-190 | C-54 |
| T1c-5977 | I-3 | II-191 | C-54 |
| T1c-5978 | I-3 | II-192 | C-54 |
| T1c-5979 | I-3 | II-193 | C-54 |
| T1c-5980 | I-3 | II-194 | C-54 |
| T1c-5981 | I-3 | II-195 | C-54 |
| T1c-5982 | I-3 | II-196 | C-54 |
| T1c-5983 | I-3 | II-197 | C-54 |
| T1c-5984 | I-3 | II-198 | C-54 |
| T1c-5985 | I-3 | II-199 | C-54 |
| T1c-5986 | I-3 | II-200 | C-54 |
| T1c-5987 | I-3 | II-201 | C-54 |
| T1c-5988 | I-3 | II-202 | C-54 |
| T1c-5989 | I-3 | II-203 | C-54 |
| T1c-5990 | I-3 | II-91 | C-55 |
| T1c-5991 | I-3 | II-92 | C-55 |
| T1c-5992 | I-3 | II-93 | C-55 |
| T1c-5993 | I-3 | II-94 | C-55 |
| T1c-5994 | I-3 | II-95 | C-55 |
| T1c-5995 | I-3 | II-96 | C-55 |
| T1c-5996 | I-3 | II-97 | C-55 |
| T1c-5997 | I-3 | II-98 | C-55 |
| T1c-5998 | I-3 | II-99 | C-55 |
| T1c-5999 | I-3 | II-100 | C-55 |
| T1c-6000 | I-3 | II-101 | C-55 |
| T1c-6001 | I-3 | II-102 | C-55 |
| T1c-6002 | I-3 | II-103 | C-55 |
| T1c-6003 | I-3 | II-104 | C-55 |
| T1c-6004 | I-3 | II-105 | C-55 |
| T1c-6005 | I-3 | II-106 | C-55 |
| T1c-6006 | I-3 | II-107 | C-55 |
| T1c-6007 | I-3 | II-108 | C-55 |
| T1c-6008 | I-3 | II-109 | C-55 |
| T1c-6009 | I-3 | II-110 | C-55 |
| T1c-6010 | I-3 | II-111 | C-55 |
| T1c-6011 | I-3 | II-112 | C-55 |
| T1c-6012 | I-3 | II-113 | C-55 |
| T1c-6013 | I-3 | II-114 | C-55 |
| T1c-6014 | I-3 | II-115 | C-55 |
| T1c-6015 | I-3 | II-116 | C-55 |
| T1c-6016 | I-3 | II-117 | C-55 |
| T1c-6017 | I-3 | II-118 | C-55 |
| T1c-6018 | I-3 | II-119 | C-55 |
| T1c-6019 | I-3 | II-120 | C-55 |
| T1c-6020 | I-3 | II-121 | C-55 |
| T1c-6021 | I-3 | II-122 | C-55 |
| T1c-6022 | I-3 | II-123 | C-55 |
| T1c-6023 | I-3 | II-124 | C-55 |
| T1c-6024 | I-3 | II-125 | C-55 |
| T1c-6025 | I-3 | II-126 | C-55 |
| T1c-6026 | I-3 | II-127 | C-55 |
| T1c-6027 | I-3 | II-128 | C-55 |
| T1c-6028 | I-3 | II-129 | C-55 |
| T1c-6029 | I-3 | II-130 | C-55 |
| T1c-6030 | I-3 | II-131 | C-55 |
| T1c-6031 | I-3 | II-132 | C-55 |
| T1c-6032 | I-3 | II-133 | C-55 |
| T1c-6033 | I-3 | II-134 | C-55 |
| T1c-6034 | I-3 | II-135 | C-55 |
| T1c-6035 | I-3 | II-136 | C-55 |
| T1c-6036 | I-3 | II-137 | C-55 |
| T1c-6037 | I-3 | II-138 | C-55 |
| T1c-6038 | I-3 | II-139 | C-55 |
| T1c-6039 | I-3 | II-140 | C-55 |
| T1c-6040 | I-3 | II-141 | C-55 |
| T1c-6041 | I-3 | II-142 | C-55 |
| T1c-6042 | I-3 | II-143 | C-55 |
| T1c-6043 | I-3 | II-144 | C-55 |
| T1c-6044 | I-3 | II-145 | C-55 |
| T1c-6045 | I-3 | II-146 | C-55 |
| T1c-6046 | I-3 | II-147 | C-55 |
| T1c-6047 | I-3 | II-148 | C-55 |
| T1c-6048 | I-3 | II-149 | C-55 |
| T1c-6049 | I-3 | II-150 | C-55 |
| T1c-6050 | I-3 | II-151 | C-55 |
| T1c-6051 | I-3 | II-152 | C-55 |
| T1c-6052 | I-3 | II-153 | C-55 |
| T1c-6053 | I-3 | II-154 | C-55 |
| T1c-6054 | I-3 | II-155 | C-55 |
| T1c-6055 | I-3 | II-156 | C-55 |
| T1c-6056 | I-3 | II-157 | C-55 |
| T1c-6057 | I-3 | II-158 | C-55 |
| T1c-6058 | I-3 | II-159 | C-55 |
| T1c-6059 | I-3 | II-160 | C-55 |
| T1c-6060 | I-3 | II-161 | C-55 |
| T1c-6061 | I-3 | II-162 | C-55 |
| T1c-6062 | I-3 | II-163 | C-55 |
| T1c-6063 | I-3 | II-164 | C-55 |
| T1c-6064 | I-3 | II-165 | C-55 |
| T1c-6065 | I-3 | II-166 | C-55 |
| T1c-6066 | I-3 | II-167 | C-55 |
| T1c-6067 | I-3 | II-168 | C-55 |
| T1c-6068 | I-3 | II-169 | C-55 |
| T1c-6069 | I-3 | II-170 | C-55 |
| T1c-6070 | I-3 | II-171 | C-55 |
| T1c-6071 | I-3 | II-172 | C-55 |
| T1c-6072 | I-3 | II-173 | C-55 |
| T1c-6073 | I-3 | II-174 | C-55 |
| T1c-6074 | I-3 | II-175 | C-55 |
| T1c-6075 | I-3 | II-176 | C-55 |
| T1c-6076 | I-3 | II-177 | C-55 |
| T1c-6077 | I-3 | II-178 | C-55 |
| T1c-6078 | I-3 | II-179 | C-55 |
| T1c-6079 | I-3 | II-180 | C-55 |
| T1c-6080 | I-3 | II-181 | C-55 |
| T1c-6081 | I-3 | II-182 | C-55 |
| T1c-6082 | I-3 | II-183 | C-55 |
| T1c-6083 | I-3 | II-184 | C-55 |
| T1c-6084 | I-3 | II-185 | C-55 |
| T1c-6085 | I-3 | II-186 | C-55 |
| T1c-6086 | I-3 | II-187 | C-55 |
| T1c-6087 | I-3 | II-188 | C-55 |
| T1c-6088 | I-3 | II-189 | C-55 |
| T1c-6089 | I-3 | II-190 | C-55 |
| T1c-6090 | I-3 | II-191 | C-55 |
| T1c-6091 | I-3 | II-192 | C-55 |
| T1c-6092 | I-3 | II-193 | C-55 |
| T1c-6093 | I-3 | II-194 | C-55 |
| T1c-6094 | I-3 | II-195 | C-55 |
| T1c-6095 | I-3 | II-196 | C-55 |
| T1c-6096 | I-3 | II-197 | C-55 |
| T1c-6097 | I-3 | II-198 | C-55 |
| T1c-6098 | I-3 | II-199 | C-55 |
| T1c-6099 | I-3 | II-200 | C-55 |
| T1c-6100 | I-3 | II-201 | C-55 |
| T1c-6101 | I-3 | II-202 | C-55 |
| T1c-6102 | I-3 | II-203 | C-55 |
| T1c-6103 | I-3 | II-91 | C-56 |
| T1c-6104 | I-3 | II-92 | C-56 |
| T1c-6105 | I-3 | II-93 | C-56 |
| T1c-6106 | I-3 | II-94 | C-56 |
| T1c-6107 | I-3 | II-95 | C-56 |
| T1c-6108 | I-3 | II-96 | C-56 |
| T1c-6109 | I-3 | II-97 | C-56 |
| T1c-6110 | I-3 | II-98 | C-56 |
| T1c-6111 | I-3 | II-99 | C-56 |
| T1c-6112 | I-3 | II-100 | C-56 |
| T1c-6113 | I-3 | II-101 | C-56 |
| T1c-6114 | I-3 | II-102 | C-56 |
| T1c-6115 | I-3 | II-103 | C-56 |
| T1c-6116 | I-3 | II-104 | C-56 |

TABLE T1c-continued

Three-component compositions T1c-1 to T1c-6215 comprising compound I-3, one component II and one component III, in particular ternary compositions containing compound I-3, II and III as only active ingredients.

| composition | I | II | III |
|---|---|---|---|
| T1c-6117 | I-3 | II-105 | C-56 |
| T1c-6118 | I-3 | II-106 | C-56 |
| T1c-6119 | I-3 | II-107 | C-56 |
| T1c-6120 | I-3 | II-108 | C-56 |
| T1c-6121 | I-3 | II-109 | C-56 |
| T1c-6122 | I-3 | II-110 | C-56 |
| T1c-6123 | I-3 | II-111 | C-56 |
| T1c-6124 | I-3 | II-112 | C-56 |
| T1c-6125 | I-3 | II-113 | C-56 |
| T1c-6126 | I-3 | II-114 | C-56 |
| T1c-6127 | I-3 | II-115 | C-56 |
| T1c-6128 | I-3 | II-116 | C-56 |
| T1c-6129 | I-3 | II-117 | C-56 |
| T1c-6130 | I-3 | II-118 | C-56 |
| T1c-6131 | I-3 | II-119 | C-56 |
| T1c-6132 | I-3 | II-120 | C-56 |
| T1c-6133 | I-3 | II-121 | C-56 |
| T1c-6134 | I-3 | II-122 | C-56 |
| T1c-6135 | I-3 | II-123 | C-56 |
| T1c-6136 | I-3 | II-124 | C-56 |
| T1c-6137 | I-3 | II-125 | C-56 |
| T1c-6138 | I-3 | II-126 | C-56 |
| T1c-6139 | I-3 | II-127 | C-56 |
| T1c-6140 | I-3 | II-128 | C-56 |
| T1c-6141 | I-3 | II-129 | C-56 |
| T1c-6142 | I-3 | II-130 | C-56 |
| T1c-6143 | I-3 | II-131 | C-56 |
| T1c-6144 | I-3 | II-132 | C-56 |
| T1c-6145 | I-3 | II-133 | C-56 |
| T1c-6146 | I-3 | II-134 | C-56 |
| T1c-6147 | I-3 | II-135 | C-56 |
| T1c-6148 | I-3 | II-136 | C-56 |
| T1c-6149 | I-3 | II-137 | C-56 |
| T1c-6150 | I-3 | II-138 | C-56 |
| T1c-6151 | I-3 | II-139 | C-56 |
| T1c-6152 | I-3 | II-140 | C-56 |
| T1c-6153 | I-3 | II-141 | C-56 |
| T1c-6154 | I-3 | II-142 | C-56 |
| T1c-6155 | I-3 | II-143 | C-56 |
| T1c-6156 | I-3 | II-144 | C-56 |
| T1c-6157 | I-3 | II-145 | C-56 |
| T1c-6158 | I-3 | II-146 | C-56 |
| T1c-6159 | I-3 | II-147 | C-56 |
| T1c-6160 | I-3 | II-148 | C-56 |
| T1c-6161 | I-3 | II-149 | C-56 |
| T1c-6162 | I-3 | II-150 | C-56 |
| T1c-6163 | I-3 | II-151 | C-56 |
| T1c-6164 | I-3 | II-152 | C-56 |
| T1c-6165 | I-3 | II-153 | C-56 |
| T1c-6166 | I-3 | II-154 | C-56 |
| T1c-6167 | I-3 | II-155 | C-56 |
| T1c-6168 | I-3 | II-156 | C-56 |
| T1c-6169 | I-3 | II-157 | C-56 |
| T1c-6170 | I-3 | II-158 | C-56 |
| T1c-6171 | I-3 | II-159 | C-56 |
| T1c-6172 | I-3 | II-160 | C-56 |
| T1c-6173 | I-3 | II-161 | C-56 |
| T1c-6174 | I-3 | II-162 | C-56 |
| T1c-6175 | I-3 | II-163 | C-56 |
| T1c-6176 | I-3 | II-164 | C-56 |
| T1c-6177 | I-3 | II-165 | C-56 |
| T1c-6178 | I-3 | II-166 | C-56 |
| T1c-6179 | I-3 | II-167 | C-56 |
| T1c-6180 | I-3 | II-168 | C-56 |
| T1c-6181 | I-3 | II-169 | C-56 |
| T1c-6182 | I-3 | II-170 | C-56 |
| T1c-6183 | I-3 | II-171 | C-56 |
| T1c-6184 | I-3 | II-172 | C-56 |
| T1c-6185 | I-3 | II-173 | C-56 |
| T1c-6186 | I-3 | II-174 | C-56 |
| T1c-6187 | I-3 | II-175 | C-56 |
| T1c-6188 | I-3 | II-176 | C-56 |
| T1c-6189 | I-3 | II-177 | C-56 |
| T1c-6190 | I-3 | II-178 | C-56 |
| T1c-6191 | I-3 | II-179 | C-56 |
| T1c-6192 | I-3 | II-180 | C-56 |
| T1c-6193 | I-3 | II-181 | C-56 |
| T1c-6194 | I-3 | II-182 | C-56 |
| T1c-6195 | I-3 | II-183 | C-56 |
| T1c-6196 | I-3 | II-184 | C-56 |
| T1c-6197 | I-3 | II-185 | C-56 |
| T1c-6198 | I-3 | II-186 | C-56 |
| T1c-6199 | I-3 | II-187 | C-56 |
| T1c-6200 | I-3 | II-188 | C-56 |
| T1c-6201 | I-3 | II-189 | C-56 |
| T1c-6202 | I-3 | II-190 | C-56 |
| T1c-6203 | I-3 | II-191 | C-56 |
| T1c-6204 | I-3 | II-192 | C-56 |
| T1c-6205 | I-3 | II-193 | C-56 |
| T1c-6206 | I-3 | II-194 | C-56 |
| T1c-6207 | I-3 | II-195 | C-56 |
| T1c-6208 | I-3 | II-196 | C-56 |
| T1c-6209 | I-3 | II-197 | C-56 |
| T1c-6210 | I-3 | II-198 | C-56 |
| T1c-6211 | I-3 | II-199 | C-56 |
| T1c-6212 | I-3 | II-200 | C-56 |
| T1c-6213 | I-3 | II-201 | C-56 |
| T1c-6214 | I-3 | II-202 | C-56 |
| T1c-6215 | I-3 | II-203 | C-56 |

Table T2c: Three-component compositions T2c-1 to T2c-6215 corresponding to the respective compositions T1c-1 to T1c-6215, wherein component I is I-2 instead of I-3. Consequently, Table T2c contains compositions T2c-1 to T2c-6215 comprising compound I-2, component II and component III, in particular ternary compositions containing compound I-2, II and III as only active ingredients.

Table T3c: Three-component compositions T3c-1 to T3c-6215 corresponding to the respective compositions T1c-1 to T1c-6215, wherein component I is I-1 instead of I-3. Consequently, Table T3c contains compositions T3c-1 to T3c-6215 comprising compound I-1, component II and component III, in particular ternary compositions containing compound I-1, II and III as only active ingredients.

Table T4c: Three-component compositions T4c-1 to T4c-6215 corresponding to the respective compositions T1c-1 to T1c-6215, wherein component I is I-4 instead of I-3. Consequently, Table T4c contains compositions T4c-1 to T4c-6215 comprising compound I-4, component II and component III, in particular ternary compositions containing compound I-4, II and III as only active ingredients.

Table T5c: Three-component compositions T5c-1 to T5c-6215 corresponding to the respective compositions T1c-1 to T1c-6215, wherein component I is I-5 instead of I-3. Consequently, Table T5c contains compositions T5c-1 to T5c-6215 comprising compound I-5, component II and component III, in particular ternary compositions containing compound I-5, II and III as only active ingredients.

Table T6c: Three-component compositions T6c-1 to T6c-6215 corresponding to the respective compositions T1c-1 to T1c-6215, wherein component I is I-6 instead of I-3. Consequently, Table T6c contains compositions T6c-1 to T6c-6215 comprising compound I-6, component II and component III, in particular ternary compositions containing compound I-6, II and III as only active ingredients.

Table T7c: Three-component compositions T7c-1 to T7c-6215 corresponding to the respective compositions T1c-1 to T1c-6215, wherein component I is I-7 instead of I-3. Consequently, Table T7c contains compositions T7c-1 to T7c-6215 comprising compound I-7, component II and component III, in particular ternary compositions containing compound I-7, II and III as only active ingredients.

Table T8c: Three-component compositions T8c-1 to T8c-6215 corresponding to the respective compositions T1c-1 to T1c-6215, wherein component I is I-8 instead of I-3. Consequently, Table T8c contains compositions T8c-1 to T8c-6215 comprising compound I-8, component II and component III, in particular ternary compositions containing compound I-8, II and III as only active ingredients.

Table T9c: Three-component compositions T9c-1 to T9c-6215 corresponding to the respective compositions T1c-1 to T1c-6215, wherein component I is I-9 instead of I-3. Consequently, Table T9c contains compositions T9c-1 to T9c-6215 comprising compound I-9, component II and component III, in particular ternary compositions containing compound I-9, II and III as only active ingredients.

Table T10c: Three-component compositions T10c-1 to T10c-6215 corresponding to the respective compositions T1c-1 to T1c-6215, wherein component I is I-10 instead of I-3. Consequently, Table T10c contains compositions T10c-1 to T10c-6215 comprising compound I-10, component II and component III, in particular ternary compositions containing compound I-10, II and III as only active ingredients.

Table T11c: Three-component compositions T11c-1 to T11c-6215 corresponding to the respective compositions T1c-1 to T1c-6215, wherein component I is I-11 instead of I-3. Consequently, Table T11c contains compositions T11c-1 to T11c-6215 comprising compound I-11, component II and component III, in particular ternary compositions containing compound I-11, II and III as only active ingredients.

Table T12c: Three-component compositions T12c-1 to T12c-6215 corresponding to the respective compositions T1c-1 to T1c-6215, wherein component I is I-12 instead of I-3. Consequently, Table T12c contains compositions T12c-1 to T12c-6215 comprising compound I-12, component II and component III, in particular ternary compositions containing compound I-12, II and III as only active ingredients.

Table T13c: Three-component compositions T13c-1 to T13c-6215 corresponding to the respective compositions T1c-1 to T1c-6215, wherein component I is I-13 instead of I-3. Consequently, Table T13c contains compositions T13c-1 to T13c-6215 comprising compound I-13, component II and component III, in particular ternary compositions containing compound I-13, II and III as only active ingredients.

Table T14c: Three-component compositions T14c-1 to T14c-6215 corresponding to the respective compositions T1c-1 to T1c-6215, wherein component I is I-14 instead of I-3. Consequently, Table T14c contains compositions T14c-1 to T14c-6215 comprising compound I-14, component II and component III, in particular ternary compositions containing compound I-14, II and III as only active ingredients.

Table T15c: Three-component compositions T15c-1 to T15c-6215 corresponding to the respective compositions T1c-1 to T1c-6215, wherein component I is I-15 instead of I-3. Consequently, Table T15c contains compositions T15c-1 to T15c-6215 comprising compound I-15, component II and component III, in particular ternary compositions containing compound I-15, II and III as only active ingredients.

Table T16c: Three-component compositions T16c-1 to T16c-6215 corresponding to the respective compositions T1c-1 to T1c-6215, wherein component I is I-16 instead of I-3. Consequently, Table T16c contains compositions T16c-1 to T16c-6215 comprising compound I-16, component II and component III, in particular ternary compositions containing compound I-16, II and III as only active ingredients.

Table T17c: Three-component compositions T17c-1 to T17c-6215 corresponding to the respective compositions T1c-1 to T1c-6215, wherein component I is I-17 instead of I-3. Consequently, Table T17c contains compositions T17c-1 to T17c-6215 comprising compound I-17, component II and component III, in particular ternary compositions containing compound I-17, II and III as only active ingredients.

Table T18c: Three-component compositions T18c-1 to T18c-6215 corresponding to the respective compositions T1c-1 to T1c-6215, wherein component I is I-18 instead of I-3. Consequently, Table T18c contains compositions T18c-1 to T18c-6215 comprising compound I-18, component II and component III, in particular ternary compositions containing compound I-18, 11 and 11 as only active ingredients.

Table T19c: Three-component compositions T19c-1 to T19c-6215 corresponding to the respective compositions T1c-1 to T1c-6215, wherein component I is I-19 instead of I-3. Consequently, Table T19c contains compositions T19c-1 to T19c-6215 comprising compound I-19, component II and component III, in particular ternary compositions containing compound I-19, II and III as only active ingredients.

Table T20c: Three-component compositions T20c-1 to T20c-6215 corresponding to the respective compositions T1c-1 to T1c-6215, wherein component I is I-20 instead of I-3. Consequently, Table T20c contains compositions T20c-1 to T20c-6215 comprising compound I-20, component II and component III, in particular ternary compositions containing compound I-20, II and III as only active ingredients.

Table T21c: Three-component compositions T21c-1 to T21c-6215 corresponding to the respective compositions T1c-1 to T1c-6215, wherein component I is I-21 instead of I-3. Consequently, Table T21c contains compositions T21c-1 to T21c-6215 comprising compound I-21, component II and component III, in particular ternary compositions containing compound I-21, II and III as only active ingredients.

Table T22c: Three-component compositions T22c-1 to T22c-6215 corresponding to the respective compositions T1c-1 to T1c-6215, wherein component I is I-22 instead of I-3. Consequently, Table T22c contains compositions T22c-1 to T22c-6215 comprising compound I-22, component II and component III, in particular ternary compositions containing compound I-22, II and III as only active ingredients.

Table T23c: Three-component compositions T23c-1 to T23c-6215 corresponding to the respective compositions T1c-1 to T1c-6215, wherein component I is I-23 instead of I-3. Consequently, Table T23c contains compositions T23c-1 to T23c-6215 comprising compound I-23, component II and component III, in particular ternary compositions containing compound I-23, II and III as only active ingredients.

Table T24c: Three-component compositions T24c-1 to T24c-6215 corresponding to the respective compositions T1c-1 to T1c-6215, wherein component I is I-24 instead of I-3. Consequently, Table T24c contains compositions T24c-1 to T24c-6215 comprising compound I-24, component II and component III, in particular ternary compositions containing compound I-24, II and III as only active ingredients.

Table T25c: Three-component compositions T25c-1 to T25c-6215 corresponding to the respective compositions T1c-1 to T1c-6215, wherein component I is I-25 instead of I-3. Consequently, Table T25c contains compositions T25c-1 to T25c-6215 comprising compound I-25, component II and component III, in particular ternary compositions containing compound I-25, II and III as only active ingredients.

Table T26c: Three-component compositions T26c-1 to T26c-6215 corresponding to the respective compositions T1c-1 to T1c-6215, wherein component I is I-26 instead of I-3. Consequently, Table T26c contains compositions T26c-1 to T26c-6215 comprising compound I-26, component II and component III, in particular ternary compositions containing compound I-26, II and III as only active ingredients.

Table T27c: Three-component compositions T27c-1 to T27c-6215 corresponding to the respective compositions T1c-1 to T1c-6215, wherein component I is I-27 instead of I-3. Consequently, Table T27c contains compositions T27c-1 to T27c-6215 comprising compound I-27, component II and component III, in particular ternary compositions containing compound I-27, II and III as only active ingredients.

Table T28c: Three-component compositions T28c-1 to T28c-6215 corresponding to the respective compositions T1c-1 to T1c-6215, wherein component I is I-28 instead of I-3. Consequently, Table T28c contains compositions T28c-1 to T28c-6215 comprising compound I-28, component II and component III, in particular ternary compositions containing compound I-28, II and III as only active ingredients.

Table T29c: Three-component compositions T29c-1 to T29c-6215 corresponding to the respective compositions T1c-1 to T1c-6215, wherein component I is I-29 instead of I-3. Consequently, Table T29c contains compositions T29c-1 to T29c-6215 comprising compound I-29, component II and component III, in particular ternary compositions containing compound I-29, II and III as only active ingredients.

Table T30c: Three-component compositions T30c-1 to T30c-6215 corresponding to the respective compositions T1c-1 to T1c-6215, wherein component I is I-30 instead of I-3. Consequently, Table T30c contains compositions T30c-1 to T30c-6215 comprising compound I-30, component II and component III, in particular ternary compositions containing compound I-30, II and III as only active ingredients.

Table T31c: Three-component compositions T31c-1 to T31c-6215 corresponding to the respective compositions T1c-1 to T1c-6215, wherein component I is I-31 instead of I-3. Consequently, Table T31c contains compositions T31c-1 to T31c-6215 comprising compound I-31, component II and component III, in particular ternary compositions containing compound I-31, II and III as only active ingredients.

According to a further aspect, the present invention relates to four-component compositions, i.e. compositions comprising component I, i.e a compound I, in particular a compound selected from compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30 and I-31 or any group of compounds I detailed above, a component II as defined herein, a component III as defined herein and a component IV.

A further aspect of the invention are compositions comprising more than four active ingredients, such as, in particular five-component-compositions. In addition to the four components I, II, III and IV as detailed above, these inventive compositions comprise a component V.

The compositions comprising component I and biochemical pesticide component II selected from groups L2), L4) and L6) as defined herein can be prepared as compositions comprising besides the active ingredients at least one inert ingredient (auxiliary) by usual means, e. g. by the means given for the compositions of compounds I as detailed below. Concerning usual ingredients of such compositions reference is made to the explanations given for the compositions containing compounds I.

According to one embodiment, the microbial pesticides selected from groups L1), L3) and L5) embrace not only the isolated, pure cultures of the respective micro-organism as defined herein, but also its cell-free extract, its suspensions in a whole broth culture or as a metabolite-containing supernatant or a purified metabolite obtained from a whole broth culture of the microorganism or microorganism strain.

According to a further embodiment, the microbial pesticides selected from groups L1), L3 and L5) embraces not only the isolated, pure cultures of the respective micro-organism as defined herein, but also a cell-free extract thereof or at least one metabolite thereof, and/or a mutant of the respective micro-organism having all the identifying characteristics thereof and also a cell-free extract or at least one metabolite of the mutant.

"Whole broth culture" refers to a liquid culture containing both cells and media. In particular, as used herein, "whole culture broth" refers to a liquid culture of a microorganism containing vegetative cells and/or spores suspended in the culture medium and optionally metabolites produced by the respective microorganism.

As used herein, "culture medium", refers to a medium obtainable by culturing the microorganism in said medium, preferably a liquid broth, and remaining when cells grown in the medium are removed, e. g., the supernatant remaining when cells grown in a liquid broth are removed by centrifugation, filtration, sedimentation, or other means well known in the art; comprising e. g. metabolites produced by the respective microorganism and secreted into the culture medium. The "culture medium" sometimes also referred to as "supernatant" can be obtained e. g. by centrifugation at temperatures of about 2 to 30° C. (more preferably at temperatures of 4 to 20° C.) for about 10 to 60 min (more preferably about 15 to 30 min) at about 5,000 to 20,000×g (more preferably at about 15,000×g).

As used herein, "supernatant" refers to the liquid broth remaining when cells grown in broth are removed by centrifugation, filtration, sedimentation, or other means well known in the art.

The term "cell-free extract" refers to an extract of the vegetative cells, spores and/or the whole culture broth of a microorganism comprising cellular metabolites produced by the respective microorganism obtainable by cell disruption methods known in the art such as solvent-based (e.g. organic solvents such as alcohols sometimes in combination with suitable salts), temperature-based, application of shear forces, cell disruption with an ultrasonicator. The desired extract may be concentrated by conventional concentration techniques such as drying, evaporation, centrifugation or alike. Certain washing steps using organic solvents and/or water-based media may also be applied to the crude extract preferably prior to use.

The term "metabolite" refers to any compound, substance or byproduct produced by a microorganism (such as fungi and bacteria) that has improves plant growth, water use efficiency of the plant, plant health, plant appearance, or the population of beneficial microorganisms in the soil around the plant activity. In particular, as used herein, the term "metabolite" refers to any component, compound, substance or byproduct (including but not limited to small molecule secondary metabolites, polyketides, fatty acid synthase products, non-ribosomal peptides, ribosomal peptides, proteins and enzymes) produced by a microorganism (such as fungi and bacteria, in particular the strains of the invention) that has any beneficial effect as described herein such as pesticidal activity or improvement of plant growth, water use efficiency of the plant, plant health, plant appearance, or the population of beneficial microorganisms in the soil around the plant activity herein.

As used herein, "isolate" refers to a pure microbial culture separated from its natural origin, such an isolate obtained by culturing a single microbial colony. An isolate is a pure culture derived from a heterogeneous, wild population of microorganisms.

The term "mutant" refers a microorganism obtained by direct mutant selection but also includes microorganisms that have been further mutagenized or otherwise manipulated (e.g., via the introduction of a plasmid). Accordingly, embodiments include mutants, variants, and or derivatives of the respective microorganism, both naturally occurring and artificially induced mutants. For example, mutants may be induced by subjecting the microorganism to known mutagens, such as N-methyl-nitrosoguanidine, using conventional methods.

The compositions comprising cell-free extracts and/or metabolites of microbial pesticides selected from groups L1), L3) and L5) as defined herein can be prepared as compositions comprising besides the active ingredients at least one inert ingredient by usual means, e. g. by the means given for the compositions of compounds I. Concerning usual ingredients of such compositions reference is made to the explanations given for the compositions containing compounds I.

The compositions comprising at least one compound I and cells, spores and/or whole broth culture of at least one microbial pesticide selected from groups L1), L3) and L5) as defined herein can be prepared as compositions comprising besides the active ingredients at least one inert ingredient (auxiliary) by usual means (see e.g. H. D. Burges: Formulation of Microbial Biopesticides, Springer, 1998,), e. g. by the means given for the compositions of compounds I. Suitable customary types of such compositions are suspensions, dusts, powders, pastes, granules, pressings, capsules, and compositions thereof. Examples for composition types are suspensions (e.g. SC, OD, FS), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). Herein, it has to be taken into account that each formulation type or choice of auxiliary should not influence the viability of the microorganism during storage of the composition and when finally applied to the soil, plant or plant propagation material. Suitable formulations are e. g. mentioned in WO 2008/002371, U.S. Pat. Nos. 6,955,912, 5,422,107.

Examples for suitable auxiliaries are besides those mentioned earlier herein stabilizers or nutrients and UV protectants. Examples for suitable auxiliaries are those mentioned earlier herein, wherein it must be taken care that choice and amounts of such auxiliaries should not influence the viability of the microbial pesticides in the composition. Especially for bactericides and solvents, compatibility with the respective microorganism of the respective microbial pesticide has to be taken into account. In addition, compositions with microbial pesticides may further contain stabilizers or nutrients and UV protectants.

Suitable stabilizers or nutrients are e.g. alpha-tocopherol, trehalose, glutamate, potassium sorbate, various sugars like glucose, sucrose, lactose and maltodextrine (H. D. Burges: Formulation of Microbial Biopesticides, Springer, 1998). Suitable UV protectants are e.g. inorganic compounds like titan dioxide, zinc oxide and iron oxide pigments or organic compounds like benzophenones, benzotriazoles and phenyltriazines. The compositions may in addition to auxiliaries mentioned for compositions comprising compounds I herein optionally comprise 0.1-80% stabilizers or nutrients and 0.1-10% UV protectants.

According to the invention, the solid material (dry matter) of the biopesticides (with the exception of oils such as Neem oil, *Tagetes* oil, etc.) are considered as active components (e.g. to be obtained after drying or evaporation of the extraction medium or the suspension medium in case of liquid formulations of the microbial pesticides).

In accordance with the present invention, the weight ratios and percentages used herein for biological extract such as Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calculate the total weight of the respective active component with the following equation that $1 \times 10^{10}$ CFU equals one gram of total weight of the respective active component. Colony forming unit is measure of viable microbial cells, in particular fungal and bacterial cells. In addition, here "CFU" may also be understood as the number of (juvenile) individual nematodes in case of (entomopathogenic) nematode biopesticides, such as *Steinernema feltiae*.

In the binary compositions and compositions according to the invention the weight ratio of the component I and the component II generally depends from the properties of the active components used, usually it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to further embodiments of the binary compositions and compositions, the weight ratio of the component I and the component II usually is in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiments of the binary compositions and compositions, the weight ratio of the component I and the component II usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

According to further embodiments of the compositions and compositions, the weight ratio of the component I and the component II generally depends from the properties of the active components used, usually it is in the range of from 1:10,000 to 10,000:1, regularly in the range of from 1:100 to 10,000:1, preferably in the range of from 1:100 to 5,000:1, more preferably in the range of from 1:1 to 1,000:1, even more preferably in the range of from 1:1 to 500:1 and in particular in the range of from 10:1 to 300:1.

According to further embodiments of the compositions and compositions, the weight ratio of the component I and the component II usually is in the range of from 20,000:1 to 1:10, often in the range of from 10,000:1 to 1:1, regularly in the range of from 5,000:1 to 5:1, preferably in the range of from 5,000:1 to 10:1, more preferably in the range of from 2,000:1 to 30:1, even more preferably in the range of from 2,000:1 to 100:1 and in particular in the range of from 1,000:1 to 100:1.

According to further embodiments of the compositions and compositions, the weight ratio of the component I and the component II usually is in the range of from 1:20,000 to 10:1, often in the range of from 1:10,000 to 1:1, regularly in the range of from 1:5,000 to 1:5, preferably in the range of from 1:5,000 to 1:10, more preferably in the range of from 1:2,000 to 1:30, even more preferably in the range of from 1:2,000 to 1:100 and in particular in the range of from 1:1,000 to 1:100.

In the ternary compositions, i.e. compositions according to the invention comprising the component I and component II and a component III, the weight ratio of component I and component II depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component I and component III usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component I.

These ratios are also suitable for inventive compositions applied by seed treatment.

For microbial pesticides II selected from groups L1), L3) and L5), weight ratios and/or percentages refer to the total weight of a preparation of the respective biopesticide II with at least $1 \times 10^6$ CFU/g ("colony forming units per gram total weight"), preferably with at least $1 \times 10^8$ CFU/g, even more preferably from $1 \times 10^8$ to $1 \times 10^{12}$ CFU/g dry matter. Colony forming unit is a measure of viable microbial cells, in particular fungal and bacterial cells. In addition, here CFU may also be understood as number of (juvenile) individual nematodes in case of (entomopathogenic) nematode biopesticides, such as Steinernema feltiae.

Herein, microbial pesticides II selected from groups L1), L3) and L5) may be supplied in any physiological state such as active or dormant. Such dormant active component may be supplied for example frozen, dried, or lyophilized or partly desiccated (procedures to produce these partly desiccated organisms are given in WO2008/002371) or in form of spores.

Microbial pesticides II selected from groups L1), L3) and L5) used as organism in an active state can be delivered in a growth medium without any additional additives or materials or in combination with suitable nutrient compositions.

According to a further embodiment, microbial pesticides II selected from groups L1), L3) and L5) are delivered and formulated in a dormant stage, more preferably in form of spores.

The total weight ratios of compositions wherein component 3) is selected from groups L1), L3) and L5) can be determined based on the total weight of the solid material (dry matter) of component 1) and using the amount of CFU of component 2) to calculate the total weight of component 2) with the following equation that $1 \times 10^9$ CFU equals one gram of total weight of component 2).

According to one embodiment, the compositions, wherein component 3) is selected from groups L1), L3) and L5), comprise between 0.01 and 90% (w/w) of dry matter (solid material) of component 1) and from $1 \times 10^5$ CFU to $1 \times 10^{12}$ CFU of component 2) per gram total weight of the composition.

According to another embodiment, the compositions, wherein component 3) is selected from groups L1), L3) and L5), comprise between 5 and 70% (w/w) of dry matter (solid material) of component 1) and from $1 \times 10^6$ CFU to $1 \times 10^{10}$ CFU of component 2) per gram total weight of the composition.

According to another embodiment, the compositions, wherein component 3) is selected from groups L1), L3) and L5), comprise between 25 and 70% (w/w) of dry matter (solid material) of component 1) and from $1 \times 10^7$ CFU to $1 \times 10^9$ CFU of component 2) per gram total weight of the composition.

In the case of compositions comprising microbial pesticides II selected from groups L1), L3) and L5), the application rates preferably range from about $1 \times 10^6$ to $5 \times 10^{15}$ (or more) CFU/ha. Preferably, the spore concentration is about $1 \times 10^7$ to about $1 \times 10^{11}$ CFU/ha. In the case of (entomopathogenic) nematodes as microbial pesticides (e.g. Steinernema feltiae), the application rates preferably range inform about $1 \times 10^5$ to $1 \times 10^{12}$ (or more), more preferably from $1 \times 10^8$ to $1 \times 10^{11}$, even more preferably from $5 \times 10^8$ to $1 \times 10^{10}$ individuals (e.g. in the form of eggs, juvenile or any other live stages, preferably in an infective juvenile stage) per ha.

In the case of compositions comprising microbial pesticides II selected from groups L1), L3) and L5), the application rates with respect to plant propagation material preferably range from about $1 \times 10^6$ to $1 \times 10^{12}$ (or more) CFU/seed. Preferably, the concentration is about $1 \times 10^6$ to about $1 \times 10^{11}$ CFU/seed. In the case of microbial pesticides III selected from groups L1), L3) and L5), the application rates with respect to plant propagation material also preferably range from about $1 \times 10^7$ to $1 \times 10^{14}$ (or more) CFU per 100 kg of seed, preferably from $1 \times 10^9$ to about $1 \times 10^{11}$ CFU per 100 kg of seed.

In the case of compositions comprising microbial pesticides II selected from groups L1), L3) and L5), the microorganisms as used according to the invention can be cultivated continuously or discontinuously in the batch process or in the fed batch or repeated fed batch process. A review of known methods of cultivation will be found in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)). The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D. C., USA, 1981). These culture media that can be used according to the invention generally comprise one or more sources of carbon, sources of nitrogen, inorganic salts, vitamins and/or trace elements. Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add compositions of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid. Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soybean protein, yeast extract, meat extract and others. The sources of nitrogen can be used separately or as a composition. Inorganic salt compounds that may be present in the media comprise the chloride, phosphate or sulfate salts of calcium, magnesium, sodium, cobalt, molybdenum, potassium, manganese, zinc, copper and iron. Inorganic sulfur-containing compounds, for example sulfates, sulfites, dithionites, tetrathionates, thiosulfates, sulfides, but also organic sulfur compounds, such as mercaptans and thiols, can be used as sources of sulfur. Phosphoric acid, potassium dihydrogenphosphate or dipotassium hydrogenphosphate or the corresponding sodium-containing salts can be used as sources of phosphorus. Chelating agents can be added to the medium, in order to keep the metal ions in solution. Especially suitable chelating agents comprise dihydroxyphenols, such as catechol or protocatechuate, or organic acids, such as citric acid. The culture media used may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (Publ. P. M. Rhodes, P. F. Stanbury, IRL Press (1997) p. 53-73, ISBN 0 19 963577 3). Growing media can also be obtained from commercial suppliers, such as Standard 1 (Merck) or BHI (Brain heart infusion, DIFCO) etc. All components of the medium are sterilized, either by heating (20 min at 2.0 bar and 121° C.) or by sterile filtration. The components can be sterilized either together, or if necessary separately. All the components of the medium can be present at the start of growing, or optionally can be added continuously or by batch feed. The temperature of the culture of the respective microorganism is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas compositions, e.g. the ambient air, are fed into the culture in order to maintain aerobic conditions. The temperature of the culture is normally from 20° C. to 45° C. Culture is continued until a maximum of the desired product has formed. This is normally achieved within 10 hours to 160 hours. To obtain cell-free extracts, the cells can be disrupted optionally by high-frequency ultrasound, by high pressure, e.g. in a French pressure cell, by osmolysis, by the action of detergents, lytic enzymes or organic solvents, by means of homogenizers or by a combination of several of the methods listed. The methodology of the present invention can further include a step of recovering individual compositions such as cell-free extracts, supernatants, metabolites or alike. The term "recovering" includes extracting, harvesting, isolating or purifying of an extract, supernatant or metabolite e.g. from whole culture broth. Recovering can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like. For example the agent can be recovered from culture media by first removing the microorganisms. The remaining broth is then passed through or over a cation exchange resin to remove unwanted cations and then through or over an anion exchange resin to remove unwanted inorganic anions and organic acids.

The compositions according to the invention are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. *Fungi imperfecti*). Some are systemically effective and they can be used in crop protection as foliar fungicides, fungicides for seed dressing and soil fungicides. Moreover, they are suitable for controlling harmful fungi, which inter alia occur in wood or roots of plants.

The compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e. g. conifers; and on the plant propagation material, such as seeds, and the crop material of these plants.

Preferably, the inventive compositions are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with the components of the inventive compositions and the inventive compositions, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the CryIAb toxin), YieldGard® Plus (corn cultivars producing CryIAb and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, Bite-Gard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S. A., Belgium (corn cultivars producing the Cry3Bb1 toxin), IPC 531 from Monsanto Europe S. A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozyme (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The compositions are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis*(syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e.g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypi*), corn (e. g. *C. graminicola*: Anthracnose stalk rot), soft fruits, potatoes (e. g. *C. coccodes*: black dot), beans (e. g. *C. lindemuthianum*) and soybeans (e. g. *C. truncatum* or *C. gloeosporioides*); *Corticium* spp., e. g. *C. sasaki* (sheath blight) on rice; *Corynespora cassilcola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; *Dematophora* (teleomorph: *Rosellinia*) necatrix (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. a *tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophllum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. glycines now syn. *F. virguliforme*) and *F. tucumaniae* and *F. brasiliense* each causing sudden death syndrome on soybeans and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fufikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseo-*

*lina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria Septoria* blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. P. destructor), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans* late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnni* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni*(*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici*(*Septoria* blotch) on wheat and S. (syn. *Stagonospora*) *nodorum* (*Stagonospora* blotch) on cereals; *Uncinula* (syn. *Erysiphe*) necator (powdery mildew, anamorph: *Oidium tuckeri*) on vines; *Setosphaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Vertiallium* spp. (wilt) on various plants, such as fruits and ornamentals, vines, soft fruits, vegetables and field crops, e. g. *V. dahliae* on strawberries, rape, potatoes and tomatoes.

The compositions are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecllomyces* spp. and Zygomycetes such as *Mucor* spp., and in addition in the protection of stored products and harvest the following yeast fungi are worthy of note: *Candida* spp. and *Saccharomyces cerevisae*.

The compositions may be used for improving the health of a plant. The invention also relates to a method for improving plant health by treating a plant, its propagation material and/or the locus where the plant is growing or is to grow with an effective amount of the components of the inventive compositions or the inventive compositions, respectively.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. Compositions comprising such modifications of compounds I are likewise subject matter of the present invention.

The compositions are used by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with the components of the inventive compositions and the inventive compositions, respectively, prophylactically either at or before planting or transplanting.

The invention also relates to agrochemical compositions comprising an auxiliary and the components of the respective inventive composition or the inventive composition, respectively.

An agrochemical composition comprises a fungicidally effective amount of the components of the inventive compositions or the inventive composition, respectively. The term "effective amount" denotes an amount of the composition or of the components, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The components of the inventive compositions or the inventive compositions, respectively, their N-oxides and salts can be converted into customary types of agrochemical compositions, e. g. solutions, emulsions, suspensions, dusts, powders, pastes, granules, pressings, capsules, and compositions thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and compositions thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and compositions thereof.

Suitable surfactants are surface-active compounds, such as anionic, cationic, nonionic and amphoteric surfactants, block polymers, polyelectrolytes, and compositions thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and compositions thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and compositions thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkyliso-thiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for general composition types and their preparation are (wherein active substances denote the respective components (=active ingredients) of the inventive composition):

i) Water-Soluble Concentrates (SL, LS)

10-60 wt % active substances and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % active substances and 1-10 wt % dispersant (e. g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % active substances and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % active substances and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This composition is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % active substances are comminuted with addition of 2-10 wt % dispersants and wetting agents (e.g. sodium lignosulfonate and alcohol ethoxylate), 0.1-2 wt % thickener (e.g. xanthan gum) and ad water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % active substances are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % active substances are ground in a rotor-stator mill with addition of I-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % active substances are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % active substances are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100 wt %. This composition is stirred for 1 h to produce spontaneously a thermodynamically stable microemulsion.

iv) Microcapsules (CS)

An oil phase comprising 5-50 wt % active substances, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth) acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable Powders (DP, DS)

1-10 wt % active substances are ground finely and mixed intimately with solid carrier (e.g. finely divided kaolin) ad 100 wt %.

x) Granules (GR, FG)

0.5-30 wt % active substances are ground finely and associated with solid carrier (e.g. silicate) ad 100 wt %. Granulation is achieved by extrusion, spray-drying or fluidized bed.

xi) Ultra-Low Volume Liquids (UL)

1-50 wt % active substances are dissolved in organic solvent (e.g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha. from 0.1 to 10 kg active ingredients per 100 kg of seed In treatment of plant propagation materials such as seeds, e. g. by dusting, coating or drenching seed, amounts of active substance of from 0.1 to 10 kg active substances per 100 kg of seed, in particular from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of composition may be mixed by the user himself in a spray tank or any other kind of vessel used for applications (e. g. seed treater drums, seed pelleting machinery, knapsack sprayer) and further auxiliaries may be added, if appropriate.

When living microorganisms, such as microbial pesticides from groups L1), L3) and L5), form part of such kit, it must be taken care that choice and amounts of the components (e. g. chemical pesticides) and of the further auxiliaries should not influence the viability of the microbial pesticides in the composition mixed by the user. Especially for bactericides and solvents, compatibility with the respective microbial pesticide has to be taken into account.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

In the compositions, the ratios of the components are sometimes advantageously chosen so as to produce a synergistic effect.

The term "synergstic effect" is understood to refer in particular to that defined by Colby's formula (Colby, S. R., "Calculating synergistic and antagonistic responses of herbicide combinations", Weeds, 15, pp. 20-22, 1967).

The term "synergistic effect" is also understood to refer to that defined by application of the Tammes method, (Tammes, P. M. L., "Isoboles, a graphic representation of synergism in pesticides", Netherl. J. Plant Pathol. 70, 1964).

The components can be used individually or already partially or completely mixed with one another to prepare the composition according to the invention. It is also possible for them to be packaged and used as combination such as a kit of parts.

The fungicidal action of the compositions according to the invention can be shown by the tests described below.

The active compounds, separately or jointly, are prepared as a stock solution comprising 25 mg of active compound which is made up to 10 ml using a composition of acetone and/or DMSO and the emulsifier Uniperol® EL (wetting agent having an emulsifying and dispersing action based on ethoxylated alkylphenols) in a ratio by volume of solvent/emulsifier of 99:1. The composition is then made up to 100 ml with water. This stock solution is diluted with the solvent/emulsifier/water composition described to give the concentration of active compound stated below.

The visually determined percentages of infected leaf areas are converted into efficacies in % of the untreated control.

The efficacy (E) is calculated as follows using Abbots formula:

$$E=(1-\alpha/\beta)\cdot 100$$

$\alpha$ corresponds to the fungicidal infection of the treated plants in % and
$\beta$ corresponds to the fungicidal infection of the untreated (control) plants in %

An efficacy of 0 means that the infection level of the treated plants corresponds to that of the untreated control plants; an efficacy of 100 means that the treated plants were not infected.

The expected efficacies of active compound combinations were determined using Colby's formula (Colby, S. R. "Calculating synergistic and antagonistic responses of herbicide combinations", Weeds, 15, pp. 20-22, 1967) and compared with the observed efficacies.

$$E=x+y-x\cdot y/100 \qquad \text{Colby's formula:}$$

E expected efficacy, expressed in % of the untreated control, when using the composition of the active compounds A and B at the concentrations a and b
x efficacy, expressed in % of the untreated control, when using the active compound A at the concentration a
y efficacy, expressed in % of the untreated control, when using the active compound B at the concentration b.

Microtests

The active compounds were formulated separately as a stock solution having a concentration of 10000 ppm in dimethyl sulfoxide.

The product orysastrobin was used as commercial finished formulation and diluted with water to the stated concentration of the active compound.

The stock solutions were mixed according to the ratio, pipetted onto a micro titer plate (MTP) and diluted with water to the stated concentrations. A spore suspension of the respective pathogen in the respective nutrient medium was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds. These percentages were converted into efficacies.

The expected efficacies of active compound compositions were determined using Colby's formula [R. S. Colby, "Calculating synergistic and antagonistic responses of herbicide combinations", Weeds 15, 20-22 (1967)] and compared with the observed efficacies.

The invention claimed is:

1. A composition comprising,
   1) as component I
   2-[4-(4 chlorophenoxy)-2-(trifluoromethyl)phenyl]-1-(1,2,4-triazol-1-yl)propan-2-ol;
   and
   2) as component II a biopesticide selected from the group consisting of:
   *Bacillus amyloliquefaciens* ssp. *Plantarum* MBI 600,
   *Bacillus subtilis* FB17,
   *B. amyloliquefaciens* ssp. *Plantarum* QST 713, and
   *Bacillus pumilus* QST 2808; wherein component I and component II are present in a synergistically effect amount.

2. The composition of claim 1, wherein the biopesticide is *Bacillus amyloliquefaciens* ssp. *Plantarum* MBI 600.

3. The composition of claim 1, wherein the biopesticide is *Bacillus subtilis* FB17.

4. The composition of claim 1, wherein component I and component II are present in a total weight ratio of from 100:1 to 1:100 wherein the total weight of component II is based on the amount of the solid material (dry matter) of component II.

5. The composition of claim 1, wherein component I and component II are present in a total weight ratio of from 100:1 to 1:100, wherein the total weight of component II is calculated on the basis of the amount of colony forming units (CFU) of component II, wherein $1 \times 10^9$ CFU equals one gram of total weight of component II.

6. The composition of claim 1, further comprising a component III selected from biopesticides.

7. The composition of claim 1, further comprising an agrochemical auxiliary.

8. The composition of claim 1, wherein the biopesticide is *B. amyloliquefaciens* ssp. *Plantarum* QST 713.

9. The composition of claim 1, wherein the biopesticide is *Bacillus pumilus* QST 2808.

10. A method for combating phytopathogenic fungi, comprising treating the fungi or materials, plants, soil or seeds to be protected against fungal attack with an effective amount of the composition of claim 1.

11. The method of claim 10, wherein the biopesticide is *Bacillus amyloliquefaciens* ssp. *Plantarum* MBI 600.

12. The method of claim 10, wherein the biopesticide is *Bacillus subtilis* FB17.

13. The method of claim 10, wherein the biopesticide is *B. amyloliquefaciens* ssp. *Plantarum* QST 713.

14. The method of claim 10, wherein the biopesticide is *Bacillus pumilus* QST 2808.

15. Plant propagation material, coated with the composition of claim 1, in an amount of from 0.1 to 10 kg active substances per 100 kg of seed.

16. The plant propagation material of claim 15, wherein the biopesticide is *Bacillus amyloliquefaciens* ssp. *Plantarum* MBI 600.

17. The plant propagation material of claim 15, wherein the biopesticide is *Bacillus subtilis* FB17.

18. The plant propagation material of claim 15, wherein the biopesticide is *B. amyloliquefaciens* ssp. *Plantarum* QST 713.

19. The plant propagation material of claim 15, wherein the biopesticide is *Bacillus pumilus* QST 2808.

* * * * *